(12) United States Patent
Tang et al.

(10) Patent No.: US 11,471,455 B2
(45) Date of Patent: Oct. 18, 2022

(54) COMPOUNDS AND COMPOSITIONS FOR TREATING CONDITIONS ASSOCIATED WITH APJ RECEPTOR ACTIVITY

(71) Applicant: Annapurna Bio, Inc., South San Francisco, CA (US)

(72) Inventors: Haifeng Tang, Metuchen, NJ (US); Michael Hanson, San Marcos, CA (US); Sarah Boyce, New York, NY (US); Zhe Nie, San Diego, CA (US)

(73) Assignee: ANNAPURNA BIO, INC., South San Francisco, CA (US)

( * ) Notice: Subject to any disclaimer, the term of this patent is extended or adjusted under 35 U.S.C. 154(b) by 0 days.

(21) Appl. No.: 17/572,531

(22) Filed: Jan. 10, 2022

(65) Prior Publication Data
US 2022/0125787 A1 Apr. 28, 2022

Related U.S. Application Data

(63) Continuation of application No. 17/282,619, filed as application No. PCT/US2019/054880 on Oct. 4, 2019, now abandoned.

(60) Provisional application No. 62/742,218, filed on Oct. 5, 2018.

(51) Int. Cl.
| | |
|---|---|
| C07D 471/04 | (2006.01) |
| C07D 487/04 | (2006.01) |
| A61K 31/4985 | (2006.01) |
| A61K 31/5377 | (2006.01) |
| A61K 31/506 | (2006.01) |
| A61K 31/5025 | (2006.01) |
| A61K 31/444 | (2006.01) |

(52) U.S. Cl.
CPC ........ *A61K 31/4985* (2013.01); *A61K 31/444* (2013.01); *A61K 31/506* (2013.01); *A61K 31/5025* (2013.01); *A61K 31/5377* (2013.01); *C07D 471/04* (2013.01); *C07D 487/04* (2013.01)

(58) Field of Classification Search
CPC .............. C07D 471/04; C07D 487/04; A61K 31/4985; A61K 31/5377
USPC .................................................... 514/210.21
See application file for complete search history.

(56) References Cited

U.S. PATENT DOCUMENTS

| | | |
|---|---|---|
| 5,434,150 A | 7/1995 | Austel et al. |
| 5,482,960 A | 1/1996 | Berryman et al. |
| 5,780,496 A | 7/1998 | Tang et al. |
| 6,358,634 B1 | 3/2002 | Igarashi et al. |
| 6,534,503 B1 | 3/2003 | Dines et al. |
| 6,630,496 B1 | 10/2003 | Seehra et al. |
| 7,569,700 B2 | 8/2009 | Defossa et al. |
| 7,981,893 B2 * | 7/2011 | Mortensen ............... A61P 11/06 514/249 |
| 8,003,668 B2 | 8/2011 | Defossa et al. |
| 8,138,207 B2 | 3/2012 | Defossa et al. |
| 8,188,282 B2 | 5/2012 | Alonso et al. |
| 8,362,019 B2 | 1/2013 | Winfield |
| 8,735,586 B2 | 5/2014 | Alonso et al. |
| 8,975,247 B2 | 3/2015 | Choong et al. |
| 9,156,796 B2 | 10/2015 | Hachtel et al. |
| 10,072,015 B2 | 9/2018 | Guillemont et al. |

(Continued)

FOREIGN PATENT DOCUMENTS

| | | |
|---|---|---|
| CA | 2563116 | 1/2008 |
| CN | 101016294 | 8/2007 |

(Continued)

OTHER PUBLICATIONS

Database Registry [Online], "6-ethyl-1-(1-ethylpropyl)-5-[4-methoxy-6-(trifluoromethyl)-3-pyridinyl]-2-methyl-1H-imidazo[4,5-b]pyrazine", Chemical Abstracts Service, Dec. 7, 2011, Database accession No. 1350255-25-2 (1 page).
Ackermann et al., "Palladium-catalyzed sequential indole synthesis using sterically hindered amines," Tetrahedron, Oct. 31, 2009, 65(44):8930-8939.
Ashwell et al., "Discovery and optimization of a series of 3-(3-Phenyl-3 H-imidazo [4,5-b] pyridin-2-yl)pyridin-2-amines: orally bioavailable, selective, and potent ATP-independent Akt inhibitors," Journal of medicinal chemistry, Jun. 14, 2012, 55(11):5291-5310.
Coquerel et al., "The apelinergic system as an alternative to catecholamines in low-output septic shock," Critical care, Dec. 2018, 22(1):1-7.

(Continued)

*Primary Examiner* — Niloofar Rahmani
(74) *Attorney, Agent, or Firm* — Sheppard Mullin Richter & Hampton LLP

(57) ABSTRACT

This disclosure features chemical entities (e.g., a compound or a pharmaceutically acceptable salt and/or hydrate and/or prodrug of the compound) that modulate (e.g., agonize) the apelin receptor (also referred to herein as the APJ receptor, gene symbol APLNR). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

20 Claims, No Drawings

(56) References Cited

U.S. PATENT DOCUMENTS

| | | |
|---|---|---|
| 2003/0109714 A1 | 6/2003 | Wishart et al. |
| 2003/0232843 A1 | 12/2003 | Cole et al. |
| 2005/0267108 A1 | 12/2005 | Hsieh et al. |
| 2005/0267194 A1 | 12/2005 | Hsieh et al. |
| 2005/0282733 A1 | 12/2005 | Prins et al. |
| 2006/0035945 A1 | 2/2006 | Attardo et al. |
| 2006/0156486 A1 | 7/2006 | Lim |
| 2006/0160884 A1 | 7/2006 | Park et al. |
| 2006/0189606 A1 | 8/2006 | Karp et al. |
| 2006/0205706 A1 | 9/2006 | Prat et al. |
| 2006/0229355 A1 | 10/2006 | Bjeldanes et al. |
| 2006/0247230 A1 | 11/2006 | Martyres et al. |
| 2007/0299069 A1 | 12/2007 | Karp et al. |
| 2008/0027044 A1 | 1/2008 | Lewis et al. |
| 2008/0132501 A1 | 6/2008 | Sun et al. |
| 2008/0161254 A1 | 7/2008 | Green et al. |
| 2009/0264457 A1 | 10/2009 | Codony-Soler et al. |
| 2009/0311217 A1 | 12/2009 | Bursavich et al. |
| 2010/0028299 A1 | 2/2010 | Einav et al. |
| 2010/0061982 A1 | 3/2010 | Ayral-Kaloustin et al. |
| 2011/0053973 A1 | 3/2011 | Guo et al. |
| 2011/0082143 A1 | 4/2011 | Sun et al. |
| 2011/0207750 A1 | 8/2011 | Chu et al. |
| 2011/0281865 A1 | 11/2011 | Muthuppalaniappan et al. |
| 2012/0095037 A1 | 4/2012 | Winfield |
| 2012/0202785 A1 | 8/2012 | Heald et al. |
| 2012/0220575 A1 | 8/2012 | Chang et al. |
| 2012/0258951 A1 | 10/2012 | Sato et al. |
| 2013/0165458 A1 | 6/2013 | Huang et al. |
| 2014/0194407 A1 | 7/2014 | Sato et al. |
| 2014/0336108 A1 | 11/2014 | Guo et al. |
| 2018/0057456 A1 | 3/2018 | Grindrod et al. |
| 2018/0093976 A1 | 4/2018 | Cole et al. |
| 2019/0127365 A1 | 5/2019 | Coburn et al. |
| 2019/0201561 A1 | 7/2019 | Marik et al. |
| 2019/0314390 A1 | 10/2019 | Manfredi et al. |
| 2019/0315717 A1 | 10/2019 | Hummel et al. |
| 2020/0017486 A1 | 1/2020 | Cole et al. |
| 2020/0087283 A1 | 3/2020 | Romero et al. |
| 2021/0009579 A1 | 1/2021 | Strack et al. |
| 2021/0053936 A1 | 2/2021 | Tang et al. |

FOREIGN PATENT DOCUMENTS

| | | |
|---|---|---|
| CN | 104418849 | 3/2015 |
| CN | 105732464 | 7/2016 |
| CN | 109232362 | 1/2019 |
| CN | 110835333 | 2/2020 |
| DE | 102007048447 | 4/2009 |
| DE | 102007049157 | 4/2009 |
| EP | 165588 | 12/1985 |
| EP | 501269 | 9/1992 |
| EP | 547556 | 6/1993 |
| EP | 946948 | 6/1998 |
| EP | 1388541 | 2/2004 |
| EP | 1532980 | 5/2005 |
| EP | 1632491 | 3/2006 |
| EP | 1878724 | 1/2008 |
| EP | 1902733 | 3/2008 |
| EP | 2020230 | 2/2009 |
| JP | 08157461 | 6/1996 |
| JP | 5959330 | 8/2016 |
| WO | WO-93/18765 | 9/1993 |
| WO | WO-95/07263 | 3/1995 |
| WO | WO-95/13266 | 5/1995 |
| WO | WO-98/22457 | 5/1998 |
| WO | WO-98/39342 | 9/1998 |
| WO | WO-98/55479 | 12/1998 |
| WO | WO-99/21553 | 5/1999 |
| WO | WO-99/43651 | 9/1999 |
| WO | WO-99/43654 | 9/1999 |
| WO | WO-99/43672 | 9/1999 |
| WO | WO-99/51225 | 10/1999 |
| WO | WO-2000/002550 | 1/2000 |
| WO | WO-2000/028993 | 5/2000 |
| WO | WO-2001/021634 | 3/2001 |
| WO | WO-2001/028993 | 4/2001 |
| WO | WO-2001/029025 | 4/2001 |
| WO | WO-2001/030778 | 5/2001 |
| WO | WO-2001/047935 | 7/2001 |
| WO | WO-2001/049688 | 7/2001 |
| WO | WO-2001/051473 | 7/2001 |
| WO | WO-2001/070743 | 9/2001 |
| WO | WO-2002/009702 | 2/2002 |
| WO | WO-2002/016353 | 2/2002 |
| WO | WO-2002/020013 | 3/2002 |
| WO | WO-2002/032422 | 4/2002 |
| WO | WO-2002/032900 | 4/2002 |
| WO | WO-2002/046168 | 6/2002 |
| WO | WO-2002/046183 | 6/2002 |
| WO | WO-2002/076960 | 10/2002 |
| WO | WO-2003/000695 | 1/2003 |
| WO | WO-2003/006438 | 1/2003 |
| WO | WO-2003/020276 | 3/2003 |
| WO | WO-2003/024899 | 3/2003 |
| WO | WO-2003/040114 | 5/2003 |
| WO | WO-2003/066622 | 8/2003 |
| WO | WO-2003/068225 | 8/2003 |
| WO | WO-2003/080610 | 10/2003 |
| WO | WO-2003/086371 | 10/2003 |
| WO | WO-2003/095452 | 11/2003 |
| WO | WO-2003/103663 | 12/2003 |
| WO | WO-2004/054582 | 7/2004 |
| WO | WO-2004/063151 | 7/2004 |
| WO | WO-2004/084813 | 10/2004 |
| WO | WO-2005/013976 | 2/2005 |
| WO | WO-2005/014000 | 2/2005 |
| WO | WO-2005/014045 | 2/2005 |
| WO | WO-2005/021510 | 3/2005 |
| WO | WO-2005/023761 | 3/2005 |
| WO | WO-2005/025579 | 3/2005 |
| WO | WO-2005/028624 | 3/2005 |
| WO | WO-2005/041951 | 5/2005 |
| WO | WO-2005/054213 | 6/2005 |
| WO | WO-2005/065686 | 7/2005 |
| WO | WO-2005/105788 | 11/2005 |
| WO | WO-2005/108370 | 11/2005 |
| WO | WO-2005/112932 | 12/2005 |
| WO | WO-2005/118580 | 12/2005 |
| WO | WO-2006/010008 | 1/2006 |
| WO | WO-2006/015867 | 2/2006 |
| WO | WO-2006/019831 | 2/2006 |
| WO | WO-2006/030031 | 2/2006 |
| WO | WO-2006/043145 | 4/2006 |
| WO | WO-2006/060737 | 6/2006 |
| WO | WO-2006/089397 | 8/2006 |
| WO | WO-2006/120573 | 11/2006 |
| WO | WO-2007/024021 | 3/2007 |
| WO | WO-2007/040166 | 4/2007 |
| WO | WO-2007/042321 | 4/2007 |
| WO | WO-2007/056279 | 5/2007 |
| WO | WO-2007/056281 | 5/2007 |
| WO | WO-2007/075629 | 7/2007 |
| WO | WO-2007/084435 | 7/2007 |
| WO | WO-2007/084841 | 7/2007 |
| WO | WO-2007/091106 | 8/2007 |
| WO | WO-2007/102126 | 9/2007 |
| WO | WO-2007/106436 | 9/2007 |
| WO | WO-2007/106938 | 9/2007 |
| WO | WO-2007/117715 | 10/2007 |
| WO | WO-2007/147883 | 12/2007 |
| WO | WO-2007/149727 | 12/2007 |
| WO | WO-2008/056150 | 5/2008 |
| WO | WO-2008/089459 | 7/2008 |
| WO | WO-2008/120661 | 10/2008 |
| WO | WO-2009/000413 | 12/2008 |
| WO | WO-2009/006839 | 1/2009 |
| WO | WO-2009/013010 | 1/2009 |
| WO | WO-2009/019504 | 2/2009 |
| WO | WO-2009/023179 | 2/2009 |
| WO | WO-2009/029622 | 3/2009 |
| WO | WO-2009/039248 | 3/2009 |
| WO | WO-2009/123776 | 10/2009 |
| WO | WO-2009/126691 | 10/2009 |

(56) References Cited

FOREIGN PATENT DOCUMENTS

| WO | WO-2009/134850 | 11/2009 |
|---|---|---|
| WO | WO-2009/158118 | 12/2009 |
| WO | WO-2010/006086 | 1/2010 |
| WO | WO-2010/030360 | 3/2010 |
| WO | WO-2010/035032 | 4/2010 |
| WO | WO-2010/051245 | 5/2010 |
| WO | WO-2010/051781 | 5/2010 |
| WO | WO-2010/068287 | 6/2010 |
| WO | WO-2010/094755 | 8/2010 |
| WO | WO-2010/107739 | 9/2010 |
| WO | WO-2010/115279 | 10/2010 |
| WO | WO-2010/117932 | 10/2010 |
| WO | WO-2010/117935 | 10/2010 |
| WO | WO-2010/117936 | 10/2010 |
| WO | WO-2010/117939 | 10/2010 |
| WO | WO-2010/118009 | 10/2010 |
| WO | WO-2010/123049 | 10/2010 |
| WO | WO-2010/124648 | 11/2010 |
| WO | WO-2010/132684 | 11/2010 |
| WO | WO-2010/142801 | 12/2010 |
| WO | WO-2011/002520 | 1/2011 |
| WO | WO-2011/002635 | 1/2011 |
| WO | WO-2011/019738 | 2/2011 |
| WO | WO-2011/074658 | 6/2011 |
| WO | WO-2011/082270 | 7/2011 |
| WO | WO-2011/102149 | 8/2011 |
| WO | WO-2011/116176 | 9/2011 |
| WO | WO-2011/123693 | 10/2011 |
| WO | WO-2011/127833 | 10/2011 |
| WO | WO-2011/153310 | 12/2011 |
| WO | WO-2012/003576 | 1/2012 |
| WO | WO-2012/009258 | 1/2012 |
| WO | WO-2012/044567 | 4/2012 |
| WO | WO-2012/048058 | 4/2012 |
| WO | WO-2012/065065 | 5/2012 |
| WO | WO-2012/080220 | 6/2012 |
| WO | WO-2012/080221 | 6/2012 |
| WO | WO-2012/102405 | 8/2012 |
| WO | WO-2012/106343 | 8/2012 |
| WO | WO-2012/122383 | 9/2012 |
| WO | WO-2012/124825 | 9/2012 |
| WO | WO-2012/126181 | 9/2012 |
| WO | WO-2012/129562 | 9/2012 |
| WO | WO-2012/146667 | 11/2012 |
| WO | WO-2012/154888 | 11/2012 |
| WO | WO-2013/052395 | 4/2013 |
| WO | WO-2013/053045 | 4/2013 |
| WO | WO-2013/078254 | 5/2013 |
| WO | WO-2013/169907 | 11/2013 |
| WO | WO-2013/186229 | 12/2013 |
| WO | WO-2014/025688 | 2/2014 |
| WO | WO-2014/047427 | 3/2014 |
| WO | WO-2014/049364 | 4/2014 |
| WO | WO-2014/078733 | 5/2014 |
| WO | WO-2014/144455 | 9/2014 |
| WO | WO-2014/148053 | 9/2014 |
| WO | WO-2014/179785 | 11/2014 |
| WO | WO-2014/187922 | 11/2014 |
| WO | WO-2015/000715 | 1/2015 |
| WO | WO-2015/017502 | 2/2015 |
| WO | WO-2015/031608 | 3/2015 |
| WO | WO-2015/073528 | 5/2015 |
| WO | WO-2015/086507 | 6/2015 |
| WO | WO-2015/086509 | 6/2015 |
| WO | WO-2015/138273 | 9/2015 |
| WO | WO-2015/173225 | 11/2015 |
| WO | WO-2016/141122 | 9/2016 |
| WO | WO-2016/168682 | 10/2016 |
| WO | WO-2016/176460 | 11/2016 |
| WO | WO-2016/176657 | 11/2016 |
| WO | WO-2016/196890 | 12/2016 |
| WO | WO-2017/025989 | 2/2017 |
| WO | WO-2017/064068 | 4/2017 |
| WO | WO-2017/089453 | 6/2017 |
| WO | WO-2017/093727 | 6/2017 |
| WO | WO-2017/144517 | 8/2017 |
| WO | WO-2017/171234 | 10/2017 |
| WO | WO-2017/178844 | 10/2017 |
| WO | WO-2018/009625 | 1/2018 |
| WO | WO-2018/093579 | 5/2018 |
| WO | WO-2018/114710 | 6/2018 |
| WO | WO-2018/140730 | 8/2018 |
| WO | WO-2018/175906 | 9/2018 |
| WO | WO-2018/215800 | 11/2018 |
| WO | WO-2018/237084 | 12/2018 |
| WO | WO-2019/005617 | 1/2019 |
| WO | WO-2019/028164 | 2/2019 |
| WO | WO-2019/060693 | 3/2019 |
| WO | WO-2019/060742 | 3/2019 |
| WO | WO-2019/075086 | 4/2019 |
| WO | WO-2019/078619 | 4/2019 |
| WO | WO-2019/113523 | 6/2019 |
| WO | WO-2019/136442 | 7/2019 |
| WO | WO-2019/169193 | 9/2019 |
| WO | WO-2019/195118 | 10/2019 |
| WO | WO-2019/199979 | 10/2019 |
| WO | WO-2019/222272 | 11/2019 |
| WO | WO-2020/006296 | 1/2020 |
| WO | WO-2020/069330 | 4/2020 |
| WO | WO-2020/146532 | 7/2020 |
| WO | WO-2020/160225 | 8/2020 |
| WO | WO-2020/181050 | 9/2020 |
| WO | WO-2020/201773 | 10/2020 |
| WO | WO-2020/243457 | 12/2020 |
| WO | WO-2021/081207 | 4/2021 |
| WO | WO-2021/096314 | 5/2021 |
| WO | WO-2021/127302 | 6/2021 |
| WO | WO-2021/154796 | 8/2021 |
| WO | WO-2021/178362 | 9/2021 |
| WO | WO-2021/183760 | 9/2021 |

OTHER PUBLICATIONS

Crawford et al., "BippyPhos: A single ligand with unprecedented scope in the Buchwald-Hartwig amination of (hetero)aryl chlorides," Chemistry—A European Journal, Dec. 2, 2013, 19(49):16760-16771.

Farrant et al., "A solid-phase synthetic route to substituted 7-azabenzimidazoles suitable for combinatorial library synthesis," Tetrahedron Letters, Jul. 8, 2000, 41(28):5383-5386.

International Preliminary Reporton Patentability in International Appln. No. PCT/US2019/054880, dated Apr. 15, 2021, 10 pages.

International Search Report and Written Opinion in International Appln. No. PCT/US2019/054880, dated Jan. 21, 2020 10 pages.

Keivanloo et al., "Highly efficient synthesis of 5,6-disubstituted-5H-pyrrolo [2, 3-b] pyrazine-2, 3-dicarbonitriles through a one-pot palladium-catalyzed coupling reaction/cyclization in water," Tetrahedron Letters, Jun. 20, 2012, 53(25):3126-3130.

Kim, "Apelin-APJ signaling: a potential therapeutic target for pulmonary arterial hypertension," Molecules and cells, Mar. 31, 2014, 37(3):196-201.

Kolli et al., "Ligand-free Pd-catalyzed C—N cross-coupling/cyclization strategy: An unprecedented access to 1-thienyl pyrroloquinoxalines for the new approach towards apoptosis," European journal of medicinal chemistry, Oct. 30, 2014, 86:270-278.

Lau et al., "Cancer stem cells and their microenvironment: biology and therapeutic implications." Stem cells international, Oct. 2017, 2017:1-12.

Lu et al., "Manganese (I)-Catalyzed C—H (2-Indolyl) methylation: Expedient Access to Diheteroarylmethanes," Angewandte Chemie International Edition, Jan. 26, 2018, 57(5):1399-1403.

O'Carroll et al., "The apelin receptor APJ: journey from an orphan to a multifaceted regulator of homeostasis," JEndocrinol, Oct. 1, 2013, 219(1):RI3-R35.

Pham et al., "Facile synthesis of 4-and 7-azaindoles from the corresponding imines by palladium-catalyzed cascade C—C and C—N coupling," Organic & biomolecular chemistry, 2015, 13(21): 28 pages.

Pires et al., "Synthesis of substituted 4-, 5-, 6-, and 7-azaindoles from aminopyridines via a cascade C—N cross-coupling/heck reaction," Organic letters, Jul. 1, 2016, 18(13): 4 pages.

(56) References Cited

OTHER PUBLICATIONS

Purificacao et al., "One-pot synthesis of 1,2-disubstituted 4-, 5-, 6-, and 7-azaindoles from amino-o-halopyridines via N-arylation/Sonogashira/cyclization reaction," Organic letters, Oct. 6, 2017, 19(19):5118-5121.

Revesz et al., "Novel p38 inhibitors with potent oral efficacy in several models of rheumatoid arthritis," Bioorganic & medicinal chemistry letters, Jul. 5, 2004 14(13):3595-3599.

Rosenberg et al., "Synthesis of 2-amino-imidazo [4,5-b] pyridines," Organic & biomolecular chemistry, 2013, 11(18):3064-3072.

Scimia et al., "APJ acts as a dual receptor in cardiac hypertrophy," Nature, Aug. 2012, 488(7411):394-398.

Zhao et al., "Regiospecific synthesis of 1,2-disubstituted (hetero)aryl fused imidazoles with tunable fluorescent emission," Organic letters, Dec. 16, 2011, 13(24):6516-6519.

\* cited by examiner

COMPOUNDS AND COMPOSITIONS FOR TREATING CONDITIONS ASSOCIATED WITH APJ RECEPTOR ACTIVITY

CROSS REFERENCE TO RELATED APPLICATIONS

This application is a continuation of U.S. application Ser. No. 17/282,619, filed on Apr. 2, 2021, which is a National Stage application under 35 U.S.C. § 371 of International Patent Application No. PCT/US2019/054880, filed on Oct. 4, 2019, which claims the benefit of U.S. Provisional Application No. 62/742,218, filed on Oct. 5, 2018, which are incorporated herein by reference in their entirety.

TECHNICAL FIELD

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

BACKGROUND

Pulmonary arterial hypertension (PAH) is a severe cardiopulmonary disorder characterized by the vascular remodeling of the pulmonary arterioles, including formation of plexiform and concentric lesions comprised of proliferative vascular cells. PAH is believed to be caused by cellular proliferation and fibrosis of the small pulmonary arteries. Clinically, PAH leads to increased pulmonary arterial pressure and subsequent right ventricular failure, which is one of the major causes of morbidity and mortality. Mortality rates remain exceedingly high with 15%, 30%, and 45% mortality at 1, 2, and 3 years after diagnosis, respectively. See, e.g., Kim, J., *Mol. Cells* 2014; 37(3): 196-201 and Lau, E. M. T., *Nature Reviews*, 2017, 1-12.

Diabetes mellitus type 2 (type-2 diabetes) is characterized by high blood glucose and insulin resistance. Type 2 diabetes as well as conditions that are co-morbid or sequela with type-2 diabetes affect tens of millions of people in the United States alone. Type-2 diabetes is frequently associated with obesity.

The apelin or APJ receptor is a G protein-coupled receptor containing seven hydrophobic transmembrane domains (see, e.g., Kim, supra). Apelin (also known as APLN) is a 36 amino acid peptide that in humans is encoded by the APLN gene and is the endogenous ligand for the APJ receptor (see, e.g., O'Carroll, A-M., et al., *J Endocrinol* 2013, 219, R13-R35).

The apelin/APJ system is present in many tissues such as heart, kidney, pancreas, lung, vasculature, central nervous system, liver, adipose, gastrointestinal tract, brain, adrenal glands, endothelium, and human plasma.

Additionally, there is evidence showing that both apelin and APJ are regulators of central and peripheral responses to multiple homeostatic perturbations such as cardiovascular control and function; angiogenesis; fluid homeostasis; water balance; hypothalamic-pituitary-adrenal (HPA) axis regulation; metabolic homeostasis; energy metabolism; and kidney function. For example, there is emerging evidence that APJ-apelin signaling plays a role in the maintenance of pulmonary vascular homeostasis (see, e.g., Kim supra). Evidence also points to a nexus between apelinergic system (e.g., apelin and APJ receptor) and the treatment of conditions such as sepsis, septic shock, and renal failure (see, e.g., Coquerel, D., et al., *Critical Care* 2018, 22: 10). As another example, apelin, synthesized and secreted by adipocytes, has been described as a beneficial adipokine related to obesity, and there is additional evidence of a potential role for apelin and APJ receptor in glucose and energy metabolism (see e.g., O'Carroll supra).

SUMMARY

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type 11 diabetes; renal failure; sepsis; systemic hypertension; idiopathic pulmonary fibrosis (IPF); and systemic sclerosis.

An "agonist" of the APJ receptor includes compounds that, at the protein level, directly bind or modify the APJ receptor such that an activity of the APJ receptor is increased, e.g., by activation, stabilization, altered distribution, or otherwise.

Certain chemical entities described herein that agonize the APJ receptor to a lesser extent than an APJ receptor full agonist can function in assays as antagonists as well as agonists. These chemical entities antagonize activation of the APJ receptor by an APJ receptor full agonist because they prevent the full effect of APJ receptor interaction. However, the chemical entities also, on their own, activate some APJ receptor activity, typically less than a corresponding amount of the APJ receptor full agonist. Such chemical entities are sometimes referred to herein as "partial agonists of the APJ receptor".

In some embodiments, the chemical entities described herein are agonists (e.g. full agonists) of the APJ receptor. In other embodiments, the chemical entities described herein are partial agonists of the APJ receptor.

In other embodiments, the chemical entities described herein modulate (e.g., agonize) the APJ receptor in a pathway-specific manner. Accordingly, this disclosure also features chemical entities that exhibit activity as ligand-biased modulators (e.g., ligand-biased agonists). APJ receptor activity can modulate (e.g., alter or bias) competing levels of downstream G-protein signaling (activation) and β-arrestin recruitment. APJ receptor signaling through β-arrestin has been shown to mediate stretch-induced myocardial hypertrophy. See, e.g., Scimia, M. C., et al., *Nature* 2012, 488, 394-398. In certain embodiments, the chemical entities described herein modulate (e.g., reduce, e.g., attenuate, disrupt, inhibit) β-arrestin signaling. In certain embodiments, the chemical entities described herein modulate (e.g., reduce, e.g., attenuate, disrupt, inhibit) recruitment of β-arrestin.

In certain embodiments, the chemical entities described herein activate or increase the levels of downstream G-protein signaling.

In certain embodiments, the chemical entities described herein inhibit or decrease the levels of β-arrestin recruitment.

In certain embodiments, the chemical entities described herein activate or increase the levels of β-arrestin recruitment.

In certain embodiments, the chemical entities described herein selectively modulate (e.g., increase) one of the pathways over the other. For example, the chemical entities described herein can activate or increase the levels of downstream G-protein signaling, and inhibit or decrease the levels of β-arrestin recruitment.

In other embodiments, the chemical entities described herein can activate or increase the levels of downstream G-protein signaling, and activate or increase the levels of β-arrestin recruitment. For example, the chemical entities described herein can fully agonize both β-arrestin and G protein signaling pathways.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In one aspect, the featured chemical entities include compounds of Formula I, or a pharmaceutically acceptable salt thereof:

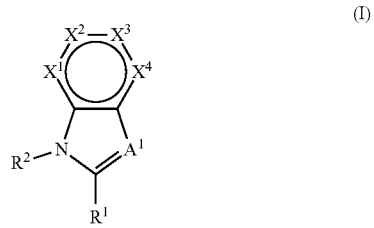

in which $R^1$, $R^2$, $A^1$, $X^1$, $X^2$, $X^3$, and $X^4$ can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing,) APJ receptor activity are featured that include contacting the APJ receptor with a chemical entity described herein (e.g., a compound described generically or specifically herein or a pharmaceutically acceptable salt thereof or compositions containing the same). Methods include in vitro methods, e.g., contacting a sample that includes one or more cells, each independently comprising one or more APJ receptors with the chemical entity. Methods can also include in vivo methods. Such methods can include, e.g., administering the chemical entity to a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition (e.g., PAH; heart failure; type II diabetes; sepsis; renal failure; and systemic hypertension). In vivo methods include, but are not limited to modulating (e.g., decreasing) right ventricular afterload; modulating (e.g., decreasing) mean pulmonary artery pressure; modulating (e.g., increasing) insulin levels; and modulating (e.g., decreasing) glucose levels in a subject (e.g., a human).

In a further aspect, methods of treatment of a disease, disorder, or condition are featured, in a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. The methods include administering to a subject in need of such treatment an effective amount of a chemical entity described herein (e.g., a compound described generically or specifically herein, a pharmaceutically acceptable salt thereof, or compositions containing the same).

In another aspect, this disclosure features methods of treating a subject having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. The methods include administering a chemical entity described herein (e.g., a compound described generically or specifi- cally herein, a pharmaceutically acceptable salt thereof or compositions containing the same) in an amount effective to treat the disease, disorder, or condition.

In a further aspect, methods of treatment are featured that include administering to a subject chemical entity described herein (e.g., a compound described generically or specifically herein, a pharmaceutically acceptable salt thereof, or compositions containing the same). The methods include administering the chemical entity in an amount effective to treat a disease, disorder, or condition, wherein a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition, thereby treating the disease, disorder, or condition.

A non-limiting example of such diseases, disorders, and conditions is PAH. In some embodiments, the PAH is idiopathic. In other embodiments, the PAH is heritable PAH, toxin or drug-induced PAH; or a PAH associated with one or more of the following: congenital heart disease, connective tissue disorders (e.g., scleroderma, systemic lupus erythematosus, systemic sclerosis, Hashimoto's thyroiditis, Sjogren's Syndrome, and the antiphospholipid antibody syndrome), portal hypertension, BMPR2 mutations, Schistosomiasis, and HIV infection.

Another non-limiting example of such diseases, disorders, and conditions is cardiovascular disease, e.g., coronary heart disease and heart failure. In certain embodiments, the cardiovascular disease is heart failure; e.g., systolic heart failure, diastolic heart failure, diabetic heart failure and heart failure with preserved ejection fraction, cardiomyopathy, myocardial infarction, left ventricular dysfunction including left ventricular dysfunction after myocardial infarction, right ventricular dysfunction, right ventricular failure, cardiac hypertrophy, myocardial remodeling including myocardial remodeling after infarction or after cardiac surgery, and valvular heart diseases.

Still another non-limiting example of such diseases, disorders, and conditions is a metabolic disorder, such as metabolic syndrome; diabetes (e.g., type 2 diabetes); obesity; obesity-related disorders; impaired glucose tolerance; and insulin resistance.

Other non-limiting examples of such diseases, disorders, and conditions include sepsis, septic shock, renal failure, systemic hypertension, idiopathic pulmonary fibrosis (IPF), and systemtic sclerosis.

Further non-limiting examples include coronary artery disease (CAD), non-CAD atherosclerotic conditions, including peripheral vascular disease (PVD), aortic atherosclerosis, and cerebral arteriosclerosis, diabetic retinopathy, ischemia-reperfusion injury, emphysema, radiation-induced organ and tissue injury, corpus luteum regression, scleroderma, systemic sclerosis, and diseases of immune dysregulation.

In one aspect, this disclosure features methods for identifying and/or selecting a subject (e.g., a human) likely to benefit from the methods described herein, as well as methods for determining whether a subject (e.g., a human) is responding to such methods. In certain embodiments, a biological sample, which may be, for example and without limitation, a breath, sputum, tissue, plasma or serum sample, urine, is obtained from the subject, and the level of a particular parameter in the sample is determined and compared to a control value. In some instances, the control value may be determined from one or more normal individuals not suffering from the disease, disorder, or conditions being treated. In other instances, the control value can also be determined from a sample previously obtained from the subject. Generally, higher (or elevated) levels of the measured parameter relative to a control value determined from a normal, non-diseased individual or population indicate that a subject will benefit from methods described herein. Lower levels generally indicate that a patient is responding to therapy or, for a subject not on such therapy, that the therapeutic methods may not be as beneficial for that subject.

In certain of the foregoing embodiments, the subject is suffering from, or at risk of suffering from PAN. Non-limiting, exemplary parameters related to PAH are delineated below.

In certain embodiments, the parameter is LTB4 level. For example, a baseline or reference value of LTB4 can be 100 pg/mL or greater, 200 pg/mL or greater, 300 pg/mL or greater, 400 pg/mL or greater, 500 pg/mL or greater, 600 pg/mL or greater, or 100 pg/mL or greater. In certain embodiments, the treatment provided is efficacious if, after treatment has started, the endpoint LTB4 level of the subject decreases from the baseline or reference LTB4 level. For example, the endpoint LTB4 level of the subject decreases to 600 pg/mL or less, 500 pg/mL or less, 400 pg/mL or less, 300 pg/mL or less, 200 pg/mL or less, or 100 pg/mL or less. In certain embodiments, the treatment provided is efficacious if, after treatment has started, the endpoint LTB4 level is 30 pg/mg of tissue or lower, 20 pg/mg of tissue of lower, 10 pg/mg of tissue or lower, 7.5 pg/mg of tissue or lower, or 5 pg/mg of tissue or lower. In other embodiments, the treatment provided is efficacious if, after treatment has started, the endpoint LTB4 level is lower than the baseline LTB4 level by 2-fold or more, 3-fold or more, 4-fold or more, or 5-fold or more.

In certain embodiments, the parameter is pulmonary vascular resistance (PVR). The baseline or reference PVR level can be 200 dynsec/cm$^5$ or greater, 240 dynsec/cm$^5$ or greater, 300 dynsec/cm$^5$ or greater, 400 dynsec/cm$^5$ or greater, 500 dynsec/cm$^5$ or greater, 600 dynsec/cm$^5$ or greater, 700 dynsec/cm$^5$ or greater, or 800 dynsec/cm$^5$ or greater. In certain embodiments, the treatment provided is efficacious if, after treatment has started, the endpoint PVR level of the subject decreases from the baseline or reference PVR level by 70 dynsec/cm$^5$ or more, 100 dynsec/cm$^5$ or more, 130 dynsec/cm$^5$ or more, or 160 dynsec/cm$^5$ or more.

In certain embodiments, the parameter is pulmonary arterial pressure (PAP). The baseline or reference PAP level can be 20 mmHg or greater, 25 mmHg or greater, 30 mmHg or greater, 35 mmHg or greater, 40 mmHg or greater, 45 mmHg or greater, 50 mmHg or greater, 60 mmHg or greater, or 70 mmHg or greater. In certain embodiments, the treatment provided is efficacious if, after treatment has started, the endpoint PAP level of the subject decreases from the baseline or reference PAP level by 0.5 mmHg or more, 1 mmHg or more, 1.5 mmHg or more, 5 mmHg or more, 10 mmHg or more, 20 mmHg or more, 30 mmHg or more, 40 mmHg or more, or 50 mmHg. In certain embodiments, the subject exhibits a mean pulmonary artery pressure of greater than 25 mmHg.

In certain embodiments, the parameter is cardiac index (CI). A baseline or reference CI level can be 5 L/min/m.sup.2 or lower, 2.5 L/min/m.sup.2 or lower, 2 L/min/m.sup.2 or lower, 1.5 L/min/m.sup.2 or lower, or 1 L/min/m.sup.2 or lower. In certain embodiments, the treatment provided is efficacious if, after treatment has started, the endpoint CI level increases from the baseline or reference CI level by 0.1 or more, 0.2 or more, 0.3 or more, 0.4 or more, 0.5 or more, 1 or more, or 2 or more.

In certain embodiments, the parameter is pulmonary capillary wedge pressure (PCWP). A baseline or reference PCWP level can be 36 mmHg or less, 24 mmHg or less, 18 mmHg or less, 10 mmHg, or 5 mmHg or less. In certain embodiments, the treatment provided is efficacious if, after treatment has started, the endpoint PCWP level increases from the baseline or reference PCWP level by 0.2 mmHg or more, 0.3 mmHg or more, 0.4 mmHg or more, 0.5 mmHg or more, 0.6 mmHg or more, 1 mmHg or more, or 5 mmHg or more.

In certain embodiments, the parameter is right atrial pressure (RAP). A baseline or reference RAP level can be 4 mmHg or more, 6 mmHg or more, 8 mmHg or more, 10 mmHg or more, 12 mmHg or more, 16 mmHg or more, 20 mmHg or more, or 25 mmHg or more. In certain embodiments, the treatment provided is efficacious if, after treatment has started, the endpoint RAP level of the subject decreases from the baseline or reference RAP level by 5 mmHg or more 2.5 mmHg or more, 1 mmHg or more, 0.5 mmHg or more, or 0.2 mmHg or more.

In certain embodiments, the parameter is the six-minute walk distance (6 MWD). A baseline or reference 6 MWD can be 50 m or less, 100 m or less, 200 m or less, 300 m or less, 400 m or less, or 500 m or less. In certain embodiments, the treatment provided is efficacious it after treatment has started, the endpoint 6 MWD of the subject increases from the baseline or reference 6 MWD by 10 m or more, 15 m or more, 20 m or more, 25 m or more, 30 m or more, or 50 m or more. Alternatively or in addition, treatment provided in the invention is efficacious if, after treatment has started, the endpoint 6 MWD of the subject increases by 3% or more, 4% or more, 5% or more, 10% or more, or 20% or more of the baseline level.

In certain embodiments, the parameter is brain natriuretic peptide (BNP) level. A baseline or reference BNP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. In certain embodiments, the treatment provided is efficacious if, after treatment has started, the endpoint BNP level of the subject decreases from the baseline or reference BNP level. For example, the endpoint BNP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

In certain embodiments, the parameter is atrial natriuretic peptide (ANP) level. A baseline or reference ANP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. In certain embodiments, the treatment provided is efficacious if, after treatment has started, the endpoint ANP level of the subject decreases from the baseline or reference ANP level. For example, the endpoint ANP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

In certain embodiments, the parameter is Diffusion of lung capacity (DLCO), or diffusion capacity of CO, can also be used in the methods as a parameter to determine efficacy. A baseline or reference DLCO can be 90% or less, 80% or less, 70% or less, 50% or less, 45% or less, or 40% or less. In certain embodiments, the treatment provided is efficacious if, after treatment has started, the endpoint DLCO is increased from the baseline level. For example, the endpoint DLCO can be increased from the baseline or reference DLCO by 1% or more, 5% or more, 10% or more, 15% or more, 20% or more, or 50% or more.

In another aspect, this disclosure features methods for reducing the risk of right ventricular failure in a subject in need of such reducing, the method comprising administering to the subject an effective amount of a chemical entity described herein.

The methods described herein can further include treating one or more conditions that are associated, co-morbid or sequela with any one or more of the conditions described herein.

For example, the methods can further include treating one or more conditions that are associated, co-morbid or sequela with PAH, e.g., coronary heart disease or heart failure. In certain embodiments, the cardiovascular disease is heart failure, e.g., systolic heart failure, diastolic heart failure, diabetic heart failure and heart failure with preserved ejection fraction, cardiomyopathy, myocardial infarction, left ventricular dysfunction including left ventricular dysfunction after myocardial infarction, right ventricular dysfunction, right ventricular failure, cardiac hypertrophy, myocardial remodeling including myocardial remodeling after infarction or after cardiac surgery, and valvular heart diseases.

As another example, the methods can further include treating one or more conditions that are co-morbid or sequela with diabetes (e.g., type 2 diabetes), such as obesity, obesity-related disorders, metabolic syndrome, impaired glucose tolerance; insulin resistance; cardiovascular risk factors. (e.g., coronary artery disease, peripheral artery disease, cerebrovascular disease, hypertension, and risk factors related to unmanaged cholesterol and/or lipid levels, and/or inflammation), retinopathy, nephropathy, neuropathy, NASH, bone fracture and cognitive dysfunction.

The methods can further include administering one or more other therapeutic agents (e.g., in combination with a chemical entity described herein).

Embodiments can include one of more of the following advantageous properties.

Apelin peptide is labile; as such, only acute pharmacodynamics effect of apelin peptide is observable. In some embodiments, the compounds described herein exhibit relatively high metabolic stability to allow observations of non-acute pharmacodynamics effect.

In some embodiments, the compounds described herein can lead to reduced atrial pressure in addition to enhancing cardiac output.

In some embodiments, the compounds described herein can selectively activate the G-protein pathway through APJ receptor, thereby reducing tachyphylaxis often associated with dosing potent agonists. As such, in certain embodiments, compounds described herein can reduce arrestin-associated cardiac hypertrophy.

In some embodiments, the compounds described herein can exhibit pleiotropic properties (e.g., inodilator activity, cardio-renal protection, and control of fluid homeostasis).

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "APJ receptor" is meant to include, without limitation, nucleic acids, polynucleotides, oligonucleotides, sense and antisense polynucleotide strands, complementary sequences, peptides, polypeptides, proteins, homologous and/or orthologous APJ or APJ receptor molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The term "IC50" or "EC50" refers an amount, concentration, or dosage of a compound that is required for 50% inhibition or activation of a maximal response in an assay that measures such response.

The terms "effective amount" or "therapeutically effective amount," as used herein, refer to a sufficient amount of a chemical entity (e.g., a compound described generically or specifically herein, a pharmaceutically acceptable salt thereof, or compositions containing the same) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21*st ed.*; Lippincott Williams & Wilkins: Philadelphia, Pa., 2005; *Handbook of Pharmaceutical Excipients,* 6*th ed.*; Rowe et al., Eds.; The Pharmaceutical Press and the American Pharmaceutical Association: 2009; *Handbook of Pharmaceutical Additives,* 3*rd ed.*; Ash and Ash Eds.; Gower Publishing Company: 2007; *Pharmaceutical Preformulation and Formulation,* 2*nd ed.*; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl radical (e.g., —OCH$_3$).

The term "alkylene" refers to a branched or unbranched divalent alkyl (e.g., —CH$_2$—).

The term "arylene" and the like refer to divalent forms of the ring system, here divalent aryl.

The term "alkenyl" refers to a hydrocarbon chain that may be a straight chain or branched chain having one or more carbon-carbon double bonds. The alkenyl moiety contains the indicated number of carbon atoms. For example, C$_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, C$_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene [1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The compounds provided herein may encompass various stereochemical forms. The compounds also encompass diastereomers as well as optical isomers, e.g., mixtures of enantiomers (including atropisomers) including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound. For example, —S(O) (=NH)—R$^4$ is intended to encompass enantiomer:

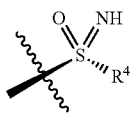

and enantiomer:

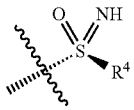

as well as a mixture thereof (e.g., racemic mixture).

The details of one or more embodiments of the invention are set forth in the description below and in the accompanying Appendix, which is expressly considered part of this disclosure. Other features and advantages will also be apparent from the claims.

DETAILED DESCRIPTION

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

Formula (I) Compounds

In one aspect, this disclosure features compounds of Formula (I), or a pharmaceutically acceptable salt thereof:

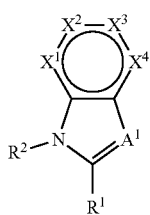

(I)

or a pharmaceutically acceptable salt thereof;
wherein:
$A^1$ is CH or N;
each of $X^1$, $X^2$, $X^3$, and $X^4$ is independently selected from the group consisting of N and $CR^3$;
$R^1$ is:
(i) —$(Y^1)_n$—$Y^2$, wherein:
  n is 0 or 1;
  $Y^1$ is $C_{1-6}$ alkylene, which is optionally substituted with from 1-6 $R^a$; and
  $Y^2$ is:
    (a) $C_{3-10}$ cycloalkyl, which is optionally substituted with from 1-4 $R^b$;
    (b) $C_{6-10}$ aryl, which is optionally substituted with from 1-4 $R^c$;
    (c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
    (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
OR
(ii) —$Z^1$—$Z^2$—$Z^3$, wherein:
  $Z^1$ is $C_{1-3}$ alkylene, which is optionally substituted with from 1-4 $R^a$;
  $Z^2$ is —N(H)—, —N($R^d$)—, —O—, or —S—; and
  $Z^3$ is $C_{2-7}$ alkyl, which is optionally substituted with from 1-4 $R^a$;
OR
(iii) $C_{3-10}$ alkyl, optionally substituted with from 1-6 independently selected $R^a$;
OR
(iv) —$Z^4$—$Z^5$—$Z^6$—$Y^2$ wherein:
  $Z^4$ is $C_{1-3}$ alkylene, which is optionally substituted with from 1-4 $R^a$;
  $Z^5$ is —N(H)—, —N($R^d$)—, —O—, or —S—;

$Z^6$ is $C_{1-4}$ alkylene, which is optionally substituted with from 1-4 $R^a$; and
$Y^2$ is as defined above;
$R^2$ is:
(i) $C_{6-10}$ aryl, which is optionally further substituted with from 1-4 $R^c$;
(ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$;
(iii) $C_{3-10}$ cycloalkyl, which is optionally substituted with from 1-4 $R^b$;
(iv) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$; or
(v) $C_{1-10}$ alkyl, which is optionally substituted with from 1-6 independently selected $R^a$;
each occurrence of $R^3$ is independently selected from the group consisting of -$L^4$-$R^4$, H and, $R^{c'}$;
each occurrence of $L^4$ is independently selected from the group consisting of:
(i) a single bond;
(ii) N(H), N($R^d$), or N($R^4$);
(iii) —N(H)S(O)$_{1-2}$— or —N($R^d$)S(O)$_{1-2}$—;
(iv) —S(O)$_{1-2}$N(H)— or —S(O)$_{1-2}$N($R^d$)—;
(v) —O—;
(vi) —S(O)$_{0-2}$—;
(vii) —C(O)NH— or —C(O)N($R^d$)
(viii) —N(H)C(O)— or —N($R^d$)C(O)—;
(ix) —C≡C;
(x) —N(H)S(O)(=NH)—, —N($R^d$)S(O)(=NH), —N(H)S(O)(=N$R^d$)—, or —N($R^d$)S(O)(=N$R^d$)—
(xi) —S(O)(=NH)NH—, —S(O)(=N$R^d$)NH—, —S(O)(=NH)N$R^d$—, or —S(O)(=N$R^d$)N$R^d$—;
(xii) —S(O)(=NH)— or —S(O)(=N$R^d$); and
(xiii) —N(H)S(O)$_{1-2}$N(H)—, —N($R^d$)S(O)$_{1-2}$N(H)—, —N(H)S(O)$_{1-2}$N($R^d$)—, or —N($R^d$)S(O)$_{1-2}$N($R^d$)—;
each occurrence of $R^4$ is, independently:
(i) —$(Y^3)_p$—$Y^4$, wherein:
  p is 0 or 1;
  $Y^3$ is $C_{1-6}$ alkylene or $C_{1-6}$ alkenylene, each of which is optionally substituted with from 1-6 $R^a$; and
  $Y^4$ is:
    (a) $C_{3-6}$ cycloalkyl, which is optionally substituted with from 1-4 $R^b$,
    (b) $C_{6-10}$ aryl, which is optionally substituted with from 1-4 $R^c$;
    (c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
    (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,

OR (ii) $C_{1-10}$ alkyl, $C_{1-10}$ alkenyl, or $C_{1-10}$ alkynyl, each of which is optionally substituted with from 1-6 independently selected $R^a$;

each occurrence of $R^a$ is independently selected from the group consisting of: —OH; —F; —Cl; —Br; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;

each occurrence of $R^b$ is independently selected from the group consisting of: $C_{1-6}$ alkyl; $C_{1-4}$ haloalkyl; —OH; oxo; —F; —Cl; —Br; —NR$^e$R$^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl;

each occurrence of $R^c$ is independently selected from the group consisting of:

(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —S(O)$_{1-2}$($C_{1-4}$ alkyl);
(xi) —NR$^e$R$^f$;
(xii) —OH;
(xiii) —S(O)$_{1-2}$(NR'R'');
(xiv) —$C_{1-4}$ thioalkoxy;
(xv) —NO$_2$;
(xvi) —C(=O)($C_{1-4}$ alkyl);
(xvii) —C(=O)O($C_{1-4}$ alkyl);
(xviii) —C(=O)OH,
(xix) —C(=O)N(R')(R''), and
(xx) $C_{3-6}$ cycloalkoxy;

each occurrence of $R^{c'}$ is independently selected from the group consisting of:

(i) halo;
(ii) cyano;
(iii) —OH;
(iv) —NO$_2$;
(v) —C(=O)($C_{1-4}$ alkyl);
(vi) —C(=O)O($C_{1-4}$ alkyl);
(vii) —C(=O)OH; and
(viii) —NH$_2$;

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N(R$^d$), O, and S; and each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N(R$^d$), O, and S.

In some embodiments, this disclosure features compounds of Formula (I), or a pharmaceutically acceptable salt thereof:

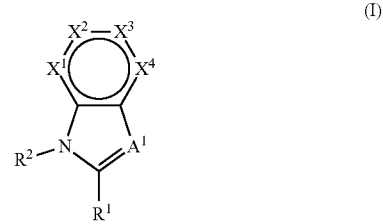

(I)

wherein:

$A^1$ is CH or N;

each of $X^1$, $X^2$, $X^3$, and $X^4$ is independently selected from the group consisting of N and CR$^3$ (e.g., each of $X^1$ and $X^4$ is independently CH or N; and each of $X^2$ and $X^3$ is independently CR$^3$ or N), provided that from 1-3 of $X^1$, $X^2$, $X^3$, and $X^4$ is N;

$R^1$ is:

(i) —(Y$^1$)$_n$—Y$^2$, wherein:
n is 0 or 1;
$Y^1$ is $C_{1-6}$ alkylene, which is optionally substituted with from 1-6 $R^a$; and
$Y^2$ is:
(a) $C_{3-10}$ cycloalkyl, which is optionally substituted with from 1-4 $R^b$,
(b) $C_{6-10}$ aryl, which is optionally substituted with from 1-4 $R^c$;
(c) heteroaryl including from 5-10 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-4 independently selected $R^c$, or
(d) heterocyclyl including from 3-10 ring atoms, wherein from 1-3 ring atoms are heteroatoms, each independently selected from the group consisting of N, N(H), N(R$^d$), and O, and wherein one or more of the heterocyclyl ring carbon atoms are optionally substituted with from 1-4 independently selected $R^b$,

OR (ii) —Z$^1$—Z$^2$—Z$^3$, wherein:
$Z^1$ is $C_{1-3}$ alkylene, which is optionally substituted with from 1-4 $R^a$;
$Z^2$ is —N(H)—, —N(R$^d$)—, —O—, or —S—; and
$Z^3$ is $C_{2-7}$ alkyl, which is optionally substituted with from 1-4 $R^a$;

OR (iii) $C_{3-10}$ alkyl, optionally substituted with from 1-6 independently selected $R^a$;

OR (iv) —Z$^4$—Z$^5$—Z$^6$—Y$^2$ wherein:
$Z^4$ is $C_{1-3}$ alkylene, which is optionally substituted with from 1-4 $R^a$;

$Z^5$ is —N(H)—, —N($R^d$)—, —O—, or —S—;

$Z^6$ is $C_{1-4}$ alkylene, which is optionally substituted with from 1-4 $R^a$; and $Y^2$ is as defined above;

$R^2$ is:
  (i) $C_{6-10}$ aryl, which is optionally further substituted with from 1-4 $R^c$;
  (ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$;
  (iii) $C_{3-10}$ cycloalkyl, which is optionally substituted with from 1-4 $R^b$;
  (iv) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$; or
  (v) $C_{1-10}$ alkyl, which is optionally substituted with from 1-6 independently selected $R^a$ each occurrence of $R^3$ is independently selected from the group consisting of -$L^4$-$R^4$, H and, $R^{c'}$;

each occurrence of $L^4$ is independently selected from the group consisting of:
  (i) a single bond;
  (ii) N(H), N($R^d$), or N($R^4$);
  (iii) —N(H)S(O)$_{1-2}$— or —N($R^d$)S(O)$_{1-2}$—;
  (iv) —S(O)$_{1-2}$N(H)— or —S(O)$_{1-2}$N($R^d$)—;
  (v) —O—;
  (vi) —S(O)$_{0-2}$—;
  (vii) —C(O)NH— or —C(O)N($R^d$);
  (viii) —N(H)C(O)— or —N($R^d$)C(O)—;
  (ix) —C≡C—;
  (x) —N(H)S(O)(=NH)—, —N($R^d$)S(O)(=NH), —N(H)S(O)(=N$R^d$)—, or —N($R^d$)S(O)(=N$R^d$)—
  (xi) —S(O)(=NH)NH—, —S(O)(=N$R^d$)NH—, —S(O)(=NH)N$R^d$—, or —S(O)(=N$R^d$)N$R^d$—; and
  (xii) —S(O)(=NH)— or —S(O)(=N$R^d$);

each occurrence of R' is, independently:
  (i) —($Y^3$)$_p$—$Y^4$, wherein:
    p is 0 or 1;
    $Y^3$ is $C_{1-6}$ alkylene or $C_{1-6}$ alkenylene, each of which is optionally substituted with from 1-6 $R^a$; and
    $Y^4$ is:
      (a) $C_{3-6}$ cycloalkyl, which is optionally substituted with from 1-4 $R^b$,
      (b) $C_{6-10}$ aryl, which is optionally further substituted with from 1-4 $R^c$;
      (c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
      (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$, OR
  (ii) $C_{1-10}$ alkyl, $C_{1-10}$ alkenyl, or $C_{1-10}$ alkynyl, each of which is optionally substituted with from 1-6 independently selected $R^a$;

each occurrence of $R^a$ is independently selected from the group consisting of: —OH; —F; —Cl; —Br; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;

each occurrence of $R^b$ is independently selected from the group consisting of: $C_{1-6}$ alkyl; $C_{1-4}$ haloalkyl; —OH; oxo; —F; —Cl; —Br; —NR$^e$R$^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl;

each occurrence of $R^c$ is independently selected from the group consisting of:
  (i) halo;
  (ii) cyano;
  (iii) $C_{1-6}$ alkyl;
  (iv) $C_{2-6}$ alkenyl;
  (v) $C_{2-6}$ alkynyl;
  (vi) $C_{1-4}$ haloalkyl;
  (vii) $C_{1-4}$ alkoxy;
  (viii) $C_{1-4}$ haloalkoxy;
  (ix) —($C_{0-3}$ alkylene)-$C_{3-6}$ cycloalkyl optionally substituted with from 1-4 independently selected $C_{1-4}$ alkyl;
  (x) —S(O)$_{1-2}$($C_{1-4}$ alkyl);
  (xi) —NR$^e$R$^f$;
  (xii) —OH;
  (xiii) —S(O)$_{1-2}$(NR'R'');
  (xiv) —$C_{1-4}$ thioalkoxy;
  (xv) —NO$_2$;
  (xvi) —C(=O)($C_{1-4}$ alkyl);
  (xvii) —C(=O)O($C_{1-4}$ alkyl);
  (xviii) —C(=O)OH;
  (xix) —C(=O)N(R')(R''); and
  (xx) $C_{3-6}$ cycloalkoxy;

each occurrence of $R^{c'}$ is independently selected from the group consisting of:
  (i) halo;
  (ii) cyano;
  (iii) —OH;
  (iv) —NO$_2$;
  (v) —C(=O)($C_{1-4}$ alkyl);
  (vi) —C(=O)O($C_{1-4}$ alkyl);
  (vii) —C(=O)OH; and
  (viii) —NH$_2$;

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S; and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of $N(R^d)$, O, and S.

In some embodiments, it is provided that when the compound is of Formula (I-1):

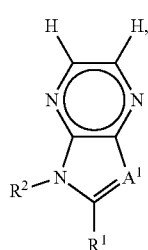

(I-1)

$R^1$ is other than unsubstituted phenyl, para-dimethylaminophenyl, para-aminosulfonylphenyl, and unsubstituted 4-pyridinyl.

In some embodiments, it is provided that when the compound of of Formula (I-1):

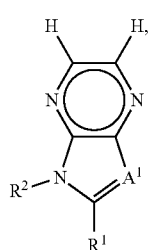

(I-1)

$R^1$ is other than unsubstituted phenyl, para-mono-substituted phenyl, and unsubstituted pyridinyl.

In some embodiments, it is provided that when the compound of Formula (I-2):

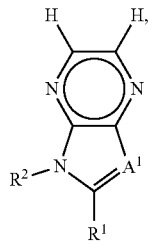

(I-2)

$R^1$ is other than unsubstituted phenyl.

In some embodiments, it is provided that the compound is other than a compound of Formula (I-1) or Formula (I-2):

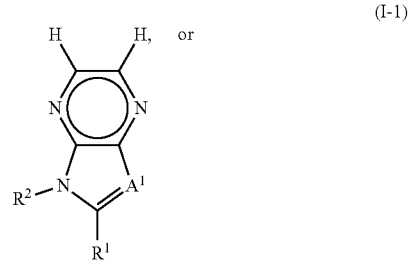

(I-1)

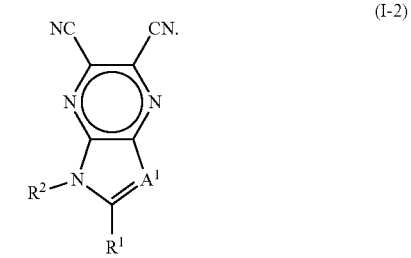

(I-2)

In some embodiments, it is provided that the compound is not of Formula (I-3):

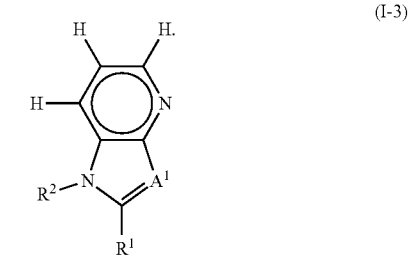

(I-3)

In some embodiments, it is provided that when the compound is of Formula (I-4):

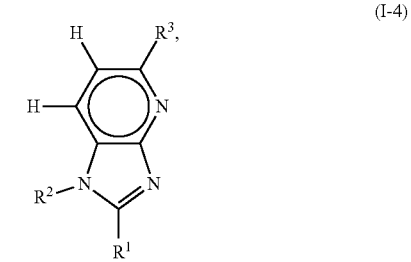

(I-4)

$R^1$ is other than para-monosubstituted phenyl (e.g., para-fluorophenyl).

In some embodiments, it is provided that when the compound is of Formula (I-5):

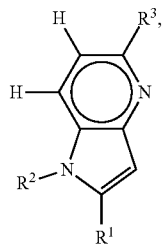
(I-5)

R³ is other than trifluoromethyl.

In some embodiments, it is provided that when the compound is of Formula (I-6):

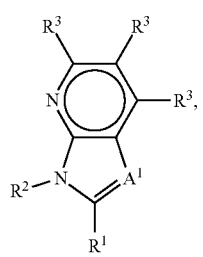
(I-6)

R² is other than:
(i) unsubstituted phenyl;

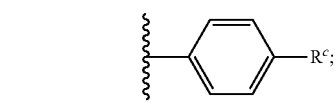
(ii)

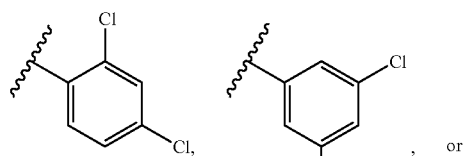
(iii)

, or

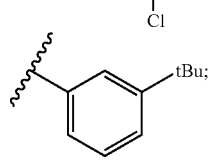

(iv) unsubstituted pyridinyl;

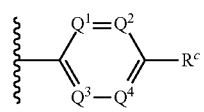
(v)

wherein each of Q¹, Q², Q³, and Q⁴ is independently selected from N and CH; or (vi) heteroaryl including from 9-10 ring atoms, wherein from 1-2 ring atoms are heteroatoms, each independently selected from the group consisting of N, N(H), N(R$^a$), O, and S, and wherein one or more of the heteroaryl ring carbon atoms are optionally substituted with from 1-2 independently selected R$^c$.

In some embodiments, the compound is other than one or more of the following:

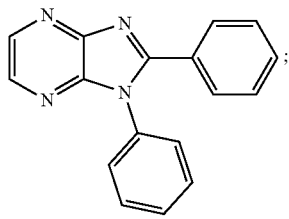
;

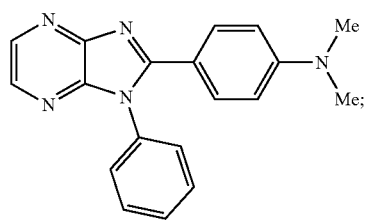
;

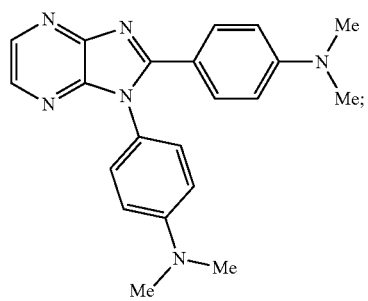
;

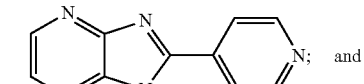
; and

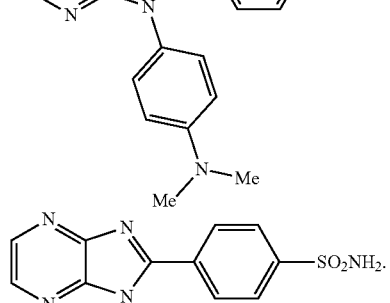

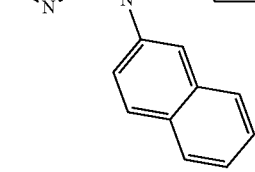
.

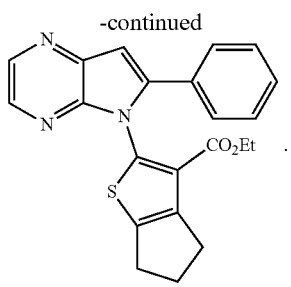

In some embodiments, the compound is other than one or more of the following:

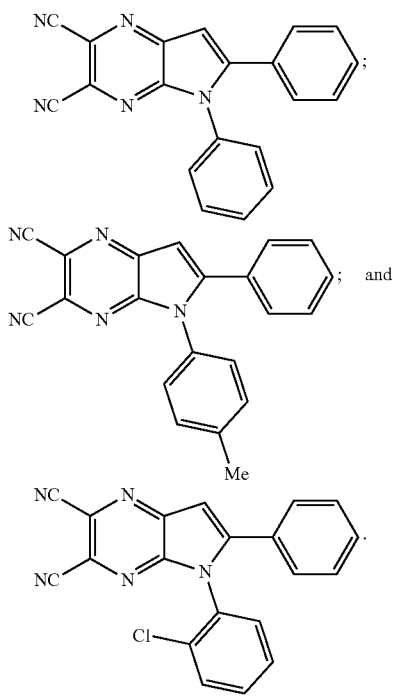

In certain embodiments, the compound is other than those disclosed in *European Journal of Medicinal Chemistry* (2014), 86, 270-278. In certain embodiments, the compound is other than those disclosed in *Tetrahedron Letters* (2012), 53(25), 3126-3130. In certain embodiments, the compound is other than those disclosed in *Organic Letters* (2011), 13(24), 6516-6519. In certain embodiments, the compound is other than those disclosed in U.S. Patent Application Publication No. 2012/0095037 and/or U.S. Pat. No. 8,362,019.

In certain embodiments, the compound is other than those disclosed in *Angewandte Chemie, International Edition* (2018), 57(5), 1399-1403. In certain embodiments, the compound is other than those disclosed in *Organic Letters* (2017), 19(19), 5118-5121. In certain embodiments, the compound is other than those disclosed in *Tetrahedron* (2009), 65(44), 8930-8939. In certain embodiments, the compound is other than those disclosed in *Organic Letters* (2016), 18(13), 3250-3253. In certain embodiments, the compound is other than those disclosed in *Organic & Biomolecular Chemistry* (2015), 13(21), 6047-6058. In certain embodiments, the compound is other than those disclosed in *Chemistry—A European Journal* (2013), 19(49), 16760-16771. In certain embodiments, the compound is other than those disclosed in *Organic & Biomolecular Chemistry* (2013), 11(18), 3064-3072. In certain embodiments, the compound is other than those disclosed in *Organic Letters* (2011), 13(24), 6516-6519. In certain embodiments, the compound is other than those disclosed in *Bioorganic & Medicinal Chemistry Letters* (2004), 14(13), 3595-3599. In certain embodiments, the compound is other than those disclosed in International Patent Application Publication No. 2015/073528. In certain embodiments, the compound is other than those disclosed in International Patent Application Publication No. 2012/146667. In certain embodiments, the compound is other than those disclosed in International Patent Application Publication No. 2001/030778. In certain embodiments, the compound is other than those disclosed in U.S. Patent Application Publication No. 2012/0095037.

In certain embodiments, the compound is other than those disclosed in *Journal of Medicinal Chemistry* (2012), 55(11), 5291-5310. In certain embodiments, the compound is other than those disclosed in *Tetrahedron Letters* (2000), 41(28), 5383-5386. In certain embodiments, the compound is other than those disclosed in International Patent Application Publication No. WO 2017/171234. In certain embodiments, the compound is other than those disclosed in International Patent Application Publication No. WO 2016/176460. In certain embodiments, the compound is other than those disclosed in Japanese Patent Application Publication No. JP 2013/018771 and/or JP 5,959,330. In certain embodiments, the compound is other than those disclosed in International Patent Application Publication No. WO 2011/153310. In certain embodiments, the compound is other than those disclosed in International Patent Application Publication No. WO 2011/082270. In certain embodiments, the compound is other than those disclosed in Australia Patent Application Publication No. AU 2010/331175 and/or U.S. Patent Application Publication No. US 2012/0258951 and/or U.S. 2014/0194407. In certain embodiments, the compound is other than those disclosed in International Patent Application Publication No. WO 2010/051245 and/or U.S. Patent Application Publication No. US 2011/0207750. In certain embodiments, the compound is other than those disclosed in WO 2010/030360. In certain embodiments, the compound is other than those disclosed in European Patent Application No. EP 1878724 and/or U.S. Pat. No. 8,188,282. In certain embodiments, the compound is other than those disclosed in International Patent Application No. WO 2007/075629. In certain embodiments, the compound is other than those disclosed in Japan Patent Application Publication No. JP 2000/302754 and/or U.S. Pat. No. 6,358,634.

Variable $A^1$ and $X^1$-$X^4$

In some embodiments, $A^1$ is N.

In other embodiments, $A^1$ is CH.

In some embodiments, each of $X^1$ and $X^4$ is independently selected from CH and N.

In some embodiments, from 1-2 of $X^1$, $X^2$, $X^3$, and $X^4$ are independently N.

In certain embodiments from 1-2 of $X^1$, $X^2$, $X^3$, and $X^4$ are independently N; and from 2-3 of $X^1$, $X^2$, $X^3$, and $X^4$ are each an independently selected $CR^3$.

In certain embodiments, from 1-2 of $X^1$, $X^2$, $X^3$, and $X^4$ are independently N; and each of $X^1$ and $X^4$ is independently N or CH.

In some embodiments, two of $X^1$, $X^2$, $X^3$, and $X^4$ are independently N; and the other two of $X^1$, $X^2$, $X^3$, and $X^4$ are independently selected from N and $CR^3$.

In certain embodiments, a compound of Formula (I) is of Formula (I-a):

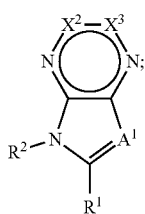
(I-a)

or a pharmaceutically acceptable salt thereof.

In certain embodiments, a compound of Formula (I) is of Formula (I-b):

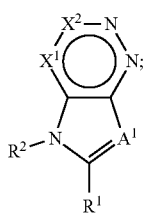
(I-b)

or a pharmaceutically acceptable salt thereof.

In certain of the foregoing embodiments when two of $X^1$, $X^2$, $X^3$, and $X^4$ are independently N, the other two of $X^1$, $X^2$, $X^3$, and $X^4$ are independently selected $CR^3$.

In certain embodiments, a compound of Formula (I) is of Formula (I-a1):

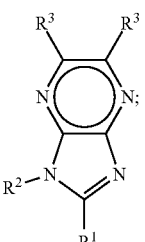
(I-a1)

or a pharmaceutically acceptable salt thereof.

In certain embodiments, a compound of Formula (I) is of Formula (I-a2):

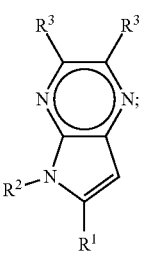
(I-a2)

or a pharmaceutically acceptable salt thereof.

In certain embodiments, a compound of Formula (I) is of Formula (I-b1):

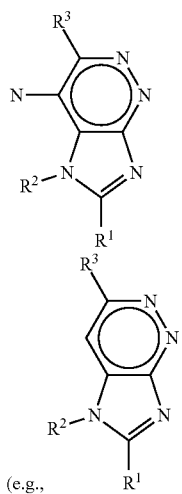
(I-b1)

(e.g., );

or a pharmaceutically acceptable salt thereof.

In some embodiments, one of $X^1$, $X^2$, $X^3$, and $X^4$ is independently N; and the other three of $X^1$, $X^2$, $X^3$, and $X^4$ are independently selected from N and $CR^3$.

In certain embodiments, a compound of Formula (I) is of Formula (I-c):

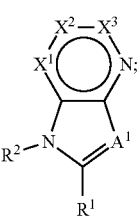
(I-c)

or a pharmaceutically acceptable salt thereof.

In certain embodiments, a compound of Formula (I) is of Formula (I-d):

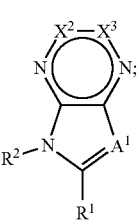
(I-d)

or a pharmaceutically acceptable salt thereof.

In certain of the foregoing embodiments when one of $X^1$, $X^2$, $X^3$, and $X^4$ is independently N, the other three of $X^1$, $X^2$, $X^3$, and $X^4$ are independently selected $CR^3$.

In certain embodiments, a compound of Formula (I) is of Formula (I-c1):

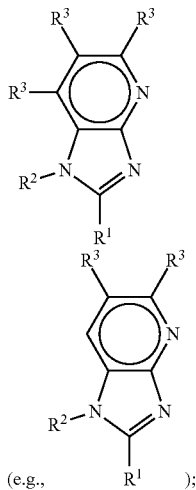

(I-c1)

(e.g., R¹ );

or a pharmaceutically acceptable salt thereof.

In certain embodiments, a compound of Formula (I) is of Formula (I-d1):

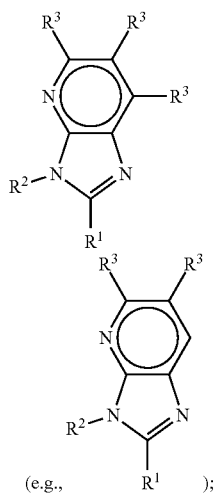

(I-d1)

(e.g., R¹ );

or a pharmaceutically acceptable salt thereof.

In certain embodiments, the compound of Formula (I-d1) has the following formula:

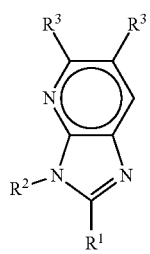

wherein: one $R^3$ is independently selected from -$L^4$-$R^4$ and $R^{c'}$;

the other $R^3$ is independently selected from H, -$L^4$-$R^4$, and $R^{c'}$;

$R^1$ is (i) —$(Y^1)_n$—$Y^2$, wherein:

n is 0;

$Y^2$ is:
(a) partially unsaturated $C_{3-10}$ cycloalkyl, which is optionally substituted with from 1-4 $R^b$,
(b) $C_{6-10}$ aryl, which is optionally substituted with from 1-4 $R^c$;
(c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
(d) partially unsaturated heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$; and $R^2$ is:
(i) $C_{6-10}$ aryl, which is optionally further substituted with from 1-4 $R^c$;
(ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$;
(iii) partially unsaturated $C_{3-10}$ cycloalkyl, which is optionally substituted with from 1-4 $R^b$; or
(iv) partially unsaturated heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

Variable $R^1$

In some embodiments, $R^1$ is —$(Y^1)_n$—$Y^2$.

In some embodiments, n is 0.

In other embodiments, n is 1. In certain of these embodiments, $Y^1$ is $C_{1-3}$ alkylene.

In some embodiments, $Y^2$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$. In certain of the foregoing embodiments, n is 0.

In some embodiments, $Y^2$ is heteroaryl including from 6 ring atoms, wherein from 1-4 ring atoms are heteroatoms, each independently selected from the group consisting of N, N(H), N($R^d$), O, and S, and wherein one or more of the heteroaryl ring carbon atoms are substituted with from 1-4 independently selected $R^c$; or heteroaryl including 5 or from 9-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$; In certain of the foregoing embodiments, n is 0.

In certain embodiments, $Y^2$ is heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$. In certain of these embodiments, n is 0.

In certain embodiments, $Y^2$ is heteroaryl including 6 ring atoms, wherein from 1-2 ring atoms are N, and wherein one or more of the heteroaryl ring carbon atoms are optionally substituted with from 1-4 independently selected $R^c$. For example, $Y^2$ can be pyridyl (e.g., 2-pyridyl or 6-pyridyl), wherein one or more of the ring carbon atoms are optionally substituted with from 1-4 (e.g., 1, 2, 3, or 4) independently selected $R^c$ (e.g., $Y^2$ is pyridyl (e.g., 2-pyridyl or 6-pyridyl), wherein one or more of the ring carbon atoms are optionally substituted with one independently selected $R^c$). In certain of these embodiments, n is 0.

In certain embodiments, $Y^2$ is heteroaryl including 5 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$. For example, $Y^2$ can be pyrazolyl, oxazolyl, or thiazolyl, wherein any substitutable nitrogen atom is optionally substituted with $R^d$, and wherein one or more of the ring carbon atoms are optionally substituted with from 1-2 independently selected $R^c$. In certain of these embodiments, n is 0.

In certain embodiments, $Y^2$ is heteroaryl including 5 ring atoms, wherein from 1-3 ring atoms are heteroatoms, each independently selected from the group consisting of N, N(H), N($R^d$), O, and S, and wherein one or more of the heteroaryl ring carbon atoms are optionally substituted with from 1-3 independently selected $R^c$. In certain of these embodiments, n is 0.

In certain of these embodiments, $Y^2$ is furanyl, wherein one or more of the ring carbon atoms are optionally substituted with from 1-2 (e.g., 1) independently selected $R^c$.

In certain of these embodiments, n is 0.

In certain of the foregoing embodiments when $Y^2$ is heteroaryl, each occurrence of $R^c$ is independently selected from the group consisting of:
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(xiv) —$C_{1-4}$ thioalkoxy;
and
(xx) $C_{3-6}$ cycloalkoxy.

In certain of the foregoing embodiments when $Y^2$ is heteroaryl, each occurrence of $R^c$ is independently selected from the group consisting of:
(vii) $C_{1-4}$ alkoxy;
(viii) $C_{1-4}$ haloalkoxy (e.g., $OCH_2CF_3$ or $OCF_3$);
(xiv) —$C_{1-4}$ thioalkoxy; and
(xx) $C_{3-6}$ cycloalkoxy (e.g., cyclopropoxy).

For example, each occurrence of $R^c$ is an independently selected $C_{1-4}$ alkoxy (e.g., —$OCH_3$, —$OCH_2CH_3$).

As another example, each occurrence of $R^c$ is an independently selected $C_{1-6}$ alkyl (e.g., methyl).

In certain of the foregoing embodiments when $Y^2$ is heteroaryl, each occurrence of $R^d$ is an independently selected $C_{1-6}$ alkyl.

In certain of the foregoing embodiments when $Y^2$ is heteroaryl and n is 0, $R^1$ can be selected from the group consisting of:

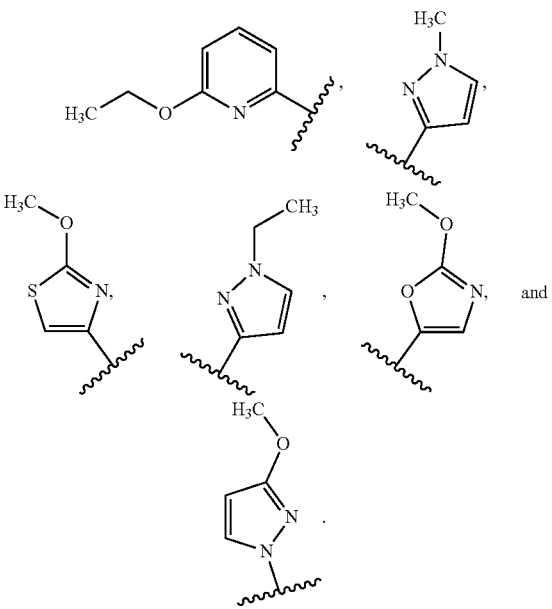

In certain of the foregoing embodiments when $Y^2$ is heteroaryl and n is 0, $R^1$ can be selected from the group consisting of:

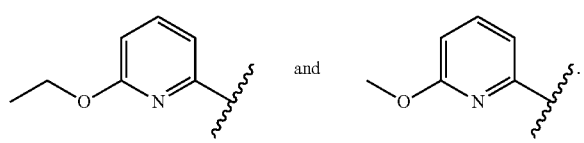

As a non-limiting example of the foregoing embodiments, when $Y^2$ is heteroaryl and n is 0, $R^1$ can be:

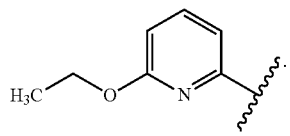

In certain embodiments, when $Y^2$ is heteroaryl and n is 0, $R^1$ can be:

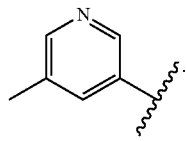 [SMILES: *c1cncc(C)c1]

In certain embodiments, when $Y^2$ is heteroaryl and n is 0, $R^1$ can be:

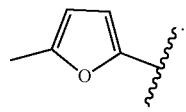

In some embodiments, $Y^2$ is $C_{3-10}$ cycloalkyl, which is optionally substituted with from 1-4 $R^b$. In certain of these embodiments, n is 0.

In some embodiments, $Y^2$ is $C_{6-10}$ aryl, which is optionally substituted with from 1-4 $R^c$.

In certain embodiments, $Y^2$ is phenyl, which is substituted with from 1-4 $R^c$.

In certain embodiments when $Y^2$ is phenyl; and the ring carbon atom para to the point of attachment to $Y^1$ is substituted with $R^c$, then one or more of the other ring carbon atoms is optionally substituted with from 1-3 $R^c$.

In some embodiments, $R^1$ is $-Z^1-Z^2-Z^3$.

In some embodiments, $Z^1$ is $CH_2$.

In some embodiments, $Z^2$ is $-O-$, or $-S-$. For example, $Z^2$ can be $-O-$.

In some embodiments, $Z^3$ is $C_{2-3}$ alkylene.

In certain embodiments, $Z^1$ is $CH_2$, and $Z^2$ is $-O-$, or $-S-$ (e.g., $-O-$).

In certain embodiments, $Z^2$ is $-O-$, or $-S-$ (e.g., $-O-$), and $Z^3$ is $C_{2-3}$ alkylene.

In certain embodiments, $Z^1$ is $CH_2$, and $Z^2$ is $-O-$, or $-S-$ (e.g., $-O-$), and $Z^3$ is $C_{2-3}$ alkylene.

In certain of the foregoing embodiments when $R^1$ is $-Z^1-Z^2-Z^3$, $R^1$ is

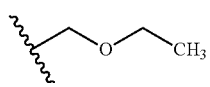

Variable $R^2$

In some embodiments, $R^2$ is:

(i) $C_{6-10}$ aryl, which is optionally further substituted with from 1-4 $R^c$;

(ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with 1-4 independently selected $R^c$;

(iii) partially unsaturated $C_{3-10}$ cycloalkyl, which is optionally substituted with from 1-4 $R^b$; or (iv) partially unsaturated heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

In some embodiments, $R^2$ is $C_{6-10}$ aryl, which is optionally substituted with from 1-4 $R^c$.

In certain embodiments, $R^2$ is phenyl, which is optionally substituted with from 1-4 $R^c$. In certain of the foregoing embodiments, $R^2$ can be phenyl, which is optionally substituted with from 1-2 $R^c$. As a non-limiting example, $R^2$ can be phenyl, which is optionally substituted with 2 $R^c$.

In certain of the foregoing embodiments when $R^2$ is aryl (e.g., phenyl), each occurrence of $R^c$ is independently selected from the group consisting of:

(i) halo (e.g., F);

(vi) $C_{1-4}$ haloalkyl (e.g., $CF_3$);

(vii) $C_{1-4}$ alkoxy;

(viii) $C_{1-4}$ haloalkoxy; and (xiv) $-C_{1-4}$ thioalkoxy.

As a non-limiting example, each occurrence of $R^c$ can be independently selected from halo, $C_{1-4}$ alkoxy, and $C_{1-4}$ haloalkyl (e.g., each occurrence of $R^c$ is independently $-OCH_3$, $CF_3$, or F).

In certain of the foregoing embodiments when $R^2$ is aryl (e.g., phenyl), $R^2$ has the following formula (A):

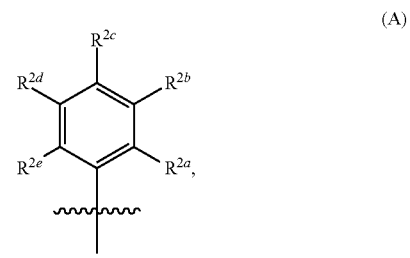

(A)

in which each of $R^2$, $R^{2b}$, $R^{2c}$, $R^{2d}$, and $R^{2e}$ are each independently selected from the group consisting of H and $R^c$.

In certain embodiments, four of $R^{2a}$, $R^{2b}$, $R^{2c}$, $R^{2d}$, and $R^{2e}$ are each an independently selected $R^c$, and the other is H.

In certain embodiments, three of $R^{2a}$, $R^{2b}$, $R^{2c}$, $R^{2d}$, and $R^{2e}$ are each an independently selected $R^c$, and the others are H.

In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; $-C_{1-4}$ thioalkoxy; $C_{1-4}$ haloalkyl and halo e.g., each occurrence of $R^c$ is an independently selected $C_{1-4}$ alkoxy (e.g., $-OCH_3$). For example, $R^{2a}$ and $R^{2c}$ are each $OCH_3$.

In certain embodiments, $R^2$ is:

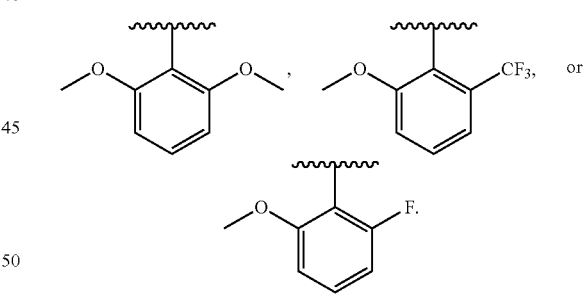

In certain of the foregoing embodiments when $R^2$ is aryl (e.g., phenyl), $R^2$ has formula (B)

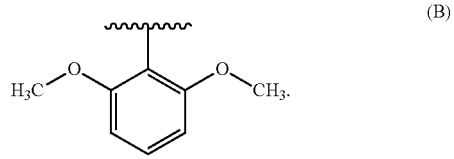 [SMILES: *c1c(OC)cccc1OC]

(B)

In some embodiments, when $R^2$ is aryl (e.g., phenyl); and $R^2$ has the following formula (A):

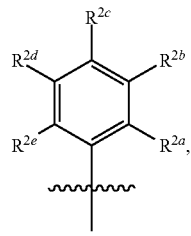

(A)

from 1-4 of $R^{2a}$, $R^{2b}$, $R^{2d}$, and $R^{2e}$ is an independently selected $R^c$.

In certain of the foregoing embodiments, each $R^c$ is independently selected from:
(i) —F;
(ii) cyano;
(iii) $C_{1-3}$ alkyl, $C_{5-6}$ alkyl, n-butyl, sec-butyl, iso-butyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —$S(O)_{1-2}(C_{1-4}$ alkyl);
(xii) —OH;
(xiv) —$C_{1-4}$ thioalkoxy;
(xv) —$NO_2$;
(xvi) —C(=O)($C_{1-4}$ alkyl);
(xvii) —C(=O)O($C_{1-4}$ alkyl);
(xviii) —C(=O)OH;
(xix) —C(=O)N(R')(R''); and
(xx) $C_{3-6}$ cycloalkoxy.

In some embodiments, $R^2$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

In certain of the foregoing embodiments, $R^2$ is heteroaryl including from 6 ring atoms, wherein from 1-3 ring atoms are heteroatoms, each independently selected from the group consisting of N, N(H), and N($R^d$), and wherein one or more of the heteroaryl ring carbon atoms are optionally substituted with from 1-4 independently selected $R^c$.

As a non-limiting example, $R^2$ can be pyridinyl optionally substituted with from 1-2 independently selected $R^c$.

In certain of the foregoing embodiments when $R^2$ is heteroaryl as defined above (e.g., $R^2$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$), each $R^c$ is independently selected from:
(i) halo
(vi) $C_{1-4}$ haloalkyl (e.g., $CF_3$);
(vii) $C_{1-4}$ alkoxy;
(viii) $C_{1-4}$ haloalkoxy; and
(xiv) —$C_{1-4}$ thioalkoxy.

As a non-limiting example, each $R^c$ can be independently $C_{1-4}$ alkoxy (e.g., methoxy).

In certain of the foregoing embodiments when $R^2$ is heteroaryl, $R^2$ is:

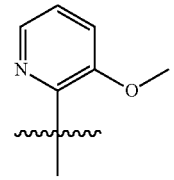 [SMILES: *c1ncccc1OC]

or

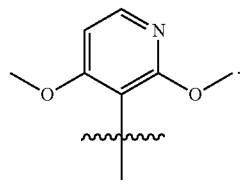

In certain of the foregoing embodiments when $R^2$ is heteroaryl, $R^2$ is:

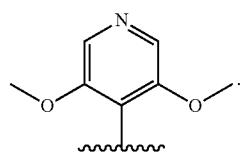

In some embodiments (e.g., when the compound has Formula I-d1), when $R^2$ is heteroaryl as defined elsewhere herein, $R^2$ is selected from:

(a) heteroaryl including 5 ring atoms, wherein from 1-2 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$;

(b)

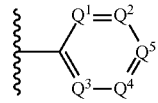

wherein each of $Q^1$, $Q^2$, $Q^3$, $Q^4$, and $Q^5$ is independently selected from N, CH, and $CR^c$, provided that:
from 1-4 of $Q^1$, $Q^2$, $Q^3$, $Q^4$, and $Q^5$ is independently $CR^c$;
one or more of $Q^1$, $Q^2$, $Q^3$, $Q^4$, and $Q^5$ is independently N; and
when $Q^5$ is $CR^c$, one or more of $Q^1$, $Q^2$, $Q^3$, and $Q^4$ is $CR^c$; and (c) heteroaryl including from 9-10 ring atoms, wherein from 1-4 ring atoms are heteroatoms, each independently selected from the group consisting of N, N(H), N($R^d$), O, and S, and wherein one or more of the heteroaryl ring carbon atoms are substituted with from 1-4 independently selected $R^c$, wherein each occurrence of $R^c$ is independently selected from:

(i) —F;
(ii) cyano;
(iii) $C_{2-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —S(O)$_{1-2}$($C_{1-4}$ alkyl);
(xi) —NR$^c$R$^{f}$;
(xiii) —S(O)$_{1-2}$(NR'R");
(xiv) —$C_{1-4}$ thioalkoxy;
(xv) —NO$_2$;
(xvi) —C(=O)($C_{1-4}$ alkyl);
(xvii) —C(=O)O($C_{1-4}$ alkyl);
(xviii) —C(=O)OH;
(xix) —C(=O)N(R')(R"); and
(xx) $C_{3-6}$ cycloalkoxy.

Variable $R^3$

In some embodiments, one or more occurrences of $R^3$ is each independently selected from $R^{c'}$ and -$L^4$-$R^4$.

In some embodiments, one occurrence of $R^3$ is -$L^4$-$R^4$.

In certain of the foregoing embodiments when one occurrence $R^3$ is -$L^4$-$R^4$, each of the remaining occurrences of $R^3$ is independently selected from the group consisting of H and $R^{c'}$ (e.g., $R^{c'}$ can be halo, e.g., Br or Cl; or $R^{c'}$ can be —OH or NH$_2$). For example, each of the remaining occurrences of $R^3$ can be H.

In some embodiments, one occurrence of $R^3$ is -$L^4$-$R^4$, and one occurrence of $R^3$ is H or $R^{c'}$ (e.g., $R^{c'}$ can be halo, e.g., Br or Cl; or $R^{c'}$ can be NH$_2$).

In some embodiments, one occurrence of $R^3$ is -$L^4$-$R^4$, and one occurrence of $R^3$ is $R^{c'}$ (e.g., $R^{c'}$ can be halo, e.g., Br or Cl (e.g., $R^{c'}$ can be Cl)).

In some embodiments, one occurrence of $R^3$ is -$L^4$-$R^4$, and one occurrence of $R^3$ is H.

In some embodiments, two occurrences of $R^3$ are independently selected -$L^4$-$R^4$.

In certain of the foregoing embodiments, any remaining occurrence of $R^3$ is selected from the group consisting of H and $R^{c'}$. For example, any remaining occurrence of $R^3$ can be H.

As a non-limiting example of the foregoing embodiments, each of $X^2$ and $X^3$ can be CR$^3$, wherein each $R^a$ is an independently selected -$L^4$-$R^4$ (in certain embodiments, each of $X^1$ and $X^4$ is independently CH or N).

In some embodiments, one occurrence of $R^3$ is H or $R^{c'}$ (e.g., $R^{c'}$ can be halo, e.g., Br or Cl; or $R^{c'}$ can be —OH or NH$_2$).

In certain embodiments, when one occurrence of $R^3$ is $R^{c'}$, each of the remaining occurrences of $R^3$ is independently H or $R^{c'}$. For example, each of the remaining occurrences of $R^3$ can be H.

In certain embodiments, when one occurrence of $R^3$ is $R^{c'}$; and one or more occurrences of the remaining $R^3$ is independently selected from -$L^4$-$R^4$ and $R^{c'}$.

In some embodiments, one occurrence of $R^6$ is H.

Non-Limiting Combinations of $X^1$-$X^4$ and $R^3$

In some embodiments, the moiety

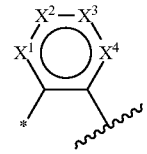

(the originally provided structure in U.S. Provisional Application Ser. No. 62/742,218

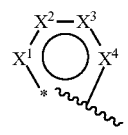

has been redrawn to further clarify points of connection) is

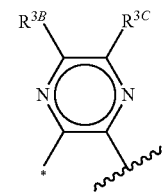

(the originally provided structure

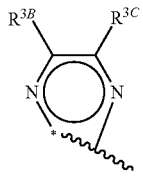

in U.S. Provisional Application Ser. No. 62/742,218 has been redrawn to further clarify points of connection), wherein * denotes point of attachment to NR$^2$; and ⁓ denotes point of attachment to $A^1$.

In certain embodiments, $R^{3B}$ is -$L^4$-$R^4$; and $R^{3C}$ is H (e.g., -$L^4$ can be NHS(O)$_2$).

In certain embodiments, $R^{3B}$ is -$L^4$-$R^4$; and $R^{3C}$ is $R^{c'}$ (e.g., $R^{c'}$ can be halo such as —Cl; and/or -$L^4$ can be NHS(O)$_2$).

In certain embodiments, $R^{3B}$ is -$L^4$-$R^4$; and $R^{3C}$ is an independently selected -$L^4$-$R^4$. In certain of the foregoing embodiments, the -$L^4$ of $R^{3B}$ is different from the -$L^4$ of $R^{3C}$. As a non-limiting example, the -$L^4$ of $R^{3B}$ can be NHS(O)$_2$; and the -$L^4$ of $R^{3C}$ can be a bond.

In certain embodiments, $R^{3B}$ is H; and $R^{3C}$ is -$L^4$-$R^4$ (e.g., -$L^4$ can be NHS(O)$_2$).

In certain embodiments, $R^{3B}$ is $R^{c'}$; and $R^{3C}$ is -$L^4$-$R^4$ (e.g., -$L^4$ can be NHS(O)$_2$).

In certain embodiments, $R^3$ is H; and $R^{3C}$ is $R^{c'}$.

In some embodiments, the moiety

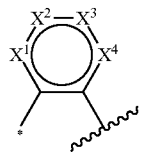

the originally provided structure

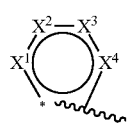

in U.S. Provisional Application Ser. No. 62/742,218 has been redrawn to further clarify points of connection) is

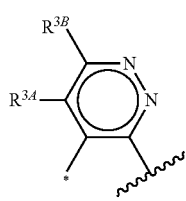

(the originally provided structure

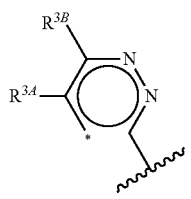

in U.S. Provisional Application Ser. No. 62/742,218 has been redrawn to further clarify points of connection), wherein * denotes point of attachment to NR$^2$; and denotes point of attachment to A$^1$.

In certain embodiments, $R^{3A}$ is H.

In certain of the foregoing embodiments, $R^{3B}$ is -$L^4$-$R^4$ (e.g., -$L^4$ can be NHS(O)$_2$).

In some embodiments, the moiety

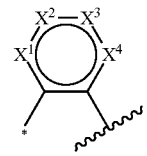

(the originally provided structure

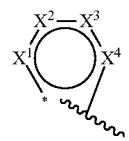

in U.S. Provisional Application Ser. No. 62/742,218 has been redrawn to further clarify points of connection)

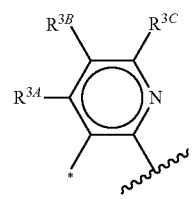

is (the originally provided structure

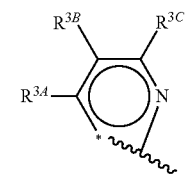

in U.S. Provisional Application Ser. No. 62/742,218 has been redrawn to further clarify points of connection), wherein * denotes point of attachment to NR$^2$; and denotes point of attachment to A$^1$.

In certain of the foregoing embodiments, $R^{3B}$ is -$L^4$-$R^4$ (e.g., -$L^4$ can be NHS(O)$_2$).

In certain of the foregoing embodiments, $R^{3B}$ is -$L^4$-$R^4$ (e.g., -$L^4$ can be NHS(O)$_2$); and $R^{3C}$ is H.

In certain of the foregoing embodiments, $R^{3B}$ is -$L^4$-$R^4$ (e.g., -$L^4$ can be NHS(O)$_2$); and $R^{3C}$ is $R^{c'}$.

In certain of the foregoing embodiments, $R^{3B}$ is -$L^4$-$R^4$ (e.g., -$L^4$ can be NHS(O)$_2$); and $R^{3C}$ is an independently selected -$L^4$-$R^4$. In certain of the foregoing embodiments, the -$L^4$ of $R^{3B}$ is different from the -$L^4$ of $R^{3C}$. As a non-limiting example, the -$L^4$ of $R^{3B}$ can be NHS(O)$_2$; and the -$L^4$ of $R^{3C}$ can be a bond.

In some embodiments, the moiety

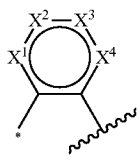

(the originally provided structure

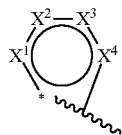

in U.S. Provisional Application Ser. No. 62/742,218 has been redrawn to further clarify points of connection) is

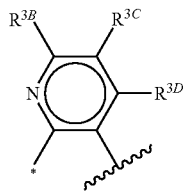

(the originally provided structure

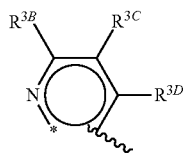

in U.S. Provisional Application Ser. No. 62/742,218 has been redrawn to further clarify points of connection), wherein * denotes point of attachment to $NR^2$; and

denotes point of attachment to $A^1$.

In certain embodiments, $R^{3D}$ is H.
In certain of the foregoing embodiments, $R^{3B}$ is -$L^4$-$R^4$ (e.g., -$L^4$ can be $NHS(O)_2$).
In certain of the foregoing embodiments, $R^{3B}$ is -$L^4$-$R^4$ (e.g., -$L^4$ can be $NHS(O)_2$); and $R^{3C}$ is H.
In certain of the foregoing embodiments, $R^{3B}$ is -$L^4$-$R^4$ (e.g., -$L^4$ can be $NHS(O)_2$); and $R^{3C}$ is $R^c$.
In certain of the foregoing embodiments, $R^{3B}$ is -$L^4$-$R^4$ (e.g., -$L^4$ can be $NHS(O)_2$); and $R^{3C}$ is an independently selected -$L^4$-$R^4$. In certain of the foregoing embodiments, the -$L^4$ of $R^{3B}$ is different from the -$L^4$ of $R^c$. As a non-limiting example, the -$L^4$ of $R^{3B}$ can be $NHS(O)_2$; and the -$L^4$ of $R^{3C}$ can be a bond.

Variable $L^4$

In some embodiments, -$L^4$ is —N(H)S(O)$_{1-2}$— or —N($R^d$)S(O)$_{1-2}$. (e.g., N($C_{1-3}$ alkyl)S(O)$_2$).
In certain of the foregoing embodiments, -$L^4$ is —N(H)S(O)$_2$—.

In some embodiments, -$L^4$ is —N(H)S(O)(=NH)—, —N($R^d$)S(O)(=NH), N(H)S(O)(=N$R^d$)—, or —N($R^d$)S(O)(=N$R^d$)—.
In certain of the foregoing embodiments, -$L^4$ is —N(H)S(O)(=NH)—.
In some embodiments, -$L^4$ is —S(O)(=NH)NH—, —S(O)(=N$R^d$)NH—, —S(O)(=NH)N$R^d$—, or —S(O)(=N$R^d$)N$R^d$—.
In certain of the foregoing embodiments, -$L^4$ is —S(O)(=NH)NH—.
In some embodiments, -$L^4$ is —S(O)$_{1-2}$N(H)— or —S(O)$_{1-2}$N($R^d$)—.
In certain of the foregoing embodiments, -$L^4$ is —S(O)$_2$N(H)—.
In some embodiments, -$L^4$ is —N(H)C(O)— or —N($R^d$)C(O).
In certain of the foregoing embodiments, -$L^4$ is —N(H)C(O)—.
In some embodiments, $L^4$ is —C(O)NH— or —C(O)N($R^d$)—.
In some embodiments, -$L^4$ is —N(H)—, —N($R^d$)—, or —N($R^4$)—.
In certain embodiments, -$L^4$ is —N(H)— or —N($R^4$)—.
In some embodiments, -$L^4$ is a single bond.
In some embodiments, -$L^4$ is C≡C.
In some embodiments, -$L^4$ is —O—.
In some embodiments, $L^4$ is selected from the group consisting of: —N(H)S(O)$_{1-2}$N(H)—, —N($R^d$)S(O)$_{1-2}$N(H)—, —N(H)S(O)$_{1-2}$N($R^d$)—, and —N($R^d$)S(O)$_{1-2}$N($R^d$)—.
In some embodiments, $L^4$ is —N(H)S(O)$_{1-2}$N(H)— (e.g., —N(H)S(O)$_2$N(H)—).
In some embodiments, $L^4$ is —N(H)S(O)$_{1-2}$N($R^d$)— (e.g., —N(H)S(O)$_2$N($R^d$)—, e.g., —N(H)S(O)$_2$N($C_{1-3}$ alkyl)-).
In some embodiments, -$L^4$ is selected from the group consisting of —N(H)S(O)$_2$—, C≡C, a single bond, —C(O)N(H)—, —N(H)—, —N($R^4$)—, —N($R^d$)—, and —N(H)C(O)—.
In certain of the foregoing embodiments, -$L^4$ is selected from the group consisting of —N(H)S(O)$_2$—, a single bond, —NH—, —N($R^4$)—, and —N(H)C(O)—.
In some embodiments, -$L^4$ is selected from:
(i) a bond (in certain embodiments, when -$L^4$ is a bond; and $R^4$ is —$(Y^3)_p$—$Y^4$, then p is 1).
(ii) N($R^4$);
(iii) —N(H)S(O)$_{1-2}$— or —N($R^d$)S(O)$_{1-2}$—;
(iv) —S(O)$_{1-2}$N(H)— or —S(O)$_{1-2}$N($R^d$)—.
(vi) —S(O)$_{1-2}$—;
(viii) —N(H)C(O)— or —N($R^d$)C(O)—;
(ix) —C≡C;
(x) —N(H)S(O)(=NH)—, —N($R^d$)S(O)(=NH), —N(H)S(O)(=N$R^d$)—, or —N($R^d$)S(O)(=N$R^d$)—
(xi) —S(O)(=NH)NH—, —S(O)(=N$R^d$)NH—, —S(O)(=NH)N$R^d$—, or —S(O)(=N$R^d$)N$R^d$—; and
(xii) —S(O)(=NH)— or —S(O)(=N$R^d$).

Variable $R^4$

In some embodiments, $R^4$ is —$(Y^3)_p$—$Y^4$.
In some embodiments, p is 0.
In other embodiments, p is 1. In certain of these embodiments, $Y^3$ is $C_{1-3}$ alkylene. For example, $Y^3$ can be $CH_2$ or $CH_2$—$CH_2$.
In some embodiments, $Y^4$ is $C_{6-10}$ aryl, which is optionally substituted with from 1-4 $R^c$.
In some embodiments, $Y^4$ is phenyl, which is optionally substituted with from 1-2 (e.g., 1) $R^c$.
In certain embodiments when $Y^4$ is $C_{6-10}$ aryl, which is optionally substituted with from 1-4 $R^c$ (e.g., when $Y^4$ is phenyl, which is optionally substituted with from 1-2 (e.g., 1) $R^c$), each occurrence of $R^c$ is independently selected from the group consisting of:
- (i) halo;
- (ii) cyano;
- (iii) $C_{1-6}$ alkyl;
- (iv) $C_{2-6}$ alkenyl;
- (v) $C_{2-6}$ alkynyl;
- (vi) $C_{1-4}$ haloalkyl;
- (vii) $C_{1-4}$ alkoxy;
- (viii) $C_{1-4}$ haloalkoxy;
- (ix) —($C_{0-3}$ alkylene)-$C_{3-6}$ cycloalkyl optionally substituted with from 1-4 independently selected $C_{1-4}$ alkyl;
- (xiv) —$C_{1-4}$ thioalkoxy, and
- (xx) $C_{3-6}$ cycloalkoxy.

In certain embodiments when $Y^4$ is $C_{6-10}$ aryl, which is optionally substituted with from 1-4 $R^c$ (e.g., when $Y^4$ is phenyl, which is optionally substituted with from 1-2 (e.g., 1) $R^c$), each occurrence of $R^c$ is independently selected from the group consisting of:
- (i) halo;
- (iii) $C_{1-6}$ alkyl;
- (vi) $C_{1-4}$ haloalkyl;
- (vii) $C_{1-4}$ alkoxy; and
- (viii) $C_{1-4}$ haloalkoxy.

In certain embodiments when $Y^4$ is $C_{6-10}$ aryl, each occurrence of $R^c$ is independently selected from the group consisting of:
- (vii) $C_{1-4}$ alkoxy;
- (viii) $C_{1-4}$ haloalkoxy; and
- (xiv) —$C_{1-4}$ thioalkoxy.

In certain embodiments, $Y^4$ is $C_{6-10}$ aryl (e.g., phenyl), which is unsubstituted.

In certain embodiments when p=1 and $Y^4$ is $C_{6-10}$ aryl, $R^4$ is selected from the group consisting of:

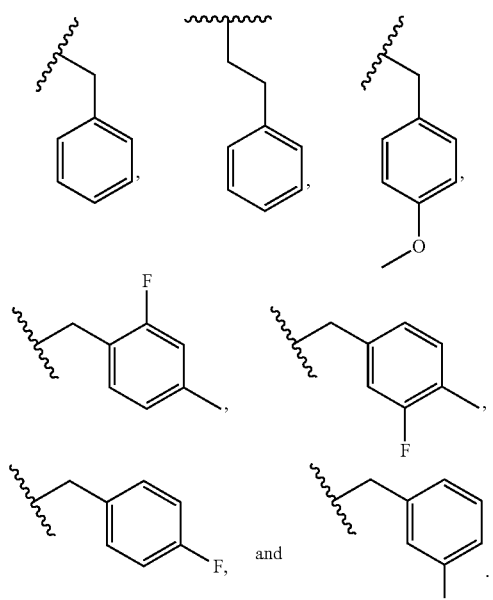

In certain embodiments when p=1 and $Y^4$ is $C_{6-10}$ aryl, $R^4$ is selected from the group consisting of:

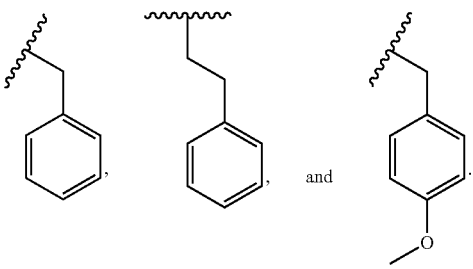

In certain embodiments when p=0 and $Y^4$ is $C_{6-10}$ aryl, $R^4$ is:

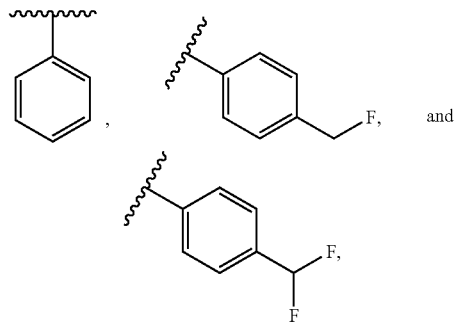

In certain embodiments when p=0 and $Y^4$ is $C_{6-10}$ aryl, $R^4$ is:

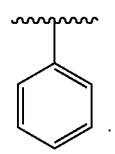

In some embodiments, $Y^4$ is $C_{3-6}$ (e.g., $C_{3-6}$ or $C_6$) cycloalkyl, which is optionally substituted with from 1-4 $R^b$.

In certain of the foregoing embodiments, $Y^4$ is cyclopropyl, which is optionally substituted with from 1-2 $R^b$. For example, $Y^4$ is unsubstituted cyclopropyl.

In some embodiments, $Y^4$ is $C_6$ cycloalkyl (e.g., cyclohexyl), which is optionally substituted with from 1-2 $R^b$.

In certain of the foregoing embodiments when $Y^4$ is cycloalkyl which is optionally substituted with from 1-4 $R^b$, each occurrence of $R^b$ is independently selected from the group consisting of: —F, $C_{1-6}$ alkyl, $C_{1-4}$ haloalkyl, and —OH (e.g., $R^b$ can be OH; and/or $R^b$ can be $C_{1-6}$ alkyl such as methyl).

In certain embodiments when p=1 and $Y^4$ is $C_{3-6}$ cycloalkyl optionally substituted with from 1-4 $R^b$, $R^4$ is selected from the group consisting of:

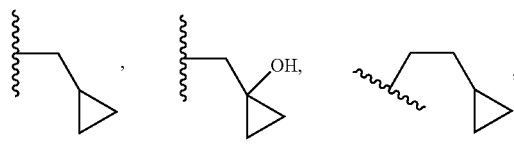

-continued

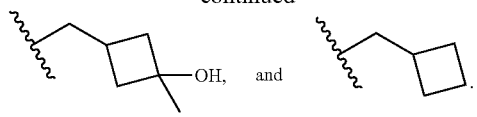

In certain embodiments when p=1 and $Y^4$ is $C_{3-6}$ cycloalkyl optionally substituted with from 1-4 $R^b$, $R^4$ is selected from the group consisting of:

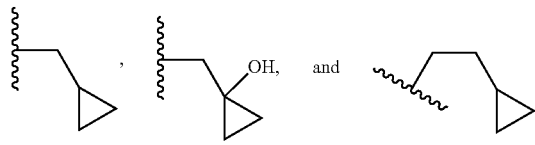

In certain embodiments when p=0 and $Y^4$ is $C_{3-6}$ cycloalkyl optionally substituted with from 1-4 $R^b$, $R^4$ is selected from the group consisting of:

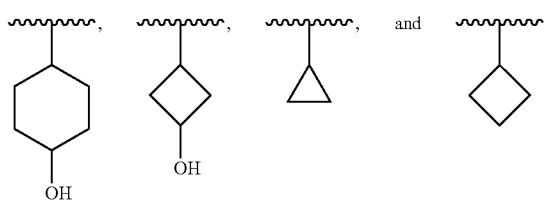

In certain embodiments, $Y^4$ is $C_{3-6}$ (e.g., $C_{3-4}$ or $C_6$) cycloalkyl, which is unsubstituted.

In certain of these embodiments, $Y^4$ is unsubstituted cyclopropyl or unsubstituted cyclobutyl (e.g., unsubstituted cyclopropyl).

In some embodiments, $Y^4$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

In certain of the foregoing embodiments, $Y^4$ is heteroaryl including 6 ring atoms, wherein from 1-4 ring atoms are heteroatoms, each independently selected from the group consisting of N, N(H), and N($R^d$), and wherein one or more of the heteroaryl ring carbon atoms are optionally substituted with from 1-4 independently selected $R^c$.

As non-limiting examples of the foregoing, $Y^4$ can be pyridinyl (e.g., 2-pyridinyl, 3-pyridinyl, or 4-pyridinyl), pyrimidinyl (e.g., 2-pyrimidinyl or 5-pyrimidinyl), or pyrazinyl, each of which is optionally substituted with from 1-2 independently selected $R^c$.

For example $Y^4$ can be pyridinyl, pyrimidinyl, or pyrazinyl, each of which is unsubstituted.

In certain embodiments when $Y^4$ is heteroaryl optionally substituted with one or more independently selected $R^c$ as defined supra, each occurrence of $R^c$ is independently selected from the group consisting of:
  (i) halo;
  (ii) cyano;
  (iii) $C_{1-6}$ alkyl;
  (iv) $C_{2-6}$ alkenyl;
  (v) $C_{2-6}$ alkynyl;
  (vi) $C_{1-4}$ haloalkyl;
  (vii) $C_{1-4}$ alkoxy;
  (viii) $C_{1-4}$ haloalkoxy;
  (ix) —($C_{0-3}$ alkylene)-$C_{3-6}$ cycloalkyl optionally substituted with from 1-4 independently selected $C_{1-4}$ alkyl;
  (xii) OH;
  (xiv) —$C_{1-4}$ thioalkoxy, and
  (xx) $C_{3-6}$ cycloalkoxy.

In certain of these embodiments, each occurrence of $R^c$ is independently selected from the group consisting of:
  (i) halo (e.g., F, Cl);
  (iii) $C_{1-6}$ alkyl (e.g., methyl); and
  (xii) OH.

In certain embodiments when p=1; and $Y^4$ is heteroaryl, $R^4$ is selected from the group consisting of:

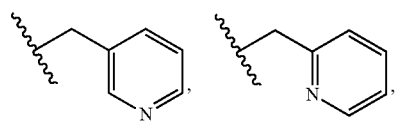

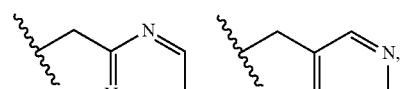

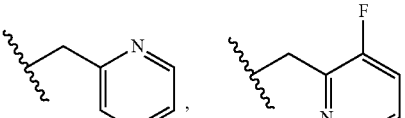

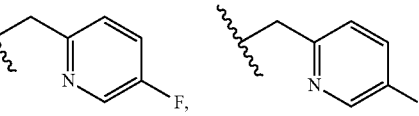

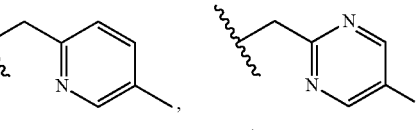

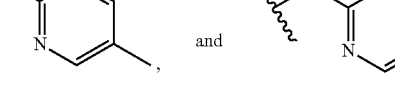

In certain embodiments when p=1; and $Y^4$ is heteroaryl, $R^4$ is selected from the group consisting of:

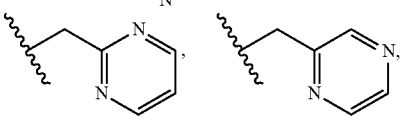

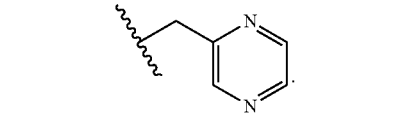

In certain embodiments when p=0; and $Y^4$ is heteroaryl, $R^4$ is selected from the group consisting of:

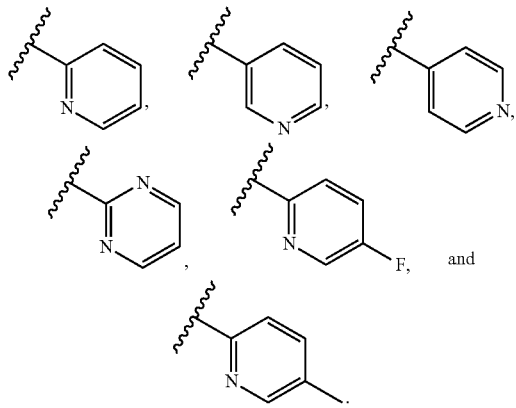

In certain embodiments when p=0; and $Y^4$ is heteroaryl, $R^4$ is selected from the group consisting of:

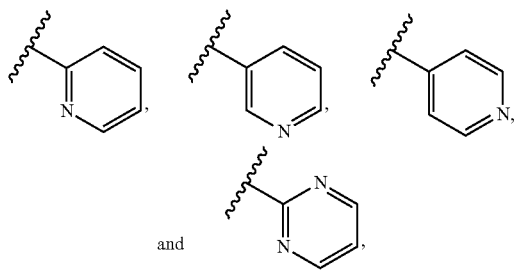

In some embodiments, $Y^4$ is heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

In certain of the foregoing embodiments, $Y^4$ is heterocyclyl including from 4-6 ring atoms, wherein from 1-2 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

In certain embodiments, $Y^4$ heterocyclyl including from 4 ring atoms, wherein 1 ring atom is a heteroatom, independently selected from the group consisting of N, N(H), N($R^d$), and O, and wherein one or more of the heterocyclyl ring carbon atoms are optionally substituted with from 1-2 independently selected $R^b$.

As a non-limiting example, $Y^4$ can be oxetanyl optionally substituted with from 1-2 independently selected $R^b$ (e.g., unsubstituted oxetanyl).

As another non-limiting example, $Y^4$ can be azetidinyl optionally substituted with from 1-2 independently selected $R^b$ (e.g., azetidinyl substituted with one $R^b$).

In some embodiments, $Y^4$ is heterocyclyl including from 6 ring atoms, wherein from 1-2 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

As non-limiting examples, $Y^4$ can be selected from the group consisting of tetrahydropyranyl, piperidinyl, piperazinyl, and morpholinyl, each of which is optionally substituted with from 1-2 independently selected $R^b$.

As non-limiting examples, $Y^4$ can be selected from tetrahydropyranyl, piperidinyl, and morpholinyl, each of which is optionally substituted with from 1-2 independently selected $R^b$.

In certain of the foregoing embodiments when $Y^4$ is heterocyclyl optionally substituted with from 1-4 independently selected $R^b$, each occurrence of $R^b$ is independently selected from the group consisting of: —F, $C_{1-6}$ alkyl, $C_{1-4}$ haloalkyl, oxo, and —OH.

In certain of the foregoing embodiments when $Y^4$ is heterocyclyl optionally substituted with from 1-4 independently selected $R^b$, each occurrence of $R^b$ is independently selected from the group consisting of: —F, $C_{1-6}$ alkyl, $C_{1-4}$ haloalkyl, and —OH (e.g., $R^b$ can be OH).

In certain embodiments when p=1; and $Y^4$ is heterocyclyl optionally substituted with from 1-4 independently selected $R^b$, $R^4$ is selected from the group consisting of:

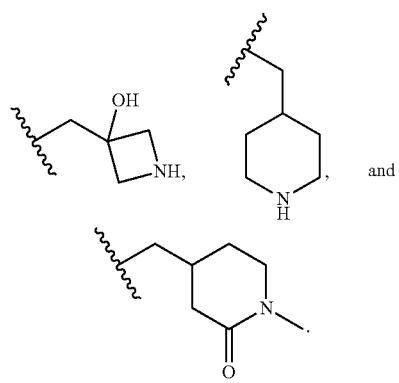

In certain embodiments when p=1; and $Y^4$ is heterocyclyl optionally substituted with from 1-4 independently selected $R^b$, $R^4$ is

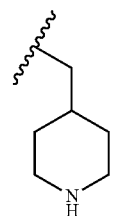

In certain embodiments when p=0; and $Y^4$ is heterocyclyl optionally substituted with from 1-4 independently selected $R^b$, $R^4$ is selected from the group consisting of:

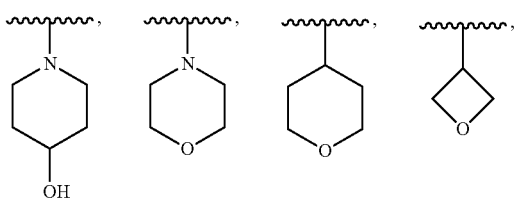

-continued

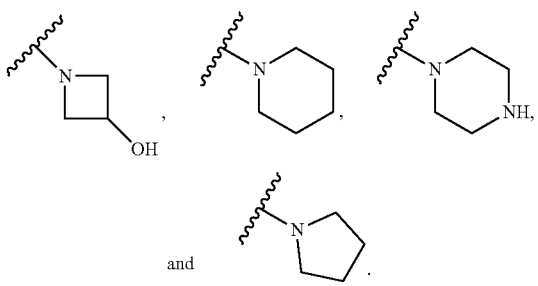

In certain embodiments when p=0; and $Y^4$ is heterocyclyl optionally substituted with from 1-4 independently selected $R^b$, $R^4$ is selected from the group consisting of:

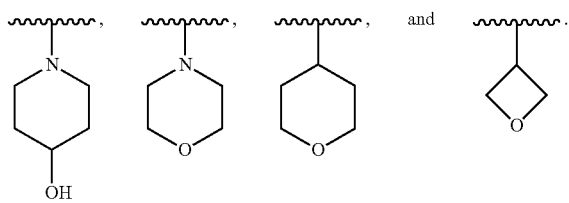

In some embodiments, $R^4$ is $C_{1-10}$ alkyl, optionally substituted with from 1-6 independently selected $R^a$.

In certain embodiments, $R^4$ is $C_{1-6}$ alkyl, optionally substituted with from 1-6 independently selected $R^a$.

In certain embodiments, $R^4$ is $C_{1-6}$ alkyl, optionally substituted with from 1-2 independently selected $R^a$. For example, $R^4$ can be methyl.

In certain of the foregoing embodiments when $R^4$ is $C_{1-6}$alkyl, each occurrence of $R^a$ is independently selected from the group consisting of: —F, —OH; $C_{1-4}$ alkoxy; and $C_{1-4}$ haloalkoxy.

In certain embodiments, each occurrence of $R^a$ is independently —OH. For example, $R^4$ is

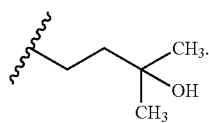 [SMILES: *CCC(C)(C)O]

In some embodiments, $R^4$ is selected from the group consisting of methyl, ethyl,

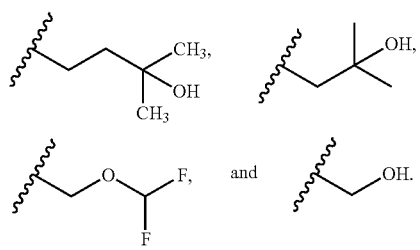

In some embodiments, $R^4$ is selected from methyl and

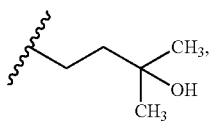

In some embodiments, $R^4$ is $C_{2-10}$ (e.g., $C_{2-4}$) alkynyl, which is optionally substituted with from 1-6 (e.g., from 1-3) independently selected $R^a$ (e.g., unsubstituted $C_{2-4}$ alkynyl such as

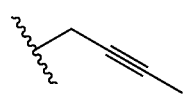 [SMILES: *CC#CC]

In some embodiments, $R^4$ is $C_{2-10}$ (e.g., $C_{2-4}$) alkenyl, which is optionally substituted with from 1-6 (e.g., from 1-3) independently selected $R^a$ (e.g., unsubstituted $C_{2-4}$ alkenyl such as vinyl).

In some embodiments (e.g., when -$L^4$ is a bond or —O—), $R^4$ is $C_{2-10}$ alkyl, optionally substituted with from 1-6 independently selected $R^a$; or methyl optionally substituted with from 1-2 independently selected $R^a$.

In certain embodiments (e.g., when -$L^4$ is a bond or —O—), $R^4$ is $C_{2-10}$ alkyl, optionally substituted with from 1-6 independently selected $R^a$; or methyl substituted with from 1-2 independently selected $R^a$.

Non-Limiting Combinations of -$L^4$ and $R^4$
Non-Limiting Combination [A]

In some embodiments, -$L^4$ is selected from the group consisting of —N(H)S(O)$_2$—, —N(H)S(O)$_2$N(H)—, —N(H)S(O)$_2$N($R^d$)—, C≡C, a single bond, —C(O)N(H)—, —N(H)—, —N($R^4$)—, —N($R^d$)—, and —N(H)C(O)—; and $R^4$ is selected from the group consisting of:
(i) $C_{1-6}$ alkyl optionally substituted with 1-2 $R^a$;
(ii) —($Y^3$)$_p$—$Y^4$; and
(iii) $C_{2-10}$ alkenyl or $C_{2-10}$ alkynyl, each of which is optionally substituted with from 1-3 independently selected $R^a$.

In certain embodiments, -$L^4$ is selected from the group consisting of —N(H)S(O)$_2$—, —N(H)S(O)$_2$N(H)—, and —N(H)S(O)$_2$N($R^d$)—; and $R^4$ is selected from the group consisting of:
(i) $C_{1-6}$ alkyl optionally substituted with 1-2 $R^a$;
(ii) —($Y^3$)$_p$—$Y^4$; and
(iii) $C_{2-10}$ alkenyl or $C_{2-10}$ alkynyl, each of which is optionally substituted with from 1-3 independently selected $R^a$.

In some embodiments, -$L^4$ is selected from the group consisting of —N(H)S(O)$_2$—, C≡C, a single bond, —C(O)N(H)—, —N(H)—, —N($R^4$)—, —N($R^d$)—, and —N(H)C(O)—; and $R^4$ is selected from the group consisting of:
(i) $C_{1-6}$ alkyl optionally substituted with 1-2 $R^a$; and
(ii) —($Y^3$)$_p$—$Y^4$.

In certain embodiments, -$L^4$ is selected from the group consisting of —N(H)S(O)$_2$—, a single bond, —NH—, —N($R^4$)—, and —N(H)C(O)—; and $R^4$ is selected from the group consisting of:
(i) $C_{1-6}$ alkyl optionally substituted with 1-2 $R^a$; and
(ii) —($Y^3$)$_p$—$Y^4$.

In certain embodiments, -$L^4$ is —N(H)S(O)$_2$—; and $R^4$ is selected from the group consisting of:

(i) $C_{1-6}$ alkyl optionally substituted with 1-2 $R^a$; and
(ii) —$(Y^3)_p$—$Y^4$.

In certain embodiments, -$L^4$ is a single bond; and $R^4$ is selected from the group consisting of:
(i) $C_{1-6}$ alkyl optionally substituted with 1-2 $R^a$; and
(ii) —$(Y^3)_p$—$Y^4$.

In certain embodiments, -$L^4$ is —NH— or —N($R^4$)—; and $R^4$ is selected from the group consisting of:
(i) $C_{1-6}$ alkyl optionally substituted with 1-2 $R^a$; and
(ii) —$(Y^3)_p$—$Y^4$.

In certain embodiments, -$L^4$ is —N(H)C(O)—; and $R^4$ is selected from the group consisting of:
(i) $C_{1-6}$ alkyl optionally substituted with 1-2 $R^a$; and
(ii) —$(Y^3)_p$—$Y^4$.

In certain of these embodiments, -$L^4$ is —N(H)S(O)$_2$N(H)— or —N(H)S(O)$_2$N($R^d$)—; and
$R^4$ is selected from the group consisting of:
(i) $C_{1-6}$ alkyl optionally substituted with 1-2 $R^a$; and
(ii) —$(Y^3)_p$—$Y^4$.

In certain embodiments, -$L^4$ is —N(H)S(O)$_2$—; and $R^4$ is selected from the group consisting of:
$R^4$ is selected from the group consisting of:
(i) $C_{1-6}$ alkyl optionally substituted with 1-2 $R^a$;
(ii) —$(Y^3)_p$—$Y^4$; and
(iii) $C_{2-10}$ alkenyl or $C_{2-10}$ alkynyl, each of which is optionally substituted with from 1-3 independently selected $R^a$.

In certain embodiments, -$L^4$ is a single bond; and $R^4$ is selected from the group consisting of:
$R^4$ is selected from the group consisting of:
(i) $C_{1-6}$ alkyl optionally substituted with 1-2 $R^a$;
(ii) —$(Y^3)_p$—$Y^4$; and
(iii) $C_{2-10}$ alkenyl or $C_{2-10}$ alkynyl, each of which is optionally substituted with from 1-3 independently selected $R^a$.

In certain embodiments, -$L^4$ is —NH— or —N($R^4$)—; and $R^4$ is selected from the group consisting of:
$R^4$ is selected from the group consisting of:
(i) $C_{1-6}$ alkyl optionally substituted with 1-2 $R^a$;
(ii) —$(Y^3)_p$—$Y^4$; and
(iii) $C_{2-10}$ alkenyl or $C_{2-10}$ alkynyl, each of which is optionally substituted with from 1-3 independently selected $R^a$.

In certain embodiments, -$L^4$ is —N(H)C(O)—; and $R^4$ is selected from the group consisting of:
$R^4$ is selected from the group consisting of:
(i) $C_{1-6}$ alkyl optionally substituted with 1-2 $R^a$;
(ii) —$(Y^3)_p$—$Y^4$; and
(iii) $C_{2-10}$ alkenyl or $C_{2-10}$ alkynyl, each of which is optionally substituted with from 1-3 independently selected $R^a$.

In certain embodiments, -$L^4$ is —N(H)S(O)$_2$N(H)— or —N(H)S(O)$_2$N($R^d$)—; and
$R^4$ is selected from the group consisting of:
(i) $C_{1-6}$ alkyl optionally substituted with 1-2 $R^a$;
(ii) —$(Y^3)_p$—$Y^4$; and
(iii) $C_{2-10}$ alkenyl or $C_{2-10}$ alkynyl, each of which is optionally substituted with from 1-3 independently selected $R^a$.

In some embodiments of [A], $R^4$ is $C_{1-6}$ alkyl optionally substituted with 1-2 $R^a$.

In some embodiments of [A], $R^4$ is $C_{2-10}$ alkenyl or $C_{2-10}$ alkynyl, each of which is optionally substituted with from 1-3 independently selected $R^a$.

In certain of these embodiments, $R^4$ is $C_{2-10}$ (e.g., $C_{2-5}$) alkynyl, which is optionally substituted with from 1-3 independently selected $R^a$ (e.g., unsubstituted $C_{2-5}$ alkynyl such as

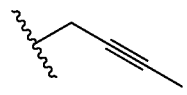

In some embodiments of [A], $R^4$ is —$(Y^3)_p$—$Y^4$. In certain embodiments, $Y^4$ is $C_{6-10}$ aryl, which is optionally substituted with from 1-4 $R^c$. For example, $Y^4$ can be phenyl which is optionally substituted with from 1-2 (e.g., 1) $R^c$.

In some embodiments of [A] when $R^4$ is —$(Y^3)_p$—$Y^4$, $Y^4$ is is $C_{3-6}$ (e.g., $C_{3-6}$ or $C_6$) cycloalkyl, which is optionally substituted with from 1-4 $R^b$. In certain embodiments, $Y^4$ is $C_{3-4}$ cycloalkyl or $C_6$ cycloalkyl, each of which is optionally substituted with from 1-2 $R^b$ (e.g., $R^b$ can be —OH).

In some embodiments of [A], $R^4$ is —$(Y^3)_p$—$Y^4$. In certain embodiments, $Y^4$ is heterocyclyl including from 4-6 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-2 independently selected $R^b$. In certain embodiments, $Y^4$ is heterocyclyl including 6 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-2 independently selected $R^b$ (e.g., $Y^4$ can be tetrahydropyranyl, piperidinyl, or morpholinyl, each of which is optionally substituted with from 1-2 independently selected $R^b$). In certain embodiments, $Y^4$ is heterocyclyl including 4 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-2 independently selected $R^b$ (e.g., $Y^4$ can be oxetanyl; or $Y^4$ can be azetidinyl).

In some embodiments of [A], $R^4$ is —$(Y^3)_p$—$Y^4$. In certain embodiments, $Y^4$ is heteroaryl including 6 ring atoms, wherein from 1-4 ring atoms are heteroatoms, each independently selected from the group consisting of N, N(H), and N($R^d$), and wherein one or more of the heteroaryl ring carbon atoms are optionally substituted with from 1-4 independently selected $R^c$. In certain embodiments, $Y^4$ is pyridinyl (e.g., 2-pyridinyl, 3-pyridinyl, or 4-pyridinyl), pyrimidinyl (e.g., 2-pyrimidinyl or 5-pyrimidinyl), or pyrazinyl, each of which is optionally substituted with from 1-2 independently selected $R^c$.

In certain of the foregoing embodiments of [A] when $R^4$ is —$(Y^3)_p$—$Y^4$, p=0.

In other embodiments of [A] when $R^4$ is —$(Y^3)_p$—$Y^4$, p=1. In certain of these embodiments, V is $C_{1-3}$ alkylene (e.g., CH$_2$, CH$_2$—CH$_2$).

In some embodiments when $R^3$ is -$L^4$-$R^4$, $R^3$ is selected from the group consisting of:

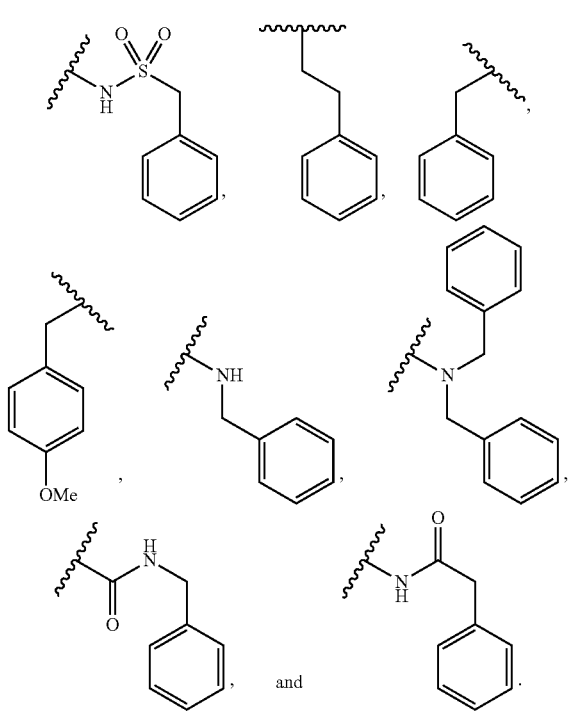
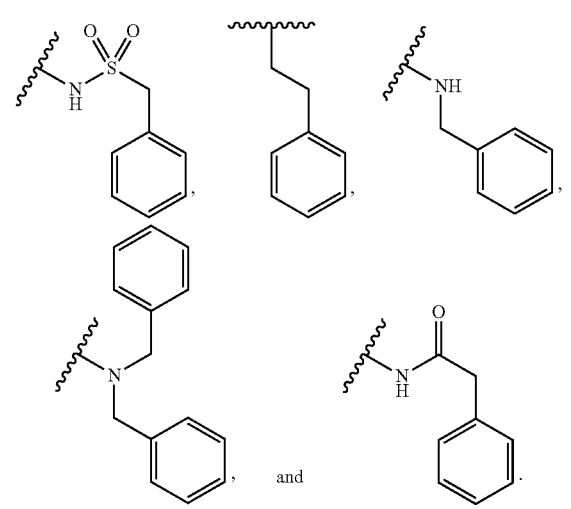
In some embodiments when $R^3$ is $-L^4-R^4$, $R^3$ is selected from the group consisting of:
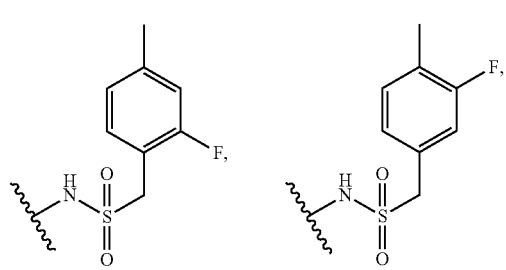
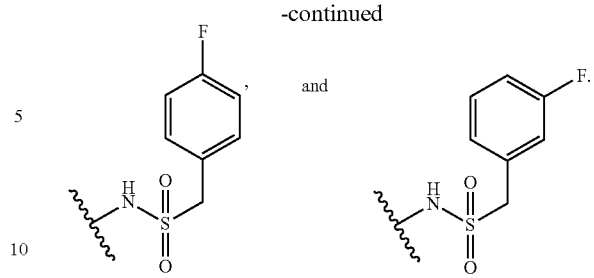
In some embodiments when $R^3$ is $-L^4-R^4$, $R^3$ is selected from the group consisting of:
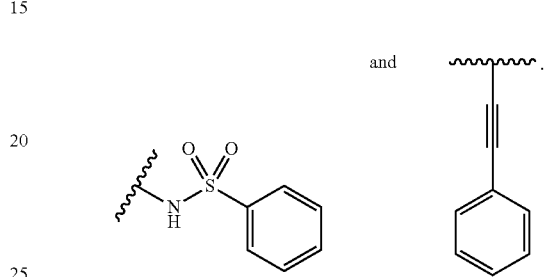
In some embodiments when $R^3$ is $-L^4-R^4$, $R^3$ is selected from the group consisting of:
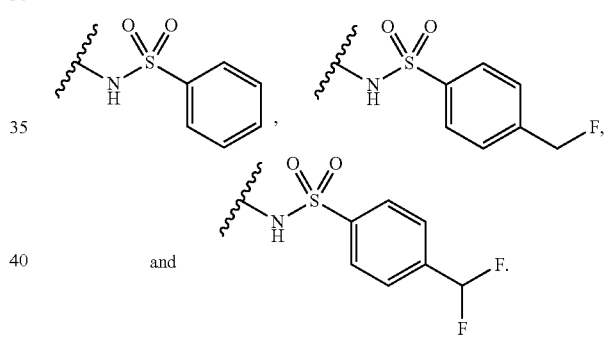
In some embodiments when $R^3$ is $-L^4-R^4$, $R^3$ is selected from the group consisting of:
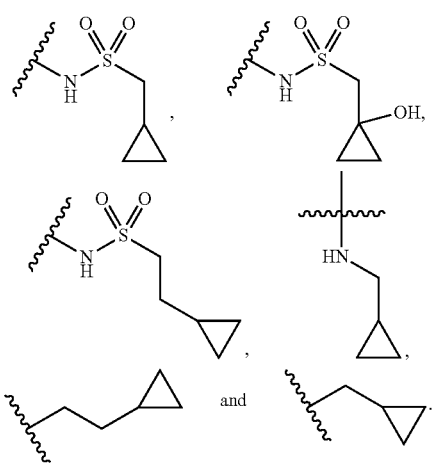

In some embodiments when $R^3$ is $-L^4-R^4$, $R^3$ is selected from the group consisting of:

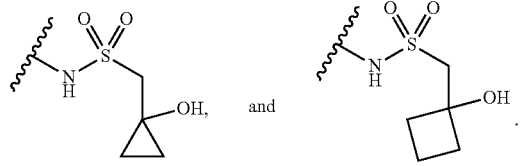 [SMILES: *NS(=O)(=O)CC1(O)CC1 ; *NS(=O)(=O)CC1(O)CCC1]

In some embodiments when $R^3$ is $-L^4-R^4$, $R^3$ is selected from the group consisting of:

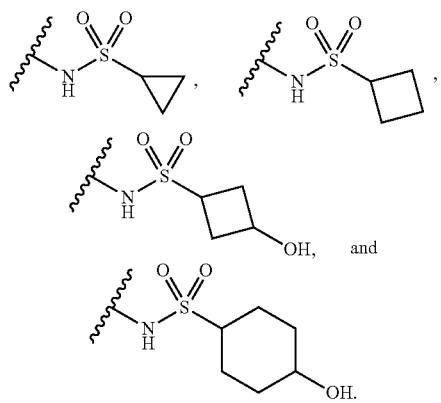

In some embodiments when $R^3$ is $-L^4-R^4$, $R^3$ is selected from the group consisting of:

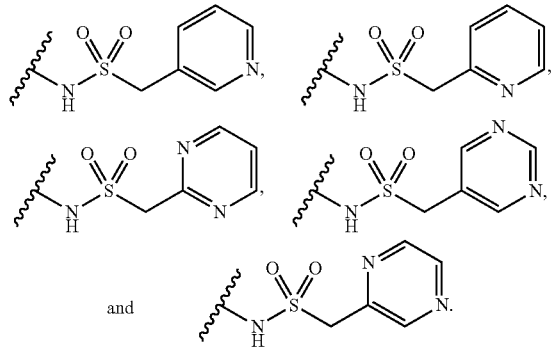

In some embodiments when $R^3$ is $-L^4-R^4$, $R^3$ is selected from the group consisting of:

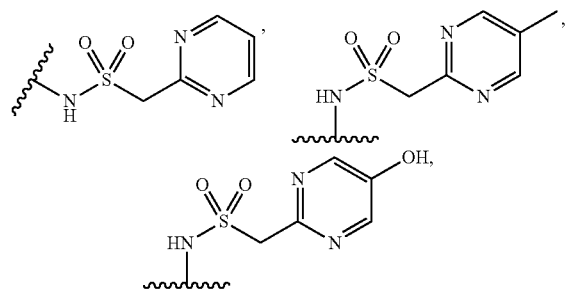

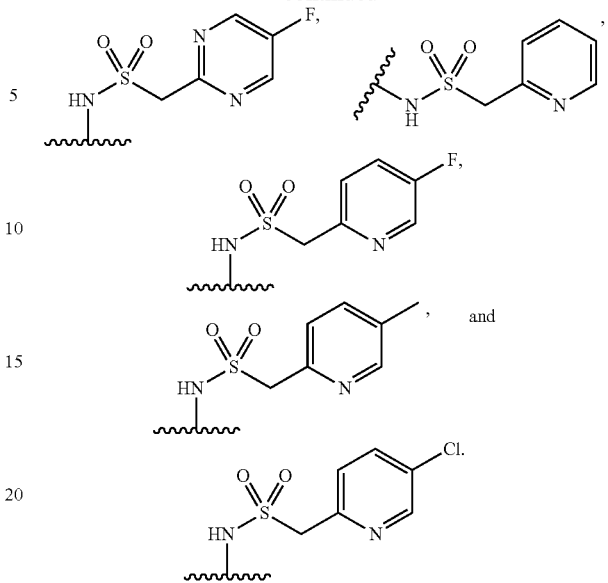

In some embodiments when $R^3$ is $-L^4-R^4$, $R^3$ is selected from the group consisting of:

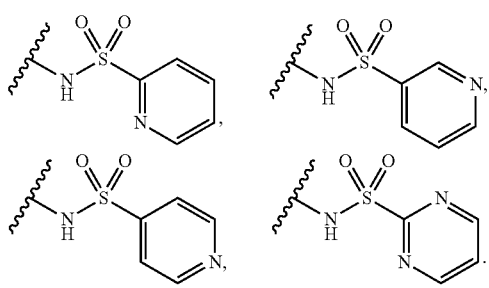

In some embodiments when $R^3$ is $-L^4-R^4$, $R^3$ is selected from the group consisting of:

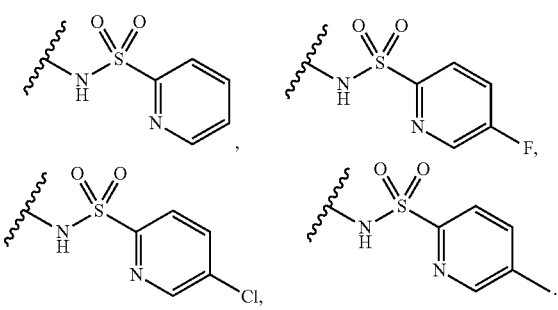

In some embodiments when $R^3$ is $-L^4-R^4$, $R^3$ is selected from the group consisting of:

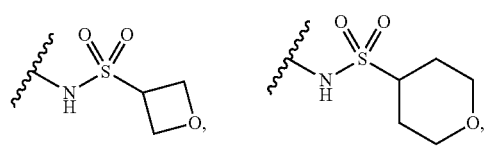

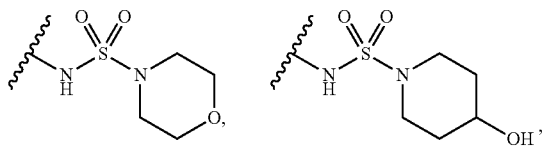

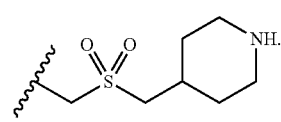

In some embodiments when $R^3$ is $-L^4-R^4$, $R^3$ is selected from the group consisting of:

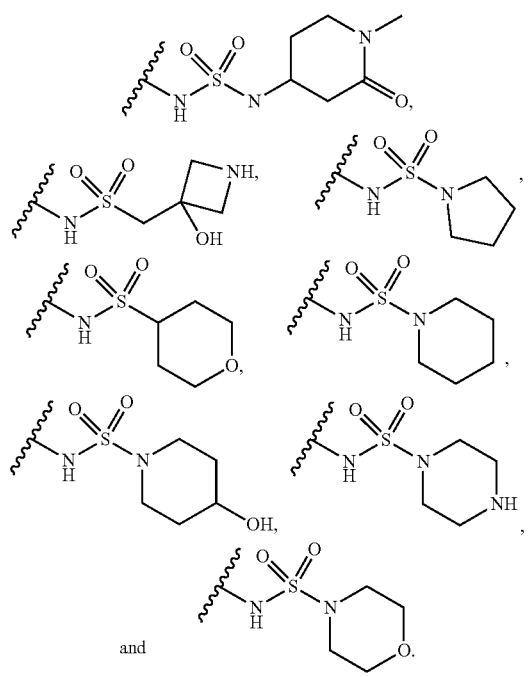

In some embodiments when $R^3$ is $-L^4-R^4$, $R^3$ is selected from the group consisting of:

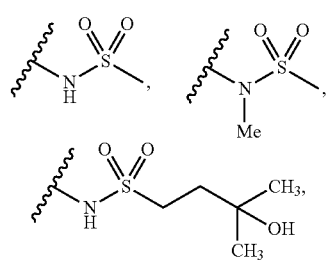

NHMe, and NMe₂.

In some embodiments when $R^3$ is $-L^4-R^4$, $R^3$ is selected from the group consisting of:

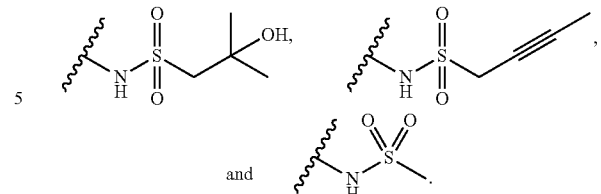

and

In some embodiments when $R^3$ is $-L^4-R^4$, $R^3$ is selected from the group consisting of:

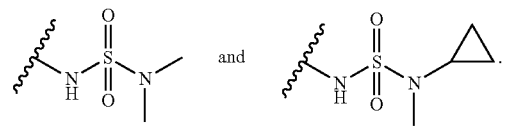

In certain of the foregoing embodiments, $R^3$ is

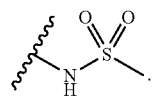

Variable $R^{c'}$

In some embodiments, each occurrence of $R^{c'}$ is independently selected from the group consisting of:
(i) halo (e.g., —F, Cl);
(ii) cyano;
(iii) —OH;
(iv) —NO$_2$;
(v) —C(=O)(C$_{1-4}$ alkyl);
(vi) —C(=O)O(C$_{1-4}$ alkyl);
(vii) —C(=O)OH; and
(viii) —NH$_2$.

In certain embodiments, each occurrence of $R^{c'}$ is independently selected from the group consisting of:
(i) halo (e.g., —F, Cl);
(iii) —OH;
(iv) —NO$_2$;
(v) —C(=O)(C$_{1-4}$ alkyl); and
(vi) —C(=O)O(C$_{1-4}$ alkyl).

In certain embodiments, each occurrence of $R^{c'}$ is independently selected from halo (e.g., —F, Cl).

In certain embodiments, each occurrence of $R^{c'}$ is independently selected from OH and NH$_2$.

Non-Limiting Combinations

Non-Limiting Combinations [1]

In some embodiments:
$R^1$ is $-(Y^1)_n-Y^2$; and
$R^2$ is C$_{6-10}$ aryl, which is optionally substituted with from 1-4 $R^c$.

In certain of these embodiments, n is 0.

In certain of the foregoing embodiments of [1], from 1-2 of $X^1$, $X^2$, $X^3$, and $X^4$ are N; and from 2-3 of $X^1$, $X^2$, $X^3$, and $X^4$ are each an independently selected CR$^3$.

In certain of the foregoing embodiments of [1], one of $X^1$, $X^2$, $X^3$, and $X^4$ is N; and each of the remaining $X^1$, $X^2$, $X^3$, and $X^4$ is an independently selected CR$^3$; or
two of X, $X^2$, $X^3$, and $X^4$ are N; and each of the remaining $X^1$, $X^2$, $X^3$, and $X^4$ is an independently selected CR$^3$.

In certain embodiments, from 1-2 of $X^2$ and $X^3$ is independently $CR^3$, such as wherein both of $X^2$ and $X^3$ are each an independently selected $CR^3$. In certain of the foregoing embodiments, each of $X^1$ and $X^4$ is independently CH or N (e.g., each of $X^1$ and $X^4$ is N).

In certain of the foregoing embodiments of [1], one occurrence of $R^3$ is -$L^4$-$R^4$.

In certain of the foregoing embodiments of [1], $R^4$ is —$(Y^3)_p$—$Y^4$.

In certain of the foregoing embodiments when $R^4$ is $(Y^3)_p$—$Y^4$, p=1. In other embodiments, p=0.

In certain of the foregoing embodiments of [1], $R^4$ is $C_{1-10}$ alkyl optionally substituted with from 1-6 independently selected $R^a$.

In certain of the foregoing embodiments of [1], each of the remaining occurrences of $R^3$ is independently selected from the group consisting of H and $R^{c'}$. For example, each of the remaining occurrences of $R^3$ can be independently H.

In certain of the foregoing embodiments of [1], when one occurrence of $R^3$ is -$L^4$-$R^4$, one occurrence of $R^a$ is H.

In certain of the foregoing embodiments of [1], when one occurrence of $R^3$ is -$L^4$-$R^4$, one occurrence of $R^a$ is $R^{c'}$ (e.g., halo (e.g., Br or Cl, e.g., Cl)).

In some embodiments of [1], one occurrence of $R^3$ is $R^{c'}$ (e.g., Br or Cl, e.g., Cl); and each of the remaining occurrences of $R^3$ is H.

In some embodiments of [1], $Y^2$ is as defined in any one of claims 14-20 and 26-28; and each $R^c$, when present, is independently as defined in any one of claims 21-24.

In some embodiments of [1], $Y^2$ is as defined in any one of claims 14-18; and each $R^c$, when present, is as defined in any one of claims 21-23.

In some embodiments of [1], $Y^2$ is as defined in any one of claims 16-18; and each $R^c$, when present, is as defined in any one of claims 21-23.

In some embodiments of [1], $Y^2$ is as defined in claim 18; and each $R^c$, when present, is as defined in claim 23.

In certain embodiments of [1], $R^1$ is $R^1$ is

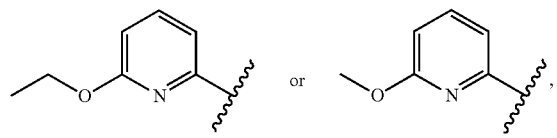

such as

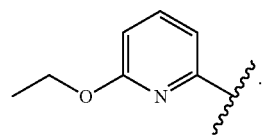 [SMILES: *c1cccc(OCC)n1]

In some embodiments of [1], $R^1$ is as defined in any one of claims 10-23 of U.S. 62/742,218, filed Oct. 5, 2018. In certain of the foregoing embodiments, $R^1$ is as defined in any one of claims 16-23 U.S. 62/742,218, filed Oct. 5, 2018. For example, $R^1$ can be as defined in claim 23 U.S. 62/742,218, filed Oct. 5, 2018. In some embodiments of [1], $R^2$ is $C_{6-10}$ aryl, which is optionally substituted with from 1-4 $R^c$, such as phenyl, which is optionally substituted with from 1-4 $R^c$ or 1-2 $R^c$ or 2 $R^c$; and $R^c$, when present, is as defined in any one of claims 33-35.

In some embodiments of [1], $R^2$ is as defined in any one of claims 24-31 of U.S. 62/742,218, filed Oct. 5, 2018. In certain of the foregoing embodiments, $R^2$ is phenyl, which is optionally substituted with 2 $R^c$, such as wherein $R^2$ is

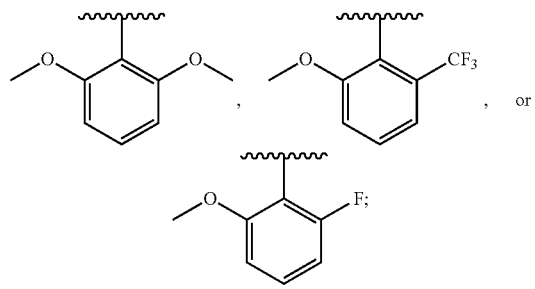

and $R^c$, when present, is as defined in any one of claims 33-35.

In certain embodiments of [1], $R^2$ is as defined in any one of claims 27-31 of U.S. 62/742,218, filed Oct. 5, 2018. For example, $R^2$ can be

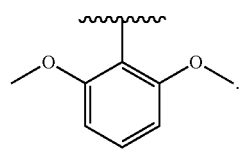

In some embodiments of [1], $R^2$ is heteroaryl including from 5-10 (such as 6) ring atoms, wherein from 1-4 (such as 1-3) ring atoms are heteroatoms, each independently selected from the group consisting of N, N(H), N($R^d$), O, and S (such as the group consisting of N, N(H), and N($R^d$)), and wherein one or more of the heteroaryl ring carbon atoms are optionally substituted with from 1-4 independently selected $R^c$, such as wherein $R^2$ is pyridinyl which is optionally substituted with from 1-2 independently selected $R^c$, or such as wherein $R^2$ is

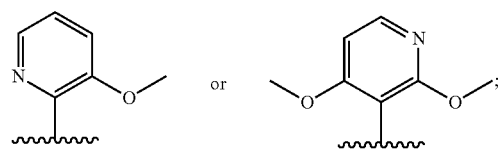

and $R^c$, when present, is as defined in any one of claims 40-41.

In certain embodiments of [1], $R^2$ is

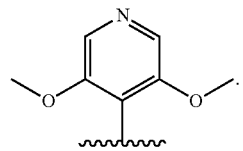

In some embodiments of [1], $R^2$ is as defined in any one of claims 32-37 of U.S. 62/742,218, filed Oct. 5, 2018. In certain of the foregoing embodiments, $R^2$ is as defined in any one of claims 34-37 of U.S. 62/742,218, filed Oct. 5, 2018.

For example, $R^2$ can be as defined in claim 37 of U.S. 62/742,218, filed Oct. 5, 2018.

In some embodiments of [1] when one occurrence of $R^3$ is $-L^4-R^4$, $-L^4$ is selected from the group consisting of:
—N(H)S(O)$_{1-2}$— or —N(R$^d$)S(O)$_{1-2}$ (e.g., N(C$_{1-3}$ alkyl) S(O)$_2$), such as wherein $L^4$ is —N(H)S(O)$_2$—;
—N(H)C(O)— or —N(R$^d$)C(O), such as wherein $L^4$ is —N(H)C(O)—;
—C(O)NH— or —C(O)N(R$^d$)—;
—N(H)—, —N(R$^d$)—, or —N(R$^4$)—;
a single bond;
C≡C;
—O—; and
—N(H)S(O)$_{1-2}$N(H)—, —N(R$^d$)S(O)$_{1-2}$N(H)—, —N(H)S(O)$_{1-2}$N(R$^d$)—, and —N(R$^d$)S(O)$_{1-2}$N(R$^d$)—, such as wherein $L^4$ is —N(H)S(O)$_{1-2}$N(H)— (e.g., —N(H)S(O)$_2$N(H)—) or wherein $L^4$ is —N(H)S(O)$_{1-2}$N(R$^d$)— (e.g., —N(H)S(O)$_2$N(R$^d$)— (e.g., —N(H)S(O)$_2$N(C$_{1-3}$ alkyl)-));
as well as defined in any one of claims 48-55 of U.S. 62/742,218, filed Oct. 5, 2018.

In some embodiments of [1] when one occurrence of $R^3$ is $-L^4-R^4$, $-L^4$ is selected from the group consisting of:
—N(H)S(O)$_{1-2}$— or —N(R$^d$)S(O)$_{1-2}$ (e.g., N(C$_{1-3}$ alkyl) S(O)$_2$), such as wherein $L^4$ is —N(H)S(O)$_2$—;
—N(H)C(O)— or —N(R$^d$)C(O), such as wherein $L^4$ is —N(H)C(O)—;
—C(O)NH— or —C(O)N(R$^d$)—;
—N(H)—, —N(R$^d$)—, or —N(R$^4$)—;
a single bond; and
C≡C.

In some embodiments of [1] when one occurrence of $R^3$ is $-L^4-R^4$, $-L^4$ is selected from the group consisting of:
N(H)S(O)$_2$—;
—N(H)C(O)—; and
—N(H)—, —N(R$^d$)—, or —N(R$^4$)—.

In certain embodiments of [1], $-L^4$ is as defined in any one of claims 49, 51, and 53 of U.S. 62/742,218, filed Oct. 5, 2018. For example, $L^4$ can be as defined in claim 49 of U.S. 62/742,218, filed Oct. 5, 2018. In some embodiments of [1] when one occurrence of $R^3$ is $-L^4-R^4$, $-L^4$ is —NHS(O)(=NH)—.

In some embodiments of [1] when one occurrence of $R^3$ is $-L^4-R^4$, $-L^4$ is selected from the group consisting of:
—N(H)S(O)$_{1-2}$— or —N(R$^d$)S(O)$_{1-2}$ (e.g., N(C$_{1-3}$ alkyl) S(O)$_2$), such as wherein $L^4$ is —N(H)S(O)$_2$—; and
—N(H)S(O)$_{1-2}$N(H)—, —N(R$^d$)S(O)$_{1-2}$N(H)—, —N(H)S(O)$_{1-2}$N(R$^d$)—, and —N(R$^d$)S(O)$_{1-2}$N(R$^d$)—, such as wherein $L^4$ is —N(H)S(O)$_{1-2}$N(H)— (e.g., —N(H)S(O)$_2$N(H)—) or wherein $L^4$ is —N(H)S(O)$_{1-2}$N(R$^d$)— (e.g., —N(H)S(O)$_2$N(R$^d$)— (e.g., —N(H)S(O)$_2$N(C$_{1-3}$ alkyl)-)).

In some embodiments of [1] when one occurrence of $R^3$ is $-L^4-R^4$; and $R^4$ is $(Y^3)_p$—$Y^4$, $Y^4$ is $C_{6-10}$ aryl, which is optionally substituted with from 1-4 $R^c$, such as phenyl, which is optionally substituted with from 1-2 (e.g., 1) $R^c$, or wherein $Y^4$ is unsubstituted $C_{6-10}$ aryl such as unsubstituted phenyl; and $R^c$, when present, is as defined in any one of claims 73-75

In some embodiments of [1] when one occurrence of $R^3$ is $-L^4-R^4$; and $R^4$ is $(Y^3)_p$—$Y^4$, $Y^4$ is $C_{6-10}$ aryl, which is optionally substituted with from 1-4 $R^c$, such as phenyl optionally substituted with from 1-4 $R^c$; and wherein each occurrence of $R^c$, when present, is independently selected from the group consisting of:
(vii) $C_{1-4}$ alkoxy;
(viii) $C_{1-4}$ haloalkoxy; and
(xiv) —$C_{1-4}$ thioalkoxy.

In some embodiments of [1] when one occurrence of $R^3$ is $-L^4-R^4$; and $R^4$ is $(Y^3)_p$—$Y^4$, $Y^4$ is as defined in any one of claims 77, 78, 79, 81, and 82, and wherein $R^b$, when present, is as defined in claim 80.

In some embodiments of [1] when one occurrence of $R^3$ is $-L^4-R^4$; and $R^4$ is $(Y^3)_p$—$Y^4$, $Y^4$ is as defined in any one of claims 77-79; and $R^b$, when present, is as defined in claim 80.

In some embodiments of [1] when one occurrence of $R^3$ is $-L^4-R^4$; and R is $(Y^3)_p$—$Y^4$, $Y^4$ is as defined in any one of claims 83-85 and 88; and $R^c$, when present, is as defined in any one of claims 86-87.

In some embodiments of [1] when one occurrence of $R^3$ is $-L^4-R^4$; and $R^4$ is $(Y^3)_p$—$Y^4$, $Y^4$ is as defined in any one of claims 83-85, and 88.

In some embodiments of [1] when one occurrence of $R^3$ is $-L^4-R^4$; and $R^4$ is $(Y^3)_9$—$Y^4$, $Y^4$ is as defined in any one of claims 89-96; and $R^b$, when present, is as defined in any one of claims 97-98.

In some embodiments of [1] when one occurrence of $R^3$ is $-L^4-R^4$; and $R^4$ is $(Y^3)_p$—$Y^4$, $Y^4$ is as defined in any one of claims 89-92, 94, and 96; and $R^b$, when present, is as defined in claim 98.

In some embodiments of [1], $R^4$ is selected from the group consisting of the structures delineated in claims 99-113.

In some embodiments of [1], $R^4$ is selected from the group consisting of the structures delineated in claims 100, 101, 104-105, 107, 109, 111, and 113.

In some embodiments of [1] when one occurrence of $R^3$ is $-L^4-R^4$,
$R^4$ is $C_{1-10}$ alkyl, optionally substituted with from 1-6 independently selected $R^a$; or
$R^4$ is $C_{1-6}$ alkyl, optionally substituted with from 1-6 independently selected $R^a$; or
$R^4$ is $C_{1-6}$ alkyl, optionally substituted with from 1-2 independently selected $R^a$, such as wherein $R^4$ is selected from the group consisting of: methyl, ethyl,

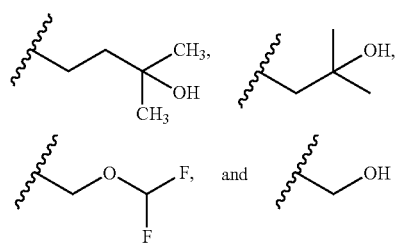

(such as methyl and

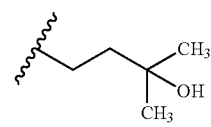

or $R^4$ is $C_{2-10}$ alkynyl (e.g., $C_{2-4}$ alkynyl), which is optionally substituted with from 1-6 (e.g., from 1-3) independently selected $R^a$ (e.g., unsubstituted $C_{2-4}$ alkynyl such as

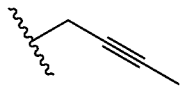 [SMILES: *CC#CC]

or

R⁴ is C₂₋₁₀ alkenyl (e.g., C₂₋₆ alkenyl), which is optionally substituted with from 1-6 (e.g., from 1-3) independently selected Rᵃ (e.g., unsubstituted C₂₋₄ alkenyl such as vinyl); and wherein each Rᵃ, when present, is independently selected from the group consisting of: —F; —OH; C₁₋₄ alkoxy; and C₁₋₄ haloalkoxy, such as wherein each occurrence of Rᵃ is independently —OH.

In some embodiments of [1] when one occurrence of R³ is -L⁴-R⁴,

R⁴ is C₁₋₁₀ alkyl, optionally substituted with from 1-6 independently selected Rᵃ; or R⁴ is C₁₋₆ alkyl, optionally substituted with from 1-6 independently selected Rᵃ; or R⁴ is C₁₋₆ alkyl, optionally substituted with from 1-2 independently selected Rᵃ, such as methyl and

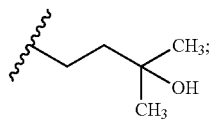

and wherein each Rᵃ, when present, is independently selected from the group consisting of: —F; —OH; C₁₋₄ alkoxy; and C₁₋₄ haloalkoxy, such as —OH.

In some embodiments of [1] when one occurrence of R³ is -L⁴-R⁴, R⁴ is as defined in any one of claims 56-60 and 61-63 of U.S. 62/742,218, filed Oct. 5, 2018.

In some embodiments of [1] when one occurrence of R³ is -L⁴-R⁴, R⁴ is as defined in any one of claims 56-60 and 64-67 of U.S. 62/742,218, filed Oct. 5, 2018.

In some embodiments of [1] when one occurrence of R³ is -L⁴-R⁴, R⁴ is as defined in any one of claims 56-60 and 68-71 of U.S. 62/742,218, filed Oct. 5, 2018.

In some embodiments of [1] when one occurrence of R³ is -L⁴-R⁴, R⁴ is as defined in any one of claims 56-60 and 72-78 of U.S. 62/742,218, filed Oct. 5, 2018.

In some embodiments of [1] when one occurrence of R³ is-L⁴-R⁴, R⁴ is as defined in any one of claims 56-60 and 79-86 of U.S. 62/742,218, filed Oct. 5, 2018.

In some embodiments of [1] when one occurrence of R³ is -L⁴-R⁴, R⁴ is as defined in any one of claims 56-60 and 87-92 of U.S. 62/742,218, filed Oct. 5, 2018.

In certain embodiments of [1], -L⁴ is selected from the group consisting of —N(H)S(O)₂—, —N(H)S(O)₂N(H)—, —N(H)S(O)₂N(Rᵈ)—, C≡C, a single bond, —C(O)N(H)—, —N(H)—, —N(R⁴)—, —N(Rᵈ)—, and —N(H)C(O)—; and R⁴ is selected from the group consisting of:
(i) C₁₋₆ alkyl optionally substituted with 1-2 Rᵃ;
(ii) —(Y³)ₚ—Y⁴; and
(iii) C₂₋₁₀ alkenyl or C₂₋₁₀ alkynyl, each of which is optionally substituted with from 1-3 independently selected Rᵃ.

In certain embodiments of [1], -L⁴ is selected from the group consisting of —N(H)S(O)₂—, —N(H)S(O)₂N(H)—, and —N(H)S(O)₂N(Rᵈ)—; and R⁴ is selected from the group consisting of:
(i) C₁₋₆ alkyl optionally substituted with 1-2 Rᵃ;
(ii) —(Y³)ₚ—Y⁴; and
(iii) C₂₋₁₀ alkenyl or C₂₋₁₀ alkynyl, each of which is optionally substituted with from 1-3 independently selected Rᵃ.

In some embodiments of [1], Rᵃ is selected from the group consisting of structures delineated in claims 148-165; or wherein R3 is selected from the group consisting of structures delineated in claims 148-149, 151, 153, 155-156, 158, 160, 162, and 165.

In some embodiments of [1], R³ is as defined in any one of claims 113-122 of U.S. 62/742,218, filed Oct. 5, 2018.

[1-1]

In some embodiments of [1], each of X² and X³ is an independently selected CR³; and each of X¹ and X⁴ is independently N, or CH. In certain of these embodiments, each of X¹ and X⁴ is N. In certain of the foregoing embodiments, each R³ is an independently selected -L⁴-R⁴.

In some embodiments of [1-1], one occurrence of -L⁴-R⁴ is —R⁴ (i.e., one occurrence of L⁴ is a bond).

In certain of these embodiments, the other occurrence of -L⁴ is selected from the group consisting of:
—N(H)S(O)₁₋₂— or —N(Rᵈ)S(O)₁₋₂ (e.g., N(C₁₋₃ alkyl) S(O)₂), such as wherein L⁴ is —N(H)S(O)₂—;
—N(H)C(O)— or —N(Rᵈ)C(O), such as wherein L⁴ is —N(H)C(O)—;
—C(O)NH— or —C(O)N(Rᵈ)—;
—N(H)—, —N(Rᵈ)—, or —N(R⁴)—;
a single bond;
C≡C;
—O—; and
—N(H)S(O)₁₋₂N(H)—, —N(Rᵈ)S(O)₁₋₂N(H)—, —N(H)S(O)₁₋₂N(Rᵈ)—, and —N(Rᵈ)S(O)₁₋₂N(Rᵈ)—, such as wherein L⁴ is —N(H)S(O)₁₋₂N(H)— (e.g., —N(H)S(O)₂N(H)—) or wherein L⁴ is —N(H)S(O)₁₋₂N(Rᵈ)— (e.g., —N(H)S(O)₂N(Rᵈ)— (e.g., —N(H)S(O)₂N(C₁₋₃ alkyl)-)).

In certain embodiments, the other occurrence of -L⁴ is selected from the group consisting of:
—N(H)S(O)₁₋₂— or —N(Rᵈ)S(O)₁₋₂ (e.g., N(C₁₋₃ alkyl) S(O)₂), such as wherein L⁴ is —N(H)S(O)₂—;
—N(H)C(O)— or —N(Rᵈ)C(O), such as wherein L⁴ is —N(H)C(O)—;
—C(O)NH— or —C(O)N(Rᵈ)—;
—N(H)—, —N(Rᵈ)—, or —N(R⁴)—;
a single bond; and
C≡C.

In certain embodiments, the other occurrence of -L⁴ is selected from the group consisting of:
—N(H)S(O)₂—;
—N(H)C(O)—; and
—N(H)—, —N(Rᵈ)—, or —N(R⁴)—, such as wherein the other occurrence of -L⁴ is N(H)S(O)₂—.

In certain embodiments, the other occurrence of -L⁴ is selected from the group consisting of:
—N(H)S(O)₁₋₂— or —N(Rᵈ)S(O)₁₋₂ (e.g., N(C₁₋₃ alkyl) S(O)₂), such as wherein L⁴ is —N(H)S(O)₂—; and
—N(H)S(O)₁₋₂N(H)—, —N(Rᵈ)S(O)₁₋₂N(H)—, —N(H)S(O)₁₋₂N(Rᵈ)—, and —N(Rᵈ)S(O)₁₋₂N(Rᵈ)—, such as wherein L⁴ is —N(H)S(O)₁₋₂N(H)— (e.g., —N(H)S(O)₂N(H)—) or wherein L⁴ is —N(H)S(O)₁₋₂N(Rᵈ)— (e.g., —N(H)S(O)₂N(Rᵈ)— (e.g., —N(H)S(O)₂N(C₁₋₃ alkyl)-)).

In certain of the foregoing embodiments, the other occurrence of -L⁴ is as defined in any one of claims defined in claims 48-55 of U.S. 62/742,218, filed Oct. 5, 2018. For example, the other occurrence of -$L^4$ can be as defined in any one of claims 49, 51, and 53 (e.g., claim 49) of U.S. 62/742,218, filed Oct. 5, 2018.

In some embodiments of [1-1], each $R^4$ is independently as defined in any one of claims 56-60 and 61-63 of U.S. 62/742,218, filed Oct. 5, 2018.

In some embodiments of [1-1], each $R^4$ is independently as defined in any one of claims 56-60 and 64-67 of U.S. 62/742,218, filed Oct. 5, 2018.

In some embodiments of [1-1], each $R^4$ is independently as defined in any one of claims 56-60 and 68-71 of U.S. 62/742,218, filed Oct. 5, 2018.

In some embodiments of [1-1], each $R^4$ is independently as defined in any one of claims 56-60 and 72-78 of U.S. 62/742,218, filed Oct. 5, 2018.

In some embodiments of [1-1], each $R^4$ is independently as defined in any one of claims 79-86 of U.S. 62/742,218, filed Oct. 5, 2018.

In some embodiments of [1-1], each $R^4$ is independently as defined in any one of claims 87-92 of U.S. 62/742,218, filed Oct. 5, 2018.

In some embodiments of [1-1], $R^1$ is as defined in any one of claims 10-23 of U.S. 62/742,218, filed Oct. 5, 2018.

In some embodiments of [1-1], $R^1$ is as defined in any one of claims 16-23 of U.S. 62/742,218, filed Oct. 5, 2018.

In some embodiments of [1-1], $R^1$ is as defined in claim 23 of U.S. 62/742,218, filed Oct. 5, 2018.

In some embodiments of [1-1], $R^2$ is as defined in any one of claims 24-31 of U.S. 62/742,218, filed Oct. 5, 2018.

In some embodiments of [1-1], $R^2$ is as defined in any one of claims 27-31 of U.S. 62/742,218, filed Oct. 5, 2018.

In some embodiments of [1-1], $R^2$ is as defined in any one of claims 32-37 (e.g., 34-37) of U.S. 62/742,218, filed Oct. 5, 2018.

[1-2]

In some embodiments of [1], each of $X^2$ and $X^3$ is an independently selected $CR^3$; and each of $X^1$ and $X^4$ is independently N, or CH. In certain of these embodiments, each of $X^1$ and $X^4$ is N.

In some embodiments of [1-2], one occurrence of $R^3$ is -$L^4$-$R^4$ (e.g., -$L^4$ is as defined in claim 49); and the other occurrence of $R^3$ is $R^{c'}$ (e.g., $R^{c'}$ can be halo such as —Cl).

In certain of these embodiments, -$L^4$ is selected from the group consisting of:
—N(H)S(O)$_{1-2}$— or —N($R^d$)S(O)$_{1-2}$ (e.g., N($C_{1-3}$ alkyl)S(O)$_2$), such as wherein $L^4$ is —N(H)S(O)$_2$—;
—N(H)C(O)— or —N($R^d$)C(O), such as wherein $L^4$ is —N(H)C(O)—;
—C(O)NH— or —C(O)N($R^d$)—;
—N(H)—, —N($R^d$)—, or —N($R^4$)—;
a single bond;
C≡C;
—O—; and
—N(H)S(O)$_{1-2}$N(H)—, —N($R^d$)S(O)$_{1-2}$N(H)—, —N(H)S(O)$_{1-2}$N($R^d$)—, and —N($R^d$)S(O)$_{1-2}$N($R^d$)—, such as wherein $L^4$ is —N(H)S(O)$_{1-2}$N(H)— (e.g., —N(H)S(O)$_2$N(H)—) or wherein $L^4$ is —N(H)S(O)$_{1-2}$N($R^d$)— (e.g., —N(H)S(O)$_2$N($R^d$)— (e.g., —N(H)S(O)$_2$N($C_{1-3}$ alkyl)-)).

In certain embodiments, -$L^4$ is selected from the group consisting of:
—N(H)S(O)$_{1-2}$— or —N($R^d$)S(O)$_{1-2}$ (e.g., N($C_{1-3}$ alkyl)S(O)$_2$), such as wherein $L^4$ is —N(H)S(O)$_2$—;
—N(H)C(O)— or —N($R^d$)C(O), such as wherein $L^4$ is —N(H)C(O)—;
—C(O)NH— or —C(O)N($R^d$)—;
—N(H)—, —N($R^d$)—, or —N($R^4$)—;
a single bond; and
C≡C.

In certain embodiments, -$L^4$ is selected from the group consisting of:
—N(H)S(O)$_2$—;
—N(H)C(O)—; and
—N(H)—, —N($R^d$)—, or —N($R^4$)—, such as wherein the other occurrence of -$L^4$ is N(H)S(O)$_2$—.

In certain embodiments, -$L^4$ is selected from the group consisting of:
—N(H)S(O)$_{1-2}$— or —N($R^d$)S(O)$_{1-2}$ (e.g., N($C_{1-3}$ alkyl)S(O)$_2$), such as wherein $L^4$ is —N(H)S(O)$_2$—; and
—N(H)S(O)$_{1-2}$N(H)—, —N($R^d$)S(O)$_{1-2}$N(H)—, —N(H)S(O)$_{1-2}$N($R^d$)—, and —N($R^d$)S(O)$_{1-2}$N($R^d$)—, such as wherein $L^4$ is —N(H)S(O)$_{1-2}$N(H)— (e.g., —N(H)S(O)$_2$N(H)—) or wherein $L^4$ is —N(H)S(O)$_{1-2}$N($R^d$)— (e.g., —N(H)S(O)$_2$N($R^d$)— (e.g., —N(H)S(O)$_2$N($C_{1-3}$ alkyl)-)).

In certain of the foregoing embodiments, the other occurrence of -$L^4$ is as defined in any one of claims defined in claims 48-55 of U.S. 62/742,218, filed Oct. 5, 2018. For example, the other occurrence of -$L^4$ can be as defined in any one of claims 49, 51, and 53 (e.g., claim 49) of U.S. 62/742,218, filed Oct. 5, 2018.

In some embodiments of [1-2], each $R^4$ is independently as defined in any one of claims 56-60 and 61-63 of U.S. 62/742,218, filed Oct. 5, 2018.

In some embodiments of [1-2], each $R^4$ is independently as defined in any one of claims 56-60 and 64-67 of U.S. 62/742,218, filed Oct. 5, 2018.

In some embodiments of [1-2], each $R^4$ is independently as defined in any one of claims 56-60 and 68-71 of U.S. 62/742,218, filed Oct. 5, 2018.

In some embodiments of [1-2], each $R^4$ is independently as defined in any one of claims 56-60 and 72-78 of U.S. 62/742,218, filed Oct. 5, 2018.

In some embodiments of [1-2], each $R^4$ is independently as defined in any one of claims 79-86 of U.S. 62/742,218, filed Oct. 5, 2018.

In some embodiments of [1-2], each $R^4$ is independently as defined in any one of claims 87-92 of U.S. 62/742,218, filed Oct. 5, 2018.

In some embodiments of [1-2], $R^1$ is as defined in any one of claims 10-23 of U.S. 62/742,218, filed Oct. 5, 2018.

In some embodiments of [1-2], $R^1$ is as defined in any one of claims 16-23 of U.S. 62/742,218, filed Oct. 5, 2018.

In some embodiments of [1-2], $R^1$ is as defined in claim 23 of U.S. 62/742,218, filed Oct. 5, 2018.

In some embodiments of [1-2], $R^2$ is as defined in any one of claims 24-31 of U.S. 62/742,218, filed Oct. 5, 2018.

In some embodiments of [1-2], $R^2$ is as defined in any one of claims 27-31 of U.S. 62/742,218, filed Oct. 5, 2018.

In some embodiments of [1-2], $R^2$ is as defined in any one of claims 32-37 (e.g., 34-37) of U.S. 62/742,218, filed Oct. 5, 2018.

Non-Limiting Combinations [2]

In some embodiments, a compound of Formula (I) is of Formula (I-a1-a):

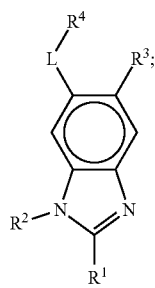

(I-a1-a)

or a pharmaceutically acceptable salt thereof.

In some embodiments of [2], -$L^4$ is selected from the group consisting of:

—N(H)S(O)$_{1-2}$— or —N(R$^d$)S(O)$_{1-2}$ (e.g., N(C$_{1-3}$ alkyl)S(O)$_2$), such as wherein $L^4$ is —N(H)S(O)$_2$—; and —N(H)S(O)$_{1-2}$N(H)—, —N(R$^d$)S(O)$_{1-2}$N(H)—, —N(H)S(O)$_{1-2}$N(R$^d$)—, and —N(R$^d$)S(O)$_{1-2}$N(R$^d$)—, such as wherein L is —N(H)S(O)$_{1-2}$N(H)— (e.g., —N(H)S(O)$_2$N(H)—) or wherein $L^4$ is —N(H)S(O)$_{1-2}$N(R$^d$)— (e.g., —N(H)S(O)$_2$N(R$^d$)— (e.g., —N(H)S(O)$_2$N(C$_{1-3}$ alkyl)-)).

In certain embodiments of [2], a compound of Formula (I-a1-a) is of Formula (I-a1-a1):

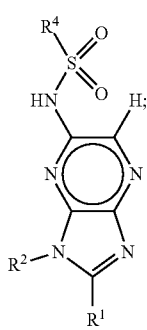

(I-a1-a1)

or a pharmaceutically acceptable salt thereof.

In certain embodiments of [2], a compound of Formula (I-a1-a) is of Formula (I-a1-a2):

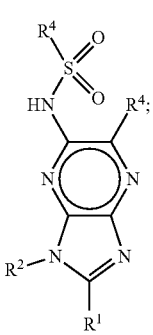

(I-a1-a2)

or a pharmaceutically acceptable salt thereof.

In certain embodiments of [2], a compound of Formula (I-a1-a) is of Formula (I-a1-a3):

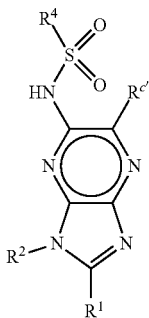

(I-a1-a3)

(e.g., R$^{c'}$ is halo, e.g., —Cl);
or a pharmaceutically acceptable salt thereof.

In certain of the foregoing embodiments of [2], $R^1$ is as defined in any one of claims 10-23 of U.S. 62/742,218, filed Oct. 5, 2018; and/or $R^2$ is as defined in any one of claims 24-37 of U.S. 62/742,218, filed Oct. 5, 2018; and/or $R^4$ is as defined in any one of claims 56-92 of U.S. 62/742,218, filed Oct. 5, 2018.

In certain embodiments of [2], a compound of Formula (I-a1-a) is of Formula (I-a1-a4):

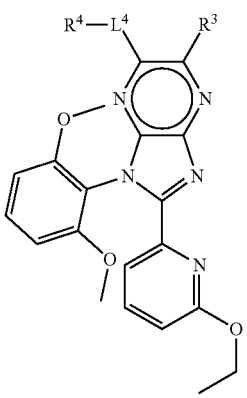

(I-a1-a4)

(e.g., $R^3$ is R$^{c'}$; or $R^3$ is -$L^4$-$R^4$);
or a pharmaceutically acceptable salt thereof.

In certain embodiments of Formula (I-a1-a4), $L^3$ is NHS(O)$_2$.

In certain embodiments of Formula (I-a1-a4), $R^3$ is H.

In certain embodiments of Formula (I-a1-a4), $R^3$ is R$^{c'}$, such as halo (e.g., —Cl).

In certain embodiments of Formula (I-a1-a4), $R^3$ is -$L^4$-$R^4$.

In certain of the foregoing embodiments of [2] (e.g., when the compound has Formula (I-a1-a4)), $L^4$ is as defined in any one of claims 48-55 of U.S. 62/742,218, filed Oct. 5, 2018; and/or $R^4$ is as defined in any one of claims 56-60 of U.S. 62/742,218, filed Oct. 5, 2018 and 61-63 of U.S. 62/742,218, filed Oct. 5, 2018; or 56-60 of U.S. 62/742,218, filed Oct. 5, 2018 and 64-67 of U.S. 62/742,218, filed Oct. 5, 2018; or 56-60 of U.S. 62/742,218, filed Oct. 5, 2018 and 68-71 of U.S. 62/742,218, filed Oct. 5, 2018; or 56-60 and 72-78 of U.S. 62/742,218, filed Oct. 5, 2018; or 79-86 of U.S. 62/742,218, filed Oct. 5, 2018; or 87-92 of U.S. 62/742,218, filed Oct. 5, 2018.

[2-1]

In some embodiments of [2], the compound of Formula (I-a1-a) is of Formula (I-a1-a5):

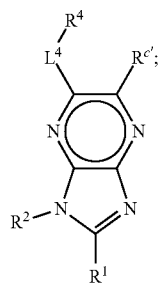

(I-a1-a5)

or a pharmaceutically acceptable salt thereof.

In some embodiments of [2-1], $R^{c'}$ is halo (e.g., —Cl).

In some embodiments of [2-1], $R^1$ is as defined in any one of claims 10-23 of U.S. 62/742,218, filed Oct. 5, 2018.

In some embodiments of [2-1], $R^2$ is as defined in any one of claims 24-37 (e.g., claims 24-31) of U.S. 62/742,218, filed Oct. 5, 2018.

In some embodiments of [2-1], $R^4$ is as defined in any one of claims 56-92 (e.g., claims 87-92) of U.S. 62/742,218, filed Oct. 5, 2018. In some embodiments of [2-1], $L^4$ is —NHS(O)$_2$—.

In some embodiments of [2-1], $L^4$ is —N(H)S(O)$_2$N(H)— or —N(H)S(O)$_2$N(R$^d$)—.

[2-2]

In some embodiments of [2], compound of Formula (I-a1-a) is of Formula (I-a1-a6):

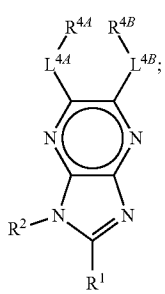

(I-a1-a6)

wherein each of $L^{4A}$ and $L^{4B}$ is an independently selected $L^4$; and
each of $R^{4A}$ and $R^{4B}$ is an independently selected $R^4$;
or a pharmaceutically acceptable salt thereof.

In some embodiments of [2-2], $L^{4B}$ is a bond.

In some embodiments of [2-2], $R^1$ is as defined in any one of claims 10-23 of U.S. 62/742,218, filed Oct. 5, 2018.

In some embodiments of [2-2], $R^2$ is as defined in any one of claims 24-37 (e.g., claims 24-31) of U.S. 62/742,218, filed Oct. 5, 2018.

In some embodiments of [2-2], $R^4$ is as defined in any one of claims 56-92 of U.S. 62/742,218, filed Oct. 5, 2018.

In some embodiments of [2-2], $L^{4A}$ is —NHS(O)$_2$—.

In some embodiments of [2-2], $L^4$ is —N(H)S(O)$_2$N(H)— or —N(H)S(O)$_2$N(R$^d$)—.

In some embodiments of [2-2], $R^{4B}$ is as defined in any one of claims 56-92 (e.g., claims 56-60 and 64-67) of U.S. 62/742,218, filed Oct. 5, 2018.

[2-3]

In some embodiments of [2], compound of Formula (I-a1-a) is of Formula (I-a1-a7), (I-a1-a8) or (I-a1-a9):

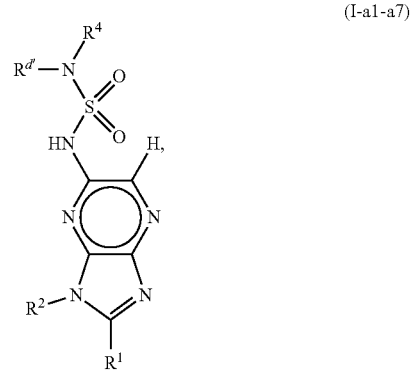

(I-a1-a7)

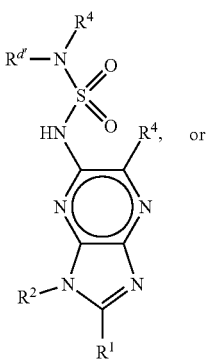

(I-a1-a8)

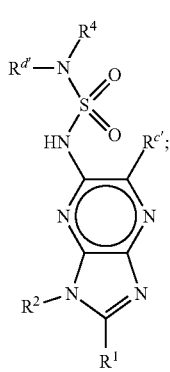

(I-a1-a9)

wherein $R^{d'}$ is H or $R^d$ (e.g., H or $C_{1-3}$ alkyl); or a pharmaceutically acceptable salt thereof.

Non-Limiting Combinations [3]

In some embodiments, a compound of Formula (I) is of Formula (I-a1-b):

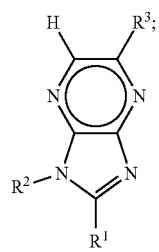

(I-a1-b)

or a pharmaceutically acceptable salt thereof.

In certain embodiments of [3], a compound of Formula (I-a1-b) is of Formula (I-a1-b1) or Formula (I-a1-b2):

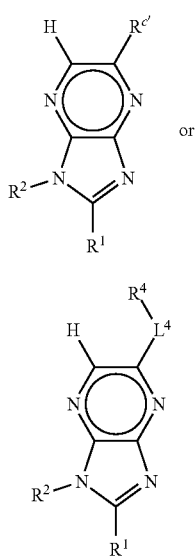

(I-a1-b1)

or (I-a1-b2)

(e.g., $L^4$ is N(H)SO$_2$, —N(H)—, or NHC(O));

or a pharmaceutically acceptable salt thereof.

In some embodiments of [3], -$L^4$ is selected from the group consisting of:

—N(H)S(O)$_{1-2}$— or —N(R$^d$)S(O)$_{1-2}$— (e.g., N(C$_{1-3}$ alkyl)S(O)$_2$), such as wherein $L^4$ is —N(H)S(O)$_2$—; and —N(H)S(O)$_{1-2}$N(H)—, —N(R$^d$)S(O)$_{1-2}$N(H)—, —N(H)S(O)$_{1-2}$N(R$^d$)—, and —N(R$^d$)S(O)$_{1-2}$N(R$^d$)—, such as wherein $L^4$ is —N(H)S(O)$_{1-2}$N(H)— (e.g., —N(H)S(O)$_2$N(H)—) or wherein $L^4$ is —N(H)S(O)$_{1-2}$N(R$^d$)— (e.g., —N(H)S(O)$_2$N(R$^d$)— (e.g., —N(H)S(O)$_2$N(C$_{1-3}$ alkyl)-)).

In certain of the foregoing embodiments of [3], $R^1$ is as defined in any one of claims 10-23 of U.S. 62/742,218, filed Oct. 5, 2018; and/or $R^2$ is as defined in any one of claims 24-37 of U.S. 62/742,218, filed Oct. 5, 2018; and/or $R^4$ is as defined in any one of claims 56-92 of U.S. 62/742,218, filed Oct. 5, 2018.

In certain of the foregoing embodiments of [3], $R^{c'}$ is selected from halo (e.g., Cl, Br), —OH, and NH$_2$.

Non-Limiting Combinations [4]

In some embodiments, a compound of Formula (I) is of Formula (I-a2-a):

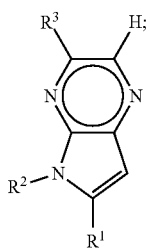

(I-a2-a)

or a pharmaceutically acceptable salt thereof.

In certain embodiments of [4], a compound of Formula (I-a2-a1) is a compound of Formula (I-a2-a1):

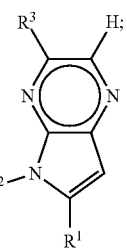

(I-a2-a1)

or a pharmaceutically acceptable salt thereof.

In certain of the foregoing embodiments of [4], $R^1$ is as defined in any one of claims 10-23 of U.S. 62/742,218, filed Oct. 5, 2018; and/or $R^2$ is as defined in any one of claims 24-37 of U.S. 62/742,218, filed Oct. 5, 2018; and/or $R^4$ is as defined in any one of claims 56-92 of U.S. 62/742,218, filed Oct. 5, 2018.

In certain embodiments of [4], a compound of Formula (I-a2-a) is of Formula (I-a1-a2):

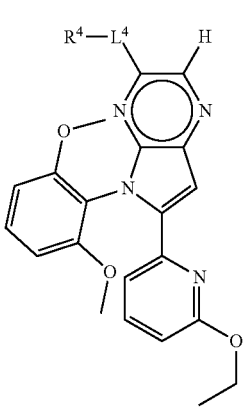

(I-a2-a2)

(e.g., $L^4$ is NHS(O)$_2$);

or a pharmaceutically acceptable salt thereof.

In certain of the foregoing embodiments of [4] (e.g., when the compound has Formula (I-a2-a2)), L⁴ is as defined in any one of claims 48-55 (e.g., 49) of U.S. 62/742,218, filed Oct. 5, 2018; and/or R⁴ is as defined in any one of claims 56-60 of U.S. 62/742,218, filed Oct. 5, 2018 and 61-63 of U.S. 62/742,218, filed Oct. 5, 2018; or 56-60 of U.S. 62/742,218, filed Oct. 5, 2018 and 64-67 of U.S. 62/742,218, filed Oct. 5, 2018; or 56-60 of U.S. 62/742,218, filed Oct. 5, 2018 and 68-71 of U.S. 62/742,218, filed Oct. 5, 2018; or 56-60 of U.S. 62/742,218, filed Oct. 5, 2018 and 72-78 of U.S. 62/742,218, filed Oct. 5, 2018; or 79-86 of U.S. 62/742,218, filed Oct. 5, 2018; or 87-92 of U.S. 62/742,218, filed Oct. 5, 2018.

Non-Limiting Combinations [5]

In some embodiments, a compound of Formula (I) is of Formula (I-b1-a):

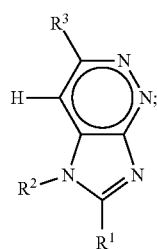

(I-b1-a)

or a pharmaceutically acceptable salt thereof.

In certain embodiments of [5], a compound of Formula (I-b1-a) is of Formula (I-b1-a1):

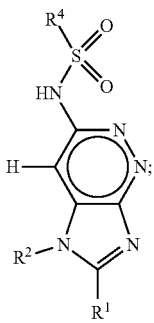

(I-b1-a1)

or a pharmaceutically acceptable salt thereof.

In certain of the foregoing embodiments of [5], R¹ is as defined in any one of claims 10-23 of U.S. 62/742,218, filed Oct. 5, 2018; and/or R² is as defined in any one of claims 24-37 of U.S. 62/742,218, filed Oct. 5, 2018; and/or R⁴ is as defined in any one of claims 56-92 of U.S. 62/742,218, filed Oct. 5, 2018.

In certain embodiments of [5], a compound of Formula (I-b1-a) is of Formula (I-b1-a3):

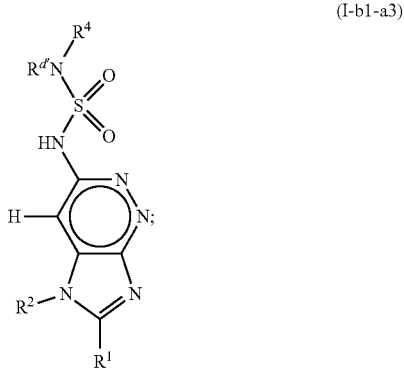

(I-b1-a3)

wherein $R^{d'}$ is H or $R^d$ (e.g., H or $C_{1-3}$ alkyl); or a pharmaceutically acceptable salt thereof.

In certain embodiments of [5], a compound of Formula (I-b1-a) of Formula (I-b1-a2):

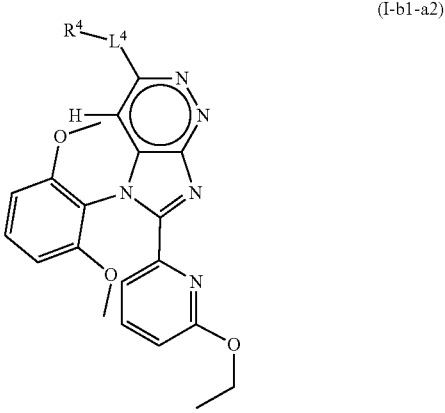

(I-b1-a2)

e.g., L is $NHS(O)_2$);

or a pharmaceutically acceptable salt thereof.

In certain embodiments of Formula (I-b1-a2), L⁴ is $NHS(O)_2$.

In certain of the foregoing embodiments of [5] (e.g., when the compound has Formula (I-b1-a2)), L⁴ is as defined in any one of claims 48-55 (e.g., 49) of U.S. 62/742,218, filed Oct. 5, 2018; and/or R⁴ is as defined in any one of claims 56-60 of U.S. 62/742,218, filed Oct. 5, 2018 and 61-63 of U.S. 62/742,218, filed Oct. 5, 2018; or 56-60 of U.S. 62/742,218, filed Oct. 5, 2018 and 64-67 of U.S. 62/742,218, filed Oct. 5, 2018; or 56-60 of U.S. 62/742,218, filed Oct. 5, 2018 and 68-71 of U.S. 62/742,218, filed Oct. 5, 2018; or 56-60 of U.S. 62/742,218, filed Oct. 5, 2018 and 72-78 of U.S. 62/742,218, filed Oct. 5, 2018; or 79-86 of U.S. 62/742,218, filed Oct. 5, 2018; or 87-92 of U.S. 62/742,218, filed Oct. 5, 2018.

Non-Limiting Combinations [6]

In some embodiments, a compound of Formula (I) is of Formula (I-c1-a):

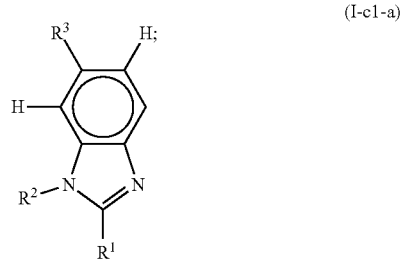

or a pharmaceutically acceptable salt thereof.

In certain embodiments of [6], a compound of Formula (I-c1-a) is of Formula (I-c1-a1):

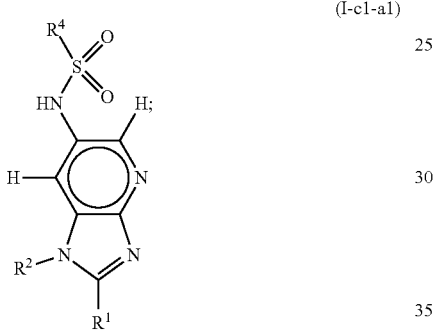

or a pharmaceutically acceptable salt thereof.

In certain of the foregoing embodiments of [6], $R^1$ is as defined in any one of claims 10-23 of U.S. 62/742,218, filed Oct. 5, 2018; and/or $R^2$ is as defined in any one of claims 24-37 of U.S. 62/742,218, filed Oct. 5, 2018; and/or $R^4$ is as defined in any one of claims 56-92 of U.S. 62/742,218, filed Oct. 5, 2018.

In certain embodiments of [6], a compound of Formula (I-c1-a) of Formula (I-c1-a2):

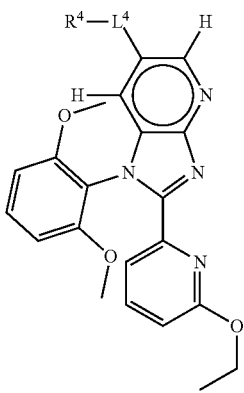

(e.g., $L^4$ is $NHS(O)_2$);
or a pharmaceutically acceptable salt thereof.

In certain of the foregoing embodiments of [6] (e.g., when the compound has Formula (I-c1-a2)), $L^4$ is as defined in any one of claims 48-55 (e.g., 49) of U.S. 62/742,218, filed Oct. 5, 2018; and/or $R^4$ is as defined in any one of claims 56-60 of U.S. 62/742,218, filed Oct. 5, 2018 and 61-63 of U.S. 62/742,218, filed Oct. 5, 2018; or 56-60 of U.S. 62/742,218, filed Oct. 5, 2018 and 64-67 of U.S. 62/742,218, filed Oct. 5, 2018; or 56-60 of U.S. 62/742,218, filed Oct. 5, 2018 and 68-71 of U.S. 62/742,218, filed Oct. 5, 2018; or 56-60 of U.S. 62/742,218, filed Oct. 5, 2018 and 72-78 of U.S. 62/742,218, filed Oct. 5, 2018; or 79-86 of U.S. 62/742,218, filed Oct. 5, 2018; or 87-92 of U.S. 62/742,218, filed Oct. 5, 2018.

Non-Limiting Combinations [7]

In some embodiments, the compound of Formula (I) is of Formula (I-d1-a):

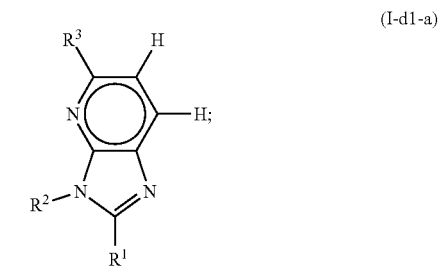

or a pharmaceutically acceptable salt thereof.

In certain embodiments of [7], the compound of Formula (I-d1-a) is of Formula (I-d1-a1):

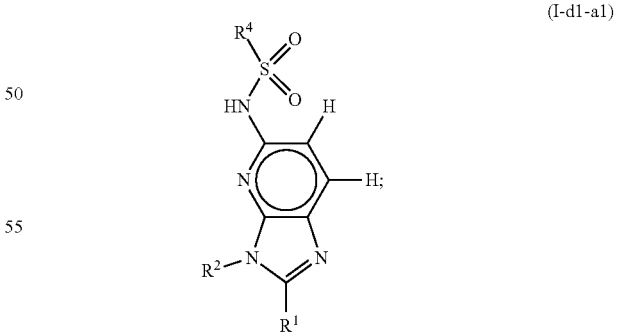

or a pharmaceutically acceptable salt thereof.

In certain embodiments of [7], $R^1$ is as defined in any one of claims 10-23 of U.S. 62/742,218, filed Oct. 5, 2018; and/or $R^2$ is as defined in any one of claims 24-37 of U.S. 62/742,218, filed Oct. 5, 2018; and/or $R^4$ is as defined in any one of claims 56-92 of U.S. 62/742,218, filed Oct. 5, 2018.

In certain embodiments of [7], a compound of Formula (I-d1-a) of Formula (I-d1-a2):

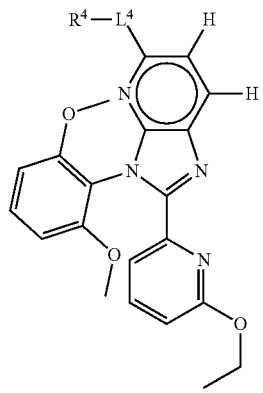

(I-d1-a2)

(e.g., $L^4$ is $NHS(O)_2$);
or a pharmaceutically acceptable salt thereof.

In certain of the foregoing embodiments of [7] (e.g., when the compound has Formula (I-c1-a2)), $L^4$ is as defined in any one of claims 48-55 (e.g., 49) of U.S. 62/742,218, filed Oct. 5, 2018; and/or $R^4$ is as defined in any one of claims 56-60 of U.S. 62/742,218, filed Oct. 5, 2018 and 61-63 of U.S. 62/742,218, filed Oct. 5, 2018; or 56-60 of U.S. 62/742,218, filed Oct. 5, 2018 and 64-67 of U.S. 62/742,218, filed Oct. 5, 2018; or 56-60 of U.S. 62/742,218, filed Oct. 5, 2018 and 68-71 of U.S. 62/742,218, filed Oct. 5, 2018; or 56-60 of U.S. 62/742,218, filed Oct. 5, 2018 and 72-78 of U.S. 62/742,218, filed Oct. 5, 2018; or 79-86 of U.S. 62/742,218, filed Oct. 5, 2018; or 87-92 of U.S. 62/742,218, filed Oct. 5, 2018.

In certain embodiments of any one or more of [1-1], [1-2], [2], [2-1], [2-2], [2-3], [3], [4], [5], [6], and [7], $R^4$ is selected from the group consisting of:
  (i) $C_{1-10}$ alkyl, optionally substituted with from 1-6 independently selected $R^a$;
  (ii) —$(Y^3)_p$—$Y^4$; and
  (iii) $C_{2-10}$ alkenyl or $C_{2-10}$ alkynyl, each of which is optionally substituted with from 1-3 independently selected $R^a$.

In certain embodiments of any one or more of [1-1], [1-2], [2], [2-1], [2-2], [2-3], [3], [4], [5], [6], and [7], $R^4$ is —$(Y^3)_p$—$Y^4$.

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is $C_{6-10}$ aryl, which is optionally substituted with from 1-4 $R^c$, such as phenyl, which is optionally substituted with from 1-2 (e.g., 1) $R^c$, or wherein $Y^4$ is unsubstituted $C_{6-10}$ aryl such as unsubstituted phenyl; and $R^c$, when present, is as defined in any one of claims 73-75 (e.g., claim 75).

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is $C_{6-10}$ aryl, which is optionally substituted with from 1-4 $R^c$, such as phenyl optionally substituted with from 1-4 $R^c$; and wherein each occurrence of $R^c$, when present, is independently selected from the group consisting of:
  (vii) $C_{1-4}$ alkoxy;
  (viii) $C_{1-4}$ haloalkoxy; and
  (xiv) —$C_{1-4}$ thioalkoxy.

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is as defined in any one of claims 77, 78, 79, 81, and 82, and wherein $R^b$, when present, is as defined in claim 80.

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is as defined in any one of claims 77-79; and $R^b$, when present, is as defined in claim 80.

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is as defined in any one of claims 83-85 and 88; and $R^c$, when present, is as defined in any one of claims 86-87.

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is as defined in any one of claims 83-85, and 88.

In certain embodiments of any one or more of [1-1], [1-2], [2], 12-11, 12-21, [2-3], [3], [4], [5], [6], and [7] when $R^4$ is —$(Y^3)_p$—$Y^4$, $Y^4$ is as defined in any one of claims 89-96; and $R^b$, when present, is as defined in any one of claims 97-98.

In certain embodiments of any one or more of [1-1], [1-2], [2], [2-1], [2-2], [2-3], [3], [4], [5], [6], and [7] when $R^4$ is —$(Y^3)_p$—$Y^4$, $Y^4$ is as defined in any one of claims 89-92, 94, and 96; and $R^b$, when present, is as defined in claim 98.

In certain embodiments of any one or more of [1-1], [1-2], [2], [2-1], [2-2], [2-3], [3], [4], [5], [6], and [7] when $R^4$ is —$(Y^3)_p$—$Y^4$, p is 0.

In other embodiments, p is 1. In certain of these embodiments, $Y^3$ is $C_{1-3}$ alkylene, such as $CH_2$ or $CH_2$—$CH_2$.

In certain embodiments of any one or more of [1-1], [1-2], [2], [2-1], [2-2], [2-3], [3], [4], [5], [6], and [7], $R^4$ is selected from the group consisting of the structures delineated in claims 99-113.

In certain embodiments of any one or more of [1-1], [1-2], [2], [2-1], [2-2], [2-3], [3], [4], [5], [6], and [7], each $R^4$ is selected from the group consisting of the structures delineated in claims 100, 101, 104-105, 107, 109, 111, and 113.

In certain embodiments of any one or more of [1-1], [1-2], [2], [2-1], [2-2], [2-3], [3], [4], [5], [6], and [7],
  $R^4$ is $C_{1-10}$ alkyl, optionally substituted with from 1-6 independently selected $R^a$; or
  $R^4$ is $C_{1-6}$ alkyl, optionally substituted with from 1-6 independently selected $R^a$; or
  $R^4$ is $C_{1-6}$ alkyl, optionally substituted with from 1-2 independently selected $R^a$, such as wherein $R^4$ is selected from the group consisting of: methyl, ethyl,

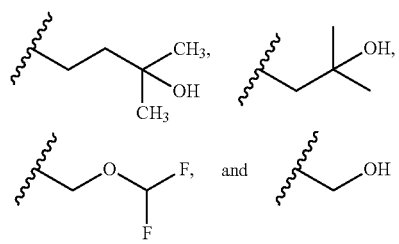

(such as methyl and

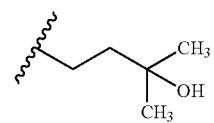

or

R⁴ is C$_{2-10}$ (e.g., C$_{2-4}$ alkynyl) alkynyl, which is optionally substituted with from 1-6 (e.g., from 1-3) independently selected R$^a$ (e.g., unsubstituted C$_{2-4}$ alkynyl such as

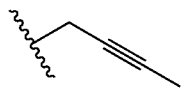 [SMILES: *CC#CC]

or

R⁴ is C$_{2-10}$ (e.g., C$_{2-4}$ alkenyl) alkenyl, which is optionally substituted with from 1-6 (e.g., from 1-3) independently selected R$^a$ (e.g., unsubstituted C$_{2-4}$ alkenyl such as vinyl); and wherein each R$^a$, when present, is independently selected from the group consisting of: —F; —OH; C$_{1-4}$ alkoxy; and C$_{1-4}$ haloalkoxy, such as wherein each occurrence of R$^1$ is independently —OH.

In certain embodiments of any one or more of [1-1], [1-2], [2], [2-1], [2-2], [2-3], [3], [4], [5], [6], and [7], R⁴ is C$_{1-10}$ alkyl, optionally substituted with from 1-6 independently selected R$^a$; or R⁴ is C$_{1-6}$ alkyl, optionally substituted with from 1-6 independently selected R$^a$; or R⁴ is C$_{1-6}$ alkyl, optionally substituted with from 1-2 independently selected R$^a$, such as methyl

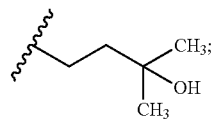 [SMILES: *CCC(C)(C)O]

and wherein each R$^a$, when present, is independently selected from the group consisting of: —F; —OH; C$_{1-4}$ alkoxy; and C$_{1-4}$ haloalkoxy, such as —OH.

In certain embodiments of any one or more of [1-1], [1-2], [2], [2-1], [2-2], [2-3], [3], [4], [5], [6], and [7], R¹ is —(Y$^1$)$_n$—Y$^2$.

In certain of these embodiments, Y$^2$ is as defined in any one of claims 14-20; and each R$^c$, when present, is independently as defined in any one of claims 21-24.

In certain embodiments of any one or more of [1-1], [1-2], [2], [2-1], [2-2], [2-3], [3], [4], [5], [6], and [7] when R¹ is —(Y$^1$)$_n$—Y$^2$, Y$^2$ is as defined in any one of claims 14-18 and 26; and each R$^d$, when present, is as defined in any one of claims 21-23.

In certain embodiments of any one or more of [1-1], [1-2], [2], [2-1], [2-2], [2-3], [3], [4], [5], [6], and [7] when R¹ is —(Y$^1$)$_n$—Y$^2$, Y$^2$ is as defined in any one of claims 16-18; and each R$^c$, when present, is as defined in any one of claims 21-23.

In certain embodiments of any one or more of [1-1], [1-2], [2], [2-1], [2-2], [2-3], [3], [4], [5], [6], and [7] when R¹ is —(Y$^1$)$_n$—Y$^2$, n is 0.

In certain embodiments of any one or more of [1-1], [1-2], [2], [2-1], [2-2], [2-3], [3], [4], [5], [6], and [7] when R¹ is —(Y$^1$)$_n$—Y$^2$, R¹ is

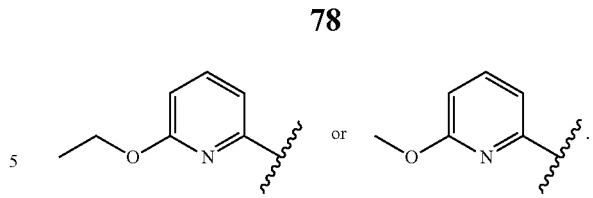

As a non-limiting example, R¹ can be

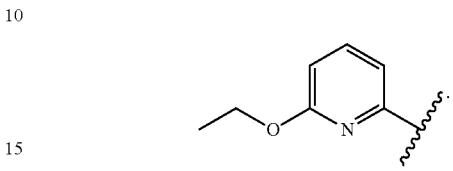

In certain embodiments of any one or more of [1-1], [1-2], [2], [2-1], [2-2], [2-3], [3], [4], [5], [6], and [7], R² is C$_{6-10}$ aryl, which is optionally substituted with from 1-4 R$^c$, such as phenyl, which is optionally substituted with from 1-4 R$^c$ or 1-2 R$^c$ or 2 R$^c$; and R$^c$, when present, is as defined in any one of claims 33-35.

In certain embodiments of any one or more of [1-1], [1-2], [2], [2-1], [2-2], [2-3], [3], [4], [5], [6], and [7], R² is phenyl, which is optionally substituted with 2 R$^c$, such as wherein R² is

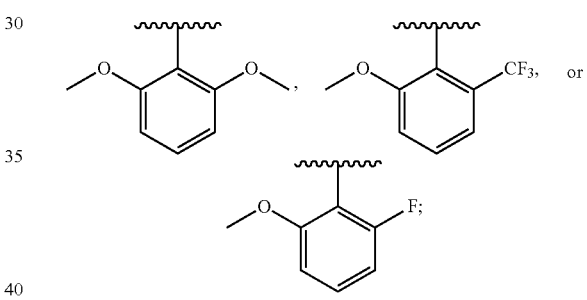

and R$^c$, when present, is as defined in any one of claims 33-35.

In certain embodiments of any one or more of [1-1], [1-2], [2], [2-1], [2-2], [2-3], [3], [4], [5], [6], and [7], R² is heteroaryl including from 5-10 (such as 6) ring atoms, wherein from 1-4 (such as 1-3) ring atoms are heteroatoms, each independently selected from the group consisting of N, N(H), N(R$^d$), O, and S (such as the group consisting of N, N(H), N(R$^d$), and O), and wherein one or more of the heteroaryl ring carbon atoms are optionally substituted with from 1-4 independently selected R$^c$, such as wherein R² is pyridinyl which is optionally substituted with from 1-2 independently selected R$^c$, or such as wherein R² is

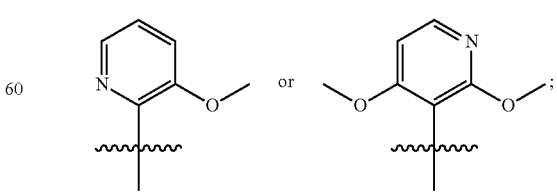

and R$^c$, when present, is as defined in any one of claims 40-41.

In certain embodiments of any one or more of [1-1], [1-2], [2], [2-1], [2-2], [2-3], [3], [4], [5], [6], and [7], $R^2$ is

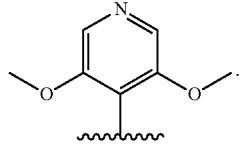

In certain embodiments of any one or more of [1-1], [1-2], [2], [2-1], [2-2], [2-3], [3], [4], [5], [6], and [7], $R^1$ is $-(Y^1)_n-Y^2$; and $R^2$ is $C_{6-10}$ aryl, which is optionally substituted with from 1-4 $R^c$.

In certain of these embodiments, n is 0.

In certain embodiments of any one or more of [1-1], [1-2], [2], [2-1], [2-2], [2-3], [3], [4], [5], [6], and [7] when $R^1$ is $-(Y^1)_n-Y^2$, $Y^2$ is heteroaryl including 6 ring atoms, wherein from 1-2 ring atoms are N, and wherein one or more of the heteroaryl ring carbon atoms are optionally substituted with from 1-4 independently selected $R^c$.

In certain embodiments of any one or more of [1-1], [1-2], [2], [2-1], [2-2], [2-3], [3], [4], [5], [6], and [7] when $R^1$ is $-(Y^1)_n-Y^2$, $Y^2$ is pyridyl (e.g., 2-pyridyl or 6-pyridyl), wherein one or more of the ring carbon atoms are optionally substituted with from 1-4 (e.g., 1) independently selected $R^c$.

In certain embodiments of any one or more of [1-1], [1-2], [2], [2-1], [2-2], [2-3], [3], [4], [5], [6], and [7] when $R^1$ is $-(Y^1)_n-Y^2$; and $Y^2$ is heteroaryl such as pyridyl optionally substituted with 1-4 independently selected $R^c$ as defined supra, each occurrence of $R^c$ is an independently selected $C_{1-4}$ alkoxy (e.g., $-OCH_3$, $-OCH_2CH_3$).

As a non-limiting example, $R^1$ is:

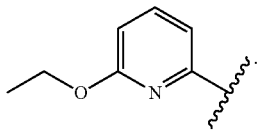 [SMILES: *c1cccc(OCC)n1]

In certain embodiments of any one or more of [1-1], [1-2], [2], [2-1], [2-2], [2-3], [3], [4], [5], [6], and [7] (when $R^1$ is $-(Y^1)_n-Y^2$; and $R^2$ is $C_{6-10}$ aryl, which is optionally substituted with from 1-4 $R^c$), such as $R^2$ is phenyl, which is optionally substituted with from 1-4 $R^c$.

In certain of these embodiments, $R^2$ is phenyl, which is optionally substituted with 2 $R^c$. For example, $R^2$ can be:

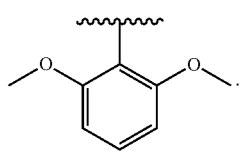

In certain embodiments of any one or more of [1-1], [1-2], [2], [2-1], [2-2], [2-3], [3], [4], [5], [6], and [7], $R^1$ is

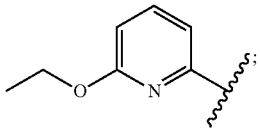 [SMILES: *c1cccc(OCC)n1]

and $R^2$ is

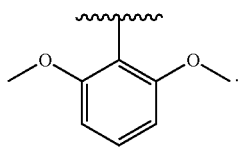

This specification concludes with 302 claims. For ease of exposition, certain variable definitions refer to one or more specific claim numbers, and as such, it is understood that the entire subject matter of each claim referenced is incorporated by reference in its entirety into the portion of the disclosure, in which it is referenced. For the avoidance of doubt and as a non-limiting example, use of a phrase, such as "$Y^4$ is as defined in any one of claims 77, 78, 79, 81, and 82" is intended to represent a short-hand recitation for the following set of defintions:

$Y^4$ is $C_{3-6}$ (e.g., $C_{3-4}$ or $C_6$) cycloalkyl, which is optionally substituted with from 1-4 $R^b$.

$Y^4$ is cyclopropyl or cyclobutyl which is optionally substituted with from 1-2 $R^b$.

$Y^4$ is $C_6$ cycloalkyl (e.g., cyclohexyl), which is optionally substituted with from 1-2 $R^b$.

$Y^4$ is $C_{3-6}$ (e.g., $C_{3-6}$ or $C_6$) cycloalkyl, which is unsubstituted.

$Y^4$ is unsubstituted cyclopropyl or unsubstituted cyclobutyl (e.g., unsubstituted cyclopropyl).

$Y^4$ is selected from the group consisting of $C_{3-6}$ (e.g., $C_{3-4}$ or $C_6$) cycloalkyl, which is optionally substituted with from 1-4 $R^b$; cyclopropyl or cyclobutyl which is optionally substituted with from 1-2 $R^b$; $C_6$ cycloalkyl (e.g., cyclohexyl), which is optionally substituted with from 1-2 $R^b$; is $C_{3-6}$ (e.g., $C_{3-4}$ or $C_6$) cycloalkyl, which is unsubstituted; and unsubstituted cyclopropyl or unsubstituted cyclobutyl (e.g., unsubstituted cyclopropyl).

The same also applies to claims referenced from the priority document U.S. 62/742,218, filed on Oct. 5, 2018.

Pharmaceutical Compositions and Administration

General

In some embodiments, a chemical entity (e.g., a compound or a pharmaceutically acceptable salt and/or hydrate and/or prodrug of the compound) that modulates (e.g., agonizes) the APJ receptor is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In general, the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules, sterility is not required. The USP/NF standard is usually sufficient.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Proper dosage for a particular situation can be determined by one skilled in the medical arts. In some cases, the total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

This disclosure features methods for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. In certain embodiments, the methods described herein can include or further include treating one or more conditions associated, co-morbid or sequela with any one or more of the conditions described herein.

In some embodiments, the method further comprises identifying the subject. In some embodiments, identifying comprises determining the level of one or more of the following parameters in the subject: leukotriene B4 level, pulmonary vascular resistance, pulmonary arterial pressure, cardiac index, pulmonary capillary wedge pressure, right atrial pressure, six-minute walk distance, brain natriuretic peptide level, atrial natriuretic peptide, and diffusion of lung capacity.

In certain embodiments, the chemical entities described herein modulate (e.g., decrease) pulmonary vascular resistance, modulate (e.g., decrease) right ventricular afterload, and modulate (e.g., decrease) mean pulmonary artery pressure. In certain embodiments, the chemical entities described herein reduce the risk of right ventricular failure.

In certain embodiments, the chemical entities described herein modulate vascular tone, modulate fluid homeostasis, modulate kidney function, modulate energy metabolism, modulate inflammatory response, and modulate thrombosis.

Indications

Pulmonary Hypertension

In some embodiments, the condition, disease or disorder is pulmonary arterial hypertension (PAH). Non-limiting examples of PAH and related conditions include idiopathic PAH, heritable PAH (e.g., BMPR2 mutations and other mutations), drug-induced or toxin-induced PAH, and PAH associated with conditions including but not limited to connective tissue diseases (CTD) (e.g., scleroderma, systemic lupus erythematosus, systemic sclerosis, Hashimoto's thyroiditis, Sjogren's Syndrome, and the antiphospholipid antibody syndrome), HIV infection, portal hypertension, congenital heart disease, and schistosomiasis.

In some embodiments, the PAH is idiopathic.

In other embodiments, the PAH is heritable PAH, toxin or drug-induced PAH; or a PAH associated with one or more of the following: congenital heart disease, connective tissue disorders (e.g., scleroderma, systemic lupus erythematosus, systemic sclerosis, Hashimoto's thyroiditis, Sjogren's Syndrome, and the antiphospholipid antibody syndrome), portal hypertension, BMPR2 mutations, Schistosomiasis, and HIV infection.

In some embodiments, the condition, disease or disorder is pulmonary hypertension other than PAM. Examples of such conditions include, without limitation, pulmonary hypertension due to left heart disease (e.g., left ventricular systolic dysfunction, left ventricular diastolic dysfunction, valvular heart disease, and congenital/acquired left heart inflow/outflow obstruction and congenital cardiomyopathies), pulmonary hypertension due to lung disease and/or hypoxia (e.g., choronic obstructive pulmonary disease, interstitial lung disease, other pulmonary disease with mixed restrictive and obstructive pattern, sleep-disordered breathing, alveolar hypoventilation disorders, chronic exposure to high altitude, developmental lung disease), chronic thromboembolic pulmonary hypertension and other pulmonary artery obstructions (e.g., chronic thromboembolic pulmonary hypertension, other pulmonary artery obstructions), and pulmonary hypertension with unclear multifactorial mechanisms (e.g., haematologic disorders, systemic disorders, metabolic disorders, and others).

Cardiovascular Conditions, Diseases or Disorders

In some embodiments, the condition, disease or disorder is a cardiovascular condition, disease or disorder. Non-limiting examples of cardiovascular condition, disease or disorder include coronary heart disease, acute coronary syndrome, peripheral vascular disease, angina, stroke, cerebrovascular accidents, transient ischemic attacks, heart failure, cardiomyopathy, myocardial infarction, myocardial remodeling after cardiac surgery, valvular heart disease, hypertension (e.g., systemic hypertension, essential hypertension, pulmonary hypertension, portal hypertension, systolic hypertension), aortic aneurysm (e.g., abdominal aortic aneurysm), atrial fibrillation, arrhythmia, atherosclerosis, Brugada syndrome, ischemic cardiovascular diseases, peripheral arterial disease, preeclampsia, ventricular tachycardia, and cardiac fibrosis.

In some embodiments, the cardiovascular condition, disease or disorder is heart failure. Non-limiting examples of heart failure include chronic heart failure, systolic heart failure, diastolic heart failure, diabetic heart failure, congestive heart failure, heart failure with preserved ejection fraction, heart failure with reduced ejection fraction, left ventricular dysfunction (e.g., left ventricular dysfunction after myocardial infarction), right ventricular dysfunction, cardiac hypertrophy, myocardial remodeling, and acute decompensated heart failure (ADHF).

In some embodiments, the cardiovascular condition, disease or disorder is a condition, disease or disorder with vascular pathology (e.g., with increased vascular permeability and nonfunctional blood vessels). Non-limiting examples of such condition, disease or disorder include vascular hypertrophy, vascular remodeling (e.g., vascular stiffness), atherosclerosis, peripheral arterial occlusive disease (PAOD), restenosis (e.g., angioplastic restenosis), thrombosis and vascular permeability disorders, and ischemia and/or reperfusion damage (e.g., ischemia and/or reperfusion damage of the heart, kidney and retina). In some embodiments, the conditions, disease or disorder is vein related. Non-limiting examples of such condition, disease or disorder include angioma, venous insufficiency, stasis, or thrombosis.

In some embodiments, the chemical entities described herein can improve cardiac contractility (e.g., cardiac relaxation), ventricular arterial coupling, inotropic function, or luistropic function in a subject suffering from a cardiovascular condition. In some embodiments, the chemical entities described herein can increase ejection fraction in a subject suffering from a cardiovascular condition.

Metabolic and Homeostatic Dysfunction and Related Conditions, Diseases or Disorders In some embodiments, the condition, disease or disorder is associated with metabolic dysfunction. Non-limiting examples of such condition, disease or disorder include metabolic dysfunction, obesity, diabetes (e.g., type II diabetes mellitus, gestational diabetes), complications of diabetes (e.g., metabolic syndrome, insulin resistance, organ damages of micro- or macrovascular origins such as macro- and microvaculopathies, diabetic neuropathy, diabetic retinopathy, cardiac autonomic neuropathy), kidney disease (e.g., chronic kidney disease), edema, dyslipidemia, anorexia, hyperphagia, polyphagia, hypercholesterolemia, hyperglyceridemia, hyperlipemia, growth hormone disorder (e.g., gigantism, aromegaly), galactorrhea, and cardiac wasting.

In some embodiments, the condition, disease or disorder is associated with inappropriate vasopressin secretions (SIADH). Non-limiting examples of such condition, disease or disorder include neurogenic diabetes mellitus (e.g. diabetic complications such as diabetic nephropathy, diabetic neuropathy, diabetic retinopathy, etc.), lung cancer, septic shock, and thirst troubles.

In some embodiments, the condition, disease or disorder is associated with systemic inflammation. Non-limiting examples of such condition, disease or disorder include systemic inflammatory response syndrome (SIRs), sepsis (e.g., severe sepsis), and septic shock. In some embodiments, the condition, disease or disorder is associated with sepsis (e.g., a complication, co-morbidity, or sequela of sepsis). Non-limiting examples of conditions, diseases or disorders associated with sepsis include sepsis-induced myocardial dysfunction, sepsis-related inflammatory response (e.g., systemic inflammation), sepsis-related hemodynamic alterations, hypovolemia, sepsis-related organ failures (e.g., multi-organ failure, renal failure), acute kidney injury, vasoplegia, lung injury, inappropriate vasopressin secretions, persistent hypertension related to generalized vasodilation, refractory constrictive responsiveness, huge plasma capillary leak syndrome, coagulation/fibrinolysis imbalance, and metabolic disturbance highlighted by elevated blood-stream lactates. See. e.g., Coquerel et al. Critical Care (2018) 22:10.

In some embodiments, the chemical entities described herein can regulate arginine vasopressin (AVP) or angiotensin receptor.

In some embodiments, the condition, disease or disorder is associated with disturbed body's fluid homeostasis by CNS-dependent and -independent effects. Non-limiting examples of such condition, disease or disorder include renal failure (e.g., acute and chronic renal failure), renal perfusion, renal dysfunction (e.g., polycystic kidney disease), aquaresis, and diuresis.

Dementia and Related Conditions, Diseases or Disorders

In some embodiments, the condition, disease or disorder is dementia. Non-limiting examples of such condition, disease or disorder include senile dementia, cerebrovascular dementia, dementia due to genealogical denaturation degenerative diseases (e.g. Alzheimer's disease, Parkinson's disease, Pick's disease, Huntington's disease, etc.), dementia resulting from infectious diseases (e.g. delayed virus infections such as Creutzfeldt-Jakob disease), dementia associated with endocrine diseases, metabolic diseases, or poisoning (e.g. hypothyroidism, vitamin B12 deficiency, alcoholism, poisoning caused by various drugs, metals, or organic compounds), dementia caused by tumors (e.g. brain tumor), and dementia due to traumatic diseases (e.g. chronic subdural hematoma), depression, hyperactive child syndrome (microencephalopathy), disturbance of consciousness, anxiety disorder, schizophrenia, and phobia.

Connective Tissue Disorder

In some embodiments, the condition, disease or disorder is a connective tissue disorder. In certain embodiments, the connective tissue disorder is selected from the group consisting of: scleroderma, systemic lupus erythematosus, systemic sclerosis, Hashimoto's thyroiditis, Sjogren's Syndrome, and the antiphospholipid antibody syndrome. In certain embodiments, the condition, disease or disorder is systemic sclerosis.

Fibrosis

In some embodiments, the condition, disease or disorder is fibrosis. In certain embodiments, the fibrosis is associated with an organ or tissue selected from the group consisting of: lung, liver, heart, mediastinum, bone marrow, retroperitoneaum, skin, intestine, joint, a reproductive organ, and a combination thereof. In certain embodiments, the fibrosis is idiopathic pulmonary fibrosis (IPF). In certain embodiments, the fibrosis is liver fibrosis. In certain embodiments, the fibrosis is associated with non-alcoholic fatty liver disease (NAFLD)

Other Conditions, Diseases or Disorders

In some embodiments, the condition, disease or disorder is a liver disease. Non-limiting examples of such condition, disease or disorder include alcoholic liver disease, toxicant-induced liver disease, viral induced liver disease, and liver cirrhosis.

In some embodiments, the condition, disease or disorder is a pulmonary disease. Non-limiting examples of such condition, disease or disorder include chronic obstructive pulmonary disease (COPD), asthma, acute respiratory dystress syndrome (ARDS), and amyotrophiclateral sclerosis. In some embodiments, the condition, disease or disorder is a retinal disease (e.g., macular degeneration).

In some embodiments, the condition, disease or disorder is HIV infection, HIV neurodegeneration, neurodegenerative disease, cancer (e.g., mammary cancer, lymphocytic leukemia, bladder cancer, ovary cancer, carcinoma of prostate, etc.), asthma, burn injuries (e.g., sun burn), traumatic brain injuries, pancreatitis, Turner's syndrome, neurosis, rheumatoid arthritis, spinal cord injury, immune function, inflammation, spinocerebellar degeneration, bone fracture, wounds, atopic dermatitis, osteoporosis, asthma, epilepsy, and sterility.

Activating Stem Cells

The chemical entities described herein can also be used to activate stem cells (e.g., cardiac stem cells such as endogenous cardiac stem cells). In some embodiments, the chemical entities described herein can be used in regrowing tissue, assisting functional recovery after transplanting cells (e.g., cells with bone marrow-derived mesenchymal stem cells), increasing cardiac stem cell proliferation (e.g., in patents that have suffered a myocardial infarction), reducing infarct size, promoting cardiac repair, activating stem cells and progenitors in postmyocardial infarction subjects, or reducing reperfusion injury (e.g., during surgeries such as heart bypass surgery or heart transplant procedures).

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the compound described herein can be administered in combination with one or more of additional therapeutic agents.

Representative additional therapeutic agents include, but are not limited to, therapeutic agents for PAH, pulmonary hypertension, heart failure (e.g., ADHF, chronic heart failure), hypertension (e.g., systemic hypertension), amyotrophic lateral sclerosis, arrhythmia, asthma, atherosclerosis, atrial fibrillation, Brugada syndrome, burn injuries (e.g., sunburn), cancer, cardiac fibrosis, cardiomyopathy, cerebrovascular accidents, diabetes (e.g., gestational diabetes), septic shock, sepsis, renal failure, dyslipidemia, HIV neurodegeneration, inflammation, ischemic cardiovascular disease, liver disease, metabolic disorder, neurodegenerative disease, obesity, peripheral arterial disease, preeclampsia, restenosis, transient ischemic attacks, traumatic brain injuries, ventricular tachycardia, edema, or immune function.

In some embodiments, the one or more additional therapeutic agents include those useful, e.g., as therapeutics for PAH. Non-limiting examples include:
- prostacyclin analogues (e.g., Epoprostenol, Treprostinil, Iloprost);
- prostacyclin IP receptor (e.g., Selexipag);
- endothelin receptor antagonists (e.g., Bosentan, Ambrisentan, Macitentan);
- PDE 5 inhibitors (e.g., Sildenafil, Tadalafil);
- soluble guanylate cyclase stimulator (e.g., Riociguat);
- therapeutics for mitochondria dysfunction (e.g., Bardoxolone methyl);
- anti-inflammation agents (e.g., Rituximab, Tocilizumab, Ubenimex); and
- agents that modulate oxidative stress (e.g., dimethyl fumarate, intravenous iron).

In some embodiments, the one or more additional therapeutic agents include those useful, e.g., as therapeutics for heart failure or hypertension. Non-limiting examples include:
- α-blockers (e.g., doxazosin, prazosin, tamsulosin, terazosin);
- β-blockers (e.g., acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol);
- calcium channel blockers including but not limited to dihydropyridines (DHPs) (e.g., amlodipine, felodipine, isradipine, lacidipine, nicardipine, nifedipine, nigulpidine, nilutipine, nimodiphine, nisoldipine, nitrendipine, nivaldipine, ryosidine) and non-DHPs (e.g., anipamil, diltiazem, fendiline, flunarizine, gallpamil, mibefradil, prenylamine, tiapamil, verapamil);
- diuretics (e.g., thiazide derivatives such as, but not limited to, amiloride, chlorothalidon, chlorothiazide, hydrochlorthiazide, and methylchlorothiazide)
- centrally acting hypertensive agents (e.g., clonidine, guanabenz, guanfacine, methyldopa);
- angiotensin converting enzyme (ACE) inhibitors (alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril) and dual ACE/NEP inhibitors (e.g., omapatrilat, fasidotril, and fasidotrilat);
- angiotensin receptor blockers (ARBs) (e.g., candesartan, eprosartan, irbesartan, losartan, olmesartan, tasosartan, telmisartan, valsartan) and dual ARB/NEP inhibitors (e.g., combinations of valsartan and sacubitril);
- neutral endopeptidase (NEP) inhibitor (e.g., sacubitril);
- aldosterone synthase inhibitors (e.g., anastrozole, fadrozole, exemestane);
- endothelin antagonists (e.g., bosentan, enrasentan, atrasentan, darusentan, macitentan, sitaxentan, tezosentan);
- inhibitors of funny current (e.g., ivabradine);
- myosin activators (e.g., cardiac myosin activators);
- natriuretic;
- saluretic;
- vasodilator/vasorelaxation agents (e.g., nitrates)
- mineralocorticoid receptor antagonists;
- renin inhibitors;
- digitalis compounds;
- inotropic agents and β-receptor agonists;
- anti-hyperlipidemic agents;
- plasma HDL-raising agents;
- anti-hypercholesterolemic agents;
- cholesterol biosynthesis inhibitors (e.g., HMG CoA reductase inhibitors) LXR agonist;
- probucol;
- raloxifene;
- nicotinic acid;
- niacinamide;
- cholesterol absorption inhibitors;
- bile acid sequestrants (e.g., anion exchange resins, or quaternary amines such as cholestyramine or colestipol);
- low density lipoprotein receptor inducers;
- clofibrate;
- fenofibrate;
- bezafibrate;
- ciprofibrate;
- gemfibrizol;
- vitamins (e.g., vitamin $B_6$, vitamin $B_{12}$, anti-oxidant vitamins);
- platelet aggregation inhibitors;
- fibrinogen receptor antagonists;
- aspirin; and
- fibric acid derivatives.

In some embodiments, the one or more additional therapeutic agents include those useful, e.g., for treating diabetes. Non-limiting examples include:
- sulfonylureas (e.g., chlorpropamide, tolbutamide, acetohexamide, tolazamide, glyburide, gliclazide, glynase, glimepiride, glipizide);
- biguanides (e.g., metformin);
- thiazolidinediones (e.g., ciglitazone, pioglitazone, troglitazone, rosiglitazone)
- insulin sensitizers related to the above (e.g., selective and non-selective activators of PPAR-alpha, PPAR-beta and PPAR-gamma);
- dehydroepiandrosterone (also referred to as DHEA or its conjugated sulfate ester, DHEA-$SO_4$);
- anti-glucocorticoids;
- TNF-alpha inhibitors;
- dipeptidyl peptidase IV (DPP4) inhibitors (e.g.; sitagliptin, saxagliptin);
- GLP-1 agonists or analogs (such as exenatide);
- alpha-glucosidase inhibitors (such as acarbose, miglitol, and voglibose);
- pramlintide (a synthetic analog of the human hormone amylin);
- other insulin secretagogues (such as repaglinide, gliquidone, and nateglinide); and
- insulin.

In some embodiments, the one or more additional therapeutic agents include those useful, e.g., for treating obesity. Non-limiting examples include phenylpropanolamine, phentermine, diethylpropion, mazindol, fenfluramine, dexfenfluramine, phentiramine, beta3-adrenergic receptor agonist agents, sibutramine, gastrointestinal lipase inhibitors (e.g., orlistat), leptins, neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin, and gamma amino butyric acid (GABA).

Other additional therapeutic agents include:
anti-atherosclerotic agents;
anti-dyslipidemic agents;
antihyperinsulinemic agents;
anti-thrombotic agents;
anti-retinopathic agents;
anti-neuropathic agents;
anti-nephropathic agents;
anti-ischemic agents;
anti-hyperlipidemic agents;
anti-hypertriglyceridemic agents;
anti-hypercholesterolemic agents;
anti-restenotic-agents;
anti-pancreatic agents;
anorectic agents;
memory enhancing agents;
antidementia agents;
cognition promoting agents;
appetite suppressants;
agents for treating peripheral arterial disease;
agents for treating malignant tumors;
anti-innammatory agents;
aquaretics;
digoxin;
nitric oxide donors;
hydralazines;
a ionotropes;
vasopressin receptor antagonists;
statins;
anti-arrhythmics;
phosphodiesterase inhibitors (e.g., PDE5 inhibitors); and
nephro-protectives.

Non-limiting examples of additional therapeutic agents can also include those described in U.S. Pat. No. 9,156, 796B2, which is incorporated herein by reference.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In some embodiments, intermediates useful for preparing the compounds described herein can be prepared using the chemistries delineated in any one or more of the following schemes and non-limiting examples.

Compound Preparation

For illustrative purposes, Schemes 1-4 show general methods for preparing the compounds provided herein as well as intermediates. For a more detailed description of the individual reaction steps, see the Synthetic Examples section below. Those skilled in the art will appreciate that other synthetic routes may be used to synthesize the inventive compounds. Although specific starting materials and reagents are depicted in the Scheme and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

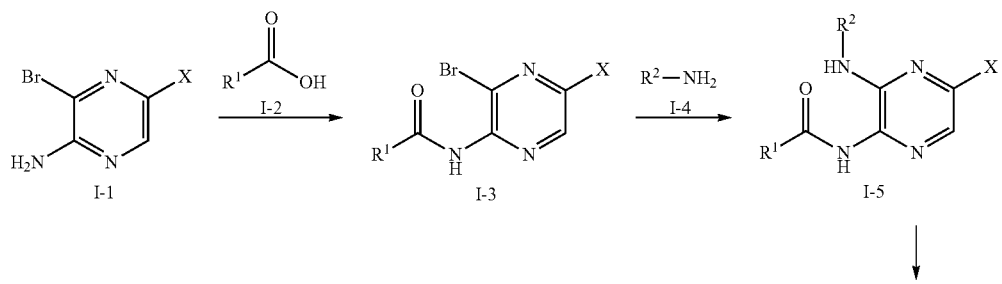

Non-limiting example of I-7:

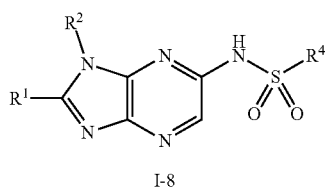

I-8

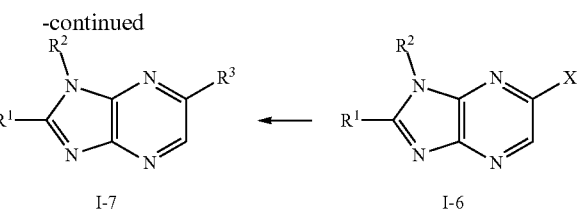

I-7    I-6

Referring to Scheme 1, a compound of Formula (I) (shown as I-6 and I-7) may be prepared from compound I-1, I-2, and I-4 wherein $R^1$ and $R^2$ are as defined herein. Aminopyrazine I-1 can be reacted with carboxylic acid I-2 to afford amide I-3 (wherein X is a halo such as bromo or chloro) under standard conditions (e.g., in the presence of oxalyl chloride which converts I-2 into an acyl chloride or in the presence of peptide coupling reagents). Then a reaction under $S_NAr$ or metal catalyzed cross-coupling conditions (e.g., Buchwald Hartwig coupling using Xantphos and Pd(OAc)$_2$) between I-3 and amine I-4 can provide compound I-5. Condensation of the carbonyl moiety in I-5 onto the amino group can provide I-6, a compound of Formula (I).

Alternatively, I-3 may be obtained through the coupling between I-1 and an ester of I-2 (e.g., alkyl ester, e.g., methyl or ethyl ester) under appropriate conditions (e.g., in the presence of AlMe$_3$).

Optionally, the X moiety in I-6 can be converted into other $R^3$ groups to provide I-7, another compound of Formula (I). As non-limiting examples for the transformation between I-6 and I-7, I-6 can be reacted with a sulfonamide under Ullmann coupling conditions to provide compound I-8 (vide supra, Scheme 1).

The following starting materials can be used in place of I-1 and subjected to the sequence depicted in Scheme 1.

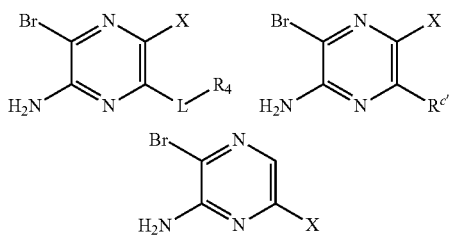

Scheme 2

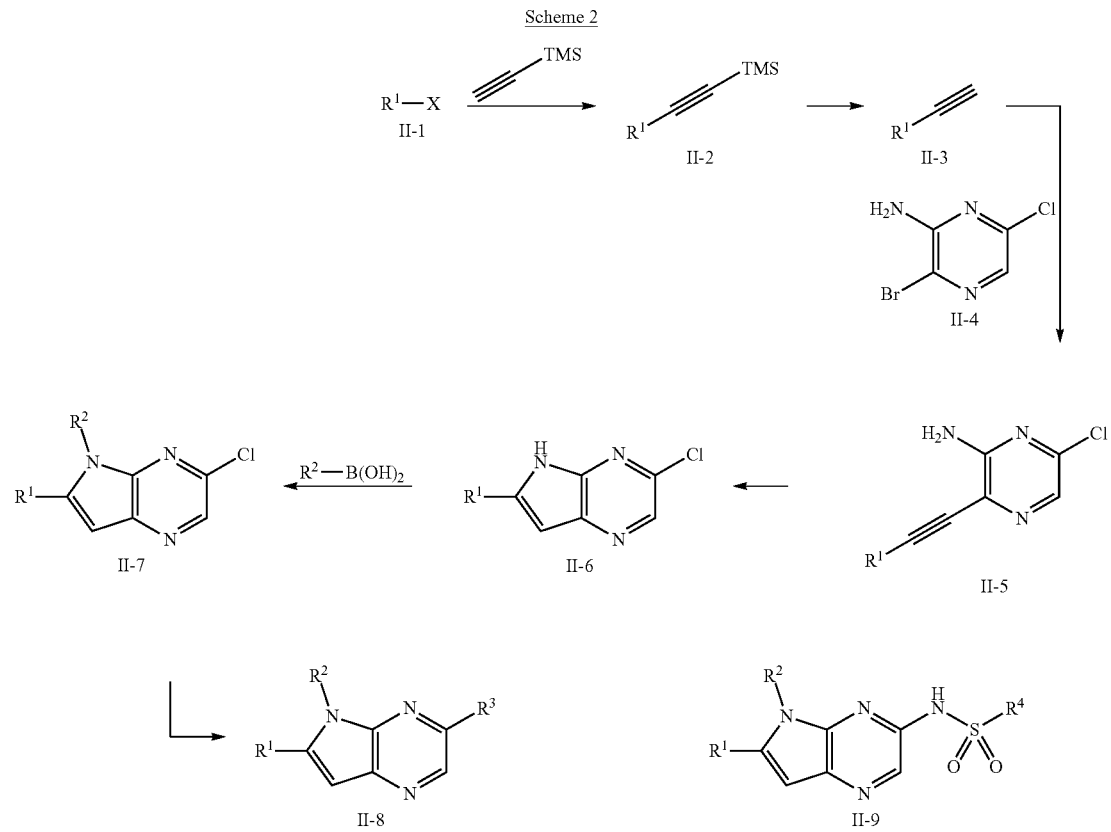

Referring to Scheme 2, a compound of Formula (I) (shown as compounds II-7 to II-9) in Scheme 2 may be prepared from compound II-1 wherein $R^1$ is as defined elsewhere herein, and X is a halo (e.g., Br) or pseudohalo (e.g., OTf) group. II-1 can be subjected to a Sonogashira coupling or equivalent thereof with a protected acetylene (e.g., TMS-acetylene) to provide compound II-2. Subsequent removal of the alkyne protecting group can afford II-3 which can be coupled with pyrazine derivative II-4 to furnish compound II-5. Cyclization of the amino group in II-5 onto the alkynyl moiety can result in compound II-6, which can be subjected to cross-coupling with a boronic acid of the formula $R^2$—$B(OH)_2$ wherein $R^2$ is as defined elsewhere herein or a boronate ester thereof (e.g., under Chan-Lam coupling conditions) to afford compound II-7, which is a compound of Formula (I). Compound II-7 can be further functionalized provide compound II-8, also a compound of Formula (I).

As an non-limiting example for the transformation of II-7 to II-8, II-7 can be coupled with a compound of formula $H_2NS(O)_2R^4$ wherein $R^4$ is as defined elsewhere herein (e.g., under Ullmann coupling conditions) to afford compound II-9, a non-limiting example of compound II-8.

Scheme 3

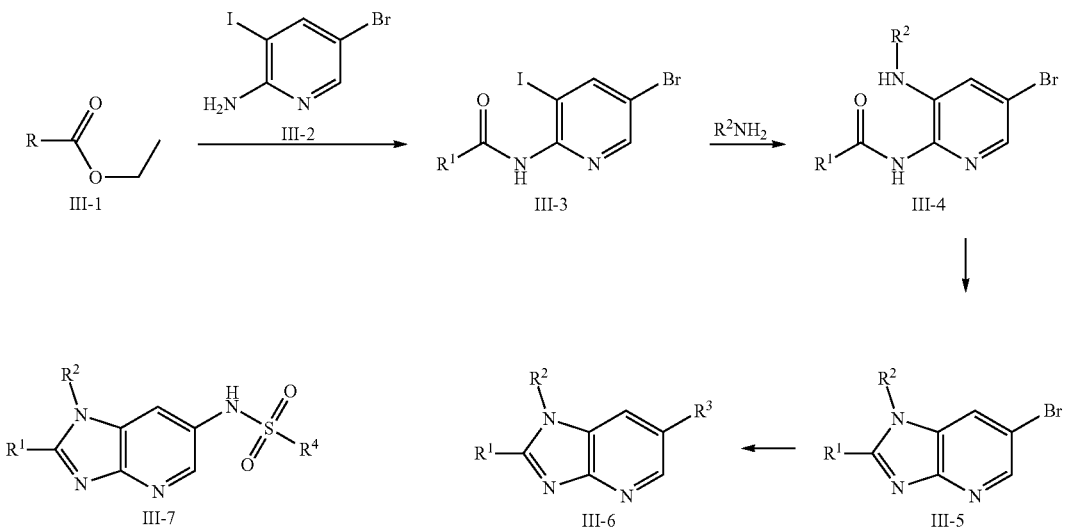

Referring to Scheme 3, a compound of Formula (I) (shown as compounds III-5 to III-7 in Scheme 3) may be prepared from compound III-1 wherein $R^1$ is as defined elsewhere herein. Coupling between III-1 and III-2 (e.g., in the presence of a Lewis acid such as $AlMe_3$) can provide compound III-3, which can be subjected to cross-coupling with a compound of formula $R^2NH_2$ wherein $R^2$ is as defined elsewhere herein to afford compound III-4. Cyclization of the amino group in III-4 onto the amide moiety (e.g., in the presence of $P(O)Cl_3$ under heat) can provide III-5, which is a compound of Formula (I). III-5 can functionalized to provide III-6, also a compound of Formula (I).

As an non-limiting example for the transformation of III-5 to III-6, II-5 can be coupled with a compound of formula $H_2NS(O)_2R^4$ wherein $R^4$ is as defined elsewhere herein (e.g., under Ullmann coupling conditions) to afford compound III-7, a non-limiting example of compound III-6.

Scheme 4

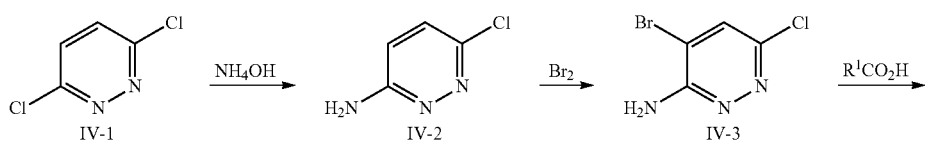

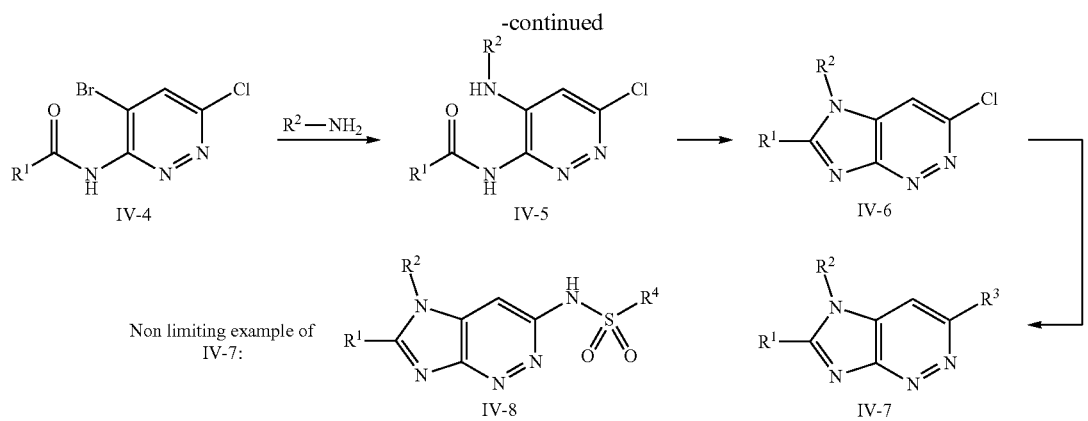

Referring to Scheme 4, a compound of Formula (I) (shown as compounds IV-6 to IV-8 in Scheme 4) may be prepared from pyridazine derivative IV-1. Sequential treatment of IV-1 with ammonium hydroxide and bromine can provide IV-3, whereupon the coupling of IV-3 and $R^1CO_2H$ (wherein $R^1$ is as defined elsewhere herein) can provide IV-4. IV-4 can be subjected to coupling with $R^2NH_2$ wherein $R^2$ is as defined elsewhere herein (e.g., under Buchwald-Hartwig coupling conditions) to provide IV-5 which can undergo cyclization (e.g., under heat and/or microwave irradiation) to afford IV-6, a compound of Formula (I). Compound IV-6 may be functionalized to provide IV-7, also a compound of Formula (I).

As an non-limiting example for the transformation of IV-6 to IV-7, IV-6 can be coupled with a compound of formula $H_2NS(O)_2R^4$ wherein $R^4$ is as defined elsewhere herein (e.g., under Ullmann coupling conditions) to afford compound IV-8, a non-limiting example of compound IV-7.

Buchwald Hartwig coupling using Xantphos and $Pd(OAc)_2$) between V-3 and amine V-4 can provide compound V-5. Condensation of the carbonyl moiety in V-5 onto the amino group can provide V-6, a compound of Formula (I).

Alternatively, V-3 may be obtained through the coupling between V-1 and an ester of V-2 (e.g., alkyl ester, e.g., methyl or ethyl ester) under appropriate conditions (e.g., in the presence of $AlMe_3$).

Optionally, the X moiety in V-6 can be converted into other $R^3$ groups to provide I-7, another compound of Formula (I). As non-limiting examples for the transformation between V-6 and V-7, V-6 can be reacted with a sulfonamide under Ullmann coupling conditions to provide compound V-8 (vide supra, Scheme 5).

General Procedures

Reactions sensitive to moisture or air were performed under nitrogen or argon using anhydrous solvents and reagents. The progress of reactions was determined by either

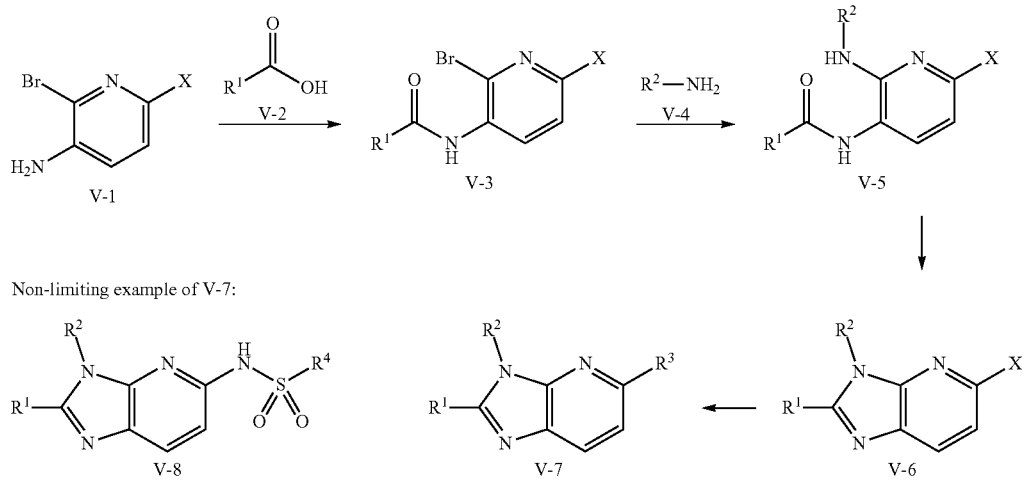

Referring to Scheme 5, a compound of Formula (I) (shown as V-6 and V-7) may be prepared from compound V-1, V-2, and V-4 wherein $R^1$ and $R^2$ are as defined herein. Aminopyrazine V-1 can be reacted with carboxylic acid V-2 to afford amide V-3 (wherein X is a halo such as bromo or chloro) under standard conditions. Then a reaction under $S_NAr$ or metal catalyzed cross-coupling conditions (e.g., analytical thin layer chromatography (TLC) usually performed with Sanpont precoated TLC plates, silica gel GF-254, layer thickness 0.25 mm or liquid chromatography-mass spectrometry (LC-MS).

Typically the analytical LC-MS system used consisted of an Agilent 6120 platform with electrospray ionization in positive ion detection mode with an Agilent 1260 series HPLC with autosampler. The column was usually an Agilent poroshell C18, 3.0×50 mm, 2.7 μm. The flow rate was 0.6 mL/min, and the injection volume was 5 μL. UV detection was in the range 190-400 nm. The mobile phase consisted of solvent A (water plus 0.1% TFA) and solvent B (acetonitrile plus 0.05% TFA) with a gradient of 90% solvent A changing to 95% solvent B over 1.7 min, maintained for 1.8 min, then reverting to 90% solvent A over 0.1 min and maintained for 1.4 mins.

Preparative HPLC purifications were usually performed Waters 2555-2767 system with a 2489 UV detector. The column was Welch C-18, 21.2×150 mm, 5 μm. The mobile phases consisted of mixtures of acetonitrile (5-95%) in water containing 0.05% TFA. Flow rates were maintained at 20 mL/min, the injection volume was 1800 μL, and the UV detector used two channels 254 nm and 280 nm. Mobile phase gradients were optimized for the individual compounds.

Reactions performed using microwave irradiation were normally carried out using an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (40-63 mM, 60 Å pore size) in pre-packed cartridges of the size noted. $^1$H NMR spectra were acquired at 400 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions.

ABBREVIATIONS

—C(O)CH$_3$ (Ac); acetic acid (AcOH); —OC(O)CH$_3$ (OAc); aqueous (aq); Cbz (benzyloxycarbonyl); N,N-diisopropylethylamine (DIEA); N;N-dimethylformamide (DMF); 1-Ethyl-3-(3-dimethylaminopropyl)carbodiimide (EDCI); ethyl acetate (EtOAc); diethyl ether (ether or Et$_2$O); petroleum ether (PE); gram(s) (g); hour(s) (h or hr); 2-propanol (IPA); mass spectrum (ms or MS); microliter(s) (μL); milligram(s) (mg); milliliter(s) (mL); millimole (mmol); minute(s) (min); methyl t-butylether (MTBE); (benzotriazol-1-yloxy)tripyrrolidino-phosphonium hexafluorophosphate (PyBOP); retention time (R$_t$); room temperature (rt or RT); saturated aq sodium chloride solution (brine); trifluoroacetic acid (TFA); tetrahydrofuran (THF); flash chromatography (FC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); dichloromethane (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC).

SYNTHETIC EXAMPLES

The following are representative procedures for the preparation of the compounds used in the following Examples, or which can be substituted for the compounds used in the following Examples which may not be commercially available.

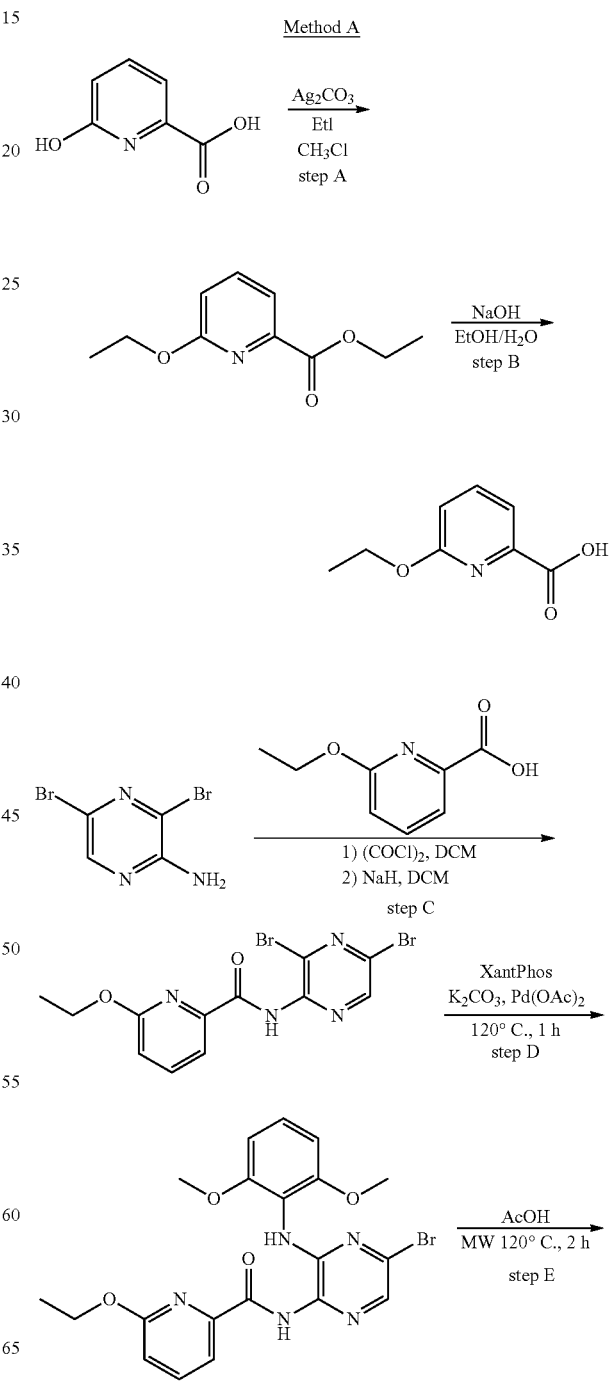

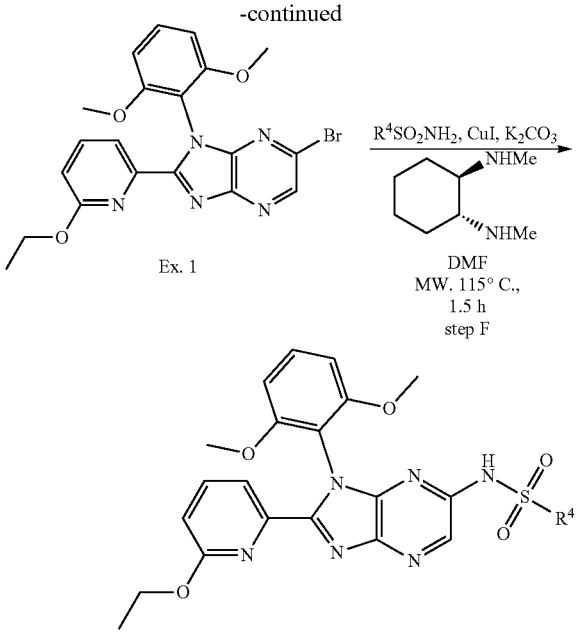

Example 1: 6-bromo-1-(2,6-dimethoxyphenyl)-2-(6-ethoxypyridin-2-yl)-1H-imidazo[4,5-b]pyrazine

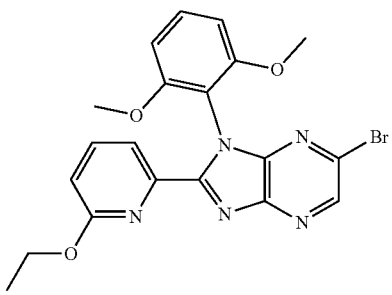 [SMILES: CCOc1cccc(-c2nc3ncc(Br)nc3n2-c2c(OC)cccc2OC)n1]

And

Example 2: N-(1-(2,6-dimethoxyphenyl)-2-(6-ethoxypyridin-2-yl)-1H-imidazo[4,5-b]pyrazin-6-yl)methanesulfonamide

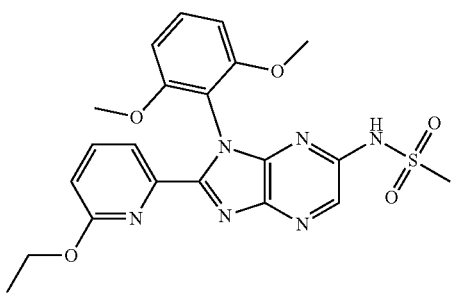 [SMILES: CCOc1cccc(-c2nc3ncc(NS(C)(=O)=O)nc3n2-c2c(OC)cccc2OC)n1]

Step A: ethyl 6-ethoxypicolinate

Ethyl iodide (112.2 g, 720 mmol, 4 equiv) was added to a suspension of 6-hydroxy-pyridine-2-carboxylic acid (25.0 g, 180 mmol, 1 equiv) and silver(I) carbonate (100 g, 360 mmol, 2 equiv) in CHCl$_3$ (400 mL). The mixture was stirred at 30° C. for 1 day. Insoluble material was removed by filtration and the solid was washed with CHCl$_3$. The filtrate was concentrated in vacuo to afford the title compound ethyl 6-ethoxypicolinate as light yellow oil which was used in the next step without further purification.

LC-MS: m/z 196.0 (M+H)$^+$

Step B: 6-ethoxypicolinic acid

To a solution of ethyl 6-ethoxypicolinate (25 g, 128 mmol, 1 equiv) in EtOH (30 mL) was added sodium hydroxide solution (1 mol/L, 384 mL, 384 mmol, 3 equiv). The reaction mixture was stirred at room temperature for 3 hours. The reaction mixture was neutralized with 1 N HCl (aq.) solution and extracted with ethyl acetate. The extract was washed with brine, dried over MgSO$_4$ and concentrated in vacuo to afford the title compound 6-ethoxypicolinic acid.

LC-MS: m/z 168.0 (M+H)$^+$

Step C: N-(3,5-dibromopyrazine-2-yl)-6-ethoxypicolinamide

A solution of 6-ethoxypicolinic acid (10 g, 59.9 mmol, 1 equiv) in DCM (100 mL) was added oxalyl chloride (11.4 g, 89.8 mmol, 1.5 equiv) and DMF (1 mL) dropwise at 0° C. The resulted mixture was stirred at room temperature for 1 hour. The reaction solution was concentrated to afford the crude 6-ethoxypicolinic chloride as a light yellow solid. A suspension of 3,5-dibromopyrazin-2-amine (14.4 g, 56.9 mmol, 0.95 equiv) and NaH (6.8 g, 170.7 mmol, 2.85 equiv) in DMF (100 mL) was stirred at room temperature for 1 hour. Then the crude 6-ethoxypicolinic chloride in DMF (100 mL) was added dropwise over a period of 30 min. After the addition, the mixture was stirred at room temperature overnight. The mixture was quenched with saturated NH$_4$Cl (aq.) (100 mL) and extracted with DCM (3*150 mL). The extract was washed with brine (100 mL), dried over anhydrous Na$_2$SO$_4$ and concentrated in vacuo. The residue was recrystalized in DCM to afford the compound N-(3,5-dibromopyrazin-2-yl)-6-ethoxypicolinamide.

LC-MS: m/z 400.9, 402.9, 404.9 (M+H)$^+$

Step D: N-(5-bromo-3-((2,6-dimethoxyphenyl)amino)pyrazin-2-yl)-6-ethoxypicolinamide A suspension of N-(3,5-dibromopyrazin-2-yl)-6-ethoxypicolinamide (1.0 g, 2.5 mmol, 1 equiv), 2,6-dimethoxyaniline (380 mg, 2.5 mmol, 1 equiv), Pd(OAc)$_2$ (112 mg, 0.5 mmol, 0.2 equiv), Xantphos (576 mg, 1.0 mmol, 0.4 equiv) and K$_2$CO$_3$ (680 mg, 3.0 mmol, 2 equiv) in 1,4-dioxane (10 mL) was stirred at 120° C. via microwave irradiation for 2 hours under N$_2$ atmosphere. The mixture was diluted with DCM (20 mL) and filtered through celite. The filtrate was concentrated in vacuo and the residue was purified by flash chromatography (PE/EtOAc=4/1) to afford the title compound N-(5-bromo-3-((2,6-dimethoxyphenyl)amino)pyrazin-2-yl)-6-ethoxypicolinamide.

LC-MS: m/z 474.0, 476.0 (M+H)$^+$

Step E: 6-bromo-1-(2,6-dimethoxyphenyl)-2-(6-ethoxypyridin-2-yl)-1H-imidazo[4,5-b]pyrazine (Example 1)

A solution of N-(5-bromo-3-((2,6-dimethoxyphenyl)amino)pyrazin-2-yl)-6-ethoxypicolinamide (1.0 g, 2.1 mmol, 1 equiv) in AcOH (10 mL) was stirred at 120° C. via microwave irradiation for 2 hours. The mixture was cooled to room temperature. The precipitate was filtered off and washed with a mixture of EtOAc/PE=1/2 (3*1 mL) to afford the title compound as a white solid.

¹H NMR (400 MHz, DMSO-d₆) δ: 8.75 (s, 1H), 8.04 (dd, J=7.4, 0.8 Hz, 1H), 7.89 (dd, J=8.4, 7.4 Hz, 1H), 7.50 (t, J=8.4 Hz, 1H), 6.89 (d, J=8.4 Hz, 3H), 3.60 (s, 6H), 3.40 (q, J=7.0 Hz, 2H), 1.05 (t, J=7.0 Hz, 3H).

LC-MS: m/z 456.1, 458.1 (M+H)⁺

Step F: N-(1-(2,6-dimethoxyphenyl-2-(6-ethoxy-pyridin-2-yl)-1H-imidazo[4,5-b]pyrazin-6-yl)methanesulfonamide (Example 2)

A suspension of 6-bromo-1-(2,6-dimethoxyphenyl)-2-(6-ethoxypyridin-2-yl)-1H-imidazo[4,5-b]pyrazine (150 mg, 0.33 mmol), methanesulfonamide (62 mg, 0.66 mmol, 2 equiv), CuI (125 mg, 0.66 mmol, 2 equiv), trans-N,N'-Dimethylcyclohexane-1,2-diamine (94 mg, 0.66 mmol, 2 equiv) and K₂CO₃ (137 mg, 0.99 mmol, 3 equiv) in DMF (5 mL) was stirred at 115° C. via microwave irradiation for 1.5 hour under N₂ atmosphere. The reaction was washed with water (150 mL), followed by extraction with EtOAc (3*100 mL). The combined organic layer was dried over anhydrous Na₂SO₄ and concentrated in vacuo. The residue was purified by flash chromatography (eluting with PE/EtOAc=20/1~5/1) to obtain the title compound as a yellow solid.

¹H NMR (400 MHz, DMSO-d₆) δ: 11.05 (s, 1H), 8.27 (s, 1H), 7.95 (dd, J=7.4 Hz, J=0.8 Hz, 1H), 7.86 (t, J=7.8 Hz, 1H), 7.45 (t, J=8.4 Hz, 1H), 6.81-6.87 (m, 3H), 3.57 (s, 6H), 3.39 (q, J=7.0 Hz, 2H), 3.20 (s, 3H), 1.03 (t, J=7.0 Hz, 3H). LC-MS: m/z 471.0 (M+H)⁺

Example 3: N-(1-(2,6-dimethoxyphenyl)-2-(6-ethoxypyridin-2-yl)-1H-imidazo[4,5-b]pyrazin-6-yl)-1-phenylethanesulfonamide

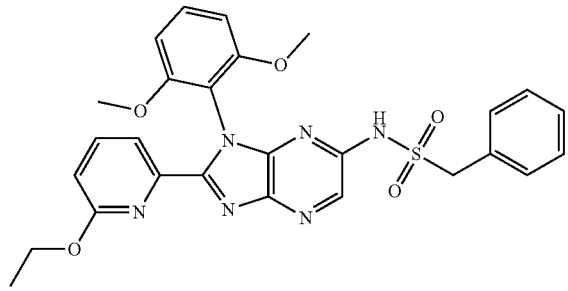 [SMILES: CCOc1cccc(-c2nc3ncc(NS(=O)(=O)Cc4ccccc4)nc3n2-c2c(OC)cccc2OC)n1]

The title compound was prepared according to general procedure A, step F, starting from Example 1 by using benzylsulfonamide.

¹H NMR (400 MHz, DMSO-d₆) δ: 11.04 (s, 1H), 8.14 (s, 1H), 7.97 (dd, J=7.4 Hz, 0.8 Hz, 1H), 7.87 (t, J=7.8 Hz, 1H), 7.49 (t, J=8.4 Hz, 1H), 7.31-7.33 (m, 3H), 7.12-7.14 (m, 2H), 6.83-6.90 (m, 3H), 4.68 (s, 2H), 3.58 (s, 6H), 3.41 (q, J=7.0 Hz, 2H), 1.03 (t, J=7.0 Hz, 3H). LC-MS: m/z 547.0 (M+H)⁺

Example 4: 1-cyclopropyl-N-(1-(2,6-dimethoxyphenyl)-2-(6-ethoxypyridin-2-yl)-1H-imidazo[4,5-b]pyrazin-6-yl)methanesulfonamide

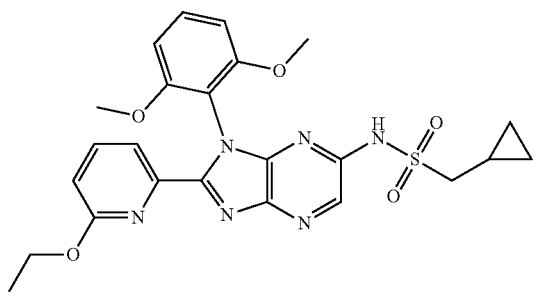 [SMILES: CCOc1cccc(-c2nc3ncc(NS(=O)(=O)CC4CC4)nc3n2-c2c(OC)cccc2OC)n1]

The title compound was prepared according to general procedure A, step F, starting from Example 1 by using 1-cyclopropylmethanesulfonamide.

¹H NMR (400 MHz, DMSO-d₆) δ: 11.03 (s, 1H), 8.30 (s, 1H), 7.94 (dd, J=7.4 Hz, 0.8 Hz, 1H), 7.85 (t, J=7.8 Hz, 1H), 7.45 (t, J=8.4 Hz, 1H), 6.81-6.87 (m, 3H), 3.57 (s, 6H), 3.39 (q, J=7.0 Hz, 2H), 3.27 (d, J=3.4 Hz, 2H), 1.02 (t, J=7.0 Hz, 3H), 0.47 (d, J=4.0 Hz, 3H), 0.13 (d, J=2.2 Hz, 2H). LC-MS: m/z 511.0 (M+H)⁺

Example 5: N-(1-(2,6-dimethoxyphenyl)-2-(6-ethoxypyridin-2-yl)-1H-imidazo[4,5-b]pyrazin-6-yl)benzenesulfonamide

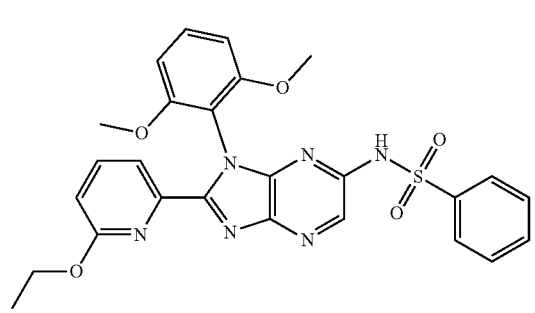 [SMILES: CCOc1cccc(-c2nc3ncc(NS(=O)(=O)c4ccccc4)nc3n2-c2c(OC)cccc2OC)n1]

The title compound was prepared according to general procedure A, step F, starting from Example 1 by using benzenesulfonamide.

¹H NMR (400 MHz, DMSO-d₆) δ: 11.53 (s, 1H), 8.24 (s, 1H), 7.93 (dd, J=7.4 Hz, 0.8 Hz, 1H), 7.83 (t, J=7.8 Hz, 1H), 7.66 (dd, J=8.4 Hz, 0.8 Hz, 2H), 7.55 (t, J=8.4 Hz, 2H), 7.38 (t, J=7.8 Hz, 2H), 6.93 (d, J=4.4 Hz, 2H), 6.81 (d, J=4 Hz 1H), 3.54 (s, 6H), 3.38 (q, J=7.0 Hz, 2H), 1.03 (t, J=7.0 Hz, 3H). LC-MS: m/z 533.0 (M+H)⁺

Example 6: 1-(2,6-dimethoxyphenyl)-2-(6-ethoxypyridin-2-yl)-6-(phenylethynyl)-1H-imidazo[4,5-b]pyrazine

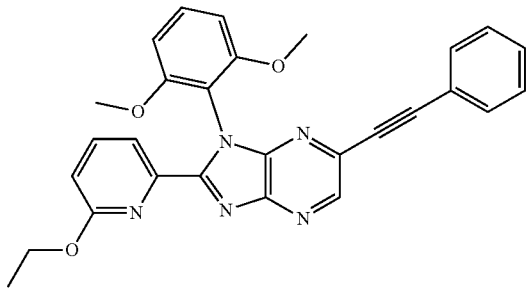 [SMILES: CCOc1cccc(-c2nc3ncc(C#Cc4ccccc4)nc3n2-c2c(OC)cccc2OC)n1]

And

Example 7: 1-(2,6-dimethoxyphenyl)-2-(6-ethoxypyridin-2-yl)-6-phenethyl-1H-imidazo[4,5-b]pyrazine

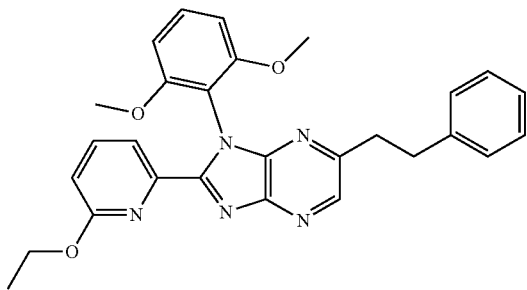 [SMILES: CCOc1cccc(-c2nc3ncc(CCc4ccccc4)nc3n2-c2c(OC)cccc2OC)n1]

Step A: 1-(2,6-dimethoxyphenyl)-2-(6-ethoxypyridin-2-yl)-6-(phenylethynyl)-1H-imidazo[4,5-b]pyrazine (Example 6)

A suspension of 6-bromo-1-(2,6-dimethoxyphenyl)-2-(6-ethoxypyridin-2-yl)-1H-imidazo[4,5-b]pyrazine (Example 1, 100 mg, 0.22 mmol, 1 equiv), ethynylbenzene (44.5 mg, 0.44 mmol, 2 equiv), Pd(PPh$_3$)$_2$Cl$_2$ (15.3 mg, 0.022 mmol, 0.1 equiv), CuI (8.3 mg, 0.044 mmol, 0.2 equiv) and Et$_3$N (66 mg, 0.66 mmol, 3.0 equiv) in DMF (5 mL) was bubbled with N$_2$ for 1 min followed by stirred at 80° C. for 4 hours. The reaction mixture was diluted with water (50 mL) and extracted with ethyl ether (3*100 mL). The combined organic phase was washed with brine (30 mL), dried over anhydrous Na$_2$SO$_4$, filtered and concentrated. The residue was purified by flash chromatography on silica gel (PE/EtOAc=1/1) to afford the title compound.

$^1$H NMR (400 MHz, DMSO-d$_6$) δ: 8.85 (s, 1H), 8.07 (d, J=7.0 Hz, 1H), 7.87-7.93 (m, 1H), 7.64-7.68 (m, 2H), 7.49-7.53 (m, 1H), 7.43-7.49 (m, 3H), 6.90 (dd, J=8.4, 1.6 Hz, 3H), 3.61 (s, 6H), 3.41 (q, J=7.0 Hz, 2H), 1.06 (t, J=7.0 Hz, 3H). LC-MS: m/z 478.2 (M+H)$^+$

Step B: 1-(2,6-dimethoxyphenyl)-2-(6-ethoxypyridin-2-yl)-6-phenethyl-1H-imidazo[4,5-b]pyrazine (Example 7)

A mixture of 1-(2,6-dimethoxyphenyl)-2-(6-ethoxypyridin-2-yl)-6-(phenylethynyl)-1H-imidazo[4,5-b]pyrazine (70 mg, 0.157 mmol) and 10% Pd/C (7 mg) in EtOAc (10 mL) was stirred under H$_2$ at room temperature overnight. The reaction mixture was filtered through celite and the filtrate was concentrated in vacuo. The residue was purified by flash chromatography on silica gel (PE/EtOAc=1/1) to afford the title compound.

$^1$H NMR (400 MHz, DMSO-d$_6$) δ: 8.40 (s, 1H), 7.98 (d, J=7.4 Hz, 1H), 7.86 (t, J=7.8 Hz, 1H), 7.47 (t, J=8.4 Hz, 1H), 7.19-7.26 (m, 2H), 7.09-7.18 (m, 3H), 6.86 (dd, J=17.4, 8.4 Hz, 3H), 3.59 (s, 6H), 3.41 (q, J=7.0 Hz, 2H), 3.13 (dd, J=8.4, 6.8 Hz, 2H), 2.96 (t, J=7.6 Hz, 2H), 1.05 (t, J=7.0 Hz, 3H).

LC-MS: m/z 482.2 (M+H)$^+$

Example 8: N-Benzyl-1-(2,6-dimethoxyphenyl)-2-(6-ethoxypyridin-2-yl)-1H-imidazo[4,5-b]pyrazine-6-carboxamide

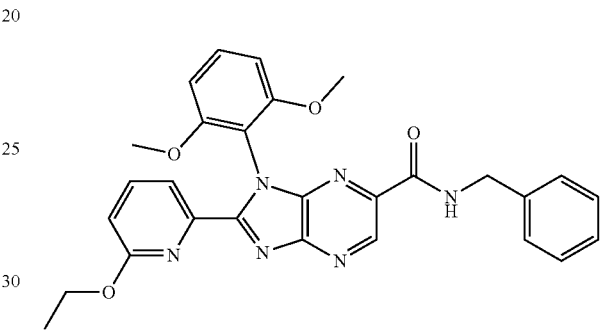

Step A: Methyl 1-(2,6-dimethoxyphenyl)-2-(6-ethoxypyridin-2-yl)-1H-imidazo[4,5-b]pyrazine-6-carboxylate 6-Bromo-1-(2,6-dimethoxyphenyl)-2-(6-ethoxypyridin-2-yl)-1H-imidazo[4,5-b]pyrazine (105 mg, 0.23 mmol, 1 equiv) was dissolved in MeOH. Then Pd(dppf)Cl$_2$ (33 mg, 0.046 mmol, 0.2 equiv) and triethylamine (70 mg, 0.69 mmol, 3 equiv) were added. The suspension was degassed and purged with CO three times. Then the reaction mixture was stirred at 90° C. under 3 MPa overnight. The reaction mixture was filtered, concentrated and purified via column chromatography (silica gel, eluting with 25% EtOAc in PE) to afford the title compound methyl 1-(2,6-dimethoxyphenyl)-2-(6-ethoxypyridin-2-yl)-1H-imidazo[4,5-b]pyrazine-6-carboxylate.

LC-MS: m/z 436.1 (M+H)$^+$

Step B: N-Benzyl-1-(2,6-dimethoxyphenyl)-2-(6-ethoxypyridin-2-yl)-1H-imidazo[4,5-b]pyrazine-6-carboxamide (Example 8)

Methyl 1-(2,6-dimethoxyphenyl)-2-(6-ethoxypyridin-2-yl)-1H-imidazo[4,5-b]pyrazine-6-carboxylate (32.4 mg, 0.074 mmol, 1 equiv) and benzylamine (15 mg, 0.148 mmol, 2 equiv) were charged into sealed tube and the mixture was heated at 90° C. for 2 h. Then the reaction mixture was purified via column chromatography (silica gel, eluting with 25% EtOAc in PE) to afford the title compound.

$^1$H NMR (400 MHz, DMSO-d$_6$) δ: 9.21 (s, 1H), 8.85 (t, J=6.4 Hz, 1H), 8.04 (d, J=6.8 Hz, 1H), 7.90 (t, J=7.2 Hz, 1H), 7.46 (t, J=8.4 Hz, 1H), 7.23-7.30 (m, 5H), 6.88 (t, J=8.4

Hz, 3H), 4.50 (d, J=6.4 Hz, 2H), 3.59 (s, 6H), 3.41 (q, J=7.0 Hz, 2H), 1.05 (t, J=7.0 Hz, 3H). LC-MS: m/z 511.2 (M+H)+

Example 9: 1-(2,6-dimethoxyphenyl)-2-(6-ethoxypyridin-2-yl)-N-methyl-1H-imidazo[4,5-b]pyrazin-6-amine

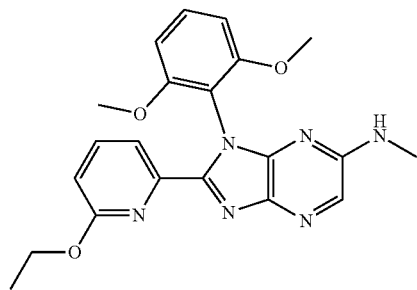 [SMILES: CCOc1cccc(-c2nc3ncc(NC)nc3n2-c2c(OC)cccc2OC)n1]

A mixture of 6-bromo-1-(2,6-dimethoxyphenyl)-2-(6-ethoxypyridin-2-yl)-1H-imidazo[4,5-b]pyrazine (Example 1, 60 mg, 0.1 mmol, equiv), and CH$_3$NH$_2$ (aq., 40 wt %, 5 mL) was stirred at 120° C. via microwave irradiation for 2 hours. The reaction mixture was concentrated and residue was purified by flash chromatography on silica gel (PE/EtOAc=1/2) to afford the title compound.

$^1$H NMR (400 MHz, DMSO-d$_6$) δ: 7.84 (s, 1H), 7.82 (dd, J=7.4, 1.0 Hz, 1H), 7.73-7.79 (m, 1H), 7.40 (t, J=8.4 Hz, 1H), 7.19 (q, J=4.8 Hz, 1H), 6.83 (d, J=8.4 Hz, 2H), 6.69 (dd, J=8.0, 1.0 Hz, 1H), 3.58 (s, 6H), 3.37 (q, J=7.0 Hz, 2H), 2.70 (d, J=4.8 Hz, 3H), 1.02 (t, J=7.0 Hz, 3H). LC-MS: m/z 407.2 (M+H)+

Method B

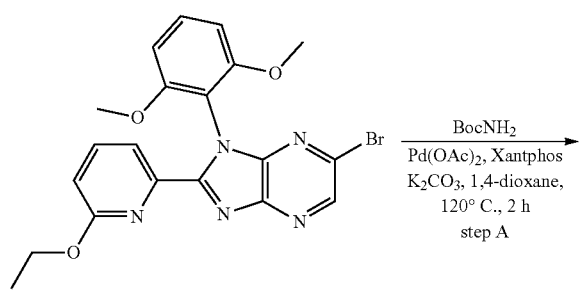

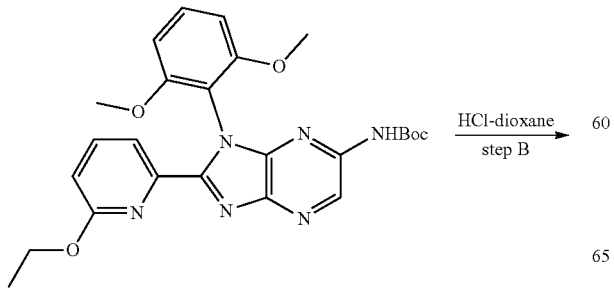

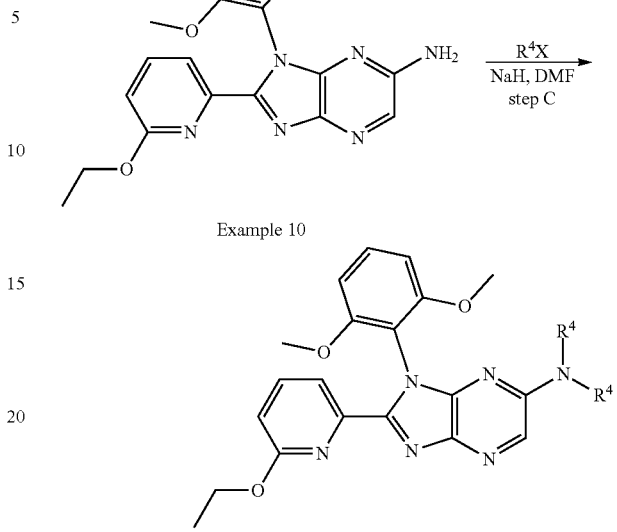

Step A: tert-butyl (1-(2,6-dimethoxyphenyl)-2-(6-ethoxypyridin-2-yl)-1H-imidazo[4,5-b]pyrazin-6-yl)carbamate A suspension of 6-bromo-1-(2,6-dimethoxyphenyl)-2-(6-ethoxypyridin-2-yl)-1H-imidazo[4,5-b]pyrazine (500 mg, 1.09 mmol, 1 equiv), BocNH$_2$ (255 mg, 2.18 mmol, 2 equiv), Pd(OAc)$_2$ (49 mg, 0.22 mmol, 0.2 equiv), Xantphos (252 mg, 0.44 mmol, 0.4 equiv) and Cs$_2$CO$_3$ (711 mg, 2.18 mmol, 2 equiv) in 1,4-dioxane (10 mL) was stirred at 120° C. via microwave irradiation for 2 hours under N$_2$ atmosphere. The mixture was filtered through celite and the filtrate was concentrated in vacuo. The residue was purified by flash chromatography (PE/EtOAc=2/1) to afford the title compound tert-butyl (1-(2,6-dimethoxyphenyl)-2-(6-ethoxypyridin-2-yl)-1H-imidazo[4,5-b]pyrazin-6-yl)carbamate.

LC-MS: m/z 493.2 (M+H)+

Step B: 1-(2,6-dimethoxyphenyl)-2-(6-ethoxypyridin-2-yl)-1H-imidazo[4,5-b]pyrazin-6-amine (Example 10)

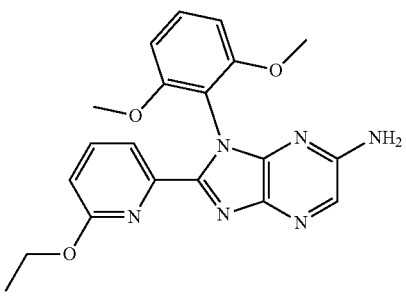 [SMILES: CCOc1cccc(-c2nc3ncc(N)nc3n2-c2c(OC)cccc2OC)n1]

A mixture of tert-butyl (1-(2,6-dimethoxyphenyl)-2-(6-ethoxypyridin-2-yl)-1H-imidazo[4,5-b]pyrazin-6-yl)carbamate (350 mg, 0.71 mmol, 1 equiv) and HCl in dioxane (4 mol/L, 20 mL) at 0° C. The mixture was then stirred at room temperature for 4 hours. The reaction mixture was concentrated and residue was purified by flash chromatography on silica gel (100% EtOAc) to afford Example 10.

¹H NMR (400 MHz, DMSO-d$_6$) δ: 7.83-7.89 (m, 2H), 7.79 (t, J=7.8 Hz, 1H), 7.41 (t, J=8.4 Hz, 1H), 6.83 (d, J=8.4 Hz, 2H), 6.72 (d, J=8.0 Hz, 1H), 6.64 (s, 2H), 3.60 (s, 6H), 3.42 (q, J=7.0 Hz, 2H), 1.04 (t, J=7.0 Hz, 3H).

LC-MS: m/z 393.2 (M+H)⁺

Example 11: N,N-dibenzyl-1-(2,6-dimethoxyphenyl)-2-(6-ethoxypyridin-2-yl)-1H-imidazo[4,5-b]pyrazin-6-amine

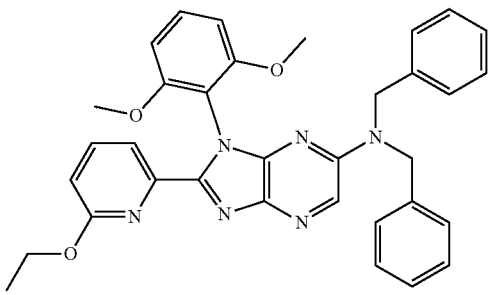 [SMILES: CCOc1cccc(-c2nc3ncc(N(Cc4ccccc4)Cc4ccccc4)nc3n2-c2c(OC)cccc2OC)n1]

A mixture of compound Example 10 (50 mg, 0.13 mmol, 1 equiv) and NaH (10.2 mg, 0.26 mmol, 2 equiv) in DMF (5 mL) was stirred at 0° C. for 30 minutes. Bromomethylbenzene (24 mg, 0.14 mmol, 1.1 equiv) was added and the mixture was stirred at room temperature overnight. The reaction mixture was diluted with water (30 mL) and extracted with ethyl ether (3*50 mL). The combined organic phase was washed with brine (30 mL), dried over anhydrous Na$_2$SO$_4$, filtered and concentrated in vacuo. The residue was purified by flash chromatography on silica gel (PE/EtOAc=1/1) to afford the title compound.

¹H NMR (400 MHz, DMSO-d$_6$) δ: 7.90 (s, 1H), 7.85 (dd, J=7.4, 0.8 Hz, 1H), 7.78 (t, J=7.8 Hz, 1H), 7.43 (t, J=8.4 Hz, 1H), 7.18-7.32 (m, 10H), 6.85 (d, J=8.4 Hz, 2H), 6.73 (dd, J=8.0, 0.8 Hz, 1H), 4.77 (s, 4H), 3.55 (s, 6H), 3.37 (q, J=7.0 Hz, 2H), 1.01 (t, J=7.0 Hz, 3H). LC-MS: m/z 573.2 (M+H)⁺

Example 12: 1-(2,6-dimethoxyphenyl)-2-(6-ethoxypyridin-2-yl)-N,N-dimethyl-1H-imidazo[4,5-b]pyrazin-6-amine

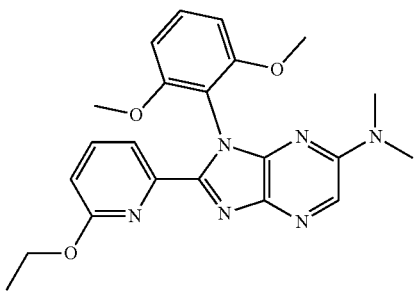 [SMILES: CCOc1cccc(-c2nc3ncc(N(C)C)nc3n2-c2c(OC)cccc2OC)n1]

A mixture of compound Example 10 (50 mg, 0.13 mmol, 1 equiv), and NaH (15.3 mg, 0.38 mmol, 3 equiv) in DMF (5 mL) was stirred at 0° C. for 30 min. iodomethane (54.3 mg, 0.38 mmol, 3 equiv) was added and the mixture was stirred at room temperature overnight. The reaction mixture was diluted with water (30 mL) and extracted with ethyl ether (3*50 mL). The combined organic phase was washed with brine (30 mL), dried over anhydrous Na$_2$SO$_4$, filtered and concentrated in vacuo. The residue was purified by flash chromatography on silica gel (PE/EtOAc=3/7) to afford the desired product.

¹H NMR (400 MHz, DMSO-d$_6$) δ: 8.08 (s, 1H), 7.84 (dd, J=7.4, 1.0 Hz, 1H), 7.75-7.82 (m, 1H), 7.40 (t, J=8.4 Hz, 1H), 6.83 (d, J=8.4 Hz, 2H), 6.71 (dd, J=8.0, 1.0 Hz, 1H), 3.57 (s, 6H), 3.40-3.34 (m, 2H), 3.02 (s, 6H), 1.02 (t, J=7.0 Hz, 3H). LC-MS: m/z 421.2 (M+H)⁺

Example 13: N-benzyl-1-(2,6-dimethoxyphenyl)-2-(6-ethoxypyridin-2-yl)-1H-imidazo[4,5-b]pyrazin-6-amine

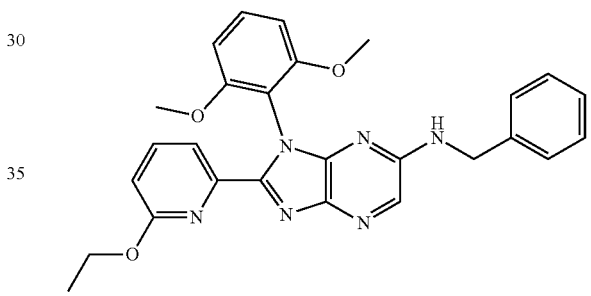

To a well-stirred red suspension of 1-(2,6-dimethoxyphenyl)-2-(6-ethoxypyridin-2-yl)-1H-imidazo[4,5-b]pyrazin-6-amine (Example 10, 60 mg, 0.15 mmol, 1 equiv) in 1,2-dichloroethane (20 mL), benzylaldehyde (65 mg, 0.61 mmol, 4 equiv) was added, and the reaction flask was immersed in an ice bath. Then AcOH (37 mg, 0.61 mmol, 4 equiv) was added followed by the addition of sodium triacetoxyborohydride (130 mg, 0.61 mmol, 4 equiv) in small portions over a 15 min period. The resulting suspension was slowly allowed to warm to 50° C. and stirred overnight. The reaction was quenched by a slow addition of saturated NaHCO$_3$ (20 mL) while stirring at 0° C. The biphasic mixture was stirred for 30 min and extracted with DCM (3*25 mL). The combined organic phase was washed with brine (30 mL), dried over anhydrous Na$_2$SO$_4$, filtered and concentrated in vacuo. The residue was purified by flash chromatography on silica gel (PE/EtOAc=1/1) to afford the desired product.

¹H NMR (400 MHz, DMSO-d$_6$) δ: 7.88 (s, 1H), 7.74-7.84 (m, 3H), 7.42 (t, J=8.4 Hz, 1H), 7.28-7.17 (m, 5H), 6.83 (d, J=8.4 Hz, 2H), 6.70 (dd, J=8.0, 1.0 Hz, 1H), 4.30 (d, J=6.0 Hz, 2H), 3.54 (s, 6H), 3.34-3.40 (m, 2H), 1.01 (t, J=7.0 Hz, 3H). LC-MS: m/z 483.2 (M+H)⁺

Example 14: N-(1-(2,6-dimethoxyphenyl)-2-(6-ethoxypyridin-2-yl)-1H-imidazo[4,5-b]pyrazin-6-yl)-2-phenylacetamide

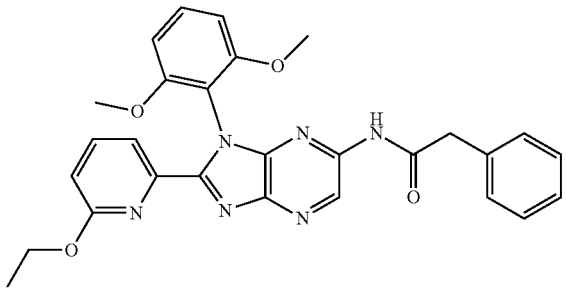 [SMILES: CCOc1cccc(-c2nc3ncc(NC(=O)Cc4ccccc4)nc3n2-c2c(OC)cccc2OC)n1]

A mixture of 1-(2,6-dimethoxyphenyl)-2-(6-ethoxypyridin-2-yl)-1H-imidazo[4,5-b]pyrazin-6-amine (Example 10, 50 mg, 0.13 mmol, 1 equiv), and NaH (15.3 mg, 0.38 mmol, 3 equiv) in DMF (5 mL) was stirred at 0° C. for 30 min. 2-Phenylacetyl chloride (21 mg, 0.13 mmol, 1 equiv) was added and the mixture was stirred at room temperature overnight. The reaction mixture was diluted with water (30 mL) and extracted with ethyl ether (3*50 mL). The combined organic phase was washed with brine (30 mL), dried over anhydrous $Na_2SO_4$, filtered and concentrated in vacuo. The residue was purified by flash chromatography on silica gel (PE/EtOAc=3/7) to afford the desired product.
$^1$H NMR (400 MHz, DMSO-$d_6$) δ: 11.11 (s, 1H), 9.33 (s, 1H), 7.99 (d, J=7.4 Hz, 1H), 7.85 (t, J=7.8 Hz, 1H), 7.46 (t, J=8.4 Hz, 1H), 7.18-7.37 (m, 6H), 6.86 (d, J=8.4 Hz, 2H), 3.74 (s, 2H), 3.60 (s, 6H), 3.39 (q, J=7.0 Hz, 2H), 1.05 (t, J=7.0 Hz, 3H). LC-MS: m/z 511.2 (M+H)$^+$

Example 15: 5-chloro-1-(2,6-dimethoxyphenyl)-2-(6-ethoxypyridin-2-yl)-1H-imidazo[4,5-b]pyrazine

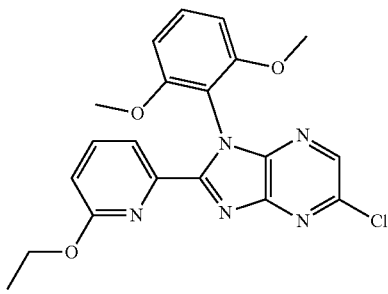 [SMILES: CCOc1cccc(-c2nc3nc(Cl)cnc3n2-c2c(OC)cccc2OC)n1]

And

Example 16: 1-(2,6-dimethoxyphenyl)-2-(6-ethoxypyridin-2-yl)-1H-imidazo[4,5-b]pyrazin-5-amine

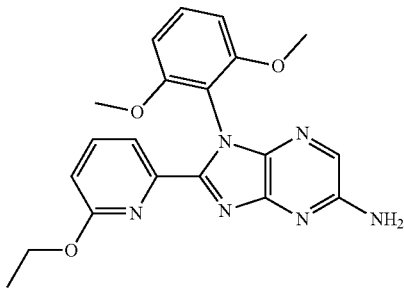 [SMILES: CCOc1cccc(-c2nc3nc(N)cnc3n2-c2c(OC)cccc2OC)n1]

Step A: N-(3-bromo-6-chloropyrazin-2-yl)-6-ethoxypicolinamide

The mixture of ethyl 6-ethoxypicolinate (500 mg, 2.56 mmol, 1 equiv) and 3-bromo-6-chloropyrazin-2-amine (530 mg, 2.56 mmol, 1 equiv) in toluene was cooled to 0° C. and $AlMe_3$ was added dropwise. Then the mixture was stirred at 100° C. for 16 hours. The mixture was quenched with $NH_4Cl$ solution and extracted with EtOAc (3*20 mL). The combined organic layer was dried over anhydrous $Na_2SO_4$ and concentrated in vacuo. The residue was purified by flash chromatography on silica gel (PE/EtOAc=10/1) to afford the title compound N-(3-bromo-6-chloropyrazin-2-yl)-6-ethoxypicolinamide.
$^1$H NMR (400 MHz, DMSO-$d_6$) δ: 10.94 (s, 1H), 8.50 (s, 1H), 7.99 (d, J=7.6 Hz, 1H), 7.68-7.82 (m, 1H), 7.07-7.27 (m, 1H), 4.52 (d, J=7.0 Hz, 2H), 1.40 (t, J=7.0 Hz, 3H). LC-MS: m/z 357.7 (M+H)$^+$

Step B: N-(6-chloro-3-((2,6-dimethoxyphenyl)amino)pyrazin-2-yl)-6-ethoxypicolinamide The mixture of N-(3-bromo-6-chloropyrazin-2-yl)-6-ethoxypicolinamide (500 mg, 1.4 mmol, 1 equiv), 2,6-dimethoxyaniline (430 mg, 2.8 mmol, 2 equiv), Xantphos (162 mg, 0.28 mmol, 2 equiv), $Pd_2(dba)_3$ (128 mg, 0.14 mmol, 0.1 equiv), potassium 2-methylpropan-2-olate (297 mg, 2.8 mmol, 2 equiv) in toluene (10 mL) was stirred at 110° C. for 16 hours under $N_2$ atmosphere. The mixture was filtered and concentrated in vacuo. The residue was purified by flash column chromatography on silica gel (PE/EtOAc=10/1) to afford the title compound N-(6-chloro-3-((2,6-dimethoxyphenyl)amino)pyrazin-2-yl)-6-ethoxypicolinamide.
$^1$H NMR (400 MHz, $CDCl_3$) δ: 10.11 (s, 1H), 8.40 (s, 1H), 8.02 (s, 1H), 7.92 (d, J=7.2 Hz, 1H), 7.77 (t, J=8.8 Hz, 1H), 7.13 (t, J=8.4 Hz, 1H), 6.97 (d, J=8.0 Hz, 1H), 6.65 (d, J=8.4 Hz, 2H), 4.48 (q, J=7.2 Hz, 2H), 3.82 (s, 6H), 1.46-1.52 (m, 3H). LC-MS: m/z 429.7 (M+H)$^+$

Step C: 5-chloro-1-(2,6-dimethoxyphenyl)-2-(6-ethoxypyridin-2-yl)-1H-imidazo[4,5-b]pyrazine (Example 15)

N-(6-chloro-3-((2,6-dimethoxyphenyl)amino)pyrazin-2-yl)-6-ethoxypicolinamide (280 mg, 0.56 mmol, 1 equiv) in AcOH (20 mL) was stirred at 120° C. for 1 hour under MW. The mixture was concentrated in vacuo. The residue was washed with ether, filtered and dried to afford the desired product.
$^1$H NMR (400 MHz, $CDCl_3$) δ: 8.27 (s, 1H), 8.13-8.20 (m, 1H), 7.69 (t, J=8.4 Hz, 1H), 7.39 (t, J=8.4 Hz, 1H), 6.65-6.77 (m, 3H), 3.62 (s, 6H), 3.43 (q, J=7.2 Hz, 2H), 1.09 (t, J=7.2 Hz, 3H). LC-MS: m/z 411.7 (M+H)$^+$

Step D: tert-butyl (1-(2,6-dimethoxyphenyl)-2-(6-ethoxypyridin-2-yl)-1H-imidazo[4,5-b]pyrazin-5-yl)carbamate The mixture of 5-chloro-1-(2,6-dimethoxyphenyl)-2-(6-ethoxypyridin-2-yl)-1H-imidazo[4,5-b]pyrazine (80 mg, 0.19 mmol, 1 equiv), tert-butyl carbamate (46 mg, 0.38 mmol, 2 equiv), Xantphos (22 mg, 0.038 mmol, 0.2 equiv), $Pd_2(dba)_3$ (17 mg, 0.019 mmol, 0.1 equiv), potassium 2-methylpropan-2-olate (43 mg, 0.38 mmol, 2 equiv) in toluene (5 mL) was stirred at 110° C. for 16 hours under $N_2$ atmosphere. The mixture was filtered and concentrated in vacuo. The residue was purified by flash chromatography on silica gel (PE/EtOAc=3/1) to afford the title compound tert-butyl (1-(2,6-dimethoxyphenyl)-2-(6-ethoxypyridin-2-yl)-1H-imidazo[4,5-b]pyrazin-5-yl)carbamate.

$^1$H NMR (400 MHz, CD$_3$OD) δ: 8.91 (s, 1H), 7.89-7.87 (d, J=7.2 Hz, 1H), 7.79-7.77 (t, J=7.2 Hz, 1H), 7.46-7.44 (t, J=8.4 Hz, 1H), 6.84-6.75 (m, 3H), 3.64 (s, 6H), 3.51-3.46 (m, 2H), 1.55 (s, 9H), 1.11-1.09 (t, J=7.2 Hz, 3H). LC-MS: m/z 492.7 (M+H)$^+$

Step E: 1-(2,6-dimethoxyphenyl)-2-(6-ethoxypyridin-2-yl)-1H-imidazo[4,5-b]pyrazin-5-amine (Example 16)

tert-butyl (1-(2,6-dimethoxyphenyl)-2-(6-ethoxypyridin-2-yl)-1H-imidazo[4,5-b]pyrazin-5-yl) carbamate (30 mg, 0.06 mmol, 1 equiv) in HCl/MeOH (4 mol/L, 10 mL) was stirred at room temperature for 6 hours. The mixture was concentrated in vacuo and residue was washed with ether to afford the desired product.

$^1$H NMR (400 MHz, CD$_3$OD) δ: 7.96 (s, 1H), 7.80 (t, J=8.0 Hz, 1H), 7.52-7.63 (m, 2H), 6.85-6.97 (m, 3H), 3.80 (q, J=7.2 Hz, 2H), 3.70 (s, 6H), 1.19 (t, J=7.2 Hz, 3H). LC-MS: m/z 393.3 (M+H)$^+$

Example 17: N-(1-(2,6-dimethoxyphenyl)-2-(6-ethoxypyridin-2-yl)-1H-imidazo[4,5-b]pyrazin-5-yl)-2-phenylacetamide

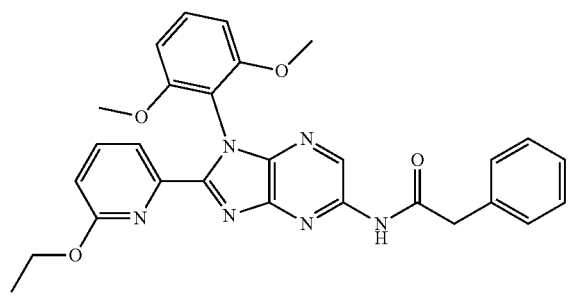 [SMILES: CCOc1cccc(-c2nc3nc(NC(=O)Cc4ccccc4)cnc3n2-c2c(OC)cccc2OC)n1]

The mixture of 5-chloro-1-(2,6-dimethoxyphenyl)-2-(6-ethoxypyridin-2-yl)-1H-imidazo[4,5-b]pyrazine (Example 15, 60 mg, 0.15 mmol, 1 equiv), 2-phenylacetamide (19.7 mg, 0.15 mmol, 1 equiv), Xantphos (17 mg, 0.03 mmol, 0.2 equiv), Pd$_2$(dba)$_3$ (13 mg, 0.015 mmol, 0.1 equiv), Cs$_2$CO$_3$ (95 mg, 0.3 mmol, 2 equiv) in dioxane (5 mL) was stirred at 110° C. for 16 hours under N$_2$ atmosphere. The mixture was filtered and concentrated in vacuo. The residue was purified by flash chromatography on silica gel (PE/EtOAc=3/1) to afford the title compound.

$^1$H NMR (400 MHz, CDCl$_3$) δ: 9.34 (s, 1H), 8.12 (d, J=7.2 Hz, 2H), 7.66 (t, J=7.2 Hz, 1H), 7.33-7.41 (m, 5H), 6.63-6.73 (m, 3H), 3.85 (s, 2H), 3.55-3.66 (m, 6H), 3.43 (q, J=7.2 Hz, 2H), 1.08 (t, J=7.2 Hz, 3H). LC-MS: m/z 511.3 (M+H)$^+$

Example 18: 1-(2,6-dimethoxyphenyl)-2-(6-ethoxypyridin-2-yl)-1H-imidazo[4,5-b]pyrazine

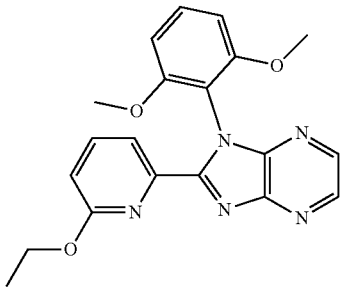 [SMILES: CCOc1cccc(-c2nc3nccnc3n2-c2c(OC)cccc2OC)n1]

Step A: ethyl 6-ethoxypicolinate

To a solution of 6-hydroxypicolinic acid (12 g, 86.33 mmol) in DCM (250 ml) was added Ag$_2$CO$_3$ (48 g, 174 mmol), followed by adding EtI (27.6 ml, 345.32 mmol) dropwise. The mixture was stirred at 25° C. for 12 hr. and filtered. The filtrate was concentrated in vacuum to give ethyl 6-ethoxypicolinate as a gray oil, which was used in the next step without further purification.

LC-MS: m/z 196.3 (M+H)$^+$

Step B: (6-ethoxypyridin-2-yl)methanol

To a solution of ethyl 6-ethoxypicolinate (5.8 g, 29.7 mmol) in THF (60 ml) was added LiAlH$_4$ (15 ml, 1M THF sol.) dropwise at 0° C. The reaction mixture was stirred at 25° C. for 3 hr and quenched with H$_2$O/EA. The collected organic layers were dried over Na$_2$SO$_4$ and concentrated in vacuum. The residue was purified by silica gel chromatograph to give (6-ethoxypyridin-2-yl)methanol.

LC-MS: m/z 154.3 (M+H)$^+$

Step C: 6-ethoxypicolinaldehyde

To a solution of (6-ethoxypyridin-2-yl)methanol (3 g, 19.61 mmol) in 1,4-dioxane (30 ml) was added MnO$_2$ (12 g, 137.25 mmol) and the reaction mixture was refluxed for 3 hr. The reaction mixture was filtered and the filtrate was concentrated in vacuum to give 6-ethoxypicolinaldehyde.

LC-MS: m/z 152.3 (M+H)$^+$

Step D: 3-chloro-N-(2,6-dimethoxyphenyl)pyrazin-2-amine

To a solution of 2,3-dichloropyrazine (0.918 g, 6 mmol) in THF (15 mL) was added KHMDS (1 N in TMF, 6 mL, 6 mmol) slowly at 0° C. and the mixture was stirred at 0° C. for 15 min, followed by adding a solution of 3-5 (0.74 g, 5 mmol) in THF (5 mL) dropwise at 0° C. The dark-green mixture was stirred at room temperature for 3 h, poured into ice-water (40 mL) and extracted with EA (10 mL*3). The combined organic layer was dried over Na$_2$SO$_4$ and concentrated in vacuum to get the residue, which was purified by column chromatography (PE:EA=97:3~66:34) to give 3-chloro-N-(2,6-dimethoxyphenyl)pyrazin-2-amine.

Step E: N-(2,6-dimethoxyphenyl)tetrazolo[1,5-a]pyrazin-8-amine

A mixture of 3-chloro-N-(2,6-dimethoxyphenyl)pyrazin-2-amine (0.14 g, 0.53 mmol) and NaN$_3$ (86 mg, 1.32 mmol)

in DMSO (3 mL) was stirred at 130° C. for 18 hr. The solution was poured into 10 mL of ice-water and extracted with EA. The organic layer was dried and evaporated to afford dark-red oil which was used to the next step without any purification.

LC-MS: m/z 273.1 (M+H)+

Step F: N-(2,6-dimethoxyphenyl)tetrazolo[1,5-a]pyrazin-8-amine

To a solution of crude N-(2,6-dimethoxyphenyl)tetrazolo[1,5-a]pyrazin-8-amine (143.7 mg, 0.53 mmol) in con.HCl aq. (3 mL) was added SnCl$_2$.H$_2$O (1.19 g, 5.3 mmol) and the mixture was stirred at 115° C. for 2 h. After cooled to room temperature, the mixture was added K$_2$CO$_3$ to adjust pH=8-9 and filtered. The filtrate was extracted by EA and the organic layer was dried over Na$_2$SO$_4$ and concentrated in vacuum to get the residue, which was purified by column chromatography (PE:EA=97:3~66:34) to afford N-(2,6-dimethoxyphenyl)tetrazolo[1,5-a]pyrazin-8-amine.

LC-MS: m/z 247.1 (M+H)+

Step G: 1-(2,6-dimethoxyphenyl)-2-(6-ethoxypyridin-2-yl)-1H-imidazo[4,5-b]pyrazine A mixture of N-(2,6-dimethoxyphenyl)tetrazolo[1,5-a]pyrazin-8-amine (70 mg, 0.285 mmol) and 6-ethoxypicolinaldehyde (43 mg, 0.285 mmol) in AcOH (1 mL) and stirred at 110° C. for 10 min under MW. The mixture was concentrated and the residue was purified by prep-HPLC to give 1-(2,6-dimethoxyphenyl)-2-(6-ethoxypyridin-2-yl)-1H-imidazo[4,5-b]pyrazine.

LC-MS: m/z 378.2 (M+H)+

Example 19: N-(5-(2,6-dimethoxyphenyl)-6-(6-ethoxypyridin-2-yl)-5H-pyrrolo[2,3-b]pyrazin-3-yl)methanesulfonamide

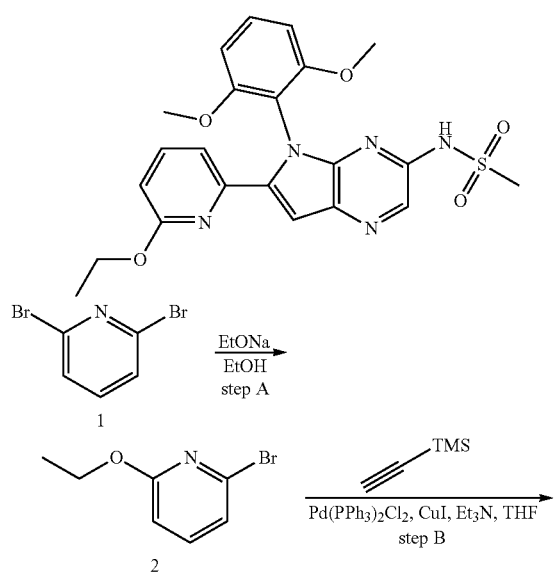

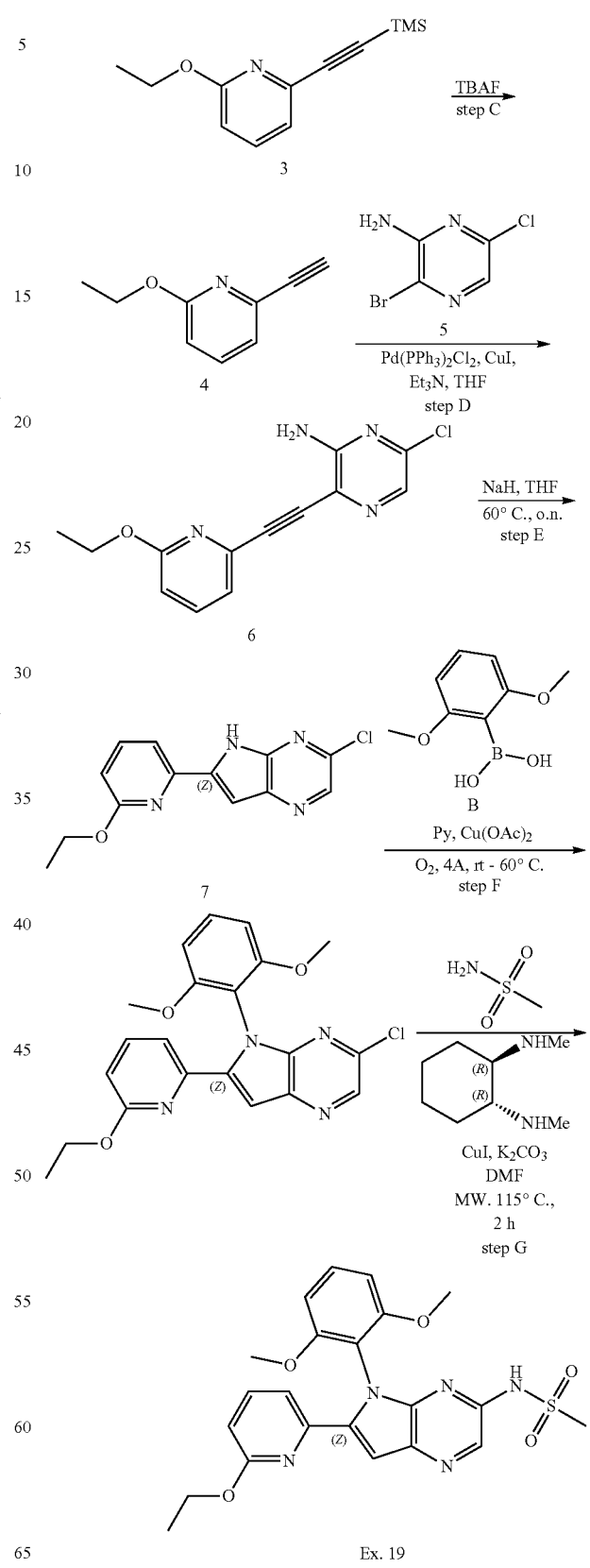

Ex. 19

Step A: 2-bromo-6-ethoxypyridine

To a solution of 2,6-dibromopyridine (20 g, 84 mmol, 1 equiv) in EtOH (200 mL) was added sodium ethanolate (22.9 g, 336 mmol, 4 equiv). The mixture was stirred at reflux temperature for 3 days. The reaction mixture was concentrated in vacuo. To the residue was added water (300 mL) and the mixture was extracted with DCM (2*300 mL). The combined organic layers was dried over $Na_2SO_4$, filtered and concentrated in vacuo. The residue was purified by silica gel chromatography (100% PE) to afford the title compound.

LC-MS: m/z 202.0, 204.0 $(M+H)^+$

Step B: 2-ethoxy-6-((trimethylsilyl)ethynyl)pyridine

A suspension of 2-bromo-6-ethoxypyridine (13.0 g, 64 mmol, 1 equiv), ethynyltrimethylsilane (10.11 g, 103 mmol, 1.6 equiv), $Pd(PPh_3)_2Cl_2$ (1.13 g, 1.6 mmol, 0.025 equiv) and CuI (610 mg, 3.2 mmol, 0.05 equiv) in $Et_3N$ (230 mL) was stirred at 85° C. for 2.5 hours under $N_2$ atmosphere. The mixture was filtered through celite. The filtrate was concentrated in vacuo and the residue was purified by flash chromatography (100% PE) to afford the title compound 6-chloro-3-((6-ethoxypyridin-2-yl)ethynyl)pyrazin-2-amine.

LC-MS: m/z 220.3 $(M+H)^+$

Step C: 2-ethoxy-6-ethynylpyridine

To a solution of 2-ethoxy-6-((trimethylsilyl)ethynyl)pyridine (11 g, 50.2 mmol, 1 equiv) in THF (100 mL) was added TBAF (50 mL, 50.2 mmol, 1 equiv). The resulted mixture was stirred at room temperature for 16 hours. The reaction solution was concentrated in vacuo and the residue was purified by flash chromatography (PE/EtOAc=100/1) to afford the title compound 2-ethoxy-6-ethynylpyridine.

LC-MS: m/z 148.1 $(M+H)^+$

Step D: 6-chloro-3-((6-ethoxypyridin-2-yl)ethynyl)pyrazin-2-amine

A suspension of 2-ethoxy-6-ethynylpyridine (2.0 g, 13.6 mmol, 1 equiv), 3-bromo-6-chloropyrazin-2-amine (2.8 g, 13.6 mmol, 1 equiv), $Pd(PPh_3)_2Cl_2$ (238 mg, 0.34 mmol, 0.03 equiv) and CuI (129 mg, 0.68 mmol, 0.06 equiv) in $Et_3N$ (80 mL) was stirred at 85° C. for 2 hours under $N_2$ atmosphere. The mixture was diluted with EtOAc (120 mL) and filtered through celite. The filtrate was concentrated in vacuo and the residue was purified by flash chromatography (PE/EtOAc=6/1) to afford the title compound 6-chloro-3-((6-ethoxypyridin-2-yl)ethynyl)pyrazin-2-amine.

LC-MS: m/z 275.1 $(M+H)^+$

Step E: 3-chloro-6-(6-ethoxypyridin-2-yl)-5H-pyrrolo[2,3-b]pyrazine

To a solution of 6-chloro-3-((6-ethoxypyridin-2-yl)ethynyl)pyrazin-2-amine (2.3 g, 8.4 mmol, 1 equiv) in THF (50 mL) was added NaH (0.5 g, 12.6 mmol, 1.5 equiv) at 0° C. The mixture was stirred at room temperature for 1 hour then heated to 60° C. for overnight. The mixture was quenched with 0.5 mL $H_2O$, then concentrated under vacuo to dry to give a residue, which was purified by flash chromatography (PE/EtOAc=5/1) to afford the title compound 3-chloro-6-(6-ethoxypyridin-2-yl)-5H-pyrrolo[2,3-b]pyrazine.

LC-MS: m/z 275.1 $(M+H)^+$

Step F: 3-chloro-5-(2,6-dimethoxyphenyl)-6-(6-ethoxypyridin-2-yl)-5H-pyrrolo[2,3-b]pyrazine A suspension of 3-chloro-6-(6-ethoxypyridin-2-yl)-5H-pyrrolo[2,3-b]pyrazine (1 g, 3.65 mmol, 1.0 equiv), (2,6-dimethoxyphenyl)boronic acid (1.3 g, 7.3 mmol, 2 equiv), $Cu(OAc)_2$ (1.3 g, 7.3 mmol, 2 equiv), dry pyridine (865 mg, 11 mmol, 3 equiv) and 4 Å molecular sieve in dry DCE (10 mL) was stirred at 25° C. for 30 hours under O2 atmosphere. The reaction was diluted with DCM (50 mL) and filtered through celite. The filtrate was concentrated in vacuo and the residue was purified by flash chromatography (PE/EtOAc=5/1) to afford the title compound 3-chloro-5-(2,6-dimethoxyphenyl)-6-(6-ethoxypyridin-2-yl)-5H-pyrrolo[2,3-b]pyrazine.

LC-MS: m/z 411.1 $(M+H)^+$

Step G: N-(5-(2,6-dimethoxyphenyl)-6-(6-ethoxypyridin-2-yl)-5H-pyrrolo[2,3-b]pyrazin-3-yl)methanesulfonamide A suspension of 3-chloro-5-(2,6-dimethoxyphenyl)-6-(6-ethoxypyridin-2-yl)-5H-pyrrolo[2,3-b]pyrazine (30 mg, 0.07 mmol, 1.0 equiv), methanesulfonamide (28 mg, 0.28 mmol, 4 equiv), trans-N,N'-Dimethylcyclohexane-1,2-diamine (22 mg, 0.14 mmol, 2 equiv), CuI (29 mg, 0.14 mmol, 2 equiv) and $K_2CO_3$ (30 mg, 0.22 mmol, 3 equiv) in DMF (2 mL) was stirred at 115° C. via microwave irradiation for 2 hours under $N_2$ atmosphere. The reaction mixture was poured into $H_2O$ (20 mL) and extracted with EtOAc (3*20 mL). The extracts were washed with water (10 mL) and brine (10 mL), dried over $MgSO_4$ and concentrated in vacuo. The residue was purified by flash chromatography (PE/EtOAc=1/1) to afford the title compound N-(5-(2,6-dimethoxyphenyl)-6-(6-ethoxypyridin-2-yl)-5H-pyrrolo[2,3-b]pyrazin-3-yl)methanesulfonamide.

$^1$H NMR (DMSO-$d_6$) δ: 8.17 (s, 1H), 7.69 (t, J=7.6 Hz, 1H), 7.36-7.40 (m, 2H), 7.31 (s, 1H), 6.78 (d, J=8.4 Hz, 2H), 6.61 (d, J=8.0 Hz, 1H), 3.53-3.55 (m, 2H), 3.52 (s, 6H), 3.12 (s, 3H), 1.08 (t, J=7.2 Hz, 3H).

LC-MS: m/z 470.0 $(M+H)^+$

Example 20: N-(1-(2,6-dimethoxyphenyl)-2-(6-ethoxypyridin-2-yl)-1H-imidazo[4,5-b]pyridin-6-yl)methanesulfonamide

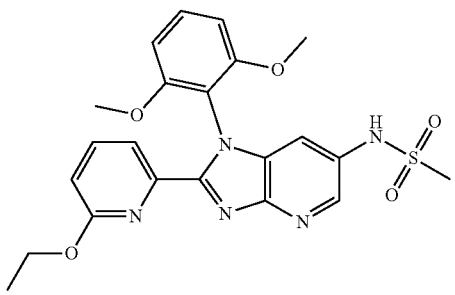

-continued

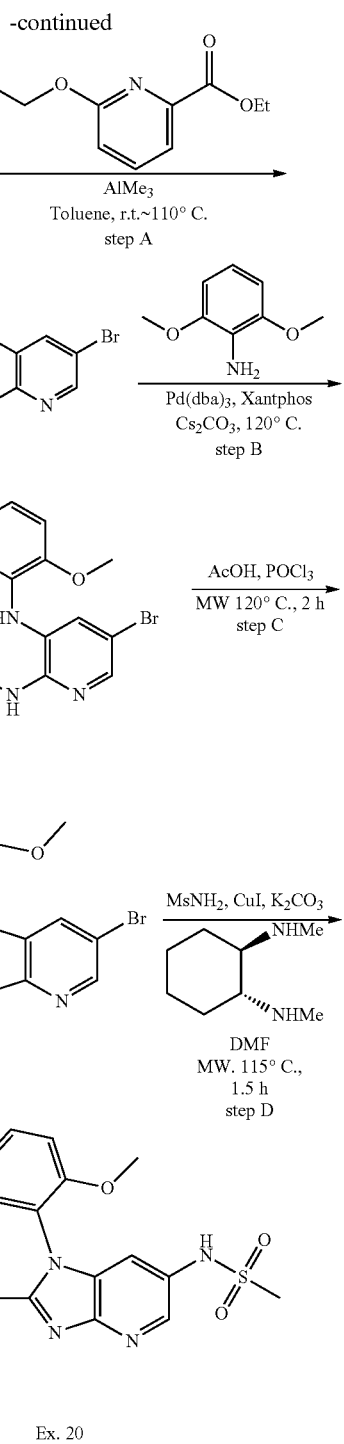

Ex. 20

Step A: N-(5-bromo-3-iodopyridin-2-yl)-6-ethoxypicolinamide

To a solution of 5-bromo-3-iodopyridin-2-amine compound (2 g, 6.7 mmol, 1.1 equiv) in toluene (50 mL) was added Al(Me)$_3$ (1.6 mol/L in toluene, 7.6 mL, 12.2 mmol, 2 equiv) drop wise at room temperature. After the mixture was stirred at 50° C. for 30 min, ethyl 6-ethoxypicolinate (1.19 g, 6.1 mmol, 1 equiv) was added and the mixture was stirred at 110° C. for 2 hours. The reaction mixture was quenched with water (50 mL), followed by extraction with EtOAc (3*50 mL). The combined organic layers was washed with brine (50 mL), dried over anhydrous Na$_2$SO$_4$ and concentrated in vacuo. The residue was purified by flash chromatography eluting with PE/EtOAc (20/1-5/1) to afford the title compound N-(5-bromo-3-iodopyridin-2-yl)-6-ethoxypicolinamide.

LC-MS: m/z 447.9, 449.9 (M+H)$^+$

Step B: N-(5-bromo-3-((2,6-dimethoxyphenyl)amino)pyridin-2-yl)-6-ethoxypicolinamide A suspension of N-(5-bromo-3-iodopyridin-2-yl)-6-ethoxypicolinamide (200 mg, 0.45 mmol, 1 equiv), 2,6-dimethoxyaniline (68 mg, 0.45 mmol, 1 equiv), Pd$_2$(dba)$_3$ (82 mg, 0.09 mmol, 0.1 equiv), Xantphos (208 mg, 0.36 mmol, 0.8 equiv) and Cs$_2$CO$_3$ (292 mg, 0.87 mmol, 2 equiv) in 1,4-dioxane (50 mL) was stirred at 120° C. via microwave irradiation for 2 hours under N$_2$ atmosphere. The mixture was diluted with water (30 mL), followed by extraction with EtOAc (3*20 mL). The combined organic layers was dried over anhydrous Na$_2$SO$_4$ and concentrated in vacuo. The residue was purified by prep-TLC (PE/EtOAc=5/1) to afford the title compound N-(5-bromo-3-((2,6-dimethoxyphenyl)amino)pyridin-2-yl)-6-ethoxypicolinamide.

LC-MS: m/z 473.0, 475.0 (M+H)$^+$

Step C: 6-bromo-1-(2,6-dimethoxyphenyl)-2-(6-ethoxypyridin-2-yl)-1H-imidazo[4,5-b]pyridine To a solution of N-(5-bromo-3-((2,6-dimethoxyphenyl)amino)pyrazin-2-yl)-6-ethoxypicolinamide (100 mg, 0.21 mmol, 1 equiv) in AcOH (10 mL) was added 1 drop of POCl$_3$. The mixture was stirred at 120° C. via microwave irradiation for 2 hours. The mixture was cooled to room temperature, evaporated and the residue was purified by prep TLC (PE/EtOAc=1/1) to afford the title compound 6-bromo-1-(2,6-dimethoxyphenyl)-2-(6-ethoxypyridin-2-yl)-1H-imidazo[4,5-b]pyridine.

LC-MS: m/z 455.0, 457.0 (M+H)$^+$

Step D: N-(1-(2,6-dimethoxyphenyl)-2-(6-ethoxypyridin-2-yl)-1H-imidazo[4,5-b]pyridin-6-yl)methanesulfonamide A suspension of 6-bromo-1-(2,6-dimethoxyphenyl)-2-(6-ethoxypyridin-2-yl)-1H-imidazo[4,5-b]pyrazine (40 mg, 0.09 mmol, 1 equiv), methanesulfonamide (17 mg, 0.18 mmol, 2 equiv), CuI (34 mg, 0.18 mmol, 2 equiv), trans-N,N'-Dimethylcyclohexane-1,2-diamine (25 mg, 0.18 mmol, 2 equiv) and K$_2$CO$_3$ (37 mg, 0.27 mmol, 3 equiv) in DMF (5 mL) was stirred at 115° C. via microwave irradiation for 1.5 hour under N$_2$ atmosphere. The reaction was diluted with water (15 mL) and extracted with EtOAc (3*50 mL). The combined organic layers was dried over anhydrous Na$_2$SO$_4$ and concentrated in vacuo. The residue was purified by prep TLC (PE/EtOAc=1/2) to obtain the title compound N-(1-(2,6-dimethoxyphenyl)-2-(6-ethoxypyridin-2-yl)-1H-imidazo[4,5-b]pyridin-6-yl)methanesulfonamide.

$^1$H NMR (DMSO-d$_6$) δ: 9.88 (br. s., 1H), 8.38 (d, J=2.4 Hz, 1H), 7.91 (dd, J=7.4 Hz, 0.8 Hz, 1H), 7.84 (t, J=7.8 Hz, 1H), 7.47 (t, J=8.4 Hz, 1H), 7.19 (d, J=2.4 Hz, 1H), 6.89 (d, J=8.5 Hz, 2H), 6.79 (dd, J=8.1, 0.9 Hz, 1H), 3.58 (s, 6H), 3.39 (q, J=7.2 Hz, 2H), 2.96 (s, 3H), 1.02 (t, J=7.2 Hz, 3H).

LC-MS: m/z 470.1 (M+H)$^+$

Example 21: N-(5-(2,6-dimethoxyphenyl)-6-(6-ethoxypyridin-2-yl)-5H-imidazo[4,5-c]pyridazin-3-yl)methanesulfonamide

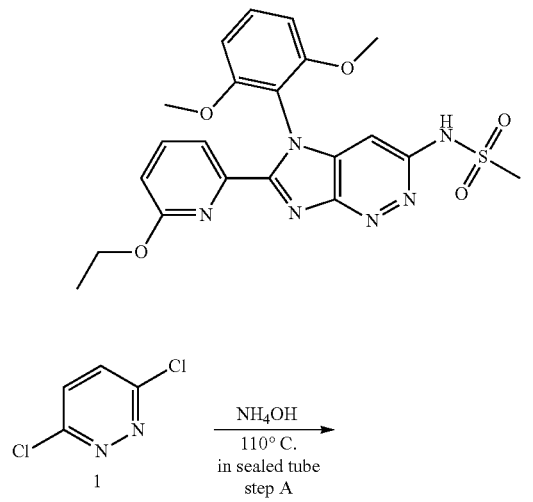

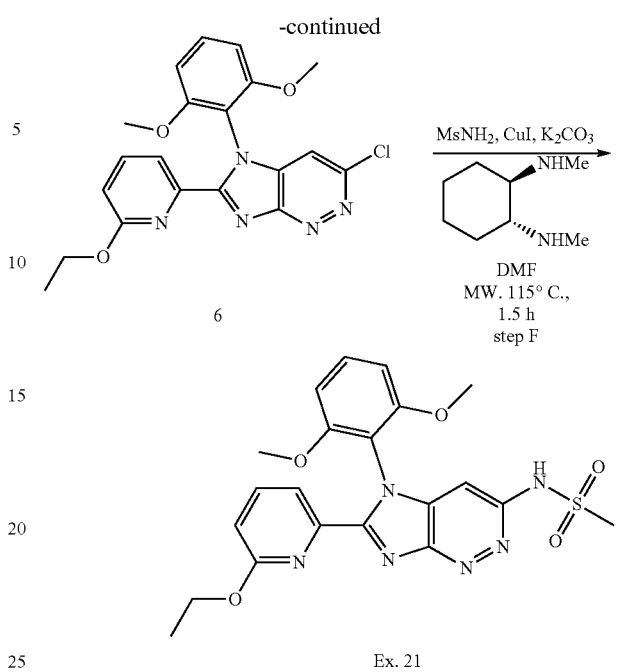

Step A: 6-chloropyridazin-3-amine

A suspension of 3,6-dichloropyridazine (10 g, 67 mmol, 1 equiv) in 25% aqueous ammonia (50 mL) was heated at 120° C. for about 12 h in a PTFE-lined pressure reactor. Upon cooling to room temperature, the resulting crystalline solids were collected by filtration, washed with water and dried to afford the title compound 6-chloropyridazin-3-amine.

LC-MS: m/z 130.0 (M+H)$^+$

Step B: 4-bromo-6-chloropyridazin-3-amine

To a solution of 6-chloropyridazin-3-amine (6.2 g, 48 mmol, 1 equiv) in methanol (200 mL) was added NaHCO$_3$ (8.1 g, 96 mmol, 2 equiv). After the mixture was stirred at room temperature for 30 min, bromine (11.5 g, 72 mmol, 1.5 equiv) was added drop wise. Then reaction mixture was stirred for another 16 h and concentrated under vacuum to obtain a residue. The residue was purified by silica gel column chromatography (eluting with 40 percent EtOAc in hexane) to afford the title compound 4-bromo-6-chloro-pyridazin-3-amine.

LC-MS: m/z 207.9, 209.9 (M+H)$^+$

Step C: N-(4-bromo-6-chloropyridazin-3-yl)-6-ethoxypicolinamide

To a solution of 6-ethoxypicolinic acid (2.3 g, 13.9 mmol, 1.2 equiv) and Oxalyl chloride (2.2 g, 17.4 mmol, 1.5 equiv) in DCM (50 mL) was added DMF (0.1 mL) at 0° C. The resulted mixture was stirred at room temperature for 1 h. The reaction solution was concentrated in vacuo to afford 6-ethoxypicolinoyl chloride which was used directly. To a solution of 4-bromo-6-chloropyridazin-3-amine (2.4 g, 11.6 mmol, 1 equiv) in DMF (50 mL) was added NaH (1.4 g, 34.8 mmol, 3 equiv) at RT. The mixture was stirred at room temperature for 1 h, then a solution of 6-ethoxypicolinoyl chloride in DMF (50 mL) was added. The mixture was stirred at room temperature for overnight. The reaction mixture was quenched with ammonium chloride solution (aq., 100 mL) and extracted with DCM (3*150 mL). The combined organic layers was washed with brine (100 mL), dried over anhydrous $Na_2SO_4$, and concentrated in vacuo. The residue was recrystalized in DCM to afford the title compound N-(4-bromo-6-chloropyridazin-3-yl)-6-ethoxypicolinamide.

LC-MS: m/z 356.9, 358.9 $(M+H)^+$

Step D: N-(6-chloro-4-((2,6-dimethoxyphenyl)amino)pyridazin-3-yl)-6-ethoxypicolinamide A suspension of N-(4-bromo-6-chloropyridazin-3-yl)-6-ethoxypicolinamide (500 mg, 1.4 mmol, 1 equiv), 2,6-dimethoxyaniline (214 mg, 1.4 mmol, 1 equiv), $Pd(OAc)_2$ (63 mg, 0.28 mmol, 0.2 equiv), Xantphos (324 mg, 0.56 mmol, 0.4 equiv) and $K_2CO_3$ (386 mg, 2.8 mmol, 2.0 equiv) in 1,4-dioxane (10 mL) was stirred at 120° C. via microwave irradiation for 2 hours under $N_2$ atmosphere. The mixture was filtered through celite and the filtrate was concentrated in vacuo. The residue was purified by flash chromatography (DCM/MeOH=100/1) to afford the desired product N-(6-chloro-4-((2,6-dimethoxyphenyl)amino)pyridazin-3-yl)-6-ethoxypicolinamide.

LC-MS: m/z 430.1 $(M+H)^+$

Step E: chloro-7-(2,6-dimethoxyphenyl)-8-(6-ethoxypyridin-2-yl)-7H-imidazo[4,5-c]pyridazine A solution of N-(6-chloro-4-((2,6-dimethoxyphenyl)amino)pyridazin-3-yl)-6-ethoxypicolinamide (110 mg, 0.25 mmol) in AcOH (10 mL) was stirred at 120° C. via microwave irradiation for 2 hours. After the reaction solution was cooled to room temperature, the light yellow precipitate was filtered off and rinsed with EtOAc/PE=1/2 (2*0.5 mL) to afford the title compound chloro-7-(2,6-dimethoxyphenyl)-8-(6-ethoxypyridin-2-yl)-7H-imidazo[4,5-c]pyridazine.

$^1$H NMR (400 MHz, DMSO-d&) S 8.05 (dd, J=7.4, 0.8 Hz, 1H), 7.93 (dd, J=8.4, 7.4 Hz, 1H), 7.67 (s, 1H), 7.50 (t, J=8.4 Hz, 1H), 6.93 (dd, J=8.4, 0.8 Hz, 1H), 6.89 (d, J=8.4 Hz, 2H), 6.60 (s, 6H), 3.40 (q, J=7.2 Hz, 2H), 1.04 (t, J=7.2 Hz, 3H).

LC-MS: m/z 412.1 $(M+H)^+$

Step E: N-(7-(2,6-dimethoxyphenyl)-8-(6-ethoxypyridin-2-yl)-7H-imidazo[4,5-c]pyridazinyl)methanesulfonamide A suspension of chloro-7-(2,6-dimethoxyphenyl)-8-(6-ethoxypyridin-2-yl)-7H-imidazo[4,5-c]pyridazine (48 mg, 0.12 mmol, 1 equiv), methanesulfonamide (22 mg, 0.23 mmol, 2 equiv), CuI (44 mg, 0.23 mmol, 2 equiv), trans-N,N'-Dimethylcyclohexane-1,2-diamine (33 mg, 0.23 mmol, 2 equiv) and $K_2CO_3$ (48 mg, 0.23 mmol, 3 equiv) in DMF (2 mL) was stirred at 130° C. via microwave irradiation for 1.5 hour under $N_2$ atmosphere. The reaction solution was diluted with water (150 mL) and extracted with EtOAc (3*100 mL). The combined organic layers was dried over anhydrous $Na_2SO_4$ and concentrated in vacuo. The residue was purified by flash chromatography (eluting with DCM/MeOH=100/1) to afford the title compound as yellow solid (30 mg, 55% yield).

$^1$H NMR (400 MHz, DMSO-$d_6$) δ 10.78 (s, 1H), 8.01 (dd, J=7.4, 0.8 Hz, 1H), 7.91 (dd, J=8.4, 7.4 Hz, 1H), 7.50 (t, J=8.4 Hz, 1H), 6.91 (dd, J=8.4, 1.2 Hz, 4H), 3.61 (s, 6H), 3.39 (q, J=7.2 Hz, 2H), 3.22 (s, 3H), 1.03 (t, J=7.2 Hz, 3H).

LC-MS: m/z 471.1 $(M+H)^+$

Method C

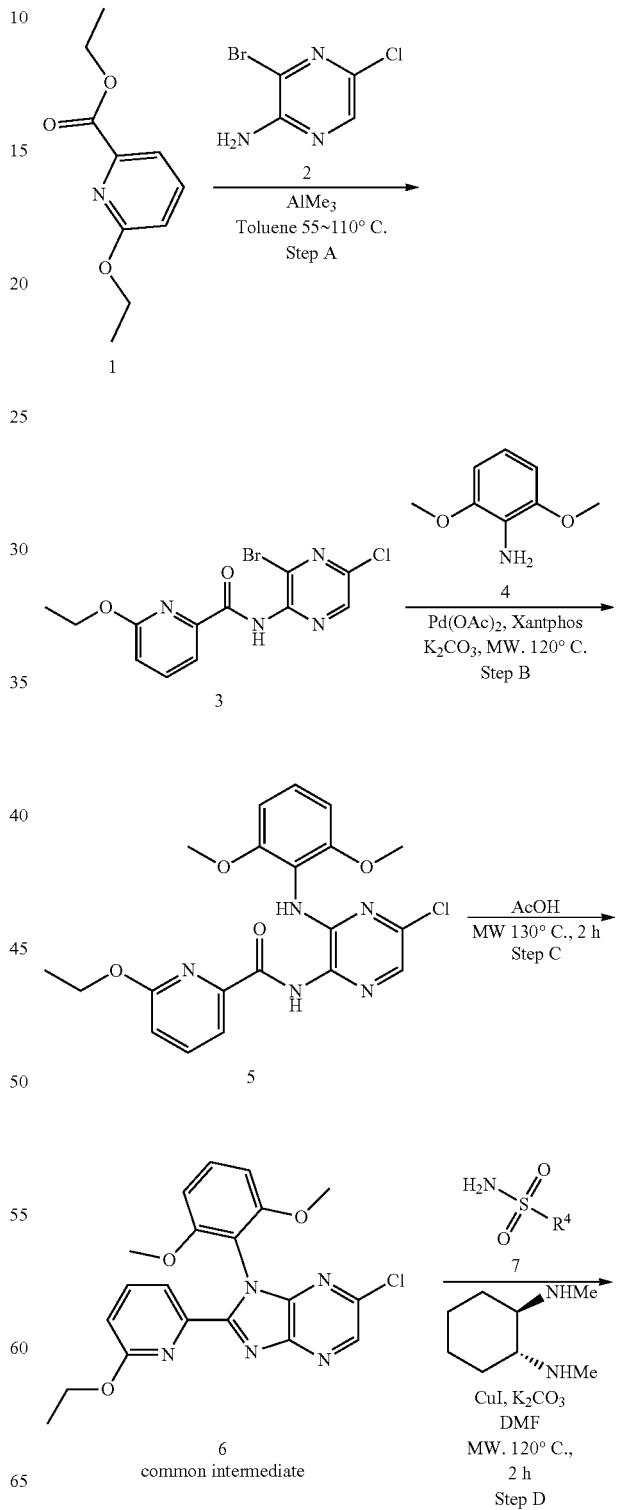

-continued

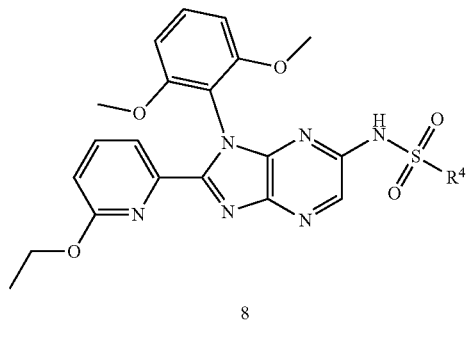

8

Step A: N-(3-bromo-5-chloropyrazin-2-yl)-6-ethoxypicolinamide

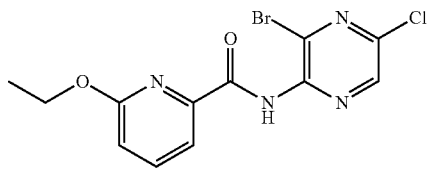 [SMILES: CCOc1cccc(C(=O)Nc2ncc(Cl)nc2Br)n1]

To a mixture of 3-bromo-5-chloropyrazin-2-amine (14.1 g, 67.6 mmol, 1.0 equiv) and toluene (60 mL) was added AlMe$_3$ (2 mol/L, 51 mL, 102 mmol, 1.5 equiv) and the resulted mixture was stirred at 55° C. for 30 mins. Ethyl 6-ethoxypicolinate (14.5 g, 74.4 mmol, 1.1 equiv) was added, and the mixture was stirred at 110° C. for 1.5 h. The mixture was quenched with 1N HCl (102 mL, 102 mmol, 1.5 equiv) and extracted with DCM (3*500 mL). The combined organic layers were washed with brine, dried over anhydrous sodium sulfate, filtered and concentrated in vacuo. The residue was re-slurried in DCM to afford the title compound N-(3-bromo-5-chloropyrazin-2-yl)-6-ethoxypicolinamide as a light yellow solid (12 g, 50% yield).
LC-MS: m/z 356.9, 358.9 (M+H)$^+$ Step B: N-(5-chloro-3-((2,6-dimethoxyphenyl)amino)pyrazin-2-yl)-6-ethoxypicolinamide

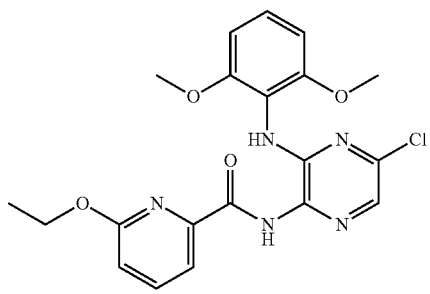 [SMILES: CCOc1cccc(C(=O)Nc2ncc(Cl)nc2Nc2c(OC)cccc2OC)n1]

A suspension of N-(3-bromo-5-chloropyrazin-2-yl)-6-ethoxypicolinamide (1 g, 2.8 mmol, 1.0 equiv), 2,6-dimethoxyaniline (475 mg, 3.4 mmol, 1.1 equiv), Pd(OAc)$_2$ (126 mg, 0.56 mmol, 0.2 equiv), Xantphos (650 mg, 1.12 mmol, 0.4 equiv) and K$_2$CO$_3$ (772 mg, 5.6 mmol, 2.0 equiv) in 1,4-dioxane (15 mL) was stirred at 120° C. via microwave irradiation under N$_2$ atmosphere for 2 h. The mixture was filtered through celite and the filtrate was concentrated in vacuo. The residue was purified by flash column chromatography (100% DCM) to afford the desired product N-(5-chloro-3-((2,6-dimethoxyphenyl)amino)pyrazin-2-yl)-6-ethoxypicolinamide as a yellow solid (6.3 g, 52% yield).
LC-MS: m/z 430.1 (M+H)$^+$ Step C: 6-chloro-1-(2,6-dimethoxyphenyl)-2-(6-ethoxypyridin-2-yl)-1H-imidazo[4,5-b]pyrazine

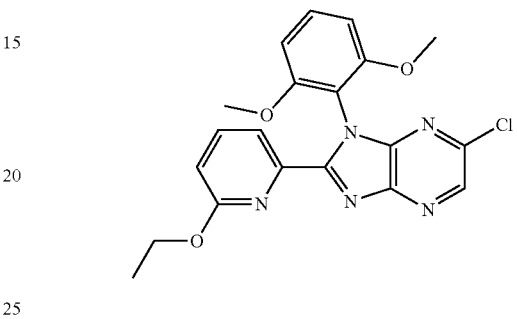

A solution of N-(5-chloro-3-((2,6-dimethoxyphenyl)amino)pyrazin-2-yl)-6-ethoxypicolinamide (2.0 g, 4.66 mmol) in AcOH (10 mL) was stirred at 130° C. via microwave irradiation for 2 hours. The mixture was cooled to room temperature, the precipitate was filtered off and washed with EtOAc/PE=1/2 to afford the title compound 6-chloro-1-(2,6-dimethoxyphenyl)-2-(6-ethoxypyridin-2-yl)-1H-imidazo[4,5-b]pyrazine as a light yellow solid (1.6 g, 83% yield).
LC-MS: m/z 412.1 (M+H)$^+$ Step D: N-(1-(2,6-dimethoxyphenyl-2-(6-ethoxypyridin-2-yl)-1H-imidazo[4,5-b]pyrazin-6-yl)methanesulfonamide (Example 2)

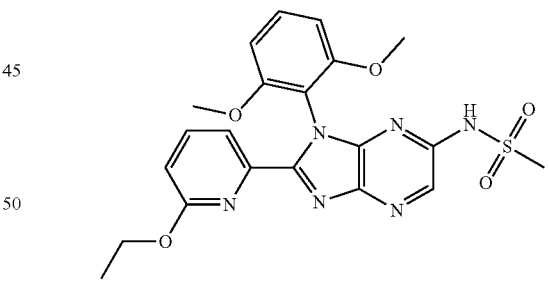

A suspension of 6-chloro-1-(2,6-dimethoxyphenyl)-2-(6-ethoxypyridin-2-yl)-1H-imidazo[4,5-b]pyrazine (1 g, 2.43 mmol), methanesulfonamide (462 mg, 4.87 mmol, 3.0 equiv), CuI (924 mg, 4.87 mmol, 3.0 equiv), trans-N,N'-Dimethylcyclohexane-1,2-diamine (691 mg, 4.87 mmol, 3.0 equiv) and K$_2$CO$_3$ (1006 mg, 7.29 mmol, 3 equiv) in DMF (10 mL) was stirred at 130° C. via microwave irradiation for 1.5 hour under N$_2$ atmosphere. The mixture was diluted with EtOAc (30 mL) and filtered through celite. The filtrate was poured onto aqueous K$_2$CO$_3$ (2 mol/L, 50 mL), stirred for 15 mins. Then the aqueous phase was separated and washed by EtOAc (2*30 mL). The aqueous phase was adjusted to pH=4 with formic acid and extracted with DCM (3*100 mL). The combined organic layers were dried over anhydrous Na$_2$SO$_4$ and concentrated in vacuo. The residue was purified by flash column chromatography eluting with DCM/MeOH=20/1~10/1 to afford the title compound N-(1-(2,6-dimethoxyphenyl)-2-(6-ethoxypyridin-2-yl)-1H-imidazo[4,5-b]pyrazin-6-yl)methanesulfonamide (Example 2) as a yellow solid (800 mg, 70% yield).

$^1$H NMR (400 MHz, DMSO-d$_6$) δ: 11.05 (s, 1H), 8.27 (s, 1H), 7.95 (dd, J=7.6 Hz, J=0.8 Hz, 1H), 7.86 (t, J=7.6 Hz, 1H), 7.45 (t, J=8.4 Hz, 1H), 6.81-6.87 (m, 3H), 3.57 (s, 6H), 3.39 (q, J=7.2 Hz, 2H), 3.20 (s, 3H), 1.03 (t, J=7.2 Hz, 3H). LC-MS: m/z 471.0 (M+H)$^+$

Example 22: N-(1-(2,6-dimethoxyphenyl)-2-(6-ethoxypyridin-2-yl)-1H-imidazo[4,5-b]pyrazin-6-yl)cyclopropanesulfonumide

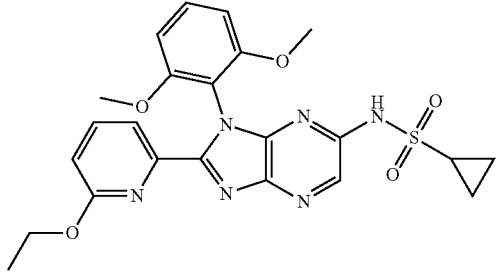 [SMILES: CCOc1cccc(-c2nc3ncc(NS(=O)(=O)C4CC4)nc3n2-c2c(OC)cccc2OC)n1]

The title compound was prepared according to Method C, step D, starting from N-(5-chloro-3-((2,6-dimethoxyphenyl)amino)pyrazin-2-yl)-6-ethoxypicolinamide by using cyclopropanesulfonamide (22 mg, 37% yield).

$^1$H NMR (400 MHz, DMSO-d$_6$) δ: 8.25 (s, 1H), 8.02 (s, 1H), 7.86 (d, J=7.2 Hz, 1H), 7.78 (t, J=7.6 Hz, 1H), 7.41 (t, J=8.4 Hz, 1H), 6.82 (d, J=8.4 Hz, 2H), 6.72 (d, J=8.0 Hz, 1H), 3.55 (s, 6H), 3.37 (q, J=7.2 Hz 2H), 2.52-2.54 (m, 1H), 1.01 (t, J=7.2 Hz, 3H), 0.79-0.83 (m, 2H), 0.64-0.69 (m, 2H). LCMS: m/z 497.1 (M+H)$^+$

Example 23: N-(1-(2,6-dimethoxyphenyl)-2-(6-ethoxypyridin-2-yl)-1H-imidazo[4,5-b]pyrazin-6-yl)pyridine-2-sulfonamide

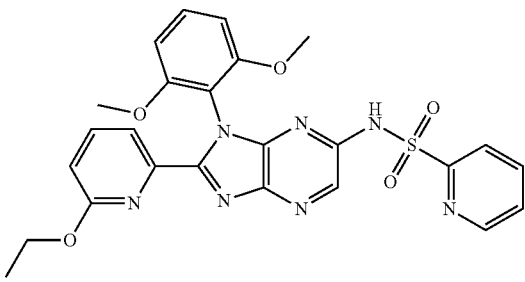 [SMILES: CCOc1cccc(-c2nc3ncc(NS(=O)(=O)c4ccccn4)nc3n2-c2c(OC)cccc2OC)n1]

The title compound was prepared according to Method C, step D, starting from N-(5-chloro-3-((2,6-dimethoxyphenyl)amino)pyrazin-2-yl)-6-ethoxypicolinamide by using pyridine-2-sulfonamide (30 mg, 23% yield).

$^1$HNMR (400 MHz, DMSO-d$_6$) δ:11.77 (s, 1H), 8.55 (d, J=4.0 Hz, 1H), 8.21 (s, 1H), 7.89 (d, J=7.6 Hz, 1H), 7.80 (t, J=7.6 Hz, 1H), 7.71 (d, J=7.6 Hz, 1H), 7.60 (d, J=7.6 Hz, 1H), 7.49 (t, J=8.4 Hz, 2H), 6.86 (d, J=8.4 Hz, 2H), 6.77 (d, J=8.0 Hz, 1H), 3.51 (s, 6H), 3.37 (q, J=7.2 Hz, 2H), 1.01 (t, J=7.2 Hz, 3H). LC-MS: m/z 534 (M+H)$^+$

Example 24: N-(1-(2,6-dimethoxyphenyl)-2-(6-ethoxypyridin-2-yl)-1H-imidazo[4,5-b]pyrazin-6-yl)pyridine-3-sulfonamide

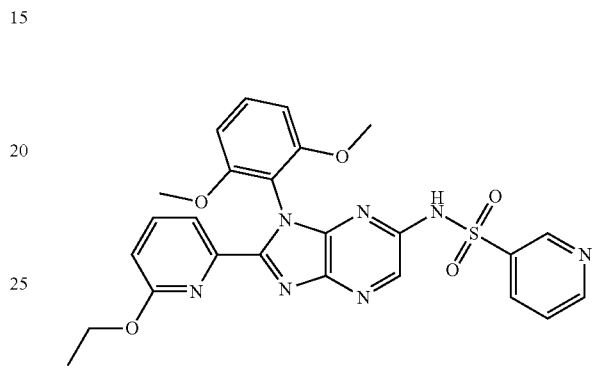

The title compound was prepared according to Method C, step D, starting from N-(5-chloro-3-((2,6-dimethoxyphenyl)amino)pyrazin-2-y)-6-ethoxypicolinamide by using pyridine-3-sulfonamide (58 mg, 54% yield).

$^1$H NMR (400 MHz, DMSO-d$_6$) δ:11.81 (s, 1H), 8.79-8.90 (m, 1H), 8.65-8.78 (m, 1H), 8.23 (s, 1H), 7.93 (t, J=8.4 Hz, 2H), 7.84 (t, J=8.0 Hz, 1H), 7.55 (t, J=8.0 Hz, 1H), 7.37 (dd, J=8.0, 4.8 Hz, 1H), 6.93 (d, J=8.0 Hz, 2H), 6.80-6.83 (m, 1H), 3.55 (s, 6H), 3.39 (q, J=7.1 Hz, 2H), 1.03 (t, J=7.1 Hz, 3H). LC-MS: m/z 534.0 (M+H)$^+$

Example 25: N-(1-(2,6-dimethoxyphenyl)-2-(6-ethoxypyridin-2-yl)-1H-imidazo[4,5-b]pyrazin-6-yl)pyridine-4-sulfonamide

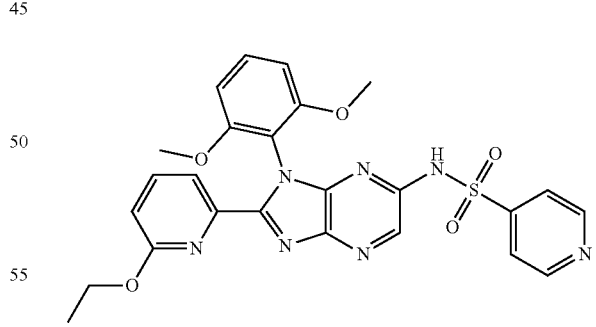

The title compound was prepared according to Method C, step D, starting from N-(5-chloro-3-((2,6-dimethoxyphenyl)amino)pyrazin-2-yl)-6-ethoxypicolinamide by using pyridine-4-sulfonamide (45 mg, 57% yield).

$^1$H NMR (400 MHz, DMSO-d$_6$) δ: 8.40 (s, 2H), 7.79-7.86 (m, 2H), 7.75 ((t, J=8.0 Hz, 1H), 7.53 (t, J=8.4 Hz, 1H), 7.43 (d, J=4.8 Hz, 2H), 6.93 (d, J=8.4 Hz, 2H), 6.69 (d, J=8.0 Hz, 1H), 3.53 (s, 6H), 3.38 (d, J=7.2 Hz, 2H), 1.01 (t, J=7.2 Hz, 3H). LC-MS: m/z 534.0 (M+H)$^+$

Example 26: N-(1-(2,6-dimethoxyphenyl)-2-(6-ethoxypyridin-2-yl)-1H-imidazo[4,5-b]pyrazin-6-yl)-1-(pyridin-3-yl)methanesulfonamide

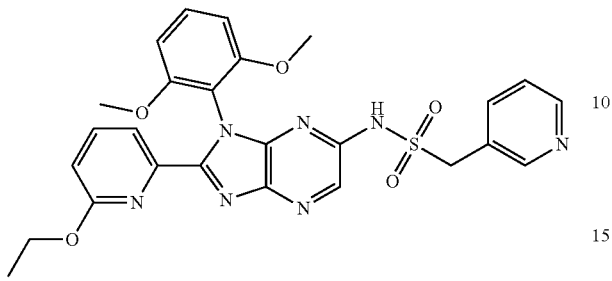

The title compound was prepared according to Method C, step D, starting from N-(5-chloro-3-((2,6-dimethoxyphenyl)amino)pyrazin-2-yl)-6-ethoxypicolinamide by using pyridin-3-ylmethanesulfonamide (24 mg, 25% yield).

$^1$H NMR (400 MHz, DMSO-$d_6$) δ:11.13 (s, 1H), 8.32-8.54 (m, 8.8 Hz, 2H), 8.17 (s, 1H), 7.97 (dd, J=7.4, 0.9 Hz, 1H), 7.87 (dd, J=8.2, 7.6 Hz, 1H), 7.44-7.5 (m, 2H), 7.38 (s, 1H), 6.89 (d, J=4.0 Hz, 2H), 6.84 (dd, J=4.0, 8.0 Hz, 3H), 4.72 (s, 2H), 3.58 (s, 6H), 3.40 (q, J=6.6 Hz, 2H), 1.03 (t, J=7.2 Hz, 3H). LC-MS: m/z 548.0 (M+H)$^+$

Example 27: N-(1-(2,6-dimethoxyphenyl-2-(6-ethoxypyridin-2-yl)-1H-imidazo[4,5-b]pyrazin-6-y)-1-(pyridin-2-yl)methanesulfonamide

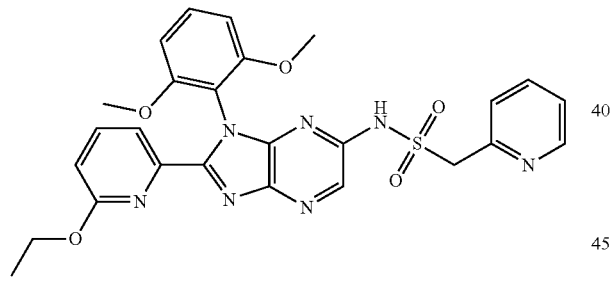

The title compound was prepared according to Method C, step D, starting from N-(5-chloro-3-((2,6-dimethoxyphenyl)amino)pyrazin-2-yl)-6-ethoxypicolinamide by using pyridin-2-ylmethanesulfonamide (30 mg, 37% yield).

$^1$H NMR (400M, DMSO-$d_6$) δ: 11.12 (br, 1H), 8.45-8.47 (m, 1H), 8.14 (s, 1H), 7.94 (dd, J=7.6 Hz, J=0.8 Hz, 1H), 7.86 (t, J=7.6 Hz, 1H), 7.75 (td, J=7.6 Hz, J=1.6 Hz, 1H), 7.47 (t, J=8.4 Hz, 1H), 7.31-7.34 (m, 1H), 7.2 (d, J=7.6 Hz, 1H), 6.87 (d, J=8.4 Hz, 1H), 6.82 (dd, J=8.0 Hz, J=0.8 Hz, 1H), 4.79 (s, 2H), 3.56 (s, 6H), 3.40 (q, J=7.2 Hz, 2H), 1.03 (t, J=7.2 Hz, 3H). LC-MS: m/z 548.6 (M+H)$^+$

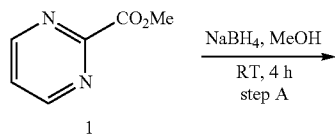

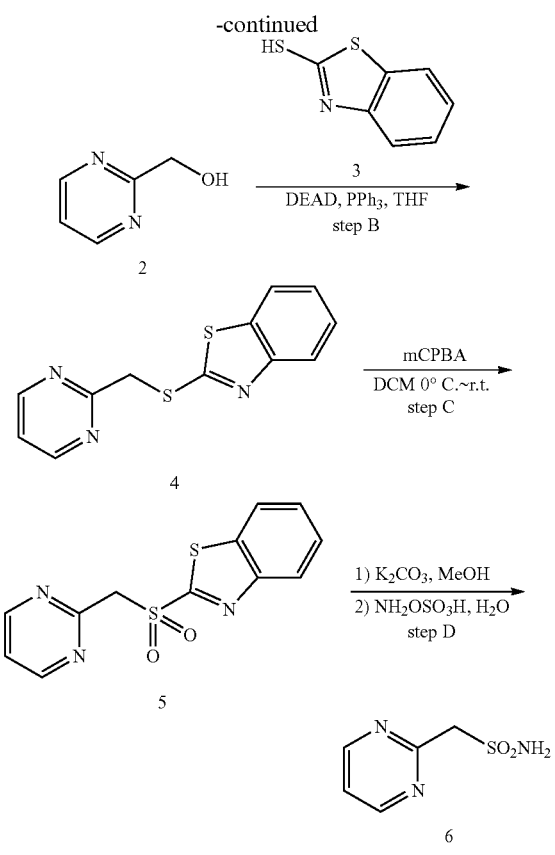

Step A: pyrimidin-2-ylmethanol

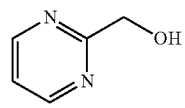

To a solution of methyl pyrimidine-2-carboxylate (25 g, 181 mmol, 1.0 equiv) in MeOH (500 mL) was added NaBH$_4$ (8.2 g, 217 mmol, 1.2 equiv) at 0° C. The reaction mixture was stirred at room temperature for 3 hours. The reaction mixture was quenched with H$_2$O (10 mL), concentrated in vacuo and the residue was purified by flash column chromatography (PE/EtOAc=1/1) to afford the title compound pyrimidin-2-ylmethanol as a yellow oil (16 g, 80% yield).

LC-MS: m/z 111.0 (M+H)$^+$

Step B: 2-((pyrimidin-2-ylmethyl)thio)benzo[d]thiazole

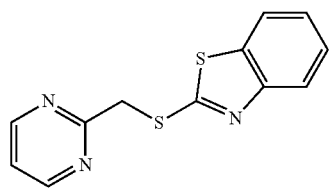 [SMILES: c1cnc(CSc2nc3ccccc3s2)nc1]

To a solution of pyrimidin-2-ylmethanol (16.6 g, 151 mmol, 1.0 equiv), benzo[d]thiazole-2-thiol (30 g, 181 mmol, 1.2 equiv) and PPh$_3$ (47.4 g, 181 mmol, 1.2 equiv) in THF (500 mL) was added DEAD (36.6 g, 181 mmol, 1.2 equiv) at 0° C. The mixture was stirred at room temperature for 16 hours. The reaction mixture was quenched with HCl-dioxane and the white precipitate was filtered off. The solid was then dissolved in 1N Na$_2$CO$_3$ aqueous solution (100 mL) and extracted with EtOAc (3*200 mL). The combined organic phase was concentrated in vacuo to afford the title compound 2-((pyrimidin-2-ylmethyl)thio)benzo[d]thiazole as a crude yellow solid (27 g, 77% yield).

LC-MS: m/z 260.0 (M+H)$^+$

Step C: 2-((pyrimidin-2-ylmethyl)sulfonyl)benzo[d]thiazole

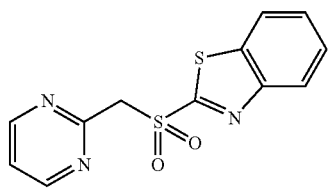 [SMILES: O=S(=O)(Cc1ncccn1)c1nc2ccccc2s1]

To a solution of 2-((pyrimidin-2-ylmethyl)thio)benzo[d]thiazole (27 g, 104 mmol, 1.0 equiv) in DCM (500 mL) was added m-CPBA (51 g, 249 mmol, 2.4 equiv). The mixture was stirred at room temperature for 16 hours and quenched with 1N Na$_2$SO$_3$ aqueous solution. The organic phase was separated, washed with saturated Na$_2$CO$_3$ and concentrated in vacuo. The residue was purified by flash column chromatography (PE/EtOAc=5/1) to afford the title compound 2-((pyrimidin-2-ylmethyl)sulfonyl)benzo[d]thiazole as a white solid (17 g, 80% yield).

LC-MS: m/z 292.0 (M+H)$^+$

Step D: pyrimidin-2-ylmethanesulfonamide

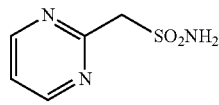 [SMILES: NS(=O)(=O)Cc1ncccn1]

To a solution of 2-((pyrimidin-2-ylmethyl)sulfonyl)benzo[d]thiazole (500 mg, 1.7 mmol, 1.0 equiv) in MeOH (10 mL) was added K$_2$CO$_3$ (1.2 g, 8.5 mmol, 5.0 equiv). After the mixture was stirred at room temperature for 10 mins, NH$_2$OSO$_3$H (250 mg, 2.0 mmol, 1.2 equiv) in H$_2$O (1 mL) was added. The mixture was stirred at room temperature for 15 mins and another batch of NH$_2$OSO$_3$H (250 mg, 2.0 mmol, 1.2 equiv) in H$_2$O (1 mL) was added. The resulting mixture was stirred at room temperature for 60 hours. The mixture was evaporated and the residue was purified by flash column chromatography (DCM/MeOH=50/1) to afford the title compound pyrimidin-2-ylmethanesulfonamide as a white solid (100 mg, 34% yield).

$^1$H NMR (400 MHz, DMSO) δ 8.83 (d, J=4.8 Hz, 2H), 7.49 (t, J=4.8 Hz, 1H), 7.01 (s, 2H), 4.55 (s, 2H). LC-MS: m/z 174.0 (M+H)$^+$

Example 28: N-(1-(2,6-dimethoxyphenyl)-2-(6-ethoxypyridin-2-yl)-1H-imidazo[4,5-b]pyrazin-6-yl)-1-(pyrimidin-2-yl)methanesulfonamide

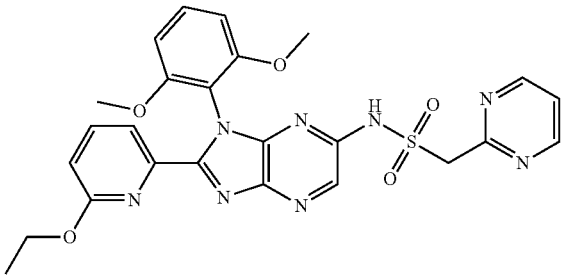

The title compound was prepared according to Method C, step D, starting from N-(5-chloro-3-((2,6-dimethoxyphenyl)amino)pyrazin-2-yl)-6-ethoxypicolinamide by using pyrimidin-2-ylmethanesulfonamide (27 mg, 34% yield).

$^1$H NMR (400 MHz, DMSO-d$_6$) δ: 11.19 (s, 1H), 8.74 (d, J=4.8 Hz, 2H), 8.21 (s, 1H), 7.94 (d, J=7.2 Hz, 1H), 7.86 (t, J=8.0 Hz, 1H), 7.40-7.49 (m, 2H), 6.85 (d, J=8.4 Hz, 2H), 6.82 (dd, J=8.2, 0.8 Hz, 1H), 3.55 (s, 6H), 3.39 (q, J=7.2 Hz, 2H), 1.02 (t, J=7.2 Hz, 3H). LCMS: m/z 548.9 (M+H)$^+$ 2-cyclopropylethanesulfonamide

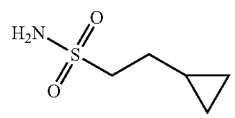

The title compound was prepared according to the preparation of pyrimidin-2-ylmethanesulfonamide by using 2-cyclopropylethanol in step A.

LC-MS: m/z 150.2 (M+H)$^+$

Example 29: 2-cyclopropyl-N-(1-(2,6-dimethoxyphenyl)-2-(6-ethoxypyridin-2-yl)-1H-imidazo[4,5-b]pyrazin-6-yl)ethanesulfonamide

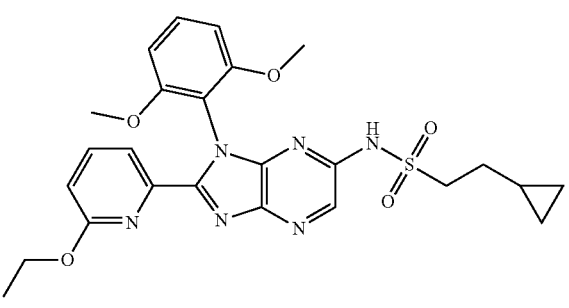 [SMILES: CCOc1cccc(-c2nc3ncc(NS(=O)(=O)CCC4CC4)nc3n2-c2c(OC)cccc2OC)n1]

The title compound was prepared according to Method C, step D, starting from 6-bromo-1-(2,6-dimethoxyphenyl)-2-(6-ethoxypyridin-2-yl)-1H-imidazo[4,5-b]pyrazine (Example 1) by using 2-cyclopropylethanesulfonamide (50 mg, 47% yield).

$^1$H NMR (400M, DMSO-d$_6$) δ:10.98 (br, 1H), 8.27 (s, 1H), 7.95 (d, J=7.2 Hz, 1H), 7.85 (t, J=8.4 Hz, 1H), 7.45 (t,

J=8.4 Hz, 1H), 6.86 (d, J=8.4 Hz, 2H), 6.82 (d, J=8.4 Hz, 1H), 3.58 (s, 6H), 3.36-3.42 (m, 4H), 1.47-1.52 (m, 2H), 1.03 (t, J=7.2 Hz, 3H), 0.63-0.68 (m, 1H), 0.29-0.33 (m, 2H), 0.06-0.1 (m, 2H). LC-MS: m/z 525.4 (M+H)+ oxetane-3-sulfonamide

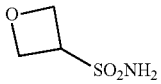

The title compound was prepared according to the preparation of pyrimidin-2-ylmethanesulfonamide by using oxetan-3-ol in step A.

$^1$H NMR (400 MHz, DMSO) δ: 7.17 (s, 2H), 4.79 (dd, J=8.0, 7.2 Hz, 2H), 4.68-4.65 (m, 2H), 4.47-4.40 (m, 1H).

Example 30: N-(1-(2,6-dimethoxyphenyl)-2-(6-ethoxypyridin-2-yl)-1H-imidazo[4,5-b]pyrazin-6-yl)oxetane-3-sulfonamide

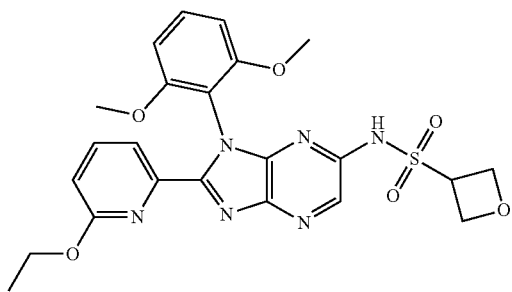 [SMILES: CCOc1cccc(-c2nc3ncc(NS(=O)(=O)C4COC4)nc3n2-c2c(OC)cccc2OC)n1]

The title compound was prepared according to Method C, step D, starting from N-(5-chloro-3-((2,6-dimethoxyphenyl)amino)pyrazin-2-yl)-6-ethoxypicolinamide by using oxetane-3-sulfonamide (36.3 mg, 35% yield).

$^1$H NMR (400 MHz, DMSO-d$_6$) δ: 8.05 (s, 1H), 7.91 (d, J=7.6 Hz, 1H), 7.81 (t, J=7.6 Hz, 1H), 7.43 (t, J=8.4 Hz, 1H), 6.86 (d, J=8.4 Hz, 2H), 6.76 (d, J=8.0 Hz, 1H), 4.49-4.67 (m, 3H), 4.34 (t, J=6.6 Hz, 2H), 3.60 (s, 6H), 3.38 (q, J=7.2 Hz, 2H), 1.02 (t, J=7.2 Hz, 3H). LC-MS: m/z 513.1 (M+H)+

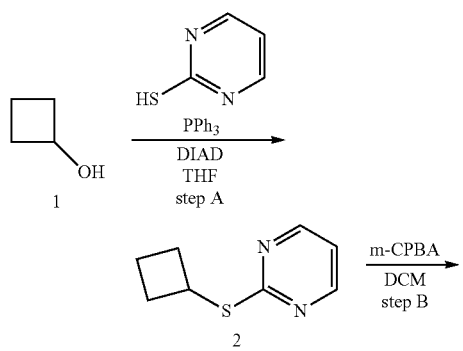

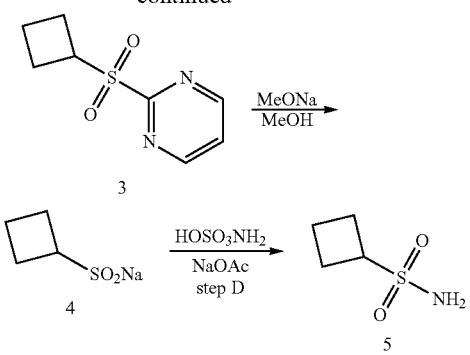

Step A: 2-(cyclobutylthio)pyrimidine

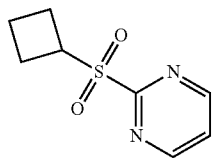 [SMILES: O=S(=O)(c1ncccn1)C1CCC1]

To a solution of PPh$_3$ (4.37 g, 16.7 mmol, 1.2 equiv) in THF (30 mL) at 0° C. was added DIAD (3.37 g, 16.7 mmol, 1.2 equiv) dropwise under N$_2$ atmosphere. After the mixture was stirred at 0° C. for 10 mins, a mixture of pyrimidine-2-thiol (1.867 g, 16.7 mmol, 1.2 equiv) and cyclobutanol (1.0 g, 13.9 mmol, 1.0 equiv) in THF (10 mL) was added. The resulting mixture was stirred at 0° C. for 10 mins and at room temperature for 1 h. The reaction solution was concentrated and the residue was purified by flash column chromatography (PE/EtOAc=6/1) to afford the desired 2-(cyclobutylthio)pyrimidine as a yellow oil (2.0 g, 87% yield).

LC-MS: m/z 167.0 (M+H)+

Step B: 2-(cyclobutylsulfonyl)pyrimidine

To a solution of m-CPBA (5.7 g, 33.1 mmol, 3 equiv) in DCM (80 mL) was added 2-(cyclobutylthio)pyrimidine (1.83 g, 11.0 mmol, 1.0 equiv). The reaction mixture was stirred at room temperature for 16 h. Saturated Na$_2$S$_2$O$_3$ aqueous solution (20 mL) was added and the mixture was stirred at room temperature for 30 mins. The organic phase was separated and washed with brine, dried over anhydrous Na$_2$SO$_4$ and concentrated in vacuo. The residue was purified by flash column chromatography (PE/EtOAc=1/1) to afford the title compound 2-(cyclobutylsulfonyl)pyrimidine as a yellow solid (1.7 g, 78% yield).

LC-MS: m/z 199.0 (M+H)+

Step C: cyclobutanesulfonamide

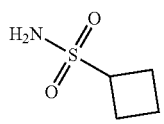

To a solution of 2-(cyclobutylsulfonyl)pyrimidine (1.75 g, 8.84 mmol, 1.0 equiv) in MeOH (40 mL) was added NaOMe (5.4 mol/L, 1.64 mL, 1.0 equiv). After the reaction mixture was stirred at 0° C. for 30 mins, a solution of NaOAc (906 mg, 11.05 mmol, 1.25 equiv) and HOSO₃NH₂ (1.25 g, 11.05 mmol, 1.25 equiv) in water (5 mL) was added. The resulting mixture was stirred at room temperature for 16 h. The reaction suspension was filtered and the filtrate was concentrated in vacuo. The residue was purified by flash column chromatography (PE/EtOAc=1/1) to afford the title compound cyclobutanesulfonamide as a white solid (300 mg, 25% yield).

LC-MS: m/z 136.0 (M+H)⁺

Example 31: N-(1-(2,6-dimethoxyphenyl)-2-(6-ethoxypyridin-2-yl)-1H-imidazo[4,5-b]pyrazin-6-yl)cyclobutanesulfonamide

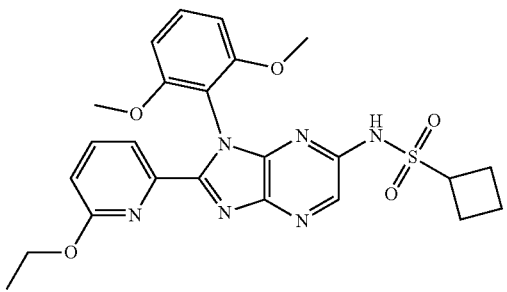 [SMILES: CCOc1cccc(-c2nc3ncc(NS(=O)(=O)C4CCC4)nc3n2-c2c(OC)cccc2OC)n1]

The title compound was prepared according to Method C, step D, starting from N-(5-chloro-3-((2,6-dimethoxyphenyl)amino)pyrazin-2-yl)-6-ethoxypicolinamide by using cyclobutanesulfonamide (85 mg, 64% yield).

¹H NMR (400 MHz, DMSO-d₆) δ: 10.87 (s, 1H), 8.31 (s, 1H), 7.95 (dd, J=7.4, 0.8 Hz, 1H), 7.86 (dd, J=8.4, 7.6 Hz, 1H), 7.46 (t, J=8.4 Hz, 1H), 6.87 (d, J=8.4 Hz, 2H), 6.83 (dd, J=8.4, 0.8 Hz, 1H), 4.09-4.22 (m, 1H), 3.59 (s, 6H), 3.39 (q, J=7.2 Hz, 2H), 2.28 (ddt, J=13.0, 10.6, 8.6 Hz, 2H), 2.02-2.13 (m, 2H), 1.75-1.92 (m, 2H), 1.03 (t, J=7.2 Hz, 3H). LC-MS: m/z 511.2 (M+H)⁺

Example 32: N-(1-(2,6-dimethoxyphenyl)-2-(6-ethoxypyridin-2-yl)-1H-imidazo[4,5-b]pyrazin-6-yl)-N-methylmethanesulfonamide

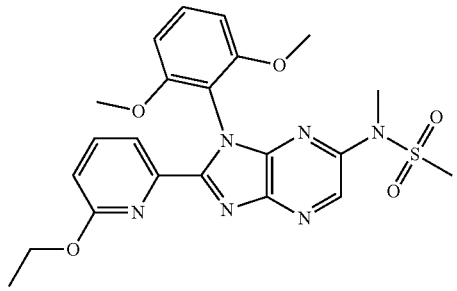 [SMILES: CCOc1cccc(-c2nc3ncc(N(C)S(C)(=O)=O)nc3n2-c2c(OC)cccc2OC)n1]

The title compound was prepared according to Method C, step D, starting from 6-bromo-1-(2,6-dimethoxyphenyl)-2-(6-ethoxypyridin-2-yl)-1H-imidazo[4,5-b]pyrazine (Example 1) by using N-methylmethanesulfonamide (40 mg, 75% yield).

¹H NMR (400 MHz, DMSO-d₆) δ: 8.63 (s, 1H), 7.98 (t, J=7.2 Hz, 1H), 7.89 (t, J=8.4 Hz, 1H), 7.47 (t, J=8.4 Hz, 1H), 6.87 (d, J=8.4 Hz, 2H), 6.86 (d, J=8.4 Hz, 2H), 3.57 (s, 6H), 3.41 (q, J=7.2 Hz, 2H), 3.26 (s, 3H), 3.12 (s, 3H), 1.03 (t, J=7.2 Hz, 3H). LC-MS: m/z 485.2 (M+H)⁺

Trans-3-(benzyloxy)cyclobutane-1-sulfonamide

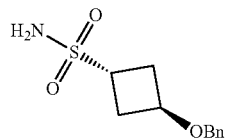 [SMILES: NS(=O)(=O)[C@H]1C[C@H](OCc2ccccc2)C1]

The title compound was prepared according to the preparation of cyclobutanesulfonamide by using cis-3-(benzyloxy)cyclobutanol in step A.

¹H NMR (400 MHz, DMSO-d₆) δ: 7.27-7.37 (m, 5H), 6.83 (s, 2H), 4.38 (s, 2H), 4.18-4.24 (m, 1H), 3.57-3.64 (m, 1H), 2.49-2.58 (m, 2H), 2.28-2.36 (m, 2H).

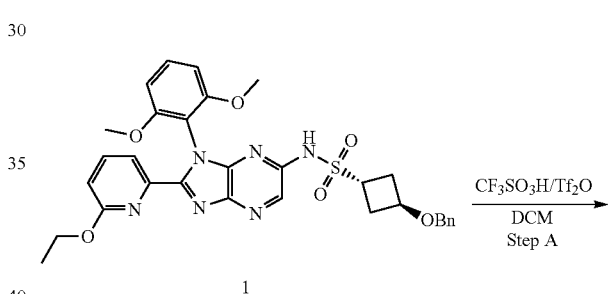

1

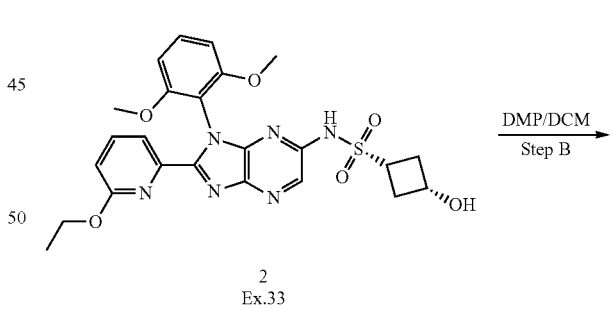

2
Ex.33

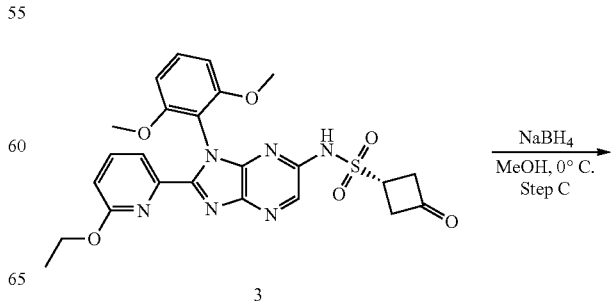

3

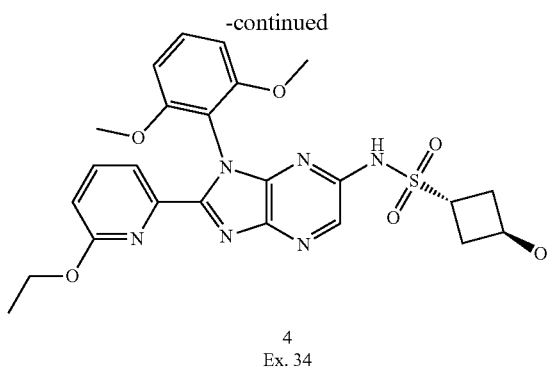

4
Ex. 34 trans-3-(benzyloxy)-N-(1-(2,6-dimethoxyphenyl)-2-(6-ethoxypyridin-2-yl)-1H-imidazo[4,5-b]pyrazin-6-yl)cyclobutane-1-sulfonamide

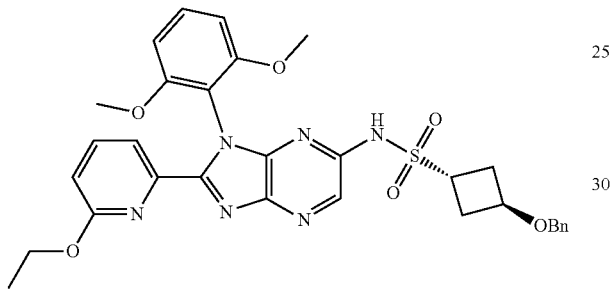

The title compound was prepared according to Method C, step D, starting from N-(5-chloro-3-((2,6-dimethoxyphenyl)amino)pyrazin-2-yl)-6-ethoxypicolinamide by using trans-3-(benzyloxy)cyclobutane-1-sulfonamide (460 mg, 48% yield).

$^1$H NMR (400 MHz, DMSO-d$_6$) δ: 11.00 (s, 1H), 8.23 (s, 1H), 7.94-7.96 (m, 1H), 7.85 (t, J=8.0 Hz, 1H), 7.43 (t, J=8.0 Hz, 1H), 7.27-7.28 (m, 5H), 6.81-6.84 (m, 3H), 4.35 (s, 2H), 4.07-4.19 (m, 2H), 3.57 (s, 6H), 3.36-3.41 (m, 2H), 2.54-2.60 (m, 2H), 2.19-2.26 (m, 2H), 1.02 (t, J=8.0 Hz, 3H). LC-MS: m/z 617.0 (M+H)$^+$

Example 33: cis-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide

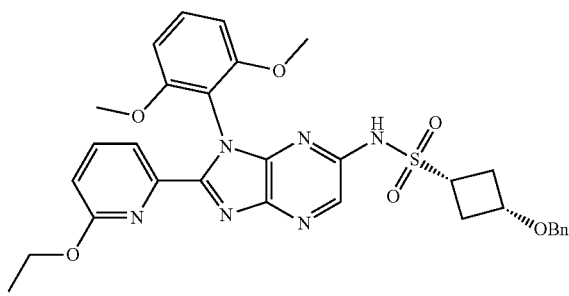 [SMILES: CCOc1cccc(-c2nc3ncc(NS(=O)(=O)[C@H]4C[C@@H](OCc5ccccc5)C4)nc3n2-c2c(OC)cccc2OC)n1]

To a mixture of trans-3-(benzyloxy)-N-(1-(2,6-dimethoxyphenyl)-2-(6-ethoxypyridin-2-yl)-1H-imidazo[4,5-b]pyrazin-6-yl)cyclobutane-1-sulfonamide (200 mg, 0.324 mmol, 1.0 equiv) in DCM (16 mL) were added trifluoromethanesulfonic acid (1 mL) and trifluoromethanesulfonic anhydride (0.5 mL) at 0° C. under N$_2$ atmosphere. The resulting mixture was stirred at 0° C. for 15 minutes under N$_2$ atmosphere. Then the mixture was adjusted to pH=6 by adding aqueous NaHCO$_3$ (3 mol/L) and DCM (60 mL) was added into the mixture. The combined organic layers were washed with brine (20 mL), dried over Na$_2$SO$_4$, filtered and evaporated under reduced pressure. The residue was purified by silica gel column chromatography (eluting with DCM/MeOH=20/1~10/1) to afford the title compound as a brown solid (50 mg, 29% yield).

$^1$H NMR (400 MHz, DMSO-d$_6$) δ: 8.19 (s, 1H), 7.90 (d, J=7.2 Hz, 1H), 7.82 (t, J=7.6 Hz, 1H), 7.43 (t, J=8.4 Hz, 1H), 6.84 (d, J=8.8 Hz, 2H), 6.77 (d, J=8.4 Hz, 1H), 5.22 (s, 1H), 4.20-4.33 (m, 1H), 3.93-3.98 (m, 1H), 3.59 (s, 6H), 3.39 (q, J=7.2 Hz, 2H), 2.42-2.50 (m, 2H), 1.97-2.12 (m, 2H), 1.02 (t, J=7.2 Hz, 3H). LC-MS: m/z 527.2 (M+H)$^+$

Step B: N-(1-(2,6-dimethoxyphenyl)-2-(6-ethoxypyridin-2-yl)-1H-imidazo[4,5-b]pyrazin-6-yl)-3-oxocyclobutane-1-sulfonamide

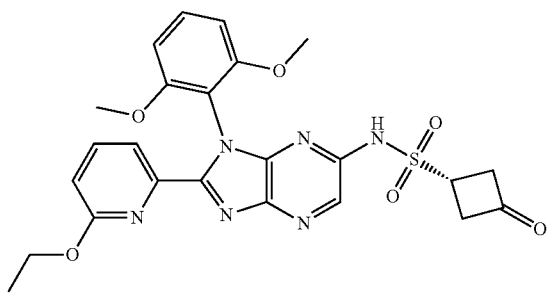

The solution of cis-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide (Example 33, 60 mg, 0.114 mmol, 1.0 equiv) in DCM (2 mL) was cooled to 0° C. and Dess-Martin periodinane (193 mg, 0.456 mmol, 4 equiv) was added. The mixture was stirred at room temperature overnight. The mixture was washed with Na$_2$SO$_3$ (aq.) brine, dried over Na$_2$SO$_4$, and concentrated in vacuo. The residue was purified by prep-TLC to give N-(1-(2,6-dimethoxyphenyl)-2-(6-ethoxypyridin-2-yl)-1H-imidazo[4,5-b]pyrazin-6-yl)-3-oxocyclobutane-1-sulfonamide as a light yellow solid (50 mg, 83% yield).

LC-MS: m/z 525.2 (M+H)$^+$

Example 34: trans-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide

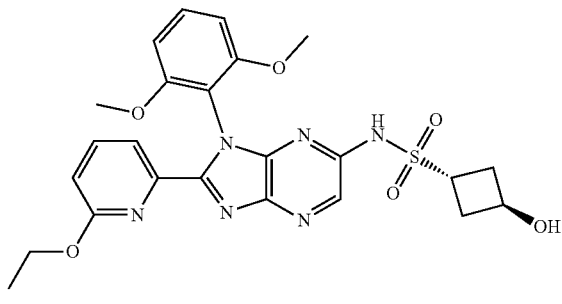 [SMILES: CCOc1cccc(-c2nc3ncc(NS(=O)(=O)[C@H]4C[C@H](O)C4)nc3n2-c2c(OC)cccc2OC)n1]

The solution of N-(1-(2,6-dimethoxyphenyl)-2-(6-ethoxypyridin-2-yl)-1H-imidazo[4,5-b]pyrazin-6-yl)-3-oxocyclobutane-1-sulfonamide (50 mg, 0.095 mmol, 1.0 equiv) in MeOH (1 mL) was cooled to 0° C. and NaBH$_4$ (7.2 mg, 0.191 mmol, 3.0 equiv) was added. The mixture was allowed to be warmed to room temperature and stirred for 2 h. After that, H$_2$O (1 mL) was added and the mixture was extracted with DCM three times. The combined organic layers were washed with brine, concentrated and purified via prep-TLC to give the title compound as a white solid (22 mg, 44% yield).

$^1$H NMR (400 MHz, CDCl$_3$) δ: 8.48 (s, 1H), 8.04 (d, J=7.6 Hz, 1H), 7.60 (t, J=7.6 Hz, 1H), 7.30 (t, J=8.4 Hz, 1H), 6.76 (s, 1H), 6.61-6.65 (m, 3H), 4.01-4.06 (m, 1H), 3.55 (s, 6H), 3.44-3.50 (m, 1H), 3.32-3.38 (m, 2H), 2.50-2.54 (m, 2H), 2.26-2.32 (m, 2H), 1.02 (t, J=7.2 Hz, 3H). LC-MS: m/z 527.2 (M+H)$^+$ pyrimidin-5-ylmethanesulfonamide

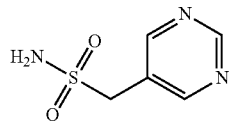

The title compound was prepared according to the preparation of cyclobutanesulfonamide by using pyrimidin-5-ylmethanol in step A.

$^1$H NMR (400 MHz, DMSO-d$_6$) δ: 9.17 (s, 1H), 8.77 (s, 2H), 7.03 (br. s, 2H), 4.38 (s, 2H). LC-MS: m/z 174.0 (M+H)$^+$

Example 35: N-(1-(2,6-dimethoxyphenyl)-2-(6-ethoxypyridin-2-yl)-1H-imidazo[4,5-b]pyrazin-6-yl)-1-(pyrimidin-5-yl)methanesulfonamide

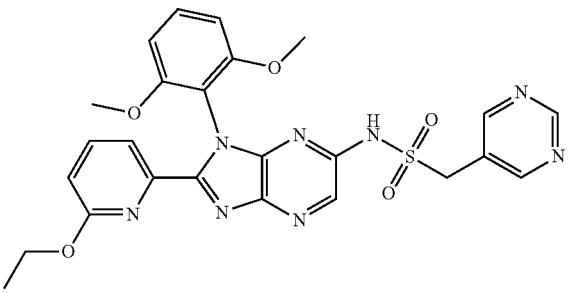 [SMILES: CCOc1cccc(-c2nc3ncc(NS(=O)(=O)Cc4cncnc4)nc3n2-c2c(OC)cccc2OC)n1]

The title compound was prepared according to Method C, step D, starting from N-(5-chloro-3-((2,6-dimethoxyphenyl)amino)pyrazin-2-yl)-6-ethoxypicolinamide by using pyrimidin-5-ylmethanesulfonamide.

$^1$H NMR (400 MHz, DMSO-d$_6$) δ: 11.20 (s, 1H), 9.15 (s, 1H), 8.54 (s, 2H), 8.27 (s, 1H), 7.98 (d, J=7.6 Hz, 1H), 7.87 (t, J=7.6 Hz, 1H), 7.48 (t, J=8.4 Hz, 1H), 6.89 (d, J=8.4 Hz, 2H), 6.84 (d, J=8.0 Hz, 1H), 4.74 (s, 2H), 3.60 (s, 6H), 3.41 (q, J=7.2 Hz, 2H), 1.03 (t, J=7.2 Hz, 3H). LC-MS: m/z 549.2 (M+H)$^+$

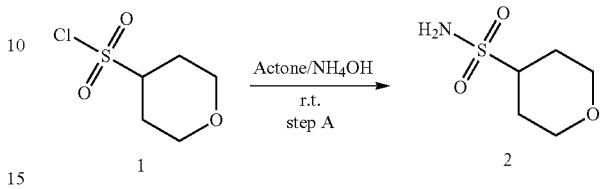

Step A: tetrahydro-2H-pyran-4-sulfonamide

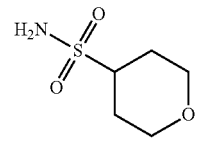

To a solution of tetrahydro-2H-pyran-4-sulfonyl chloride (300 mg, 1.6 mmol, 1.6 equiv) in acetone (5 mL) was added aqueous NH$_4$OH (34% wt., 10 mL, 140 mmol, 88 equiv). The mixture was stirred at room temperature overnight and then concentrated to dryness. The residue was purified by silica gel column chromatography (DCM/EtOAc=2/1) to afford the title compound tetrahydro-2H-pyran-4-sulfonamide as a white solid (150 mg, 56% yield).

LC-MS: m/z 166.2 (M+H)$^+$

Example 36: N-(1-(2,6-dimethoxyphenyl)-2-(6-ethoxypyridin-2-yl)-1H-imidazo[4,5-b]pyrazin-6-yl)tetrahydro-2H-pyran-4-sulfonamide

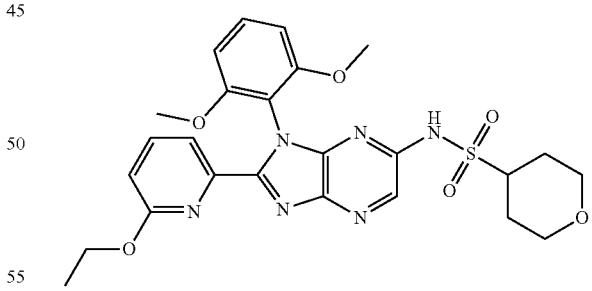

The title compound was prepared according to Method C, step D, starting from N-(5-chloro-3-((2,6-dimethoxyphenyl)amino)pyrazin-2-yl)-6-ethoxypicolinamide by using tetrahydro-2H-pyran-4-sulfonamide (25 mg, 32% yield).

$^1$H NMR (DMSO-d$_6$) δ:10.93-11.20 (m, 1H), 8.28 (s, 1H), 7.96 (d, J=8.0 Hz, 1H), 7.85 (t, J=8.0 Hz, 1H), 7.46 (t, J=7.6 Hz, 1H), 6.88 (d, J=8.8 Hz, 2H), 6.82 (d, J=8.0 Hz, 1H), 3.87-3.91 (m, 2H), 3.58 (s, 7H), 3.39 (q, J=7.2 Hz, 2H), 3.07 (t, J=11.2 Hz, 2H), 1.75-1.78 (m, 2H), 1.55-1.66 (m, 2H), 1.02 (t, J=7.2 Hz, 3H). LC-MS: m/z 541.6 (M+H)$^+$ morpholine-4-sulfonamide

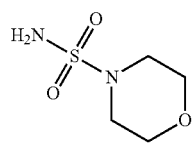

The title compound was prepared according to the preparation of tetrahydro-2H-pyran-4-sulfonamide by using morpholine-4-sulfonyl chloride.

$^1$H NMR (400 MHz, de-DMSO) δ: 6.82 (s, 2H), 3.61-3.68 (m, 4H), 2.89-2.94 (m, 4H).

Example 37: N-(1-(2,6-dimethoxyphenyl)-2-(6-ethoxypyridin-2-yl)-1H-imidazo[4,5-b]pyrazin-6-yl)morpholine-4-sulfonamide

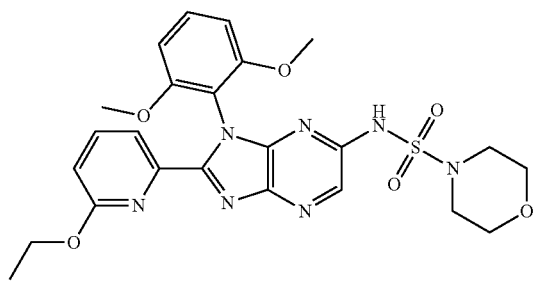 [SMILES: CCOc1cccc(-c2nc3ncc(NS(=O)(=O)N4CCOCC4)nc3n2-c2c(OC)cccc2OC)n1]

The title compound was prepared according to Method C, step D, starting from 6-bromo-1-(2,6-dimethoxyphenyl)-2-(6-ethoxypyridin-2-yl)-1H-imidazo[4,5-b]pyrazine (Example 1) by using morpholine-4-sulfonamide (39 mg, 65% yield).

$^1$H NMR (400 MHz, DMSO-d$_6$) δ: 11.03 (s, 1H), 8.24 (s, 1H), 7.97 (dd, J=7.4, 0.8 Hz, 1H), 7.85 (dd, J=8.2, 7.6 Hz, 1H), 7.45 (t, J=8.4 Hz, 1H), 6.86 (d, J=8.4 Hz, 2H), 6.82 (dd, J=8.2, 0.8 Hz, 1H), 3.60 (s, 6H), 3.42-3.46 (m, 4H), 3.38 (q, J=7.2 Hz, 2H), 2.90-2.95 (m, 4H), 1.02 (t, J=7.2 Hz, 3H). LC-MS: m/z 543.1 (M+H)$^+$ benzyl 4-(sulfamoylmethyl)piperidine-1-carboxylate

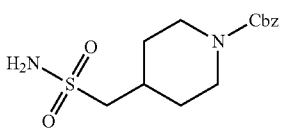 [SMILES: NS(=O)(=O)CC1CCN(C(=O)OCc2ccccc2)CC1]

The title compound was prepared according to the preparation of tetrahydro-2H-pyran-4-sulfonamide by using benzyl 4-((chlorosulfonyl)methyl)piperidine-1-carboxylate (350 mg, 56% yield).

LC-MS: m/z 313.1 (M+H)$^+$.

benzyl-4-((N-(1-(2,6-dimethoxyphenyl)-2-(6-ethoxypyridin-2-yl)-1H-imidazo[4,5-b]pyrazin-6-yl)sulfamoyl)methyl)piperidine-1-carboxylate

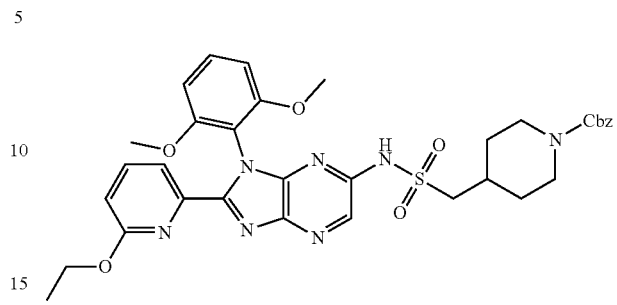

The title compound was prepared according to Method C, step D, starting from N-(5-chloro-3-((2,6-dimethoxyphenyl)amino)pyrazin-2-yl)-6-ethoxypicolinamide by using benzyl 4-(sulfamoylmethyl)piperidine-1-carboxylate (210 mg, 45% yield).

LC-MS: m/z 688.2 (M+H)$^+$

Example 38: N-(1-(2,6-dimethoxyphenyl)-2-(6-ethoxypyridin-2-yl)-1H-imidazo[4,5-b]pyrazin-6-y)-1-(piperidin-4-yl)methanesulfonamide

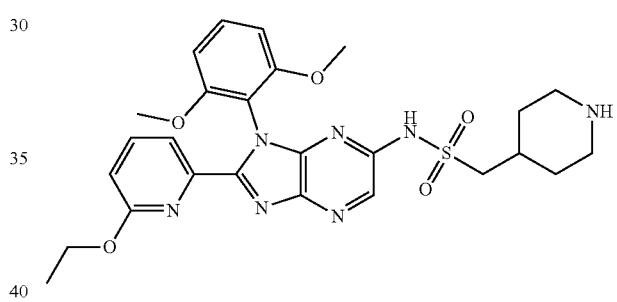

A solution of benzyl-4-((N-(1-(2,6-dimethoxyphenyl)-2-(6-ethoxypyridin-2-yl)-1H-imidazo[4,5-b]pyrazin-6-yl)sulfamoyl)methyl)piperidine-1-carboxylate (55 g, 0.08 mmol, 1.0 equiv) and con. HCl (1 mL) in EtOH (4 mL) was refluxed at 90° C. for 8 h. The reaction mixture was concentrated and residue was purified by flash column chromatography on silica gel (DCM/MeOH=10/1) to give the title compound as a yellow solid (40 mg, 90% yield).

$^1$H NMR (400 MHz, DMSO-d$_6$) δ: 8.23 (s, 1H), 7.81-7.83 (m, 2H), 7.74-7.77 (m, 1H), 7.38 (t, J=8.0 Hz, 1H), 6.81 (d, J=8.0 Hz, 2H), 6.68 (d, J=8.0 Hz, 1H), 3.57 (s, 6H), 3.36 (q, J=7.2 Hz, 2H), 3.11-3.14 (m, 2H), 2.95-2.96 (m, 2H), 2.76-2.82 (m, 2H), 1.94 (s, 1H), 1.81-1.84 (m, 2H), 1.18-1.27 (m, 2H), 1.01 (t, J=7.2 Hz, 3H). LC-MS: m/z 554.2 (M+H)$^+$.

4-oxocyclohexane-1-sulfonamide

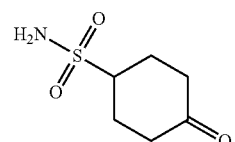

The title compound was prepared according to the preparation of tetrahydro-2H-pyran-4-sulfonamide by using 4-oxocyclohexane-1-sulfonyl chloride (150 mg, 56% yield). LC-MS: m/z 178.0 (M+H)+

N-(1-(2,6-dimethoxyphenyl)-2-(6-ethoxypyridin-2-yl)-1H-imidazo[4,5-b]pyrazin-6-yl)-4-oxocyclohexane-1-sulfonamide

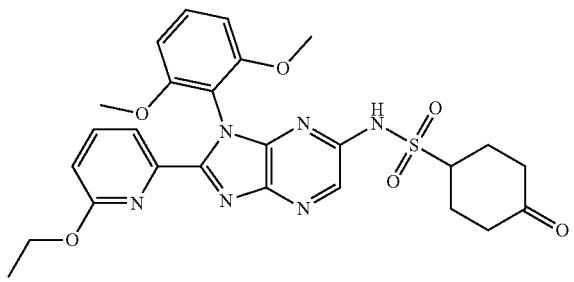 [SMILES: CCOc1cccc(-c2nc3ncc(NS(=O)(=O)C4CCC(=O)CC4)nc3n2-c2c(OC)cccc2OC)n1]

The title compound was prepared according to Method C, step D, starting from N-(5-chloro-3-((2,6-dimethoxyphenyl)amino)pyrazin-2-yl)-6-ethoxypicolinamide by using 4-oxocyclohexane-1-sulfonamide (140 mg, 69% yield).
LC-MS: m/z 553.2 (M+H)+

Example 39: trans-N-(1-(2,6-dimethoxyphenyl)-2-(6-ethoxypyridin-2-yl)-1H-imidazo[4,5-b]pyrazin-6-yl)-4-hydroxycyclohexane-1-sulfonamide Example 40: cis-N-(1-(2,6-dimethoxyphenyl)-2-(6-ethoxypyridin-2-yl)-1H-imidazo[4,5-b]pyrazin-6-yl)-4-hydroxycyclohexane-1-sulfonamide Ex. 39

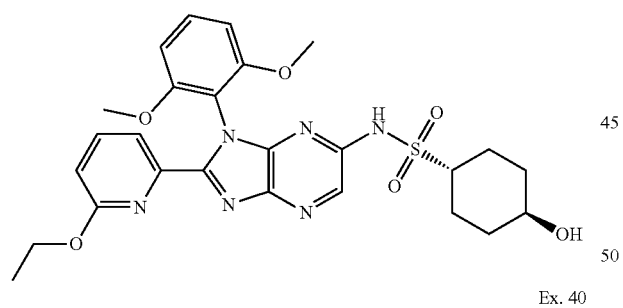

Ex. 40

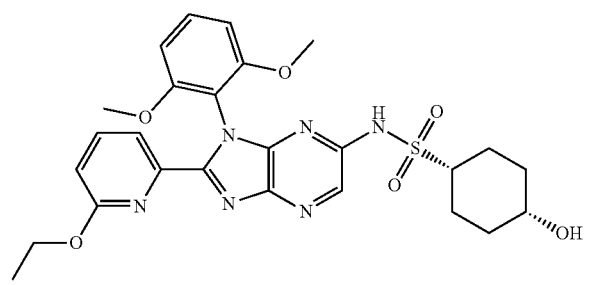

To a solution of N-(1-(2,6-dimethoxyphenyl)-2-(6-ethoxypyridin-2-yl)-1H-imidazo[4,5-b]pyrazin-6-yl)-4-oxocyclohexane-1-sulfonamide (135 mg, 0.244 mmol, 1.0 equiv) in MeOH (10 mL) was added NaBH$_4$ (18.6 mg, 0.49 mmol, 3.0 equiv). The mixture was stirred at 0° C. for 30 mins and at room temperature for 3 h. The reaction solution was quenched with 1N HCl (25 mL), extracted with DCM (3*25 mL). The combined organic phase was washed with brine (30 mL), dried over anhydrous Na$_2$SO$_4$, filtered and concentrated. The residue was purified by prep-TLC (DCM/MeOH=10/1) to give Example 39 (50 mg, 37% yield) and Example 40 (12 mg, 9% yield) as white solid.

Example 39: $^1$H NMR (400 MHz, DMSO-d$_6$) δ 10.88 (s, 1H), 8.31 (s, 1H), 7.97 (dd, J=7.4, 0.8 Hz, 1H), 7.86 (dd, J=8.2, 7.5 Hz, 1H), 7.46 (t, J=8.4 Hz, 1H), 6.77-6.98 (m, 3H), 4.66 (d, J=4.2 Hz, 1H), 3.59 (s, 6H), 3.40 (q, J=7.2 Hz, 2H), 3.30 (q, J=3.4, 2.8 Hz, 1H), 2.44-2.50 (m, 1H), 1.88 (dd, J=24.0, 12.8 Hz, 4H), 1.39-1.50 (m, 2H), 1.03 (t, J=7.2 Hz, 3H), 0.96 (dd, J=13.2, 10.0 Hz, 2H). LC-MS: m/z 555.2 (M+H)+

Example 40: $^1$H NMR (400 MHz, DMSO-d$_6$) δ 10.86 (s, 1H), 8.31 (s, 1H), 7.97 (dd, J=7.4, 0.8 Hz, 1H), 7.86 (dd, J=8.4, 7.6 Hz, 1H), 7.45 (t, J=8.4 Hz, 1H), 6.87 (d, J=8.4 Hz, 2H), 6.83 (dd, J=8.2, 0.8 Hz, 1H), 4.43 (d, J=2.8 Hz, 1H), 3.76 (d, J=5.6 Hz, 1H), 3.58 (s, 6H), 3.39 (q, J=7.2 Hz, 3H), 1.81 (q, J=14.0, 12.6 Hz, 2H), 1.59-1.74 (m, 4H), 1.19 (d, J=12.0 Hz, 2H), 1.02 (t, J=7.2 Hz, 3H). LC-MS: m/z 555.2 (M+H)+

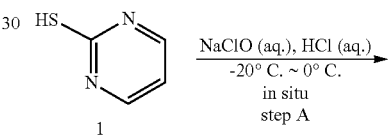

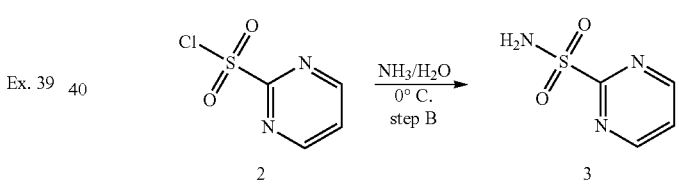

Step A: pyrimidine-2-sulfonyl chloride

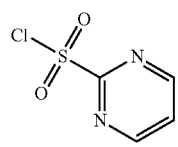

Sodium hypochlorite (30.9 mL, 60.0 mmol) was added dropwise with rapid stirring to a solution of 2-mercaptopyrimidine (1.1 g, 10 mmol) in CH$_2$Cl$_2$ (60 mL) and 1N HCl (55.0 mL, 55.0 mmol) at −20° C. After the addition was completed, the mixture was stirred at −20° C. for 15 mins. The organic layer was separated and used directly for next step.

Step B: pyrimidine-2-sulfonamide

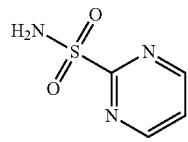

The solution of pyrimidine-2-sulfonyl chloride in CH₂Cl₂ (60 mL) was added to NH₄OH (aq., 34%, 60 mL) at 0° C. and the mixture was slowly allowed to warm to room temperature and stirred for 1 h. The mixture was concentrated under vacuum, residue was purified by silica gel chromatography (CH₂Cl₂/MeOH=20/1) to afford the title compound pyrimidine-2-sulfonamide as a light yellow solid (350 mg, 1.98 mmol, 20% yield in two steps).

LC-MS: m/z 160.0 (M+H)⁺

Example 41: N-(1-(2,6-dimethoxyphenyl)-2-(6-ethoxypyridin-2-yl)-1H-imidazo[4,5-b]pyrazin-6-yl)pyrimidine-2-sulfonamide

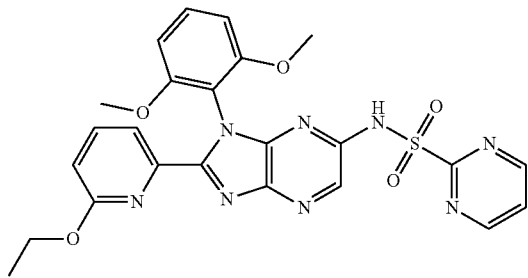 [SMILES: CCOc1cccc(-c2nc3ncc(NS(=O)(=O)c4ncccn4)nc3n2-c2c(OC)cccc2OC)n1]

The title compound was prepared according to Method C, step D, starting from 6-bromo-1-(2,6-dimethoxyphenyl)-2-(6-ethoxypyridin-2-yl)-1H-imidazo[4,5-b]pyrazine (Example 1) by using pyrimidine-2-sulfonamide (55 mg, 70%/yield).

¹H NMR (400 MHz, DMSO-d₆) δ: 11.91 (s, 1H), 8.82 (d, J=4.8 Hz, 2H), 8.35 (s, 1H), 7.92 (d, J=7.6 Hz, 1H), 7.83 (t, J=7.6 Hz, 1H), 7.67 (t, J=4.8 Hz, 1H), 7.41 (t, J=8.4 Hz, 1H), 6.78 (dd, J=11.4, 8.4 Hz, 3H), 3.50 (s, 6H), 3.35 (d, J=7.2 Hz, 2H), 1.00 (t, J=7.2 Hz, 3H). LC-MS: m/z 534.1 (M+H)⁺

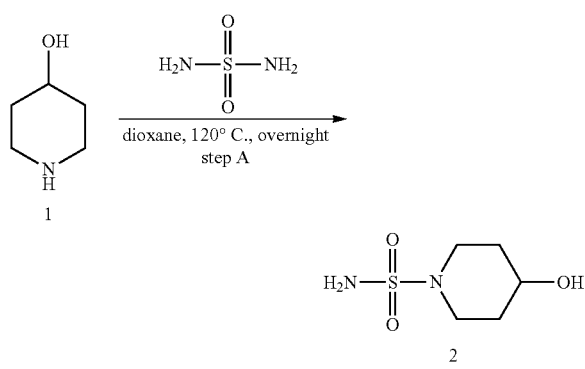

Step A: 4-hydroxypiperidine-1-sulfonamide

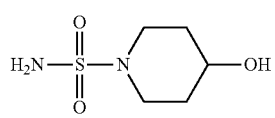 [SMILES: NS(=O)(=O)N1CCC(O)CC1]

A mixture of piperidin-4-ol (1.0 g, 10 mmol, 1.0 equiv) and sulfuric diamide (960 mg, 10 mmol, 1.0 equiv) in dioxane (20 mL) was stirred at 120° C. for 16 h. After evaporation, the residue was purified by flash column chromatography (eluting with DCM/MeOH=10/1) to afford the title compound 4-hydroxypiperidine-1-sulfonamide as a white solid, (1.09 g, 61% yield).

¹H NMR (400 MHz, DMSO-d₆) δ: 6.67 (s, 2H), 4.70 (d, J=3.6 Hz, 1H), 3.54-3.61 (m, 1H), 3.18-3.24 (m, 2H), 2.70-2.76 (m, 2H), 1.73-1.78 (m, 2H), 1.41-1.49 (m, 2H).

Example 42: N-(1-(2,6-dimethoxyphenyl)-2-(6-ethoxypyridin-2-yl)-1H-imidazo[4,5-b]pyrazin-6-yl)-4-hydroxypiperidine-1-sulfonamide

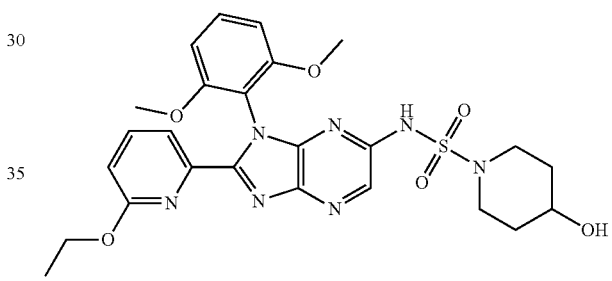

The title compound was prepared according to Method C, step D, starting from N-(5-chloro-3-((2,6-dimethoxyphenyl)amino)pyrazin-2-yl)-6-ethoxypicolinamide by using 4-hydroxypiperidine-1-sulfonamide (34.5 mg, 31% yield).

¹H NMR (400 MHz, CDCl₃) δ 8.38 (s, 1H), 8.11 (d, J=7.2 Hz, 1H), 7.65-7.69 (m, 1H), 7.35-7.40 (m, 1H), 7.18 (s, 1H), 6.67-6.70 (m, 3H), 3.67-3.73 (m, 1H), 3.63 (s, 6H), 3.39-3.49 (m, 4H), 2.96-3.03 (m, 2H), 1.74-1.81 (m, 2H), 1.44-1.53 (m, 2H), 1.08 (t, J=7.2 Hz, 3H). LC-MS: m/z 555.9 (M+H)⁺

Method D:

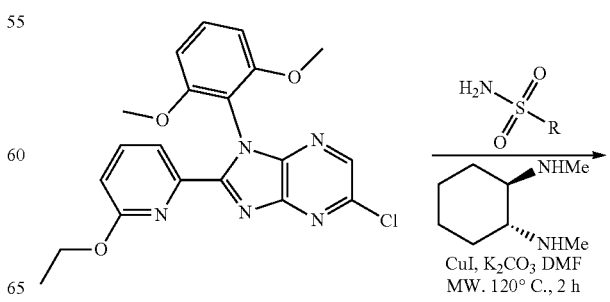

-continued

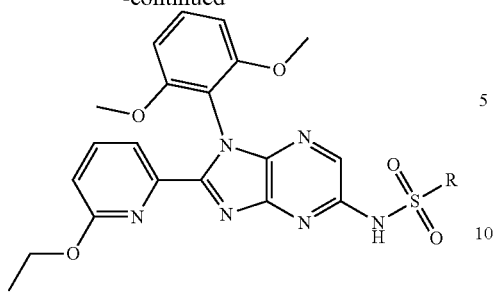

Example 43: N-(1-(2,6-dimethoxyphenyl)-2-(6-ethoxypyridin-2-yl)-1H-imidazo[4,5-b]pyrazin-5-yl)methanesulfonamide

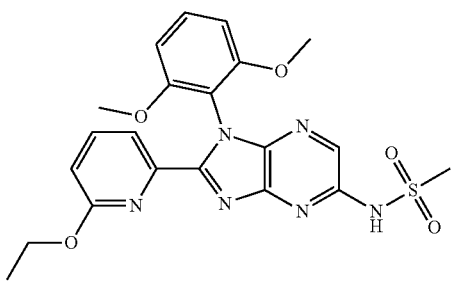 [SMILES: CCOc1cccc(-c2nc3nc(NS(C)(=O)=O)cnc3n2-c2c(OC)cccc2OC)n1]

The title compound was prepared according to Method C, step D, starting from 5-chloro-1-(2,6-dimethoxyphenyl)-2-(6-ethoxypyridin-2-yl)-1H-imidazo[4,5-b]pyrazine (Example 15) by using methanesulfonamide (26 mg, 23% yield).
$^1$H NMR (400 MHz, DMSO-d$_6$) δ: 11.11 (s, 1H), 7.98 (d, J=6.8 Hz, 1H), 7.95 (s, 1H), 7.86 (t, J=7.6 Hz, 1H), 7.45 (t, J=8.4 Hz, 1H), 6.85 (d, J=8.4 Hz, 2H), 6.82 (dd, J=8.2, 0.4 Hz, 1H), 3.58 (s, 6H), 3.39 (q, J=7.2 Hz, 2H), 3.36 (s, 3H), 1.03 (t, J=7.2 Hz, 3H). LCMS: m/z 471.0 (M+H)$^+$ Example 44: N-(1-(2,6-dimethoxyphenyl)-2-(6-ethoxypyridin-2-yl)-1H-imidazo[4,5-b]pyrazin-5-yl)methanesulfonamide

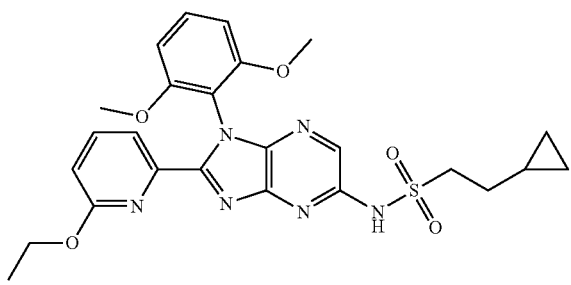 [SMILES: CCOc1cccc(-c2nc3nc(NS(=O)(=O)CCC4CC4)cnc3n2-c2c(OC)cccc2OC)n1]

The title compound was prepared according to Method C, step D, starting from 5-chloro-1-(2,6-dimethoxyphenyl)-2-(6-ethoxypyridin-2-yl)-1H-imidazo[4,5-b]pyrazine (Example 15) by using 2-cyclopropylethanesulfonamide (30 mg, 16% yield).
$^1$H NMR (400 MHz, DMSO-d$_6$) δ: 7.98-8.00 (m, 2H), 7.86 (t, J=8.0 Hz, 1H), 7.45 (t, J=8.4 Hz, 1H), 6.82-6.88 (m, 3H), 3.61-3.66 (m, 2H), 3.56 (s, 6H), 3.39 (q, J=7.2 Hz, 2H), 1.57-1.67 (m, 2H), 1.03 (t, J=7.2 Hz, 3H), 0.92-0.82 (m, 1H), 0.46-0.38 (m, 2H), 0.09 (q, J=4.8 Hz, 2H). LCMS: m/z 525.35 (M+H)$^+$ Example 45: 1-cyclopropyl-N-(1-(2,6-dimethoxyphenyl)-2-(6-ethoxypyridin-2-yl)-1H-imidazo[4,5-b]pyrazin-5-yl)methanesulfonamide

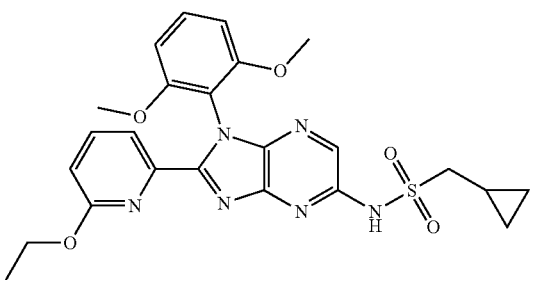 [SMILES: CCOc1cccc(-c2nc3nc(NS(=O)(=O)CC4CC4)cnc3n2-c2c(OC)cccc2OC)n1]

The title compound was prepared according to Method C, step D, starting from 5-chloro-1-(2,6-dimethoxyphenyl)-2-(6-ethoxypyridin-2-yl)-1H-imidazo[4,5-b]pyrazine (Example 15) by using cyclopropylmethanesulfonamide (20 mg, 32% yield). $^1$H NMR (400 MHz, DMSO-d$_6$) δ: 10.95 (s, 1H), 8.06 (s, 1H), 7.98-8.00 (m, 1H), 7.87 (t, J=8.0 Hz, 1H), 7.46 (t, J=8.0 Hz, 1H), 6.83-6.88 (m, 3H), 3.58 (s, 6H), 3.55 (d, J=8.0 Hz, 2H), 3.39 (q, J=7.2 Hz, 2H), 1.09-1.14 (m, 1H), 1.03 (t, J=7.2 Hz, 3H), 0.59-0.61 (m, 2H), 0.36-0.37 (m, 2H). LC-MS: m/z 511.0 (M+H)$^+$.

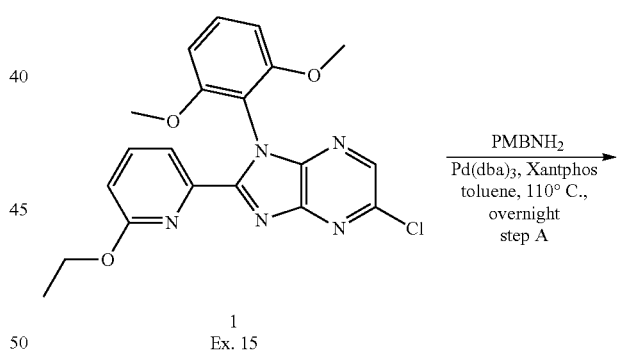

1
Ex. 15

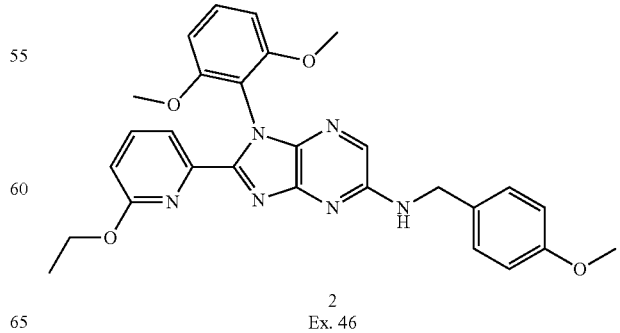

2
Ex. 46

Example 46: 1-(2,6-dimethoxyphenyl)-2-(6-ethoxy-pyridin-2-yl)-N-(4-methoxybenzyl)-1H-imidazo[4,5-b]pyrazin-5-amine

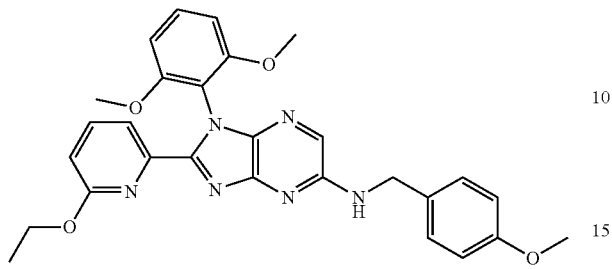

The mixture of 5-chloro-1-(2,6-dimethoxyphenyl)-2-(6-ethoxypyridin-2-yl)-1H-imidazo[4,5-b]pyrazine (Example 15, 100 mg, 0.24 mmol, 1.0 equiv), PMBNH$_2$ (67 mg, 0.48 mmol, 2.0 equiv), Xantphos (29 mg, 0.048 mmol, 0.2 equiv), Pd$_2$(dba)$_3$ (23 mg, 0.024 mmol, 0.1 equiv), $^t$BuOK (55 mg, 0.48 mmol, 2.0 equiv) in toluene (5 mL) was stirred at 110° C. for 16 hours under N$_2$ atmosphere. The mixture was filtered and the filtrate was concentrated in vacuo. The residue was purified by flash chromatography on silica gel (PE/EtOAc=10/1~1/1) to afford the title compound as a yellow solid (30 mg, 24% yield).

$^1$H NMR (400 MHz, DMSO) δ: 7.87 (d, J=7.2 Hz, 1H), 7.79 (t, J=7.6 Hz, 1H), 7.72 (s, 1H), 7.49 (t, J=5.6 Hz, 1H), 7.41 (t, J=8.4 Hz, 1H), 7.33 (d, J=8.4 Hz, 2H), 6.90 (d, J=8.4 Hz, 2H), 6.82 (d, J=8.4 Hz, 2H), 6.74 (d, J=7.6 Hz, 1H), 4.48 (d, J=5.6 Hz, 2H), 3.73 (s, 3H), 3.57 (s, 6H), 3.36 (q, J=7.2 Hz, 2H), 1.01 (t, J=7.2 Hz, 3H). LCMS: m/z 513.2 (M+H)$^+$

Method E:

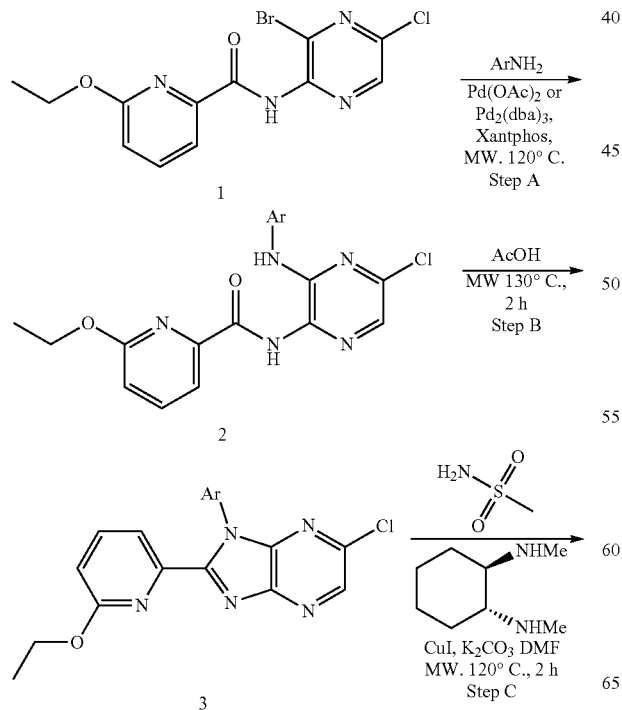

Step A: N-(5-chloro-3-((2-methoxy-6-(trifluoromethyl)phenyl)amino)pyrazin-2-yl)-6-ethoxypicolinamide

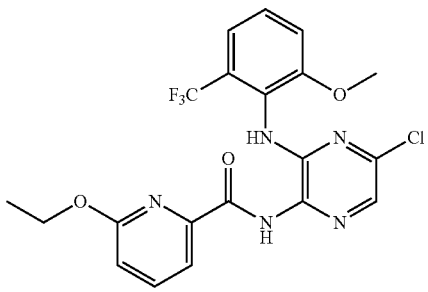 [SMILES: CCOc1cccc(C(=O)Nc2ncc(Cl)nc2Nc2c(OC)cccc2C(F)(F)F)n1]

A suspension of N-(3-bromo-5-chloropyrazin-2-yl)-6-ethoxypicolinamide (100 mg, 0.28 mmol, 1.0 equiv), 2-methoxy-6-(trifluoromethyl)aniline (53.5 mg, 0.28 mmol, 1.0 equiv), Pd$_2$(dba)$_3$ (102 mg, 0.11 mmol, 0.4 equiv), Xantphos (130 mg, 0.22 mmol, 0.8 equiv) and K$_2$CO$_3$ (77 mg, 0.56 mmol, 2.0 equiv) in 1,4-dioxane (2 mL) was stirred at 130° C. via microwave irradiation for 2 hours under N$_2$ atmosphere. The mixture was filtered through celite and the filtrate was concentrated in vacuo. The residue was purified by flash chromatography (eluting with EtOAc/PE=1/6) to afford the title compound N-(5-chloro-3-((2-methoxy-6-(trifluoromethyl)phenyl)amino)pyrazin-2-yl)-6-ethoxypicolinamide as a yellow solid (2 mg, 2% yield) and byproduct 2-(6-ethoxypyridin-2-yl)-1-(2-methoxy-6-(trifluoromethyl)phenyl)-1H-imidazo[4,5-b]pyrazin-6-ol (Example 47, 22 mg, 18% yield).

LC-MS: m/z 468.1 (M+H)$^+$

Example 47: 2-(6-ethoxypyridin-2-yl)-1-(2-methoxy-6-(trifluoromethyl)phenyl)-1H-imidazo[4,5-b]pyrazin-6-ol

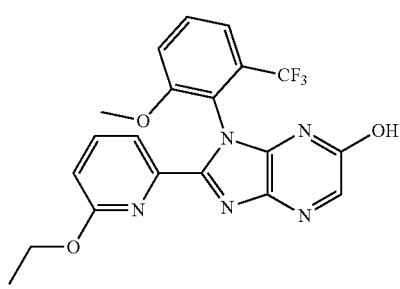 [SMILES: CCOc1cccc(-c2nc3ncc(O)nc3n2-c2c(OC)cccc2C(F)(F)F)n1]

¹H NMR (400 MHz, DMSO-d₆) δ: 9.28 (s, 1H), 8.17 (s, 1H), 7.91 (dd, J=8.2, 7.6 Hz, 1H), 7.84 (dd, J=7.6, 0.8 Hz, 1H), 7.57 (t, J=8.0 Hz, 1H), 7.49 (dd, J=8.4, 1.6 Hz, 1H), 7.40 (dd, J=8.0, 1.6 Hz, 1H), 7.00 (dd, J=8.4, 0.8 Hz, 1H), 4.41 (q, J=7.2 Hz, 2H), 3.76 (s, 3H), 1.35 (t, J=7.2 Hz, 3H). LC-MS: m/z 432.1 (M+H)⁺

Step B: 6-chloro-2-(6-ethoxypyridin-2-yl)-1-(2-methoxy-6-(trifluoromethyl)phenyl)-1H-imidazo[4,5-b]pyrazine

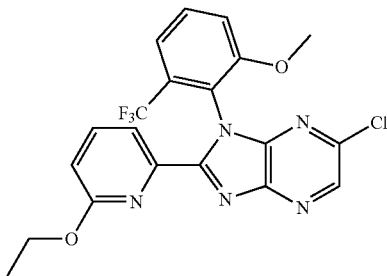 [SMILES: CCOc1cccc(-c2nc3ncc(Cl)nc3n2-c2c(OC)cccc2C(F)(F)F)n1]

A solution of N-(5-chloro-3-((2-methoxy-6-(trifluoromethyl)phenyl)amino)pyrazin-2-yl)-6-ethoxypicolinamide (35 mg, 0.075 mmol) in AcOH (2 mL) was stirred at 130° C. via microwave irradiation for 2 hours. The mixture was concentrated and the residue was purified by prep-TLC to afford the title compound 6-chloro-2-(6-ethoxypyridin-2-yl)-1-(2-methoxy-6-(trifluoromethyl)phenyl)-1H-imidazo[4,5-b]pyrazine as a yellow solid (25 mg, 74% yield). LC-MS: m/z 450.0 (M+H)⁺

Example 48: N-(2-(6-ethoxypyridin-2-yl)-1-(2-methoxy-6-(trifluoromethyl)phenyl)-1H-imidazo[4,5-b]pyrazin-6-yl) methanesulfonamide

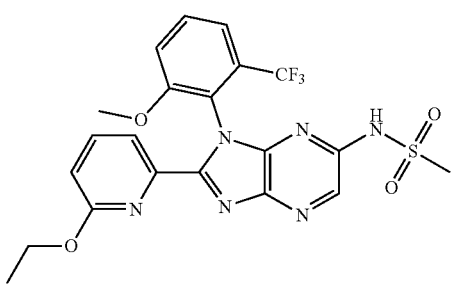 [SMILES: CCOc1cccc(-c2nc3ncc(NS(C)(=O)=O)nc3n2-c2c(OC)cccc2C(F)(F)F)n1]

A suspension of 6-chloro-2-(6-ethoxypyridin-2-yl)-1-(2-methoxy-6-(trifluoromethyl)phenyl)-1H-imidazo[4,5-b] pyrazine (25 mg, 0.056 mmol), Methanesulfonamide (11 mg, 0.112 mmol, 2 equiv), CuI (21 mg, 0.112 mmol, 2 equiv), trans-N,N'-Dimethylcyclohexane-1,2-diamine (16 mg, 0.112 mmol, 2 equiv) and K₂CO₃ (23 mg, 0.167 mmol, 3 equiv) in DMF (2 mL) was stirred at 130° C. via microwave irradiation for 2 hours under N₂ atmosphere. The mixture was diluted with EtOAc (30 mL) and filtered through celite. The filtrate was poured into aqueous K₂CO₃ (2 mol/L, 50 mL), stirred for 15 mins. Then the aqueous phase was separated and washed by EtOAc (2*30 mL). The aqueous phase was adjusted to pH=3 with 1N HCl and extracted with DCM (3*100 mL). The combined organic layers were washed with brine, dried over anhydrous Na₂SO₄ and concentrated in vacuo. The residue was purified by flash chromatography (eluting with DCM/MeOH=20/1~10/1) to afford the title compound as a white solid. (10 mg, 35% yield).

¹H NMR (400 MHz, DMSO-d₆) δ: 11.13 (s, 1H), 8.32 (s, 1H), 8.06 (dd, J=7.4, 0.8 Hz, 1H), 7.88 (dd, J=8.4, 7.6 Hz, 1H), 7.74-7.83 (m, 1H), 7.61-7.70 (m, 1H), 7.56 (dd, J=8.0, 1.2 Hz, 1H), 6.85 (dd, J=8.4, 0.8 Hz, 1H), 3.65 (s, 3H), 3.22 (q, J=7.2 Hz, 2H), 3.12 (s, 3H), 1.00 (t, J=7.2 Hz, 3H). LC-MS: m/z 509.1 (M+H)⁺

Example 49: N-(2-(6-ethoxypyridin-2-yl)-1-(3-methoxypyridin-2-yl)-1H-imidazo[4,5-b]pyrazin-6-yl)methanesulfonamide

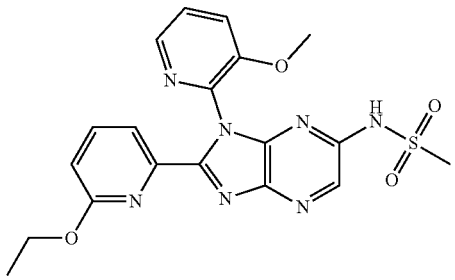 [SMILES: CCOc1cccc(-c2nc3ncc(NS(C)(=O)=O)nc3n2-c2ncccc2OC)n1]

The title compound was prepared according to Method E by using 3-methoxypyridin-2-amine in step A.

¹H NMR (400 MHz, CDCl₃) δ: 8.55 (s, 1H), 8.25 (dd, J=4.8, 1.2 Hz, 1H), 8.15 (d, J=4.0 Hz, 1H), 7.71 (t, J=8.0 Hz, 1H), 7.45-7.48 (m, 1H), 7.39-7.41 (m, 1H), 7.15 (s, 1H), 6.72 (d, J=8.0 Hz, 1H), 3.66 (s, 3H), 3.35-3.40 (m, 2H), 3.17 (s, 3H), 1.08 (t, J=8.0 Hz, 3H). LC-MS: m/z 442.0 (M+H)⁺.

Example 50: N-(benzylsulfonyl)-4-(2-fluoro-6-methoxyphenyl)-5-(6-methoxypyridin-2-yl)-4H-1,2,4-triazole-3-carboxamide

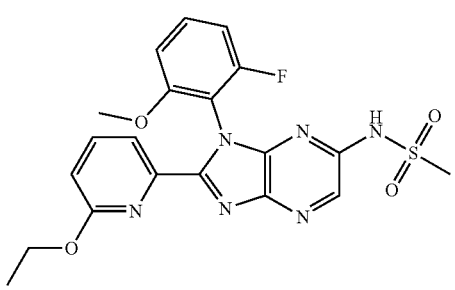 [SMILES: CCOc1cccc(-c2nc3ncc(NS(C)(=O)=O)nc3n2-c2c(F)cccc2OC)n1]

The title compound was prepared according to Method E by using 2-fluoro-6-methoxyaniline in step A.

¹H NMR (400 MHz, DMSO-d₆) δ: 11.17 (s, 1H), 8.31 (s, 1H), 7.99 (d, J=7.6 Hz, 1H), 7.89 (t, J=7.6 Hz, 1H), 7.56 (dd, J=15.2, 8.4 Hz, 1H), 7.05-7.18 (m, 2H), 6.87 (d, J=8.4 Hz, 1H), 3.61 (s, 3H), 3.41 (q, J=7.2 Hz, 2H), 3.19 (s, 3H), 1.04 (t, J=7.2 Hz, 3H). LC-MS: m/z 459.1 (M+H)⁺

Method F:

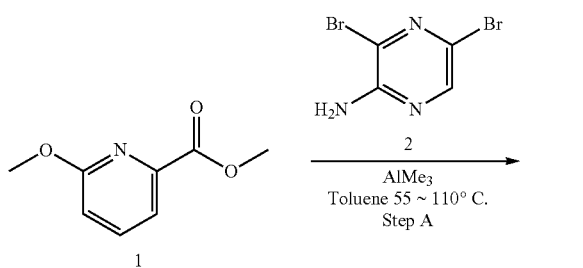

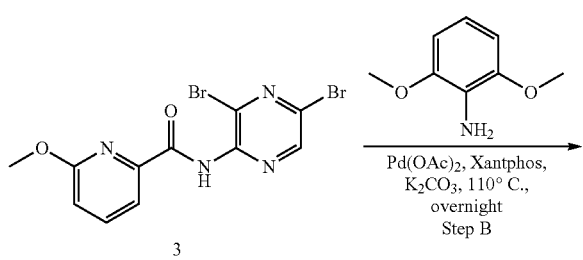

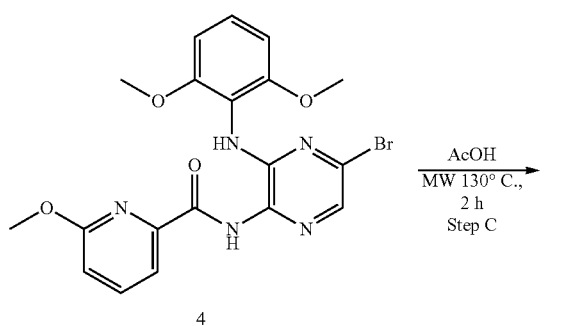

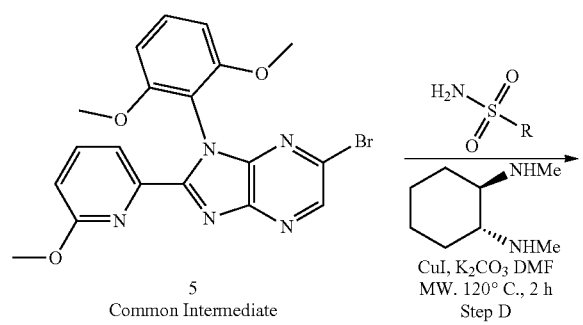

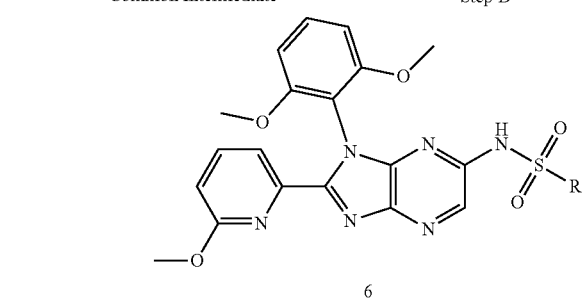

Step A:
N-(3,5-dibromopyrazin-2-yl)-6-methoxypicolinamide

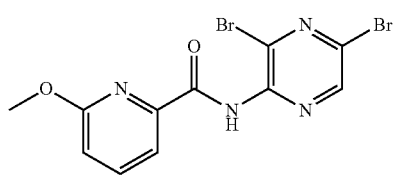 [SMILES: COc1cccc(C(=O)Nc2ncc(Br)nc2Br)n1]

To a solution of 3,5-dibromopyrazin-2-amine (13.6 g, 54 mmol, 1.3 equiv) in THF was added AlMe₃ (1.6 mol/L, 34 mL, 54 mmol, 1.3 equiv) dropwise at room temperature under argon atmosphere. The mixture was stirred at room temperature for 0.5 h. Then 3,5-dibromopyrazin-2-amine (6.8 g., 41 mmol, 1.0 equiv) was added in one portion. The mixture was stirred at 60° C. for 1.5 h, quenched with 1N HCl (aq.) and extracted with ethyl acetate for three times. The extracts were washed with brine, dried over anhydrous Na₂SO₄ and concentrated in vacuo. The residue was purified by column chromatography on silica gel to afford the title compound N-(3,5-dibromopyrazin-2-yl)-6-methoxypicolinamide as a yellow solid (14 g, 88.1% yield).

LC-MS: m/z 386.8, 388.8, 390.8 (M+H)⁺

Step B: N-(5-bromo-3-((2,6-dimethoxyphenyl) amino)pyrazin-2-yl)-6-methoxypicolinamide

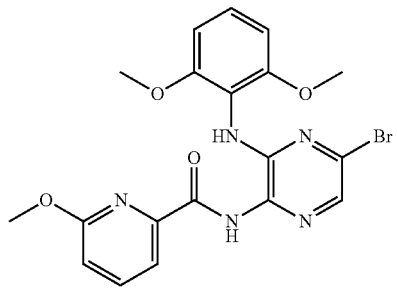 [SMILES: COc1cccc(C(=O)Nc2ncc(Br)nc2Nc2c(OC)cccc2OC)n1]

A suspension of N-(3,5-dibromopyrazin-2-yl)-6-methoxypicolinamide (600 mg, 1.54 mmol, 1.0 equiv), 2,6-dimethoxyaniline (236 mg, 1.54 mmol, 1.0 equiv), Pd(OAc)₂ (70 mg, 0.31 mmol, 0.2 equiv), Xantphos (358 mg, 0.62 mmol, 0.4 equiv) and K₂CO₃ (440 mg, 3.1 mmol, 2.0 equiv) in 1,4-dioxane (10 mL) was stirred at 120° C. via microwave irradiation for 2 hour under N₂ atmosphere. The mixture was filtered through celite and the filtrate was concentrated in vacuo. The residue was purified by flash column chromatography (PE/EtOAc=4/1) to afford the desired product N-(5-bromo-3-((2,6-dimethoxyphenyl) amino)pyrazin-2-yl)-6-methoxypicolinamide (70 mg, 10% yield).

LC-MS: m/z 459.9, 461.9 (M+H)⁺

Step C: 6-bromo-1-(2,6-dimethoxyphenyl-2-(6-ethoxypyridin-2-yl)-1H-imidazo[4,5-b]pyrazine

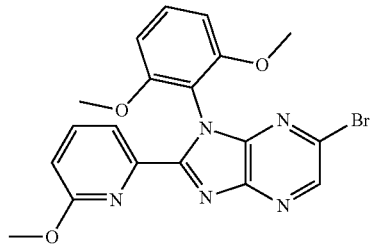 [SMILES: COc1cccc(-c2nc3ncc(Br)nc3n2-c2c(OC)cccc2OC)n1]

A solution of N-(5-bromo-3-((2,6-dimethoxyphenyl)amino)pyrazin-2-yl)-6-methoxypicolinamide (700 mg, 1.53 mmol) in AcOH (10 mL) was stirred at 120° C. via microwave irradiation for 2 hour. The reaction mixture was concentrated in vacuo and the residue was purified by column chromatography to give the desired product 6-bromo-1-(2,6-dimethoxyphenyl)-2-(6-ethoxypyridin-2-yl)-1H-imidazo[4,5-b]pyrazine as a light yellow solid (475 mg, 70%).
LC-MS: m/z 442.3, 444.3 (M+H)$^+$ Example 51: N-(1-(2,6-dimethoxyphenyl)-2-(6-methoxypyridin-2-yl)-1H-imidazo[4,5-b]pyrazin-6-yl)methanesulfonamide

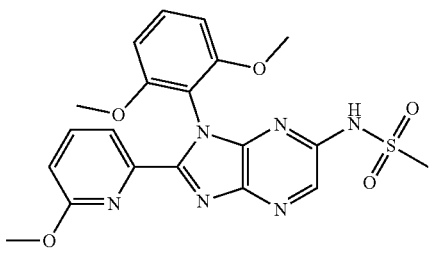

The title compound was prepared according to Method F by using methanesulfonamide in step D (72 mg, 78% yield).
$^1$H NMR (400 MHz, DMSO-d$_6$) δ: 11.05 (s, 1H), 8.30 (s, 1H), 7.95 (d, J=8.0 Hz, 1H), 7.87 (d, J=8.0 Hz, 1H), 7.44 (t, J=8.0 Hz, 1H), 6.85 (d, J=8.0 Hz, 3H), 3.57 (s, 6H), 3.20 (s, 3H), 3.11 (s, 3H). LC-MS: m/z 457.0 (M+H)$^+$ Example 52: N-(1-(2,6-dimethoxyphenyl)-2-(6-methoxypyridin-2-yl)-1H-imidazo[4,5-b]pyrazin-6-yl)pyridine-2-sulfonamide

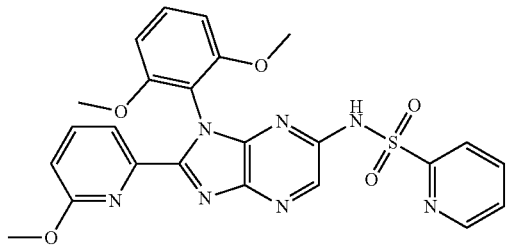 [SMILES: COc1cccc(-c2nc3ncc(NS(=O)(=O)c4ccccn4)nc3n2-c2c(OC)cccc2OC)n1]

The title compound was prepared according to Method F by using pyridine-2-sulfonamide in step D (34 mg, 33% yield).
$^1$H NMR (400 MHz, DMSO-d$_6$) δ: 11.77 (s, 1H), 8.59 (d, J=4.0 Hz, 1H), 8.29 (s, 1H), 7.91-7.96 (m, 1H), 7.81-7.86 (m, 1H), 7.77 (td, J=7.8, 1.6 Hz, 1H), 7.61 (d, J=7.6 Hz, 1H), 7.57 (dd, J=4.0, 3.2 Hz, 1H), 7.49 (t, J=8.4 Hz, 1H), 6.86 (d, J=8.4 Hz, 2H), 6.83 (dd, J=8.4, 0.8 Hz, 1H), 3.51 (s, 6H), 3.08 (s, 3H). LC-MS: m/z 520.0 (M+H)$^+$ Example 53: N-(1-(2,6-dimethoxyphenyl)-2-(6-methoxypyridin-2-yl)-1H-imidazo[4,5-b]pyrazin-6-yl)pyrimidine-2-sulfonamide

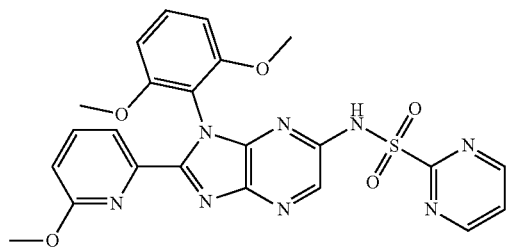 [SMILES: COc1cccc(-c2nc3ncc(NS(=O)(=O)c4ncccn4)nc3n2-c2c(OC)cccc2OC)n1]

The title compound was prepared according to Method F by using pyridine-2-sulfonamide in step D (15 mg, 29% yield).
$^1$H NMR (400 MHz, DMSO-d$_6$) δ: 11.91 (s, 1H), 8.80 (d, J=4.8 Hz, 2H), 8.32 (s, 1H), 7.91 (dd, J=7.6, 0.8 Hz, 1H), 7.83 (dd, J=8.4, 7.6 Hz, 1H), 7.63 (t, J=4.8 Hz, 1H), 7.39 (t, J=8.4 Hz, 1H), 6.79-6.85 (m, 1H), 6.76 (d, J=8.4 Hz, 2H), 3.50 (s, 6H), 3.06 (s, 3H). LC-MS: m/z 521.1 (M+H)$^+$
Method G:

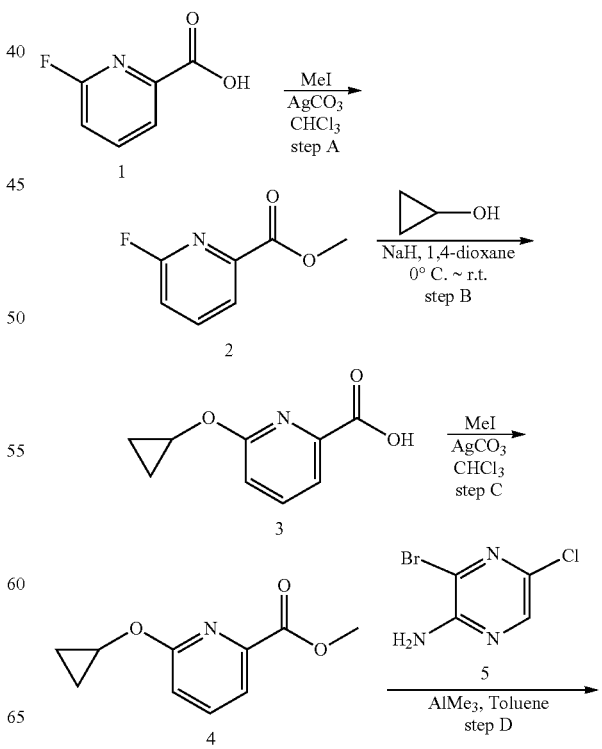

-continued

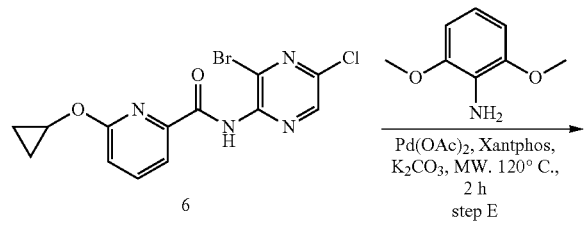
6

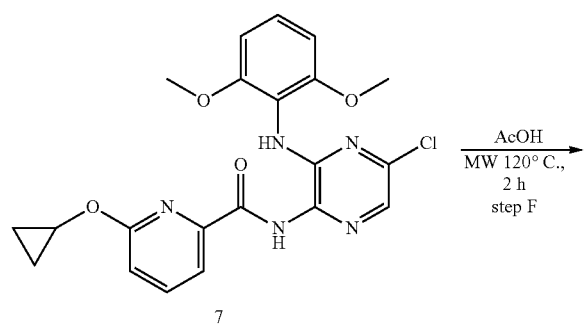
7

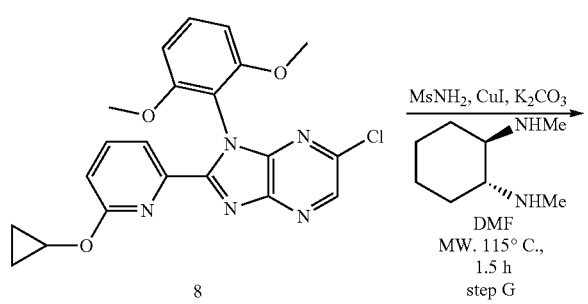
8

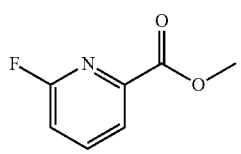
9

Step A: methyl 6-fluoropicolinate

Methyl iodide (20 g, 142 mmol, 3.0 equiv) was added to a suspension of 6-fluoropicolinic acid (10.0 g, 71 mmol, 1.0 equiv) and silver(I) carbonate (19.5 g, 71 mmol, 1.0 equiv) in CHCl$_3$ (100 mL). The suspension was stirred at 30° C. for 1 day. Insoluble material was removed by filtration and the filter cake was washed with CHCl$_3$. The filtrate was concentrated in vacuo to give the title compound as a light yellow solid (9.0 g, 82% yield). This material was used in the next step without further purification.

LC-MS: m/z 156.0 (M+H)$^+$

Step B: 6-cyclopropoxypicolinic acid

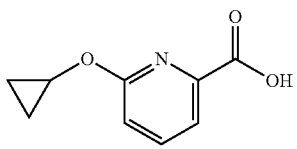 [SMILES: O=C(O)c1cccc(OC2CC2)n1]

To a mixture of cyclopropanol (1.5 g, 25.8 mmol, 3.0 equiv) in dioxane (20 mL) was added NaH (1032 mg, 25.8 mmol, 3.0 equiv) at 0° C. and the mixture was stirred at 0° C. for 30 mins. Then methyl 6-fluoropicolinate (2.0 g, 12.9 mmol, 1.0 equiv) was added and the mixture was stirred at 25° C. for 2 h. The reaction mixture was quenched with saturated aqueous NH$_4$Cl solution. The mixture was washed with EtOAc three times. The aqueous phase was acidified with concentrated hydrochloric acid and extracted with DCM (3*30 mL). The combined organic layers were washed with brine, dried over anhydrous sodium sulfate and concentrated in vacuo. The residue was purified by silica gel column chromatography to afford 6-cyclopropoxypicolinic acid as a white solid (600 mg, 13% yield).

LC-MS: m/z 180.0 (M+H)$^+$

Step C: methyl 6-cyclopropoxypicolinate

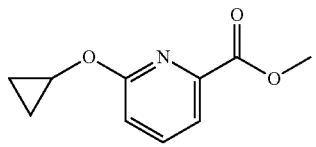

Methyl iodide (0.41 ml, 6.59 mmol, 3.0 equiv) was added to a suspension of 6-cyclopropoxypicolinic acid (590 mg, 3.29 mmol, 1.0 equiv) and silver(I) carbonate (1091 mg, 3.95 mmol, 1.2 equiv) in CHCl$_3$ (10 ml). The suspension was stirred at 30° C. for 4 h. Insoluble material was removed by filtration and the filter cake was washed with CHCl$_3$. The filtrate was concentrated to give the title compound methyl 6-cyclopropoxypicolinate as a light yellow oil (600 mg, 94% yield). This material was used in the next step without further purification.

LC-MS: m/z 194.0 (M+H)$^+$

Step D: N-(3-bromo-5-chloropyrazin-2-yl)-6-cyclopropoxypicolinamide

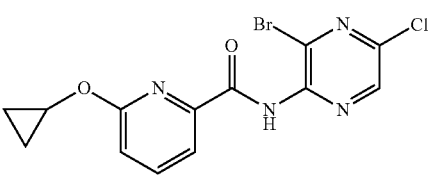 [SMILES: O=C(Nc1ncc(Cl)nc1Br)c1cccc(OC2CC2)n1]

To a mixture of 3-bromo-5-chloropyrazin-2-amine (644 mg, 3.1 mmol, 1.0 equiv) and toluene (10 mL) was added AlMe$_3$ (1.6 mol/L in toluene, 4 mL, 6.2 mmol, 2.0 equiv).

After the mixture was stirred at 50° C. for 30 mins, methyl 6-cyclopropoxypicolinate (600 mg, 3.1 mmol, 1.0 equiv) was added. The mixture was stirred at 110° C. for 1 h and was quenched with 1N aqueous HCl solution. The mixture was extracted with DCM three times. The combined organic layers were washed with brine, dried over anhydrous sodium sulfate and concentrated in vacuo. The residue was purified by silica gel column chromatography (100% DCM) to afford the title compound N-(3-bromo-5-chloropyrazin-2-yl)-6-cyclopropoxypicolinamide (500 mg, 44% yield).

LC-MS: m/z 369.0, 371.0 (M+H)+

Step E: N-(5-chloro-3-((2,6-dimethoxyphenyl)amino)pyrazin-2-yl)-6-cyclopropoxypicolinamide

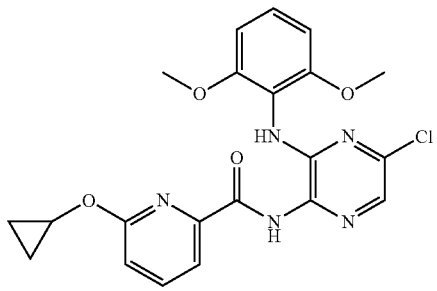 [SMILES: COc1cccc(OC)c1Nc1nc(Cl)cnc1NC(=O)c1cccc(OC2CC2)n1]

A suspension of N-(3-bromo-5-chloropyrazin-2-yl)-6-cyclopropoxypicolinamide (500 mg, 1.36 mmol, 1.0 equiv), 2,6-dimethoxyaniline (229 mg, 1.49 mmol, 1.1 equiv), Pd(OAc)$_2$ (61 mg, 0.27 mmol, 0.2 equiv), Xantphos (315 mg, 0.54 mmol, 0.4 equiv) and K$_2$CO$_3$ (375 mg, 2.72 mmol, 2.0 equiv) in 1,4-dioxane (3 mL) was stirred at 125° C. via microwave irradiation for 2 hours under N$_2$ atmosphere. The mixture was filtered through celite and the filtrate was concentrated in vacuo. The residue was purified by flash chromatography (100% DCM) to afford the title compound N-(5-chloro-3-((2,6-dimethoxyphenyl)amino)pyrazin-2-yl)-6-cyclopropoxypicolinamide as a yellow solid (247 mg, 41% yield).

LC-MS: m/z 442.1 (M+H)+

Step F: 6-chloro-2-(6-cyclopropxypyridin-2-yl)-1-(2,6-dimethoxyphenyl)-1H-imidazo[4,5-b]pyrazine

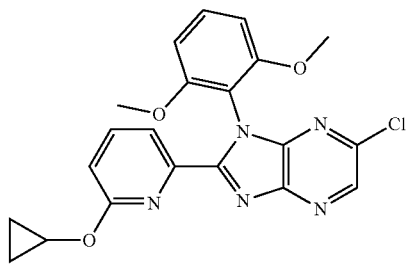 [SMILES: COc1cccc(OC)c1-n1c(-c2cccc(OC3CC3)n2)nc2ncc(Cl)nc21]

A solution of N-(5-chloro-3-((2,6-dimethoxyphenyl)amino)pyrazin-2-yl)-6-cyclopropoxypicolinamide (247 mg, 0.56 mmol, 1.0 equiv) in AcOH (2 mL) was stirred at 130° C. via microwave irradiation for 2 hours. The reaction mixture was cooled to room temperature and the precipitate was filtered off and washed with a solvent mixture of EA/PE=1/2 to afford the title compound 6-chloro-2-(6-cyclopropoxypyridin-2-yl)-1-(2,6-dimethoxyphenyl)-1H-imidazo[4,5-b]pyrazine as a light yellow solid (170 mg, 72% yield).

LC-MS: m/z 424.1 (M+H)+

Example 54: N-(2-(6-cyclopropoxypyridin-2-yl)-1-(2,6-dimethoxyphenyl)-1H-imidazo[4,5-b]pyrazin-6-yl)methanesulfonamide

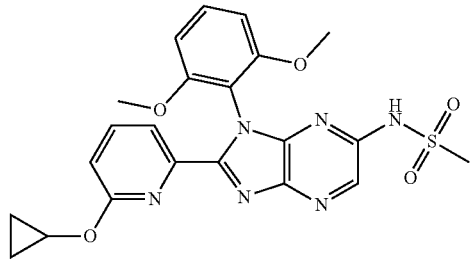 [SMILES: COc1cccc(OC)c1-n1c(-c2cccc(OC3CC3)n2)nc2ncc(NS(C)(=O)=O)nc21]

A suspension of 6-chloro-2-(6-cyclopropoxypyridin-2-yl)-1-(2,6-dimethoxyphenyl)-1H-imidazo[4,5-b]pyrazine (80 mg, 0.19 mmol 1.0 equiv), methanesulfonamide (36.1 mg, 0.38 mmol, 2.0 equiv), CuI (72 mg, 0.38 mmol, 2.0 equiv), trans-N,N'-Dimethylcyclohexane-1,2-diamine (54 mg, 0.38 mmol, 2.0 equiv) and K$_2$CO$_3$ (78 mg, 0.57 mmol, 3.0 equiv) in DMF (3 mL) was stirred at 120° C. via microwave irradiation for 2 hours under N$_2$ atmosphere. The mixture was diluted with EtOAc (30 mL) and filtered through celite. The filtrate was poured into water (50 mL). The mixture was adjusted to pH=4 with 1N HCl and extracted with EA (3*100 mL). The organic layers were dried over anhydrous Na$_2$SO$_4$ and concentrated in vacuo. The residue was purified by flash column chromatography (eluting with DCM/MeOH=20/1) to afford the title compound as write solid (55 mg, 60% yield).

$^1$H NMR (400 MHz, DMSO-d$_6$) δ: 11.06 (s, 1H), 8.27 (s, 1H), 7.97 (dd, J=7.6, 0.8 Hz, 1H), 7.87 (t, J=8.4 Hz, 1H), 7.40 (t, J=8.4 Hz, 1H), 6.77-6.87 (m, 3H), 3.56 (s, 6H), 3.15-3.22 (m, 4H), 0.42-0.50 (m, 2H), 0.27-0.41 (m, 2H).
LC-MS: m/z 483.1 (M+H)+

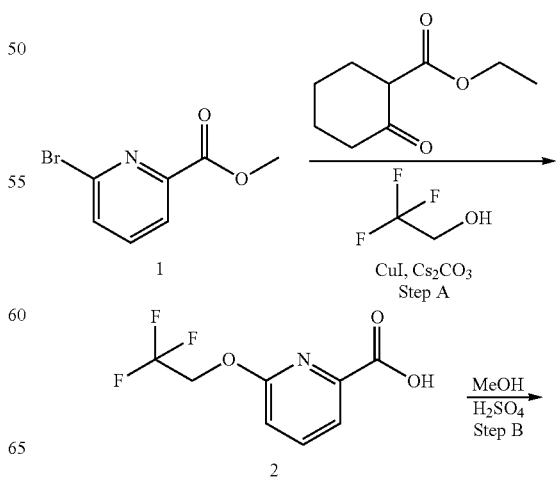

-continued

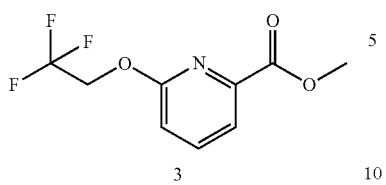

Step A: 6-(2,2,2-trifluoroethoxy)picolinic acid

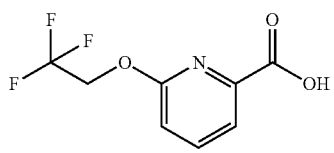 [SMILES: O=C(O)c1cccc(OCC(F)(F)F)n1]

The mixture of methyl 6-bromopicolinate (4.3 g, 20 mmol, 1.0 equiv), ethyl 2-oxocyclohexane-1-carboxylate (680 mg, 4 mmol, 0.2 equiv), CuI (380 mg, 2 mmol, 0.1 equiv) and Cs$_2$CO$_3$ (9.1 g, 28 mmol, 1.4 equiv) in 2,2,2-trifluoroethan-1-ol (14.0 g, 280 mmol, 14 equiv) was heated under nitrogen atmosphere at 78° C. for 20 hours. The reaction mixture was cooled to 20° C. and poured into water (200 mL). The mixture was adjusted to pH=5 with 1N HCl (aq.) and extracted with DCM (3*20 mL). The combined organic phase was dried over anhydrous sodium sulfate and concentrated in vacuo to afford the title compound 6-(2,2,2-trifluoroethoxy)picolinic acid as yellow solid (3.3 g, 74% yield).

LC-MS: m/z 222.0 (M+H)$^+$

Step B: methyl 6-(2,2,2-trifluoroethoxy)picolinate

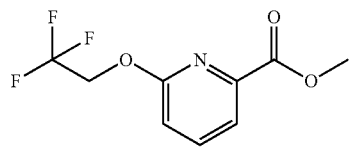 [SMILES: COC(=O)c1cccc(OCC(F)(F)F)n1]

To a solution of 6-(2,2,2-trifluoroethoxy)picolinic acid (2.2 g, 10 mmol, 1.0 equiv) in methanol (20 mL) were added 2 drops of H$_2$SO$_4$ (con.). The mixture was stirred at 20° C. for 20 hours, diluted with H$_2$O (100 mL) and extracted with DCM (3*20 mL). The combined organic phase was dried over anhydrous sodium sulfite and concentrated in vacuo. The residue was purified by silica gel chromatography (PE/EA=20/1) to afford the title compound methyl 6-(2,2,2-trifluoroethoxy)picolinate as a colorless oil (2.1 g, 88% yield).

LC-MS: m/z 236.1 (M+H)$^+$

Example 55: N-(1-(2,6-dimethoxyphenyl)-2-(6-(trifluoroethoxy)pyridin-2-yl)-1H-imidazo[4,5-b]pyrazin-6-yl)methanesulfonamide

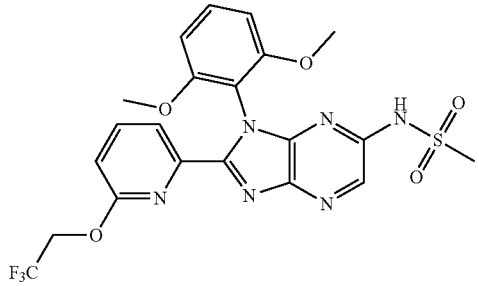 [SMILES: COc1cccc(OC)c1-n1c(-c2cccc(OCC(F)(F)F)n2)nc2ncc(NS(C)(=O)=O)nc21]

The title compound was prepared according to Method G by using methyl 6-(2,2,2-trifluoroethoxy)picolinate in step D. (15 mg, 10% yield).

$^1$H NMR (400 MHz, CDCl$_3$) δ: 8.55 (s, 1H), 8.27 (d, J=4.0 Hz, 1H), 7.79 (t, J=8.8 Hz, 1H), 7.43 (t, J=8.4 Hz, 1H), 7.07 (s, 1H), 6.86 (d, J=4.0 Hz, 1H), 6.73 (d, J=4.4 Hz, 2H), 3.74 (q, J=8.8 Hz, 2H), 3.63 (s, 6H), 3.18 (s, 3H). LC-MS: m/z 525.1 (M+H)$^+$

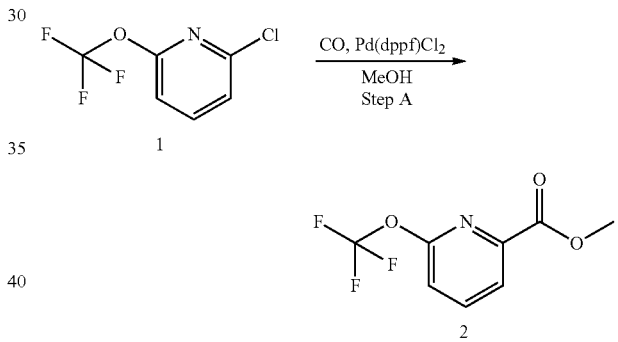

Step A: methyl 6-(trifluoromethoxy)picolinate

To a solution of 2-chloro-6-(trifluoromethoxy)pyridine (5.0 g, 25.3 mmol, 1.0 equiv) in MeOH (120 mL) was added Pd(dppf)Cl$_2$ (930 mg, 1.27 mmol, 0.05 equiv). The mixture was stirred at 100° C. under hydrogen atmosphere (50 Psi) for 48 hours. The reaction mixture was cooled to 20° C. and concentrated in vacuo. The residue was purified by silica gel chromatography (PE/EA=10/1) to afford the title compound methyl 6-(trifluoromethoxy)picolinate as yellow oil (3.85 g, 68% yield).

LC-MS: m/z 222.0 (M+H)$^+$

Example 56: N-(1-(2,6-dimethoxyphenyl)-2-(6-(trifluoromethoxy)pyridin-2-yl)-1H-imidazo[4,5-b]pyrazin-6-yl)methanesulfonamide

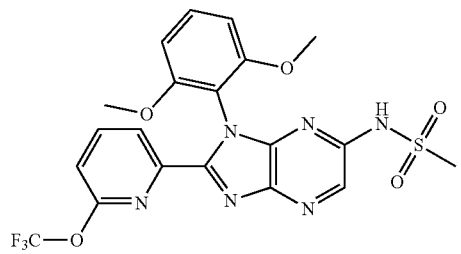 [SMILES: COc1cccc(OC)c1-n1c(-c2cccc(OC(F)(F)F)n2)nc2ncc(NS(C)(=O)=O)nc21]

The title compound was prepared according to Method G by using methyl 6-(trifluoromethoxy)picolinate in step D (30 mg, 15% yield).

$^1$H NMR (400 MHz, DMSO-$d_6$) δ: 8.26 (t, J=4.0 Hz, 1H), 8.19 (s, 1H), 8.17 (t, J=7.6 Hz, 1H), 7.43 (t, J=8.8 Hz, 1H), 7.29 (d, J=4.0 Hz, 1H), 6.79 (d, J=4.4 Hz, 2H), 3.54 (s, 6H), 3.10 (s, 3H). LC-MS: m/z 511.1 (M+H)$^+$

Example 57: N-(1-(2,6-dimethoxyphenyl)-2-(ethoxymethyl)-1H-imidazo[4,5-b]pyrazin-6-yl)benzenesulfonamide

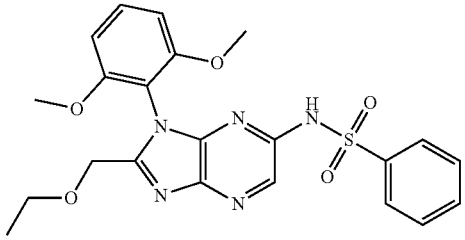

The title compound was prepared according to Method G by using ethyl 2-ethoxyacetate in step D and benzenesulfonamide in step G (39 mg, 29% yield).

$^1$H NMR (400 MHz, DMSO-$d_6$) δ: 11.52 (s, 1H), 8.16 (s, 1H), 7.69 (d, J=7.6 Hz, 2H), 7.54-7.70 (m, 2H), 7.36 (t, J=7.6 Hz, 2H), 6.94 (d, J=8.4 Hz, 2H), 4.42 (s, 2H), 3.65 (s, 6H), 3.28 (q, J=7.2 Hz, 2H), 0.92 (t, J=7.2 Hz, 3H). LC-MS: m/z 470.1 (M+H)$^+$

Method H:

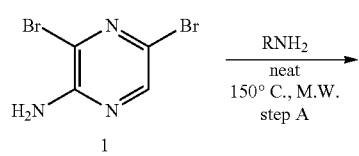

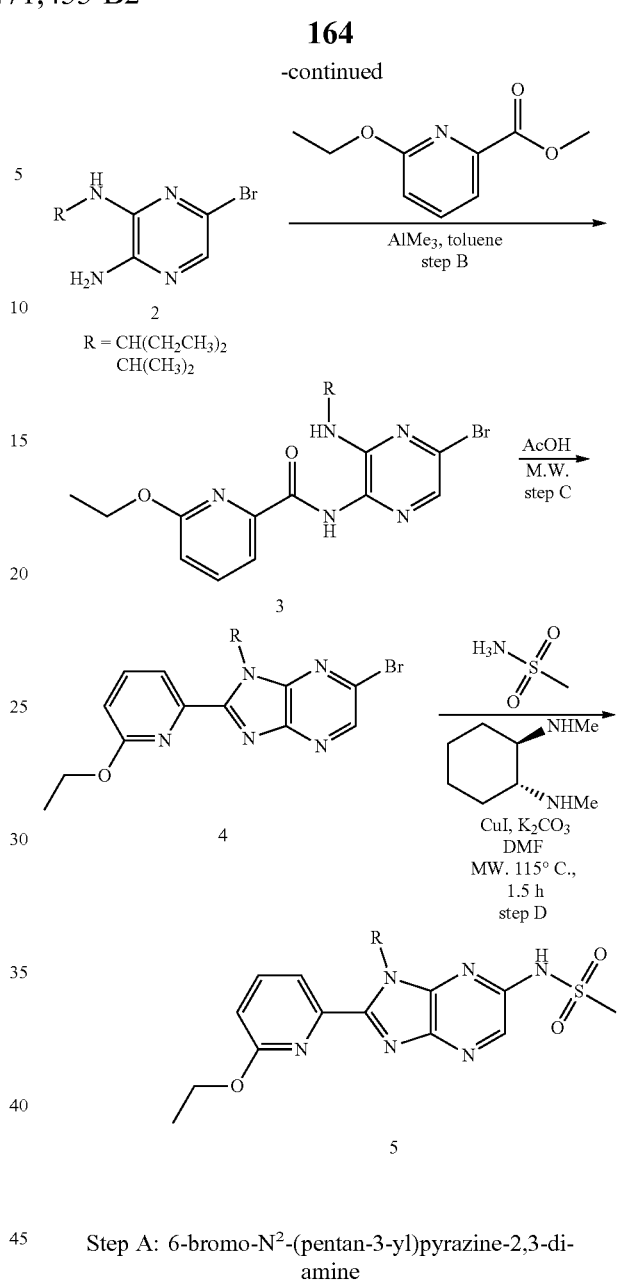

Step A: 6-bromo-N$^2$-(pentan-3-yl)pyrazine-2,3-diamine

A suspension of 3,5-dibromopyrazin-2-amine (1.0 g, 3.98 mmol, 1.0 equiv) in pentan-3-amine (10 mL) was stirred at 150° C. via microwave irradiation for 1 hour. The mixture was diluted with water (15 mL) and extracted with EtOAc (3*50 mL). The combined organic layers were dried over anhydrous Na$_2$SO$_4$ and concentrated in vacuo. The residue was purified by flash column chromatography (eluting with PE/EtOAc=20/1 to 5/1) to afford the title compound 6-bromo-N$^2$-(pentan-3-yl)pyrazine-2,3-diamine as light yellow solid (0.9 g, 88% yield). LC-MS: m/z 259.1, 261.1 (M+H)$^+$ Step B: N-(5-bromo-3-(pentan-3-ylamino)pyrazin-2-yl)-6-ethoxypicolinamide

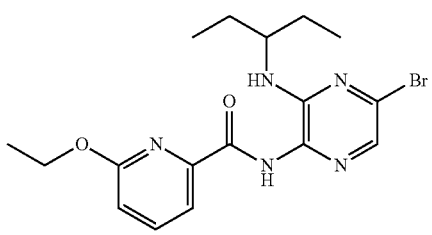 [SMILES: CCOc1cccc(C(=O)Nc2ncc(Br)nc2NC(CC)CC)n1]

To a solution of 6-bromo-N²-(pentan-3-yl)pyrazine-2,3-diamine (900 mg, 3.5 mmol, 1.1 equiv) in toluene (20 mL) was added Al(Me)₃ (1.6 mol/L in toluene, 10 mL, 15.9 mmol, 5 equiv) dropwise at room temperature. After the mixture was stirred at 50° C. for 30 mins, ethyl 6-ethoxypicolinate (686 mg, 3.2 mmol, 1.0 equiv) was added and the mixture was stirred at 110° C. for 2 hours. The reaction mixture was quenched with water (50 mL), followed by extraction with EtOAc (3*50 mL). The combined organic layers were washed with brine (50 mL), dried over anhydrous Na₂SO₄ and concentrated in vacuo. The residue was purified by flash column chromatography (eluting with PE/EtOAc=20/1 to 5/1) to afford the title compound N-(5-bromo-3-(pentan-3-ylamino)pyrazin-2-yl)-6-ethoxypicolinamide as light yellow solid (0.65 g, 46% yield). LC-MS: m/z 408.1, 410.1 (M+H)⁺

Step C: 6-bromo-2-(6-ethoxypyridin-2-yl)-1-(pentan-3-yl)-1H-imidazo[4,5-b]pyrazine

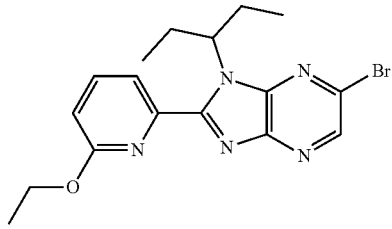 [SMILES: CCOc1cccc(-c2nc3ncc(Br)nc3n2C(CC)CC)n1]

To a solution of N-(5-bromo-3-(pentan-3-ylamino)pyrazin-2-yl)-6-ethoxypicolinamide (650 mg, 1.6 mmol, 1.0 equiv) in AcOH (10 mL) was added 1 drop of POCl₃. The mixture was stirred at 120° C. via microwave irradiation for 2 hours. The mixture was cooled to room temperature, evaporated and the residue was purified by flash column chromatography (eluting with PE/EtOAc=20/1 to 5/1) to afford the title compound 6-bromo-2-(6-ethoxypyridin-2-yl)-1-(pentan-3-yl)-1H-imidazo[4,5-b]pyrazine as a light yellow solid (450 mg, 72% yield).

LC-MS: m/z 390.1, 392.1 (M+H)⁺

Example 58: N-(2-(6-ethoxypyridin-2-yl)-1-(pentan-3-yl)-1H-imidazo[4,5-b]pyrazin-6-yl)methanesulfonamide

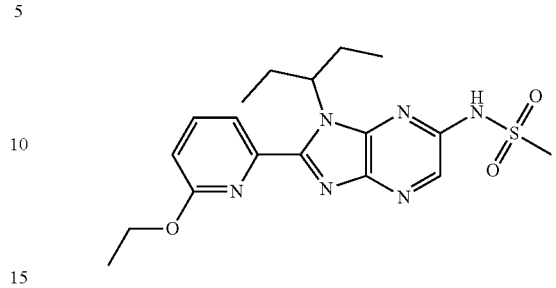

A suspension of 6-bromo-2-(6-ethoxypyridin-2-yl)-1-(pentan-3-yl)-1H-imidazo[4,5-b]pyrazine (50 mg, 0.13 mmol, 1.0 equiv), methanesulfonamide (24 mg, 0.26 mmol, 3.0 equiv), CuI (49 mg, 0.26 mmol, 3.0 equiv), trans-N,N'-Dimethylcyclohexane-1,2-diamine (37 mg, 0.26 mmol, 3.0 equiv) and K₂CO₃ (53 mg, 0.39 mmol, 3 equiv) in DMF (5 mL) was stirred at 115° C. via microwave irradiation for 1.5 h under N₂ atmosphere. The mixture was diluted with water (15 mL) and extracted with EtOAc (3*50 mL). The combined organic layers were dried over anhydrous Na₂SO₄ and concentrated in vacuo. The residue was purified by prep-TLC (PE/EtOAc=1/2) to afford the title compound N-(2-(6-ethoxypyridin-2-yl)-1-(pentan-3-yl)-1H-imidazo[4,5-b]pyrazin-6-yl)methanesulfonamide as a light yellow solid (40 mg, 76% yield).

¹H NMR (400 MHz, DMSO-d₆) δ: 11.18 (s, 1H), 8.19 (s, 1H), 7.94 (t, J=7.6 Hz, 1H), 7.89 (dd, J=7.6 Hz, 0.8 Hz, 1H), 7.01 (dd, J=8.4 Hz, 0.8 Hz, 1H), 5.74-5.79 (m, 1H), 4.40 (q, J=7.2 Hz, 2H), 3.42 (s, 3H), 2.34-2.42 (m, 2H), 2.01-1.99 (m, 2H), 1.39 (t, J=7.2 Hz, 3H), 0.70 (t, J=7.6 Hz, 6H). LC-MS: m/z 405.2 (M+H)⁺

Example 59: N-(2-(6-ethoxypyridin-2-yl)-1-isopropyl-1H-imidazo[4,5-b]pyrazin-6-yl)methanesulfonamide

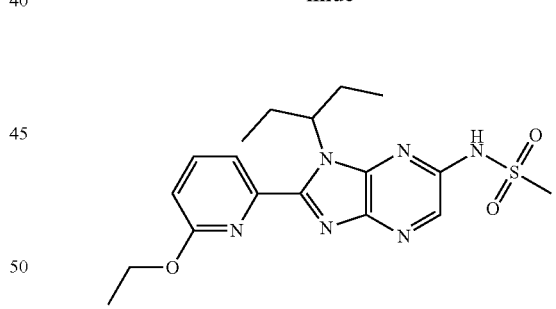

The title compound was prepared according to Method H by using propan-2-amine in step A.

¹HNMR (400 MHz, DMSO-d₆) δ: 11.17 (s, 1H), 8.18 (s, 1H), 7.95 (t, J=7.6 Hz, 1H), 7.85 (dd, J=7.6 Hz, 0.8 Hz, 1H), 7.0 (dd, J=8.4 Hz, 0.8 Hz, 1H), 5.93-6.0 (m, 1H), 4.41 (q, J=7.2 Hz, 2H), 3.45 (s, 3H), 1.73 (d, J=6.8 Hz, 6H), 1.38 (t, J=7.2 Hz, 3H). LC-MS: m/z 377.1 (M+H)⁺

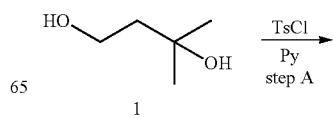

167
-continued

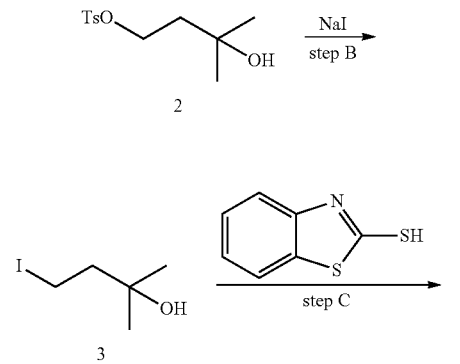

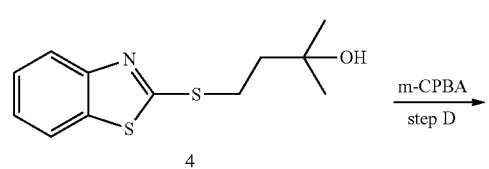

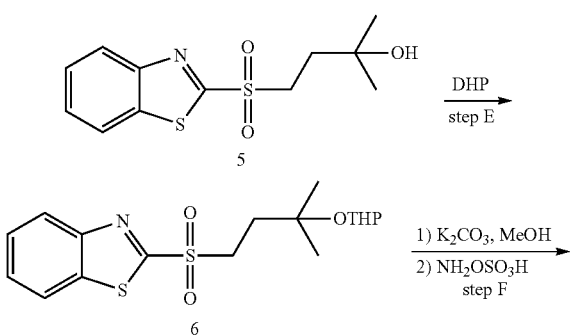

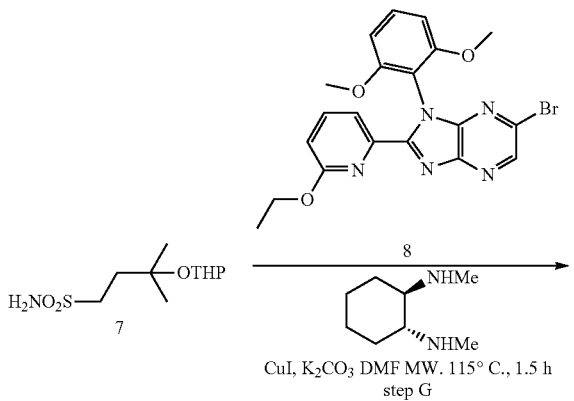

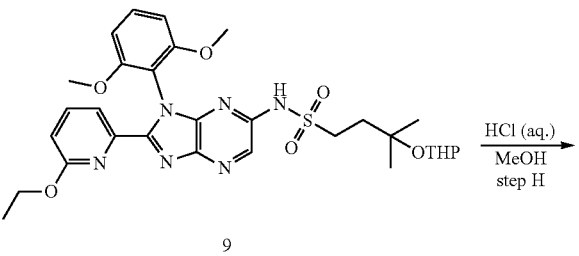

168
-continued

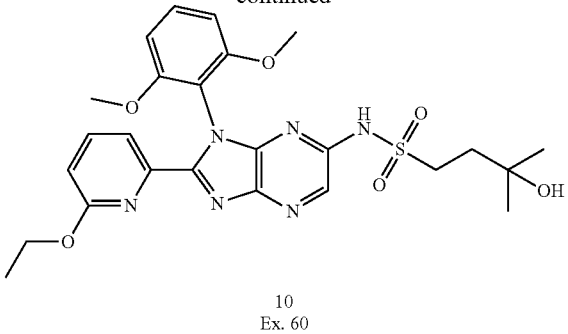

10
Ex. 60

Step A: 3-hydroxy-3-methylbutyl 4-methylbenzenesulfonate

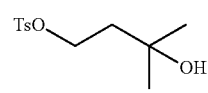 [SMILES: Cc1ccc(S(=O)(=O)OCCC(C)(C)O)cc1]

To a solution of 3-methylbutane-1,3-diol (20.8 g, 200 mmol, 1.0 equiv) in Pyridine (40 mL) was added TsCl (39.6 g, 20 mmol, 1.0 equiv) at 0° C. The reaction mixture was stirred at room temperature for 16 hours. The reaction mixture was neutralized with saturated NH₄Cl and extracted with DCM (3*100 mL). The extract was concentrate in vacuo and the residue was purified by flash chromatography (PE/EA=1/1) to afford the title compound 3-hydroxy-3-methylbutyl 4-methylbenzenesulfonate as a yellow (45 g 90% yield).

LC-MS: m/z 259.0 (M+H)⁺

Step B: 4-iodo-2-methylbutan-2-ol

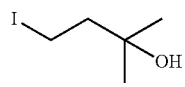

To a solution of 3-hydroxy-3-methylbutyl 4-methylbenzenesulfonate (6 g, 23.2 mmol, 1.0 equiv) in acetone (100 mL) was added NaI (8.7 g, 58 mmol, 2.5 equiv). The reaction mixture was stirred at 60° C. for 2 hours and concentrated in vacuo. The residue was diluted with EtOAc, washed with water and brine. The organic phase was concentrated in vacuo to afford the title crude compound 4-iodo-2-methylbutan-2-ol as a brown oil (3.6 g, 72% yield).

LC-MS: m/z 215.0 (M+H)⁺

Step C: 4-(benzo[d]thiazol-2-ylthio)-2-methylbutan-2-ol

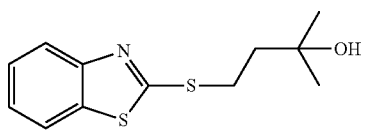 [SMILES: CC(C)(O)CCSc1nc2ccccc2s1]

To a solution of 4-iodo-2-methylbutan-2-ol (3.6 g, 11.8 mmol, 1.0 equiv) and benzo[d]thiazole-2-thiol (3.4 g, 20.2 mmol, 1.2 equiv) in THF (85 mL) was added Et₃N (3.4 g, 33.6 mmol, 2.0 equiv). The resulting mixture was stirred at 85° C. for 16 hours. The reaction solution was concentrated in vacuo and the residue was purified by flash chromatography (PE/EA=10/1) to afford the title compound 4-(benzo[d]thiazol-2-ylthio)-2-methylbutan-2-ol as a yellow solid (3.5 g, 83% yield).

LC-MS: m/z 254.0 (M+H)⁺

Step D: 4-(benzo[d]thiazol-2-ylsulfonyl)-2-methylbutan-2-ol

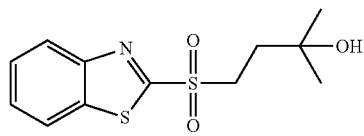 [SMILES: CC(C)(O)CCS(=O)(=O)c1nc2ccccc2s1]

To a suspension of 4-(benzo[d]thiazol-2-ylthio)-2-methylbutan-2-ol (3.3 g, 13 mmol, 1.0 equiv) in DCM (80 mL) was added m-CPBA (5.8 g, 28.7 mmol, 2.2 equiv). The resulting mixture was stirred at room temperature for 16 hours. The reaction mixture was washed with Na₂SO₃ (aq.), saturated NaHCO₃ (aq.) and brine successively, dried over Na₂SO₄, concentrated in vacuo and the residue was purified by flash column chromatography (PE/EtOAc=2/1) to afford the title compound 4-(benzo[d]thiazol-2-ylsulfonyl)-2-methylbutan-2-ol as a white solid (3.5 g, 88% yield).

LC-MS: m/z 286.0 (M+H)⁺

Step E: 24(3-methyl-3-((tetrahydro-2H-pyran-2-yl)oxy)butyl)sulfonyl)benzo[d]thiazole

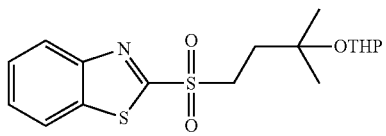

To a solution of 4-(benzo[d]thiazol-2-ylsulfonyl)-2-methylbutan-2-ol (0.5 g, 1.75 mmol, 1.0 equiv) in DCM (15 mL) were added DHP (0.2 g, 2.28 mmol, 1.3 equiv) and PPTS (50 mg) at 0° C. The mixture was stirred at room temperature for 2 hours. The mixture was concentrated and the residue was purified by flash chromatography (PE/EtOAc=7/1) to afford the title compound 2-((3-methyl-3-((tetrahydro-2H-pyran-2-yl)oxy)butyl)sulfonyl)benzo[d]thiazole as a white solid (0.6 g, 94% yield).

LC-MS: m/z 370.1 (M+H)⁺

Step F: 3-methyl-3-((tetrahydro-2H-pyran-2-yl)oxy)butane-1-sulfonamide

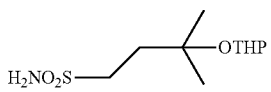

To a suspension of 2-((3-methyl-3-((tetrahydro-2H-pyran-2-yl)oxy)butyl)sulfonyl)benzo[d]thiazole (550 mg, 1.5 mmol, 1.0 equiv) in MeOH (15 mL) was added K₂CO₃ (1.0 g, 7.5 mmol, 5.0 equiv). After the mixture was stirred at 25° C. for 2 hours, NH₂OSO₃H (250 mg, 2.3 mmol, 1.5 equiv) was added. The mixture was then stirred at room temperature for 16 hours. The mixture was filtered and the filtrate was concentrated in vacuo. The residue was purified by flash chromatography (PE/EtOAc=1/1) to afford the title compound 3-methyl-3-((tetrahydro-2H-pyran-2-yl)oxy)butane-1-sulfonamide as a colorless oil (210 mg, 59% yield).

LC-MS: m/z 252.1 (M+H)⁺

Step G: N-(1-(2,6-dimethoxyphenyl)-2-(6-ethoxypyridin-2-yl)-1H-imidazo[4,5-b]pyrazin-6-yl)-3-methyl-3-((tetrahydro-2H-pyran-2-yl)oxy)butane-1-sulfonamide

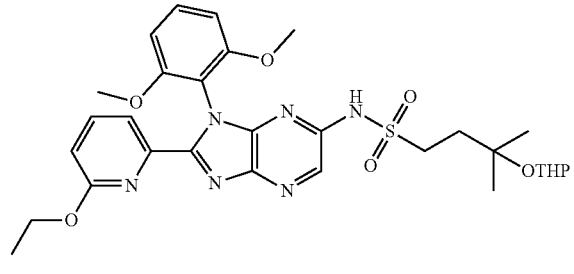

A suspension of 6-bromo-1-(2,6-dimethoxyphenyl)-2-(6-ethoxypyridin-2-yl)-1H-imidazo[4,5-b]pyrazine (100 mg, 0.22 mmol, 1.0 equiv), 3-methyl-3-((tetrahydro-2H-pyran-2-yl)oxy)butane-1-sulfonamide (100 mg, 0.22 mmol, 2.0 equiv), (1R,2R)—N¹,N²-dimethylcyclohexane-1,2-diamine (62 mg, 0.44 mmol, 3.0 equiv), CuI (84 mg, 0.44 mmol, 3.0 equiv) and K₂CO₃ (91 mg, 0.66 mmol, 3 equiv) in DMF (4 mL) was stirred at 115° C. via microwave irradiation for 2 hours under N₂ atmosphere. The reaction was poured into H₂O (20 mL) and extracted with ethyl acetate. The extract was washed with water and brine, dried over anhydrous MgSO₄ and concentrated in vacuo. The residue was purified by flash column chromatography (PE/EtOAc=1/1) to afford the title compound N-(1-(2,6-dimethoxyphenyl)-2-(6-ethoxypyridin-2-yl)-1H-imidazo[4,5-b]pyrazin-6-yl)-3-methyl-3-((tetrahydro-2H-pyran-2-yl)oxy)butane-1-sulfonamide as a yellow oil (100 mg, 73% yield).

LC-MS: m/z 627.3 (M+H)⁺

Example 60: N-(1-(2,6-dimethoxyphenyl)-2-(6-ethoxypyridin-2-yl)-1H-imidazo[4,5-b]pyrazin-6-yl)-3-hydroxy-3-methylbutane-1-sulfonamide

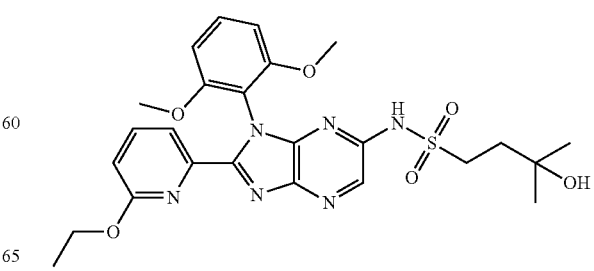

To a suspension of N-(1-(2,6-dimethoxyphenyl)-2-(6-ethoxypyridin-2-yl)-1H-imidazo[4,5-b]pyrazin-6-yl)-3-methyl-3-((tetrahydro-2H-pyran-2-yl)oxy)butane-1-sulfonamide (100 mg, 0.16 mmol, 1.0 equiv) in MeOH (4 mL) was added HCl (con. 0.3 mL) and the resulting mixture was stirred at room temperature for 10 mins. The mixture was evaporated and diluted with EtOAc, then washed with NaHCO$_3$ (aq.). The organic phase was concentrated in vacuo and the residue was purified by Prep-TLC (DCM/MeOH=20/1) to afford the title compound N-(1-(2,6-dimethoxyphenyl)-2-(6-ethoxypyridin-2-yl)-1H-imidazo[4,5-b]pyrazin-6-yl)-3-hydroxy-3-methylbutane-1-sulfonamide as a yellow solid (35 mg, 40% yield).

$^1$H NMR (400 MHz, DMSO-d$_6$) δ: 8.27 (s, 1H), 7.94 (dd, J=7.6 Hz, 1H), 7.84 (t, J=8.0 Hz, 1H), 7.42 (t, J=8.4 Hz, 1H), 6.86-6.80 (m, 3H), 4.36 (s, 1H), 3.56 (s, 6H) 3.36 (q, J=7.2 Hz, 2H), 3.30-3.28 (m, 2H), 1.68-1.64 (m, 2H), 3.52 (s, 6H), 1.03 (t, J=7.2 Hz, 3H), 0.91 (s, 6H). LC-MS: m/z 543.2 (M+H)$^+$

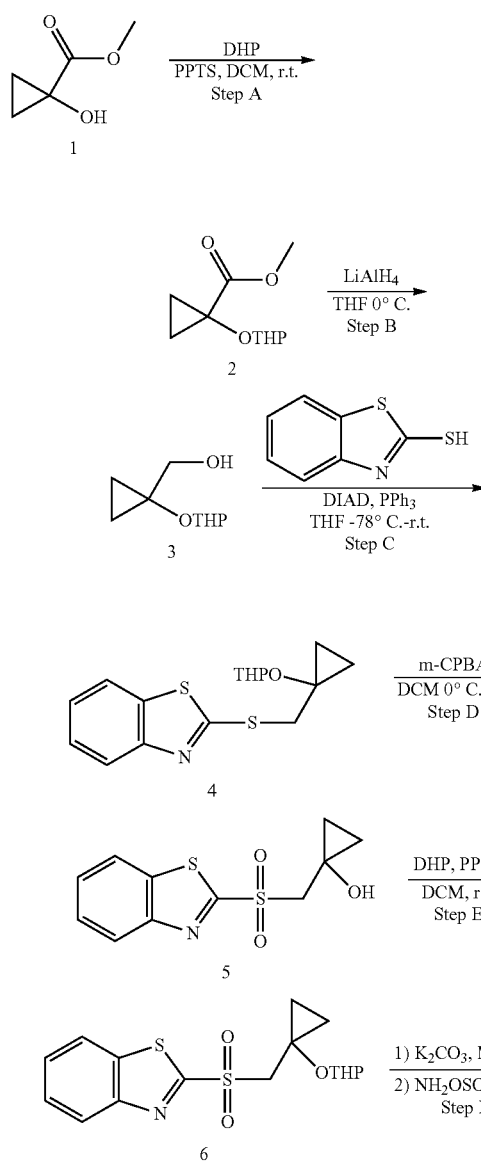

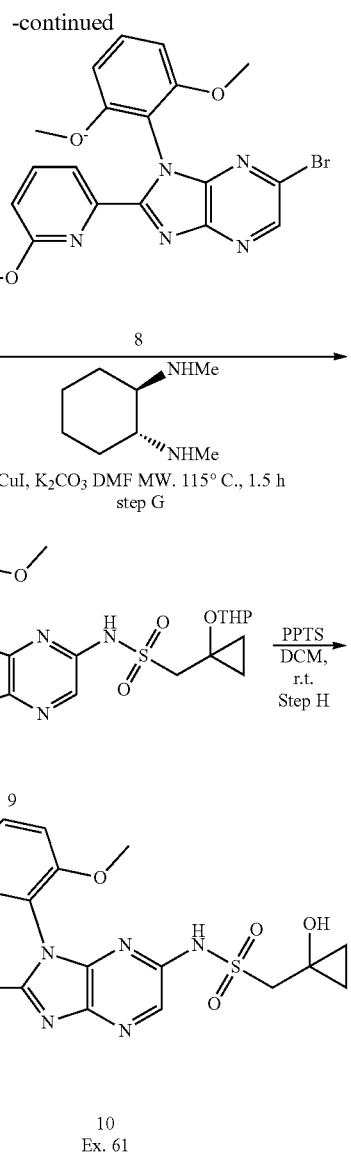

Ex. 61

Step A: methyl 1-((tetrahydro-2H-pyran-2-yl)oxy)cyclopropanecarboxylate

Methyl 1-hydroxycyclopropanecarboxylate (5 g, 43.1 mmol, 1.0 equiv) was dissolved in DCM (40 mL). Then DHP (3.8 g, 45.2 mmol, 1.05 equiv) and PPTS (1.1 g, 4.3 mmol, 0.1 equiv) were added. The mixture was stirred at room temperature for 3 hours. After that, DCM was removed and to the residue were added Et$_2$O and brine. The organic layer was separated, dried over anhydrous Na$_2$SO$_4$, concentrated and purified by column chromatography (PE/EtOAc=20/1) to afford the title compound methyl 1-((tetrahydro-2H-pyran-2-yl)oxy)cyclopropanecarboxylate as colorless oil (7.66 g, 93% yield).

LC-MS: m/z 201.1 (M+H)+

Step B: (1-((tetrahydro-2H-pyran-2-yl)oxy)cyclopropyl)methanol

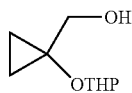

The solution of methyl 1-((tetrahydro-2H-pyran-2-yl)oxy)cyclopropanecarboxylate (7.66 g, 38.3 mmol, 1.0 equiv) in THF (30 mL) was cooled to 0° C. Then LiAlH$_4$ (1 mol/L in THF, 76.6 mL, 76.6 mmol, 3.0 equiv) was added dropwise. After stirred at 0° C. for 0.5 h, the reaction mixture was diluted with Et$_2$O and quenched by adding H$_2$O (3 mL) dropwise. After that, 4 N NaOH (aq. 3 mL) was added followed by addition of H$_2$O (3*3 mL). The resulting suspension was filtered and the filter cake was washed with EtOAc three times. The organic layer of the filtrate was separated, washed with brine, dried over Na$_2$SO$_4$ and concentrated in vacuo. The residue was purified by column chromatography (PE/EtOAc=3/1) to afford the title compound (1-((tetrahydro-2H-pyran-2-yl)oxy)cyclopropyl)methanol as colorless oil (5.8 g, 88% yield).

LC-MS: m/z 172.2 (M+H)+

Step C: 2-(((1-((tetrahydro-2H-pyran-2-yl)oxy)cyclopropyl)methyl)thio)benzo[d]thiazole

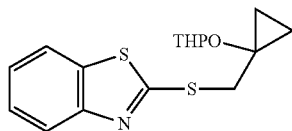

(1-((Tetrahydro-2H-pyran-2-yl)oxy)cyclopropyl)methanol (2 g, 11.6 mmol, 1.0 equiv), benzo[d]thiazole-2-thiol (2.24 g, 14.5 mmol, 1.25 equiv) and PPh$_3$ (3.8 g, 14.5 mmol, 1.25 equiv) were dissolved in anhydrous THF (12 mL). The solution was cooled to −78° C. and DIAD (2.93 g, 14.5 mmol, 1.25 equiv) was added dropwise. The mixture was stirred at room temperature overnight. After that, the mixture was filtered and the filtrate was concentrated in vacuo. The residue was purified by column chromatography to afford the title compound 2-(((1-((tetrahydro-2H-pyran-2-yl)oxy)cyclopropyl)methyl)thio)benzo[d]thiazole as light yellow solid (3.03 g, 81% yield).

LC-MS: m/z 322.1 (M+H)+

Step D: 1-((benzo[d]thiazol-2-ylsulfonyl)methyl)cyclopropanol

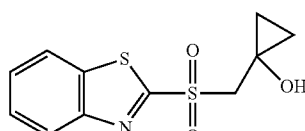

2-(((1-((Tetrahydro-2H-pyran-2-yl)oxy)cyclopropyl)methyl)thio)benzo[d]thiazole (3.03 g, 9.4 mmol, 1.0 equiv) was dissolved in DCM (10 mL) and m-CPBA (3.57 g, 20.7 mmol, 2.2 equiv) was added. The solution was stirred at room temperature overnight. The reaction mixture was washed with Na$_2$SO$_3$ (aq.), saturated NaHCO$_3$ (aq.) and brine successively, dried over Na$_2$SO$_4$, concentrated in vacuo and the residue was purified by column chromatography to afford the title compound 1-((benzo[d]thiazol-2-ylsulfonyl)methyl)cyclopropanol as colorless oil (1.4 g, 55% yield)

LC-MS: m/z 270.0 (M+H)+

Step E: 2-(((1-((tetrahydro-2H-pyran-2-yl)oxy)cyclopropyl)methyl)sulfonyl)benzo[d]thiazole

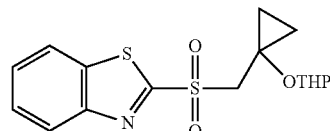

Molecular Weight: 353.45

1-((Benzo[d]thiazol-2-ylsulfonyl)methyl)cyclopropanol (1.4 g, 5.20 mmol, 1.0 equiv) was dissolved in DCM (2 mL). Then DHP (492 mg, 5.72 mmol, 1.1 equiv) and PPTS (261 mg, 1.04 mmol, 0.2 equiv) were added. The mixture was stirred at room temperature overnight. Then DCM was removed and to the residue were added Et$_2$O and brine. The organic layer was separated, dried over Na$_2$SO$_4$, concentrated and purified with column chromatography (PE/EtOAc=10/1) to give 2-(((1-((tetrahydro-2H-pyran-2-yl)oxy)cyclopropyl)methyl)sulfonyl)benzo[d]thiazole as white solid (839 mg, 45% yield).

LC-MS: m/z 354.1 (M+H)+

Step F: (1-((tetrahydro-2H-pyran-2-yl)oxy)cyclopropyl)methanesulfonamide

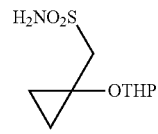

2-(((1-((tetrahydro-2H-pyran-2-yl)oxy)cyclopropyl)methyl)sulfonyl)benzo[d]thiazole (839 mg, 2.37 mmol, 1.0 equiv) was dissolved in MeOH (4 mL) and K$_2$CO$_3$ (492 mg, 3.56 mmol, 1.5 equiv) was added. The mixture was stirred at room temperature for 1.5 h. After which time, another batch K$_2$CO$_3$ (982 mg, 7.11 mmol, 3 equiv) and NH$_2$OSO$_3$ (401 mg, 3.56 mmol, 1.5 equiv) were added. The reaction mixture was stirred at room temperature overnight. Then MeOH was removed and the residue was dissolved in H$_2$O. The mixture was extracted with EtOAc three times. The organic layers were combined, washed with brine, dried over Na$_2$SO$_4$, concentrated and purified via column chromatography (PE/EtOAc=2/1) to give (1-((tetrahydro-2H-pyran-2-yl)oxy)cyclopropyl)methanesulfonamide as colorless oil (210 mg, 38% yield).

$^1$H NMR (400 MHz, CDCl$_3$) δ: 4.95 (s, 2H), 4.56 (dd, J=8.0 Hz, J=2.4 Hz, 1H), 3.97 (dd, J=14.8 Hz, J=1.6 Hz,

1H), 3.90-3.94 (m, 1H), 3.40-3.48 (m, 1H), 2.84 (d, J=14.8 Hz, 1H), 1.74-1.78 (m, 2H), 1.34-1.59 (m, 4H), 1.09-1.05 (m, 1H), 0.90-0.95 (m, 2H), 0.60-0.67 (m, 1H).

Step G: N-(1-(2,6-dimethoxyphenyl-2-(6-ethoxypyridin-2-yl)-1H-imidazo[4,5-b]pyrazin-6-yl)-1-(1-((tetrahydro-2H-pyran-2-yl)oxy)cyclopropylmethanesulfonamide

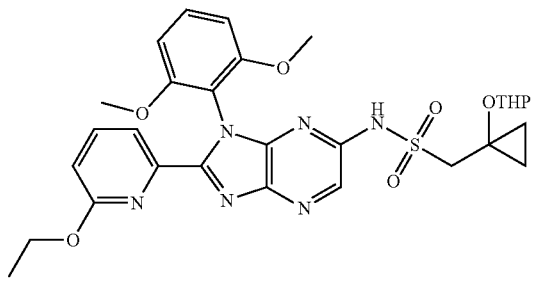

A suspension of 6-bromo-1-(2,6-dimethoxyphenyl)-2-(6-ethoxypyridin-2-yl)-1H-imidazo[4,5-b]pyrazine (69 mg, 0.15 mmol, 0.5 equiv), (1-((tetrahydro-2H-pyran-2-yl)oxy)cyclopropyl)methanesulfonamide (71 mg, 0.30 mmol, 1.0 equiv), CuI (57 mg, 0.30 mmol, 1.0 equiv), trans-N,N'-Dimethylcyclohexane-1,2-diamine (43 mg, 0.30 mmol, 1.0 equiv) and $K_2CO_3$ (68 mg, 0.45 mmol, 1.5 equiv) in DMF (1 mL) was stirred at 115° C. via microwave irradiation for 2 hours under $N_2$ atmosphere. The mixture was diluted with water (5 mL), extracted with EtOAc three times. The combined organic layers were washed with brine, dried over anhydrous $Na_2SO_4$ and concentrated in vacuo. The residue was purified by column chromatography (PE/EtOAc=4/1) to give N-(1-(2,6-dimethoxyphenyl)-2-(6-ethoxypyridin-2-yl)-1H-imidazo[4,5-b]pyrazin-6-yl)-1-(1-((tetrahydro-2H-pyran-2-yl)oxy)cyclopropyl)methanesulfonamide as a yellow solid (40 mg, 44% yield).

LC-MS: m/z 611.2 (M+H)+

Example 61: N-(1-(2,6-dimethoxyphenyl)-2-(6-ethoxypyridin-2-yl)-1H-imidazo[4,5-b]pyrazin-6-yl)-1-(1-hydroxycyclopropyl)methanesulfonamide

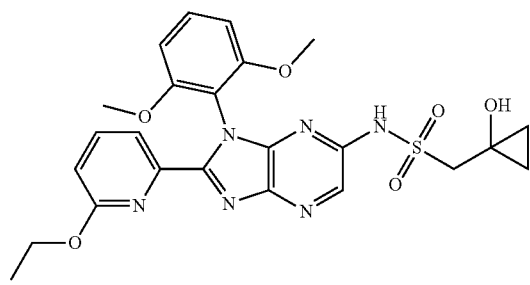 [SMILES: CCOc1cccc(-c2nc3ncc(NS(=O)(=O)CC4(O)CC4)nc3n2-c2c(OC)cccc2OC)n1]

N-(1-(2,6-dimethoxyphenyl)-2-(6-ethoxypyridin-2-yl)-1H-imidazo[4,5-b]pyrazin-6-yl)-1-(1-((tetrahydro-2H-pyran-2-yl)oxy)cyclopropyl)methanesulfonamide (45 mg, 0.074 mmol, 1.0 equiv) was dissolved in DCM (1 mL) and PPTS (19 mg, 0.037 mmol, 0.5 equiv) was added. The mixture was stirred at room temperature overnight. The mixture was concentrated and purified by reverse phase flash chromatography to give the title compound as white solid (30 mg, 77% yield).

$^1$H NMR (400 MHz, DMSO-$d_6$) δ:11.06 (br, 1H), 8.25 (s, 1H), 7.91 (d, J=7.2 Hz, 1H), 7.83 (t, J=8.0 Hz, 1H), 7.41 (t, J=8.4 Hz, 1H), 6.83 (d, J=8.4 Hz, 2H), 6.78 (d, J=7.6 Hz, 1H), 5.38 (br. s, 1H), 3.57 (s, 6H), 3.49 (s, 2H), 3.35 (q, J=7.2 Hz, 2H), 1.00 (t, J=7.2 Hz, 3H), 0.57-0.60 (m, 2H), 0.41-0.44 (m, 2H). LC-MS: m/z 527.3 (M+H)+

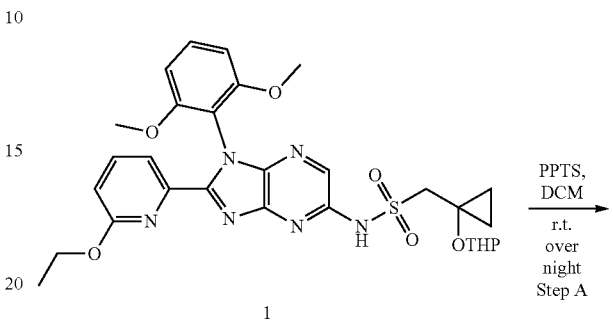

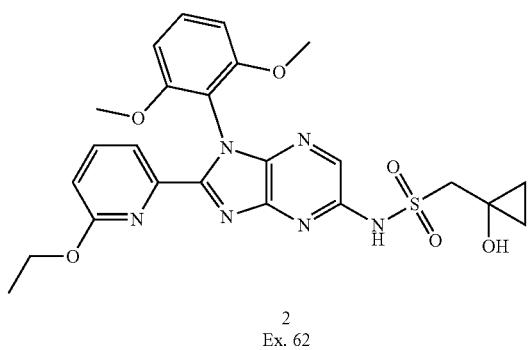

N-(1-(2,6-dimethoxyphenyl)-2-(6-ethoxypyridin-2-yl)-1H-imidazo[4,5-b]pyrazin-5-yl)-1-(1-((tetrahydro-2H-pyran-2-yl)oxy)cyclopropyl)methanesulfonamide

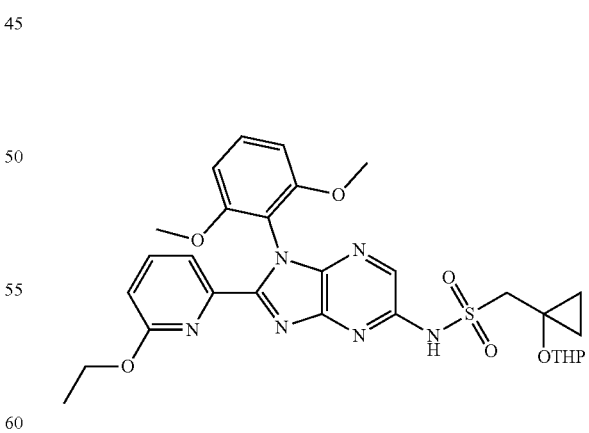

The title compound was prepared according to Method C, step D, starting from 5-chloro-1-(2,6-dimethoxyphenyl)-2-(6-ethoxypyridin-2-yl)-1H-imidazo[4,5-b]pyrazine (Example 15) by using (1-((tetrahydro-2H-pyran-2-yl)oxy)cyclopropyl)methanesulfonamide (121 mg, 66% yield).

LC-MS: m/z 611.0 (M+H)+

Example 62: N-(1-(2,6-dimethoxyphenyl)-2-(6-ethoxypyridin-2-yl)-1H-imidazo[4,5-b]pyrazin-5-yl)-1-(1-hydroxycyclopropyl)methanesulfonamide

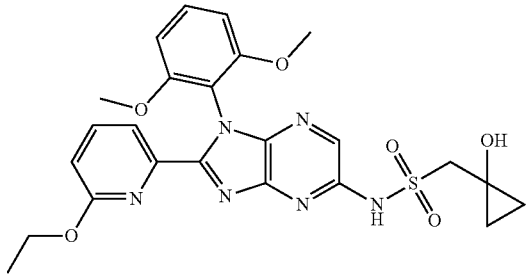 [SMILES: CCOc1cccc(-c2nc3nc(NS(=O)(=O)CC4(O)CC4)cnc3n2-c2c(OC)cccc2OC)n1]

The title compound was prepared following the same approach of the preparation of Example 61 (22 mg, 28% yield).

$^1$H NMR (400 MHz, DMSO-d$_6$) δ: 7.94-8.02 (m, 2H), 7.81-7.92 (m, 1H), 7.46 (t, J=8.4 Hz, 1H), 6.82-6.89 (m, 3H), 3.81 (s, 2H), 3.58 (s, 6H), 3.39 (q, J=7.2 Hz, 2H), 1.03 (t, J=7.2 Hz, 3H), 0.71 (d, J=7.6 Hz, 4H). LC-MS: m/z 527.3 (M+H)$^+$

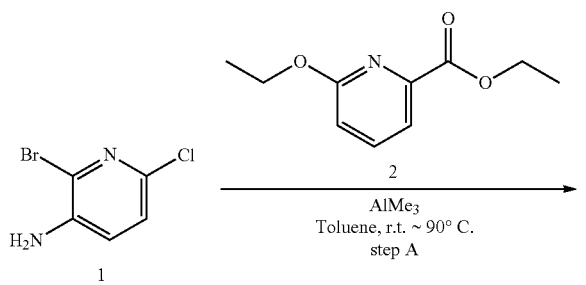

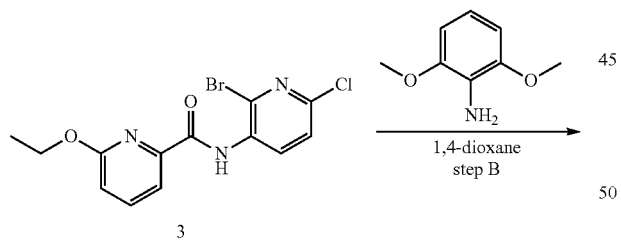

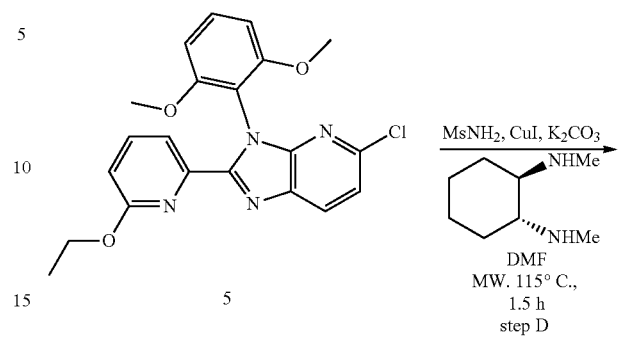

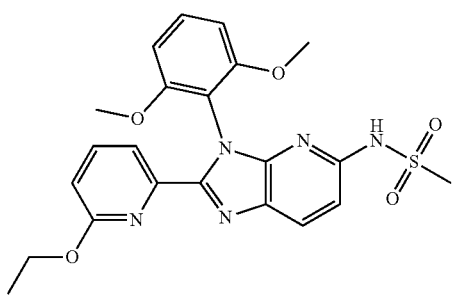

Ex. 63

Step A: N-(2-bromo-6-chloropyridin-3-yl)-6-ethoxypicolinamide

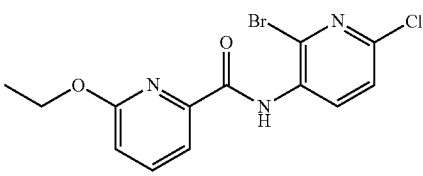 [SMILES: CCOc1cccc(C(=O)Nc2ccc(Cl)nc2Br)n1]

To a solution of 2-bromo-6-chloropyridin-3-amine (2 g, 10 mmol, 1.0 equiv) in toluene (30 mL) was added trimethylaluminum (2 mol/L in toluene, 7.5 mL, 15 mmol, 1.5 equiv) at 0° C. After the mixture was stirred at 80° C. for 1 hour, ethyl 6-ethoxypicolinate (2 g, 10 mmol, 1.0 equiv) was added. The resulting mixture was stirred at 90° C. for 16 hours. The mixture was quenched with 4N HCl (aq.) and extracted with DCM (3*80 mL). The extract was washed with brine (100 mL), dried over anhydrous Na$_2$SO$_4$ and concentrated in vacuo.

The residue was washed with MeOH to afford the title compound N-(2-bromo-6-chloropyridin-3-yl)-6-ethoxypicolinamide as a yellow solid (2.3 g, 67% yield).

LC-MS: m/z 355.0, 357.0 (M+H)$^+$

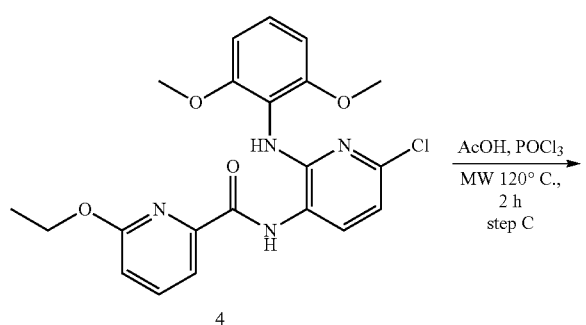

Step B: N-(6-chloro-2-((2,6-dimethoxyphenyl)amino)pyridin-3-yl)-6-ethoxypicolinamide

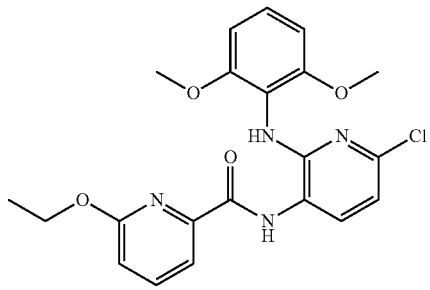 [SMILES: CCOc1cccc(C(=O)Nc2ccc(Cl)nc2Nc2c(OC)cccc2OC)n1]

A suspension of N-(2-bromo-6-chloropyridin-3-yl)-6-ethoxypicolinamide (1.2 g, 3.4 mmol, 1.0 equiv), 2,6-dimethoxyaniline (516 mg, 3.4 mmol, 1.0 equiv), Pd$_2$(dba)$_3$ (616 mg, 0.7 mmol, 0.2 equiv), Xantphos (578 mg, 1.4 mmol, 0.4 equiv) and K$_2$CO$_3$ (1.4 g, 10 mmol, 3 equiv) in 1,4-dioxane (15 mL) was stirred at 100° C. via microwave irradiation for 2 hours under N$_2$ atmosphere. The mixture was diluted with DCM (20 mL) and filtered through celite. The filtrate was concentrated in vacuo and the residue was purified by flash column chromatography (PE/EtOAc=5/1) to afford the title compound N-(6-chloro-2-((2,6-dimethoxyphenyl)amino)pyridin-3-yl)-6-ethoxypicolinamide as a white solid (1 g, 69% yield).

LC-MS: m/z 429.1 (M+H)$^+$

Step C: 5-chloro-3-(2,6-dimethoxyphenyl)-2-(6-ethoxypyridin-2-yl)-3H-imidazo[4,5-b]pyridine

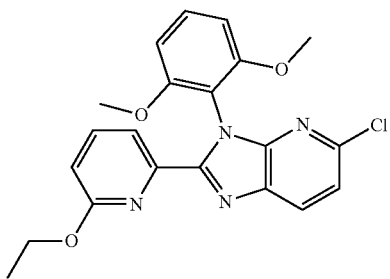 [SMILES: CCOc1cccc(-c2nc3ccc(Cl)nc3n2-c2c(OC)cccc2OC)n1]

To a solution of N-(6-chloro-2-((2,6-dimethoxyphenyl)amino)pyridin-3-yl)-6-ethoxypicolinamide (0.3 g, 0.7 mmol, 1.0 equiv) in AcOH (10 mL) was added 1 drop of POCl$_3$ (cat.). The mixture was stirred at 120° C. via microwave irradiation for 2 hours and then cooled to room temperature. The precipitate was filtered off and washed with a mixture of EtOAc/PE=1/2 to afford the title compound 5-chloro-3-(2,6-dimethoxyphenyl)-2-(6-ethoxypyridin-2-yl)-3H-imidazo[4,5-b]pyridine as a white solid (60 mg, 20% yield).

LC-MS: m/z 411 (M+H)$^+$

Example 63: N-(3-(2,6-dimethoxyphenyl)-2-(6-ethoxypyridin-2-yl)-3H-imidazo[4,5-b]pyridin-5-yl)methanesulfonamide

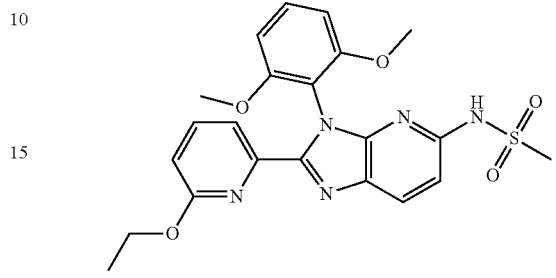

A suspension of 5-chloro-3-(2,6-dimethoxyphenyl)-2-(6-ethoxypyridin-2-yl)-3H-imidazo[4,5-b]pyridine (70 mg, 0.17 mmol, 1.0 equiv), methanesulfonamide (32 mg, 0.34 mmol, 3.0 equiv), CuI (65 mg, 0.34 mmol, 3.0 equiv), trans-N,N'-Dimethylcyclohexane-1,2-diamine (48 mg, 0.34 mmol, 3.0 equiv) and K$_2$CO$_3$ (70 mg, 0.51 mmol, 3 equiv) in DMF (3 mL) was stirred at 120° C. via microwave irradiation for 10 hours under N$_2$ atmosphere. The mixture was diluted with EtOAc (100 mL) and filtered through celite. The filtrate was poured into water (150 mL), followed by extraction with EtOAc (2*100 mL). The combined organic layers were dried over anhydrous Na$_2$SO$_4$ and concentrated in vacuo. The residue was purified by flash column chromatography (eluting with DCM/MeOH=20/1) to afford the title compound N-(3-(2,6-dimethoxyphenyl)-2-(6-ethoxypyridin-2-yl)-3H-imidazo[4,5-b]pyridin-5-yl)methanesulfonamide as a white solid (30 mg, 30% yield).

$^1$HNMR (400 MHz, DMSO-d$_6$) δ: 10.58 (s, 1H), 8.10 (d, J=8.4 Hz, 1H), 7.86 (d, J=6.8 Hz, 1H), 7.79 (t, J=7.6 Hz, 1H), 7.41 (t, J=8.4 Hz, 1H), 6.94 (d, J=8.4 Hz, 1H), 6.83 (d, J=8.4 Hz, 2H), 6.74 (d, J=7.6 Hz, 1H), 3.55 (s, 6H), 3.39 (q, J=7.2 Hz, 2H), 3.31 (s, 3H), 1.02 (t, J=7.2 Hz, 3H). LC-MS: m/z 470.1 (M+H)$^+$

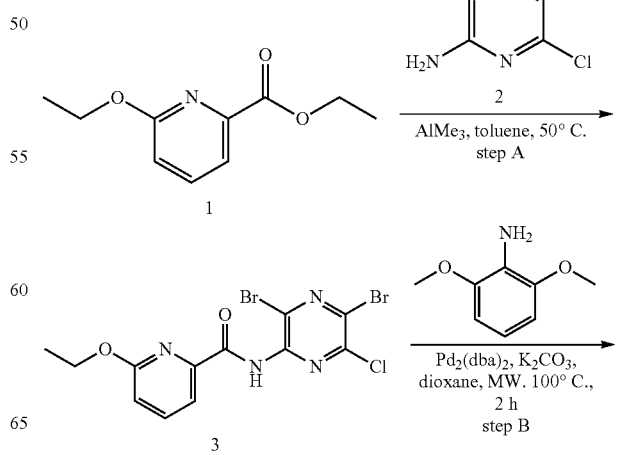

-continued

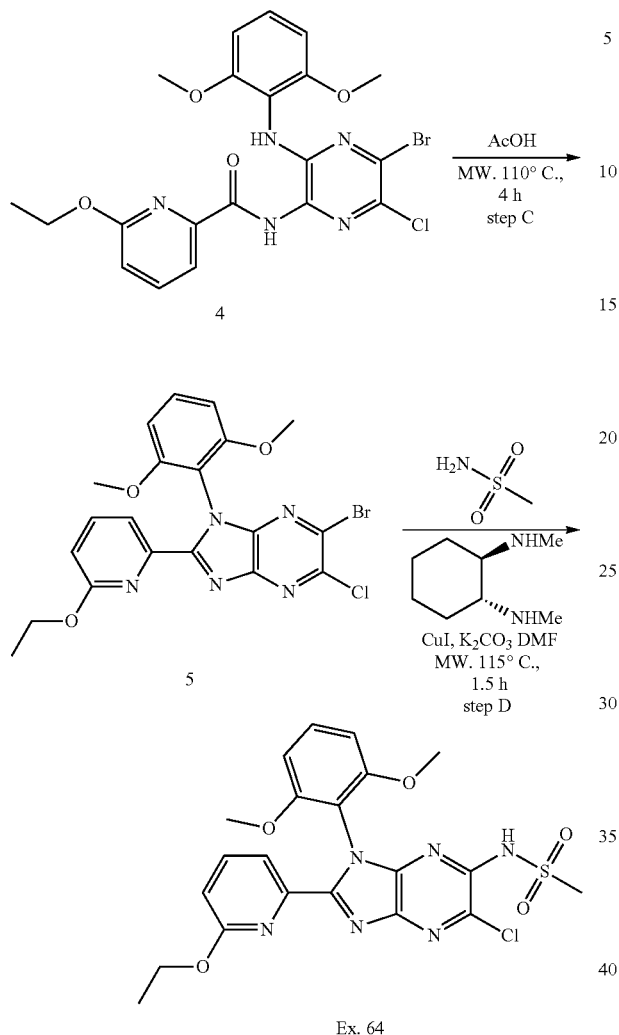

Ex. 64

Step A: N-3,5-dibromo-6-chloropyrazin-2-yl)-6-ethoxypicolinamide

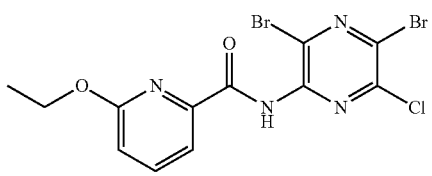 [SMILES: CCOc1cccc(C(=O)Nc2nc(Cl)c(Br)nc2Br)n1]

To a solution of 3,5-dibromo-6-chloropyrazin-2-amine (2 g, 6.97 mmol, 1.0 equiv) in toluene (50 mL) was added Al(Me)$_3$ (2 mol/L in toluene, 5.2 mL, 10.4 mmol, 1.5 equiv) dropwise at 0° C. under N$_2$ atmosphere. After the mixture was stirred at 0° C. for 30 mins and at 50° C. for 30 mins, ethyl 6-ethoxypicolinate (1.36 g, 6.97 mmol, 1.0 equiv) was added. The mixture was stirred at 50° C. for 3 hours. The reaction mixture was quenched with 1N HCl (100 mL), followed by extraction with DCM (2*50 mL). The combined organic layers were dried over anhydrous Na$_2$SO$_4$ and concentrated in vacuo. MeOH (50 mL) was added into the residue. The precipitate was filtered off to afford the title compound N-(3,5-dibromo-6-chloropyrazin-2-yl)-6-ethoxypicolinamide as a yellow solid (2.3 g, 76% yield).

LC-MS: m/z 434.9, 436.9, 438.9 (M+H)$^+$

Step B: N-(5-bromo-6-chloro-3-((2,6-dimethoxyphenylamino)pyrazin-2-yl)-6-ethoxypicolinamide

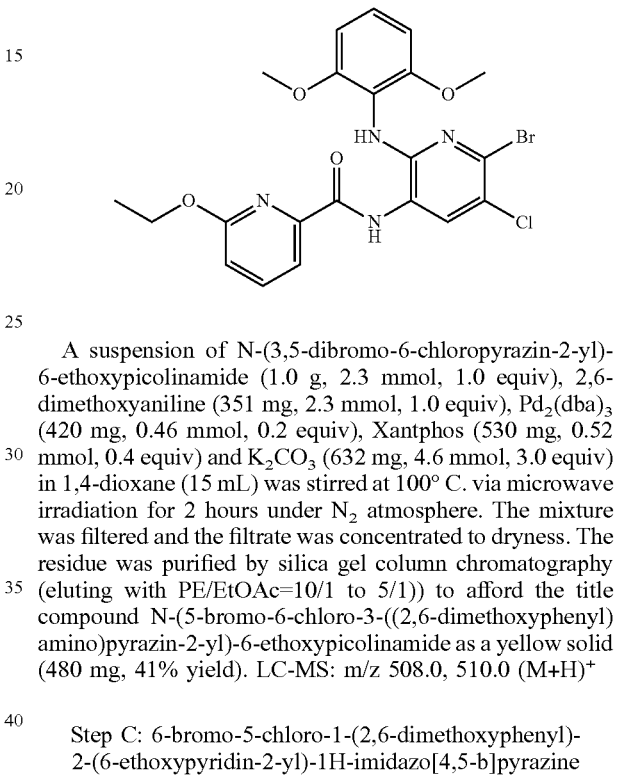

A suspension of N-(3,5-dibromo-6-chloropyrazin-2-yl)-6-ethoxypicolinamide (1.0 g, 2.3 mmol, 1.0 equiv), 2,6-dimethoxyaniline (351 mg, 2.3 mmol, 1.0 equiv), Pd$_2$(dba)$_3$ (420 mg, 0.46 mmol, 0.2 equiv), Xantphos (530 mg, 0.52 mmol, 0.4 equiv) and K$_2$CO$_3$ (632 mg, 4.6 mmol, 3.0 equiv) in 1,4-dioxane (15 mL) was stirred at 100° C. via microwave irradiation for 2 hours under N$_2$ atmosphere. The mixture was filtered and the filtrate was concentrated to dryness. The residue was purified by silica gel column chromatography (eluting with PE/EtOAc=10/1 to 5/1)) to afford the title compound N-(5-bromo-6-chloro-3-((2,6-dimethoxyphenyl)amino)pyrazin-2-yl)-6-ethoxypicolinamide as a yellow solid (480 mg, 41% yield). LC-MS: m/z 508.0, 510.0 (M+H)$^+$ Step C: 6-bromo-5-chloro-1-(2,6-dimethoxyphenyl)-2-(6-ethoxypyridin-2-yl)-1H-imidazo[4,5-b]pyrazine The solution of N-(5-bromo-6-chloro-3-((2,6-dimethoxyphenyl)amino)pyrazin-2-yl)-6-ethoxypicolinamide amide (400 mg, 0.78 mmol, 1.0 equiv) in AcOH (10 mL) was stirred at 110° C. via microwave irradiation for 4 hours. The mixture was cooled to room temperature and the precipitate was filtered off to afford the title compound 6-bromo-5-chloro-1-(2,6-dimethoxyphenyl)-2-(6-ethoxypyridin-2-yl)-1H-imidazo[4,5-b]pyrazine as a yellow solid (220 mg, 57% yield).

LC-MS: m/z 490.0, 492.0 (M+H)$^+$

Example 64: N-(5-chloro-1-(2,6-dimethoxyphenyl)-2-(6-ethoxypyridin-2-yl)-1H-imidazo[4,5-b]pyrazin-6-yl)methanesulfonamide

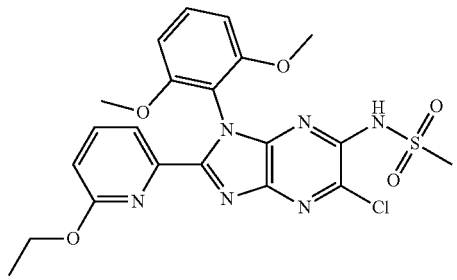 [SMILES: CCOc1cccc(-c2nc3nc(Cl)c(NS(C)(=O)=O)nc3n2-c2c(OC)cccc2OC)n1]

A suspension of 6-bromo-5-chloro-1-(2,6-dimethoxyphenyl)-2-(6-ethoxypyridin-2-yl)-1H-imidazo[4,5-b]pyrazine (200 mg, 0.41 mmol, 1.0 equiv), methanesulfonamide (38 mg, 0.41 mmol, 1.0 equiv), CuI (155 mg, 0.82 mmol, 3.0 equiv), trans-N,N'-Dimethylcyclohexane-1,2-diamine (116 mg, 0.82 mmol, 3.0 equiv) and $K_2CO_3$ (168 mg, 1.2 mmol, 3 equiv) in DMF (10 mL) was stirred at 60° C. via microwave irradiation for 1 hour under $N_2$ atmosphere. The mixture was diluted with 1N HCl (20 mL) and extracted with EtOAc (2*50 mL). The combined organic layers were dried over anhydrous $Na_2SO_4$ and concentrated in vacuo. The residue was purified by flash column chromatography to afford the title compound as a yellow solid (120 mg, 59% yield).

$^1$H NMR (400 MHz, DMSO-$d_6$) δ: 10.69 (br. s, 1H), 7.94 (d, J=7.2 Hz, 1H), 7.87 (t, J=8.0 Hz, 1H), 7.46 (t, J=8.4 Hz, 1H), 6.83-6.87 (m, 3H), 3.57 (s, 6H), 3.39 (q, J=7.2 Hz, 2H), 3.12 (s, 3H), 1.02 (t, J=7.2 Hz, 3H). LC-MS: m/z 505.0 (M+H)$^+$

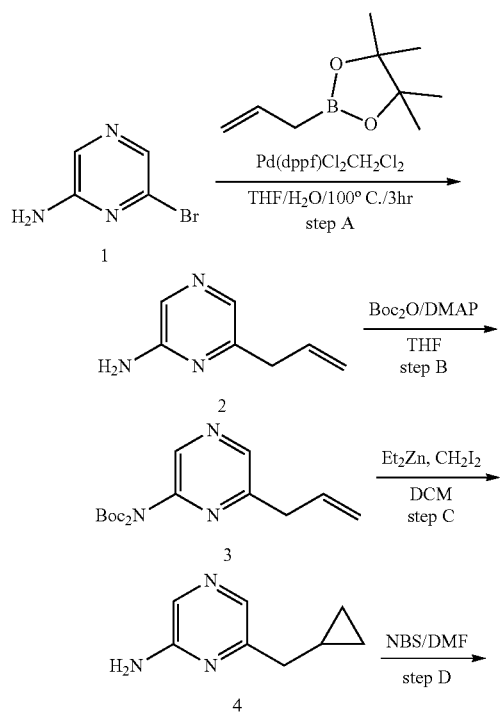

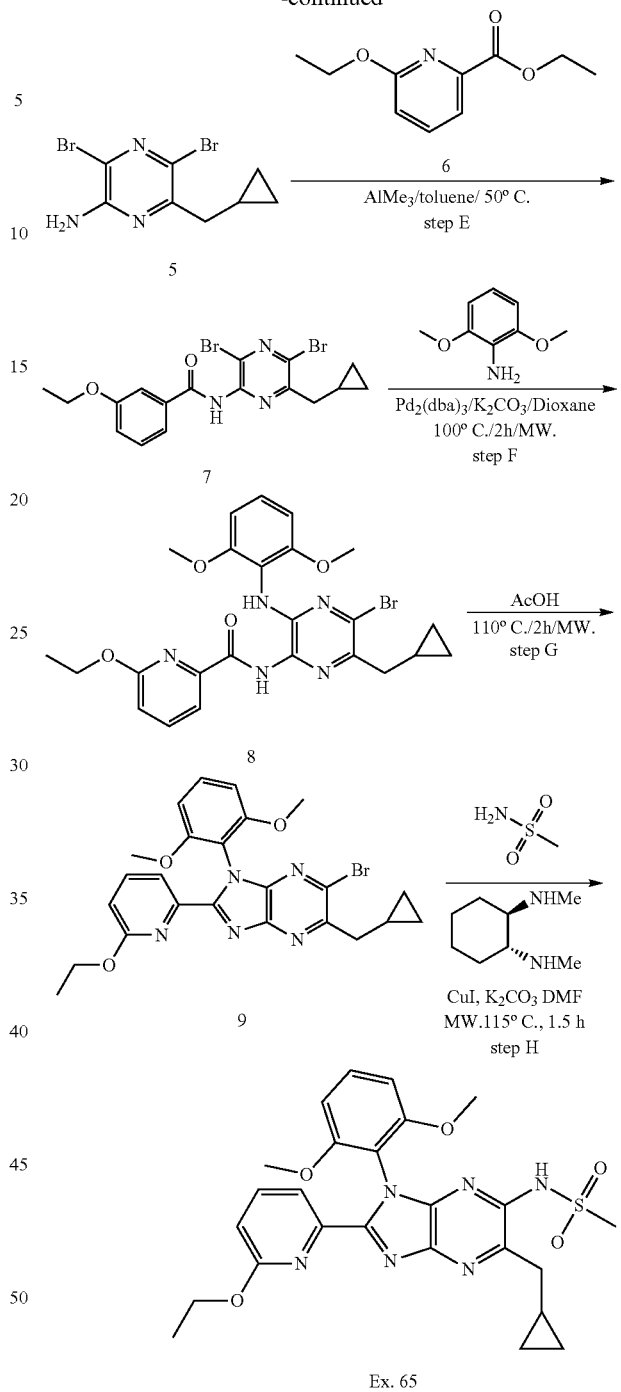

Step A: 2-amino-6-allylpyrazine

A suspension of 6-bromopyrazin-2-amine (1.0 g, 5.7 mmol, 1.0 equiv), 2-allyl-4,4,5,5-tetramethyl-1,3,2-dioxaborolane (1.9 g, 11.5 mmol, 3.0 equiv), Pd(dppf)Cl$_2$.CH$_2$Cl$_2$ (470 mg, 0.57 mmol, 0.1 equiv) and K$_2$CO$_3$ (2.37 g, 1.72 mmol, 0.06 equiv) in THF/H$_2$O (15 mL/1.5 mL) was stirred at 100° C. under N$_2$ atmosphere overnight. The reaction mixture was poured onto H$_2$O (20 mL) and extracted with EtOAc (3*20 mL). The extracts were washed with water (10 mL) and brine (10 mL), dried over MgSO$_4$ and concentrated in vacuo. The residue was purified by silica gel column chromatography (eluting with PE/EtOAc=6/1 to 2/1)) to afford the title compound 2-amino-6-allylpyrazine as a yellow solid (570 mg, 74% yield). LC-MS: m/z 136.2 (M+H)$^+$ Step B:
2-(bis(tert-butoxycarbonylamino)-6-allylpyrazine

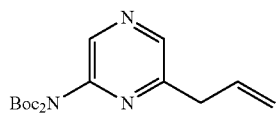

To a solution of 2-amino-6-allylpyrazine (1 g, 7.4 mmol, 1.0 equiv) in THF (30 mL) was added DMAP (181 mg, 1.48 mmol, 0.2 equiv) and Boc$_2$O (6.5 g, 29.6 mmol, 4.0 equiv) at 0° C. The resulting mixture was stirred at room temperature for 3 hours. The reaction solution was concentrated in vacuo and the residue was purified by silica gel column chromatography (eluting with PE/EtOAc=40/1) to afford the title compound 2-(bis(tert-butoxycarbonyl)amino)-6-allylpyrazine as a white solid (1.6 g, 64% yield). LC-MS: m/z 336.4 (M+H)$^+$ Step C: 2-amino-6-(cyclopropylmethyl)pyrazine

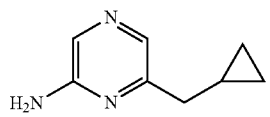

To a solution of Et$_2$Zn (9 mL, 17.9 mmol, 10.0 equiv) in DCM (100 mL) was added CH$_2$I$_2$ (4.8 g, 17.9 mmol, 10.0 equiv) at 0° C. under N$_2$ pressure. After the resulting mixture was stirred at 0° C. under N$_2$ pressure for 20 mins, 2-(bis (tert-butoxycarbonyl)amino)-6-allylpyrazine (600 mg, 1.79 mmol, 1.0 equiv) was added. The mixture was stirred at room temperature for 1 hour under N$_2$ pressure. The reaction mixture was poured onto aqueous NH$_4$Cl (50 mL) and extracted with EtOAc (2*50 mL). The extracts were dried over anhydrous MgSO$_4$ and concentrated in vacuo. The residue was purified by flash column chromatography (PE/EtOAc=10/1 to 2/1) to afford the title compound 2-amino-6-(cyclopropylmethyl)pyrazine as a white solid (120 mg, 23% yield).
LC-MS: m/z 150.2 (M+H)$^+$ Step D:
2-amino-3,5-dibromo-6-(cyclopropylmethyl)pyrazine

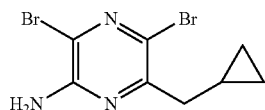

To a solution of 2-amino-6-(cyclopropylmethyl)pyrazine (230 mg, 1.5 mmol, 1.0 equiv) in THF (10 mL) was added NBS (1.1 g, 6.17 mmol, 4.0 equiv) at 0° C. under N$_2$ pressure. The mixture was stirred at room temperature for 3 hours. The mixture was concentrated in vacuo and the residue which was purified by silica gel column chromatography (eluting with PE/EtOAc=40/1 to 20/1)) to afford the title 2-amino-3,5-dibromo-6-(cyclopropylmethyl)pyrazine as yellow oil (240 mg, 49% yield).
LC-MS: m/z 305.9, 307.9, 309.9 (M+H)$^+$ Step E: N-(3,5-dibromo-6-(cyclopropylmethyl) pyrazin-2-yl)-6-ethoxypicolinamide

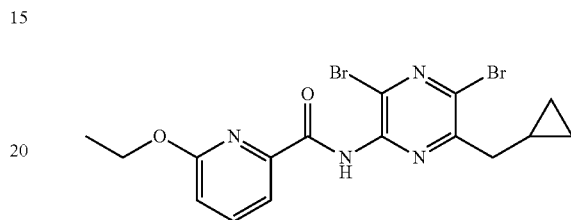

To a solution of 3,5-dibromo-6-(cyclopropylmethyl) pyrazin-2-amine (240 mg, 0.78 mmol, 1.0 equiv) in toluene (5 mL) was added Al(Me)$_3$ (2 mol/L in toluene, 0.6 mL, 1.17 mmol, 1.5 equiv) dropwise at 0° C. under N$_2$ atmosphere. After the mixture was stirred at 0° C. for 20 mins and at 50° C. for 30 mins, ethyl 6-ethoxypicolinate (230 mg, 1.17 mmol, 1.5 equiv) was added. The resulting mixture was stirred at 50° C. for 4 hours. The reaction mixture was quenched with 1N HCl (10 mL), followed by extraction with DCM (2*30 mL). The combined organic layers were dried over anhydrous Na$_2$SO$_4$ and concentrated in vacuo. The residue was purified by silica gel column chromatography (eluting with PE/EtOAc=20/1)) to afford the title compound N-(3,5-dibromo-6-(cyclopropylmethyl)pyrazin-2-yl)-6-ethoxypicolinamide as a white solid (320 mg, 89% yield).
LC-MS: m/z 455.0, 457.0, 459.0 (M+H)$^+$ Step F: N-(5-bromo-6-(cyclopropylmethyl)-3-((2,6-dimethoxyphenyl)amino)pyrazin-2-yl)-6-ethoxypicolinamide

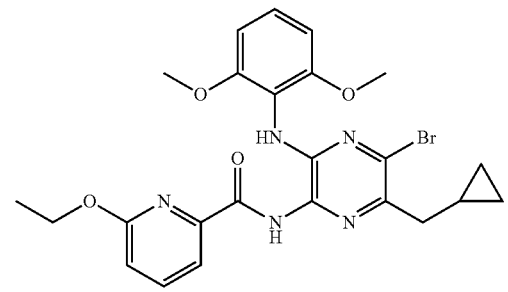 [SMILES: CCOc1cccc(C(=O)Nc2nc(CC3CC3)c(Br)nc2Nc2c(OC)cccc2OC)n1]

A suspension of N-(3,5-dibromo-6-(cyclopropylmethyl) pyrazin-2-yl)-6-ethoxypicolinamide (120 mg, 0.26 mmol, 1.0 equiv), 2,6-dimethoxyaniline (40 mg, 0.26 mmol, 1.0 equiv), Pd$_2$(dba)$_3$ (48 mg, 0.053 mmol, 0.2 equiv), Xantphos (61 mg, 0.11 mmol, 0.4 equiv) and K$_2$CO$_3$ (73 mg, 0.53 mmol, 3.0 equiv) in 1,4-dioxane (4 mL) was stirred at 100° C. via microwave irradiation for 2 hours under N$_2$ atmosphere. The mixture was filtered and the filtrate was concentrated to dryness. The residue was purified by Prep-TLC (PE/EtOAc=15/1) to afford the title compound N-(5-bromo-6-(cyclopropylmethyl)-3-((2,6-dimethoxyphenyl)amino)pyrazin-2-yl)-6-ethoxypicolinamide as yellow oil (55 mg, 40% yield)

LC-MS: m/z 528.1, 530.1 (M+H)+

Step G: 6-bromo-5-(cyclopropylmethyl)-1-(2,6-dimethoxyphenyl)-2-(6-ethoxypyridin-2-yl)-1H-imidazo[4,5-b]pyrazine

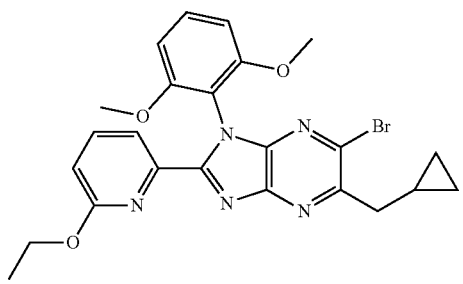 [SMILES: CCOc1cccc(-c2nc3nc(CC4CC4)c(Br)nc3n2-c2c(OC)cccc2OC)n1]

The solution of N-(5-bromo-6-(cyclopropylmethyl)-3-((2,6-dimethoxyphenyl)amino)pyrazin-2-yl)-6-ethoxypicolinamide (100 mg, 0.19 mmol, 1.0 equiv) in AcOH (5 mL) was stirred at 110° C. via microwave irradiation for 3 hours. The mixture was concentrated in vacuo. The residue was dissolved in EtOAc (40 mL) and washed with NaHCO3 (aq., 30 mL). The organic phase was dried over anhydrous MgSO4 and concentrated in vacuo. The residue was purified by Prep-TLC (100% DCM) to afford the title compound 6-bromo-5-(cyclopropylmethyl)-1-(2,6-dimethoxyphenyl)-2-(6-ethoxypyridin-2-yl)-1H-imidazo[4,5-b]pyrazine as a white solid (80 mg, 83% yield).

LC-MS: m/z 510.1, 512.1 (M+H)+

Example 65: N-(5-(cyclopropylmethyl)-1-(2,6-dimethoxyphenyl)-2-(6-ethoxypyridin-2-yl)-1H-imidazo[4,5-b]pyrazin-6-yl)methanesulfonamide

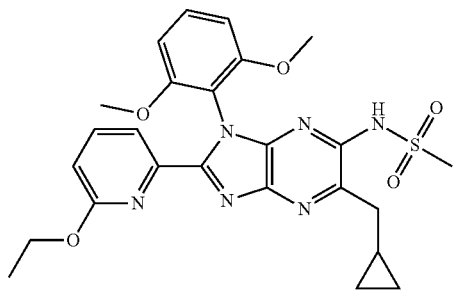 [SMILES: CCOc1cccc(-c2nc3nc(CC4CC4)c(NS(C)(=O)=O)nc3n2-c2c(OC)cccc2OC)n1]

A suspension of 6-bromo-5-(cyclopropylmethyl)-1-(2,6-dimethoxyphenyl)-2-(6-ethoxypyridin-2-yl)-1H-imidazo[4,5-b]pyrazine (80 mg, 0.16 mmol, 1.0 equiv), methanesulfonamide (30 mg, 0.31 mmol, 2.0 equiv), CuI (60 mg, 0.31 mmol, 3.0 equiv), trans-N,N'-Dimethylcyclohexane-1,2-diamine (45 mg, 0.31 mmol, 3.0 equiv) and K2CO3 (65 mg, 0.47 mmol, 3 equiv) in DMF (5 mL) was stirred at 100° C. via microwave irradiation for 2 hours under N2 atmosphere. The mixture was diluted with 1N HCl (aq., 20 mL) and extracted with EtOAc (3*20 mL). The combined organic layers were dried over anhydrous Na2SO4 and concentrated in vacuo. The residue was purified by flash chromatography to afford the title compound as a white solid (55 mg, 67% yield).

1H NMR (400 MHz, DMSO-d6) δ: 7.92 (d, J=7.2 Hz, 1H), 7.84 (t, J=8.0 Hz, 1H), 7.44 (t, J=8.0 Hz, 1H), 6.84 (d, J=8.4 Hz, 2H), 6.79 (d, J=8.0 Hz, 1H), 3.56 (s, 6H), 3.39 (q, J=7.2 Hz, 2H), 3.06 (s, 3H), 2.83 (d, J=7.2 Hz, 2H), 1.23-1.30 (m, 1H), 1.02 (t, J=7.2 Hz, 3H), 0.46-0.50 (m, 2H), 0.25-0.29 (m, 2H). LC-MS: m/z 525.2 (M+H)+

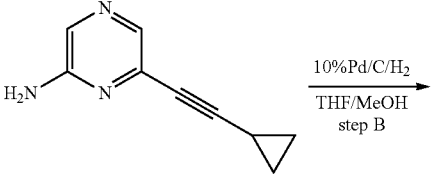

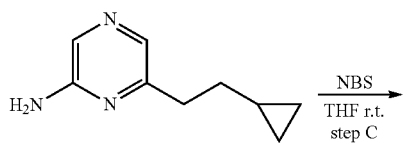

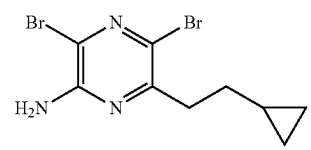

Step A: 6-(cyclopropylethynyl)pyrazin-2-amine

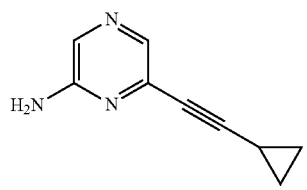 [SMILES: Nc1cncc(C#CC2CC2)n1]

To a mixture of 6-bromopyrazin-2-amine (3.48 g, 20 mmol, 1.0 equiv), ethynylcyclopropane (2.5 mL, 30 mmol, 1.5 equiv), bis(triphenylphosphine)palladium (II) chloride (1.4 g, 2 mmol, 0.1 equiv), Et₃N (8.3 mL, 60 mmol, 3 equiv) in THF (10 mL) was added Cuprous iodide (380 mg, 2 mmol, 0.1 equiv) at room temperature. The resulting mixture was stirred at 80° C. for 16 hours under N₂ atmosphere in sealed tube. The reaction mixture was evaporated and the residue was purified by silica gel column chromatography (eluting with PE/EtOAc=20/1 ro 3/1) to afford the title compound 6-(cyclopropylethynyl)pyrazin-2-amine as a brown solid (2.6 g, 82% yield).

¹H NMR (400 MHz, DMSO-d₆) δ: 7.79 (s, 1H), 7.71 (s, 1H), 6.51 (s, 2H), 1.52-1.59 (m, 1H), 0.89-0.94 (m, 2H), 0.73-0.77 (m, 2H).

Step B: 6-(2-cyclopropylethyl)pyrazin-2-amine

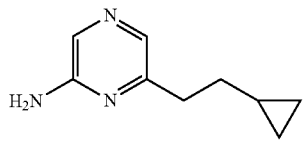 [SMILES: Nc1cncc(CCC2CC2)n1]

To a mixture of 6-(cyclopropylethynyl)pyrazin-2-amine (2.1 g, 6.8 mmol, 1.0 equiv) in THF (15 mL) and MeOH (15 mL) was added 10% Pd/C (400 mg) at room temperature. The resulting mixture was stirred at room temperature under hydrogen atmosphere (70 Psi) for 80 hours. The mixture was filtered and the filtrate was concentrated in vacuo to afford the title compound 6-(2-cyclopropylethyl)pyrazin-2-amine as a brown solid (1.5 g, 70% yield).

¹H NMR (400 MHz, DMSO-d₆) δ: 7.67 (s, 1H), 7.57 (s, 1H), 6.26 (s, 2H), 2.56 (t, J=8.8 Hz, 2H), 1.47-1.60 (m, 2H), 0.64-0.72 (m, 1H), 0.35-0.43 (m, 2H), 0.01-0.09 (m, 2H).

Step C: 3,5-dibromo-6-(2-cyclopropylethyl)pyrazin-2-amine

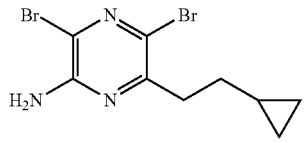 [SMILES: Nc1nc(CCC2CC2)c(Br)nc1Br]

To a mixture of 6-(2-cyclopropylethyl)pyrazin-2-amine (400 mg, 2.45 mmol, 1.0 equiv) in THF (10 mL) was added NBS (1.74 g, 9.80 mmol, 4 equiv) at room temperature. The resulting mixture was stirred at room temperature for 3.5 hours under N₂ atmosphere. The mixture was diluted with ethyl acetate (70 mL), washed with Na₂SO₃ (3 mol/L, 20 mL), water (35 mL) and brine (60 mL) successively. The organic phase was dried over anhydrous Na₂SO₄ and concentrated in vacuo. The residue was purified by silica gel column chromatography (eluting with PE/EtOAc=20/1 to 5/1) to afford the title compound 3,5-dibromo-6-(2-cyclopropylethyl)pyrazin-2-amine as a yellow solid (600 mg, yield 76%).

¹H NMR (400 MHz, DMSO-d₆) δ: 6.84 (s, 2H), 2.69-2.73 (m, 2H), 1.46-1.52 (m, 2H), 0.63-0.77 (m, 1H), 0.36-0.40 (m, 2H), 0.01-0.09 (m, 2H).

Example 66: N-(5-(2-cyclopropylethyl)-1-(2,6-dimethoxyphenyl)-2-(6-ethoxypyridin-2-yl)-1H-imidazo[4,5-b]pyrazin-6-yl)methanesulfonamide

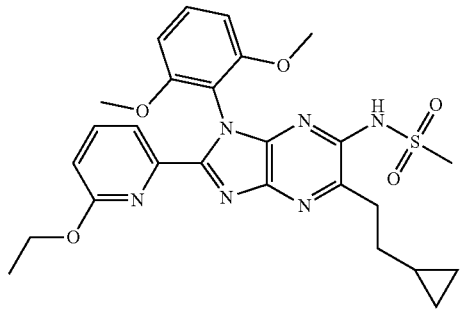 [SMILES: CCOc1cccc(-c2nc3nc(CCC4CC4)c(NS(C)(=O)=O)nc3n2-c2c(OC)cccc2OC)n1]

The title compound was prepared according to Example 65, step E~H, by using 3,5-dibromo-6-(2-cyclopropylethyl)pyrazin-2-amine in step E.

¹H NMR (400 MHz, DMSO-d₆) δ: 10.20 (s, 1H), 7.83-7.94 (m, 2H), 7.44 (t, J=8.4 Hz, 1H), 6.84 (d, J=8.4 Hz, 2H), 6.79 (d, J=8.0 Hz, 1H), 3.56 (s, 6H), 3.39 (q, J=7.2 Hz, 2H), 3.10 (s, 3H), 3.02 (t, J=7.6 Hz, 2H), 1.66 (dd, J=15.2, 7.2 Hz, 2H), 1.01 (t, J=7.2 Hz, 3H), 0.86-0.79 (m, 1H), 0.38-0.50 (m, 2H), 0.09 (q, J=5.2 Hz, 2H). LC-MS: m/z 539.2 (M+H)⁺

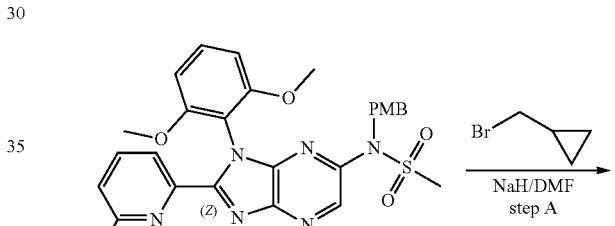

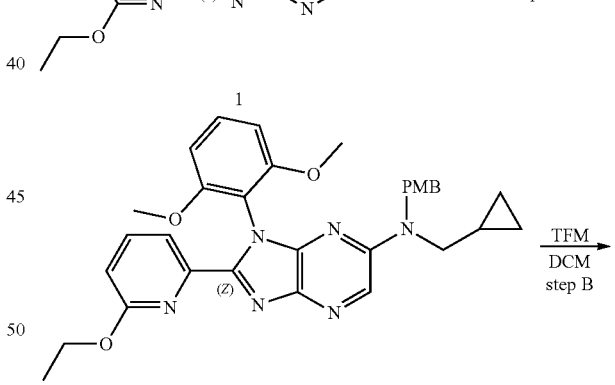

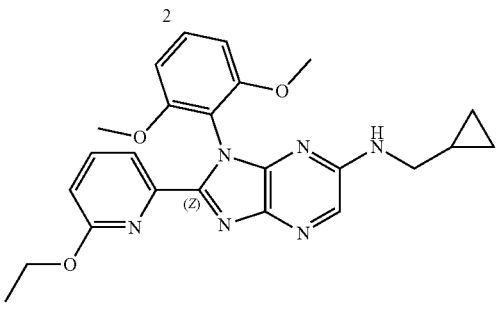

Ex. 67

N-(1-(2,6-dimethoxyphenyl)-2-(6-ethoxypyridin-2-yl)-1H-imidazo[4,5-b]pyrazin-6-yl)-N-(4-methoxybenzyl)methanesulfonamide

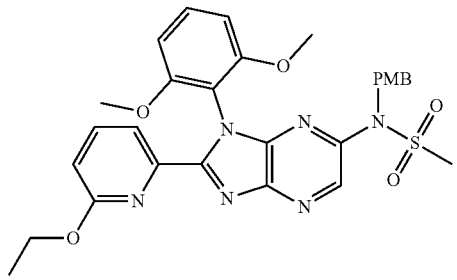

The title compound was prepared according to Method C, step D, starting from 6-bromo-1-(2,6-dimethoxyphenyl)-2-(6-ethoxypyridin-2-yl)-1H-imidazo[4,5-b]pyrazine (Example 1) by using N-(4-methoxybenzyl)methanesulfonamide (250 mg, 64% yield).

LC-MS: m/z 591.2 (M+H)+

Step A: N-(cyclopropylmethyl)-1-(2,6-dimethoxyphenyl)-2-(6-ethoxypyridin-2-yl)-N-(4-methoxybenzyl)-1H-imidazo[4,5-b]pyrazin-6-amine

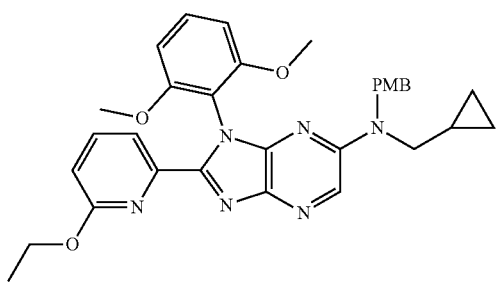

To a solution of N-(1-(2,6-dimethoxyphenyl)-2-(6-ethoxypyridin-2-yl)-1H-imidazo[4,5-b]pyrazin-6-yl)-N-(4-methoxybenzyl)methanesulfonamide (30 mg, 0.05 mmol, 1.0 equiv) in DMF (2 mL) was added NaH (3.0 mg, 0.076 mmol, 1.5 equiv). After the mixture was stirred at room temperature for 0.5 hour under N₂, (bromomethyl)cyclopropane (14 mg, 0.1 mmol, 3.0 equiv) was added. The mixture was stirred at room temperature overnight. The mixture was quenched with H₂O (10 mL), extracted with EtOAc (3*15 mL). The extracts were washed with water (10 mL) and brine (10 mL), dried over anhydrous MgSO₄ and concentrated in vacuo. The residue was purified by Prep-TLC (PE/EtOAc=3/2) to afford the title compound N-(cyclopropylmethyl)-1-(2,6-dimethoxyphenyl)-2-(6-ethoxypyridin-2-yl)-N-(4-methoxybenzyl)-1H-imidazo[4,5-b]pyrazin-6-amine as a yellow solid (23 mg, 70% yield).

LC-MS: m/z 567.3 (M+H)+

Example 67: N-(cyclopropylmethyl)-1-(2,6-dimethoxyphenyl)-2-(6-ethoxypyridin-2-yl)-1H-imidazo[4,5-b]pyrazin-6-amine

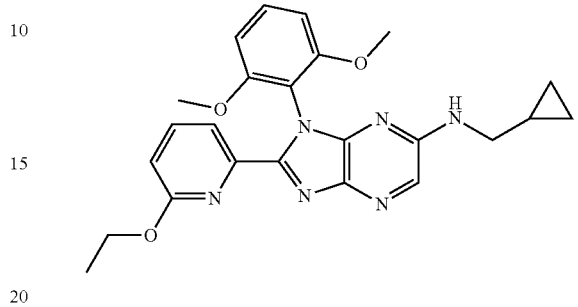

To a solution of N-(cyclopropylmethyl)-1-(2,6-dimethoxyphenyl)-2-(6-ethoxypyridin-2-yl)-N-(4-methoxybenzyl)-1H-imidazo[4,5-b]pyrazin-6-amine (20 mg, 0.03 mmol, 1.0 equiv) in DCM (5 mL) was added TFA (18 mg, 0.15 mmol, 5 equiv) at 0° C. The mixture was stirred at room temperature overnight. The mixture was concentrated to dryness. The residue was purified by Prep-TLC (PE/EtOAc=1/1) to afford the title compound as a yellow solid (3 mg, 21% yield).

¹H NMR (400 MHz, CDCl₃) δ: 8.00 (br. s, 1H), 7.85 (s, 1H), 7.62 (t, J=8.0 Hz, 1H), 7.34 (t, J=8.4 Hz, 1H), 6.67 (d, J=8.4 Hz, 2H), 6.61 (d, J=8.0 Hz, 1H), 3.61 (s, 6H), 3.42-3.44 (m, 2H), 3.13 (d, J=6.8 Hz, 1H), 1.01-1.09 (m, 4H), 0.86-0.89 (m, 1H), 0.49-0.53 (m, 2H), 0.21-0.24 (m, 2H). LC-MS: m/z 447.2 (M+H)+

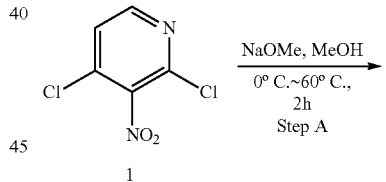

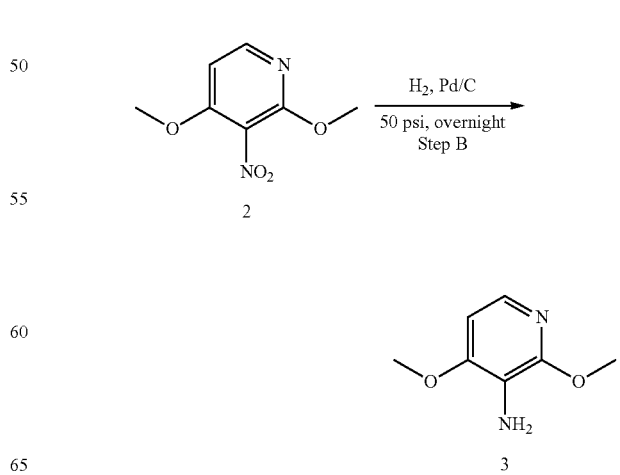

Step A: 2,4-dimethoxy-3-nitropyridine

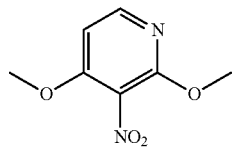

2,4-dichloro-3-nitropyridine (10 g, 51.8 mmol, 1.0 equiv) was dissolved in MeOH and the solution was cooled to 0° C. Then NaOMe solution (2 mol/L in MeOH, 78 mL, 155.4 mmol, 3.0 equiv) was added dropwise. The reaction solution was poured onto ice after stirred at 60° C. for 2 h. The resulting mixture was extracted with EtOAc (3*100 mL). The combined organic layers were washed with brine, dried over $Na_2SO_4$ and concentrated in vacuo to give the title compound 2,4-dimethoxy-3-nitropyridine as a light yellow solid (9.0 g, 94% yield). The crude product was used in next step without purification.

LC-MS: m/z 185.0 $(M+H)^+$

Step B: 2,4-dimethoxypyridin-3-amine

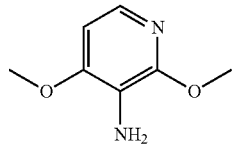

2,4-dimethoxy-3-nitropyridine (9.0 g, 48.6 mmol, 1.0 equiv) was dissolved in MeOH and 10% Pd/C (1.8 g) was added. The mixture was stirred overnight under 50 psi $H_2$ atmosphere at room temperature. The mixture was filtered and the filter cake was swashed with MeOH (3*50 mL). The filtrate was concentrated to give 2,4-dimethoxypyridin-3-amine as a gray solid (7.5 g, 99% yield). The crude product was used in next step directly.

LC-MS: m/z 155.1 $(M+H)^+$

Example 68: N-(1-(2,4-dimethoxypyridin-3-yl)-2-(6-ethoxypyridin-2-yl)-1H-imidazo[4,5-b]pyrazin-6-yl)methanesulfonamide

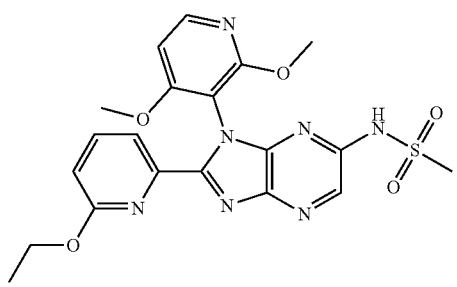 [SMILES: CCOc1cccc(-c2nc3ncc(NS(C)(=O)=O)nc3n2-c2c(OC)ccnc2OC)n1]

The title compound was prepared according to Method E by using 2,4-dimethoxypyridin-3-amine in step A.

$^1$H NMR (400 MHz, DMSO-$d_6$) δ: 11.16 (br. s, 1H), 8.26 (s, 1H), 8.24 (d, J=6.0 Hz, 1H), 7.98 (d, J=7.2 Hz, 1H), 7.87 (t, J=8.0 Hz, 1H), 7.06 (d, J=6.0 Hz, 1H), 6.85 (d, J=8.0 Hz, 1H), 3.69 (d, J=5.2 Hz, 6H), 3.42 (q, J=7.2 Hz, 2H), 3.17 (s, 3H), 1.06 (t, J=7.2 Hz, 3H). LC-MS: m/z 471.9 $(M+H)^+$

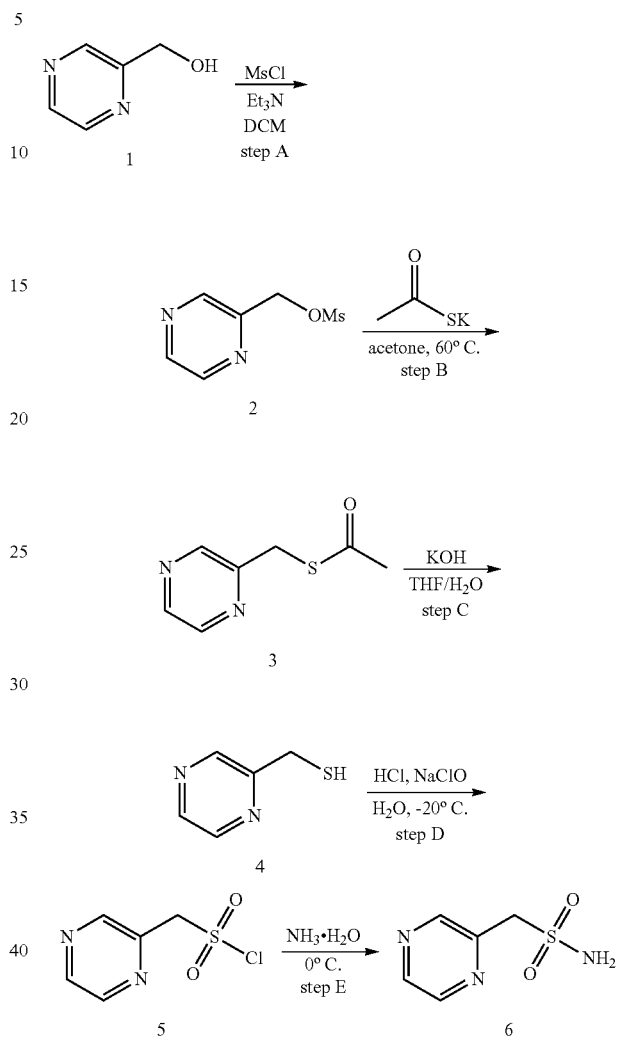

Step A: pyrazin-2-ylmethyl methanesulfonate

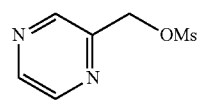 [SMILES: CS(=O)(=O)OCc1cnccn1]

To a mixture of pyrazin-2-ylmethanol (3.0 g, 27.3 mmol, 1.0 equiv) and triethylamine (5.1 g, 50 mmol, 1.8 equiv) in DCM (20 mL) was was added MsCl (5.72 g, 50 mmol, 1.8 equiv) dropwise over 10 mins. The resulting mixture was stirred at room temperature for 2 hours. Then the mixture was diluted with water and extracted with DCM (3*30 mL). The organic layers were washed with brine, dried over anhydrous $Na_2SO_4$ and concentrated in vacuo to give the title compound as a yellow oil (assumed 100% yield). The crude compound was used in the next step without any further purification. LC-MS: m/z 189.0 $(M+H)^+$ Step B: S-(pyrazin-2-ylmethyl) ethanethioate

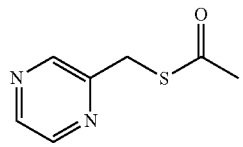

To the solution of pyrazin-2-ylmethyl methanesulfonate (5.1 g, 27.3 mmol, 1.0 equiv) in acetone (40 mL) was added potassium thioacetate (4.7 g, 40.9 mmol, 1.5 equiv) in one portion, the resulting mixture was stirred at 60° C. overnight. Then the mixture was filtered and the filtrate was concentrated in vacuo. The residue was purified by column chromatography (eluting with PE/EtOAc=1/1) to give the title compound S-(pyrazin-2-ylmethyl) ethanethioate as a yellow oil (3.6 g, 79% yield in two steps). LC-MS: m/z 169.0 (M+H)$^+$ Step C: pyrazin-2-ylmethanethiol

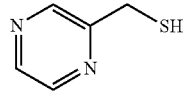

To a solution of S-(pyrazin-2-ylmethyl) ethanethioate (1.0 g, 5.95 mmol, 1.0 equiv) in THF (15 mL) was added KOH (1.0 g, 17.8 mmol, 3 equiv) in water (50 mL). The mixture was stirred at room temperature for 1 h. The reaction mixture was acidified with 1 N HCl (aq.) and extracted with DCM (3*15 mL). The combined organic phase was used directly in next step. LC-MS: m/z 127.0 (M+H)$^+$ Step D: pyrazin-2-ylmethanesulfonyl chloride

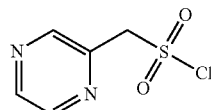

Sodium hypochlorite (26.6 mL, 35.7 mmol, 6.0 equiv) was added dropwise with rapid stirring to a solution of pyrazin-2-ylmethanethiol (750 mg, 5.95 mmol, 1.0 equiv) in DCM (45 mL) and 1N HCl (35.7 mL, 35.7 mmol, 6.0 equiv) at −20° C. After the addition was completed, the mixture was stirred at −20° C. for 2 h. The organic layer were separated and used directly in next step.

Step E: pyrazin-2-ylmethanesulfonamide

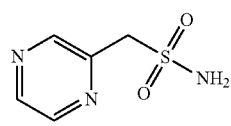

The solution of pyrimidine-2-sulfonyl chloride in DCM (45 mL) was added to NH$_4$OH (aq., 34%, 40 mL) at 0° C. The resulting mixture was allowed to slowly warm to room temperature and stirred for 1 h. The mixture was concentrated under vacuum and the residue was purified by silica gel chromatography (eluting with DCM/MeOH=20/1) to afford the title compound pyrazin-2-ylmethanesulfonamide as a light yellow solid (180 mg, 17% yield in three steps).
$^1$H NMR (400 MHz, DMSO-d$_6$) δ: 8.68-8.74 (m, 1H), 8.63-8.68 (m, 1H), 8.60-8.64 (m, 1H), 7.04 (s, 2H), 4.52 (s, 2H). LC-MS: m/z 174.0 (M+H)$^+$ Example 69: N-(1-(2,6-dimethoxyphenyl)-2-(6-ethoxypyridin-2-yl)-1H-imidazo[4,5-b]pyrazin-6-yl)-1-(pyrazin-2-yl)methanesulfonamide

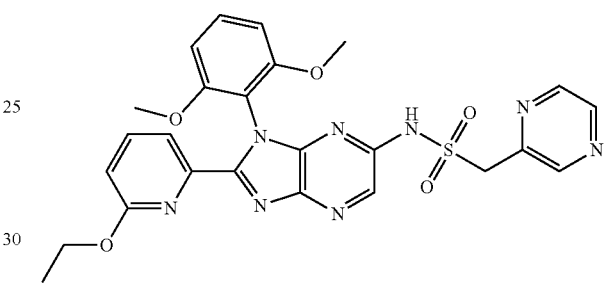

The title compound was prepared according to Method C, step D, starting from N-(5-chloro-3-((2,6-dimethoxyphenyl)amino)pyrazin-2-yl)-6-ethoxypicolinamide by using pyrazin-2-ylmethanesulfonamide (45 mg, 48% yield). $^1$H NMR (400 MHz, DMSO-d$_6$) δ: 11.21 (s, 1H), 8.59-8.62 (m, 1H), 8.56-8.58 (m, 1H), 8.46-8.50 (m, 1H), 8.21 (s, 1H), 7.97 (d, J=7.6 Hz, 1H), 7.87 (t, J=7.6 Hz, 1H), 7.47 (t, J=8.4 Hz, 1H), 6.87 (d, J=8.4 Hz, 2H), 6.83 (dd, J=7.6, 0.8 Hz, 1H), 4.93 (s, 2H), 3.57 (s, 6H), 3.40 (q, J=7.2 Hz, 3H), 1.03 (t, J=7.2 Hz, 3H). LC-MS: m/z 549.2 (M+H)$^+$

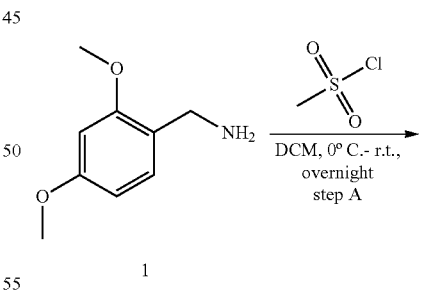

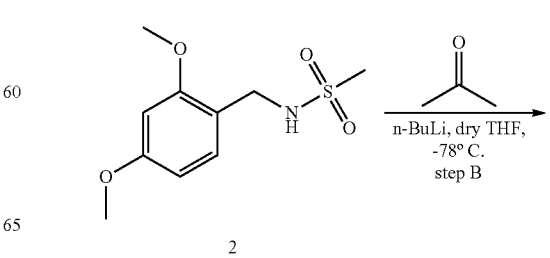

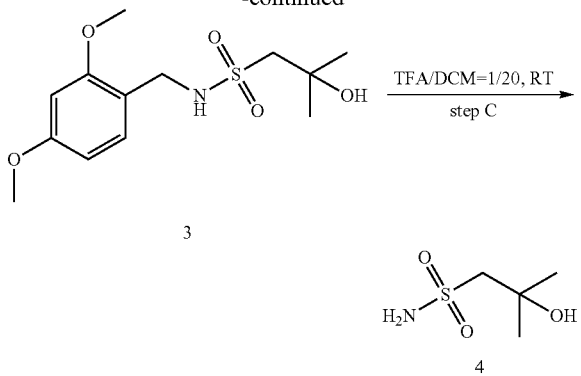

Step A: N-(2,4-Dimethoxybenzyl)methanesulfonamide

A solution of (2,4-dimethoxyphenyl)methanamine (5.00 g, 29.9 mmol, 1.0 equiv) in DCM (50 mL) was cooled to 0° C. Then triethyl amine (6.10 g, 8.38 mL, 59.8 mmol, 2.0 equiv) and methanesulfonyl chloride (4.10 g, 35.9 mmol, 1.2 equiv) were added to the solution at 0° C. The mixture was stirred at room temperature overnight. The reaction mixture was poured onto sat. NaHCO$_3$ solution (60 mL) and extracted with DCM (60 mL*2). The combined organic layers were washed with 0.5 M HCl (aq., 60 mL), dried over Na$_2$SO$_4$, filtered and concentrated in vacuo to afford N-(2,4-dimethoxybenzyl)methanesulfonamide as la ight yellow solid (7.30 g, 99% yield). $^1$H NMR (400 MHz, Chloroform-d) δ: 7.17 (d, J=8.0 Hz, 1H), 6.47 (d, J=2.4 Hz, 1H), 6.44 (dd, J=8.0, 2.4 Hz, 1H), 5.00 (t, J=6.4 Hz, 1H), 4.24 (d, J=6.4 Hz, 2H), 3.84 (s, 3H), 3.80 (s, 3H), 2.73 (s, 3H).

Step B: N-(2,4-Dimethoxybenzyl)-2-hydroxy-2-methylpropane-1-sulfonamide

A solution of N-(2,4-dimethoxybenzyl)methanesulfonamide (1.50 g, 6.10 mmol, 1.0 equiv) in anhydrous THF (6 mL) was cooled to −78° C. n-BuLi (5.40 mL, 13.5 mmol, 2.5 M in hexane, 2.2 equiv) was added to the solution dropwise at −78° C. After the resulting mixture was stirred at −78° C. for 30 minutes, acetone (1.10 g, 1.40 mL, 18.3 mmol, 3.0 equiv) was added. The reaction mixture was warmed up to room temperature and stirred for 10 minutes. Then the mixture was poured onto sat. NH$_4$Cl solution (30 mL) and extracted with EtOAc (30 mL*2). The combined organic layers were washed with brine, dried over anhydrous Na$_2$SO$_4$, filtered and concentrated in vacuo. The residue was purified by chromatography on silica gel (eluted with PE/EtOAc=10/1~4/1) to afford N-(2,4-dimethoxybenzyl)-2-hydroxy-2-methylpropane-1-sulfonamide as a colorless oil (580 mg, 31% yield). $^1$H NMR (400 MHz, Chloroform-d) S: 7.17 (d, J=8.0 Hz, 1H), 6.48 (d, J=2.4 Hz, 1H), 6.46 (dd, J=8.0, 2.4 Hz, 1H), 5.00 (t, J=5.2 Hz, 1H), 4.24 (d, J=6.0 Hz, 2H), 3.84 (s, 3H), 3.81 (s, 3H), 3.35 (s, 1H), 3.01 (s, 2H), 1.32 (s, 6H).

Step C: 2-Hydroxy-2-methylpropane-1-sulfonamide

A solution of N-(2,4-dimethoxybenzyl)-2-hydroxy-2-methylpropane-1-sulfonamide (380 mg, 1.25 mmol) in DCM (10 mL) was cooled to 0° C. and then TFA (0.5 mL) was added to the solution. The mixture was stirred at room temperature for 2 hours. The reaction mixture was diluted with DCM (20 mL) and filtered. The filtrate was concentrated in vacuo. The residue was stirred in DCM/hexane (15 mL/15 mL) at room temperature for 1 hour. Then the resulting mixture was filtered. The filter cake was washed with hexane to give 2-hydroxy-2-methylpropane-1-sulfonamide as a white solid (220 mg, 90% yield). $^1$H NMR (400 MHz, DMSO-d$_6$) δ: 6.72 (s, 2H), 4.79 (s, 1H), 3.15 (s, 2H), 1.29 (s, 6H).

Example 70: N-(1-(2,6-Dimethoxyphenyl)-2-(6-ethoxypyridin-2-yl)-1H-imidazo[4,5-b]pyrazin-6-yl)-2-hydroxy-2-methylpropane-1-sulfonamide The title compound was prepared according to Method C, Step D, starting from 6-chloro-1-(2,6-dimethoxyphenyl)-2-(6-ethoxypyridin-2-yl)-1H-imidazo[4,5-b]pyrazine by using 2-hydroxy-2-methylpropane-1-sulfonamide. $^1$H NMR (400 MHz, DMSO-d$_6$) δ: 8.17 (s, 1H), 7.90 (d, J=7.2 Hz, 1H), 7.82 (t, J=7.6 Hz, 1H), 7.42 (t, J=8.4 Hz, 1H), 6.83 (d, J=8.4 Hz, 2H), 6.77 (d, J=8.0 Hz, 1H), 3.58 (s, 6H), 3.35-3.41 (m, 4H), 1.18 (s, 6H), 1.02 (t, J=7.2 Hz, 3H). LC-MS: m/z 529.2 (M+H)$^+$.

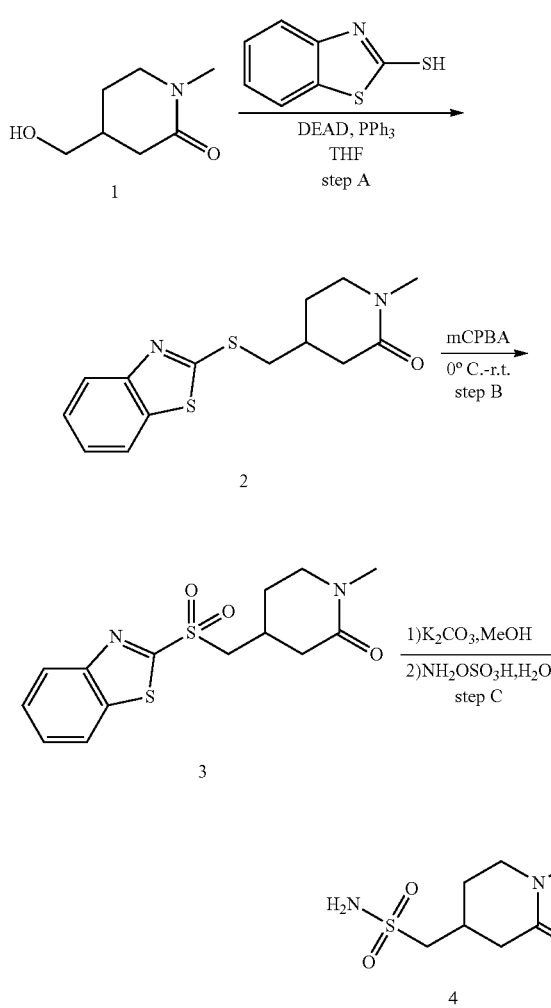

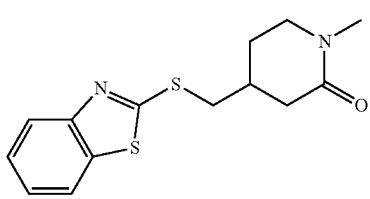 [SMILES: CN1CCC(CSc2nc3ccccc3s2)CC1=O]

Step A: 4-((Benzo[d]thiazol-2-ylthio)methyl)-1-methylpiperidin-2-one

To a solution of 4-(hydroxymethyl)-1-methylpiperidin-2-one (600 mg, 4.20 mmol, 1.0 equiv), benzo[d]thiazole-2-thiol (912 mg, 5.50 mmol, 1.3 equiv) and PPh$_3$ (1.65 g, 6.30 mmol, 1.5 equiv) in anhydrous THF (25 mL) was added DEAD (1.1 g, 6.3 mmol, 1.5 equiv) at 0° C. The resulting mixture was stirred at room temperature for 16 hours. The mixture was concentrated in vacuo and the residue was purified by flash chromatography (eluted with DCM/MeOH=30/1) to afford 4-((benzo[d]thiazol-2-ylthio)methyl)-1-methylpiperidin-2-one as a white solid (1.00 g, 86% yield). LC-MS: m/z 293.1 (M+H)$^+$ Step B: 4-((Benzo[d]thiazol-2-ylsulfonyl)methyl)-1-methylpiperidin-2-one

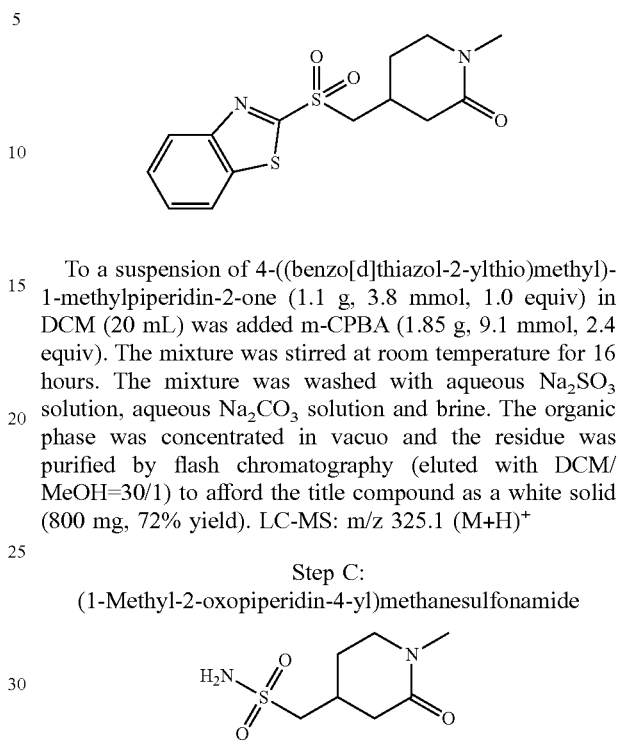

To a suspension of 4-((benzo[d]thiazol-2-ylthio)methyl)-1-methylpiperidin-2-one (1.1 g, 3.8 mmol, 1.0 equiv) in DCM (20 mL) was added m-CPBA (1.85 g, 9.1 mmol, 2.4 equiv). The mixture was stirred at room temperature for 16 hours. The mixture was washed with aqueous Na$_2$SO$_3$ solution, aqueous Na$_2$CO$_3$ solution and brine. The organic phase was concentrated in vacuo and the residue was purified by flash chromatography (eluted with DCM/MeOH=30/1) to afford the title compound as a white solid (800 mg, 72% yield). LC-MS: m/z 325.1 (M+H)$^+$ Step C: (1-Methyl-2-oxopiperidin-4-yl)methanesulfonamide To a suspension of 4-((benzo[d]thiazol-2-ylsulfonyl)methyl)-1-methylpiperidin-2-one (400 mg, 1.2 mmol, 1.0 equiv) in MeOH (10 mL) was added K$_2$CO$_3$ (840 mg, 6.10 mmol, 5.0 equiv). The resulting mixture was stirred at room temperature for 10 minutes. Then a solution of NH$_2$OSO$_3$H (330 mg, 2.9 mmol, 2.4 equiv) in H$_2$O (2 mL) was added. The mixture was stirred at room temperature for 16 hours. The resulting mixture was concentrated in vacuo and the residue was purified by reverse phase prep-HPLC (eluted with CH$_3$CN/H$_2$O=5/95~90/10) to afford the title compound (1-methyl-2-oxopiperidin-4-yl)methanesulfonamide as a white solid (190 mg, 75% yield). $^1$H NMR (400 MHz, DMSO-d$_6$) δ: 6.97 (s, 2H), 3.24-3.28 (m, 2H), 2.94-3.06 (m, 2H), 2.79 (s, 3H), 2.44-2.50 (m, 1H), 2.32-2.34 (m, 1H), 2.00-2.12 (m, 2H), 1.58-1.62 (m, 1H). LC-MS: m/z 207.1 (M+H)$^+$ Example 71: (S)—N-(1-(2,6-Dimethoxyphenyl)-2-(6-ethoxypyridin-2-yl)-1H-imidazo[4,5-b]pyrazin-6-yl)-1-(1-methyl-2-oxopiperidin-4-yl)methanesulfonamide

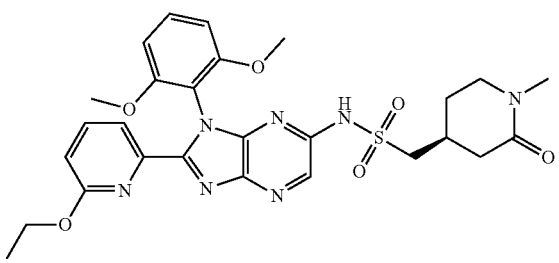

The title compound was prepared according to Method C, step D, starting from 6-chloro-1-(2,6-dimethoxyphenyl)-2-

(6-ethoxypyridin-2-yl)-1H-imidazo[4,5-b]pyrazine by using (1-methyl-2-oxopiperidin-4-yl)methanesulfonamide and separated by chiral separation.

¹H NMR (400 MHz, Chloroform-d) δ: 8.41 (s, 1H), 8.12 (d, J=7.2 Hz, 1H), 7.68 (t, J=7.6 Hz 1H), 7.46 (s, 1H), 7.38 (t, J=7.6 Hz, 1H), 6.68-6.72 (m, 3H), 3.62 (s, 3H), 3.61 (s, 3H), 3.42 (q, J=7.6 Hz, 2H), 3.38-3.22 (m, 4H), 2.93 (s, 3H), 2.52-2.46 (m, 2H), 2.16-2.10 (m, 1H), 1.98-2.02 (m, 1H), 1.22-1.26 (m, 1H), 1.07 (t, J=7.6 Hz, 3H). LC-MS: m/z 582.2 (M+H)⁺

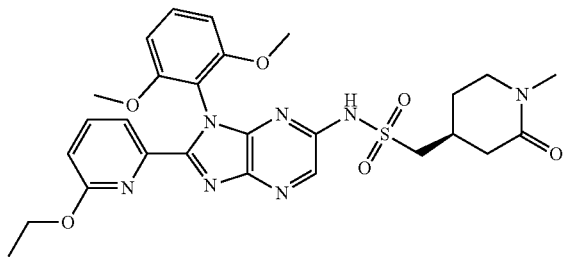 [SMILES: CCOc1cccc(-c2nc3ncc(NS(=O)(=O)C[C@H]4CCN(C)C(=O)C4)nc3n2-c2c(OC)cccc2OC)n1]

Example 72: (R)—N-(1-(2,6-dimethoxyphenyl)-2-(6-ethoxypyridin-2-yl)-1H-imidazo[4,5-b]pyrazin-6-yl)-1-(1-methyl-2-oxopiperidin-4-yl)methanesulfonamide

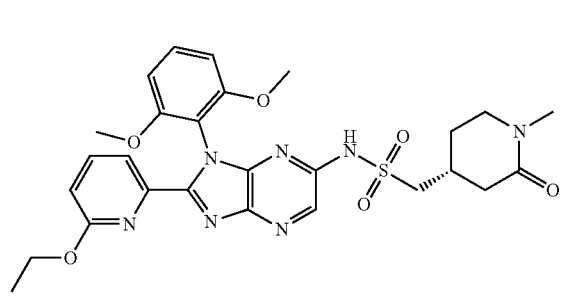 [SMILES: CCOc1cccc(-c2nc3ncc(NS(=O)(=O)C[C@@H]4CCN(C)C(=O)C4)nc3n2-c2c(OC)cccc2OC)n1]

The tile compound was prepared according to Method C, step D, starting from 6-chloro-1-(2,6-dimethoxyphenyl)-2-(6-ethoxypyridin-2-yl)-1H-imidazo[4,5-b]pyrazine by using (1-methyl-2-oxopiperidin-4-yl)methanesulfonamide and separated by chiral separation. ¹H NMR (400 MHz, Chloroform-d) δ: 8.41 (s, 1H), 8.12 (d, J=7.2 Hz, 1H), 7.68 (t, J=7.6 Hz 1H), 7.46 (s, 1H), 7.38 (t, J=7.6 Hz, 1H), 6.68-6.72 (m, 3H), 3.62 (s, 3H), 3.61 (s, 3H), 3.42 (q, J=7.6 Hz, 2H), 3.38-3.22 (m, 4H), 2.93 (s, 3H), 2.52-2.46 (m, 2H), 2.16-2.10 (m, 1H), 1.98-2.02 (m, 1H), 1.22-1.26 (m, 1H), 1.07 (t, J=7.6 Hz, 3H). LC-MS: m/z 582.2 (M+H)⁺

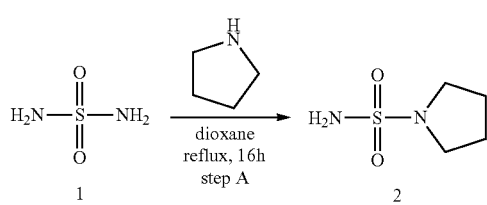 [SMILES: NS(N)(=O)=O ; C1CCNC1 ; NS(=O)(=O)N1CCCC1]

Step A: pyrrolidine-1-sulfonamide

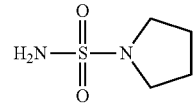

To a solution of pyrrolidine (3.30 g, 42.3 mmol, 1.0 equiv) in dioxane (100 mL) was added sulfuric diamide (10.0 g, 104 mmol, 2.5 equiv). The reaction mixture was stirred at 110° C. for 16 hours. The reaction mixture was concentrated in vacuo, reslurried in DCM and filtered to afford pyrrolidine-1-sulfonamide as a white solid (5.00 g, 71% yield). ¹H NMR (400 MHz, DMSO-d₆) δ: 6.62 (s, 2H), 3.08-3.10 (m, 4H) 1.78-1.80 (m, 4H). LC-MS: m/z 151.1 (M+H)⁺

Example 73: N-(1-(2,6-dimethoxyphenyl)-2-(6-ethoxypyridin-2-yl)-1H-imidazo[4,5-b]pyrazin-6-yl)pyrrolidine-1-sulfonamide

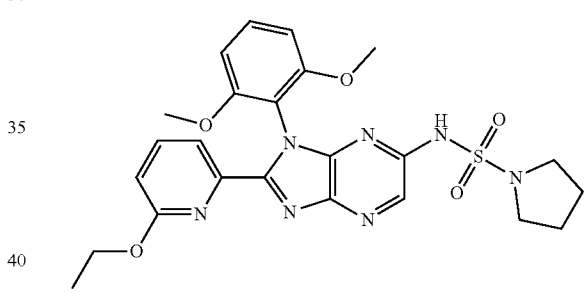

The title compound was prepared according to Method C, step D, starting from 6-chloro-1-(2,6-dimethoxyphenyl)-2-(6-ethoxypyridin-2-yl)-1H-imidazo[4,5-b]pyrazine by using pyrrolidine-1-sulfonamide. ¹H NMR (400 MHz, Chloroform-d) δ: 8.35 (s, 1H), 8.13 (d, J=7.2 Hz, 1H), 7.65-7.69 (m, 1H), 7.36 (t, J=8.4 Hz, 1H), 7.14 (s, 1H), 6.66-6.70 (m, 3H), 3.63 (s, 6H), 3.42 (q, J=7.2 Hz, 2H), 3.26-3.30 (m, 4H), 1.63-1.67 (m, 4H), 1.08 (t, J=7.2 Hz, 3H). LC-MS: m/z 526.1 (M+H)⁺ tert-Butyl 4-sulfamoylpiperazine-1-carboxylate

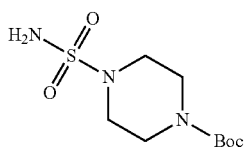

The title compound was prepared according to the preparation of pyrrolidine-1-sulfonamide by using tert-butyl piperazine-1-carboxylate. LC-MS: m/z 266.1 (M+H)⁺

203 tert-Butyl 4-(N-(1-(2,6-dimethoxyphenyl)-2-(6-ethoxypyridin-2-yl)-1H-imidazo[4,5-b]pyrazin-6-yl)sulfamoyl)piperazine-1-carboxylate

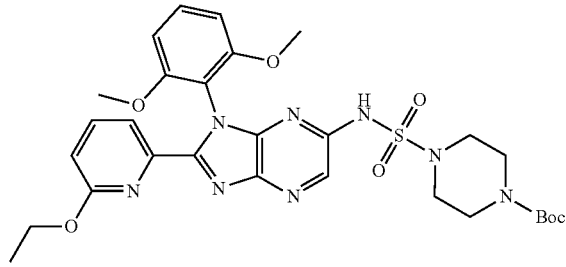 [SMILES: CCOc1cccc(-c2nc3ncc(NS(=O)(=O)N4CCN(C(=O)OC(C)(C)C)CC4)nc3n2-c2c(OC)cccc2OC)n1]

The title compound was prepared according to Method C, step D, starting from 6-chloro-1-(2,6-dimethoxyphenyl)-2-(6-ethoxypyridin-2-yl)-1H-imidazo[4,5-b]pyrazine by using tert-butyl 4-sulfamoylpiperazine-1-carboxylate. LC-MS: m/z 641.2 (M+H)⁺

Example 74: N-(1-(2,6-Dimethoxyphenyl)-2-(6-ethoxypyridin-2-yl)-1H-imidazo[4,5-b]pyrazin-6-yl)piperazine-1-sulfonamide

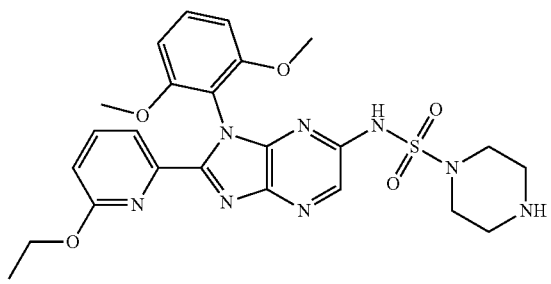 [SMILES: CCOc1cccc(-c2nc3ncc(NS(=O)(=O)N4CCNCC4)nc3n2-c2c(OC)cccc2OC)n1]

The solution of tert-butyl 4-(N-(1-(2,6-dimethoxyphenyl)-2-(6-ethoxypyridin-2-yl)-1H-imidazo[4,5-b]pyrazin-6-yl)sulfamoyl)piperazine-1-carboxylate (86.0 mg, 0.1 mmol) in HCl/MeOH (4 mol/L, 2 mL) was stirred at room temperature for 3 hours. Then the mixture was concentrated in vacuo. The residue was purified by reverse phase HPLC to afford a HCl salt of N-(1-(2,6-dimethoxyphenyl)-2-(6-ethoxypyridin-2-yl)-1H-imidazo[4,5-b]pyrazin-6-yl)piperazine-1-sulfonamide as light yellow solid (51.0 mg, 70% yield). $^1$H NMR (400 MHz, DMSO-d₆) δ: 8.19 (s, 1H), 8.16 (s, 1H), 7.90 (d, J=7.6 Hz, 1H), 7.82 (t, J=8.0 Hz, 1H), 7.42 (t, J=8.4 Hz, 1H), 6.83 (d, J=8.4 Hz, 2H), 6.75 (d, J=8.0 Hz, 1H), 3.59 (s, 6H), 3.32-3.40 (m, 2H), 2.96-2.98 (m, 4H), 2.72-2.76 (m, 4H), 1.02 (t, J=7.2 Hz, 3H). LC-MS: m/z 541.2 (M+H)⁺

Piperidine-1-sulfonamide

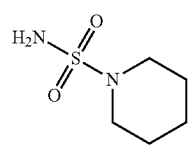

204

The title compound was prepared according to the preparation of pyrrolidine-1-sulfonamide by using piperidine. $^1$H NMR (400 MHz, Chloroform-d) δ: 4.42 (s, 2H), 3.15 (t, J=5.2 Hz, 4H), 1.63-1.77 (m, 4H), 1.47-1.59 (m, 2H).

Example 75: N-(1-(2,6-dimethoxyphenyl)-2-(6-ethoxypyridin-2-yl)-1H-imidazo[4,5-b]pyrazin-6-yl)piperidine-1-sulfonamide

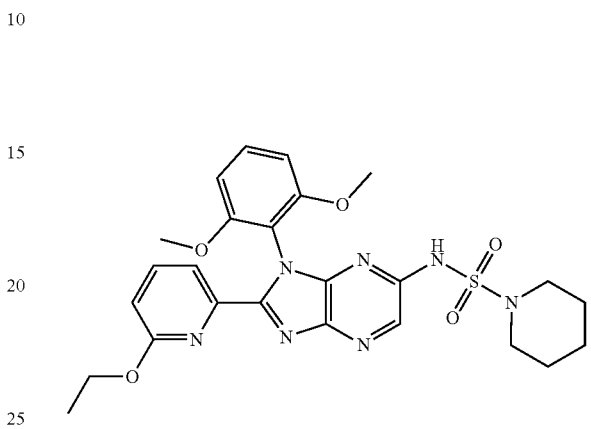

The title compound was prepared according to Method C, step D, starting from 6-chloro-1-(2,6-dimethoxyphenyl)-2-(6-ethoxypyridin-2-yl)-1H-imidazo[4,5-b]pyrazine by using piperidine-1-sulfonamide. $^1$H NMR (400 MHz, Chloroform-d) δ: 8.43 (s, 1H), 8.12 (d, J=7.2 Hz, 1H), 7.64-7.70 (m, 1H), 7.37 (t, J=8.6 Hz, 1H), 6.95 (s, 1H), 6.64-6.72 (m, 3H), 3.63 (s, 6H), 3.42 (q, J=7.2 Hz, 2H), 3.18-3.12 (m, 4H), 1.53-1.45 (m, 4H), 1.45-1.38 (m, 2H), 1.08 (t, J=7.2 Hz, 3H). LC-MS: m/z 540.2 (M+H)⁺

Example 76: N-(1-(2,6-dimethoxyphenyl)-2-(6-ethoxypyridin-2-yl)-1H-imidazo[4,5-b]pyrazin-6-yl)-N', N'-dimethylsulfamide

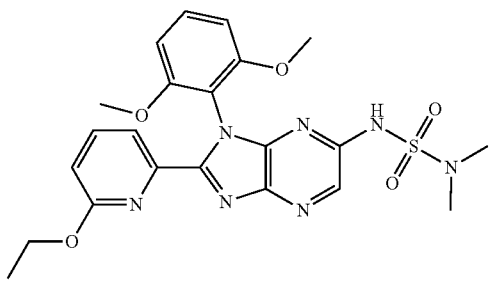 [SMILES: CCOc1cccc(-c2nc3ncc(NS(=O)(=O)N(C)C)nc3n2-c2c(OC)cccc2OC)n1]

The title compound was prepared according to Method C, step D, starting from 6-chloro-1-(2,6-dimethoxyphenyl)-2-(6-ethoxypyridin-2-yl)-1H-imidazo[4,5-b]pyrazine by using N, N-dimethylsulfamide. $^1$H NMR (400 MHz, DMSO-d₆) δ: 10.89 (s, 1H), 8.24 (s, 1H), 7.96 (d, J=8.0 Hz, 1H), 7.85 (t, J=7.6 Hz, 1H), 7.43 (t, J=8.4 Hz, 1H), 6.84 (d, J=8.4 Hz, 2H), 6.81 (dd, J=8.0, 0.8 Hz, 1H), 3.59 (s, 6H), 3.38 (t, J=7.2 Hz, 2H), 2.55 (s, 6H), 1.02 (t, J=7.2 Hz, 3H). LC-MS: m/z 500.2 (M+H)⁺

Example 77: N-(1-(2,6-dimethoxyphenyl)-2-(6-ethoxypyridin-2-yl)-1H-imidazo[4,5-b]pyrazin-6-yl)-N'-methyl-N'-cyclopropylsulfamide

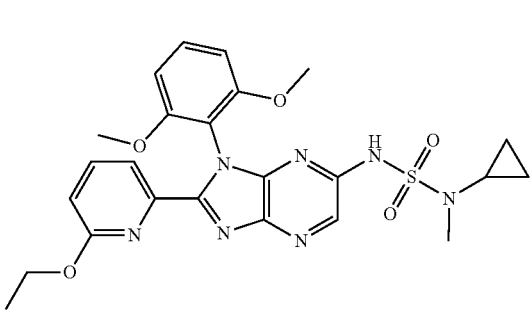 [SMILES: CCOc1cccc(-c2nc3ncc(NS(=O)(=O)N(C)C4CC4)nc3n2-c2c(OC)cccc2OC)n1]

The title compound was prepared according to Method C, step D, starting from 6-chloro-1-(2,6-dimethoxyphenyl)-2-(6-ethoxypyridin-2-yl)-1H-imidazo[4,5-b]pyrazine by using N-methyl-N-cyclopropylsulfamide. $^1$H NMR (400 MHz, DMSO-$d_6$) δ: 11.04 (br. s, 1H), 8.21 (s, 1H), 7.93 (d, J=7.2 Hz, 1H), 7.82 (t, J=7.6 Hz, 1H), 7.40 (t, J=8.4 Hz, 1H), 6.80 (d, J=8.4 Hz, 2H), 6.77 (d, J=8.0 Hz, 1H), 3.58 (s, 6H), 3.36 (q, J=7.2 Hz, 2H), 2.55 (s, 3H), 2.21-2.29 (m, 1H), 1.02 (t, J=7.2 Hz, 3H), 0.48-0.59 (m, 2H), 0.36-0.46 (m, 2H). LC-MS: m/z 526.2 (M+H)$^+$

Example 78: N-(1-(2,6-dimethoxyphenyl)-2-(6-ethoxypyridin-2-yl)-1H-imidazo[4,5-b]pyrazin-6-yl)-1-(5-fluoropyridin-2-yl)methanesulfonamide

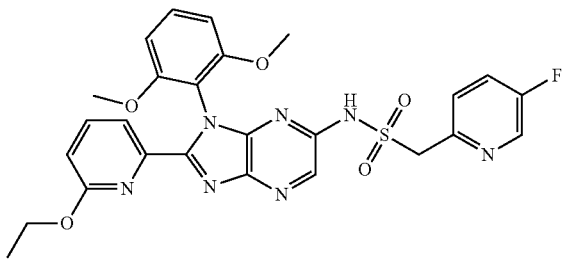 [SMILES: CCOc1cccc(-c2nc3ncc(NS(=O)(=O)Cc4ccc(F)cn4)nc3n2-c2c(OC)cccc2OC)n1]

The title compound was prepared according to Method C, step D, starting from 6-chloro-1-(2,6-dimethoxyphenyl)-2-(6-ethoxypyridin-2-yl)-1H-imidazo[4,5-b]pyrazine by using (5-fluoropyridin-2-yl)methanesulfonamide. $^1$H NMR (400 MHz, DMSO-$d_6$) δ:11.13 (s, 1H), 8.48 (d, J=4.0 Hz, 1H), 8.18 (s, 1H), 7.94-7.96 (m, 1H), 7.86 (t, J=8.0 Hz, 1H), 7.70-7.75 (m, 1H), 7.47 (t, J=8.0 Hz, 1H), 7.29 (dd, J=8.0, 4.0 Hz, 1H), 6.87 (d, J=8.0 Hz, 2H), 6.82-6.84 (m, 1H), 4.84 (s, 2H), 3.56 (s, 6H), 3.40 (q, J=7.2 Hz, 2H), 1.03 (t, J=7.2 Hz, 3H). LC-MS: m/z 566.2 (M+H)$^+$

Example 79: N-(1-(2,6-dimethoxyphenyl)-2-(6-ethoxypyridin-2-yl)-1H-imidazo[4,5-b]pyrazin-6-yl)-1-(5-fluoropyrimidin-2-yl)methanesulfonamide

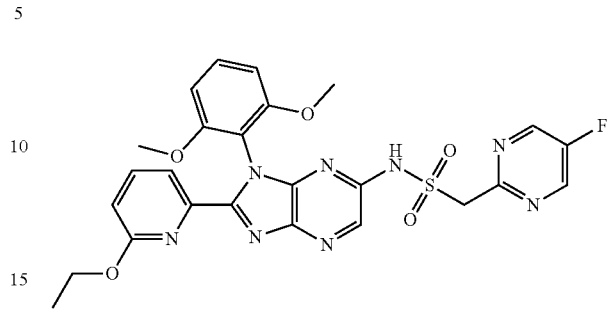

The title compound was prepared according to Method C, step D, starting from 6-chloro-1-(2,6-dimethoxyphenyl)-2-(6-ethoxypyridin-2-yl)-1H-imidazo[4,5-b]pyrazine by using (5-fluoropyrimidin-2-yl)methanesulfonamide. $^1$H NMR (400 MHz, CD$_3$OD) δ: 8.63 (s, 2H), 8.19 (s, 1H), 7.89 (d, J=7.2 Hz, 1H), 7.78 (t, J=7.6 Hz, 1H), 7.45 (t, J=8.4 Hz, 1H), 6.82 (d, J=8.4 Hz, 2H), 6.76 (dd, J=8.4, 0.4 Hz, 1H), 4.95 (s, 2H), 3.62 (s, 6H), 3.48 (q, J=7.2 Hz, 2H), 1.07 (t, J=7.2 Hz, 3H). LC-MS: m/z 567.1 (M+H)$^+$

Example 80: N-(1-(2,6-dimethoxyphenyl)-2-(6-ethoxypyridin-2-yl)-1H-imidazo[4,5-b]pyrazin-6-yl)-1-(5-methylpyrimidin-2-yl)methanesulfonamide

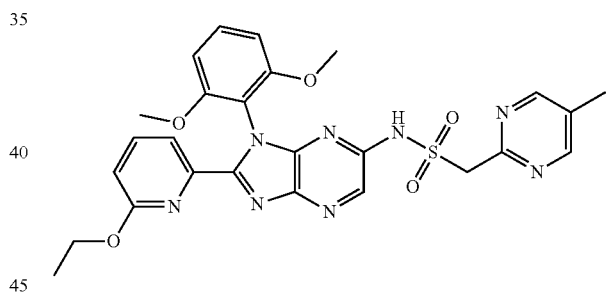

The title compound was prepared according to Method C, step D, starting from 6-chloro-1-(2,6-dimethoxyphenyl)-2-(6-ethoxypyridin-2-yl)-1H-imidazo[4,5-b]pyrazine by using (5-methylpyrimidin-2-yl)methanesulfonamide. $^1$H NMR (400 MHz, DMSO-$d_6$) δ: 11.13 (s, 1H), 8.58 (s, 2H), 8.18 (s, 1H), 7.93 (d, J=7.2 Hz, 1H), 7.85 (t, J=7.8 Hz 1H), 7.44 (t, J=8.4 Hz, 1H), 6.85 (d, J=8.4 Hz, 2H), 6.81 (d, J=8.0 Hz, 1H), 4.87 (s, 2H), 3.56 (s, 6H), 3.39 (q, J=7.2 Hz, 2H), 2.24 (s, 3H), 1.02 (t, J=7.2 Hz, 3H). LC-MS: m/z 563.1 (M+H)$^+$

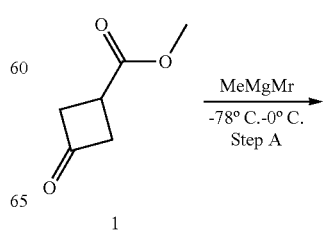

207

-continued

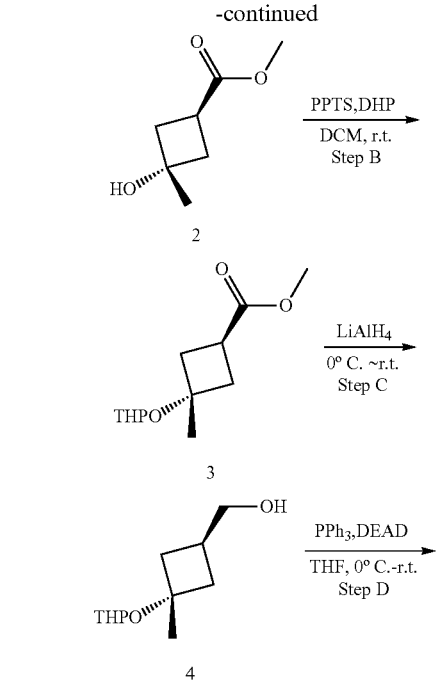

208

-continued

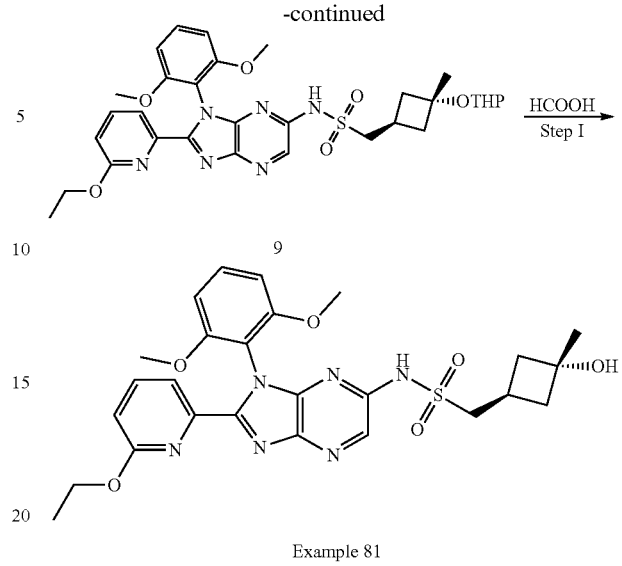

Example 81

Step A: trans-Methyl 3-hydroxy-3-methylcyclobutane-1-carboxylate

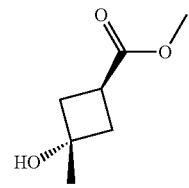

Methyl 3-oxocyclobutane-1-carboxylate (1.05 g, 8.19 mmol, 1 equiv) was dissolved in anhydrous THF (10 mL) and cooled to −78° C. MeMgBr (3 mol/L in diethyl ether) (8.2 mL, 24.6 mmol, 3 equiv) was added dropwise. The mixture was stirred at −20° C. for 2 hours. The reaction was quenched with sat. NH$_4$Cl solution (10 mL) and extracted with DCM (20 mL*3). The organic layer was washed with brine, dried over anhydrous Na$_2$SO$_4$, filtered, concentrated and purified via column chromatography (DCM/MeOH=20/1) to give trans-methyl 3-hydroxy-3-methylcyclobutane-1-carboxylate as a colorless oil (410 mg, 36.7% yield). LC-MS: m/z 145.1 (M+H)$^+$, 127.1 (M−OH)$^+$ Step B: trans-Methyl 3-methyl-3-((tetrahydro-2H-pyran-2-yl)oxy)cyclobutane-1-carboxylate

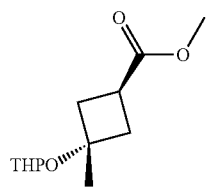

trans-Methyl 3-hydroxy-3-methylcyclobutane-1-carboxylate (410 mg, 2.84 mmol, 1 equiv) was dissolved in DCM (5 mL). Then dihydropyran (239 mg, 3.41 mmol,

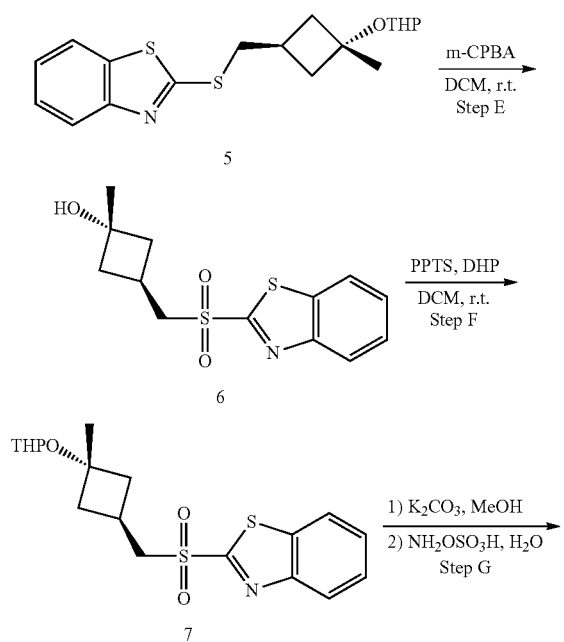

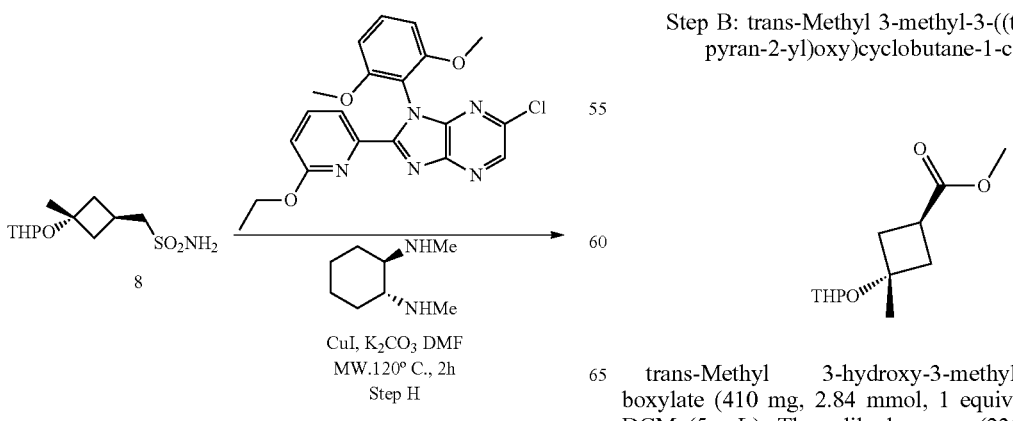

0.258 mL, 1.2 equiv) and pyridinium 4-toluenesulfonate (142 mg, 0.568 mmol, 0.2 equiv) were added. The solution was stirred at room temperature for 4 hours. The mixture was diluted with 20 mL ethyl acetate and washed with water, brine, dried over anhydrous Na$_2$SO$_4$, filtered, concentrated and purified via column chromatography (eluted with PE/EtOAc=20/1) to give trans-methyl 3-methyl-3-((tetrahydro-2H-pyran-2-yl)oxy)cyclobutane-1-carboxylate as clear oil (240 mg, 37% yield). $^1$H NMR (400 MHz, Chloroform-d) δ: 4.68-4.70 (m, 1H), 3.85-3.91 (m, 1H), 3.61 (s, 3H), 3.39-3.44 (m, 1H), 2.59-2.68 (m, 1H), 2.41-2.49 (m, 2H), 2.07-2.16 (m, 2H), 1.55-1.84 (m, 6H), 1.35 (s, 3H).

Step C: trans-(3-Methyl-3-((tetrahydro-2H-pyran-2-yl)oxy)cyclobutyl)methanol

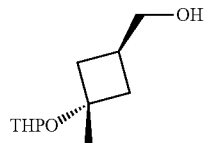

The solution of trans-methyl 3-methyl-3-((tetrahydro-2H-pyran-2-yl)oxy)cyclobutane-1-carboxylate (240 mg, 1.05 mmol, 1 equiv) in anhydrous THF (5 mL) was cooled to 0° C. 2.1 mL LiAlH$_4$ solution (1 moL/L in THF, 2.10 mmol, 2 equiv) was added dropwise. The mixture was stirred at 0° C. for 2 hours. The reaction was quenched with 1 mL water and extracted with DCM (5 mL*3). The organic layers were washed with brine, dried over anhydrous Na$_2$SO$_4$, filtered, concentrated and purified via column chromatography (eluted with PE/EtOAc=2/1) to give trans-(3-methyl-3-((tetrahydro-2H-pyran-2-yl)oxy)cyclobutyl)methanol as colorless oil (120 mg, 57% yield). $^1$H NMR (400 MHz, Chloroform-d) δ: 4.62-4.64 (m, 1H), 3.86-3.91 (m, 1H), 3.56 (d, J=5.6 Hz, 2H), 3.37-3.42 (m, 1H), 1.78-2.15 (m, 9H), 1.59-1.6 (m, 2H), 1.34 (s, 3H).

Step D: trans-2-(((3-Methyl-3-((tetrahydro-2H-pyran-2-yl)oxy)cyclobutyl)methyl)thio)benzo[d]thiazole

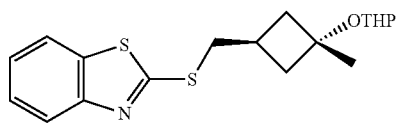

trans-(3-Methyl-3-((tetrahydro-2H-pyran-2-yl)oxy)cyclobutyl)methanol (120 mg, 0.599 mmol, 1 equiv), benzo[d]thiazole-2-thiol (120 mg, 0.719 mmol, 1.2 equiv), and PPh$_3$ (188 mg, 0.719 mmol, 1.2 equiv) were dissolved in anhydrous THF (5 mL) and cooled to −78° C. Then DIAD (145 mg, 0.142 mL, 0.719 mmol, 1.2 equiv) was added dropwise. The reaction mixture was stirred at room temperature overnight. The reaction mixture was concentrated and purified via column chromatography (eluted with PE/EtOAc=10/1) to give trans-2-(((3-methyl-3-((tetrahydro-2H-pyran-2-yl)oxy)cyclobutyl)methyl)thio)benzo[d]thiazole as colorless oil (150 mg, 72% yield). $^1$H NMR (400 MHz, Chloroform-d) δ: 7.79 (d, J=7.6 Hz, 1H), 7.68 (dd, J=8.0, 0.8 Hz, 1H), 7.34 (td, J=8.4, 1.2 Hz, 1H), 7.22 (td, J=8.0, 1.2 Hz, 1H), 4.55-4.64 (m, 1H), 3.85-3.90 (m, 1H), 3.36-3.41 (m, 3H), 2.24-2.32 (m, 1H), 2.01-2.18 (m, 3H), 1.91-1.98 (m, 1H), 1.72-1.82 (m, 1H), 1.58-1.63 (m, 1H), 1.42-1.46 (m, 4H), 1.32 (s, 3H)

Step E: trans-3-((Benzo[d]thiazol-2-ylsulfonyl)methyl)-1-methylcyclobutan-1-ol

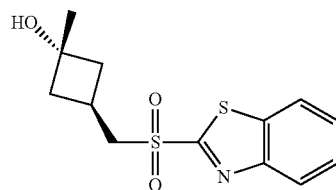 [SMILES: C[C@]1(O)C[C@H](CS(=O)(=O)c2nc3ccccc3s2)C1]

trans-2-(((3-Methyl-3-((tetrahydro-2H-pyran-2-yl)oxy)cyclobutyl)methyl)thio)benzo[d]thiazole (150 mg, 0.429 mmol, 1 equiv) was dissolved in DCM (10 mL) and m-CPBA (190 mg, 85% purity, 0.944 mmol, 2.2 equiv) was added partially. The mixture was stirred overnight at room temperature and diluted with DCM (10 mL), washed with sat. Na$_2$S$_2$O$_3$ solution, sat. NaHCO$_3$ solution, brine, dried over anhydrous Na$_2$SO$_4$, filtered, concentrated and purified via column chromatography (eluted with PE/EtOAc=4/1) to give trans-3-((benzo[d]thiazol-2-ylsulfonyl)methyl)-1-methylcyclobutan-1-ol as white solid (100 mg, 78% yield). LC-MS: m/z 298.1 (M+H)$^+$ Step F: trans-2-(((3-Methyl-3-((tetrahydro-2H-pyran-2-yl)oxy)cyclobutyl)methyl)sulfonyl)benzo[d]thiazole

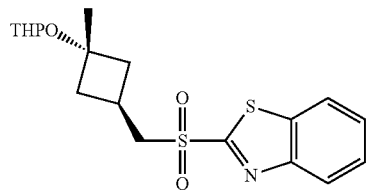

To a solution of trans-3-((benzo[d]thiazol-2-ylsulfonyl)methyl)-1-methylcyclobutan-1-ol (420 mg, 1.41 mmol, 1 equiv) in DCM (5 mL) were added dihydropyran (225 mg, 2.68 mmol, 1.9 equiv) and PPTS (67.3 mg, 0.268 mmol, 0.19 equiv). The mixture was stirred at room temperature overnight. Then the mixture was diluted with EtOAc (20 mL) and washed with brine. The organic layer was dried over Na$_2$SO$_4$, concentrated and purified via column chromatography (eluted with PE/EtOAc=5/1) to give trans-2-(((3-methyl-3-((tetrahydro-2H-pyran-2-yl)oxy)cyclobutyl)methyl)sulfonyl)benzo[d]thiazole as a white solid (180 mg, 34% yield). $^1$H NMR (400 MHz, Chloroform-d) δ: 8.15 (d, J=8.4 Hz, 1H), 7.95 (d, J=7.6 Hz, 1H), 7.51-7.60 (m, 2H), 4.49-4.56 (m, 1H), 3.79-3.84 (m, 1H), 3.60 (d, J=7.6 Hz, 2H), 3.31-3.36 (m, 1H), 2.39-2.48 (m, 2H), 2.05-2.14 (m, 3H), 1.90-1.95 (m, 1H), 1.51-1.70 (m, 5H), 1.29 (s, 3H).

Step G: trans-(3-Methyl-3-((tetrahydro-2H-pyran-2-yl)oxy)cyclobutyl)methanesulfonamide

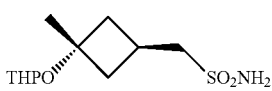

trans-2-(((3-Methyl-3-((tetrahydro-2H-pyran-2-yl)oxy)cyclobutyl)methyl)sulfonyl)benzo[d]thiazole (2.80 g, 7.34 mmol, 1.0 equiv) was dissolved in MeOH (20 mL) and K$_2$CO$_3$ (1.53 g, 11.1 mmol) was added. The mixture was stirred at room temperature for 1.5 h. The mixture was concentrated, diluted with H$_2$O (40 mL), and washed with EtOAc (20 mL). The aqueous phase was freeze-dried in vacuo to get a white to yellow solid. The solid was suspended in MeOH (8 mL) and K$_2$CO$_3$ (3.04 g, 22.0 mmol, 3.0 equiv) was added. NH$_2$OSO$_3$H (1.07 g, 9.54 mmol, 1.3 equiv) was dissolved in H$_2$O (7 mL) and added into the mixture slowly. The mixture was stirred at room temperature overnight. Then MeOH was removed and the reaction mixture was extracted with DCM (20 mL*3). The organic layer was washed with brine, dried over Na$_2$SO$_4$, concentrated and purified via column chromatography (eluted with PE/EtOAc=2/1) to give trans-(3-methyl-3-((tetrahydro-2H-pyran-2-yl)oxy)cyclobutyl)methanesulfonamide as light yellow oil (1.14 g, 59% yield). $^1$H NMR (400 MHz, Chloroform-d) δ: 4.55-4.64 (m, 3H), 3.85-3.89 (m, 1H), 3.36-3.42 (m, 1H), 3.20 (d, J=7.2 Hz, 2H), 3.31-3.36 (m, 1H), 2.08-2.26 (m, 3H), 1.97-2.02 (m, 1H), 1.73-1.82 (m, 1H), 1.58-1.63 (m, 1H), 1.44-1.46 (m, 4H), 1.35 (s, 3H).

Step H: trans-N-(1-(2,6-Dimethoxyphenyl)-2-(6-ethoxypyridin-2-yl)-1H-imidazo[4,5-b]pyrazin-6-yl)-1-((1r, 3r)-3-methyl-3-((tetrahydro-2H-pyran-2-yl)oxy)cyclobutyl)methanesulfonamide

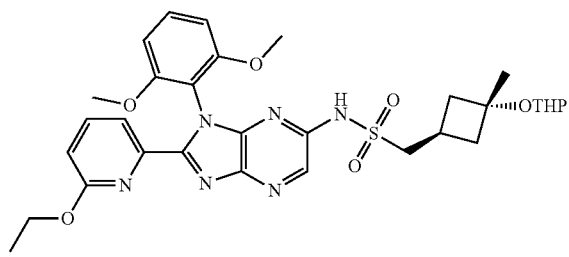

The title compound was prepared according to Method C, step D, starting from 6-chloro-1-(2,6-dimethoxyphenyl)-2-(6-ethoxypyridin-2-yl)-1H-imidazo[4,5-b]pyrazine by using trans-(3-methyl-3-((tetrahydro-2H-pyran-2-yl)oxy)cyclobutyl)methanesulfonamide. LC-MS: m/z 639.2 (M+H)$^+$

Step I: trans-N-(1-(2,6-Dimethoxyphenyl)-2-(6-ethoxypyridin-2-yl)-1H-imidazo[4,5-b]pyrazin-6-yl)-1-((1r, 3r)-3-hydroxy-3-methylcyclobutyl)methanesulfonamide (Example 81)

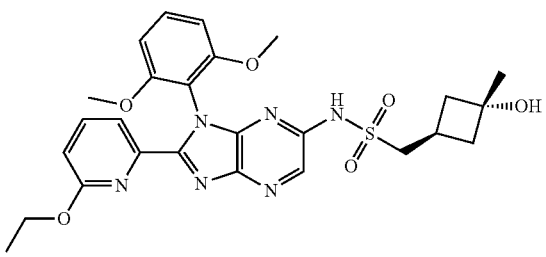 [SMILES: CCOc1cccc(-c2nc3ncc(NS(=O)(=O)C[C@H]4C[C@](C)(O)C4)nc3n2-c2c(OC)cccc2OC)n1]

A solution of trans-N-(1-(2,6-Dimethoxyphenyl)-2-(6-ethoxypyridin-2-yl)-1H-imidazo[4,5-b]pyrazin-6-yl)-1-((1r, 3r)-3-methyl-3-((tetrahydro-2H-pyran-2-yl)oxy)cyclobutyl)methanesulfonamide (150 mg, 0.235 mmol) in HCOOH (5 mL) was stirred at room temperature overnight. The mixture was concentrated in vacuo and the residue was purified by prep-TLC (eluted with DCM/MeOH=20/1) and reverse phase prep-HPLC (eluted with CH$_3$CN/H$_2$O=5/95~95/5 including 0.1% HCOOH) to afford t trans-N-(1-(2,6-dimethoxyphenyl)-2-(6-ethoxypyridin-2-yl)-1H-imidazo[4,5-b]pyrazin-6-yl)-1-((1r, 3r)-3-hydroxy-3-methylcyclobutyl)methanesulfonamide as a light yellow solid (62.0 mg, 47% yield). $^1$H NMR (400 MHz, Chloroform-d) δ: 8.50 (s, 1H), 8.13 (d, J=7.2 Hz, 1H), 7.69 (t, J=7.6 Hz, 1H), 7.40 (t, J=8.4 Hz, 1H), 6.96 (s, 1H), 6.69-6.72 (m, 3H), 3.62 (s, 6H), 3.39-3.45 (m, 4H), 2.25-2.37 (m, 3H), 1.76-1.85 (m, 2H), 1.34 (s, 3H), 1.08 (t, J=7.2 Hz, 3H). LC-MS: m/z 555.2 (M+H)$^+$

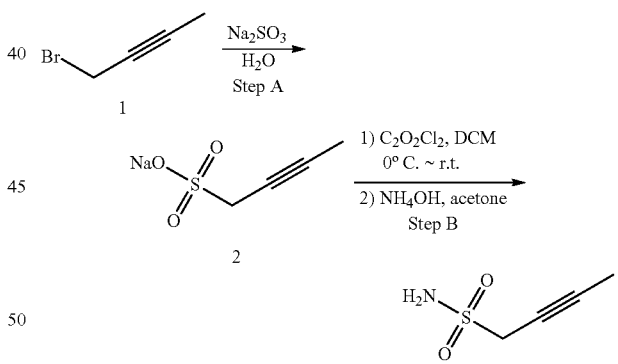

Step A: Sodium but-2-yne-1-sulfonate

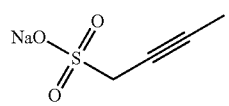

To a solution of Na$_2$SO$_3$ (947 mg, 7.5 mmol, 1.0 equiv) in H$_2$O (10 mL) was added 1-bromobut-2-yne (1.0 g, 7.5 mmol, 1.0 equiv) at room temperature. The mixture was stirred at 20° C. for 0.5 hour. The mixture was stirred at 60° C. for 1.5 hours and evaporated to dryness under reduced pressure to give the crude sodium salt of but-2-yne-1-sulfonate as a white solid (1.95 g, crude). LC-MS: m/z 156.9 (M+H)$^+$ Step B: But-2-yne-1-sulfonamide

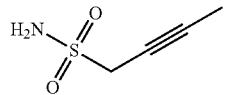

To a suspension of but-2-yne-1-sulfonate sodium salt (200 mg crude, 0.77 mmol, 1.0 equiv) in DCM (5 mL) was added (COCl)$_2$ (163 mg, 1.28 mmol, 1.7 equiv) at 0° C. under N$_2$. The mixture was stirred at room temperature for 4 hours. The mixture was added to a solution of NH$_4$OH (5 mL) in acetone (5 mL) at 0° C. The resulting mixture was stirred at 0° C. for 1 hour. The mixture was concentrated under vacuum. The residue was stirred in EtOAc (20 mL) for 5 minutes and filtered. The filtrate was concentrated in vacuo. The new residue was purified by flash chromatography on silica gel (PE/EtOAc=3/1) to give but-2-yne-1-sulfonamide as a white solid (58.0 mg, 57% yield). $^1$H NMR (400 MHz, DMSO-d$_6$) δ: 7.04 (s, 2H), 3.91 (q, J=2.4 Hz, 2H), 1.84 (t, J=2.4 Hz, 3H).

Example 82: N-(1-(2,6-Dimethoxyphenyl)-2-(6-ethoxypyridin-2-yl)-1H-imidazo[4,5-b]pyrazin-6-yl)but-2-yne-1-sulfonamide

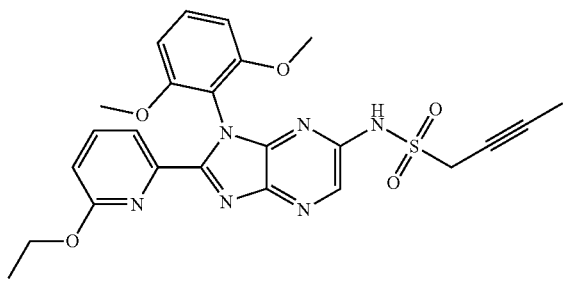 [SMILES: CC#CCS(=O)(=O)Nc1cnc2nc(-c3cccc(OCC)n3)n(-c3c(OC)cccc3OC)c2n1]

The title compound was prepared according to Method C, step D, starting from 6-chloro-1-(2,6-dimethoxyphenyl)-2-(6-ethoxypyridin-2-yl)-1H-imidazo[4,5-b]pyrazine by using but-2-yne-1-sulfonamide. $^1$H NMR (400 MHz, Chloroform-d) δ: 8.62 (s, 1H), 8.12 (d, J=7.6 Hz, 1H), 7.68 (t, J=8.0 Hz, 1H), 7.39 (t, J=8.4 Hz, 1H), 7.18 (s, 1H), 6.68-6.71 (m, 3H), 4.09 (q, J=2.4 Hz, 2H), 3.62 (s, 6H), 3.43 (q, J=7.2 Hz, 2H), 1.71 (t, J=2.4 Hz, 3H), 1.08 (t, J=7.2 Hz, 3H). LC-MS: m/z 509.2 (M+H)$^+$ Example 83: N-(1-(2,6-Dimethoxyphenyl)-2-(6-ethoxypyridin-2-yl)-1H-imidazo[4,5-b]pyrazin-6-yl)-1-(5-methylpyridin-2-yl)methanesulfonamide

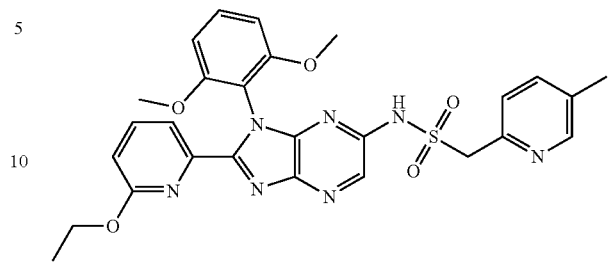

The title compound was prepared according to Method C, step D, starting from 6-chloro-1-(2,6-dimethoxyphenyl)-2-(6-ethoxypyridin-2-yl)-1H-imidazo[4,5-b]pyrazine by using (5-methylpyridin-2-yl)methanesulfonamide. $^1$H NMR (400 MHz, Chloroform-d) δ: 8.42 (s, 1H), 8.29 (s, 1H), 8.10 (d, J=7.6 Hz, 1H), 7.67 (dd, J=8.4, 7.6 Hz, 1H), 7.37-7.47 (m, 2H), 7.24 (d, J=8.0 Hz, 1H), 6.64-6.74 (m, 3H), 4.66 (s, 2H), 3.59 (s, 6H), 3.42 (q, J=7.2 Hz, 2H), 2.23 (s, 3H), 1.08 (t, J=7.2 Hz, 3H). LC-MS: m/z 562.2 (M+H)$^+$ Example 84: N-(1-(2,4-Dimethoxypyridin-3-yl)-2-(6-ethoxypyridin-2-yl)-1H-imidazo[4,5-b]pyrazin-6-yl)methanesulfonamide

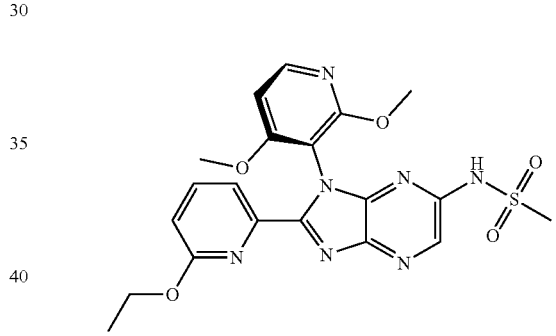

The title compound was an atropisomer of Example 68 obtained by chiral separation. The absolute configuration was arbitrarily assigned. $^1$H NMR (400 MHz, Chloroform-d) δ: 8.53 (s, 1H), 8.21 (d, J=6.0 Hz, 1H), 8.16 (d, J=7.2 Hz, 1H), 7.71 (t, J=8.0 Hz, 1H), 7.00 (s, 1H), 6.78-6.70 (m, 2H), 3.81 (s, 3H), 3.72 (s, 3H), 3.54-3.38 (m, 2H), 3.19 (s, 3H), 1.14 (t, J=7.2 Hz, 3H). LC-MS: m/z 472.1 (M+H)$^+$ Example 85: N-(1-(2,4-Dimethoxypyridin-3-yl)-2-(6-ethoxypyridin-2-yl)-1H-imidazo[4,5-b]pyrazin-6-yl)methanesulfonamide

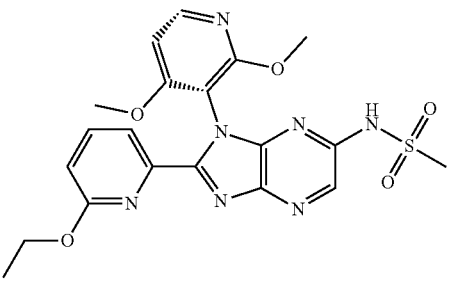

The title compound was an atropisomer of Example 68 obtained by chiral separation. The absolute configuration was arbitrarily assigned. H NMR (400 MHz, Chloroform-d) δ: 8.56 (s, 1H), 8.25 (d, J=5.6 Hz, 1H), 8.19 (d, J=7.6 Hz, 1H), 7.72 (t, J=8.0 Hz, 1H), 7.13 (s, 1H), 6.81-6.72 (m, 2H), 3.87 (s, 3H), 3.75 (s, 3H), 3.54-3.39 (m, 2H), 3.20 (s, 3H), 1.15 (t, J=7.2 Hz, 3H). LC-MS: m/z 472.1 (M+H)+
Method I

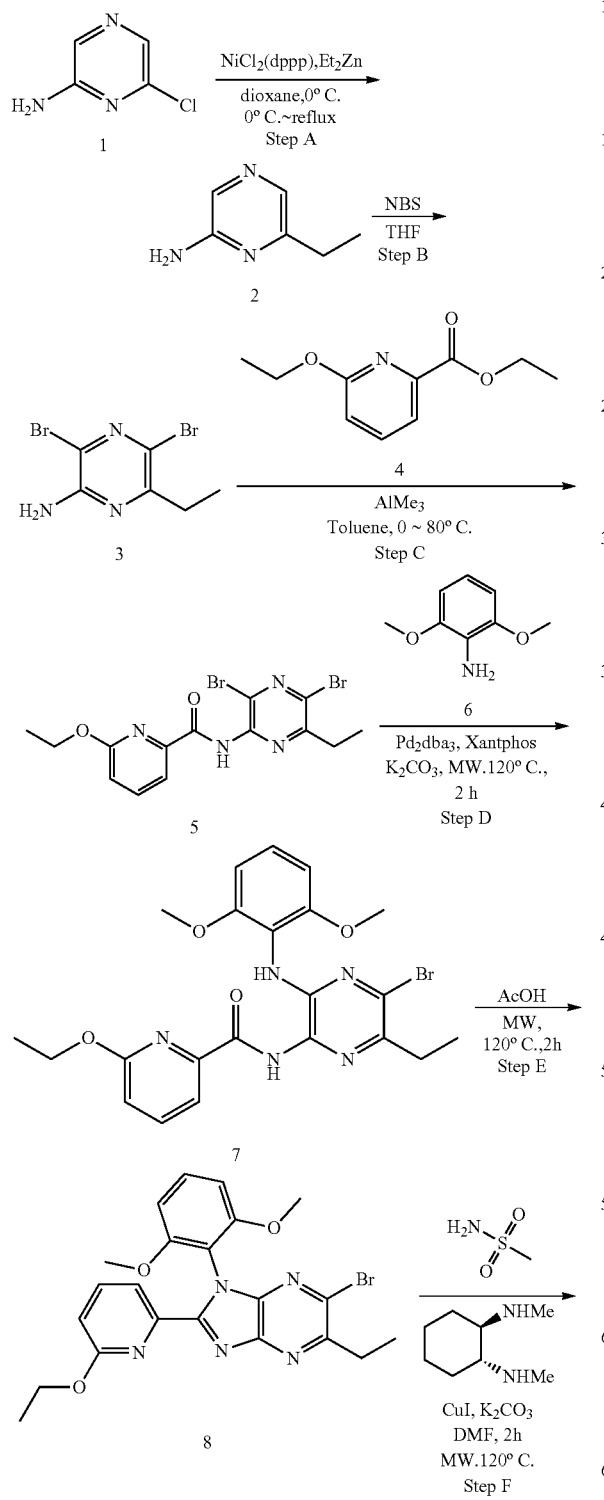

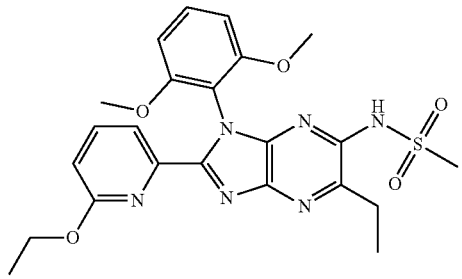

Example 86

Step A: 6-Ethylpyrazin-2-amine

To a mixture of 6-chloropyrazin-2-amine (10.0 g, 77.2 mmol, 1.0 equiv) and Ni(dppp)Cl$_2$ (4.18 g, 7.72 mmol, 0.1 equiv) in anhydrous dioxane (80 mL) at 0° C. was added Et$_2$Zn (2 mol/L in hexane, 77.0 mL, 154 mmol, 2.0 equiv) under N$_2$ atmosphere. The reaction mixture was refluxed overnight. The reaction was quenched with MeOH and concentrated in vacuo. The residue was partitioned between EtOAc and brine. The organic phase was dried over Na$_2$SO$_4$, filtered and evaporated. The residue was purified by flash chromatography (eluted with PE/EtOAc=2/1) to give 6-ethylpyrazin-2-amine as a yellow solid. (3.57 g, 37% yield). LC-MS: m/z 124.1 (M+H)+

Step B: 3,5-Dibromo-6-ethylpyrazin-2-amine

To a mixture of 6-ethylpyrazin-2-amine (3.57 g, 29.0 mmol, 1.0 equiv) in THF (50 mL) was added NBS (20.7 g, 116 mmol, 4.0 equiv) at 0° C. The resulting mixture was stirred at room temperature for 3 hours. The mixture was diluted with EtOAc (100 mL) and washed with saturated Na$_2$SO$_3$ aqueous solution and brine, dried over anhydrous Na$_2$SO$_4$ and concentrated in vacuo. The residue was purified by column chromatography on silica gel (eluted with PE/EtOAc=20/1) to afford the title compound 3,5-dibromo-6-ethylpyrazin-2-amine as yellow oil. (6.65 g, 82% yield). LC-MS: m/z 279.8, 281.8, 283.8 (M+H)+

Step C: N-(3,5-Dibromo-6-ethylpyrazin-2-yl)-6-ethoxypicolinamide

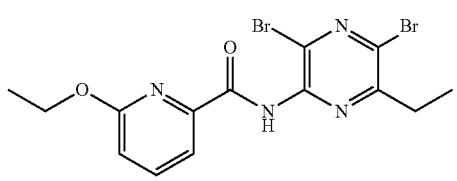 [SMILES: CCOc1cccc(C(=O)Nc2nc(CC)c(Br)nc2Br)n1]

To a solution of 3,5-dibromo-6-ethylpyrazin-2-amine (6.65 g, 23.7 mmol, 1.0 equiv) in toluene (100 mL) was added AlMe$_3$ (2 mol/L in toluene, 17.8 mL, 35.5 mmol, 1.50 equiv) dropwise at 0° C. under N$_2$ atmosphere. After the mixture was stirred at 0° C. for 30 minutes and at 80° C. for 30 minutes, ethyl 6-ethoxypicolinate (6.00 g, 30.8 mmol, 1.3 equiv) was added. The resulting mixture was stirred at 80° C. overnight. The reaction mixture was quenched with 1N aq. HCl and extracted with DCM (200 mL*2). The combined organic layers were dried over anhydrous Na$_2$SO$_4$ and concentrated in vacuo. The residue was stirred in MeOH (30 mL) for 30 mins. The mixture was filtered and the filter cake afford N-(3,5-dibromo-6-ethylpyrazin-2-yl)-6-ethoxypicolinamide as a white solid (7.87 g, 77% yield). LC-MS: m/z 428.5, 430.5, 432.5 (M+H)$^+$

Step D: N-(5-Bromo-3-((2,6-dimethoxyphenyl)amino)-6-ethylpyrazin-2-yl)-6-ethoxypicolinamide

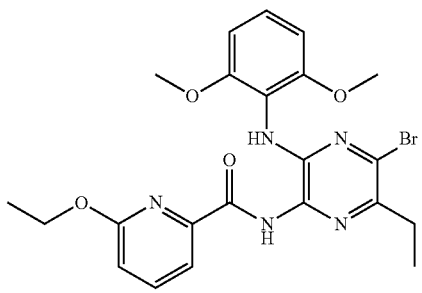 [SMILES: CCOc1cccc(C(=O)Nc2nc(CC)c(Br)nc2Nc2c(OC)cccc2OC)n1]

A suspension of N-(3,5-dibromo-6-ethylpyrazin-2-yl)-6-ethoxypicolinamide (1.00 g, 2.33 mmol, 1.0 equiv), 2,6-dimethoxyaniline (536 mg, 3.50 mmol, 1.5 equiv), Pd$_2$(dba)$_3$ (213 mg, 0.233 mmol, 0.1 equiv), Xantphos (270 mg, 0.466 mmol, 0.2 equiv) and K$_2$CO$_3$ (805 mg, 5.83 mmol, 2.5 equiv) in 1,4-dioxane (10 mL) was stirred at 120° C. via microwave irradiation for 2 hours under N$_2$ atmosphere. The mixture was filtered through celite and the filtrate was concentrated. The residue was purified by column chromatography on silica gel (eluted with PE/EtOAc=20/1) to give N-(5-bromo-3-((2,6-dimethoxyphenyl)amino)-6-ethylpyrazin-2-yl)-6-ethoxypicolinamide as a yellow solid (630 mg, 54% yield). LC-MS: m/z 501.6, 503.5 (M+H)$^+$

Step E: 6-Bromo-1-(2,6-dimethoxyphenyl)-2-(6-ethoxypyridin-2-yl)-5-ethyl-1H-imidazo[4,5-b]pyrazine

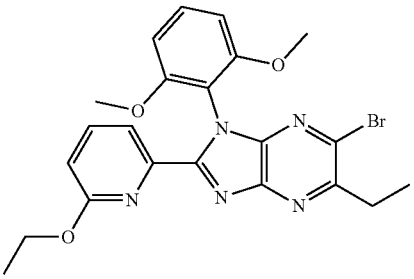 [SMILES: CCOc1cccc(-c2nc3nc(CC)c(Br)nc3n2-c2c(OC)cccc2OC)n1]

The solution of N-(5-bromo-3-((2,6-dimethoxyphenyl)amino)-6-ethylpyrazin-2-yl)-6-ethoxypicolinamide (330 mg, 0.660 mmol) in AcOH (12 mL) was stirred at 120° C. via microwave irradiation for 2 hours. The reaction mixture was poured in sat.Na$_2$CO$_3$ and extracted with DCM. The organic phase was dried over anhydrous MgSO$_4$ and concentrated in vacuo. The residue was washed with EtOAc/PE=1/2 to give 6-bromo-1-(2,6-dimethoxyphenyl)-2-(6-ethoxypyridin-2-yl)-5-ethyl-1H-imidazo[4,5-b]pyrazine as a yellow solid (520 mg, 81% yield). The crude product was used in next step without further purification. LC-MS: m/z 484.0, 486.0 (M+H)$^+$

Step F: N-(1-(2,6-dimethoxyphenyl)-2-(6-ethoxypyridin-2-yl)-5-ethyl-1H-imidazo[4,5-b]pyrazin-6-yl)methanesulfonamide (Example 86)

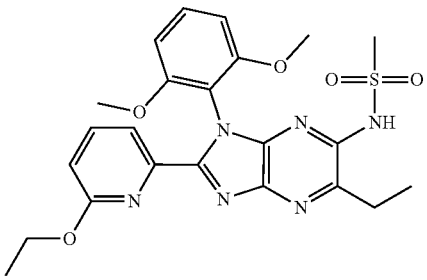 [SMILES: CCOc1cccc(-c2nc3nc(CC)c(NS(C)(=O)=O)nc3n2-c2c(OC)cccc2OC)n1]

A suspension of 6-bromo-1-(2,6-dimethoxyphenyl)-2-(6-ethoxypyridin-2-yl)-5-ethyl-1H-imidazo[4,5-b]pyrazine (100 mg, 0.21 mmol, 1.0 equiv), methanesulfonamide (80.0 mg, 0.840 mmol, 4.0 equiv), CuI (80.0 mg, 0.420 mmol, 2.0 equiv), trans-N, N'-Dimethylcyclohexane-1, 2-diamine (60.0 mg, 0.420 mmol, 2.0 equiv) and K$_2$CO$_3$ (87.0 mg, 0.630 mmol, 3.0 equiv) in DMF (4 mL) was stirred at 110° C. via microwave irradiation for 2 hours under N$_2$ atmosphere. The mixture was diluted with DCM (10 mL) and filtered. The filtrate was concentrated. The residue was purified by prep-HPLC to give N-(1-(2,6-dimethoxyphenyl)-2-(6-ethoxypyridin-2-yl)-5-ethyl-1H-imidazo[4,5-b]pyrazin-6-yl)methanesulfonamide as a yellow solid (46.9 mg, 46% yield). $^1$H NMR (400 MHz, Chloroform-d) δ: 8.15 (d, J=7.6 Hz, 1H), 7.68 (t, J=7.6 Hz, 1H), 7.36 (t, J=8.4 Hz, 1H), 6.78 (s, 1H), 6.73-6.64 (m, 3H), 3.61 (s, 6H), 3.43 (q, J=6.8 Hz, 2H), 3.23 (s, 3H), 2.91 (q, J=7.6 Hz, 2H), 1.45 (t, J=7.6 Hz, 3H), 1.07 (t, J=6.8 Hz, 3H). LC-MS: m/z 499.1 (M+H)⁺

Example 87: N-(1-(2,6-Dimethoxyphenyl)-2-(6-ethoxypyridin-2-yl)-5-methyl-1H-imidazo[4,5-b]pyrazin-6-yl)methanesulfonamide

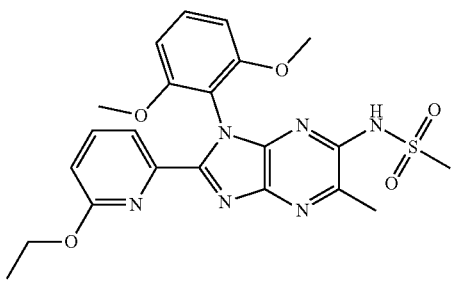 [SMILES: CCOc1cccc(-c2nc3nc(C)c(NS(C)(=O)=O)nc3n2-c2c(OC)cccc2OC)n1]

The title compound was prepared according to Method I by using 6-methylpyrazin-2-amine instead of 6-ethylpyrazin-2-amine in step B. ¹H NMR (400 MHz, Chloroform-d) δ: 8.10 (d, J=7.2 Hz, 1H), 7.67 (t, J=7.6c Hz, 1H), 7.35 (t, J=8.4 Hz, 1H), 6.71 (d, J=10.0 Hz, 2H), 6.67 (d, J=8.4 Hz, 2H), 3.61 (s, 6H), 3.42 (q, J=7.2 Hz, 2H), 3.23 (s, 3H), 2.66 (s, 3H), 1.07 (t, J=7.2 Hz, 3H). LC-MS: m/z 485.1 (M+H)⁺

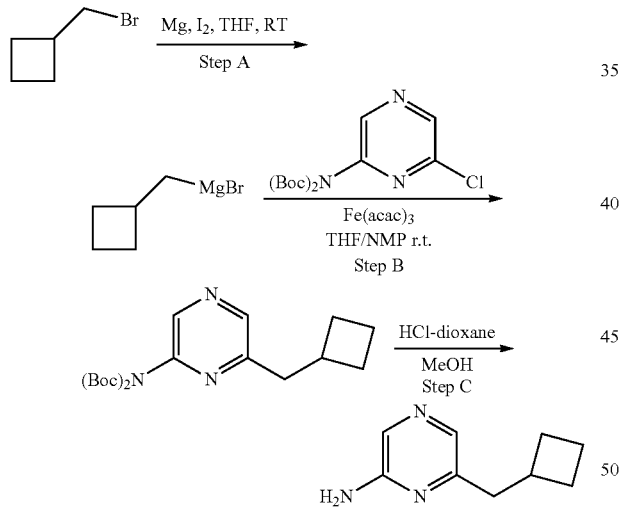

Step A: (Cyclobutylmethyl)magnesium bromide

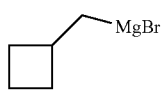

To a solution of Mg (1.60 g, 67.5 mmol, 1.5 equiv) and I2 (three pieces) in THF (40 mL) was added (bromomethyl)cyclobutane (1.10 mL, 12.0 mmol, 0.25 equiv). The mixture was heated to initiate the reaction. Then (bromomethyl)cyclobutane (3.5 mL, 33 mmol, 0.75 equiv) was added. The mixture was stirred at room temperature for 16 hours. The reaction mixture was used for the next step directly.

Step B: (6-(Cyclobutylmethyl)pyrazin-2-yl)-bis-carbamic acid tert-butyl ester

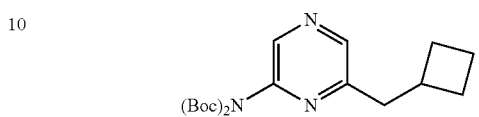

To a solution of (6-chloropyrazin-2-yl)-bis-carbamic acid tert-butyl ester (5.00 g, 15.0 mmol, 1 equiv) and Fe(acac)₃ (265 mg, 0.750 mmol, 0.05 equiv) in NMP/THF (5 mL/50 mL) was added (cyclobutylmethyl)magnesium bromide solution of last step at 0° C. The reaction mixture was stirred at room temperature for 16 hours. The reaction mixture was diluted with EtOAc and filtered. The organic phase was purified by flash chromatography (eluted with PE/EtOAc=10/1) to afford (6-(cyclobutylmethyl)pyrazin-2-yl)-bis-carbamic acid tert-butyl ester as white solid (2.40 g, 53% yield). LC-MS: m/z 364.2 (M+H)⁺

Step C: 6-(Cyclobutylmethyl)pyrazin-2-amine

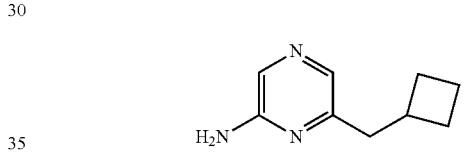

A suspension of (6-(cyclobutylmethyl)pyrazin-2-yl)-bis-carbamic acid tert-butyl ester (2.00 g, 7.60 mmol, 1.0 equiv) in MeOH (40 mL) was added HCl/dioxane (4 mol/L, 20 mL) at 0° C. The mixture was stirred at room temperature for 16 hours. The reaction mixture was concentrated then diluted with EtOAc and washed with 4 N NaHCO₃ aq. solution. The organic phase was concentrated and purified by flash chromatography (PE/EtOAc=1/1) to afford 6-(cyclobutylmethyl)pyrazin-2-amine as a white solid (770 mg, 77% yield). LC-MS: m/z 164.1 (M+H)⁺

Example 88: N-(5-(Cyclobutylmethyl)-1-(2,6-dimethoxyphenyl)-2-(6-ethoxypyridin-2-yl)-1H-imidazo[4,5-b]pyrazin-6-yl)methanesulfonamide

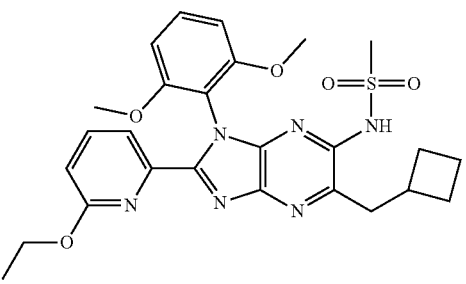 [SMILES: CCOc1cccc(-c2nc3nc(CC4CCC4)c(NS(C)(=O)=O)nc3n2-c2c(OC)cccc2OC)n1]

The title compound was prepared according to Method I by using 6-(cyclobutylmethyl)pyrazin-2-amine instead of 6-ethylpyrazin-2-amine in step B. $^1$H NMR (400 MHz, Chloroform-d) δ: 8.12 (d, J=7.2 Hz, 1H), 7.67 (t, J=8.4 Hz, 1H), 7.35 (t, J=8.4 Hz, 1H), 6.84 (s, 1H), 6.66-6.69 (m, 3H), 3.60 (s, 6H), 3.43 (q, J=7.2 Hz, 2H), 3.24 (s, 3H), 2.92-3.02 (m, 3H), 2.16-2.20 (m, 2H), 1.80-1.92 (m, 4H), 1.06 (t, J=7.2 Hz, 3H). LC-MS: m/z 539.2 (M+H)$^+$

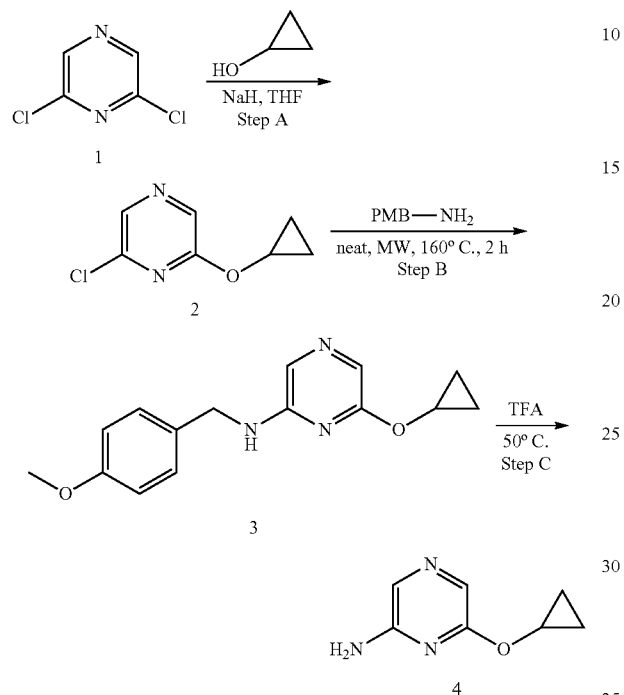

Step A: 2-Chloro-6-cyclopropoxypyrazine

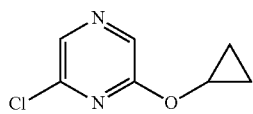 [SMILES: Clc1cncc(OC2CC2)n1]

To a solution of cyclopropanol (3.84 g, 66.2 mmol, 1.5 equiv) in THF (80 mL) was added NaH (60% in mineral oil, 2.64 g, 66.2 mmol, 1.5 equiv) at 0° C. The mixture was stirred at 0° C. for 15 minutes. A solution of 2,6-dichloropyrazine (6.57 g, 44.1 mmol, 1.0 equiv) was added. The mixture was stirred at 0° C. for 30 minutes, and then warmed up to room temperature and stirred for another 1 hour. The reaction was quenched by adding saturated NH$_4$Cl solution (50 mL) and extracted with EtOAc (50 mL*3). The combined organic phase was washed with brine (30 mL), dried over anhydrous Na$_2$SO$_4$, filtered and concentrated. The residue was purified by flash chromatography on silica gel (eluted with PE/EtOAc=20/1) to afford the title compound 2-chloro-6-cyclopropoxypyrazine as a white solid (6.19 g, 82% yield). $^1$H NMR (400 MHz, Chloroform-d) δ: 8.11 (s, 1H), 8.04 (s, 1H), 4.23 (tt, J=6.4, 3.2 Hz, 1H), 0.81-0.72 (m, 4H). LC-MS: m/z 171.0 (M+H)$^+$ Step B: 6-Cyclopropoxy-N-(4-methoxybenzyl)pyrazin-2-amine

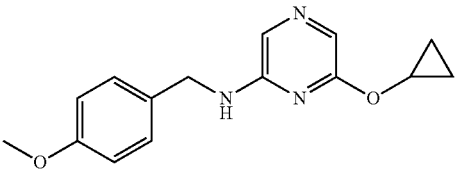 [SMILES: COc1ccc(CNc2cncc(OC3CC3)n2)cc1]

A solution of 2-chloro-6-cyclopropoxypyrazine (2.00 g, 11.8 mmol, 1.0 equiv) in PMBNH$_2$ (10 mL) was charged into a sealed tube The mixture was stirred at 160° C. via microwave irradiation for 2 hours. The mixture was purified by flash chromatography on silica gel (eluted with PE/EtOAc=1/1) to afford the title compound 6-cyclopropoxy-N-(4-methoxybenzyl)pyrazin-2-amine as a yellow solid (2.67 g, 83% yield). LC-MS: m/z 272.1 (M+H)$^+$ Step C: 6-Cyclopropoxypyrazin-2-amine

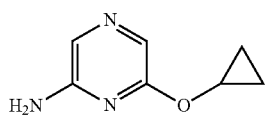

A solution of 6-cyclopropoxy-N-(4-methoxybenzyl)pyrazin-2-amine (2.67 g, 9.90 mmol, 1.0 equiv) in TFA (50 mL) was stirred at 60° C. overnight. The solvent was distilled off under vacuum. The residue was redissolved in DCM (50 mL) and washed with saturated NaHCO$_3$ solution (50 mL*3). The organic layer was dried over Na$_2$SO$_4$ and concentrated under vacuum. The residue was purified by flash chromatography on silica gel (eluted with PE/EtOAc=1/1) to afford the title compound 6-cyclopropoxypyrazin-2-amine as a yellow solid (1.46 g, 97% yield). $^1$H NMR (400 MHz, DMSO-d$_6$) δ: 7.48 (s, 1H), 7.36 (s, 1H), 6.37 (s, 2H), 4.10 (tt, J=6.4, 3.2 Hz, 1H), 0.78-0.68 (m, 2H), 0.71-0.61 (m, 2H). LC-MS: m/z 152.1 (M+H)$^+$ Example 89: N-(5-Cyclopropoxy-1-(2,6-dimethoxyphenyl)-2-(6-ethoxypyridin-2-yl)-1H-imidazo[4,5-b]pyrazin-6-yl)methanesulfonamide

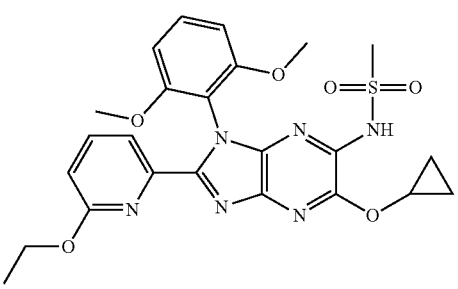 [SMILES: CCOc1cccc(-c2nc3nc(OC4CC4)c(NS(C)(=O)=O)nc3n2-c2c(OC)cccc2OC)n1]

The title compound was prepared according to Method I by using 6-cyclopropoxypyrazin-2-amine instead of 6-ethylpyrazin-2-amine in step B. $^1$H NMR (400 MHz, DMSO-d$_6$) δ: 10.30 (s, 1H), 7.86 (d, J=7.2 Hz, 1H), 7.81 (t, J=7.6

Hz, 1H), 7.42 (t, J=8.4 Hz, 1H), 6.84 (d, J=8.4 Hz, 2H), 6.74 (d, J=8.0 Hz, 1H), 4.32-4.45 (m, 1H), 3.56 (s, 6H), 3.37 (q, J=7.2 Hz, 2H), 3.09 (s, 3H), 1.01 (t, J=7.2 Hz, 3H), 0.89-0.75 (m, 4H). LC-MS: m/z 527.2 (M+H)+

Method J

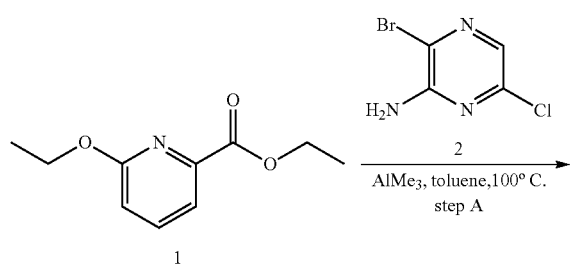

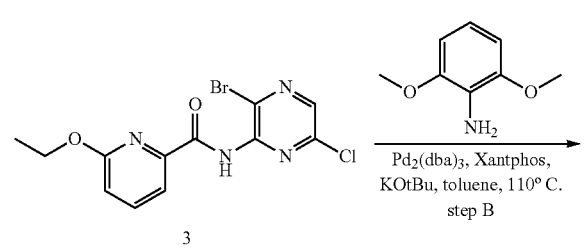

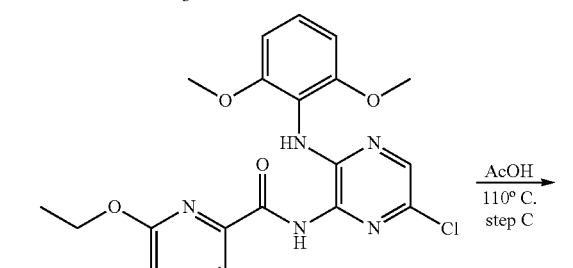

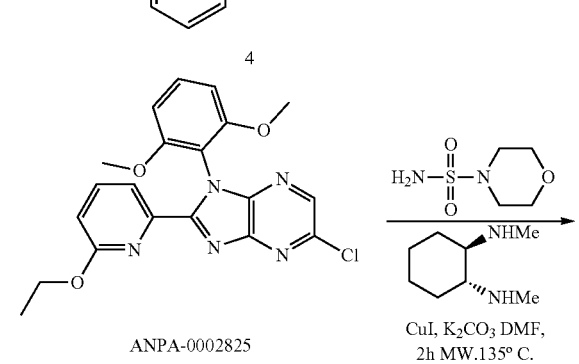

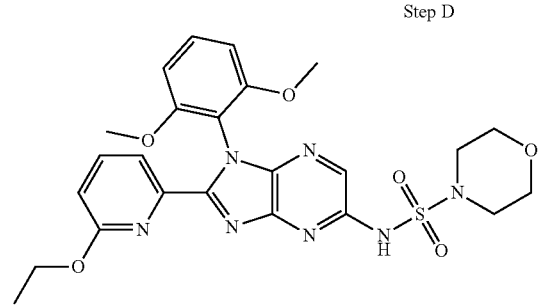

ANPA-0002825

Example 90

Step A: N-(3-Bromo-6-chloropyrazin-2-yl)-6-ethoxypicolinamide

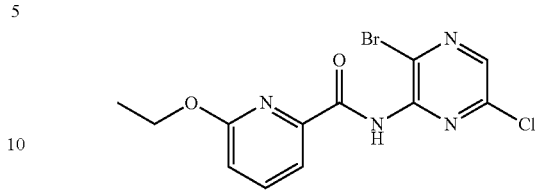

A mixture of ethyl 6-ethoxypicolinate (500 mg, 2.60 mmol, 1.0 equiv) and 3-bromo-6-chloropyrazin-2-amine (530 mg, 2.60 mmol, 1.0 equiv) in toluene was cooled to 0° C. and AlMe₃ (2.0 mol/L in toluene, 1.95 mL, 1.5 equiv) was added dropwise. The reaction mixture was stirred at 100° C. for 16 hours. The mixture was quenched with sat. NH₄Cl solution and extracted with EtOAc (20 mL*3). The combined organic layer was dried over anhydrous Na₂SO₄ and concentrated in vacuo. The residue was purified by flash chromatography on silica gel (eluted with PE/EtOAc=10/1) to afford N-(3-bromo-6-chloropyrazin-2-yl)-6-ethoxypicolinamide as a white solid (500 mg, 55% yield). ¹H NMR (400 MHz, DMSO-d₆) δ: 10.94 (s, 1H), 8.50 (s, 1H), 7.99 (d, J=7.6 Hz, 1H), 7.68-7.82 (m, 1H), 7.07-7.27 (m, 1H), 4.52 (q, J=7.2 Hz, 2H), 1.40 (t, J=7.2 Hz, 3H). LC-MS: m/z 357.7 (M+H)+

Step B: N-(6-Chloro-3-((2,6-dimethoxyphenyl)amino)pyrazin-2-yl)-6-ethoxypicolinamide

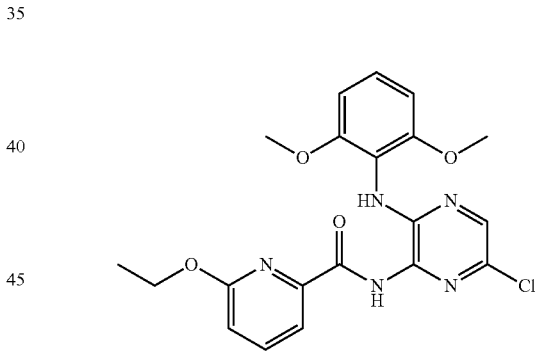

The mixture of N-(3-bromo-6-chloropyrazin-2-yl)-6-ethoxypicolinamide (500 mg, 1.40 mmol, 1.0 equiv), 2,6-dimethoxyaniline (430 mg, 2.80 mmol, 2.0 equiv), Xantphos (162 mg, 0.28 mmol, 0.2 equiv), Pd₂(dba)₃ (128 mg, 0.140 mmol, 0.1 equiv), potassium t-butoxide (297 mg, 2.80 mmol, 2.0 equiv) in toluene (10 mL) was stirred at 110° C. for 16 hours under N₂ atmosphere. The mixture was filtered and the filtrate was concentrated in vacuo. The residue was purified by flash column chromatography on silica gel (eluted with PE/EtOAc=10/1) to afford N-(6-chloro-3-((2,6-dimethoxyphenyl)amino)pyrazin-2-yl)-6-ethoxypicolinamide as a light yellow solid (80.0 mg, 13% yield). ¹H NMR (400 MHz, Chloroform-d) δ: 10.11 (s, 1H), 8.40 (s, 1H), 8.02 (s, 1H), 7.92 (d, J=7.2 Hz, 1H), 7.77 (t, J=8.8 Hz, 1H), 7.13 (t, J=8.4 Hz, 1H), 6.97 (d, J=8.0 Hz, 1H), 6.65 (d, J=8.4 Hz, 2H), 4.48 (q, J=7.2 Hz, 2H), 3.82 (s, 6H), 1.46-1.52 (m, 3H). LC-MS: m/z 429.7 (M+H)+

Step C: 5-Chloro-1-(2,6-dimethoxyphenyl)-2-(6-ethoxypyridin-2-yl)-1H-imidazo[4,5-b]pyrazine (ANPA-0002825)

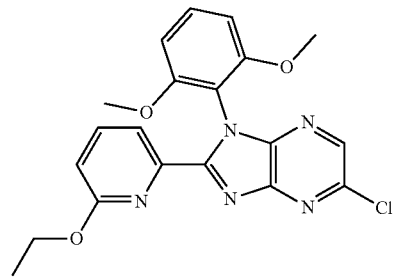 [SMILES: CCOc1cccc(-c2nc3nc(Cl)cnc3n2-c2c(OC)cccc2OC)n1]

A solution of N-(6-chloro-3-((2,6-dimethoxyphenyl)amino)pyrazin-2-yl)-6-ethoxypicolinamide (280 mg, 0.560 mmol, 1.0 equiv) in AcOH (2 mL) was stirred at 120° C. via microwave irradiation for 1 hour. The mixture was concentrated in vacuo. The residue was washed with ether, filtered and dried to afford the title compound 5-chloro-1-(2,6-dimethoxyphenyl)-2-(6-ethoxypyridin-2-yl)-1H-imidazo[4,5-b]pyrazine as a white solid (200 mg, 75% yield). $^1$H NMR (400 MHz, Chloroform-d) δ: 8.27 (s, 1H), 8.13-8.20 (m, 1H), 7.69 (t, J=8.4 Hz, 1H), 7.39 (t, J=8.4 Hz, 1H), 6.65-6.77 (m, 3H), 3.62 (s, 6H), 3.43 (q, J=7.2 Hz, 2H), 1.09 (t, J=7.2 Hz, 3H). LC-MS: m/z 411.7 (M+H)$^+$ Step D: N-(1-(2,6-Dimethoxyphenyl)-2-(6-ethoxypyridin-2-yl)-1H-imidazo[4,5-b]pyrazin-5-yl)morpholine-4-sulfonamide (Example 90)

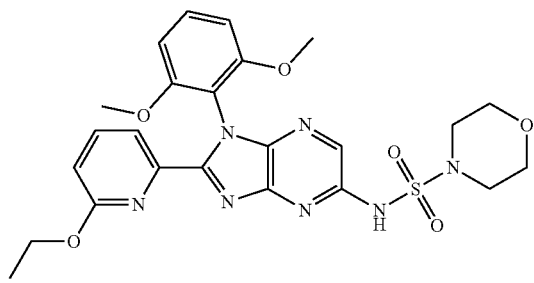 [SMILES: CCOc1cccc(-c2nc3nc(NS(=O)(=O)N4CCOCC4)cnc3n2-c2c(OC)cccc2OC)n1]

A suspension of 5-chloro-1-(2,6-dimethoxyphenyl)-2-(6-ethoxypyridin-2-yl)-1H-imidazo[4,5-b]pyrazine (42.0 mg, 0.1 mmol, 1.0 equiv), morpholine-4-sulfonamide (34.0 mg, 0.2 mmol, 2.0 equiv), CuI (38.0 mg, 0.2 mmol, 2.0 equiv), trans-N, N'-Dimethylcyclohexane-1, 2-diamine (29.0 mg, 0.2 mmol, 2.0 equiv) and K$_2$CO$_3$ (42.0 mg, 0.3 mmol, 3 equiv) in DMF (5 mL) was stirred at 135° C. via microwave irradiation for 6 hours under N$_2$ atmosphere. The reaction was quenched with 1N aq. HCOOH solution (30 mL) and extracted with EtOAc (3*60 mL). The combined organic layer was dried over anhydrous Na$_2$SO$_4$ and concentrated in vacuo. The residue was purified by prep-HPLC (eluted with CH$_3$CN/H$_2$O=5/95-90/10) to obtain N-(1-(2,6-dimethoxyphenyl)-2-(6-ethoxypyridin-2-yl)-1H-imidazo[4,5-b]pyrazin-5-yl)morpholine-4-sulfonamide as a pale yellow solid (17.0 mg, 32% yield). $^1$H NMR (400 MHz, DMSO-d$_6$) δ: 10.91 (s, 1H), 8.12 (s, 1H), 7.99 (d, J=7.2 Hz, 1H), 7.86 (t, J=7.6 Hz, 1H), 7.46 (t, J=8.4 Hz, 1H), 6.85 (d, J=8.4 Hz, 2H), 6.84 (d, J=8.4 Hz, 1H), 3.62-3.70 (m, 4H), 3.58 (s, 6H), 3.40 (q, J=6.8 Hz, 2H), 3.27-3.32 (m, 4H), 1.04 (t, J=6.8 Hz, 3H). LC-MS: m/z 542.0 (M+H)$^+$ Example 91: N-(1-(2,6-Dimethoxyphenyl)-2-(6-ethoxypyridin-2-yl)-1H-imidazo[4,5-b]pyrazin-5-yl)-1-(5-methylpyrimidin-2-yl)methanesulfonamide

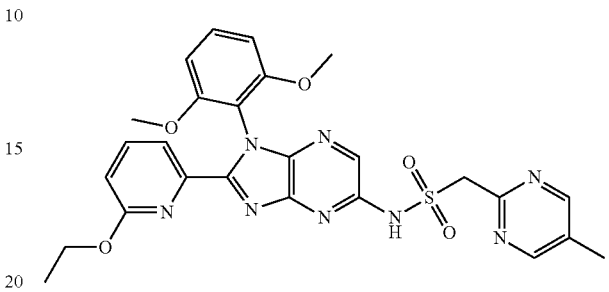

The title compound was prepared according to Method J, step D, starting from 5-chloro-1-(2,6-dimethoxyphenyl)-2-(6-ethoxypyridin-2-yl)-1H-imidazo[4,5-b]pyrazine by using (5-methylpyrimidin-2-yl)methanesulfonamide. $^1$H NMR (400 MHz, DMSO-d$_6$) δ: 11.05 (br. s, 1H), 8.64 (s, 2H), 8.01 (d, J=7.2 Hz, 1H), 7.94 (br. s, 1H), 7.87 (t, J=8.0 Hz, 1H), 7.47 (t, J=8.4 Hz, 1H), 6.83-6.89 (m, 3H), 5.12 (s, 2H), 3.60 (s, 6H), 3.40 (q, J=7.2 Hz, 2H), 2.26 (s, 3H), 1.04 (t, J=6.8 Hz, 3H). LC-MS: m/z 563.3 (M+H)$^+$ Example 92: N-(1-(2,6-Dimethoxyphenyl)-2-(6-ethoxypyridin-2-yl)-1H-imidazo[4,5-b]pyrazin-5-yl) cyclopropanesulfonamide

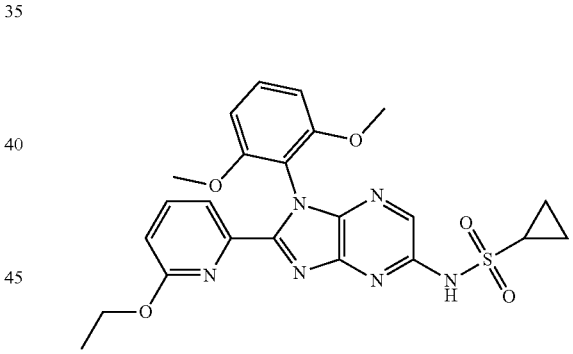

The title compound was prepared according to Method J, step D, starting from 5-chloro-1-(2,6-dimethoxyphenyl)-2-(6-ethoxypyridin-2-yl)-1H-imidazo[4,5-b]pyrazine by using cyclopropanesulfonamide. $^1$H NMR (400 MHz, Chloroform-d) δ: 8.42 (s, 1H), 8.12 (d, J=7.2 Hz, 1H), 7.75 (s, 1H), 7.67 (t, J=8.0 Hz, 1H), 7.38 (t, J=8.4 Hz, 1H), 6.68-6.72 (m, 3H), 3.62 (s, 6H), 3.44 (q, J=8.0 Hz, 2H), 2.93-2.98 (m, 1H), 1.28-1.32 (m, 2H), 1.04-1.11 (m, 5H). LC-MS: m/z 497.2 (M+H)$^+$

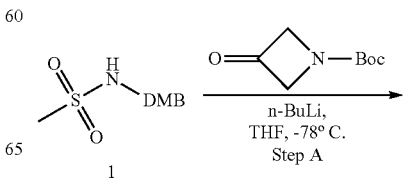

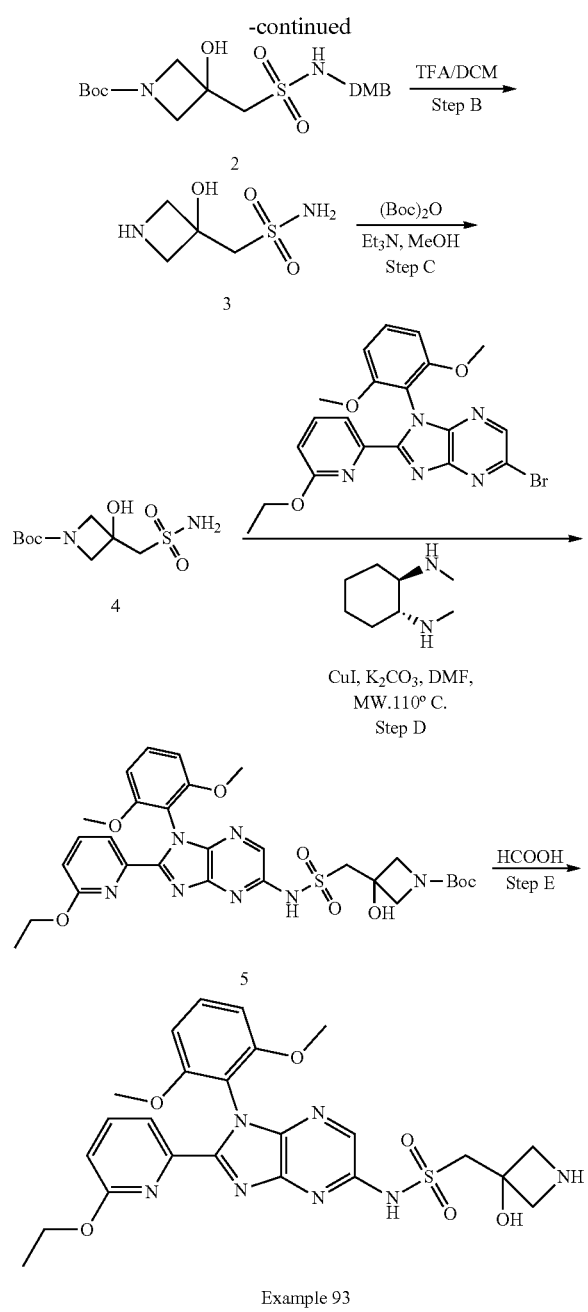

Example 93

Step A: tert-Butyl 3-((N-(2,4-dimethoxybenzyl)sulfamoylmethyl)-3-hydroxyazetidine-1-carboxylate To a solution of N-(2,4-dimethoxybenzyl)-methanesulfonamide (500 mg, 2.04 mmol, 1.0 equiv) in THF (4 mL) at −70° C. under $N_2$ was added n-BuLi (2.5 mL, 2.5 mol/L in THF, 6.25 mmol, 3.1 equiv) dropwise. The reaction mixture was stirred at −70° C. for 1 hour, and then tert-butyl 3-oxoazetidine-1-carboxylate (699 mg, 4.08 mmol, 2.0 equiv) dissolved in THF (4 mL) was added dropwise. After 1 hour at −70° C., the reaction mixture was allowed slowly to warm up to room temperature and stirred overnight. The reaction was quenched with 5 mL MeOH, concentrated in vacuo and purified by column chromatography on silica gel (eluted with EtOAc/PE=2/3) to afford tert-butyl 3-((N-(2,4-dimethoxybenzyl)sulfamoyl)methyl)-3-hydroxyazetidine-1-carboxylate as a pale yellow solid (520 mg, 61% yield). LC-MS: m/z 417.1 (M+H)⁺

Step B: (3-Hydroxyazetidin-3-yl)methanesulfonamide

To a solution of tert-butyl 3-((N-(2,4-dimethoxybenzyl)sulfamoyl)methyl)-3-hydroxyazetidine-1-carboxylate (470 mg, 1.10 mmol, 1.0 equiv) in DCM (10 mL) was added trifluoroethanoic acid (0.5 mL). The reaction mixture was stirred at room temperature overnight. It was filtered and the filter cake redissolved in methanol, filtered and the filtrated was concentrated under vacuum to give (3-hydroxyazetidin-3-yl)methanesulfonamide TFA salt as a white solid (100 mg, 54% yield). LC-MS: m/z 167.0 (M+H)⁺

Step C: (3-Hydroxy-1-methylazetidin-3-yl)methanesulfonamide

To a solution of (3-hydroxyazetidin-3-yl)methanesulfonamide (100 mg, 0.600 mmol, 1.0 equiv) in methanol (10 mL) were added triethylamine (242 mg, 2.40 mmol, 4.0 equiv) and di-tert-butyl dicarbonate (137 mg, 0.630 mmol, 1.05 equiv) at 0° C. The mixture was stirred at 40° C. overnight. The reaction mixture was concentrated under vacuum and the residue was purified by flash chromatography (eluted with DCM/MeOH=40/1) to give (3-hydroxy-1-methylazetidin-3-yl)methanesulfonamide as a white solid (80.0 mg, 47% yield). LC-MS: m/z 267.1 (M+H)⁺

Step D: tert-Butyl 3-((N-(1-(2,6-dimethoxyphenyl)-2-(6-ethoxypyridin-2-yl)-1H-imidazo[4,5-b]pyrazin-5-yl)sulfamoyl)methyl)-3-hydroxyazetidine-1-carboxylate

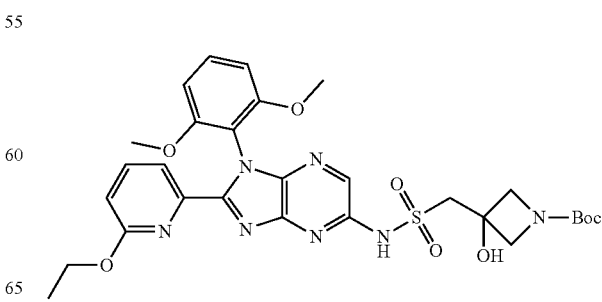

A solution of (3-hydroxy-1-methylazetidin-3-yl)methanesulfonamide (80.0 mg, 0.300 mmol, 1.0 equiv), 5-bromo-1-(2,6-dimethoxyphenyl)-2-(6-ethoxypyridin-2-yl)-1H-imidazo[4,5-b]pyrazine (273 mg, 0.600 mmol, 2.0 equiv), CuI (114 mg, 0.600 mmol, 2.0 equiv), trans-N, N'-Dimethylcyclohexane-1, 2-diamine (85.3 mg, 0.600 mmol, 2.0 equiv) and K$_2$CO$_3$ (124 mg, 0.900 mmol, 3.0 equiv) in DMF (2 mL) was stirred at 110° C. via microwave irradiation for 2 hours under N$_2$ atmosphere. The mixture was diluted with DCM (20 mL), acidified with formic acid (2 mL), and extracted with DCM (20 mL*2). The organic phase was concentrated in vacuo and the residue was purified by flash chromatography (eluted with DCM/MeOH=40/1) to afford tert-butyl 3-((N-(1-(2,6-dimethoxyphenyl)-2-(6-ethoxypyridin-2-yl)-1H-imidazo[4,5-b]pyrazin-5-yl)sulfamoyl)methyl)-3-hydroxyazetidine-1-carboxylate as a pale yellow solid. (70.0 mg, 36% yield). LC-MS: m/z 642.1 (M+H)$^+$ Step E: N-(1-(2,6-Dimethoxyphenyl)-2-(6-ethoxypyridin-2-yl)-1H-imidazo[4,5-b]pyrazin-5-yl)-1-(3-hydroxyazetidine-3-yl)methanesulfonamide (Example 93)

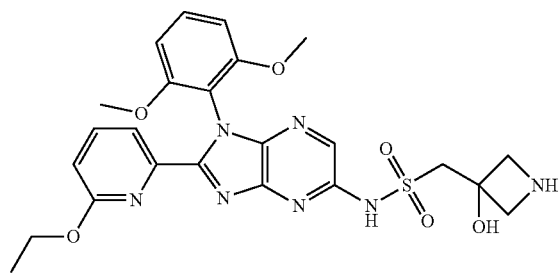 [SMILES: CCOc1cccc(-c2nc3nc(NS(=O)(=O)CC4(O)CNC4)cnc3n2-c2c(OC)cccc2OC)n1]

A solution of tert-butyl 3-((N-(1-(2,6-dimethoxyphenyl)-2-(6-ethoxypyridin-2-yl)-1H-imidazo[4,5-b]pyrazin-5-yl)sulfamoyl)methyl)-3-hydroxyazetidine-1-carboxylate (70.0 mg, 0.109 mmol) in AcOH (5 mL) was stirred at room temperature overnight. The reaction mixture was adjusted to pH=7-8 with ammonium hydroxide and concentrated under vacuum. The residue was purified by prep-HPLC to give N-(1-(2,6-dimethoxyphenyl)-2-(6-ethoxypyridin-2-yl)-1H-imidazo[4,5-b]pyrazin-5-yl)-1-(3-hydroxyazetidin-3-yl)methanesulfonamide as a yellow solid (20.0 mg, 34% yield). $^1$H NMR (400 MHz, DMSO-d$_6$) δ: 7.89 (d, J=7.2 Hz, 1H), 7.80 (t, J=7.6 Hz, 1H), 7.59 (s, 1H), 7.41 (t, J=8.4 Hz, 1H), 6.82 (d, J=8.4 Hz, 2H), 6.74 (d, J=8.0 Hz, 1H), 4.31 (d, J=11.2 Hz, 2H), 3.79 (d, J=11.2 Hz, 2H), 3.61 (s, 2H), 3.57 (s, 6H), 3.37 (d, J=7.2 Hz, 3H), 1.02 (t, J=7.2 Hz, 3H). LC-MS: m/z 542.1 (M+H)$^+$ Method K

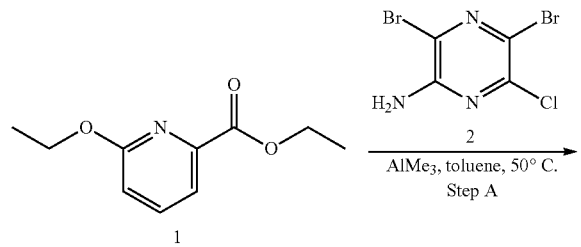

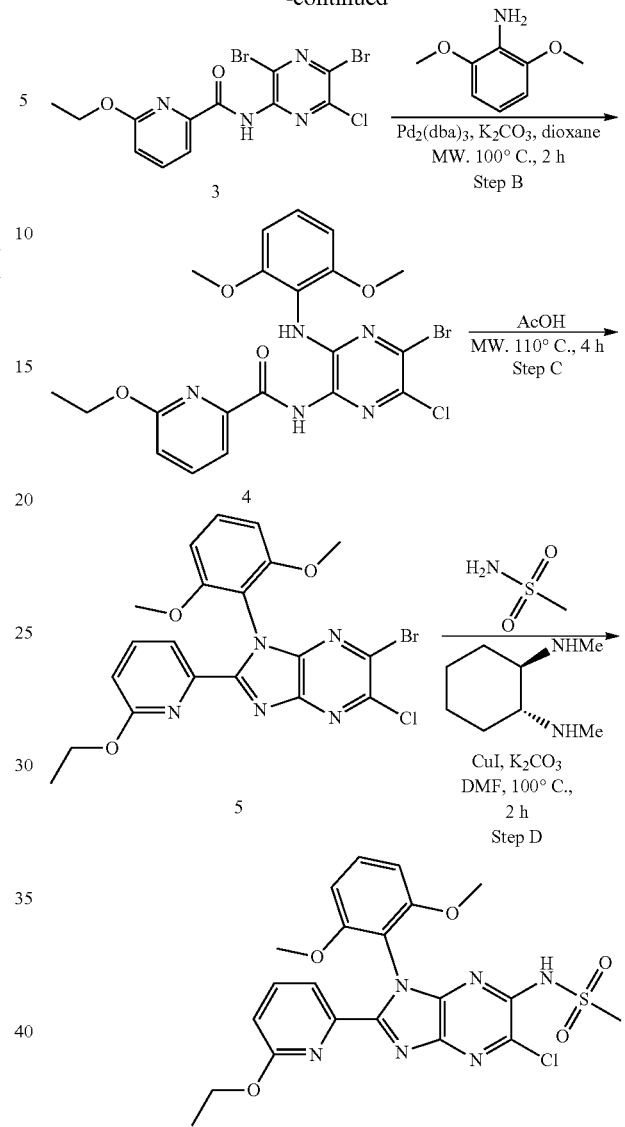

Example 64

Step A: N-(3,5-Dibromo-6-chloropyrazin-2-yl)-6-ethoxypicolinamide

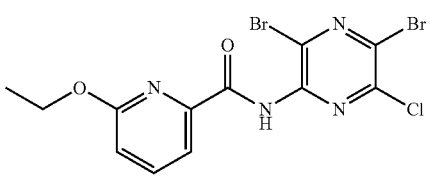 [SMILES: CCOc1cccc(C(=O)Nc2nc(Cl)c(Br)nc2Br)n1]

To a solution of 3,5-dibromo-6-chloropyrazin-2-amine (2.00 g, 6.97 mmol, 1.0 equiv) in anhydrous toluene (50 mL) was added Al(Me)$_3$ (2 mol/L in toluene, 5.20 mL, 10.4 mmol, 1.5 equiv) dropwise at 0° C. under N$_2$ atmosphere. After the mixture was stirred at 0° C. for 30 minutes and at 50° C. for 30 minutes, ethyl 6-ethoxypicolinate (1.36 g, 6.97 mmol, 1.0 equiv) was added. The mixture was stirred at 50°

C. for 3 hours. The reaction mixture was quenched with 1N HCl solution (100 mL), followed by extraction with DCM (50 mL*2). The combined organic layers were dried over anhydrous Na₂SO₄ and concentrated in vacuo. The residue was reslurried in MeOH (50 mL). The mixture was filtered to afford the title compound N-(3,5-dibromo-6-chloropyrazin-2-yl)-6-ethoxypicolinamide as a yellow solid (2.30 g, 76% yield). LC-MS: m/z 434.9, 436.9, 438.9 (M+H)⁺

Step B: N-(5-Bromo-6-chloro-3-((2,6-dimethoxyphenyl)amino)pyrazin-2-yl)-6-ethoxypicolinamide

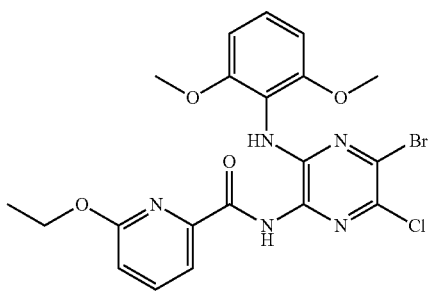 [SMILES: CCOc1cccc(C(=O)Nc2nc(Cl)c(Br)nc2Nc2c(OC)cccc2OC)n1]

A suspension of N-(3,5-dibromo-6-chloropyrazin-2-yl)-6-ethoxypicolinamide (1.00 g, 2.30 mmol, 1.0 equiv), 2,6-dimethoxyaniline (351 mg, 2.30 mmol, 1.0 equiv), Pd₂(dba)₃ (420 mg, 0.460 mmol, 0.2 equiv), Xantphos (530 mg, 0.520 mmol, 0.4 equiv) and K₂CO₃ (632 mg, 4.60 mmol, 3.0 equiv) in 1,4-dioxane (15 mL) was stirred at 100° C. via microwave irradiation for 2 hours under N₂ atmosphere. The mixture was filtered and the filtrate was concentrated to dryness. The residue was purified by silica gel column chromatography (eluted with PE/EtOAc=10/1~5/1) to afford N-(5-bromo-6-chloro-3-((2,6-dimethoxyphenyl)amino)pyrazin-2-yl)-6-ethoxypicolinamide as a yellow solid (480 mg, 41% yield). LC-MS: m/z 508.0, 510.0 (M+H)⁺

Step C: 6-Bromo-5-chloro-1-(2,6-dimethoxyphenyl-2-(6-ethoxypyridin-2-yl)-1H-imidazo[4,5-b]pyrazine

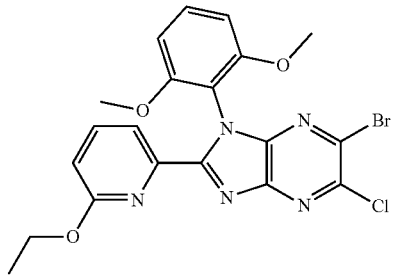 [SMILES: CCOc1cccc(-c2nc3nc(Cl)c(Br)nc3n2-c2c(OC)cccc2OC)n1]

The solution of N-(5-bromo-6-chloro-3-((2,6-dimethoxyphenyl)amino)pyrazin-2-yl)-6-ethoxypicolinamide amide (400 mg, 0.780 mmol, 1.0 equiv) in AcOH (10 mL) was stirred at 110° C. via microwave irradiation for 4 hours. The mixture was cooled to room temperature and the precipitate was filtered off to afford the title compound 6-bromo-5-chloro-1-(2,6-dimethoxyphenyl)-2-(6-ethoxypyridin-2-yl)-1H-imidazo[4,5-b]pyrazine as a yellow solid (220 mg, 57% yield). LC-MS: m/z 490.0, 492.0 (M+H)⁺

Step D: N-(5-Chloro-1-(2,6-dimethoxyphenyl-2-(6-ethoxypyridin-2-yl)-1H-imidazo[4,5-b]pyrazin-6-yl)methanesulfonamide (Example 64)

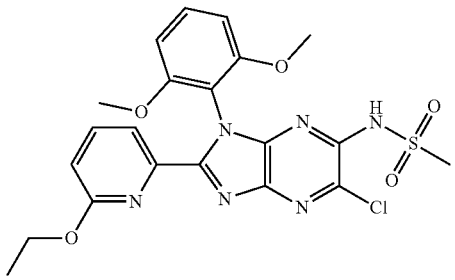 [SMILES: CCOc1cccc(-c2nc3nc(Cl)c(NS(C)(=O)=O)nc3n2-c2c(OC)cccc2OC)n1]

A suspension of 6-Bromo-5-chloro-1-(2,6-dimethoxyphenyl)-2-(6-ethoxypyridin-2-yl)-1H-imidazo[4,5-b]pyrazine (200 mg, 0.410 mmol, 1.0 equiv), methanesulfonamide (38.0 mg, 0.410 mmol, 1.0 equiv), CuI (155 mg, 0.820 mmol, 2.0 equiv), trans-N, N'-Dimethylcyclohexane-1, 2-diamine (116 mg, 0.820 mmol, 2.0 equiv) and K₂CO₃ (168 mg, 1.23 mmol, 3.0 equiv) in DMF (10 mL) was stirred at 100° C. for 2 hours under N₂ atmosphere. The mixture was diluted with 1N HCl solution (20 mL) and extracted with EtOAc (2*50 mL). The combined organic layers were dried over anhydrous Na₂SO₄ and concentrated in vacuo. The residue was purified by flash chromatography to afford N-(5-chloro-1-(2,6-dimethoxyphenyl)-2-(6-ethoxypyridin-2-yl)-1H-imidazo[4,5-b]pyrazin-6-yl)methanesulfonamide as yellow solid (120 mg, 59% yield). ¹H NMR (400 MHz, DMSO-d₆) δ: 10.69 (br. s, 1H), 7.94 (d, J=7.2 Hz, 1H), 7.87 (t, J=8.0 Hz, 1H), 7.46 (t, J=8.4 Hz, 1H), 6.83-6.87 (m, 3H), 3.57 (s, 6H), 3.39 (q, J=7.2 Hz, 2H), 3.12 (s, 3H), 1.02 (t, J=7.2 Hz, 3H). LC-MS: m/z 505.0 (M+H)⁺

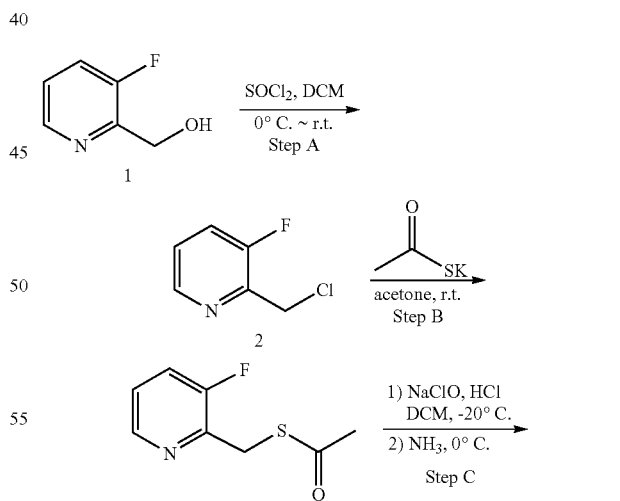

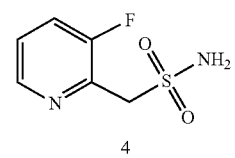

Step A: 2-(Chloromethyl)-3-fluoropyridine

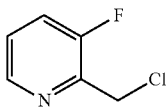

To a solution of (3-fluoropyridin-2-yl)methanol (1.80 g, 13.8 mmol, 1.0 equiv) in DCM (20 mL) was added SOCl$_2$ (2.50 mL, 35.0 mmol, 2.5 equiv) dropwise at 0° C. The resulting mixture was stirred at room temperature for 2 hours. The reaction mixture was quenched with saturated aqueous NaHCO$_3$ solution and extracted with DCM (3*20 mL). The combined organic layers were dried over anhydrous Na$_2$SO$_4$ and concentrated in vacuo. The residue was purified by column chromatography (eluted with PE/EtOAc=5/1) to afford 2-(chloromethyl)-3-fluoropyridine (1.33 g, 66% yield). LC-MS: m/z 146.0, 148.0 (M+H)$^+$

Step B: S-((3-Fluoropyridin-2-yl)methyl) ethanethioate

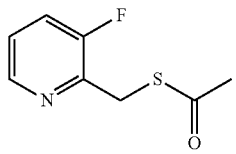

To a solution of 2-(chloromethyl)-3-fluoropyridine (1.00 g, 6.70 mmol, 1.0 equiv) in acetone (20 mL) was added potassium ethanethioate (918 mg, 8.00 mmol, 1.2 equiv) in one portion. The resulting mixture was refluxed overnight. The reaction mixture was filtered through a short silica gel column. The filtrate was concentrated in vacuo and the residue was purified by column chromatography (eluted with PE/EtOAc=5/1) to afford S-((3-fluoropyridin-2-yl)methyl) ethanethioate (1.00 g, 81% yield). LC-MS: m/z 186.0 (M+H)$^+$

Step C: (3-Fluoropyridin-2-yl)methanesulfonamide

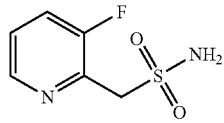 [SMILES: NS(=O)(=O)Cc1ncccc1F]

Sodium hypochlorite (9% aq. solution) (12.0 mL, 16.2 mmol, 6.0 equiv) was added dropwise to a vigorous stirring solution of S-((3-fluoropyridin-2-yl)methyl) ethanethioate (500 mg, 2.70 mmol, 1.0 equiv) in DCM (17 mL) and 1 N HCl solution (16.2 mL, 16.2 mmol, 6.0 equiv) at −20° C. After the completion of addition, the mixture was stirred at −20° C. for 1 hour. Then NH$_3$ (gas) was bubbled into the mixture at −20° C. for 10 minutes. The mixture was allowed to slowly warm up to room temperature and stirred for 1 hour. The mixture was concentrated under vacuum. The residue was purified by silica gel chromatography (eluted with DCM/MeOH=25/1) to afford (3-fluoropyridin-2-yl)methanesulfonamide as a white solid (250 mg, 49% yield). LC-MS: m/z 191.0 (M+H)$^+$ Example 94: N-(5-Chloro-1-(2,6-dimethoxyphenyl)-2-(6-ethoxypyridin-2-yl)-1H-imidazo[4,5-b]pyrazin-6-yl)-1-(3-fluoropyridin-2-yl)methanesulfonamide

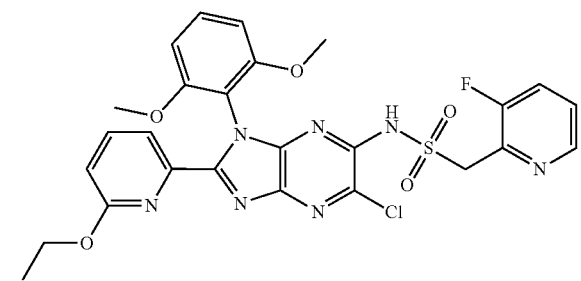 [SMILES: CCOc1cccc(-c2nc3nc(Cl)c(NS(=O)(=O)Cc4ncccc4F)nc3n2-c2c(OC)cccc2OC)n1]

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (3-fluoropyridin-2-yl)methanesulfonamide. $^1$H NMR (400 MHz, DMSO-d$_6$) δ: 10.97 (s, 1H), 8.39 (d, J=4.0 Hz, 1H), 7.97 (d, J=8.0 Hz, 1H), 7.89 (t, J=8.0 Hz, 1H), 7.70-7.75 (m, 1H), 7.43-7.50 (m, 2H), 6.84-6.87 (m, 3H), 4.89 (s, 2H), 3.56 (s, 6H), 3.40 (q, J=8.0 Hz, 2H), 1.02 (t, J=8.0 Hz, 3H). LC-MS: m/z 600.1 (M+H)$^+$ Pyridin-2-yl methanesulfonamide

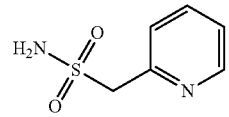 [SMILES: NS(=O)(=O)Cc1ccccn1]

Pyridin-2-ylmethanesulfonamide was prepared according to the preparation of (3-Fluoropyridin-2-yl)methanesulfonamide by using 2-(chloromethyl)pyridine at step A. LC-MS: m/z 173.0 (M+H)$^+$ Example 95: N-(5-Chloro-1-(2,6-dimethoxyphenyl)-2-(6-ethoxypyridin-2-yl)-1H-imidazo[4,5-b]pyrazin-6-yl)-1-(pyridin-2-yl)methanesulfonamide

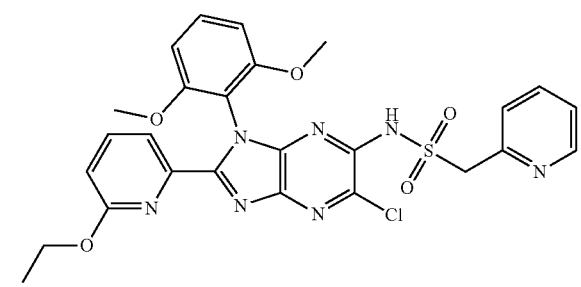 [SMILES: CCOc1cccc(-c2nc3nc(Cl)c(NS(=O)(=O)Cc4ccccn4)nc3n2-c2c(OC)cccc2OC)n1]

The title compound was prepared according to Method K, step D, starting from 6-Bromo-5-chloro-1-(2,6-dimethoxyphenyl)-2-(6-ethoxypyridin-2-yl)-1H-imidazo[4,5-b]pyrazine by using pyridin-2-ylmethanesulfonamide. ¹H NMR (400 MHz, DMSO-d₆) δ: 8.51 (d, J=4.0 Hz, 1H), 7.94 (d, J=7.2 Hz, 1H), 7.86 (t, J=8.0 Hz, 1H), 7.76-7.72 (m, 1H), 7.46 (t, J=8.8 Hz, 1H), 7.34-7.30 (m, 1H), 7.08 (d, J=7.6 Hz, 1H), 6.82-6.87 (m, 3H), 4.71 (s, 2H), 3.55 (s, 6H), 3.39 (q, J=7.2 Hz, 2H), 1.01 (t, J=7.2 Hz, 3H). LC-MS: m/z 582.1 (M+H)⁺

(5-Fluoropyridin-2-yl)methanesulfonamide

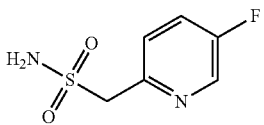 [SMILES: NS(=O)(=O)Cc1ccc(F)cn1]

(5-Fluoropyridin-2-yl)methanesulfonamide was prepared according to the preparation of (3-Fluoropyridin-2-yl)methanesulfonamide by using (5-fluoropyridin-2-yl)methanol at step A. LC-MS: m/z 191.0 (M+H)⁺

Example 96: N-(5-Chloro-1-(2,6-dimethoxyphenyl)-2-(6-ethoxypyridin-2-yl)-1H-imidazo[4,5-b]pyrazin-6-yl)-1-(5-fluoropyridin-2-yl)methanesulfonamide

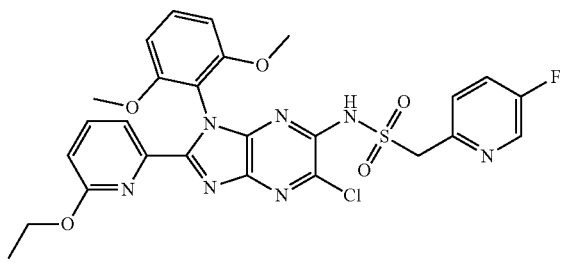

The title compound was prepared according to Method K, step D, starting from 6-Bromo-5-chloro-1-(2,6-dimethoxyphenyl)-2-(6-ethoxypyridin-2-yl)-1H-imidazo[4,5-b]pyrazine by using (3-fluoropyridin-2-yl)methanesulfonamide. ¹H NMR (400 MHz, DMSO-d₆) δ: 10.91 (s, 1H), 8.53 (d, J=2.4 Hz, 1H), 7.98 (d, J=8.0 Hz, 1H), 7.88 (t, J=8.0 Hz, 1H), 7.70-7.75 (m, 1H), 7.48 (d, J=8.0 Hz, 1H), 7.19 (dd, J=12.0, 4.0 Hz, 1H), 6.85-6.89 (m, 3H), 4.79 (s, 2H), 3.57 (s, 6H), 3.40 (q, J=8.0 Hz, 2H), 1.02 (t, J=8.0 Hz, 3H). LC-MS: m/z 600.1 (M+H)⁺

Example 97: N-(5-Chloro-1-(2,6-dimethoxyphenyl)-2-(6-ethoxypyridin-2-yl)-1H-imidazo[4,5-b]pyrazin-6-yl)cyclopropanesulfonamide

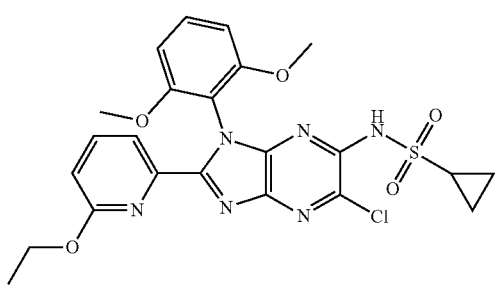 [SMILES: CCOc1cccc(-c2nc3nc(Cl)c(NS(=O)(=O)C4CC4)nc3n2-c2c(OC)cccc2OC)n1]

The title compound was prepared according to Method K, step D, starting from 6-Bromo-5-chloro-1-(2,6-dimethoxyphenyl)-2-(6-ethoxypyridin-2-yl)-1H-imidazo[4,5-b]pyrazine by using cyclopropanesulfonamide. ¹H NMR (400 MHz, DMSO-d₆) δ: 10.66 (s, 1H), 7.96 (d, J=7.6 Hz, 1H), 7.87 (t, J=7.6 Hz, 1H), 7.48 (t, J=8.4 Hz, 1H), 6.85-6.89 (m, 3H), 3.57 (s, 6H), 3.39 (q, J=7.2 Hz, 2H), 2.71-2.76 (m, 1H), 1.02 (t, J=7.2 Hz, 3H), 0.91-0.95 (m, 2H), 0.81-0.85 (m, 2H). LC-MS: m/z 531.1 (M+H)⁺

Morpholine-4-sulfonamide

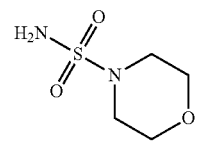

The title compound was prepared according to the preparation of pyrrolidine-1-sulfonamide by using morpholine. ¹H NMR (400 MHz, DMSO-d₆) δ: 6.82 (s, 2H), 3.61-3.68 (m, 4H), 2.89-2.94 (m, 4H).

Example 98: N-(5-Chloro-1-(2,6-dimethoxyphenyl)-2-(6-ethoxypyridin-2-yl)-1H-imidazo[4,5-b]pyrazin-6-yl)morpholine-4-sulfonamide

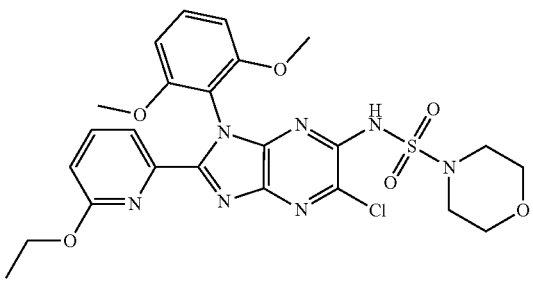 [SMILES: CCOc1cccc(-c2nc3nc(Cl)c(NS(=O)(=O)N4CCOCC4)nc3n2-c2c(OC)cccc2OC)n1]

The title compound was prepared according to Method K, step D, starting from 6-Bromo-5-chloro-1-(2,6-dimethoxyphenyl)-2-(6-ethoxypyridin-2-yl)-1H-imidazo[4,5-b]pyrazine by using morpholine-4-sulfonamide. ¹H NMR (400 MHz, DMSO-d₆) δ: 10.60 (s, 1H), 7.99 (d, J=8.0 Hz, 1H), 7.87 (t, J=7.6 Hz, 1H), 7.47 (t, J=8.4 Hz, 1H), 6.48-6.89 (m, 3H), 3.60 (s, 6H), 3.35-3.42 (m, 6H), 2.90 (t, J=4.4 Hz, 4H), 1.02 (t, J=6.8 Hz, 3H). LC-MS: m/z 576.1, 578.2 (M+H)⁺

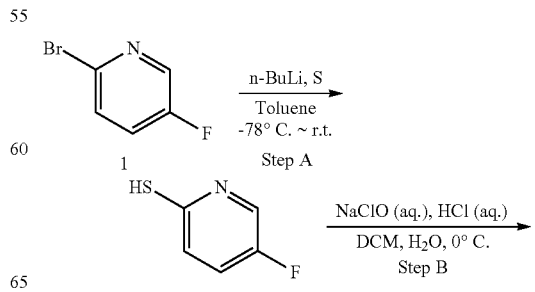

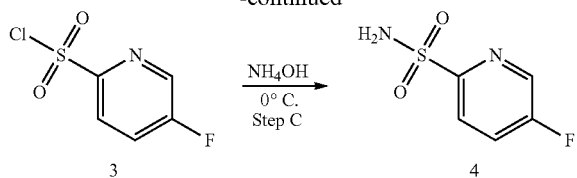

Step A: 5-Fluoropyridine-2-thiol

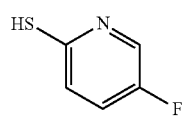

A solution of 2-bromo-5-fluoropyridine (3.00 g, 17.0 mmol, 1.0 equiv) in anhydrous toluene (2 mL) was added dropwise into a solution of n-BuLi (7.48 mL, 2.5 mol/L in hexane, 18.7 mmol, 1.1 equiv) in anhydrous toluene (38 mL) at −78° C. The reaction mixture was stirred for 5 minutes at −78° C. Sulfur power (0.550 g, 17.0 mmol, 1.0 equiv) was added to the solution and then resulting mixture was warmed up to room temperature and stirred for additional 1 hour. The reaction mixture was quenched with $H_2O$ (1 mL) and adjusted pH to 3.0 with HCl (1 N). The resulting mixture was extracted with DCM (25 mL*3). The combined organic phase was washed with brine (30 mL), dried over anhydrous $Na_2SO_4$, filtered and concentrated. The residue was purified by flash chromatography on silica gel (eluted with PE/EtOAc=2/1) to afford the title compound 5-fluoropyridine-2-thiol as a yellow solid (700 mg, 32% yield). LC-MS: m/z 130.0 $(M+H)^+$ Step B: 5-Fluoropyridine-2-sulfonyl chloride

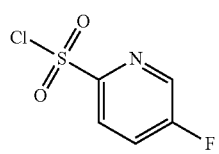 [SMILES: O=S(=O)(Cl)c1ccc(F)cn1]

Sodium hypochlorite (9% aq. solution)(10 mL, 20.1 mmol, 3.7 equiv) was added dropwise to a rapidly stirring solution of 5-fluoropyridine-2-thiol (0.700 g, 5.40 mmol, 1.0 equiv) in DCM (20 mL) and 1N HCl solution (20.1 mL, 20.1 mmol, 3.7 equiv) at 0° C. After the addition was completed, the mixture was stirred at 0° C. for 30 minutes. The organic layer was separated and used directly for the next step.

Step C: 5-Fluoropyridine-2-sulfonamide

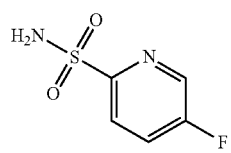 [SMILES: NS(=O)(=O)c1ccc(F)cn1]

The solution of 5-fluoropyridine-2-sulfonyl chloride in DCM (20 mL) was added to $NH_4OH$ (aq., 34%, 15 mL) at 0° C. and the mixture was allowed to warm up to room temperature slowly and stirred for 1 hour. The mixture was concentrated under vacuum and the residue was purified by silica gel chromatography (eluted with PE/EtOAc=1/1) to afford 5-fluoropyridine-2-sulfonamide as an orange solid (170 mg, 18% yield in two steps). LC-MS: m/z 177.0 $(M+H)^+$ Example 99: N-(5-Chloro-1-(2,6-dimethoxyphenyl)-2-(6-ethoxypyridin-2-yl)-1H-imidazo[4,5-b]pyrazin-6-yl)-5-fluoropyridine-2-sulfonamide

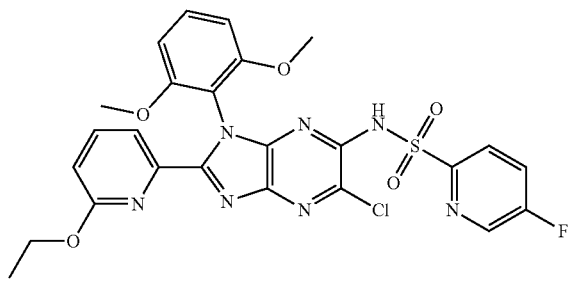 [SMILES: CCOc1cccc(-c2nc3nc(Cl)c(NS(=O)(=O)c4ccc(F)cn4)nc3n2-c2c(OC)cccc2OC)n1]

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using 5-fluoropyridine-2-sulfonamide. $^1$H NMR (400 MHz, DMSO-$d_6$) δ: 8.57 (d, J=2.4 Hz, 1H), 7.93 (d, J=7.2 Hz, 1H), 7.83 (t, J=8.0 Hz, 1H), 7.45-7.58 (m, 3H), 6.84 (dd, J=10.0, 8.4 Hz, 3H), 3.51 (s, 6H), 3.33 (q, J=7.2 Hz, 3H), 1.01 (t, J=7.2 Hz, 3H). LC-MS: m/z 586.1 $(M+H)^+$ Example 100: N-(5-Chloro-1-(2,6-dimethoxyphenyl)-2-(6-ethoxypyridin-2-yl)-1H-imidazo[4,5-b]pyrazin-6-yl)-1-(2-fluoro-4-methylphenyl)methanesulfonamide

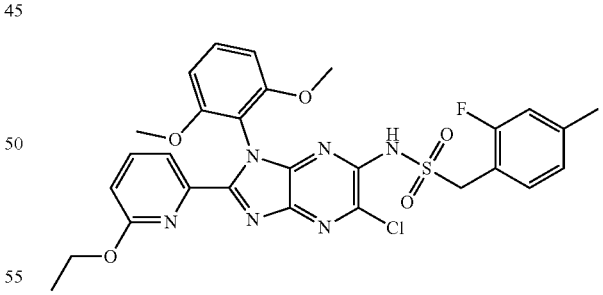

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (2-fluoro-4-methylphenyl)methanesulfonamide. $^1$H NMR (400 MHz, DMSO-$d_6$) δ: 10.92 (s, 1H), 7.99 (dd, J=7.2, 0.4 Hz, 1H), 7.89 (t, J=7.6 Hz, 1H), 7.48 (t, J=8.4 Hz, 1H), 7.04 (d, J=11.2 Hz, 1H), 6.97-7.00 (m, 2H), 6.88 (d, J=8.4 Hz, 2H), 6.87 (dd, J=8.0, 0.4 Hz, 1H), 4.64 (s, 2H), 3.57 (s, 6H), 3.40 (d, J=7.2 Hz, 2H), 2.31 (s, 3H), 1.02 (t, J=7.2 Hz, 3H). LC-MS: m/z 613.1 $(M+H)^+$

Example 101: N-(5-Chloro-1-(2,6-dmethoxyphenyl)-2-(6-ethoxypyridin-2-yl)-1H-imidazo[4,5-b]pyrazin-6-yl)-5-methylpyridine-2-sulfonamide

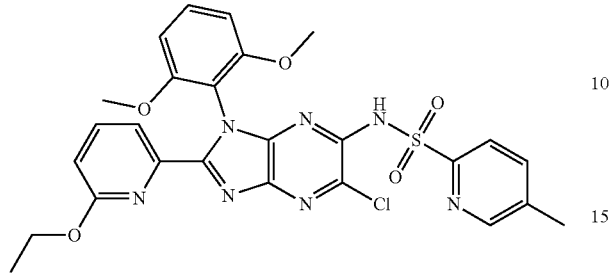

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using 5-methylpyridine-2-sulfonamide. $^1$HNMR (400 MHz, DMSO-$d_6$) δ: 11.60 (br. s, 1H), 8.38 (s, 1H), 7.92 (d, J=7.2 Hz, 1H), 7.83 (d, J=7.6 Hz, 1H), 7.56 (t, J=8.4 Hz, 1H), 7.40 (d, J=8.0 Hz, 1H), 7.31 (d, J=8.0 Hz, 1H), 6.88 (d, J=8.4 Hz, 2H), 6.82 (d, J=8.0 Hz, 1H), 3.50 (s, 6H), 3.34 (q, J=7.2 Hz, 2H), 2.35 (s, 3H), 1.01 (t, J=7.2 Hz, 3H). LC-MS: m/z 582.1 (M+H)$^+$

Example 102: N-(5-Chloro-1-(2,6-dimethoxyphenyl)-2-(6-ethoxypyridin-2-yl)-1H-imidazo[4,5-b]pyrazin-6-yl)pyridine-2-sulfonamide

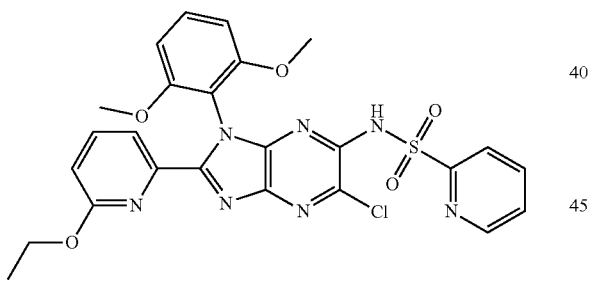

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using pyridine-2-sulfonamide. $^1$H NMR (400 MHz, DMSO-$d_6$) δ: 11.66 (s, 1H), 8.36-8.61 (m, 1H), 7.87 (d, J=7.2 Hz, 1H), 7.80 (t, J=7.6 Hz, 1H), 7.52 (t, J=8.4 Hz, 2H), 7.40 (d, J=8.0 Hz, 2H), 6.86 (d, J=8.4 Hz, 2H), 6.77 (d, J=8.0 Hz, 1H), 3.50 (s, 6H), 3.33 (q, J=7.2 Hz, 2H), 1.00 (t, J=7.2 Hz, 3H). LC-MS: m/z 568.1 (M+H)$^+$

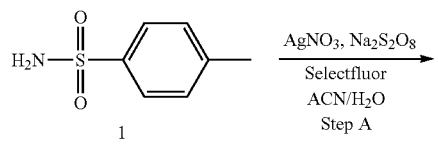

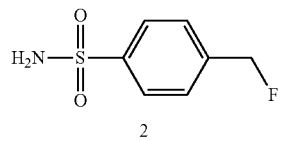

Step A: 4-(Fluoromethyl)benzenesulfonamide

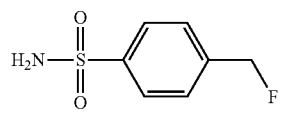

A mixture of 4-methylbenzenesulfonamide (1.71 g, 10.0 mmol, 1.0 equiv), AgNO$_3$ (340 mg, 2.00 mmol, 0.2 equiv), Na$_2$S$_2$O$_8$ (11.9 g, 50.0 mmol, 5 equiv) and Selectfluor (14.2 g, 40.0 mmol, 4 equiv) in CH$_3$CN (75 mL) and H$_2$O (75 mL) was stirred at 80° C. for 5 hours under N$_2$. The resulting mixture was extracted with DCM (3*50 mL). The combined organic phase was washed with brine (30 mL), dried over anhydrous Na$_2$SO$_4$, filtered and concentrated. The residue was purified by flash chromatography on silica gel (eluted with DCM/Et$_3$N=100/1) to afford the title compound 4-(fluoromethyl)benzenesulfonamide as a yellow solid (0.61 g, 84% purity, 27% yield). $^1$H NMR (400 MHz, DMSO-$d_6$) δ: 7.91-7.83 (m, 2H), 7.63-7.55 (m, 2H), 7.40 (s, 2H), 5.52 (d, J=47.2 Hz, 2H). LC-MS: m/z 190.0 (M+H)$^+$

Example 103: N-(5-Chloro-1-(2,6-dimethoxyphenyl)-2-(6-ethoxypyridin-2-yl)-1H-imidazo[4,5-b]pyrazin-6-yl)-4-(fluoromethyl)benzenesulfonamide

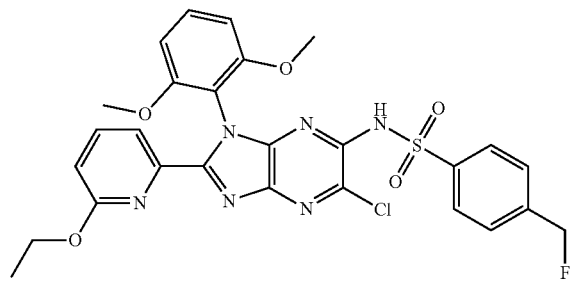 [SMILES: CCOc1cccc(-c2nc3nc(Cl)c(NS(=O)(=O)c4ccc(CF)cc4)nc3n2-c2c(OC)cccc2OC)n1]

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using 4-(fluoromethyl)benzenesulfonamide. $^1$H NMR (400 MHz, DMSO-$d_6$) δ: 11.25 (s, 1H), 7.92 (d, J=7.2 Hz, 1H), 7.83 (t, J=8.0 Hz, 1H), 7.68-7.52 (m, 3H), 7.27 (d, J=8.0 Hz, 2H), 6.98 (d, J=8.4 Hz, 2H), 6.82 (d, J=8.4 Hz, 1H), 5.47 (d, J=48.0 Hz, 2H), 3.54 (s, 6H), 3.38 (q, J=7.2 Hz, 2H), 1.03 (t, J=7.2 Hz, 3H). LC-MS: m/z 599.1 (M+H)$^+$

Example 104: N-(5-Chloro-1-(2,6-dimethoxyphenyl)-2-(6-ethoxypyridin-2-yl)-1H-imidazo[4,5-b]pyrazin-6-yl)pyridine-3-sulfonamide

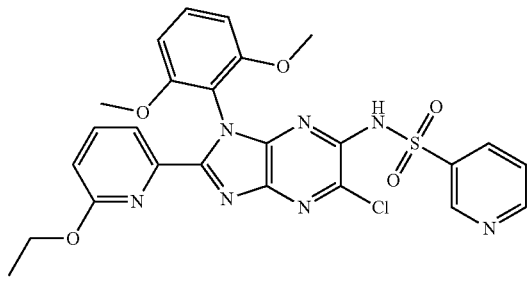 [SMILES: CCOc1cccc(-c2nc3nc(Cl)c(NS(=O)(=O)c4cccnc4)nc3n2-c2c(OC)cccc2OC)n1]

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using pyridine-3-sulfonamide. $^1$H NMR (400 MHz, DMSO-d$_6$) δ: 8.76-8.84 (m, 1H), 8.64-8.75 (m, 1H), 7.94 (d, J=7.2 Hz, 1H), 7.85 (t, J=7.6 Hz, 1H), 7.79 (dt, J=8.0, 2.0 Hz, 1H), 7.60 (t, J=8.4 Hz, 1H), 7.21-7.33 (m, 1H), 6.96 (d, J=8.4 Hz, 2H), 6.84 (d, J=8.0 Hz, 1H), 3.56 (s, 6H), 3.38 (q, J=7.2 Hz, 2H), 1.03 (t, J=7.2 Hz, 3H). LC-MS: m/z 568.2 (M+H)$^+$

Example 105: N-(5-Chloro-1-(2,6-dimethoxyphenyl)-2-(6-ethoxypyridin-2-yl)-1H-imidazo[4,5-b]pyrazin-6-yl)-1-(5-fluoropyrimidin-2-yl)methanesulfonamide

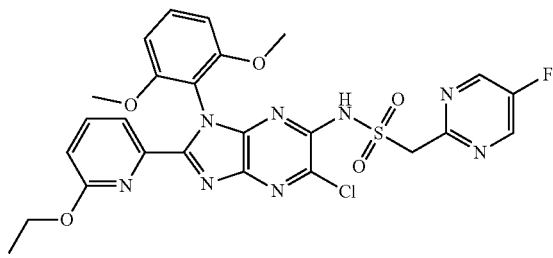

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (5-fluoropyrimidin-2-yl)methanesulfonamide. $^1$H NMR (400 MHz, Chloroform-d) δ: 8.55 (s, 2H), 8.06 (d, J=7.2 Hz, 1H), 7.68 (t, J=7.6 Hz, 1H), 7.42 (s, 1H), 7.38 (t, J=8.4 Hz, 1H), 6.70 (d, J=8.0 Hz, 1H), 6.67 (d, J=8.4 Hz, 2H), 4.99 (s, 2H), 3.59 (s, 6H), 3.42 (q, J=7.2 Hz, 2H), 1.06 (t, J=7.2 Hz, 3H). LC-MS: m/z 601.1 (M+H)$^+$

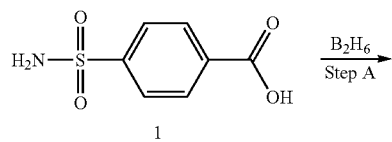

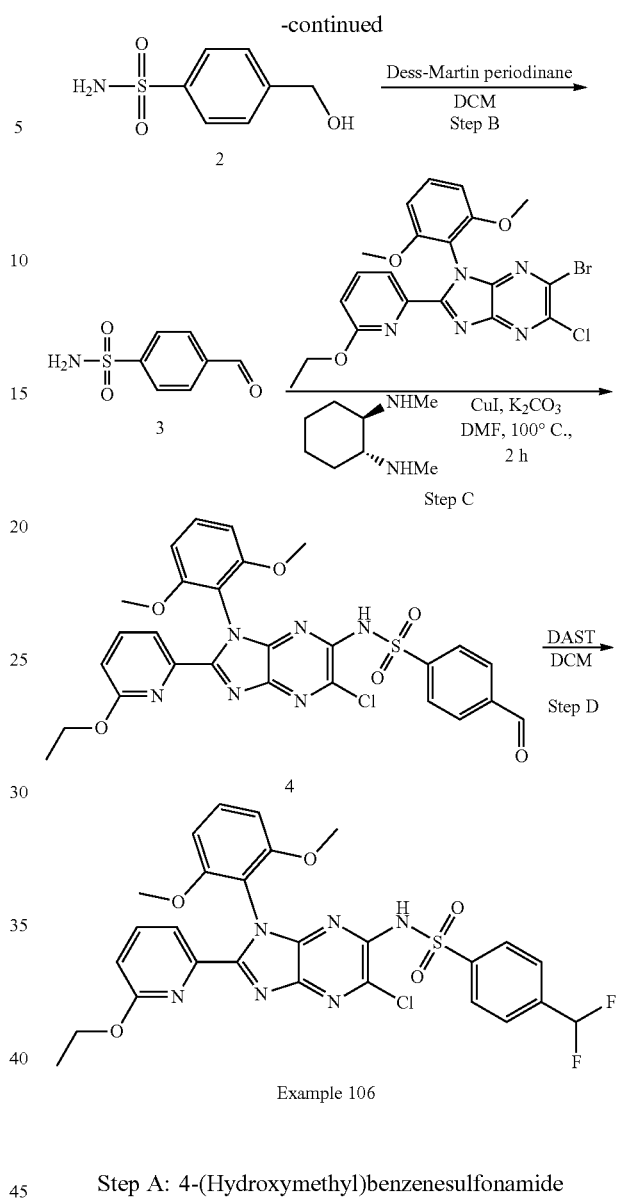

Example 106

Step A: 4-(Hydroxymethyl)benzenesulfonamide

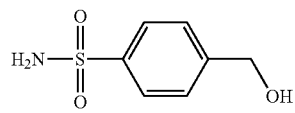 [SMILES: NS(=O)(=O)c1ccc(CO)cc1]

To a solution of 4-sulfamoylbenzoic acid (5.00 g, 25.0 mmol, 1.0 equiv) in THF (250 mL) was added B$_2$H$_6$ (100 mL, 1 mol/L in THF, 100 mmol, 4 equiv) dropwise at 0° C. The mixture was stirred for 0.5 hour at 0° C. The mixture was allowed to warm to room temperature slowly and stirred for another 18 hours. Then the mixture was cooled to 0° C. and the 50 mL MeOH was added dropwise. After refluxed for 1 h, 2 mol/L HCl (50 mL) was added to the solution and the reaction mixture was refluxed for another 30 mins. The mixture was concentrated under vacuum and the residue was purified by silica gel chromatography (eluted with DCM/MeOH=100/8) to afford 4-(hydroxymethyl)benzenesulfonamide as a white solid (3.12 g, 67% yield). $^1$H NMR (400 MHz, DMSO-d$_6$) δ: 7.77 (d, J=8.4 Hz, 2H), 7.48 (d, J=8.4

Hz, 2H), 7.29 (s, 2H), 5.37 (t, J=5.6 Hz, 1H), 4.57 (d, J=5.6 Hz, 2H). LC-MS: m/z 188.0 (M+H)+

Step B: 4-Formylbenzenesulfonamide

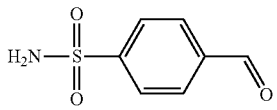

A mixture of 4-(hydroxymethyl)benzenesulfonamide (1.00 g, 5.35 mmol, 1.0 equiv) and Dess-Martin periodinane (3.40 g, 8.02 mmol, 1.5 equiv) in CH$_3$CN (40 mL) was stirred at 80° C. for 2 hours. Then aq. NaHCO$_3$ solution and aq. Na$_2$S$_2$O$_3$ solution were added. The mixture was filtered and the filtrate was concentrated. The residue was purified by flash chromatography on silica gel (eluted with PE/EtOAc=1/1) to afford 4-formylbenzenesulfonamide as a white solid (820 mg, 83% yield). $^1$H NMR (400 MHz, DMSO-d$_6$) δ: 10.10 (s, 1H), 8.10 (d, J=8.4 Hz, 2H), 8.03 (d, J=8.4 Hz, 2H), 7.60 (s, 2H). LC-MS: m/z 186.0 (M+H)+

Step C: N-(5-Chloro-1-(2,6-dimethoxyphenyl)-2-(6-ethoxypyridin-2-yl)-1H-imidazo[4,5-b]pyrazin-6-yl)-4-formylbenzenesulfonamide

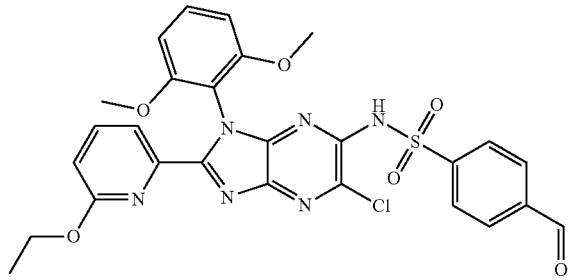 [SMILES: CCOc1cccc(-c2nc3nc(Cl)c(NS(=O)(=O)c4ccc(C=O)cc4)nc3n2-c2c(OC)cccc2OC)n1]

N-(5-Chloro-1-(2,6-dimethoxyphenyl)-2-(6-ethoxypyridin-2-yl)-1H-imidazo[4,5-b]pyrazin-6-yl)-4-formylbenzenesulfonamide was prepared according to Method K, step D, by using 4-formylbenzenesulfonamide. LC-MS: m/z 595.1 (M+H)+

Example 106: N-(5-Chloro-1-(2,6-dimethoxyphenyl)-2-(6-ethoxypyridin-2-yl)-1H-imidazo[4,5-b]pyrazin-6-yl)-4-(difluoromethyl)benzenesulfonamide

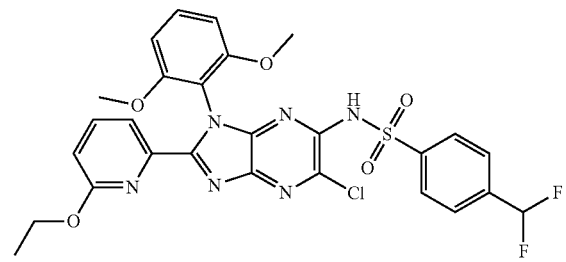 [SMILES: CCOc1cccc(-c2nc3nc(Cl)c(NS(=O)(=O)c4ccc(C(F)F)cc4)nc3n2-c2c(OC)cccc2OC)n1]

DAST (5.60*10$^{-6}$ L, 0.042 mmol, 2.5 equiv) was added to a stirred solution of N-(5-chloro-1-(2,6-dimethoxyphenyl)-2-(6-ethoxypyridin-2-yl)-1H-imidazo[4,5-b]pyrazin-6-yl)-4-formylbenzenesulfonamide (10.0 mg, 0.017 mmol, 1.0 equiv) in DCM (1 mL) at −78° C. Then the cooling bath was removed. The reaction mixture was warmed up to room temperature and stirred for 1.5 hours. Additional portion of DAST (5.60*10$^{-6}$ L, 0.042 mmol, 2.5 equiv) was added. The resulting mixture was stirred at room temperature overnight. The mixture was concentrated under vacuum and the residue was purified by prep-HPLC (eluted with eluted with CH$_3$CN/H$_2$O=5/95~95/5) to afford N-(5-chloro-1-(2,6-dimethoxyphenyl)-2-(6-ethoxypyridin-2-yl)-1H-imidazo[4,5-b]pyrazin-6-yl)-4-(difluoromethyl)benzenesulfonamide as a yellow solid (2.5 mg, 24% yield). $^1$H NMR (400 MHz, DMSO-d$_6$) δ: 11.40 (s, 1H), 7.93 (d, J=7.2 Hz, 1H), 7.84 (t, J=7.6 Hz, 1H), 7.73-7.53 (m, 3H), 7.45 (d, J=8.0 Hz, 2H), 7.10 (t, J=55.2 Hz, 1H), 6.97 (d, J=8.4 Hz, 2H), 6.83 (d, J=8.0 Hz, 1H), 3.53 (s, 6H), 3.40 (q, J=7.2 Hz, 2H), 1.03 (t, J=7.2 Hz, 3H). LC-MS: m/z 617.1 (M+H)+

Example 107: N-(5-Chloro-1-(2,6-dimethoxyphenyl)-2-(6-ethoxypyridin-2-yl)-1H-imidazo[4,5-b]pyrazin-6-yl)-1-(3-fluoro-4-methylphenyl)methanesulfonamide

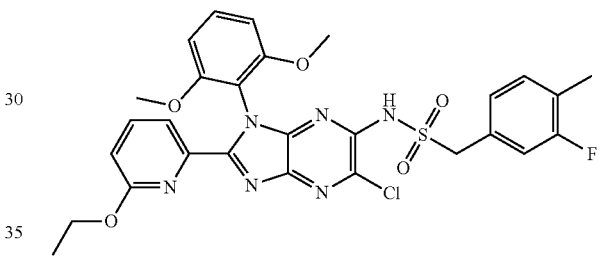

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (3-fluoro-4-methylphenyl)methanesulfonamide. $^1$H NMR (400 MHz, DMSO-d$_6$) δ: 8.00 (d, J=7.2 Hz, 1H), 7.92-7.86 (m, 1H), 7.49 (t, J=8.4 Hz, 1H), 7.23 (t, J=8.0 Hz, 1H), 7.04-6.67 (m, 5H), 4.58 (s, 2H), 3.59 (s, 6H), 3.39 (q, J=7.2 Hz, 2H), 2.21 (s, 3H), 1.07 (t, J=7.2 Hz, 3H). LC-MS: m/z 613.1 (M+H)+

Example 108: N-(5-Chloro-1-(2,6-dimethoxyphenyl)-2-(6-ethoxypyridin-2-yl)-1H-imidazo[4,5-b]pyrazin-6-yl)-1-(4-fluorophenyl)methanesulfonamide

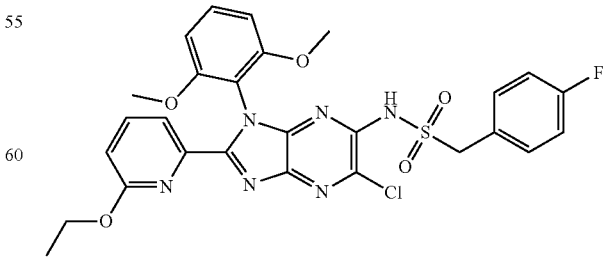

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (4-fluorophenyl)methanesulfonamide. ¹H NMR (400 MHz, Chloroform-d) δ: 8.12 (d, J=6.8 Hz, 1H), 7.70 (t, J=8.0 Hz 1H), 7.42 (t, J=8.4 Hz, 1H), 7.17 (s, 1H), 7.08-7.15 (m, 2H), 6.96-7.03 (m, 2H), 6.67-6.76 (m, 3H), 4.61 (s, 2H), 3.63 (s, 6H), 3.43 (q, J=7.2 Hz, 2H), 1.08 (t, J=7.2 Hz, 3H). LC-MS: m/z 599.1 (M+H)⁺

Example 109: N-(5-Chloro-1-(2,6-dimethoxyphenyl)-2-(6-ethoxypyridin-2-yl)-1H-imidazo[4,5-b]pyrazin-6-yl)-1-(pyrimidin-2-yl)methanesulfonamide

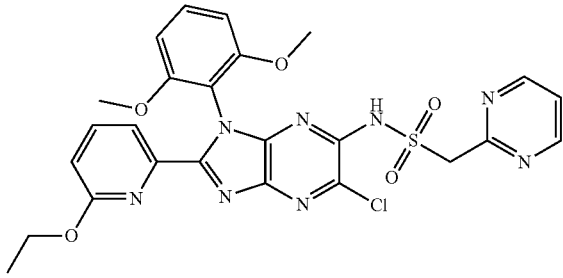

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using pyrimidin-2-ylmethanesulfonamide. ¹H NMR (400 MHz, Chloroform-d) δ: 8.70 (d, J=4.8 Hz, 2H), 8.06 (dd, J=7.6, 0.8 Hz, 1H), 7.68 (td, J=7.6, 0.8 Hz, 1H), 7.51 (s, 1H), 7.36 (t, J=8.4 Hz, 1H), 7.25-7.26 (m, 1H), 6.70 (dd, J=8.4, 0.8 Hz, 1H), 6.67 (d, J=8.4 Hz, 2H), 4.99 (s, 2H), 3.59 (s, 6H), 3.43 (q, J=7.2 Hz, 2H), 1.06 (t, J=7.2 Hz, 3H). LC-MS: m/z 583.1 (M+H)⁺

Example 110: N-(5-Chloro-1-(2,6-dimethoxyphenyl)-2-(6-ethoxypyridin-2-yl)-1H-imidazo[4,5-b]pyrazin-6-yl)but-2-yne-1-sulfonamide

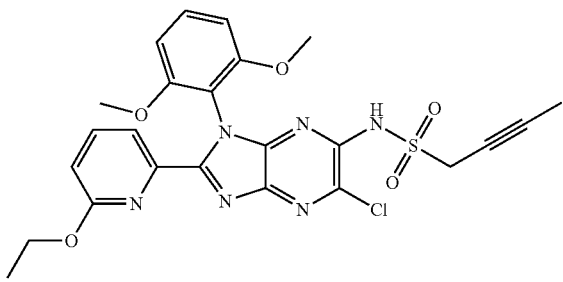 [SMILES: CC#CCS(=O)(=O)Nc1nc2c(nc1Cl)nc(-c1cccc(OCC)n1)n2-c1c(OC)cccc1OC]

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using but-2-yne-1-sulfonamide. ¹H NMR (400 MHz, DMSO-d₆) δ: 11.20 (br. s, 1H), 7.96 (dd, J=7.2, 0.8 Hz, 1H), 7.88 (t, J=8.0 Hz, 1H), 7.48 (t, J=8.4 Hz, 1H), 6.84-6.90 (m, 3H), 4.30 (d, J=2.0 Hz, 2H), 3.58 (s, 6H), 3.41 (d, J=7.2 Hz, 2H), 1.79 (t, J=2.0 Hz, 3H), 1.02 (t, J=7.2 Hz, 3H). LC-MS: m/z 543.2 (M+H)⁺

Example 111: N-(5-Chloro-1-(2,6-dimethoxyphenyl)-2-(6-ethoxypyridin-2-yl)-1H-imidazo[4,5-b]pyrazin-6-yl)tetrahydro-2H-pyran-4-sulfonamide

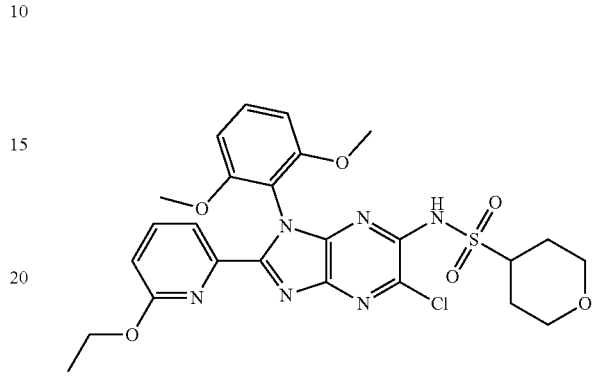

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using tetrahydro-2H-pyran-4-sulfonamide. ¹H NMR (400 MHz, Chloroform-d) δ: 8.11 (d, J=7.2 Hz, 1H), 7.69 (t, J=8.0 Hz, 1H), 7.39 (t, J=8.4 Hz, 1H), 7.29 (s, 1H), 6.66-6.76 (m, 3H), 3.95-4.04 (m, 2H), 3.74-3.86 (m, 1H), 3.63 (s, 6H), 3.42 (q, J=7.2 Hz, 2H), 3.04 (td, J=11.2, 3.2 Hz, 2H), 1.81-1.98 (m, 4H), 1.07 (t, J=7.2 Hz, 3H). LC-MS: m/z 575.1 (M+H)⁺

Example 112: N-(5-Chloro-1-(2,6-dimethoxyphenyl)-2-(6-ethoxypyridin-2-yl)-1H-imidazo[4,5-b]pyrazin-6-yl)-N'-methyl-N'-cyclopropylsulfamide

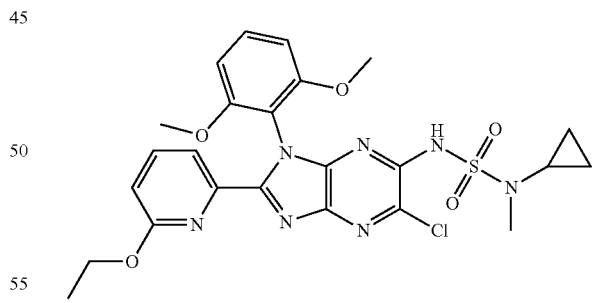

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using N-methyl-N-cyclopropylsulfamide. ¹H NMR (400 MHz, DMSO-d₆) δ:10.56 (s, 1H), 7.98 (d, J=7.2 Hz, 1H), 7.86 (t, J=8.0 Hz, 1H), 7.43 (t, J=8.4 Hz, 1H), 6.85 (d, J=8.4 Hz, 2H and 1H), 3.59 (s, 6H), 3.36 (q, J=7.2 Hz, 2H), 2.52 (s, 3H), 2.24-2.31 (m, 1H), 1.02 (t, J=7.2 Hz, 3H), 0.48-0.58 (m, 2H), 0.30-0.40 (m, 2H). LC-MS: m/z 560.2 (M+H)⁺

N-(5-Chloro-1-(2,6-dimethoxyphenyl)-2-(6-ethoxy-pyridin-2-yl)-1H-imidazo[4,5-b]pyrazin-6-yl)-1-(1-((tetrahydro-2H-pyran-2-yl)oxy)cyclopropylmethanesulfonamide

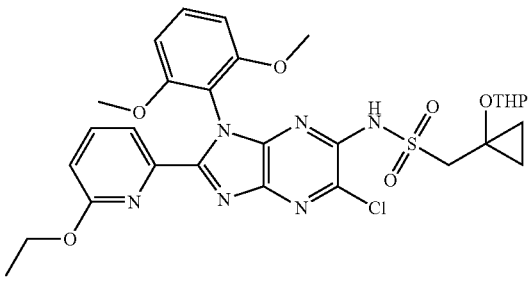

N-(5-Chloro-1-(2,6-dimethoxyphenyl)-2-(6-ethoxypyridin-2-yl)-1H-imidazo[4,5-b]pyrazin-6-yl)-1-(1-((tetrahydro-2H-pyran-2-yl)oxy)cyclopropyl)methanesulfonamide dimethoxyphenyl)-2-(6-ethoxypyridin-2-yl)-1H-imidazo[4,5-b]pyrazine by using (1-((tetrahydro-2H-pyran-2-yl)oxy)cyclopropyl)methanesulfonamide. LC-MS: m/z 645.2 (M+H)⁺

Example 113: N-(5-Chloro-1-(2,6-dimethoxyphenyl)-2-(6-ethoxypyridin-2-yl)-1H-imidazo[4,5-b]pyrazin-6-yl)-1-(1-hydroxycyclopropyl)methanesulfonamide

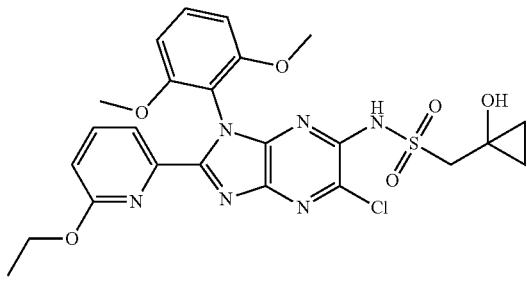 [SMILES: CCOc1cccc(-c2nc3nc(Cl)c(NS(=O)(=O)CC4(O)CC4)nc3n2-c2c(OC)cccc2OC)n1]

The title compound was prepared according to step I of synthesis of Example 81. ¹H NMR (400 MHz, DMSO-d₆) δ:10.47 (br. s, 1H), 7.93 (d, J=7.2 Hz, 1H), 7.85 (t, J=7.6 Hz, 1H), 7.45 (t, J=8.4 Hz, 1H), 6.81-6.86 (m, 3H), 5.32 (br. s, 1H), 3.57 (s, 6H), 3.46 (s, 2H), 3.37 (q, J=7.2 Hz, 2H), 1.01 (t, J=7.2 Hz, 3H), 0.59 (t, J=4.8 Hz, 2H), 0.33-0.36 (m, 2H). LC-MS: m/z 561.0 (M+H)⁺

Example 114: N-(5-Chloro-1-(2,6-dimethoxyphenyl)-2-(6-ethoxypyridin-2-yl)-1H-imidazo[4,5-b]pyrazin-6-yl)-1-(5-methylpyridin-2-yl)methanesulfonamide

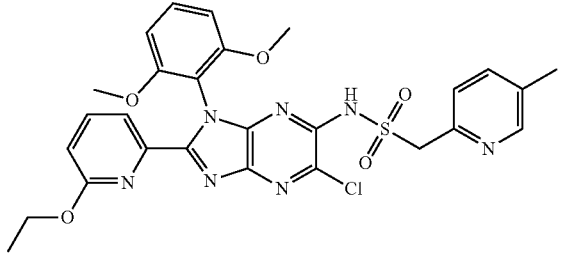 [SMILES: CCOc1cccc(-c2nc3nc(Cl)c(NS(=O)(=O)Cc4ccc(C)cn4)nc3n2-c2c(OC)cccc2OC)n1]

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (5-methylpyrimidin-2-yl)methanesulfonamide. ¹H NMR (400 MHz, DMSO-d₆) δ: 10.86 (s, 1H), 8.63 (s, 2H), 7.96 (d, J=6.8 Hz, 1H), 7.88 (t, J=7.6 Hz, 1H), 7.44 (t, J=8.4 Hz, 1H), 6.78-6.90 (m, 3H), 4.87 (s, 2H), 3.51 (s, 6H), 3.39 (q, J=7.2 Hz, 2H), 2.26 (s, 3H), 1.01 (t, J=7.2 Hz, 3H). LC-MS: m/z 597.1 (M+H)⁺

Example 115: N-(5-Chloro-1-(2,6-dimethoxyphenyl)-2-(6-ethoxypyridin-2-yl)-1H-imidazo[4,5-b]pyrazin-6-yl)-1-((1r, 3r)-3-hydroxy-3-methylcyclobutyl)methanesulfonamide

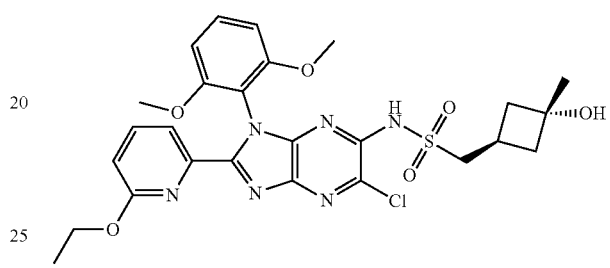

The title compound was prepared according to Example 81 using 6-bromo-5-chloro-1-(2,6-dimethoxyphenyl)-2-(6-ethoxypyridin-2-yl)-1H-imidazo[4,5-b]pyrazine in step H. ¹H NMR (400 MHz, Chloroform-d) δ: 8.09 (dd, J=7.2, 0.8 Hz, 1H), 7.68 (t, J=7.6 Hz, 1H), 7.39 (t, J=8.4 Hz, 1H), 7.31 (s, 1H), 6.69-6.72 (m, 3H), 3.63 (s, 6H), 3.54 (d, J=7.2 Hz, 2H), 3.42 (q, J=7.2 Hz, 2H), 2.22-2.33 (m, 3H), 1.65-1.71 (m, 2H), 1.35 (s, 3H), 1.07 (t, J=7.2 Hz, 3H). LC-MS: m/z 589.1 (M+H)⁺

Example 116: N-(5-Chloro-1-(2,6-dimethoxyphenyl)-2-(6-ethoxypyridin-2-yl)-1H-imidazo[4,5-b]pyrazin-6-yl)-4-hydroxypiperidine-1-sulfonamide

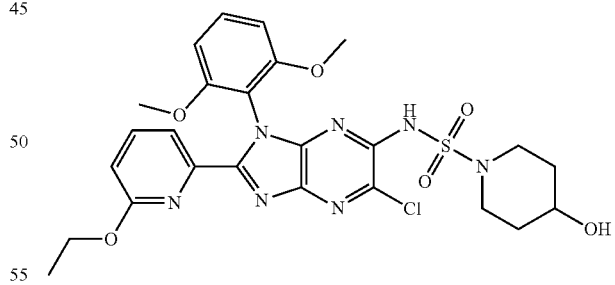

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using 4-hydroxypiperidine-1-sulfonamide. ¹H NMR (400 MHz, Chloroform-d) δ: 8.13 (d, J=7.2 Hz, 1H), 7.68 (t, J=8.0 Hz, 1H), 7.49 (s, 1H), 7.37 (t, J=8.4 Hz, 1H), 6.70 (d, J=7.6 Hz, 1H), 6.67 (d, J=8.4 Hz, 2H), 3.60-3.64 (m, 7H), 3.40 (q, J=7.2 Hz, 2H), 3.28-3.36 (m, 2H), 2.80-2.90 (m, 2H), 1.68-1.71 (m, 2H), 1.39-1.48 (m, 2H), 1.07 (t, J=7.2 Hz, 3H). LC-MS: m/z 589.9 (M+H)⁺

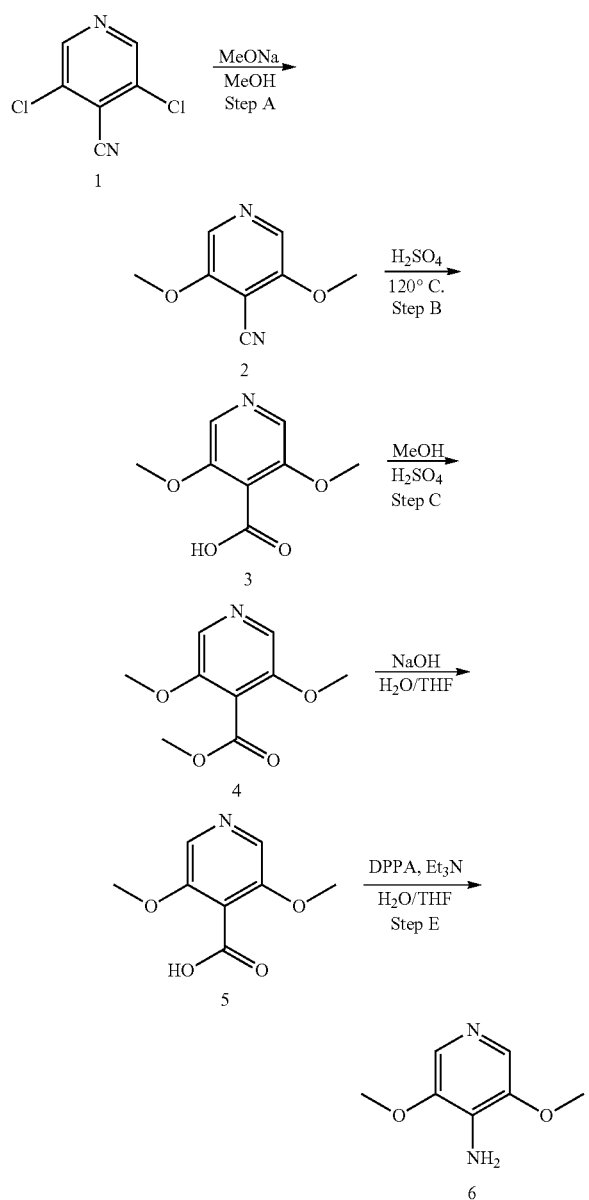

Step A: 3,5-Dimethoxyisonicotinonitrile

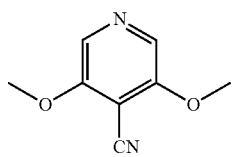

To a solution of 3,5-dichloroisonicotinonitrile (10.0 g, 57.8 mmol, 1.0 equiv) in MeOH (100 mL) was added MeONa (43.0 mL, 5.4 mol/L in MeOH, 231 mmol, 4.0 equiv). The mixture was refluxed for 4 hours. The reaction was quenched by added H$_2$O (5 mL), and concentrated under vacuum. The residue was washed by H$_2$O, dried under vacuum to afford the title compound 3,5-dimethoxyisonicotinonitrile as a white solid (8.88 g, 94% yield). LC-MS: m/z 165.1 (M+H)$^+$ Step B: 3,5-Dimethoxyisonicotinic acid

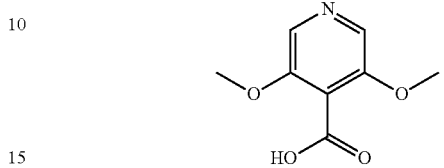

A solution of 3,5-dimethoxyisonicotinonitrile (8.88 g, 54.1 mmol, 1.0 equiv) in H$_2$SO$_4$ (8 mol/L in H$_2$O, 120 mL) was stirred at 120° C. for 6 hours. The resulting mixture was used directly for next step. LC-MS: m/z 184.1 (M+H)$^+$ Step C: Methyl 3,5-dimethoxyisonicotinate

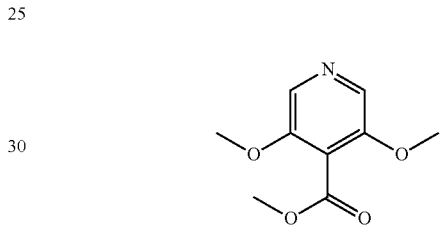

MeOH (50 mL) was added into a solution of step B. The mixture was refluxed overnight. The pH of the mixture was adjusted to 8 using 1 N aq. NaOH solution. The resulting mixture was extracted with EtOAc (3*100 mL). The combined organic phase was washed with brine (100 mL), dried over anhydrous Na$_2$SO$_4$, filtered and concentrated. The residue was purified by flash chromatography on silica gel (eluted with PE/EtOAc=1/1) to afford methyl 3,5-dimethoxyisonicotinate as a white solid (5.50 g, 52% yield in two steps). $^1$H NMR (400 MHz, DMSO-d$_6$) δ: 8.20 (s, 2H), 3.90 (s, 6H), 3.81 (s, 3H). LC-MS: m/z 198.1 (M+H)$^+$ Step D: 3,5-Dimethoxyisonicotinic acid

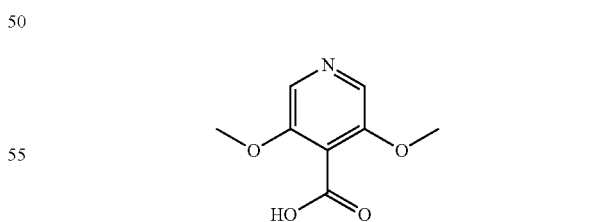

A solution of methyl 3,5-dimethoxyisonicotinate (5.50 g, 28.0 mmol, 1.0 equiv) in THF (20 mL) and H$_2$O (10 mL) was added NaOH (2.24 g, 56.0 mmol, 2.0 equiv). The mixture was stirred at 50° C. overnight. 10 mL HCl solution (5.6 mol/L in H$_2$O, 56.0 mmol, 2.0 equiv) was added and then the mixture was concentrated under vacuum. The residue was used directly for next step. LC-MS: m/z 184.1 (M+H)$^+$

Step E: 3,5-Dimethoxypyridin-4-amine

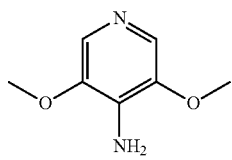

To a solution of 3,5-dimethoxyisonicotinic acid (5.12 g, 28.0 mmol, 1 equiv) in 50 mL THF was added Et₃N (12.7 g, 126 mmol, 17.4 mL, 4.5 equiv) and DPPA (11.6 g, 42.0 mmol, 1.5 equiv) under N₂. The mixture was stirred at 70° C. for 2 hours under N₂, and then H₂O (10 mL) was added. The reaction mixture was stirred overnight. The resulting mixture was extracted with DCM (50 mL*3). The combined organic phase was washed with brine (100 mL), dried over anhydrous Na₂SO₄, filtered and concentrated. The residue was purified by flash chromatography on silica gel (eluted with DCM/MeOH=20/1) to afford 3,5-dimethoxypyridin-4-amine as a white solid (2.46 g, 57% yield in two steps). ¹H NMR (400 MHz, DMSO-d₆) δ: 7.76 (s, 2H), 5.13 (s, 2H), 3.82 (s, 6H). LC-MS: m/z 155.1 (M+H)⁺

Example 117: N-(5-Chloro-1-(3,5-dimethoxypyridin-4-yl)-2-(6-ethoxypyridin-2-yl)-1H-imidazo[4,5-b]pyrazin-6-yl)methanesulfonamide

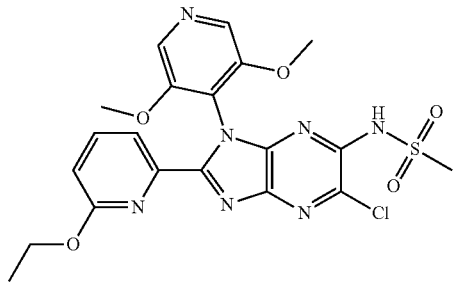 [SMILES: CCOc1cccc(-c2nc3nc(Cl)c(NS(C)(=O)=O)nc3n2-c2c(OC)cncc2OC)n1]

The title compound was prepared according to Method K, step B, starting from N-(3,5-dibromo-6-chloropyrazin-2-yl)-6-ethoxypicolinamide by using 3,5-dimethoxypyridin-4-amine. ¹H NMR (400 MHz, Chloroform-d) δ: 8.21 (s, 2H), 8.10 (d, J=7.2 Hz, 1H), 7.72 (t, J=8.0 Hz, 1H), 7.52 (s, 1H), 6.75 (d, J=8.4 Hz, 1H), 3.76 (s, 6H), 3.36 (q, J=7.2 Hz, 2H), 3.24 (s, 3H), 1.10 (t, J=7.2 Hz, 3H). LC-MS: m/z 506.1 (M+H)⁺

Example 118: N-(5-Chloro-1-(3,5-dimethoxypyridin-4-yl)-2-(6-ethoxypyridin-2-yl)-1H-imidazo[4,5-b]pyrazin-6-yl)cyclopropanesulfonamide

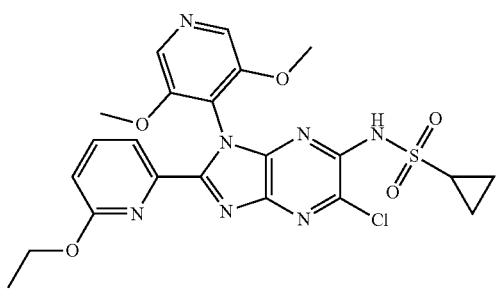 [SMILES: CCOc1cccc(-c2nc3nc(Cl)c(NS(=O)(=O)C4CC4)nc3n2-c2c(OC)cncc2OC)n1]

The title compound was prepared according to Method K, starting from N-(3,5-dibromo-6-chloropyrazin-2-yl)-6-ethoxypicolinamide by using 3,5-dimethoxypyridin-4-amine in step B and cyclopropanesulfonamide at step D. ¹H NMR (400 MHz, Chloroform-d) δ: 8.20 (s, 2H), 8.11 (d, J=7.6 Hz, 1H), 7.71 (t, J=7.6 Hz, 1H), 6.74 (d, J=8.3 Hz, 1H), 3.75 (s, 6H), 3.36 (q, J=7.2 Hz, 2H), 2.69 (tt, J=8.4, 4.8 Hz, 1H), 1.21 (dd, J=4.8, 2.4 Hz, 2H), 1.11 (t, J=7.2 Hz, 3H), 0.88 (h, J=5.6 Hz, 2H). LC-MS: m/z 532.1 (M+H)⁺

Method L

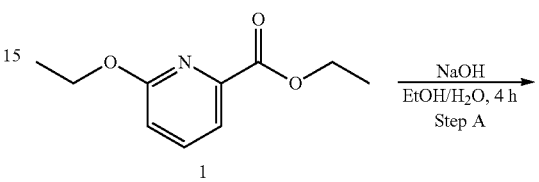

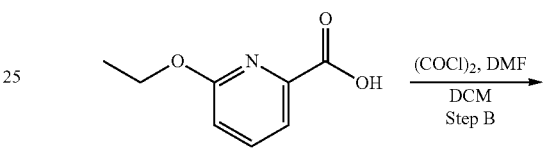

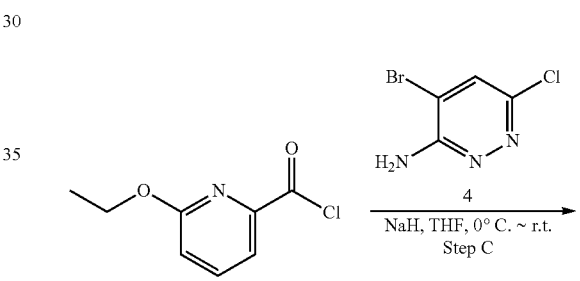

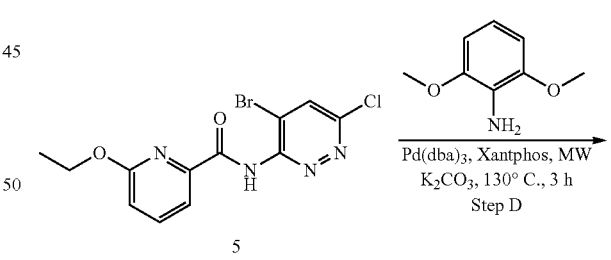

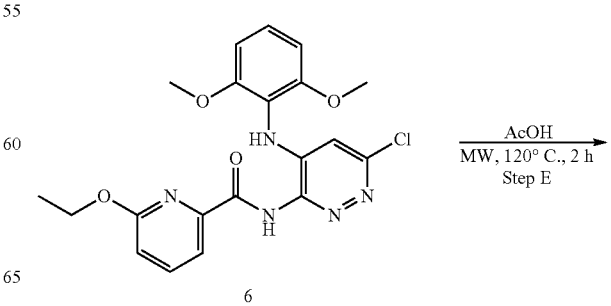

Step C: N-(4-Bromo-6-chloropyridazin-3-yl)-6-ethoxypicolinamide

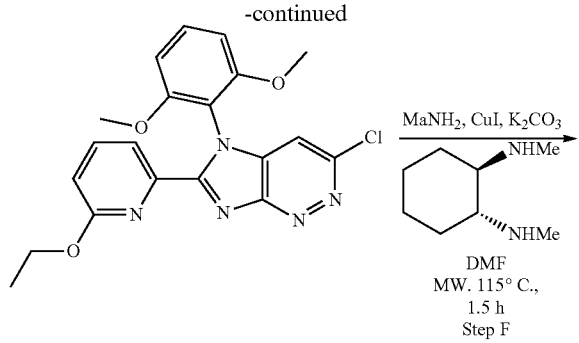

Example 21

Step A: 6-Ethoxypicolinic acid

To a solution of ethyl 6-ethoxypicolinate (2.60 g, 13.3 mmol, 1.0 equiv) in EtOH (30 mL) was added sodium hydroxide solution (1 mol/L, 40.0 mL, 40.0 mmol, 3 equiv). The reaction mixture was stirred at room temperature for 3 hours. The reaction mixture was acidified to pH=2 with 1 N HCl aqueous solution and extracted with ethyl acetate (50 mL*3). The organic layer was washed with brine, dried over anhydrous MgSO$_4$, and concentrated in vacuo to afford the title compound 6-ethoxypicolinic acid as a white solid (2.20 g, 100% yield).

Step B: 6-Ethoxypicolinoyl chloride

To the solution of 6-ethoxypicolinic acid (20.0 g, 120 mmol, 1.0 equiv) and C$_2$O$_2$Cl$_2$ (23.3 g, 180 mmol, 1.5 equiv) in DCM (100 mL) was added 6 drops of DMF dropwise at 0° C. under argon atmosphere. The resulting mixture was stirred at 0° C. for 2 hours. The mixture was concentrated to give the crude product, which was used for next step directly.

To the solution of 4-bromo-6-chloropyridazin-3-amine (25.1 g, 120 mmol, 1.0 equiv) in THF (200 mL) was added NaH (60% in mineral oil) (14.4 g, 360 mmol, 3.0 equiv) at 0° C. The resulting mixture was stirred at room temperature for 1 hour. 6-Ethoxypicolinoyl chloride (22.2 g, 120 mmol, 1.0 equiv) in DCM (30 mL) was added to the above mixture dropwise at 0° C. and then the mixture was stirred at room temperature overnight. The mixture was quenched with saturated NH$_4$Cl solution. The mixture was extracted with DCM (100 mL*3). The combined organic layers were washed with brine, dried and concentrated. The residue was purified by column chromatography (eluted with PE/EtOAc=1/1) to afford N-(4-bromo-6-chloropyridazin-3-yl)-6-ethoxypicolinamide as a white solid (29.5 g, 69% yield). LC-MS: m/z 356.9, 358.9 (M+H)$^+$

Step D: N-(6-Chloro-4-((2,6-dimethoxyphenyl)amino)pyridazin-3-yl)-6-ethoxypicolinamide A suspension of N-(4-bromo-6-chloropyridazin-3-yl)-6-ethoxypicolinamide (1.07 g, 3.00 mmol, 1.0 equiv), 2,6-dimethoxyaniline (688 mg, 4.50 mmol, 1.5 equiv), Pd$_2$(dba)$_3$ (275 mg, 0.300 mmol, 0.1 equiv), Xantphos (695 mg, 1.20 mmol, 0.4 equiv) and K$_2$CO$_3$ (828 mg, 6.0 mmol, 2.0 equiv) in 1,4-dioxane (15 mL) was stirred at 120° C. via microwave irradiation under N$_2$ atmosphere for 3 hours. The mixture was filtered through celite and the filtrate was concentrated in vacuo. The residue was purified by flash chromatography (eluted with PE/EtOAc=3/1) to afford N-(5-chloro-3-((2,6-dimethoxyphenyl)amino)pyrazin-2-yl)-6-ethoxypicolinamide as a yellow solid (800 mg, 62% yield). LC-MS: m/z 430.1 (M+H)$^+$ Step E: Chloro-7-(2,6-dimethoxyphenyl)-8-(6-ethoxypyridin-2-yl)-7H-imidazo[4,5-c]pyridazine

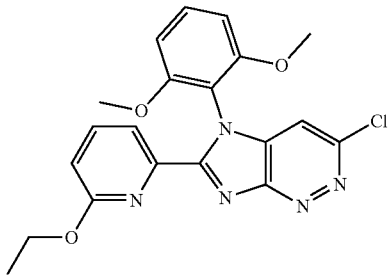 [SMILES: CCOc1cccc(-c2nc3nnc(Cl)cc3n2-c2c(OC)cccc2OC)n1]

A solution of N-(6-chloro-4-((2,6-dimethoxyphenyl) amino)pyridazin-3-yl)-6-ethoxypicolinamide (110 mg, 0.250 mmol) in AcOH (10 mL) was stirred at 120° C. via microwave irradiation for 2 hours. After the reaction mixture was cooled to room temperature, the light yellow precipitate was filtered off and rinsed with EtOAc/PE=1/2 (5 mL*2) to afford chloro-7-(2,6-dimethoxyphenyl)-8-(6-ethoxypyridin-2-yl)-7H-imidazo[4,5-c]pyridazine as light yellow solid (70.0 mg, 67% yield). $^1$H NMR (400 MHz, DMSO-d$_6$) δ: 8.05 (dd, J=7.6, 0.8 Hz, 1H), 7.93 (dd, J=8.4, 7.6 Hz, 1H), 7.67 (s, 1H), 7.50 (t, J=8.4 Hz, 1H), 6.93 (dd, J=8.4, 0.8 Hz, 1H), 6.89 (d, J=8.4 Hz, 2H), 3.60 (s, 6H), 3.40 (q, J=7.2 Hz, 2H), 1.04 (t, J=7.2 Hz, 3H). LC-MS: m/z 412.1 (M+H)$^+$ Step F: N-(7-(2,6-Dimethoxyphenyl)-8-(6-ethoxypyridin-2-yl)-7H-imidazo[4,5-c]pyridazinyl)methanesulfonamide (Example 21)

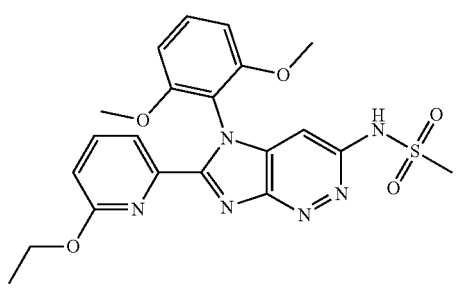

A suspension of chloro-7-(2,6-dimethoxyphenyl)-8-(6-ethoxypyridin-2-yl)-7H-imidazo[4,5-c]pyridazine (48.0 mg, 0.120 mmol, 1.0 equiv), methanesulfonamide (22.0 mg, 0.230 mmol, 2.0 equiv), CuI (44.0 mg, 0.230 mmol, 2.0 equiv), trans-N, N'-Dimethylcyclohexane-1, 2-diamine (33.0 mg, 0.230 mmol, 2.0 equiv) and K$_2$CO$_3$ (49.7 mg, 0.36 mmol, 3 equiv) in DMF (2 mL) was stirred at 130° C. via microwave irradiation for 1.5 hour under N$_2$ atmosphere. The reaction solution was diluted with water (10 mL) and extracted with EtOAc (10 mL*3). The combined organic layers were washed with brine, dried over anhydrous Na$_2$SO$_4$ and concentrated in vacuo. The residue was purified by flash chromatography (eluted with DCM/MeOH=100/1) to afford N-(7-(2,6-dimethoxyphenyl)-8-(6-ethoxypyridin-2-yl)-7H-imidazo[4,5-c]pyridazinyl)methanesulfonamide as a yellow solid (30.0 mg, 55% yield). $^1$H NMR (400 MHz, DMSO-d$_6$) δ: 10.78 (s, 1H), 8.01 (dd, J=7.6, 0.8 Hz, 1H), 7.91 (t, J=8.0 Hz, 1H), 7.50 (t, J=8.4 Hz, 1H), 6.85-6.97 (m, 4H), 3.61 (s, 6H), 3.39 (q, J=7.2 Hz, 2H), 3.22 (s, 3H), 1.03 (t, J=7.2 Hz, 3H). LC-MS: m/z 471.1 (M+H)$^+$ Example 119: N-(7-(2,6-Dimethoxyphenyl)-8-(6-ethoxypyridin-2-yl)-7H-imidazo[4,5-c]pyridazinyl) cyclopropanesulfonamide

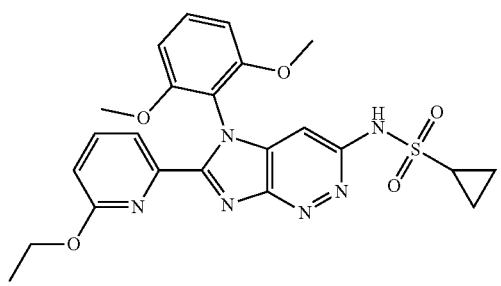 [SMILES: CCOc1cccc(-c2nc3nnc(NS(=O)(=O)C4CC4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using cyclopropanesulfonamide. $^1$H NMR (400 MHz, Chloroform-d) δ: 8.11 (dd, J=7.2, 0.8 Hz, 1H), 7.71 (dd, J=8.4, 7.2 Hz, 1H), 7.38 (t, J=8.4 Hz, 1H), 6.91 (s, 1H), 6.77 (dd, J=8.4, 0.8 Hz, 1H), 6.66 (d, J=8.4 Hz, 2H), 3.64 (s, 6H), 3.39 (q, J=7.2 Hz, 2H), 2.55-2.59 (m, 1H), 1.19-1.21 (m, 2H), 1.08 (t, J=7.2 Hz, 3H), 0.95-0.98 (m, 2H). LC-MS: m/z 497.1 (M+H)$^+$ Example 120: N-(7-(2,6-Dimethoxyphenyl)-8-(6-ethoxypyridin-2-yl)-7H-imidazo[4,5-c]pyridazinyl)-5-fluoropyridine-2-sulfonamide

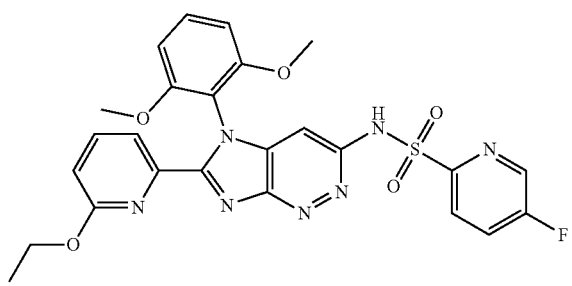 [SMILES: CCOc1cccc(-c2nc3nnc(NS(=O)(=O)c4ccc(F)cn4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using 5-fluoropyridine-2-sulfonamide. $^1$H NMR (400 MHz, Chloroform-d) δ: 8.13-8.83 (m, 2H), 8.11 (d, J=7.2 Hz, 1H), 7.73 (t, J=8.0 Hz, 1H), 7.57 (t, J=7.6 Hz, 1H), 7.38 (t, J=8.4 Hz, 1H), 6.80-6.93 (m, 1H), 6.79 (d, J=8.0 Hz, 1H), 6.65 (d, J=8.4 Hz, 2H), 3.63 (s, 6H), 3.38 (q, J=7.2 Hz, 2H), 1.07 (t, J=7.2 Hz, 3H). LC-MS: m/z 552.1 (M+H)$^+$ Example 121: N-(7-(2,6-Dimethoxyphenyl)-8-(6-ethoxypyridin-2-yl)-7H-imidazo[4,5-c]pyridazinyl)morpholine-4-sulfonamide

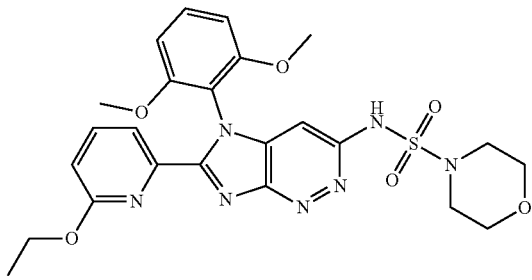 [SMILES: CCOc1cccc(-c2nc3nnc(NS(=O)(=O)N4CCOCC4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using morpholine-4-sulfonamide. $^1$H NMR (400 MHz, Chloroform-d) δ: 11.89 (br. s, 1H), 8.09 (d, J=7.2 Hz, 1H), 7.71 (t, J=7.6 Hz, 1H), 7.39 (t, J=8.4 Hz, 1H), 6.78 (d, J=8.0 Hz, 1H), 6.74 (s, 1H), 6.67 (d, J=8.4 Hz, 2H), 3.73 (t, J=4.8 Hz, 4H), 3.65 (s, 6H), 3.38 (q, J=7.2 Hz, 2H), 3.20 (t, J=4.8 Hz, 4H), 1.08 (t, J=7.2 Hz, 3H). LC-MS: m/z 542.2 (M+H)$^+$ Example 122: N-(7-(2,6-Dimethoxyphenyl)-8-(6-ethoxypyridin-2-yl)-7H-imidazo[4,5-c]pyridazinyl)-1-(4-fluorophenyl)methanesulfonamide

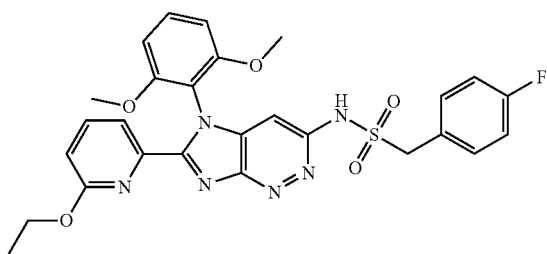 [SMILES: CCOc1cccc(-c2nc3nnc(NS(=O)(=O)Cc4ccc(F)cc4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using (4-fluorophenyl)methanesulfonamide. $^1$H NMR (400 MHz, DMSO-d$_6$) δ: 7.99 (d, J=7.2 Hz, 1H), 7.91 (t, J=8.0 Hz, 1H), 7.50 (t, J=8.4 Hz, 1H), 7.37-7.27 (m, 2H), 7.05 (br. s, 2H), 6.95-6.86 (m, 3H), 6.77 (br. s, 1H), 4.59 (br. s, 2H), 3.60 (s, 6H), 3.38 (q, J=7.2 Hz, 2H), 1.03 (t, J=7.2 Hz, 3H). LC-MS: m/z 565.1 (M+H)$^+$ (5-Chloropyridin-2-yl)methanesulfonamide

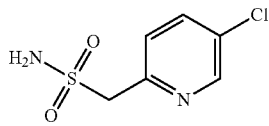 [SMILES: NS(=O)(=O)Cc1ccc(Cl)cn1]

5-Chloropyridin-2-yl)methanesulfonamide was prepared according to the preparation of (3-fluoropyridin-2-yl)methanesulfonamide by using (5-chloropyridin-2-yl)methanol at step A. $^1$H NMR (400 MHz, DMSO-d$_6$) δ: 8.61 (d, J=2.4 Hz, 1H), 7.98 (dd, J=8.0 Hz, 2.8 Hz, 1H), 7.52 (d, J=8.0 Hz, 1H), 6.95 (s, 2H), 4.45 (s, 2H). LC-MS: m/z 207.0 (M+H)$^+$ Example 123: 1-(5-Chloropyridin-2-yl)-N-(7-(2,6-dimethoxyphenyl)-8-(6-ethoxypyridin-2-yl)-7H-imidazo[4,5-c]pyridazinyl)methanesulfonamide

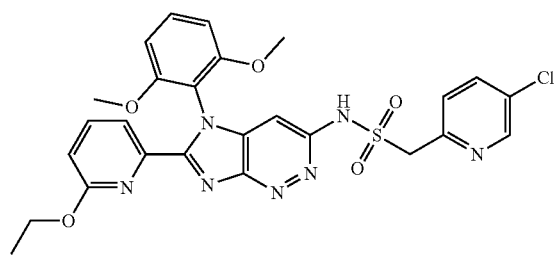 [SMILES: CCOc1cccc(-c2nc3nnc(NS(=O)(=O)Cc4ccc(Cl)cn4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using (5-chloropyridin-2-yl)methanesulfonamide. $^1$H NMR (400 MHz, Chloroform-d) δ: 8.43 (s, 1H), 8.08 (d, J=7.2 Hz, 1H), 7.71 (t, J=8.0 Hz, 1H), 7.63 (d, J=8.4 Hz, 1H), 7.54 (d, J=8.0 Hz, 1H), 7.39 (t, J=8.4 Hz, 1H), 6.78 (d, J=8.0 Hz, 2H), 6.66 (d, J=8.4 Hz, 2H), 4.56 (s, 2H), 3.65 (s, 6H), 3.40 (q, J=7.2 Hz, 2H), 1.08 (t, J=7.2 Hz, 3H). LC-MS: m/z 582.2 (M+H)$^+$ Example 124: N-(7-(2,6-Dimethoxyphenyl)-8-(6-ethoxypyridin-2-yl)-7H-imidazo[4,5-c]pyridazinyl)-1-(S-methylpyridin-2-y)methanesulfonamide

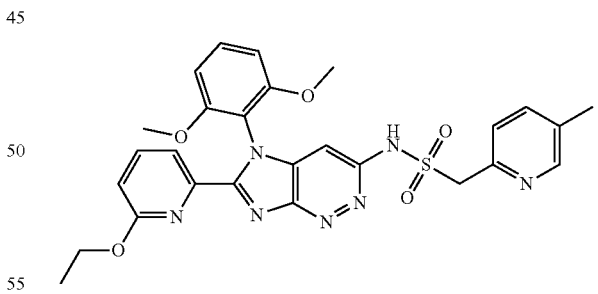

The title compound was prepared according to Method L, step F, starting from chloro-7-(2,6-dimethoxyphenyl)-8-(6-ethoxypyridin-2-yl)-7H-imidazo[4,5-c]pyridazine by using (5-methylpyridin-2-yl)methanesulfonamide. $^1$H NMR (400 MHz, DMSO-d$_6$) δ: 12.46 (br. s, 1H), 8.24 (s, 1H), 7.99 (d, J=7.2 Hz, 1H), 7.91 (t, J=8.0 Hz, 1H), 7.43-7.56 (m, 2H), 7.33 (d, J=8.0 Hz, 1H), 6.92 (d, J=7.6 Hz, 1H), 6.91 (d, J=8.4 Hz, 2H), 6.89 (s, 1H), 4.68 (s, 2H), 3.61 (s, 6H), 3.38 (q, J=7.2 Hz, 2H), 2.22 (s, 3H), 1.03 (t, J=7.2 Hz, 3H). LC-MS: m/z 562.2 (M+H)$^+$ Example 125: N-(7-(2,6-Dimethoxyphenyl)-8-(6-ethoxypyridin-2-yl)-7H-imidazo[4,5-c]pyridazinyl)-1-(5-fluoropyridin-2-y)methanesulfonamide

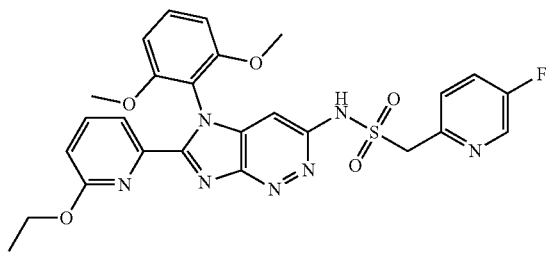 [SMILES: CCOc1cccc(-c2nc3nnc(NS(=O)(=O)Cc4ccc(F)cn4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using (5-fluoropyridin-2-yl)methanesulfonamide. $^1$H NMR (400 MHz, Chloroform-d) δ: 8.31 (br. s, 1H), 8.08 (d, J=7.6 Hz, 1H), 7.71 (t, J=8.0 Hz, 1H), 7.52-7.67 (m, 1H), 7.39 (t, J=8.4 Hz, 1H), 7.30-7.36 (m, 1H), 6.78 (d, J=8.0 Hz, 1H), 6.79 (s, 1H), 6.66 (d, J=8.4 Hz, 2H), 4.60 (s, 2H), 3.65 (s, 6H), 3.38 (q, J=8.0 Hz, 2H), 1.08 (t, J=8.0 Hz, 3H). LC-MS: m/z 566.2 (M+H)$^+$ Example 126: N-(7-(2,6-Dimethoxyphenyl)-8-(6-ethoxypyridin-2-yl)-7H-imidazo[4,5-c]pyridazinyl)-1-(S-methylpyrimidin-2-yl)methanesulfonamide

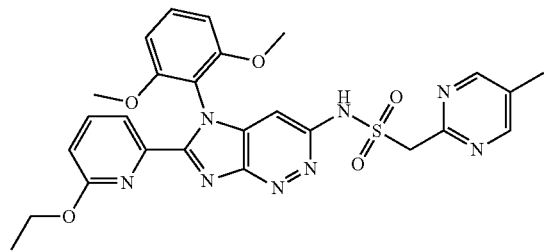 [SMILES: CCOc1cccc(-c2nc3nnc(NS(=O)(=O)Cc4ncc(C)cn4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using (5-methylpyrimidin-2-yl)methanesulfonamide. $^1$H NMR (400 MHz, DMSO-d$_6$) δ: 8.52 (s, 2H), 7.99 (d, J=7.2 Hz, 1H), 7.91 (t, J=8.0 Hz, 1H), 7.51 (t, J=8.4 Hz, 1H), 6.90-6.93 (m, 4H), 4.80 (br. s, 2H), 3.61 (s, 6H), 3.39 (q, J=7.2 Hz, 2H), 2.20 (s, 3H), 1.03 (t, J=7.2 Hz, 3H). LC-MS: m/z 563.2 (M+H)$^+$ Example 127: N-(5-(2,6-Dimethoxyphenyl)-6-(6-ethoxypyridin-2-yl)-5H-imidazo[4,5-c]pyridazin-3-yl)-1-(pyrimidin-2-yl)methanesulfonamide

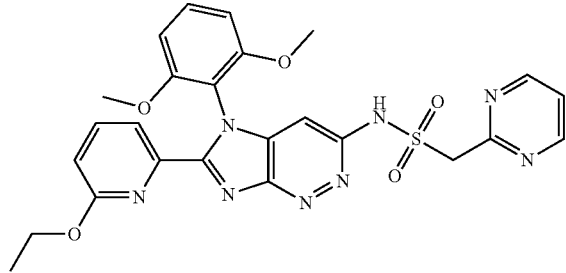 [SMILES: CCOc1cccc(-c2nc3nnc(NS(=O)(=O)Cc4ncccn4)cc3n2-c2c(OC)cccc2OC)n1]

The title compound was prepared according to Method L, step F, starting from chloro-7-(2,6-dimethoxyphenyl)-8-(6-ethoxypyridin-2-yl)-7H-imidazo[4,5-c]pyridazine by using pyrimidin-2-ylmethanesulfonamide. $^1$H NMR (400 MHz, Chloroform-d) δ: 8.72 (d, J=4.4 Hz, 2H), 8.08 (d, J=7.2 Hz, 1H), 7.71 (t, J=8.0 Hz, 1H), 7.39 (t, J=8.4 Hz, 1H), 7.20 (t, J=4.4 Hz, 1H), 6.92 (s, 1H), 6.77 (d, J=8.0 Hz, 1H), 6.67 (d, J=8.4 Hz, 2H), 4.80 (s, 2H), 3.65 (s, 6H), 3.39 (q, J=7.2 Hz, 2H), 1.08 (t, J=7.2 Hz, 3H). LC-MS: m/z 549.2 (M+H)$^+$ Example 128: N-(5-(2,6-Dimethoxyphenyl)-6-(6-ethoxypyridin-2-yl)-5H-imidazo[4,5-c]pyridazin-3-yl)-1-(3-hydroxy-3-methylcyclobutyl)methanesulfonamide

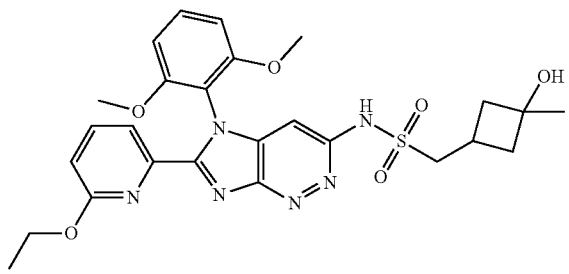 [SMILES: CCOc1cccc(-c2nc3nnc(NS(=O)(=O)CC4CC(C)(O)C4)cc3n2-c2c(OC)cccc2OC)n1]

The title compound was prepared according to Example 81 using chloro-7-(2,6-dimethoxyphenyl)-8-(6-ethoxypyridin-2-yl)-7H-imidazo[4,5-c]pyridazine in step H. $^1$H NMR (400 MHz, Chloroform-d) δ: 8.03 (d, J=7.2 Hz, 1H), 7.65 (t, J=7.2 Hz, 1H), 7.32 (t, J=8.4 Hz, 1H), 6.77 (s, 1H), 6.72 (d, J=8.0 Hz, 1H), 6.60 (d, J=8.8 Hz, 2H), 3.58 (s, 6H), 3.31 (q, J=7.2 Hz, 2H), 3.20 (d, J=7.2 Hz, 2H), 2.24-2.28 (m, 3H), 1.82-1.87 (m, 2H), 1.30 (s, 3H), 1.08 (t, J=7.2 Hz, 3H). LC-MS: m/z 555.1 (M+H)$^+$ Example 129: N-(7-(2,6-Dimethoxyphenyl)-8-(6-ethoxypyridin-2-yl)-7H-imidazo[4,5-c]pyridazinyl)-1-(5-hydroxypyrimidin-2-yl)methanesulfonamide

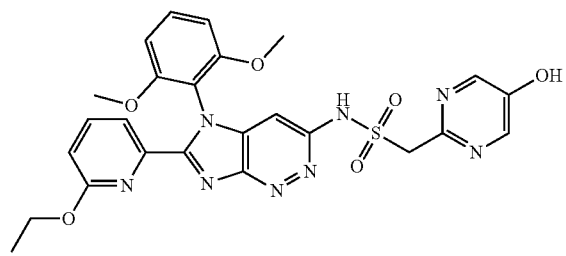 [SMILES: CCOc1cccc(-c2nc3nnc(NS(=O)(=O)Cc4ncc(O)cn4)cc3n2-c2c(OC)cccc2OC)n1]

The title compound was a byproduct prepared according to Method L, step F, starting from chloro-7-(2,6-dimethoxyphenyl)-8-(6-ethoxypyridin-2-yl)-7H-imidazo[4,5-c]pyridazine by using (5-fluoropyrimidin-2-yl)methanesulfonamide. $^1$H NMR (400 MHz, Chloroform-d) δ: 8.26 (s, 2H), 8.00 (s, 2H), 7.66-7.70 (m, 1H), 7.14 (t, J=8.4 Hz, 1H), 6.69-6.77 (m, 2H), 5.98 (d, J=8.0 Hz, 1H), 5.27 (br. s, 1H), 3.91 (s, 3H), 3.73 (q, J=6.8 Hz, 2H), 3.38-3.42 (m, 1H), 3.18 (s, 3H), 3.06-3.10 (m, 1H), 1.03 (t, J=6.8 Hz, 3H). LC-MS: m/z 565.1 (M+H)$^+$

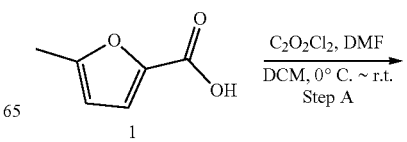

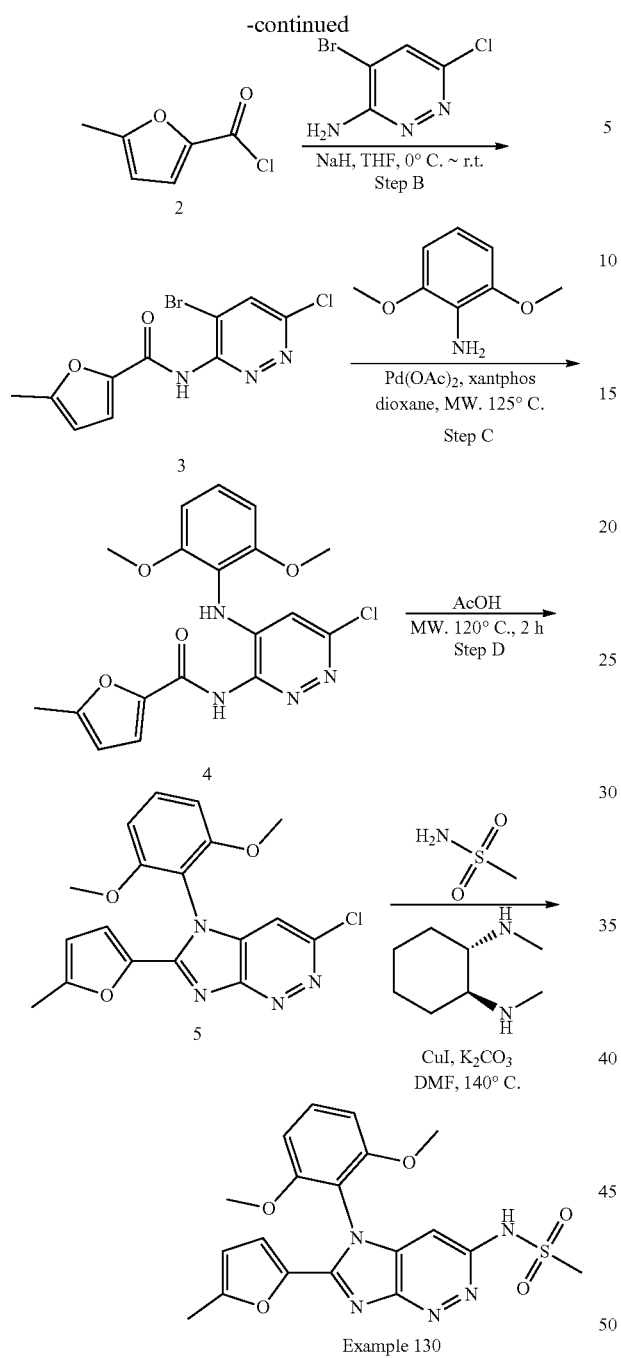

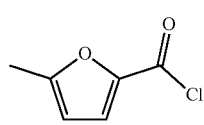

Step A: 5-Methylfuran-2-carbonyl chloride

To a solution of 5-methylfuran-2-carboxylic acid (1.50 g, 11.9 mmol, 1.0 equiv) and oxalyl chloride (3.00 g, 23.8 mmol, 2.0 equiv) in DCM (20 mL) was added DMF (0.1 mL) at 0° C. The resulting mixture was stirred at 0° C. for 1 hour. The reaction mixture was concentrated in vacuo to afford 5-methylfuran-2-carbonyl chloride which was used for next step directly.

Step B: N-(4-Bromo-6-chloropyridazin-3-yl)-5-methylfuran-2-carboxamide

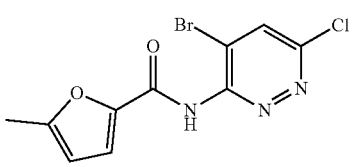 [SMILES: Cc1ccc(C(=O)Nc2nnc(Cl)cc2Br)o1]

To a solution of 4-bromo-6-chloropyridazin-3-amine (2.40 g, 11.9 mmol, 1.0 equiv) in THF (20 mL) was added NaH (60% in mineral oil) (857 mg, 34.8 mmol, 3 equiv) at 0° C. The mixture was stirred at room temperature for 1 hour, and then a solution of 5-methylfuran-2-carbonyl chloride in DCM (10 mL) was added dropwise. The mixture was stirred at room temperature for 2 hours. The reaction mixture was quenched with saturated ammonium chloride solution (10 mL) and extracted with DCM (50 mL*3). The combined organic layers were washed with brine (20 mL), dried over anhydrous $Na_2SO_4$, and concentrated in vacuo. The residue was purified by flash chromatography on silica gel (eluted with EtOAc/PE=2/3) to afford N-(4-bromo-6-chloropyridazin-3-yl)-5-methylfuran-2-carboxamide as a light yellow solid (2.20 g, 58% yield). LC-MS: m/z 315.9, 317.9 $(M+H)^+$ Step C: N-(6-Chloro-4-((2,6-dimethoxyphenyl)amino)pyridazin-3-yl)-5-methylfuran-2-carboxamide

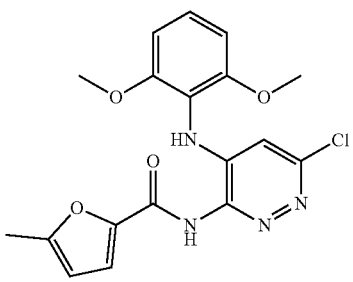 [SMILES: COc1cccc(OC)c1Nc1cc(Cl)nnc1NC(=O)c1ccc(C)o1]

A suspension of N-(4-bromo-6-chloropyridazin-3-yl)-5-methylfuran-2-carboxamide (1.20 g, 3.80 mmol, 1.0 equiv), 2,6-dimethoxyaniline (583 mg, 3.80 mmol, 1.0 equiv), $Pd(OAc)_2$ (170 mg, 0.760 mmol, 0.2 equiv), Xantphos (880 mg, 1.50 mmol, 0.4 equiv) and $K_2CO_3$ (1.05 g, 7.60 mmol, 2.0 equiv) in 1,4-dioxane (10 mL) was stirred at 100° C. via microwave irradiation for 3 hours under $N_2$ atmosphere. The mixture was filtered through celite and the filtrate was concentrated in vacuo. The residue was purified by flash chromatography (EtOAc/PE=1/2) to afford N-(6-chloro-4-((2,6-dimethoxyphenyl)amino)pyridazin-3-yl)-5-methylfuran-2-carboxamide as a yellow solid (330 mg, 22% yield). LC-MS: m/z 389.1, 391.1 $(M+H)^+$ Step D: Chloro-7-(2,6-dimethoxyphenyl)-8-(5-methylfuran-2-yl)-7H-imidazo[4,5-c]pyridazine

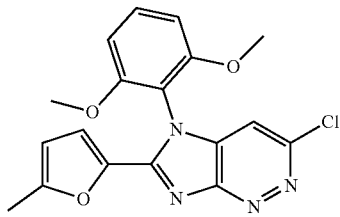 [SMILES: COc1cccc(OC)c1-n1c(-c2ccc(C)o2)nc2nnc(Cl)cc21]

A solution of N-(6-chloro-4-((2,6-dimethoxyphenyl)amino)pyridazin-3-yl)-5-methylfuran-2-carboxamide (300 mg, 0.770 mmol) in AcOH (10 mL) was stirred at 120° C. via microwave irradiation for 2 hours. After the reaction solution was cooled to room temperature, the light yellow precipitate was filtered off and rinsed with (eluted with DCM/MeOH=100/1) to afford chloro-7-(2,6-dimethoxyphenyl)-8-(5-methylfuran-2-yl)-7H-imidazo[4,5-c]pyridazine as a light yellow solid (200 mg, 70% yield). LC-MS: m/z 371.1 (M+H)+

Step E: N-(7-(2,6-Dimethoxyphenyl)-8-(5-methylfuran-2-yl)-7H-imidazo[4,5-c]pyridazinyl)methanesulfonamide (Example 130)

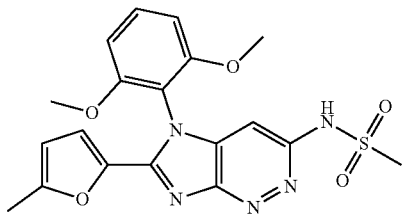

A suspension of chloro-7-(2,6-dimethoxyphenyl)-8-(5-methylfuran-2-yl)-7H-imidazo[4,5-c]pyridazine (200 mg, 0.540 mmol, 1.0 equiv), methanesulfonamide (102 mg, 1.08 mmol, 2.0 equiv), CuI (103 mg, 0.540 mmol, 1.0 equiv), trans-N, N'-Dimethylcyclohexane-1, 2-diamine (77.0 mg, 0.540 mmol, 1.0 equiv) and K$_2$CO$_3$ (224 mg, 1.62 mmol, 3.0 equiv) in DMF (10 mL) was stirred at 140° C. via microwave irradiation for 4 hour under N$_2$ atmosphere. The reaction solution was diluted with water (50 mL) and extracted with EtOAc (50 mL*3). The combined organic layers were washed with brine, dried over anhydrous Na$_2$SO$_4$ and concentrated in vacuo. The residue was purified by pre-HPLC to afford N-(7-(2,6-dimethoxyphenyl)-8-(5-methylfuran-2-yl)-7H-imidazo[4,5-c]pyridazinyl)methanesulfonamide as a yellow solid (70.0 mg, 30% yield). $^1$HNMR (400 MHz, DMSO-d$_6$) δ: 7.66 (t, J=8.4 Hz, 1H), 6.99 (d, J=8.4 Hz, 2H), 6.91 (s, 1H), 6.39 (d, J=3.6 Hz, 1H), 6.28-6.33 (m, 1H), 3.69 (s, 6H), 3.13 (s, 3H), 2.30 (s, 3H). LC-MS: m/z 430.0 (M+H)+

Method M

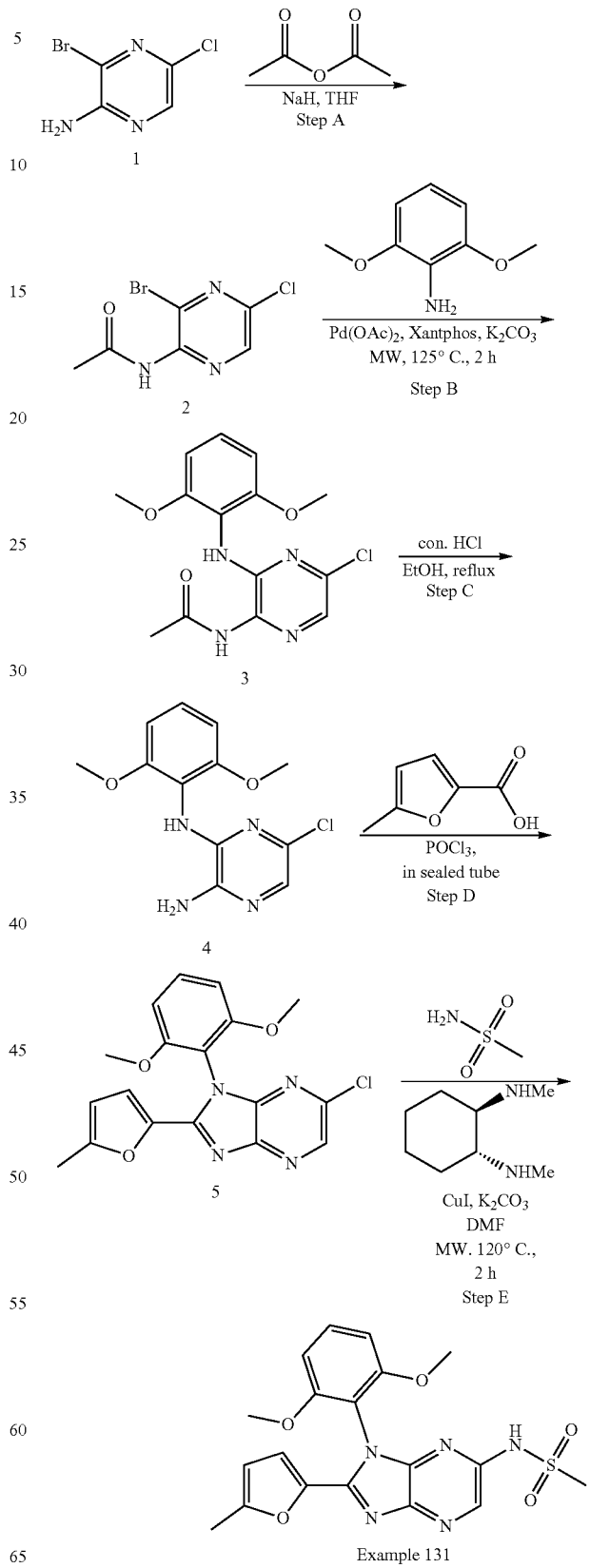

Step A: N-(3-Bromo-5-chloropyrazin-2-yl)acetamide

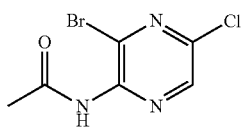

To a solution of compound 3-bromo-5-chloropyrazin-2-amine (12.4 g, 60 mmol, 1.0 equiv) in anhydrous THF (100 mL) was added NaH (60% in mineral oil, 7.20 g, 180 mmol, 3.0 equiv). The resulting mixture was stirred at 0° C. for 1 hour. Then acetic anhydride (6.80 mL, 72.0 mmol, 1.2 equiv) was added dropwise to the mixture and the mixture was stirred at room temperature for 12 hours. The mixture was quenched with 1N HCl (200 mL) and extracted with EtOAc (300 mL*3). The combined organic layers were washed with brine, dried over anhydrous $Na_2SO_4$ and concentrated in vacuo. The residue was purified by flash chromatography on silica gel (eluted with PE/EtOAc=3/1) to give N-(3-bromo-5-chloropyrazin-2-yl)acetamide as a white solid (10.0 g, 67% yield). LC-MS: m/z 249.9, 251.9 $(M+H)^+$

Step B: N-(5-chloro-3-((2,6-dimethoxyphenyl)amino)pyrazin-2-yl)acetamide

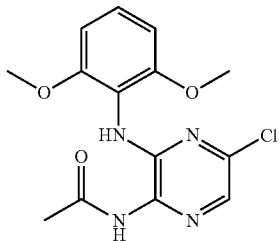 [SMILES: COc1cccc(OC)c1Nc1nc(Cl)cnc1NC(C)=O]

A suspension of N-(3-bromo-5-chloropyrazin-2-yl)acetamide (11.5 g, 46.4 mmol, 1.0 equiv), 2,6-dimethoxyaniline (7.10 g, 46.4 mmol, 1.0 equiv), $Pd(OAc)_2$ (2.10 g, 9.28 mmol, 0.2 equiv), Xantphos (8.06 g, 13.9 mmol, 0.3 equiv) and $K_2CO_3$ (12.8 g, 92.8 mmol, 2.0 equiv) in 1,4-dioxane (80 mL) was stirred at 110° C. for 3 hours under $N_2$ atmosphere. The mixture was filtered through celite and the filtrate was concentrated in vacuo. The residue was purified by flash chromatography on silica gel (eluted with PE/EtOAc=2/1) to give N-(5-chloro-3-((2,6-dimethoxyphenyl)amino)pyrazin-2-yl)acetamide as a yellow solid (4.48 g, 30% yield). LC-MS: m/z 323.1 $(M+H)^+$

Step C: 6-chloro-$N_2$-(2,6-dimethoxyphenyl)pyrazine-2, 3-diamine

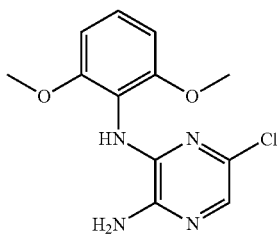 [SMILES: COc1cccc(OC)c1Nc1nc(Cl)cnc1N]

A mixture of N-(5-chloro-3-((2,6-dimethoxyphenyl)amino)pyrazin-2-yl) acetamide (1.70 g, 5.30 mmol, 1.0 equiv) and con. HCl (20 mL) in EtOH (30 mL) was refluxed at 100° C. for 4 hours. The reaction mixture was cooled to room temperature and then basified with 2N NaOH aqueous solution to pH=8~9. The mixture was extracted with EtOAc (80 mL*3). The combined organic phase was washed with brine (30 mL), dried over anhydrous $Na_2SO_4$ and concentrated in vacuo. The residue was purified by flash chromatography on silica gel (eluted with PE/EtOAc=3/1) to give 6-chloro-N2-(2,6-dimethoxyphenyl)pyrazine-2, 3-diamine as a yellow solid (1.10 g, 74% yield). LC-MS: m/z 281.0 $(M+H)^+$

Step D: 6-chloro-1-(2,6-dimethoxyphenyl)-2-(5-methylfuran-2-yl)-1H-imidazo[4,5-b]pyrazine

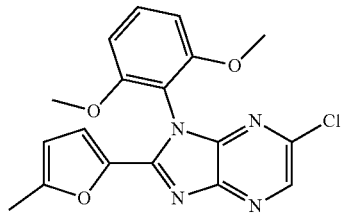 [SMILES: COc1cccc(OC)c1-n1c(-c2ccc(C)o2)nc2ncc(Cl)nc21]

A mixture of 6-chloro-$N^2$-(2,6-dimethoxyphenyl)pyrazine-2, 3-diamine (500 mg, 1.78 mmol, 1.0 equiv) and 5-methylfuran-2-carboxylic acid (1.12 g, 8.90 mmol, 5.0 equiv) in $POCl_3$ (10 mL) was stirred at 100° C. overnight under nitrogen atmosphere. The reaction mixture was concentrated in vacuo. The residue was redissolved in DCM, basified with 1 mol/L NaOH aqueous solution to pH=6. The organic phase was separated, dried over anhydrous $Na_2SO_4$ and concentrated in vacuo. The residue was purified by flash chromatography on silica gel (eluted with PE/EtOAc=1/1) to afford 6-chloro-1-(2,6-dimethoxyphenyl)-2-(5-methylfuran-2-yl)-1H-imidazo[4,5-b]pyrazine as a pale white solid (100 mg, 15% yield). LC-MS: m/z 371.1 $(M+H)^+$

Step E: N-(1-(2,6-dimethoxyphenyl)-2-(5-methylfuran-2-yl)-1H-imidazo[4,5-b]pyrazin-6-yl)methanesulfonamide (Example 131)

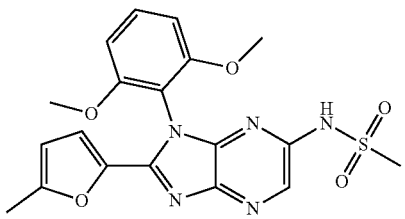

A suspension of 6-chloro-1-(2,6-dimethoxyphenyl)-2-(5-methylfuran-2-yl)-1H-imidazo[4,5-b]pyrazine (100 mg, 0.270 mmol, 1.0 equiv), methanesulfonamide (128 mg, 1.35 mmol, 5.0 equiv), CuI (102 mg, 0.540 mmol, 2.0 equiv), trans-N, N'-Dimethylcyclohexane-1, 2-diamine (76.0 mg, 0.540 mmol, 2.0 equiv) and $K_2CO_3$ (111 mg, 0.810 mmol, 3 equiv) in DMF (5 mL) was stirred at 120° C. via microwave irradiation for 2 hours under $N_2$ atmosphere. The mixture was diluted with $H_2O$ (20 mL), adjusted with HCOOH to pH=5, followed by extraction with DCM (20 mL*3). The combined organic layers were washed with brine, dried over anhydrous $Na_2SO_4$ and concentrated in vacuo. The residue was purified by pre-HPLC (eluted with $CH_3CN/H_2O$=5/95~90/10 including 0.1% HCOOH) to afford N-(1-(2,6-dimethoxyphenyl)-2-(5-methylfuran-2-yl)-

1H-imidazo[4,5-b]pyrazin-6-yl)methanesulfonamide as a white solid (45.0 mg, 39% yield). $^1$HNMR (400 MHz, DMSO-d$_6$) δ: 10.68 (br. s, 1H), 8.23 (s, 1H), 7.60 (t, J=8.4 Hz, 1H), 6.94 (d, J=8.4 Hz, 2H), 6.19-6.26 (m, 2H), 3.65 (s, 6H), 3.15 (s, 3H), 2.29 (s, 3H). LC-MS: m/z 430.0 (M+H)$^+$ Example 132: N-(1-(2,6-dimethoxyphenyl)-2-(5-methylpyridin-3-yl)-1H-imidazo[4,5-b]pyrazin-6-yl)methanesulfonamide

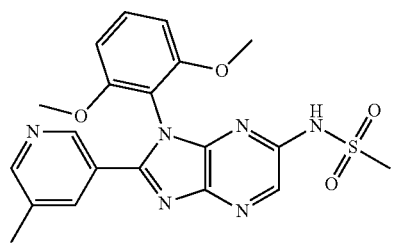 [SMILES: COc1cccc(OC)c1-n1c(-c2cncc(C)c2)nc2ncc(NS(C)(=O)=O)nc21]

The title compound was prepared according to Method M, step D, starting from 6-chloro-N$_2$-(2,6-dimethoxyphenyl)pyrazine-2,3-diamine by using 5-methylnicotinic acid. $^1$HNMR (400 MHz, DMSO-d$_6$) δ: 11.06 (s, 1H), 8.49 (d, J=1.6 Hz, 1H), 8.39 (d, J=1.6 Hz, 1H), 8.30 (s, 1H), 7.87-7.83 (m, 1H), 7.55 (t, J=8.4 Hz, 1H), 6.89 (d, J=8.4 Hz, 2H), 3.61 (s, 6H), 3.21 (s, 3H), 2.29 (s, 3H). LC-MS: m/z 441.0 (M+H)$^+$ Example 133: N-(1-(2,6-dimethoxyphenyl)-2-(5-methylpyridin-3-yl)-1H-imidazo[4,5-b]pyrazin-6-yl)cyclopropanesulfonamide

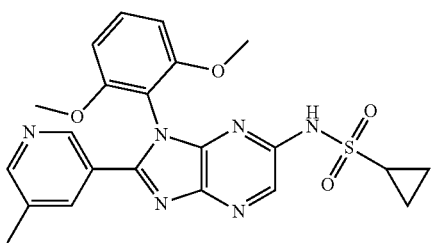

The title compound was prepared according to Method M, by using 5-methylnicotinic acid at step D and cyclopropanesulfonamide at step E. $^1$H NMR (400 MHz, DMSO-d$_6$) δ: 11.05 (s, 1H), 8.48 (d, J=1.6 Hz, 1H), 8.41 (d, J=1.6 Hz, 1H), 8.31 (s, 1H), 7.86 (s, 1H), 7.56 (t, J=8.4 Hz, 1H), 6.90 (d, J=8.4 Hz, 2H), 3.62 (s, 6H), 2.76-2.82 (m, 1H), 2.29 (s, 3H), 0.99-0.83 (m, 4H). LC-MS: m/z 467.0 (M+H)$^+$

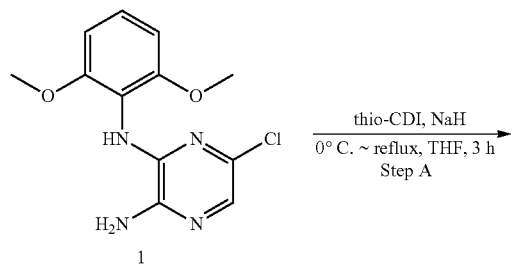

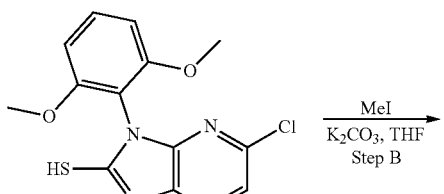

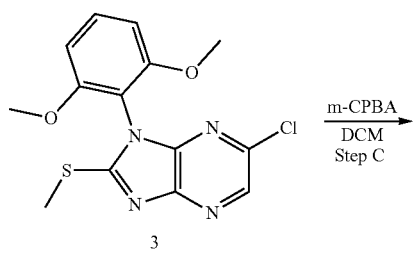

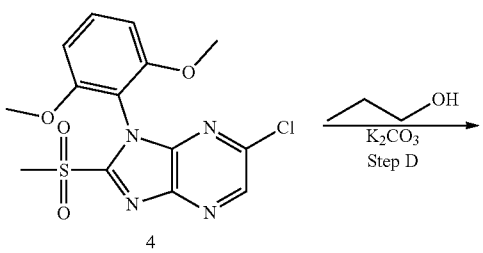

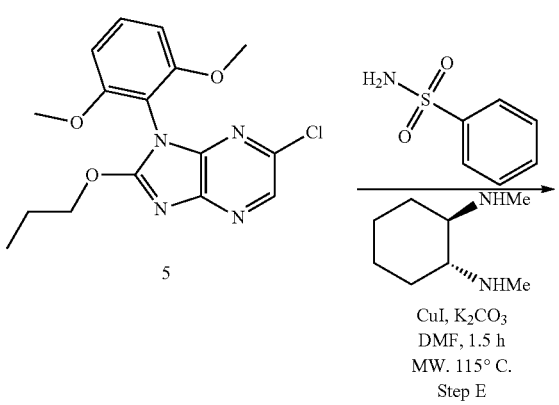

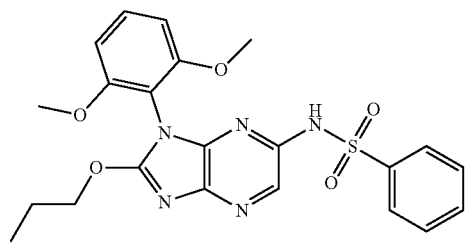

Example 134

Step A: 6-chloro-1-(2,6-dimethoxyphenyl)-1H-imidazo[4,5-b]pyrazine-2-thiol

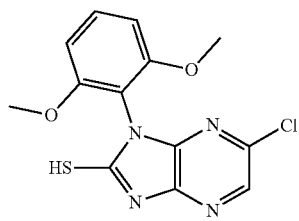 [SMILES: COc1cccc(OC)c1-n1c(S)nc2ncc(Cl)nc21]

To a solution of 6-chloro-N$_2$-(2,6-dimethoxyphenyl)pyrazine-2,3-diamine (1.12 g, 4 mmol, 1.0 equiv) in anhydrous THF (50 mL) was added NaH (60% in mineral oil, 1.60 g, 40.0 mmol, 10.0 equiv). The resulting mixture was stirred at 0° C. for 0.5 hour under N$_2$ atmosphere. Then di(1H-imidazol-1-yl)methanethione (1.42 g, 8.00 mmol, 2.0 equiv) was added at 0° C. The resulting mixture was then refluxed at 65° C. for 3 hours. The reaction mixture was cooled to room temperature and then adjusted with 2 N HCl aqueous solution to pH=5~6. The mixture was extracted with EtOAc (50 mL*3). The combined organic phase was washed with brine (30 mL), dried over anhydrous Na$_2$SO$_4$ and concentrated in vacuo. The residue was purified by flash chromatography on silica gel (eluted with PE/EtOAc=3/1) to give 6-chloro-1-(2,6-dimethoxyphenyl)-1H-imidazo[4,5-b]pyrazine-2-thiol (1.0 g, 77% yield) as a yellow solid. LC-MS: m/z 323.1 (M+H)$^+$ Step B: 6-Chloro-1-(2,6-dimethoxyphenyl)-2-(methylthio)-1H-imidazo[4,5-b]pyrazine

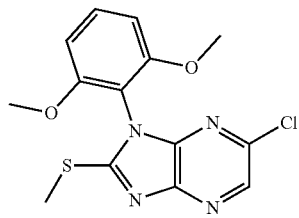 [SMILES: COc1cccc(OC)c1-n1c(SC)nc2ncc(Cl)nc21]

To a mixture of 6-chloro-1-(2,6-dimethoxyphenyl)-1H-imidazo[4,5-b] pyrazine-2-thiol (1.40 g, 4.30 mmol, 1.0 equiv) and K$_2$CO$_3$ (1.80 g, 12.9 mmol, 3.0 equiv) in anhydrous THF (20 mL) was added CH$_{3}$I (3.10 g, 21.5 mmol, 5.0 equiv) at 0° C. under N$_2$ atmosphere. The reaction mixture was stirred at room temperature for 2 h. The mixture was concentrated and residue was purified by flash chromatography on silica gel (eluted with PE/EtOAc=1/2) to give 6-chloro-1-(2,6-dimethoxyphenyl)-2-(methylthio)-1H-imidazo[4,5-b]pyrazine as a yellow solid (1.10 g, 75% yield). LC-MS: m/z 337.0, 339.0 (M+H)$^+$ Step C: 6-Chloro-1-(2,6-dimethoxyphenyl-2-(methylsulfonyl)-1H-imidazo[4,5-b]pyrazine

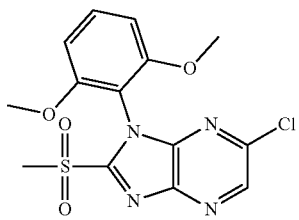 [SMILES: COc1cccc(OC)c1-n1c(S(C)(=O)=O)nc2ncc(Cl)nc21]

A solution of compound 6-chloro-1-(2,6-dimethoxyphenyl)-2-(methylthio)-1H-imidazo[4,5-b]pyrazine (1.18 g, 3.50 mmol, 1.0 equiv) and m-CPBA (85% purity) (1.56 g, 7.70 mmol, 2.2 equiv) in DCM (20 mL) was stirred at 0° C. for 5 h. The reaction was diluted with DCM (20 mL), washed with saturated Na$_2$S$_2$O$_3$ aqueous solution, Na$_2$CO$_3$ aqueous solution, brine, dried over anhydrous Na$_2$SO$_4$, filtered and concentrated. The residue was purified by flash chromatography on silica gel (eluted with PE/EtOAc=1/3) to give 6-chloro-1-(2,6-dimethoxyphenyl)-2-(methylsulfonyl)-1H-imidazo[4,5-b] pyrazine as a yellow solid (400 mg, 31% yield). LC-MS: m/z 369.1, 371.1 (M+H)$^+$ Step D: 6-Chloro-1-(2,6-dimethoxyphenyl)-2-propoxy-1H-imidazo[4,5-b]pyrazine

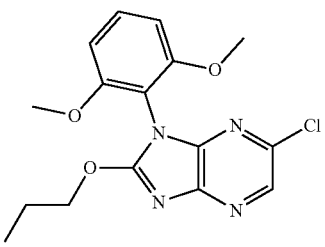 [SMILES: CCCOc1nc2ncc(Cl)nc2n1-c1c(OC)cccc1OC]

A mixture of K$_2$CO$_3$ (225 mg, 1.63 mmol, 1.5 equiv) in 1-propanol (10 mL) was stirred at room temperature for 0.5 h. Then 6-chloro-1-(2,6-dimethoxyphenyl)-2-(methylsulfonyl) -1H-imidazo[4,5-b]pyrazine (400 mg 1.09 mmol, 1.0 equiv) in 1-propanol (10 mL) was added to the mixture. The resulting mixture was stirred at room temperature for 1 h. The reaction mixture was concentrated and the residue was purified by flash chromatography on silica gel (eluted with PE/EtOAc=100/1) to give 6-chloro-1-(2,6-dimethoxyphenyl)-2-propoxy-1H-imidazo[4,5-b]pyrazine as a white solid (200 mg, 53% yield). LC-MS: m/z 349.0, 351.0 (M+H)$^+$ Step E: N-(1-(2,6-Dimethoxyphenyl)-2-propoxy-1H-imidazo[4,5-b]pyrazin-6-yl)benzenesulfonamide (Example 134)

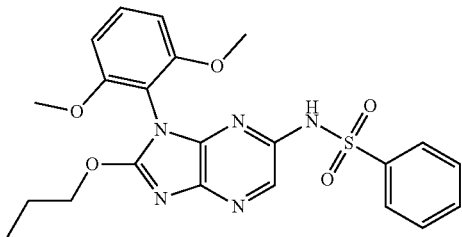

A mixture of 6-chloro-1-(2,6-dimethoxyphenyl)-2-propoxy-1H-imidazo[4,5-b]pyrazine (100 mg, 0.287 mmol, 1.0 equiv), benzenesulfonamide (90 mg, 0.574 mmol, 2.0 equiv), CuI (109 mg, 0.574 mmol, 2.0 equiv), trans-N, N'-Dimethylcyclohexane-1, 2-diamine (82 mg, 0.574 mmol, 2.0 equiv) and K$_2$CO$_3$ (119 mg, 0.861 mmol, 3.0 equiv) in DMF (1.5 mL) was stirred at 115° C. via microwave irradiation for 8 h under N$_2$ atmosphere. The reaction mixture was acidified to pH=4~6 with 2 N HCl aqueous solution and concentrated. The residue was purified by flash chromatography on silica gel (eluted with PE/EtOAc=1/1) to give N-(1-(2,6-dimethoxyphenyl)-2-propoxy-1H-imidazo[4,5-b]pyrazin-6-yl)benzenesulfonamide as white solid (9.00 mg, 7% yield).
$^1$H NMR (400 MHz, Chloroform-d) δ: 9.35 (br. s, 1H), 8.38 (s, 1H), 7.66 (d, J=4.0 Hz, 2H), 7.40-7.44 (m, 2H), 7.26-7.31 (m, 1H), 6.66 (d, J=8.0 Hz, 2H), 3.73 (s, 6H), 3.45 (t, J=4.0 Hz, 2H), 1.37-1.47 (m, 2H), 0.84 (t, J=4.0 Hz, 3H). LC-MS: m/z 470.0 (M+H)$^+$ Example 135: N-(1-(2,6-Dimethoxyphenyl)-2-(6-ethoxypyridin-2-yl)-5-hydroxy-1H-imidazo[4,5-b]pyrazin-6-yl)methanesulfonamide

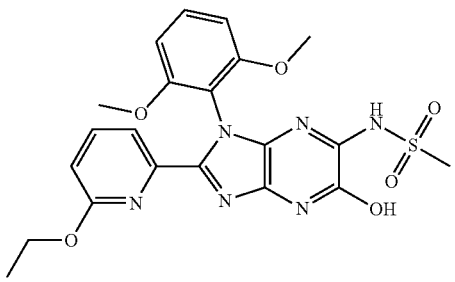

A suspension of N-(5-chloro-1-(2,6-dimethoxyphenyl)-2-(6-ethoxypyridin-2-yl)-1H-imidazo[4,5-b]pyrazin-6-yl)methanesulfonamide (200 mg, 0.400 mmol, 1.0 equiv), water (36.0 mg, 2.00 mmol, 5 equiv), CuI (152 mg, 0.800 mmol, 2.0 equiv), trans-N, N'-Dimethylcyclohexane-1, 2-diamine (114 mg, 0.800 mmol, 2.0 equiv) and K$_2$CO$_3$ (276 mg, 2.00 mmol, 5 equiv) in DMF (3 mL) was stirred at 100° C. via microwave irradiation for 2 hours under N$_2$ atmosphere. The reaction was diluted with water (60 mL), followed by extraction with EtOAc (60 mL*3). The combined organic layer was dried over anhydrous Na$_2$SO$_4$ and concentrated in vacuo. The residue was purified by flash chromatography (eluted with DCM/MeOH=80/1~20/1) to give N-(1-(2,6-dimethoxyphenyl)-2-(6-ethoxypyridin-2-yl)-5-hydroxy-1H-imidazo[4,5-b]pyrazin-6-yl)methanesulfonamide as a yellow solid (21.0 mg, 11% yield). $^1$H NMR (400 MHz, DMSO-d$_6$) δ:10.15 (s, 1H), 7.69-7.77 (m, 2H), 7.42 (t, J=8.4 Hz, 1H), 6.83 (d, J=8.4 Hz, 2H), 6.68 (d, J=8.0 Hz, 1H), 3.58 (s, 6H), 3.37 (q, J=7.2 Hz, 2H), 3.15 (s, 3H), 0.99 (t, J=7.2 Hz, 3H). LC-MS: m/z 487.1 (M+H)$^+$ Example 136: N-(1-(2,6-Dimethoxyphenyl)-2-(6-ethoxypyridin-2-yl)-5-(3-hydroxyazetidin-1-yl)-1H-imidazo[4,5-b]pyrazin-6-yl)methanesulfonamide

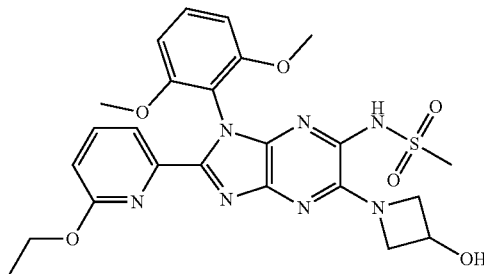

A suspension of N-(5-chloro-1-(2,6-dimethoxyphenyl)-2-(6-ethoxypyridin-2-yl)-1H-imidazo[4,5-b]pyrazin-6-yl)methanesulfonamide (270 mg, 0.534 mmol, 1.0 equiv), azetidin-3-ol hydrochloride (176 mg, 1.60 mmol, 3.0 equiv), CuI (203 mg, 1.07 mmol, 2.0 equiv), trans-N, N'-Dimethylcyclohexane-1, 2-diamine (152 mg, 1.07 mmol, 2.0 equiv) and K$_2$CO$_3$ (369 mg, 2.67 mmol, 5 equiv) in DMF (6 mL) was stirred at 115° C. via microwave irradiation for 3.5 hours under N$_2$ atmosphere. The reaction mixture was diluted with water (60 mL), followed by extraction with EtOAc (60 mL*3). The combined organic layers were dried over anhydrous Na$_2$SO$_4$ and concentrated in vacuo. The residue was purified by flash chromatography (eluted with DCM/MeOH=80/1~20/1) and prep-HPLC to give N-(1-(2,6-dimethoxyphenyl)-2-(6-ethoxypyridin-2-yl)-5-(3-hydroxyazetidin-1-yl)-1H-imidazo[4,5-b]pyrazin-6-yl)methanesulfonamide as yellow solid (1.2 mg, 0.4% yield). $^1$H NMR (400 MHz, CD$_3$OD) δ: 7.63-7.71 (m, 2H), 7.41 (t, J=8.4 Hz, 1H), 6.78 (d, J=8.4 Hz, 2H), 6.59 (d, J=7.6 Hz, 1H), 4.77-4.82 (m, 1H), 4.58-4.62 (m, 2H), 4.39 (d, J=14.4 Hz, 1H), 3.66-3.72 (m, 2H), 3.63 (s, 3H), 3.62 (s, 3H), 3.43 (q, J=7.2 Hz, 2H), 2.98 (s, 3H), 1.04 (t, J=7.2 Hz, 3H). LC-MS: m/z 542.2 (M+H)$^+$ Example 137: N-(1-(2,6-Dimethoxyphenyl)-2-(6-ethoxypyridin-2-yl)-5-vinyl-1H-imidazo[4,5-b]pyrazin-6-yl)methanesulfonamide

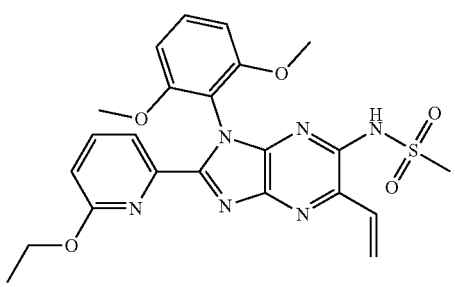 [SMILES: C=Cc1nc2nc(-c3cccc(OCC)n3)n(-c3c(OC)cccc3OC)c2nc1NS(C)(=O)=O]

To a suspension of N-(5-chloro-1-(2,6-dimethoxyphenyl)-2-(6-ethoxypyridin-2-yl)-1H-imidazo[4,5-b]pyrazin-6-yl)methanesulfonamide (50.5 mg, 0.100 mmol, 1.0 equiv), 4,4,5,5-tetramethyl-2-vinyl-1,3,2-dioxaborolane (20.0 μL, 0.120 mmol, 1.2 equiv), and K$_3$PO$_4$ (42.5 mg, 0.200 mmol, 2.0 equiv) in THF/water (2.5 mL/0.6 mL) was added Pd(dppf)Cl$_2$ (7.30 mg, 0.0100 mmol, 0.1 equiv) at room temperature. The resulting mixture was degassed and recharged with N$_2$ for three times and then stirred at 100° C. for 16 hours under N$_2$ atmosphere. The reaction mixture was diluted with water (50 mL), followed by extraction with EtOAc (50 mL*2). The combined organic layers were dried over anhydrous Na$_2$SO$_4$ and concentrated in vacuo. The residue was purified by flash chromatography (eluted with DCM/MeOH=80/1~25/1) to give N-(1-(2,6-dimethoxyphenyl)-2-(6-ethoxypyridin-2-yl)-5-vinyl-1H-imidazo[4,5-b]pyrazin-6-yl)methanesulfonamide as yellow solid (20.0 mg, 40% yield). $^1$H NMR (400 MHz, DMSO-d$_6$) δ: 10.44 (s, 1H), 7.98 (d, J=6.4 Hz, 1H), 7.88 (t, J=8.0 Hz, 1H), 7.46 (t, J=8.0 Hz, 1H), 7.24 (dd, J=10.8, 16.8 Hz, 1H), 6.84-6.87 (m, 3H), 6.42 (dd, J=2.4, 16.8 Hz, 1H), 5.57 (dd, J=2.0, 10.8 Hz, 1H), 3.57 (s, 6H), 3.39 (q, J=6.8 Hz, 2H), 3.12 (s, 3H), 1.02 (t, J=6.8 Hz, 3H). LC-MS: m/z 497.1 (M+H)$^+$

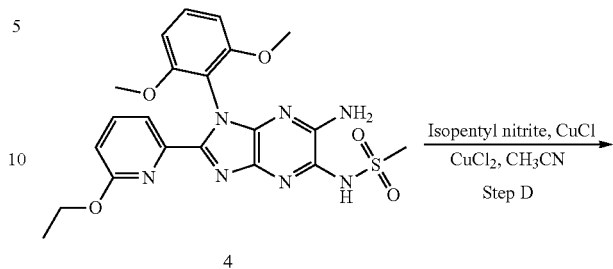

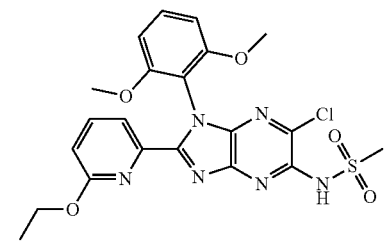

Example 138

Step A: 5-Cloro-1-(2,6-dimethoxyphenyl-2-(6-ethoxypyridin-2-yl)-N-(4-methoxybenzyl)-1H-imidazo[4,5-b]pyrazin-6-amine

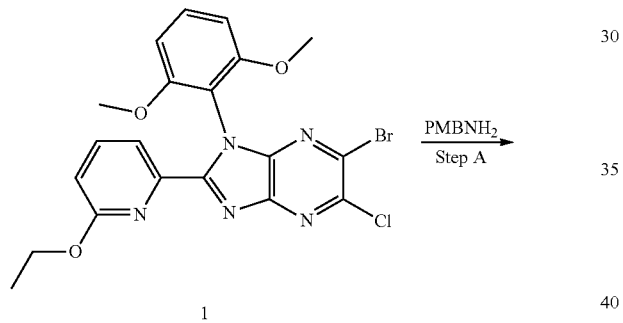

A solution of 6-bromo-5-chloro-1-(2,6-dimethoxyphenyl)-2-(6-ethoxypyridin-2-yl)-1H-imidazo[4,5-b]pyrazine (1.00 g, 2.04 mmol, 1.0 equiv) in PMBNH$_2$ (10 mL) was stirred at 105° C. via microwave irradiation for 1 hour. The reaction mixture was diluted with H$_2$O (10 mL), adjusted with HCl (aq.) to pH=4~6 and extracted with DCM (50 mL*3). The combined organic phase was washed with brine (30 mL), dried over anhydrous Na$_2$SO$_4$, filtered and concentrated. The residue was purified by flash chromatography on silica gel (eluted with PF/EtOAc=1/1) to give 5-chloro-1-(2,6-dimethoxyphenyl)-2-(6-ethoxypyridin-2-yl)-N-(4-methoxybenzyl)-1H-imidazo[4,5-b]pyrazin-6-amine as a yellow solid (790 mg, 71% yield). LC-MS: m/z 547.1 (M+H)$^+$

Step B: N-(1-(2,6-Dimethoxyphenyl)-2-(6-ethoxy-pyridin-2-yl)-6-((4-methoxybenzyl)amino)-1H-imidazo[4,5-b]pyrazin-5-yl)methanesulfonamide

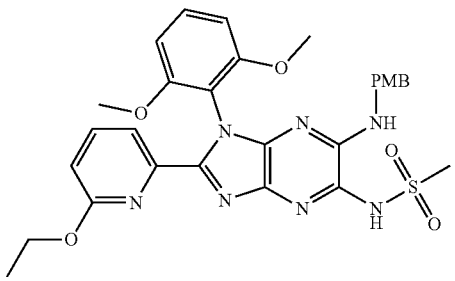

A mixture of 5-chloro-1-(2,6-dimethoxyphenyl)-2-(6-ethoxypyridin-2-yl)-N-(4-methoxybenzyl)-1H-imidazo[4,5-b]pyrazin-6-amine (790 mg, 1.45 mmol, 1.0 equiv), methanesulfonamide (276 mg, 2.90 mmol, 2.0 equiv), CuI (551 mg, 2.90 mmol, 2.0 equiv), trans-N, N'-Dimethylcyclohexane-1, 2-diamine (412 mg, 2.90 mmol, 2.0 equiv) and $K_2CO_3$ (600 mg, 4.35 mmol, 3.0 equiv) in DMF (1.5 mL) was stirred at 120° C. via microwave irradiation for 3 hours under $N_2$ atmosphere. The reaction mixture was acidified to pH=4~6 with HCOOH and concentrated. The residue was purified by flash chromatography on silica gel (eluted with DCM/MeOH=10/1) to give N-(1-(2,6-dimethoxyphenyl)-2-(6-ethoxypyridin-2-yl)-6-((4-methoxybenzyl)amino)-1H-imidazo[4,5-b]pyrazin-5-yl)methanesulfonamide as a yellow solid (350 mg, 39% yield). LC-MS: m/z 606.1 $(M+H)^+$

Step C: N-(6-Amino-1-(2,6-dimethoxyphenyl)-2-(6-ethoxypyridin-2-yl)-1H-imidazo[4,5-b]pyrazin-5-yl)methanesulfonamide

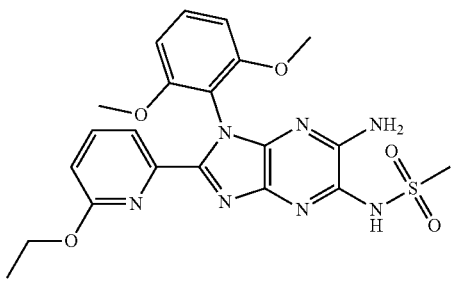 [SMILES: CCOc1cccc(-c2nc3nc(NS(C)(=O)=O)c(N)nc3n2-c2c(OC)cccc2OC)n1]

A solution of N-(1-(2,6-dimethoxyphenyl)-2-(6-ethoxy-pyridin-2-yl)-6-((4-methoxybenzyl)amino)-1H-imidazo[4,5-b]pyrazin-5-yl)methanesulfonamide (359 mg, 0.57 mmol) in TFA/DCM (5 mL/5 mL) was stirred at 50° C. for 1 h. The reaction mixture was concentrated and residue was purified by flash chromatography on silica gel (eluted with DCM/MeOH=10/1) to give N-(6-amino-1-(2,6-dimethoxyphenyl)-2-(6-ethoxypyridin-2-yl)-1H-imidazo[4,5-b]pyrazin-5-yl)methanesulfonamide as a yellow solid (160 mg, 58% yield). LC-MS: m/z 486.1 $(M+H)^+$

Step D: N-(6-Chloro-1-(2,6-dimethoxyphenyl-2-(6-ethoxypyridin-2-yl)-1H-imidazo[4,5-b]pyrazin-5-yl)methanesulfonamide (Example 138)

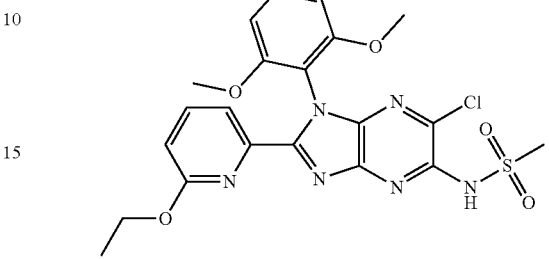

A mixture of N-(6-amino-1-(2,6-dimethoxyphenyl)-2-(6-ethoxypyridin-2-yl)-1H-imidazo[4,5-b]pyrazin-5-yl)methanesulfonamide (160 mg, 0.33 mmol, 1.0 equiv), CuCl (130 mg, 1.32 mmol, 4.0 equiv), and $CuCl_2$ (265 mg, 1.98 mmol, 6.0 equiv) in $CH_3CN$ (1.5 mL) was stirred at room temperature for 0.5 h under $N_2$ atmosphere. Then isopentyl nitrite (231 mg, 1.98 mmol, 6.0 equiv) was added to the mixture and the reaction mixture was stirred at room temperature for 24 h. The reaction mixture was concentrated and residue was purified by flash chromatography on silica gel (eluted with DCM/MeOH=10/1) and prep-HPLC to give N-(6-chloro-1-(2,6-dimethoxyphenyl)-2-(6-ethoxypyridin-2-yl)-1H-imidazo[4,5-b]pyrazin-5-yl)methanesulfonamide as white solid (3.00 mg, 1.8% yield). $^1$H NMR (400 MHz, Chloroform-d) δ: 8.10 (d, J=7.2 Hz, 1H), 7.68 (t, J=7.6 Hz, 1H), 7.42 (s, 1H), 7.38 (t, J=8.4 Hz, 1H), 6.72 (d, J=8.0 Hz, 1H), 6.68 (d, J=8.4 Hz, 1H), 3.66 (s, 3H), 3.63 (s, 6H), 3.42 (q, J=8.0 Hz, 2H), 1.09 (t, J=8.0 Hz, 3H). LC-MS: m/z 505.1 $(M+H)^+$

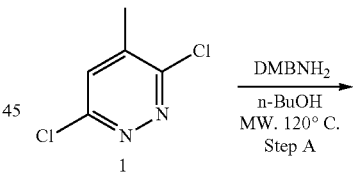

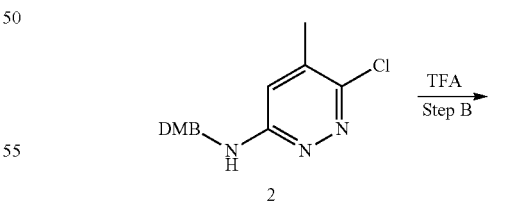

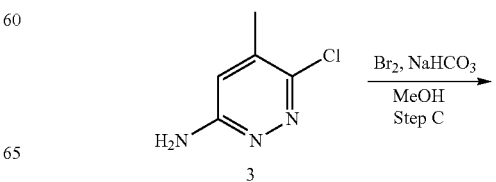

-continued

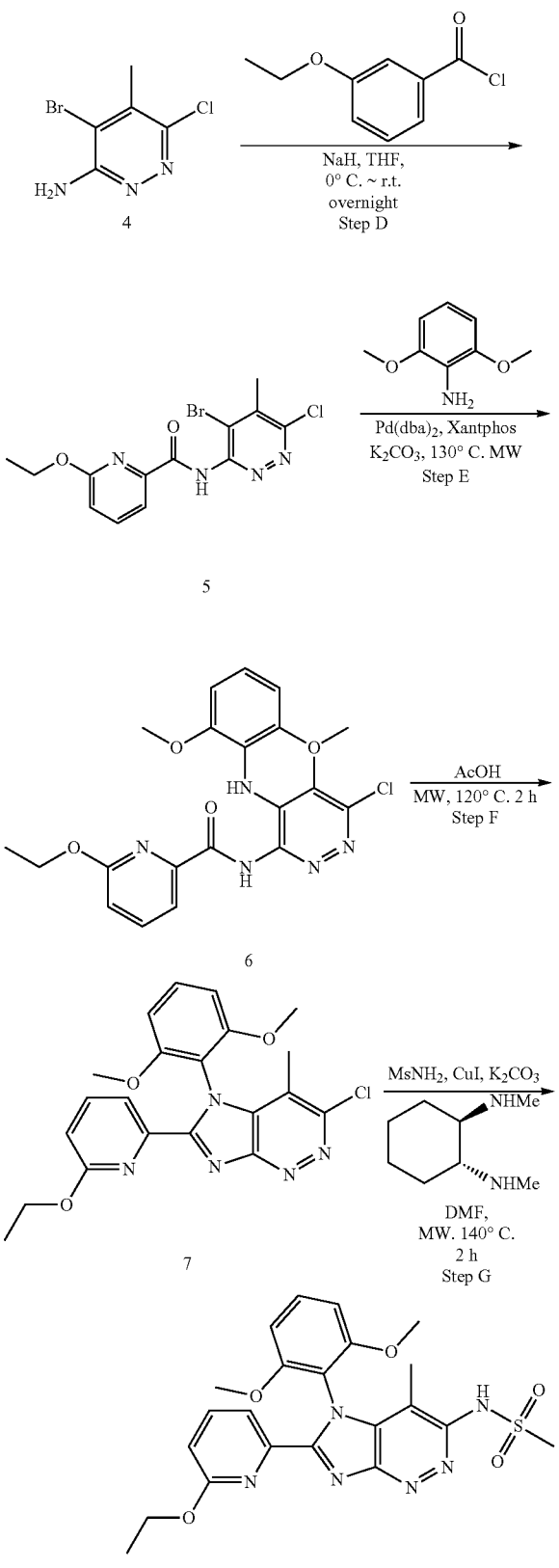

Example 139

Step A: 6-Chloro-N-(3,5-dimethoxybenzyl)-5-methylpyridazin-3-amine

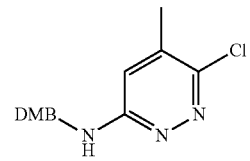

A mixture of 3,6-dichloro-4-methylpyridazine (4.00 g, 24.7 mmol, 1.0 equiv) and 2,4-dimethoxybenzylamine (32.8 g, 196 mmol, 8 equiv) in n-BuOH (40 mL) was stirred at 120° C. via microwave irradiation for 2 hours. The mixture was concentrated and the residue was purified by flash chromatography (eluted with EtOAc/PE=2/3) to afford 6-chloro-N-(3,5-dimethoxybenzyl)-5-methylpyridazin-3-amine as a light yellow solid (6.20 g, 85.7% yield). LC-MS: m/z 294.0, 296.0 (M+H)$^+$ Step B: 6-Chloro-5-methylpyridazin-3-amine

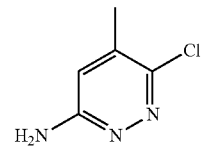

A solution of 6-chloro-N-(3,5-dimethoxybenzyl)-5-methylpyridazin-3-amine (6.20 g, 0.77 mmol, 1.0 equiv) in TFA (60 mL) was stirred at room temperature overnight. The mixture was concentrated and dissolved in DCM. The solution was basified to pH=6 with 1 mol/L NaOH aqueous solution. The organic layer was separated, washed with brine, dried over anhydrous Na$_2$SO$_4$ and concentrated in vacuo and the residue was reslurried in EtOAc to afford 6-chloro-5-methylpyridazin-3-amine as light yellow solid (2.30 g, 79% yield). LC-MS: m/z 144.0, 146.0 (M+H)$^+$ Step C: 4-Bromo-6-chloro-5-methylpyridazin-3-amine

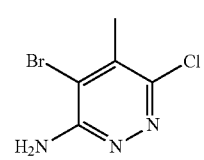

The mixture of 6-chloro-5-methylpyridazin-3-amine and 3-chloro-5-methylpyridazin-6-amine (2.30 g, 16.0 mmol, 1.0 equiv) and NaHCO$_3$ (8.40 g, 40.0 mmol, 2.5 equiv) in MeOH (100 mL) was treated with Br$_2$ (2.80 g, 17.6 mmol, 1.1 equiv) at 0° C. The mixture was stirred at 0° C. for 4 h and then filtered. The filtrate was concentrated in vacuo. The residue was purified by flash chromatography (eluted with DCM/MeOH=30/1) to afford 4-bromo-6-chloro-5-methylpyridazin-3-amine as white solid (940 mg, 26% yield). LC-MS: m/z 221.9, 223.9 (M+H)$^+$

Step D: N-(4-bromo-6-chloro-5-methylpyridazin-3-yl)-6-ethoxypicolinamide

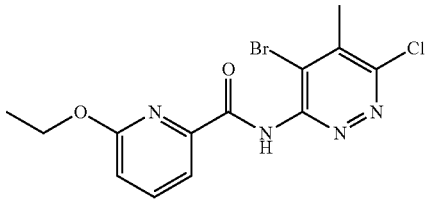 [SMILES: CCOc1cccc(C(=O)Nc2nnc(Cl)c(C)c2Br)n1]

To a solution of 4-bromo-6-chloro-5-methylpyridazin-3-amine (946 mg, 4.25 mmol, 1.0 equiv) in THF (20 mL) was added NaH (60% in mineral oil, 510 mg, 12.8 mmol, 3.0 equiv) at 0° C. After the mixture was stirred at 0° C. for 1 hour, a solution of 6-ethoxypicolinoyl chloride (946 mg, 5.1 mmol, 1.2 equiv) in DCM (10 mL) was added dropwise. The resulting mixture was stirred at room temperature overnight. The reaction mixture was quenched with NH$_4$Cl solution (aq., 10 mL) and extracted with DCM (50 mL*3). The combined organic layers were washed with brine (20 mL), dried over anhydrous Na$_2$SO$_4$ and concentrated in vacuo. The residue purified by flash chromatography on silica gel (eluted with DCM/MeOH=100/3) to afford N-(4-bromo-6-chloro-5-methylpyridazin-3-yl)-6-ethoxypicolinamide as a light yellow solid (700 mg, 44% yield). LC-MS: m/z 371.0, 373.0 (M+H)$^+$

Step E: N-(6-Chloro-4-((2,6-dimethoxyphenyl)amino)-5-methylpyridazin-3-yl)-6-ethoxypicolinamide

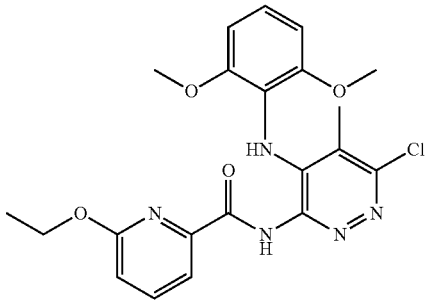 [SMILES: CCOc1cccc(C(=O)Nc2nnc(Cl)c(C)c2Nc2c(OC)cccc2OC)n1]

A suspension of N-(4-bromo-6-chloro-5-methylpyridazin-3-yl)-6-ethoxypicolinamide (600 mg, 1.60 mmol, 1.0 equiv), 2,6-dimethoxyaniline (372 mg, 2.40 mmol, 1.5 equiv), Pd$_2$(dba)$_3$ (150 mg, 0.160 mmol, 0.1 equiv), Xantphos (378 mg, 0.640 mmol, 0.4 equiv) and K$_2$CO$_3$ (450 mg, 3.20 mmol, 2.0 equiv) in 1,4-dioxane (20 mL) was stirred at 130° C. via microwave irradiation for 3 hours under N$_2$ atmosphere. The mixture was filtered through celite and the filtrate was concentrated in vacuo. The residue was purified by flash chromatography (EtOAc/DCM=1/3) to afford N-(6-chloro-4-((2,6-dimethoxyphenyl)amino)-5-methylpyridazin-3-yl)-6-ethoxypicolinamide as yellow solid (77 mg, 9% yield). LC-MS: m/z 444.1, 446.1 (M+H)$^+$

Step F: Chloro-7-(2,6-dimethoxyphenyl)-8-(6-ethoxypyridin-2-yl)-6-methyl-7H-imidazo[4,5-c]pyridazine

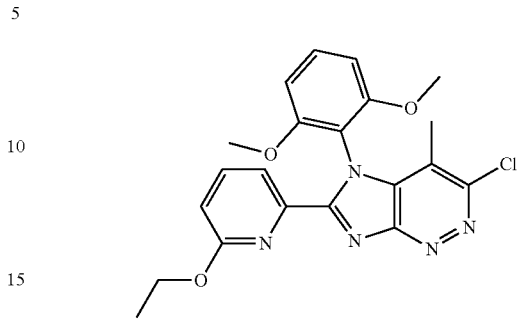

A solution of N-(6-chloro-4-((2,6-dimethoxyphenyl)amino)-5-methylpyridazin-3-yl)-6-ethoxypicolinamide (77.0 mg, 0.170 mmol) in AcOH (5 mL) was stirred at 120° C. via microwave irradiation for 2 hours. The mixture was concentrated in vacuo, and the residue was purified by pre-TLC (EtOAc/PE=1/1) to afford chloro-7-(2,6-dimethoxyphenyl)-8-(6-ethoxypyridin-2-yl)-6-methyl-7H-imidazo[4,5-c]pyridazine as white solid (15.0 mg, 20% yield). LC-MS: m/z 426.1, 428.1 (M+H)$^+$

Step G: N-(7-(2,6-Dimethoxyphenyl)-8-(6-ethoxypyridin-2-yl)-6-methyl-7H-imidazo[4,5-c]pyridazinyl)methanesulfonamide (Example 139)

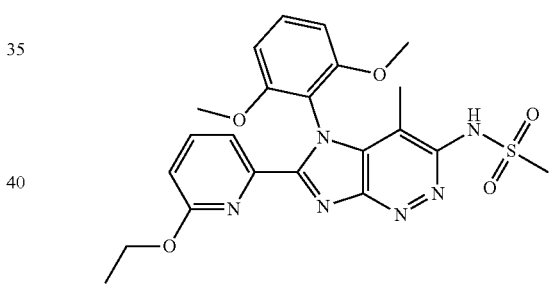

A suspension of chloro-7-(2,6-dimethoxyphenyl)-8-(6-ethoxypyridin-2-yl)-6-methyl-7H-imidazo[4,5-c]pyridazine (15.0 mg, 0.0350 mmol, 1.0 equiv), methanesulfonamide (17.0 mg, 0.180 mmol, 6 equiv), CuI (13.0 mg, 0.070 mmol, 2.0 equiv), trans-N, N'-dimethylcyclohexane-1, 2-diamine (10.0 mg, 0.070 mmol, 2.0 equiv) and K$_2$CO$_3$ (15 mg, 0.105 mmol, 3 equiv) in DMF (2 mL) was stirred at 140° C. via microwave irradiation for 4 hours under N$_2$ atmosphere. The reaction was diluted with water (10 mL) and extracted with EtOAc (10 mL*3). The combined organic layers were washed with brine, dried over anhydrous Na$_2$SO$_4$ and concentrated in vacuo. The residue was purified by pre-HPLC (eluted with CH$_3$CN/H$_2$O=5/95~90/10 including 0.1% HCOOH) to afford N-(7-(2,6-dimethoxyphenyl)-8-(6-ethoxypyridin-2-yl)-6-methyl-7H-imidazo[4,5-c]pyridazinyl)methanesulfonamide as a yellow solid (4.00 mg, 23% yield).

1H NMR (400 MHz, Chloroform-d) δ: 8.07 (d, J=7.2 Hz, 1H), 7.78-7.64 (m, 1H), 7.42 (t, J=8.4 Hz, 1H), 6.77 (d, J=8.4 Hz, 1H), 6.64 (d, J=8.4 Hz, 2H), 3.67 (s, 6H), 3.44 (q, J=7.2 Hz, 2H), 3.09 (s, 3H), 1.78 (s, 3H), 1.12 (t, J=7.2 Hz, 3H). LC-MS: m/z 485.0 (M+H)$^+$

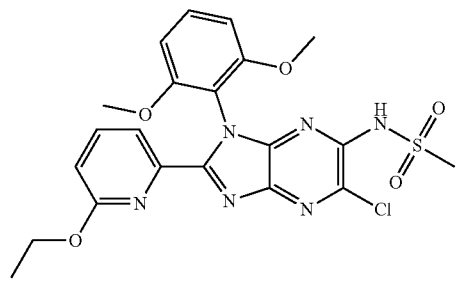
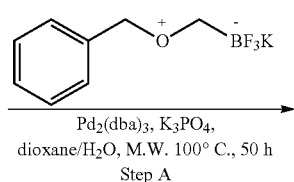

Pd₂(dba)₃, K₃PO₄,
dioxane/H₂O, M.W. 100° C., 50 h
Step A

1
SYR0007435

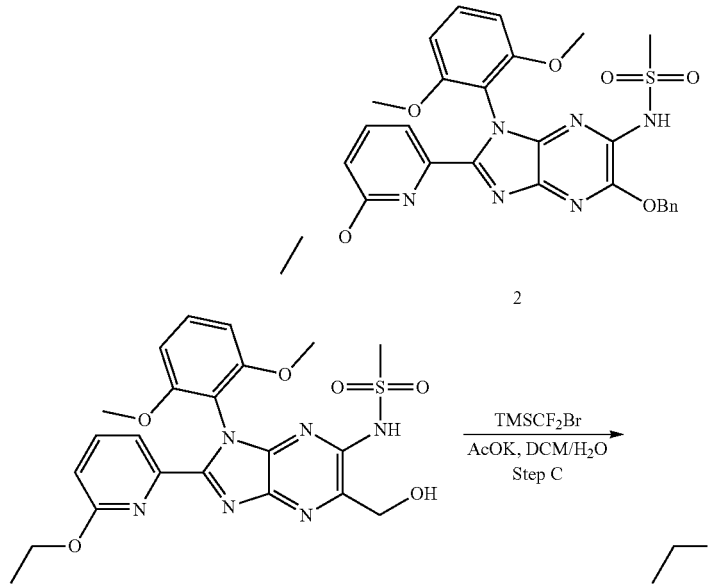

2

CF₃SO₃H/Tf₂O
-78° C./1.5 h
Step B

TMSCF₂Br
AcOK, DCM/H₂O
Step C

SYR0010543

Example 140

Step A: N-(5-((Benzyloxy)methyl)-1-(2,6-dimethoxyphenyl)-2-(6-ethoxypyridin-2-yl)-1H-imidazo[4,5-b]pyrazin-6-yl)methanesulfonamide

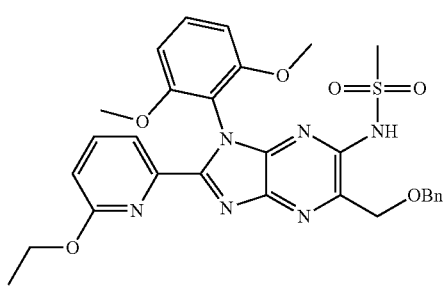 [SMILES: CCOc1cccc(-c2nc3nc(COCc4ccccc4)c(NS(C)(=O)=O)nc3n2-c2c(OC)cccc2OC)n1]

To a suspension of N-(5-chloro-1-(2,6-dimethoxyphenyl)-2-(6-ethoxypyridin-2-yl)-1H-imidazo[4,5-b]pyrazin-6-yl)methanesulfonamide (404 mg, 0.800 mmol, 1.0 equiv), potassium ((benzyloxy)methyl)trifluoroborate (456 mg, 2.00 mmol, 2.5 equiv), K₃PO₄ (509.6 mg, 2.40 mmol, 3 equiv) in dioxane/water (6 mL/2 mL) was added Pd₂(dba)₃ (146 mg, 0.16 mmol, 0.2 equiv) at room temperature. The resulting mixture was degassed and re-charged with N₂ for three times and then stirred at 100° C. for 50 hours under N₂ atmosphere. The reaction mixture was diluted with water (50 mL), followed by extraction with EtOAc (50 mL*2). The combined organic layers were dried over anhydrous Na₂SO₄ and concentrated in vacuo. The residue was purified by flash chromatography (eluted with DCM/MeOH=120/1~35/1) to give N-(5-((benzyloxy)methyl)-1-(2,6-dimethoxyphenyl)-2-(6-ethoxypyridin-2-yl)-1H-imidazo[4,5-b]pyrazin-6-yl)methanesulfonamiide as a yellow solid (70.0 mg, 14.8% yield). LC-MS: m/z 591.0 (M+H)⁺

Step B: N-(1-(2,6-Dimethoxyphenyl)-2-(6-ethoxypyridin-2-yl)-5-(hydroxymethyl)-1H-imidazo[4,5-b]pyrazin-6-yl)methanesulfonamide (Example 140)

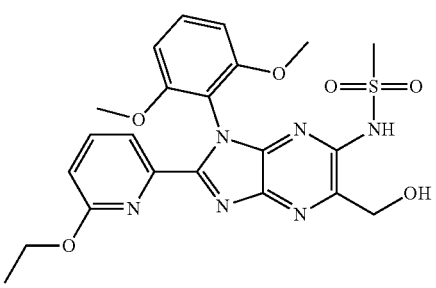 [SMILES: CCOc1cccc(-c2nc3nc(CO)c(NS(C)(=O)=O)nc3n2-c2c(OC)cccc2OC)n1]

To a mixture of N-(5-((benzyloxy)methyl)-1-(2,6-dimethoxyphenyl)-2-(6-ethoxypyridin-2-yl)-1H-imidazo[4,5-b]pyrazin-6-yl)methanesulfonamide (100 mg, 0.169 mmol, 1.0 equiv) in DCM (5 mL) were added trifluoromethanesulfonic acid (1 mL) and trifluoromethanesulfonic anhydride (0.5 mL) at −78° C. under N₂ atmosphere. The resulting mixture was stirred at −78° C. for 3.5 hours under N₂ atmosphere. Then the mixture was basified to pH=6 with aqueous NaHCO₃ solution (3 mol/L). The mixture was extracted with DCM (20 mL*3). The combined organic layers were washed with brine (20 mL), dried over Na₂SO₄, filtered and evaporated under reduced pressure. The residue was purified by column chromatography on silica gel (eluted with DCM/MeOH=50/1~25/1) to give N-(1-(2,6-dimethoxyphenyl)-2-(6-ethoxypyridin-2-yl)-5-(hydroxymethyl)-1H-imidazo[4,5-b]pyrazin-6-yl)methanesulfonamide as yellow solid (30.0 mg, 36% yield). ¹H NMR (400 MHz, CD₃OD) δ: 7.85 (d, J=7.6 Hz, 1H), 7.76 (t, J=8.4 Hz, 1H), 7.44 (t, J=8.4 Hz, 1H), 6.82 (d, J=8.4 Hz, 2H), 6.73 (d, J=8.0 Hz, 1H), 4.89 (s, 2H), 3.62 (s, 6H), 3.47 (q, J=7.2 Hz, 2H), 3.18 (s, 3H), 1.07 (t, J=7.2 Hz, 3H). LC-MS: m/z 501.1 (M+H)⁺

Step C: N-(5-(Difluoromethoxymethyl)-1-(2,6-dimethoxyphenyl)-2-(6-ethoxypyridin-2-yl)-1H-imidazo[4,5-b]pyrazin-6-yl)methanesulfonamide (Example 141)

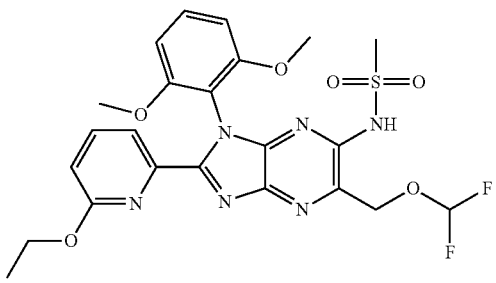 [SMILES: CCOc1cccc(-c2nc3nc(COC(F)F)c(NS(C)(=O)=O)nc3n2-c2c(OC)cccc2OC)n1]

To a mixture of N-(1-(2,6-dimethoxyphenyl)-2-(6-ethoxypyridin-2-yl)-5-(hydroxymethyl)-1H-imidazo[4,5-b]pyrazin-6-yl)methanesulfonamide (50.0 mg, 0.100 mmol, 1 equiv), KOAc (98.2 mg, 1.00 mmol, 10 equiv) in DCM/H₂O (8 mL/8 mL) was added (bromodifluoromethyl)trimethylsilane (122 mg, 0.600 mmol, 6 equiv) at room temperature under N₂ atmosphere. The resulting mixture was stirred at room temperature for 5 days under N₂ atmosphere. Then the mixture was extracted with DCM (10 mL*2). The combined organic layers were washed with brine (10 mL), dried over Na₂SO₄, filtered and evaporated under reduced pressure. The residue was purified by silica gel column chromatography (eluted with DCM/MeOH=50/1~30/1) and prep-HPLC to give N-(5-(((difluoromethoxy)methyl)-1-(2,6-dimethoxyphenyl)-2-(6-ethoxypyridin-2-yl)-1H-imidazo[4,5-b]pyrazin-6-yl)methanesulfonamide as a yellow solid (2.20 mg, 4% yield). ¹H NMR (400 MHz, Chloroform-d) δ: 8.10 (d, J=7.2 Hz, 1H), 7.69 (t, J=8.0 Hz, 1H), 7.45 (s, 1H), 7.37 (t, J=8.4 Hz, 1H), 6.66-6.72 (m, 3H), 6.39 (t, J=73.2 Hz, 1H), 5.26 (s, 2H), 3.61 (s, 6H), 3.43 (q, J=7.2 Hz, 2H), 3.25 (s, 3H), 1.07 (t, J=7.2 Hz, 3H). LC-MS: m/z 551.1 (M+H)⁺

Example 142: N-(5-Chloro-1-(2,6-dimethoxyphenyl)-2-(6-ethoxypyridin-2-yl)-1H-imidazo[4,5-b]pyrazin-6-yl)-1-(5-methylpyrimidin-2-yl)methanesulfonamide

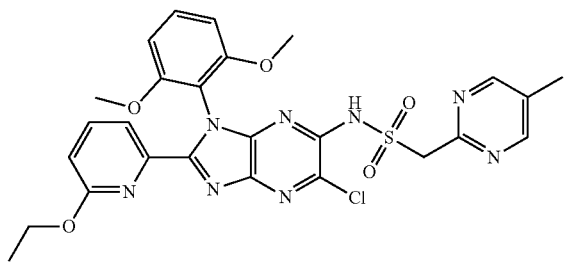

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (5-methylpyrimidin-2-yl)methanesulfonamide. ¹H NMR (400 MHz, DMSO-d₆) δ: 10.86 (s, 1H), 8.63 (s, 2H), 7.96 (d, J=6.8 Hz, 1H), 7.88 (t, J=7.6 Hz, 1H), 7.44 (t, J=8.4 Hz, 1H), 6.78-6.90 (m, 3H), 4.87 (s, 2H), 3.51 (s, 6H), 3.39 (q, J=7.2 Hz, 2H), 2.26 (s, 3H), 1.01 (t, J=7.2 Hz, 3H). LC-MS: m/z 597.1 (M+H)⁺

Example 143: N-(5-Chloro-1-(2,6-dimethoxyphenyl)-2-(6-ethoxypyridin-2-yl)-1H-imidazo[4,5-b]pyrazin-6-yl)-1-(3-fluorophenyl)methanesulfonamide

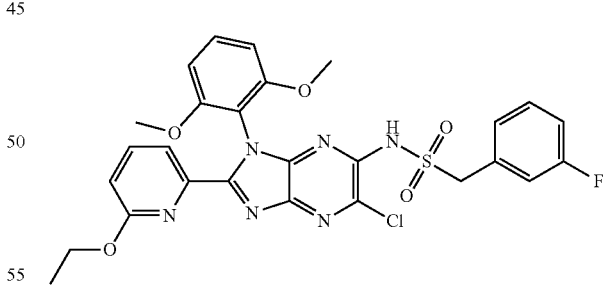

The title compound was prepared according to Method K, step D, starting from 6-bromo-5-chloro-1-(2,6-dimethoxyphenyl)-2-(6-ethoxypyridin-2-yl)-1H-imidazo[4,5-b]pyrazine by using (3-fluorophenyl)methanesulfonamide. ¹H NMR (400 MHz, Chloroform-d) δ: 8.11 (d, J=7.6 Hz, 1H), 7.70 (t, J=7.6 Hz, 1H), 7.42 (t, J=8.4 Hz, 1H), 7.26-7.28 (m, 1H), 7.18 (s, 1H), 7.04-7.06 (m, 1H), 6.98 (d, J=7.6 Hz, 1H), 6.83 (d, J=9.6 Hz, 1H), 6.72-6.74 (m, 3H), 4.62 (s, 2H), 3.64 (s, 6H), 3.43 (q, J=7.2 Hz, 2H), 1.08 (t, J=7.2 Hz, 3H). LC-MS: m/z 599.1 (M+H)

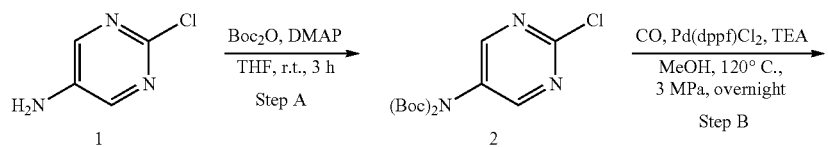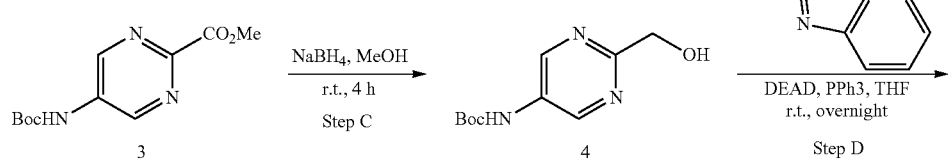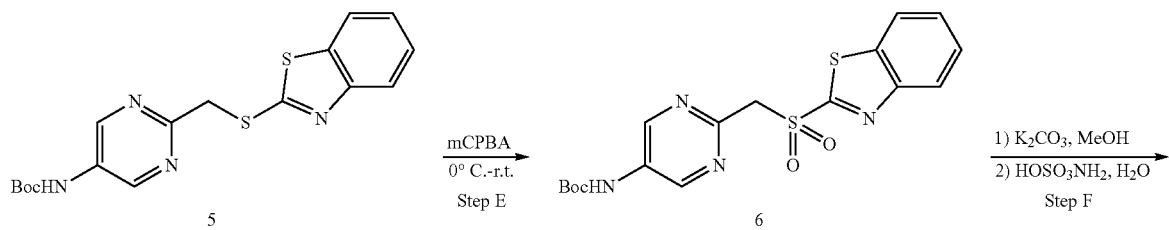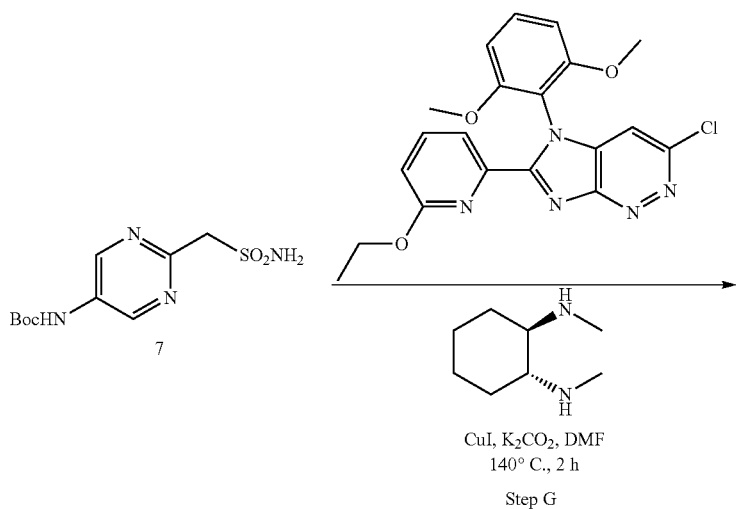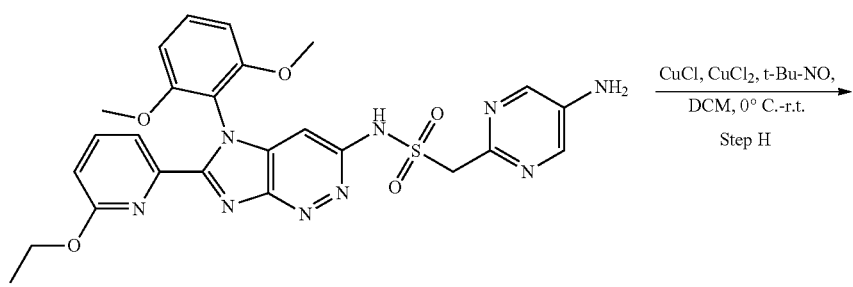

-continued

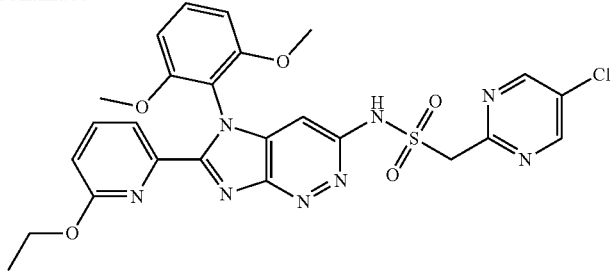

Example 144

Step A: 5-Chloro-2-amino(bis-carbamate)pyrimidine

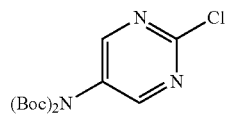

To a solution of 2-chloropyrimidin-5-amine (5.00 g, 39.0 mmol, 1.0 equiv) in THF were added Boc$_2$O (17.9 g, 82.0 mmol, 2.1 equiv) and DMAP (476 mg, 3.90 mmol, 0.10 equiv). The mixture was stirred at room temperature for 3 h. TLC showed the starting material was consumed completely. The mixture was concentrated and purified by silica gel column chromatography (PE/EA=15/1) to give 5-chloro-2-amino(bis-carbamate)pyrimidine as a white solid (11.6 g, 91% yield). LC-MS: m/z 329.8 (M+H)$^+$ Step B: Methyl 5-((tert-butoxycarbonyl)amino)pyrimidine-2-carboxylate

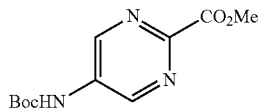

To a solution of 5-chloro-2-amino(bis-carbamate)pyrimidine (10.6 g, 32.0 mmol, 1.0 equiv) in MeOH (200 ml) and DMF (40 ml) were added TEA (9.72 g, 96.0 mol, 3.0 equiv) and Pd(dppf)Cl$_2$ (3.51 g, 5.00 mmol, 0.16 equiv). The suspension was degassed and purged with CO several times. The mixture was stirred under CO (3 MPa) at 120° C. overnight. The reaction mixture was cooled to room temperature and concentrated in vacuo. The residue was purified by silica gel column chromatography (PE/EA=2/1) to give methyl 5-((tert-butoxycarbonyl)amino)pyrimidine-2-carboxylate as a yellow solid (5.32 g, 65% yield). LC-MS: m/z 254.0 (M+H)$^+$ Step C: tert-Butyl (2-(hydroxymethyl)pyrimidin-5-yl)carbamate

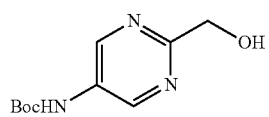

To a solution of methyl 5-((tert-butoxycarbonyl)amino)pyrimidine-2-carboxylate (5.32 g, 21.0 mmol, 1.0 equiv) in MeOH (50 mL) was added NaBH$_4$ (954 mg, 25.2 mmol, 1.2 equiv) at 0° C. The mixture was stirred at room temperature for 5 h. Then the mixture was diluted with H$_2$O (50 mL) and extracted with DCM (50 ml*3). The combined DCM layers were washed with brine, dried over anhydrous Na$_2$SO$_4$, filtered and concentrated. The crude residue was purified by silica gel column chromatography (DCM/MeOH=40/1) to give tert-butyl (2-(hydroxymethyl)pyrimidin-5-yl)carbamate as a yellow solid (2.90 g, 61% yield). LC-MS: m/z 226.01 (M+H)$^+$ Step D: tert-Butyl (2-(benzo[d]thiazol-2-ylthio)methyl)pyrimidin-5-yl)carbamate

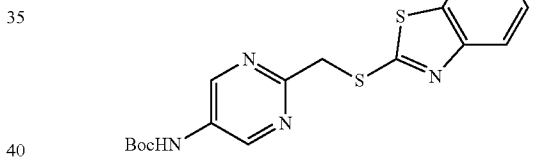

To a solution of tert-butyl (2-(hydroxymethyl)pyrimidin-5-yl)carbamate (2.93 g, 13.0 mmol, 1.0 equiv), benzo[d]thiazole-2-thiol (2.61 g, 15.6 mmol, 1.2 equiv) and PPh$_3$ (4.10 g, 15.6 mmol, 1.2 equiv) in THF was added DEAD (2.72 g, 15.6 mmol, 1.2 equiv) at 0° C. The mixture was stirred at room temperature for 16 hours. The mixture was concentrated in vacuo and purified by silica gel column chromatography (PE/EA=5/1) to give tert-butyl (2-((benzo[d]thiazol-2-ylthio)methyl)pyrimidin-5-yl)carbamate as a yellow solid (4.50 g, 92% yield). LC-MS: m/z 374.9 (M+H)$^+$ Step E: tert-Butyl (2-((benzo[d]thiazol-2-ylsulfonyl)methyl)pyrimidin-5-yl)carbamate

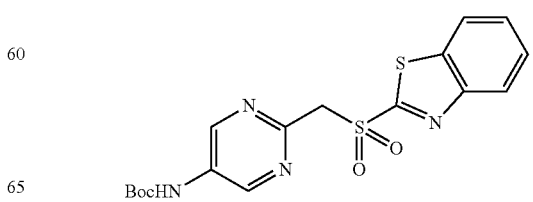

To a solution of tert-butyl (2-((benzo[d]thiazol-2-ylthio)methyl)pyrimidin-5-yl)carbamate (3.00 g, 8.02 mmol, 1.0 equiv) in DCM (60 mL) was added m-CPBA (85% purity) (1.95 g, 9.62 mmol, 1.20 equiv). The mixture was stirred at room temperature for 16 hours and quenched with 1 N $Na_2SO_3$ aqueous solution. The organic phase was separated, washed with saturated $Na_2CO_3$ aqueous solution and brine. The organic layer was dried over anhydrous $Na_2SO_4$, filtered and concentrated in vacuo. The residue was purified by flash chromatography (eluted with PE/EtOAc=3/1) to afford tert-butyl (2-((benzo[d]thiazol-2-ylsulfonyl)methyl)pyrimidin-5-yl)carbamate as a white solid (1.39 g, 43% yield). LC-MS: m/z 407.0 $(M+H)^+$

Step F: tert-Butyl (2-(sulfamoylmethyl)pyrimidin-5-yl)carbamate

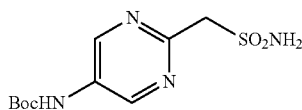

To a solution of tert-butyl (2-((benzo[d]thiazol-2-ylsulfonyl)methyl)pyrimidin-5-yl)carbamate (1.39 g, 3.42 mmol, 1.0 equiv) in MeOH (30 mL) was added $K_2CO_3$ (2.36 g, 17.1 mmol, 5.0 equiv). After the mixture was stirred at room temperature for 30 mins, 20 mL $H_2O$ and $NH_2OSO_3H$ (929 mg, 8.21 mmol, 2.4 equiv) in $H_2O$ (10 mL) were added. The resulting mixture was stirred at room temperature for 16 hours. The mixture was concentrated and the residue was purified by flash chromatography (DCM/MeOH=20/1) to afford the title compound tert-butyl (2-(sulfamoylmethyl)pyrimidin-5-yl)carbamate as a white solid (310 mg, 31% yield). $^1$H NMR (400 MHz, DMSO-d6) δ: 9.83 (s, 1H), 8.85 (s, 2H), 6.92 (s, 2H), 4.48 (s, 2H), 1.49 (s, 9H).

Step G: 1-(5-Aminopyrimidin-2-yl)-N-(7-(2,6-dimethoxyphenyl)-8-(6-ethoxypyridin-2-yl)-7H-imidazo[4,5-c]pyridazinyl)methanesulfonamide

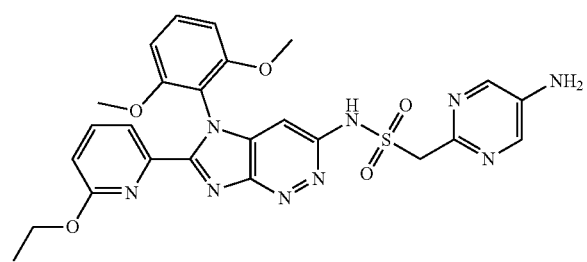 [SMILES: CCOc1cccc(-c2nc3nnc(NS(=O)(=O)Cc4ncc(N)cn4)cc3n2-c2c(OC)cccc2OC)n1]

A suspension of tert-butyl (2-(sulfamoylmethyl)pyrimidin-5-yl)carbamate (166 mg, 0.576 mmol, 1.2 equiv), chloro-7-(2,6-dimethoxyphenyl)-8-(6-ethoxypyridin-2-yl)-7H-imidazo[4,5-c]pyridazine (200 mg, 0.490 mmol, 1.0 equiv), trans-N,N'-dimethylcyclohexane-1,2-diamine (70.0 mg, 0.490 mmol, 1.0 equiv), CuI (93.0 mg, 0.490 mmol, 1.0 equiv), NaI (74.0 mg, 0.490 mmol, 1.0 equiv) and $K_2CO_3$ (135 mg, 0.980 mmol, 2.0 equiv) in DMF (4 mL) was stirred at 140° C. via microwave irradiation for 2 hours under $N_2$ atmosphere. The reaction mixture was filtered and filtrate was concentrated in vacuo. The residue was purified by prep-HPLC (eluted with $CH_3CN/H_2O$=5/95~95/5 including 0.1% HCOOH) to give 1-(5-aminopyrimidin-2-yl)-N-(7-(2,6-dimethoxyphenyl)-8-(6-ethoxypyridin-2-yl)-7H-imidazo[4,5-c]pyridazinyl)methanesulfonamide as a yellow solid (70.0 mg, 25% yield). LC-MS: m/z 564.3 (M+H)+

Step H: 1(5-Chloropyrimidin-2-yl)-N-(7-(2,6-dimethoxyphenyl)-8-(6-ethoxypyridin-2-yl)-7H-imidazo[4,5-c]pyridazinyl)methanesulfonamide (Example 144)

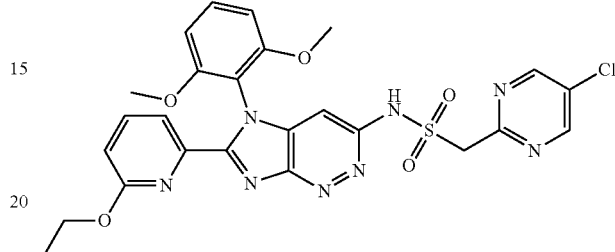

A suspension of 1-(5-aminopyrimidin-2-yl)-N-(7-(2,6-dimethoxyphenyl)-8-(6-ethoxypyridin-2-yl)-7H-imidazo[4,5-c]pyridazinyl)methanesulfonamide (80.0 mg, 0.140 mmol, 1.0 equiv), CuCl (28.0 mg, 0.280 mmol, 2.0 equiv), $CuCl_2$ (56.0 mg, 0.420 mmol, 3.0 equiv) in DCM (4 mL) was stirred at 0° C. for 10 mins. tert-Butyl nitrite (43.0 mg, 0.420 mmol, 3.0 equiv) was added. The mixture was stirred at room temperature for 4 h. The reaction mixture was filtered and filtrate was concentrated in vacuo. The residue was purified by prep-TLC (DCM/MeOH=30/1) to afford the crude product, which was further purified with prep-HPLC (eluted with $CH_3CN/H_2O$=5/95~95/5 including 0.1% HCOOH) to give 1-(5-chloropyrimidin-2-yl)-N-(7-(2,6-dimethoxyphenyl)-8-(6-ethoxypyridin-2-yl)-7H-imidazo[4,5-c]pyridazinyl)methanesulfonamide as a yellow solid (3.00 mg, 4% yield). $^1$H NMR (400 MHz, DMSO-$d_6$) δ: 8.83 (s, 2H), 8.00 (d, J=7.2 Hz, 1H), 7.92 (t, J=8.4 Hz, 1H), 7.51 (t, J=8.4 Hz, 1H), 6.80-7.03 (m, 4H), 4.70 (s, 2H), 3.61 (s, 6H), 3.37-3.42 (m, 2H), 1.03 (t, J=7.2 Hz, 3H). LC-MS: m/z 583.2 (M+H)+

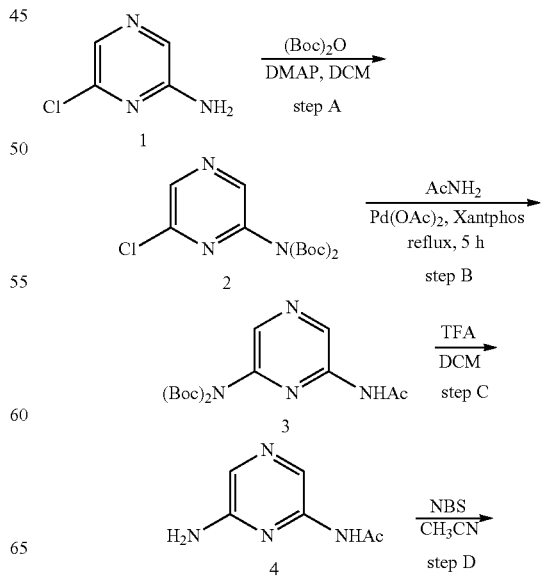

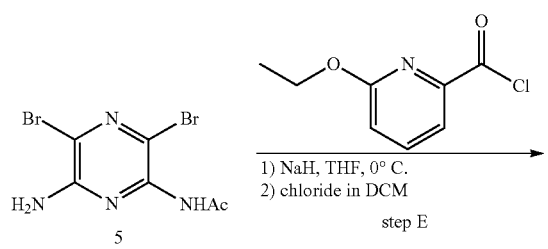

step E

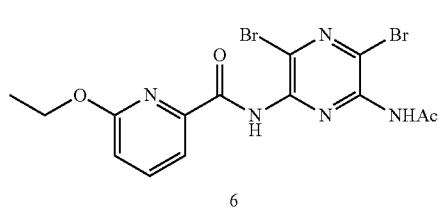

step F

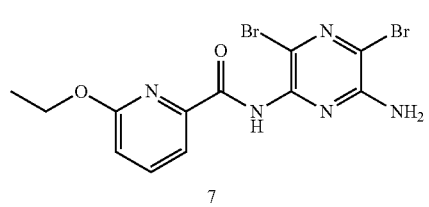

step G

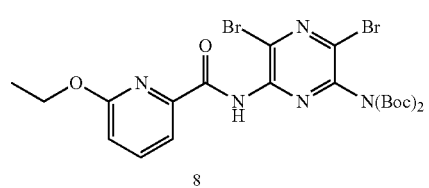

step H

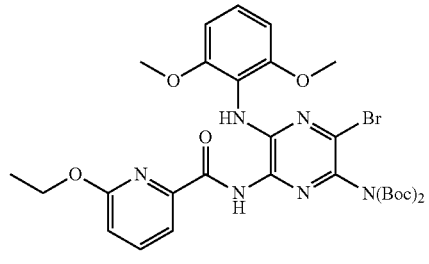

step I

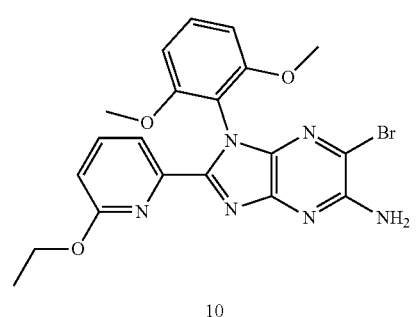

step J

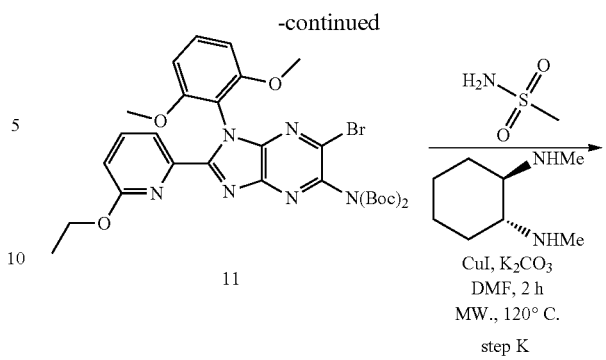

step K

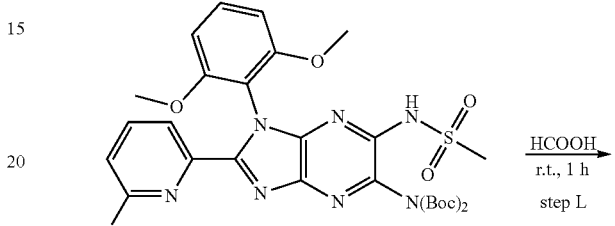

step L

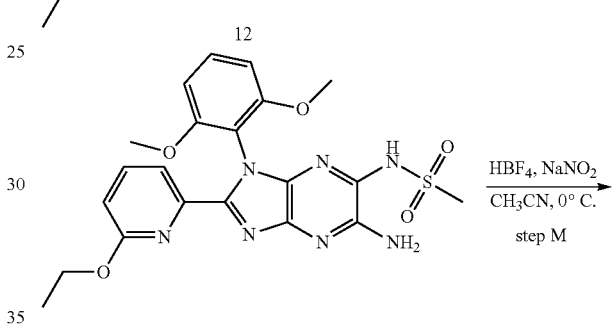

Example 145 step M

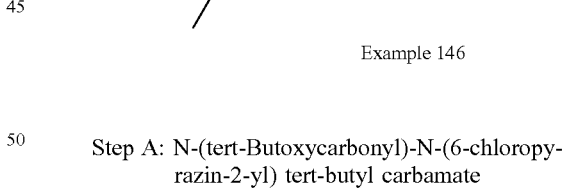

Example 146

Step A: N-(tert-Butoxycarbonyl)-N-(6-chloropyrazin-2-yl) tert-butyl carbamate

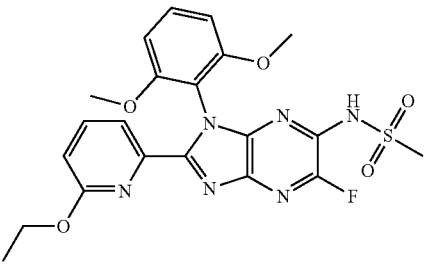

To a solution of 6-chloropyrazin-2-amine (20.0 g 154 mmol, 1.0 equiv) and (Boc)$_2$O (101 g, 462 mmol, 3.0 equiv) in DCM (250 mL) was added DMAP (1.90 g, 15.4 mmol, 0.10 equiv). The mixture was stirred at room temperature for 3 hours. The solvent was evaporated in vacuum and the residue was purified by silica gel column chromatography (eluted with PE/EtOAc=95/5) to afford the title compound N-(tert-butoxycarbonyl)-N-(6-chloropyrazin-2-yl) tert-butyl carbamate as a white solid (49.8 g, 98% yield). LC-MS: m/z 330.1 (M+H)⁺

Step B: N-(tert-Butoxycarbonyl)-N-(6-acetylamidopyrazin-2-yl) tert-butyl carbamate

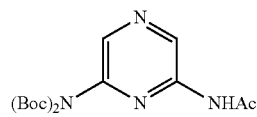

A suspension of N-(tert-butoxycarbonyl)-N-(6-chloropyrazin-2-yl) tert-butyl carbamate (15.0 g, 45.6 mmol, 1.0 equiv), acetamide (5.40 g, 91.2 mmol, 2.0 equiv), Pd(OAc)₂ (2.10 g, 9.12 mmol, 0.20 equiv), Xantphos (10.5 g, 18.2 mmol, 0.40 equiv) and K₂CO₃ (12.6 g, 91.2 mmol, 2.0 equiv) in 1,4-dioxane (250 mL) was refluxed under N₂ for 5 hours. The reaction mixture was poured into water (500 mL) and extracted with DCM (500 mL*3). The extracts were dried over anhydrous Na₂SO₄ and evaporated to dryness. The residue was purified by silica gel column chromatography (eluted with PE/EtOAc=3/1) to afford the title compound N-(tert-butoxycarbonyl)-N-(6-acetylamidopyrazin-2-yl) tert-butyl carbamate as a yellow solid (14.0 g, 87% yield). LC-MS: m/z 353.2 (M+H)⁺

Step C: N-(6-Aminopyrazin-2-yl)acetamide

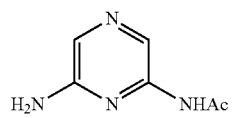

To a solution of N-(tert-butoxycarbonyl)-N-(6-acetylamidopyrazin-2-yl) tert-butyl carbamate (14.0 g, 39.8 mmol, 1.0 equiv) in DCM (200 mL) was added TFA (40 mL). The mixture was stirred at room temperature for 1 hour. Then the mixture was adjusted to pH 8 with Na₂CO₃ aqueous solution and the resulting mixture was concentrated under vacuum. The residue was purified by silica gel column chromatography (eluted with DCM/MeOH=20/1) to afford the title compound N-(6-aminopyrazin-2-yl)acetamide as a yellow solid (5.00 g, 83% yield). LC-MS: m/z 153.1 (M+H)⁺

Step D: N-(6-Amino-3,5-dibromopyrazin-2-yl)acetamide

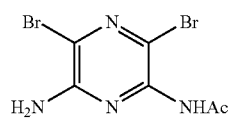

To a solution of N-(6-aminopyrazin-2-yl)acetamide (5.00 g, 32.9 mmol, 1.0 equiv) in ACN (400 mL) was added NBS (12.9 g, 72.4 mmol, 2.2 equiv) under N₂. The resulting mixture was stirred at room temperature for 4 hours. The solvent was evaporated and the residue was washed by H₂O for 3 times. The resulting mixture was purified by silica gel column chromatography (eluted with DCM/MeOH=30/1) to afford the title compound N-(6-amino-3,5-dibromopyrazin-2-yl)acetamide as a light yellow solid (7.70 g, 76% yield). LC-MS: m/z 308.9, 310.9, 312.9 (M+H)⁺. ¹H NMR (400 MHz, DMSO-d₆) δ: 10.01 (s, 1H), 6.99 (br. s, 2H), 2.03 (s, 3H).

Step E: N-(6-Acetamido-3,5-dibromopyrazin-2-yl)-6-ethoxypicolinamide

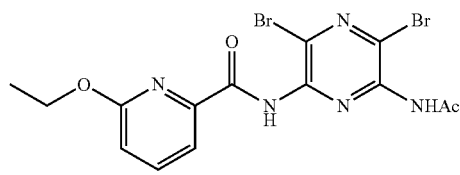 [SMILES: CCOc1cccc(C(=O)Nc2nc(NC(C)=O)c(Br)nc2Br)n1]

To a solution of N-(6-amino-3,5-dibromopyrazin-2-yl) acetamide (5.00 g, 16.1 mmol, 1.0 equiv) in THF (200 mL) was added NaH (60% in mineral oil, 3.40 g, 48.4 mmol, 3.0 equiv) at 0° C. The mixture was warmed up to room temperature and kept stirring for 1 hour. 6-Ethoxypicolinoyl chloride (3.60 g, 19.4 mmol, 1.20 equiv) in DCM (10 mL) was added dropwise at 0° C. The mixture was stirred at room temperature for another 1 hour. Then the mixture was adjusted to pH7 with HCl aqueous solution and the solvent was evaporated under vacuum. The residue was purified by silica gel column chromatography (eluted with DCM/EtOAc=4/1) to afford the title compound N-(6-acetamido-3,5-dibromopyrazin-2-yl)-6-ethoxypicolinamide as a pale yellow solid (3.20 g, 43% yield). LC-MS: m/z 457.9, 459.9, 461.9 (M+H)⁺

Step F: N-(6-Amino-3,5-dibromopyrazin-2-yl)-6-ethoxypicolinamide

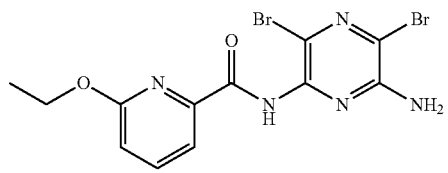 [SMILES: CCOc1cccc(C(=O)Nc2nc(N)c(Br)nc2Br)n1]

A solution of N-(6-acetamido-3,5-dibromopyrazin-2-yl)-6-ethoxypicolinamide (3.20 g, 6.97 mmol, 1.0 equiv) in HCl (15% aqueous, 60 mL) and MeOH (100 mL) was stirred at 50° C. for 5 hours. Then the mixture was adjusted to pH8 with Na₂CO₃ aqueous solution and the mixture was concentrated under vacuum. The residue was purified by silica gel column chromatography (eluted with DCM/MeOH=30/1) to afford the title compound N-(6-amino-3,5-dibromopyrazin-2-yl)-6-ethoxypicolinamide as a yellow solid (2.00 g, 67% yield). LC-MS: m/z 415.9, 417.9, 419.9 (M+H)⁺

Step G: N-(6-Bis(tert-butoxycarbonyl)amino-3,5-dibromopyrazin-2-yl)-6-ethoxypicolinamide

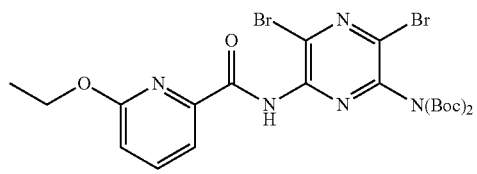

A suspension of N-(6-amino-3,5-dibromopyrazin-2-yl)-6-ethoxypicolinamide (2.00 g, 4.70 mmol, 1.0 equiv) and (Boc)$_2$O (2.00 g, 9.40 mmol, 2.0 equiv) in DCM (100 mL) was added Et$_3$N (1.50 g, 14.1 mmol, 3.0 equiv) and DMAP (57.3 mg, 0.470 mmol, 0.10 equiv). The mixture was stirred at room temperature for 3 hours. Then the mixture was concentrated in vacuo and the residue was purified by silica gel column chromatography (eluted with PE/EtOAc=4/1) to afford the title compound N-(6-bis(tert-butoxycarbonyl)amino-3,5-dibromopyrazin-2-yl)-6-ethoxypicolinamide as a white solid (1.10 g, 39% yield). LC-MS: m/z 616.0, 618.0, 620.0 (M+H)$^+$

Step H: N-(6-Bis(tert-butoxycarbonyl)amino-5-bromo-3-((2,6-dimethoxyphenyl)amino)pyrazin-2-yl)-6-ethoxypicolinamide

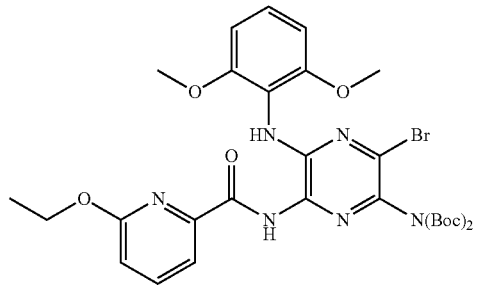

A suspension of N-(6-bis(tert-butoxycarbonyl)amino-3,5-dibromopyrazin-2-yl)-6-ethoxypicolinamide (980 mg, 1.60 mmol, 1.0 equiv), 2,6-dimethoxyaniline (487 mg, 3.20 mmol, 2.0 equiv), Pd$_2$(dba)$_3$ (293 mg, 0.300 mmol, 0.20 equiv), Xantphos (371 mg, 0.600 mmol, 0.40 equiv) and K$_2$CO$_3$ (657 mg, 4.80 mmol, 3.0 equiv) in 1,4-dioxane (12 mL) was stirred at 120° C. via microwave irradiation under N$_2$ for 2 hours. Then the mixture was concentrated in vacuo and the residue was purified by silica gel column chromatography (eluted with PE/EtOAc=5/1) to afford the title compound N-(6-bis(tert-butoxycarbonyl)amino-5-bromo-3-((2,6-dimethoxyphenyl)amino)pyrazin-2-yl)-6-ethoxypicolinamide as a yellow solid (750 mg, 69% yield).

LC-MS: m/z 689.2, 691.2 (M+H)$^+$

Step I: 6-Bromo-1-(2,6-dimethoxyphenyl)-2-(6-ethoxypyridin-2-yl)-1H-imidazo[4,5-b]pyrazin-5-amine

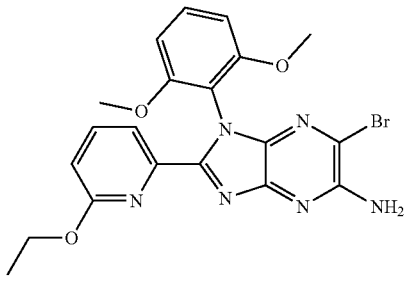 [SMILES: CCOc1cccc(-c2nc3nc(N)c(Br)nc3n2-c2c(OC)cccc2OC)n1]

A solution of N-(6-bis(tert-butoxycarbonyl)amino-5-bromo-3-((2,6-dimethoxyphenyl)amino)pyrazin-2-yl)-6-ethoxypicolinamide (750 mg, 1.10 mmol, 1.0 equiv) in AcOH (10 mL) was stirred at 145° C. via microwave irradiation for 1 hour. Then the mixture was concentrated in vacuo and the residue was purified by prep-HPLC (eluted with CH$_3$CN/H$_2$O=5/95~95/5 including 0.1% TFA) to afford the title compound 6-bromo-1-(2,6-dimethoxyphenyl)-2-(6-ethoxypyridin-2-yl)-1H-imidazo[4,5-b]pyrazin-5-amine as a yellow solid (200 mg, 39% yield). LC-MS: m/z 471.1, 473.1 (M+H)$^+$

Step J: N-(tert-Butoxycarbonyl)-N-(6-bromo-1-(2,6-dimethoxyphenyl)-2-(6-ethoxypyridin-2-yl)-1H-imidazo[4,5-b]pyrazin-5-yl) tert-butyl carbamate

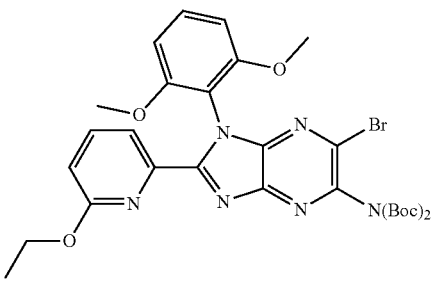

A solution of 6-bromo-1-(2,6-dimethoxyphenyl)-2-(6-ethoxypyridin-2-yl)-1H-imidazo[4,5-b]pyrazin-5-amine (200 mg, 0.400 mmol, 1.0 equiv) and (Boc)$_2$O (463 mg, 2.00 mmol, 5.0 equiv) in 1,4-dioxane (10 mL) was added Et$_3$N (139 mg, 1.20 mmol, 3.0 equiv) and DMAP (5.30 mg, 0.0400 mmol, 0.10 equiv). The mixture was stirred at 80° C. overnight. Then the reaction mixture was concentrated in vacuo and the residue was purified by silica gel column chromatography (eluted with PE/EtOAc=2/1) to afford the title compound N-(tert-butoxycarbonyl)-N-(6-bromo-1-(2,6-dimethoxyphenyl)-2-(6-ethoxypyridin-2-yl)-1H-imidazo[4,5-b]pyrazin-5-yl) tert-butyl carbamate as a yellow solid (200 mg, 71% yield). LC-MS: m/z 671.2, 673.2 (M+H)$^+$ Step K: N-(tert-Butoxycarbonyl)-N-(1-(2,6-dimethoxyphenyl)-2-(6-ethoxypyridin-2-yl)-6-(methylsulfonamido)-1H-imidazo[4,5-b]pyrazin-5-yl) tert-butyl carbamate

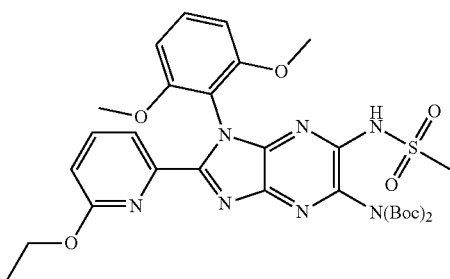

A suspension of N-(tert-butoxycarbonyl)-N-(6-bromo-1-(2,6-dimethoxyphenyl)-2-(6-ethoxypyridin-2-yl)-1H-imidazo[4,5-b]pyrazin-5-yl) tert-butyl carbamate (200 mg, 0.300 mmol, 1.0 equiv), methanesulfonamide (143 mg, 1.50 mmol, 5.0 equiv), $N^1,N^2$-dimethylcyclohexane-1,2-diamine (85.0 mg, 0.600 mmol, 2.0 equiv), CuI (114 mg, 0.600 mmol, 2.0 equiv) and $K_2CO_3$ (124 mg, 0.900 mmol, 3.0 equiv) in DMF (5 mL) was stirred at 120° C. via microwave irradiation under $N_2$ for 5 hours. The mixture was poured into a mixture of water (50 mL) and HCOOH (2 mL), and extracted with DCM (50 mL*3). The combined organic layers were dried over $Na_2SO_4$ and concentrated under vacuum. The residue was purified by prep-HPLC (eluted with $CH_3CN/H_2O=5/95\sim95/5$ including 0.1% HCOOH) to afford the title compound N-(tert-butoxycarbonyl)-N-(1-(2,6-dimethoxyphenyl)-2-(6-ethoxypyridin-2-yl)-6-(methylsulfonamido)-1H-imidazo[4,5-b]pyrazin-5-yl) tert-butyl carbamate as a yellow solid (48.0 mg, 23% yield). LC-MS: m/z 686.3 (M+H)$^+$ Step L: N-(5-Amino-1-(2,6-dimethoxyphenyl)-2-(6-ethoxypyridin-2-yl)-1H-imidazo[4,5-b]pyrazin-6-yl)methanesulfonamide (Example 145)

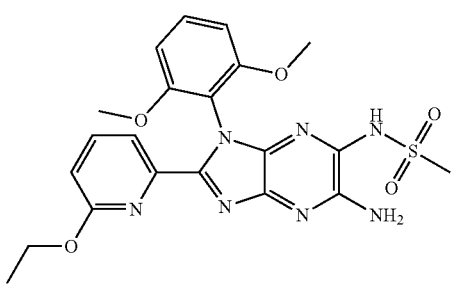 [SMILES: CCOc1cccc(-c2nc3nc(N)c(NS(C)(=O)=O)nc3n2-c2c(OC)cccc2OC)n1]

A solution of N-(tert-butoxycarbonyl)-N-(1-(2,6-dimethoxyphenyl)-2-(6-ethoxypyridin-2-yl)-6-(methylsulfonamido)-1H-imidazo[4,5-b]pyrazin-5-yl) tert-butyl carbamate (48.0 mg, 0.0700 mmol, 1.0 equiv) in HCOOH (10 mL) was stirred at room temperature for 1 hour. The mixture was concentrated under vacuum and the residue was purified by prep-HPLC (eluted with $CH_3CN/H_2O=5/95\sim95/5$ including 0.1% TFA) to afford the title compound N-(5-amino-1-(2,6-dimethoxyphenyl)-2-(6-ethoxypyridin-2-yl)-1H-imidazo[4,5-b]pyrazin-6-yl)methanesulfonamide as a yellow solid (27.0 mg, 80% yield). LC-MS: m/z 486.2 (M+H)$^+$. $^1$H NMR (400 MHz, Chloroform-d) δ: 8.05 (d, J=7.6 Hz, 1H), 7.69 (t, J=8.0 Hz, 1H), 7.41 (t, J=8.4 Hz, 1H), 6.74 (d, J=8.4 Hz, 1H), 6.69 (d, J=8.4 Hz, 2H), 3.65 (s, 6H), 3.48 (q, J=7.2 Hz, 2H), 3.15 (s, 3H), 1.09 (t, J=7.2 Hz, 3H).

Step M: N-(1-(2,6-Dimethoxyphenyl)-2-(6-ethoxypyridin-2-yl)-5-fluoro-1H-imidazo[4,5-b]pyrazin-6-yl)methanesulfonamide (Example 146)

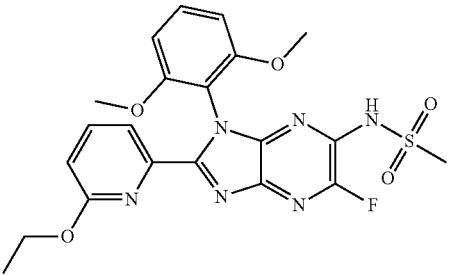 [SMILES: CCOc1cccc(-c2nc3nc(F)c(NS(C)(=O)=O)nc3n2-c2c(OC)cccc2OC)n1]

To a mixture of N-(5-amino-1-(2,6-dimethoxyphenyl)-2-(6-ethoxypyridin-2-yl)-1H-imidazo[4,5-b]pyrazin-6-yl)methanesulfonamide (27.0 mg, 0.0600 mmol, 1.0 equiv) in acetonitrile (2 mL) and $HBF_4$ (48% aqueous solution, 0.800 mL) was added $NaNO_2$ (4.70 mg, 0.0690 mmol, 1.15 equiv) at 0° C. After stirred for 1 hour at room temperature, the reaction mixture was poured into water (50 mL) and extracted with DCM (50 mL). The extracts were evaporated to dryness and the residue was purified by prep-HPLC (eluted with $CH_3CN/H_2O=5/95\sim95/5$ including 0.1% HCOOH) to afford the title compound N-(1-(2,6-dimethoxyphenyl)-2-(6-ethoxypyridin-2-yl)-5-fluoro-1H-imidazo[4,5-b]pyrazin-6-yl)methanesulfonamide as a yellow solid (5.00 mg, 20% yield). LC-MS: m/z 489.1 (M+H)$^+$. $^1$H NMR (400 MHz, Chloroform-d) δ: 8.07 (dd, J=7.6, 0.8 Hz, 1H), 7.68 (t, J=8.0 Hz, 1H), 7.37 (t, J=8.4 Hz, 1H), 7.17 (s, 1H), 6.65-6.72 (m, 3H), 3.62 (s, 6H), 3.43 (q, J=7.2 Hz, 2H), 3.28 (s, 3H), 1.07 (t, J=7.2 Hz, 3H).

Methods for Evaluating Compounds:

Activation of APJ receptor is known to inhibit forskolin-stimulated cyclic AMP (cAMP) production in cells in a pertussis toxin-sensitive manner which indicates primary coupling to the $G_{\alpha I}$ subunit of the G protein heterotrimeric complex. In addition to signaling through G protein and inhibition of cAMP, APJ receptor activation also results in β-arrestin recruitment, receptor internalization and activation of extracellular-regulated kinases (ERKs). Evidence suggests signaling through Gi induced cAMP inhibition elicits the desired inotropic and vasodilatory pharmacological response whereas arrestin recruitment results in receptor internalization, downregulation and ultimately cardiac hypertrophy.

In order to optimize functional activity directed toward Gi coupling we utilized a CHO-K1 cell line developed by DiscoverX stably expressing the APJ Receptor. Cells expressing APJR receptor were plated in a 384-well microtiter plates and incubated overnight at 37° C. with 5% $CO_2$ to allow the cells to attach and grow. Media was then aspirated from the cells and replaced with 15 uL 2:1 Hanks Balanced Salt Solution (HBSS)/10 mM Hepes:cAMP XS+ Ab reagent. Five microliters (5 uL) of previously generated compound sample stocks at 4× final concentration in assay buffer containing 4× EC80 forskolin were then added to the cells and allowed to incubate at 37° C. for 30 minutes.

After incubation the assay signal was generated using a technology termed enzyme fragment complementation (EFC). In EFC the enzyme B-galactosidase is split into two complementary portions (EA and ED). The fragment ED is fused to cAMP and in the assay format competes with endogenous cAMP for binding to a cAMP specific antibody. Activated B-Gal is formed when exogenous EA fragment binds to free ED-cAMP (not bound to cAMP specific antibody). Activated enzyme levels are detected through conversion of B-gal chemiluminescent substrate which generates a detectable luminescence signal and read on standard microtiter plate.

The methodology for detection of cAMP using EFC requires incubation with 20 uL of cAMP XS+ ED/CL lysis cocktail for one hour followed by incubation with 20 uL cAMP XS+ EA reagent for three hours at room temperature. Microplates were read following signal generation with a PerkinElmer Envision instrument utilizing chemiluminescent signal detection.

Compound activity was analyzed using CBIS data analysis suite (ChemInnovation, CA). Percentage activity was calculated using the following formula:

% Activity=100%×(1−(mean RLU of test sample−mean RLU of Max control)/(mean RLU of vehicle control−mean RLU of Max control))

The biological activity of the exemplified compounds of this invention determined by the assay described above is shown in Table 1. The APJ cAMP EC50 potency ranges are as follows: A: EC50<1 nM; B: 1≤EC50<100 nM; and C: 100≤EC50<10,000 nM.

TABLE 1

Example compounds and their potency range

| Example # | Structure | IUPAC Name | Potency Range |
|---|---|---|---|
| 1 | 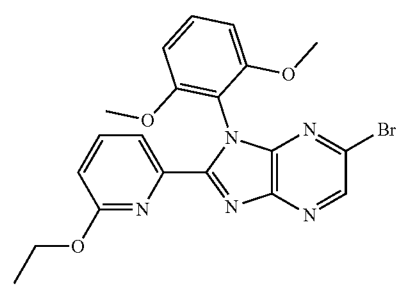 [SMILES: CCOc1cccc(-c2nc3ncc(Br)nc3n2-c2c(OC)cccc2OC)n1] | 6-bromo-1-(2,6-dimethoxyphenyl)-2-(6-ethoxypyridin-2-yl)-1H-imidazo[4,5-b]pyrazine | C |
| 2 | 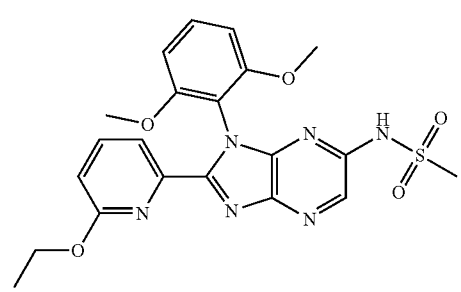 | N-(1-(2,6-dimethoxyphenyl)-2-(6-ethoxypyridin-2-yl)-1H-imidazo[4,5-b]pyrazin-6-yl)methanesulfonamide | B |
| 3 | 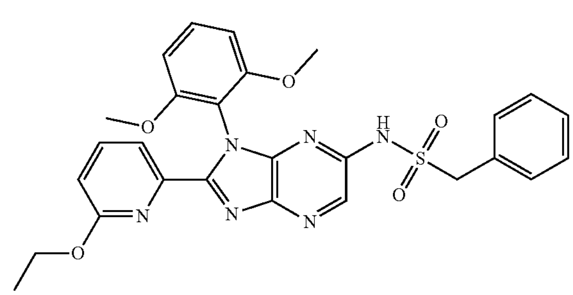 [SMILES: CCOc1cccc(-c2nc3ncc(NS(=O)(=O)Cc4ccccc4)nc3n2-c2c(OC)cccc2OC)n1] | N-(1-(2,6 dimethoxyphenyl)-2-(6-ethoxypyridin-2-yl)-1H imidazo[4,5-b]pyrazin-6-yl)-1-phenylmethanesulfonamide | B |

TABLE 1-continued

Example compounds and their potency range

| Example # | Structure | IUPAC Name | Potency Range |
|---|---|---|---|
| 4 | 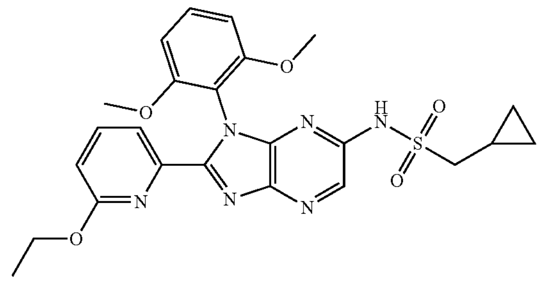 [SMILES: CCOc1cccc(-c2nc3ncc(NS(=O)(=O)CC4CC4)nc3n2-c2c(OC)cccc2OC)n1] | 1-cyclopropyl-N-(1-(2,6-dimethoxyphenyl)-2-(6-ethoxypyridin-2-yl)-1H-imidazo[4,5-b]pyrazin-6-yl)methanesulfonamide | B |
| 5 | 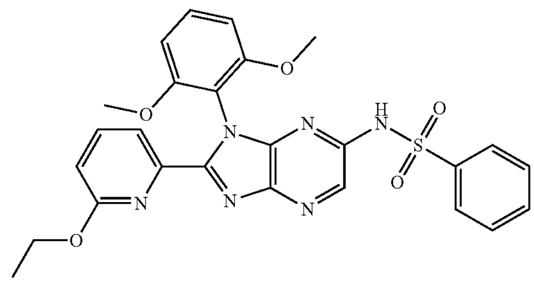 [SMILES: CCOc1cccc(-c2nc3ncc(NS(=O)(=O)c4ccccc4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)benzenesulfonamide | A |
| 6 | 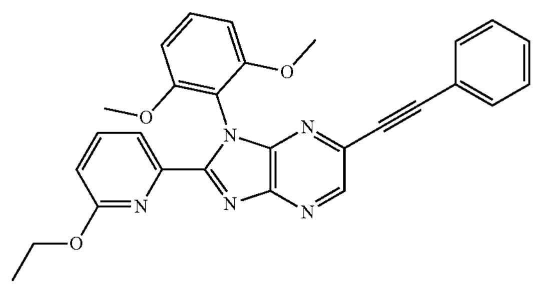 [SMILES: CCOc1cccc(-c2nc3ncc(C#Cc4ccccc4)nc3n2-c2c(OC)cccc2OC)n1] | 1-(2,6-dimethoxyphenyl)-2-(6-ethoxypyridin-2-yl)-6-(phenylethynyl)-1H-imidazo[4,5-b]pyrazine | C |
| 7 | 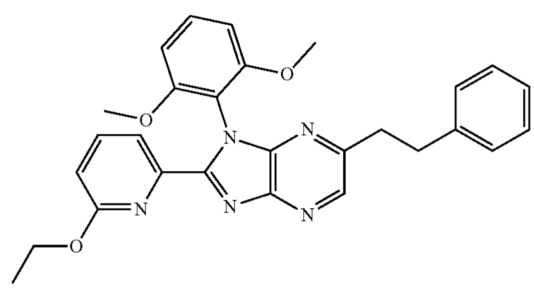 [SMILES: CCOc1cccc(-c2nc3ncc(CCc4ccccc4)nc3n2-c2c(OC)cccc2OC)n1] | 1-(2,6-dimethoxyphenyl)-2-(6-ethoxypyridin-2-yl)-6-phenethyl-1H-imidazo[4,5-b]pyrazine | B |
| 8 | 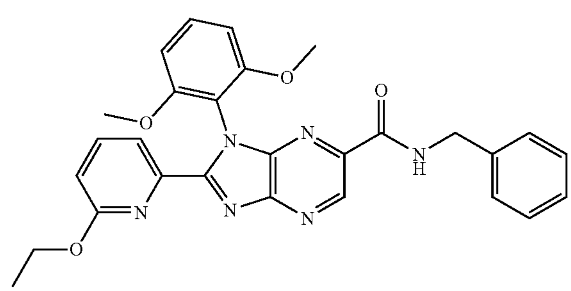 [SMILES: CCOc1cccc(-c2nc3ncc(C(=O)NCc4ccccc4)nc3n2-c2c(OC)cccc2OC)n1] | N-Benzyl-1-(2,6-dimethoxyphenyl)-2-(6-ethoxypyridin-2-yl)-1H-imidazo[4,5-b]pyrazine-6-carboxamide | C |

TABLE 1-continued

Example compounds and their potency range

| Example # | Structure | IUPAC Name | Potency Range |
|---|---|---|---|
| 9 | 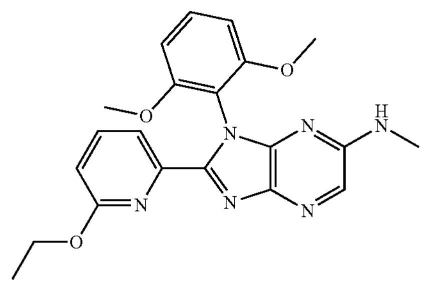 [SMILES: CCOc1cccc(-c2nc3ncc(NC)nc3n2-c2c(OC)cccc2OC)n1] | 1-(2,6-dimethoxyphenyl)-2-(6-ethoxypyridin-2-yl)-N-methyl-1H-imidazo[4,5-b]pyrazin-6-amine | B |
| 10 | 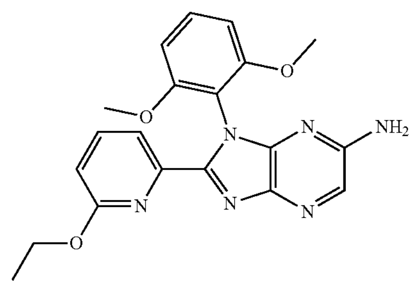 [SMILES: CCOc1cccc(-c2nc3ncc(N)nc3n2-c2c(OC)cccc2OC)n1] | 1-(2,6-dimethoxyphenyl)-2-(6-ethoxypyridin-2-yl)-1H-imidazo[4,5-b]pyrazin-6-amine | B |
| 11 | 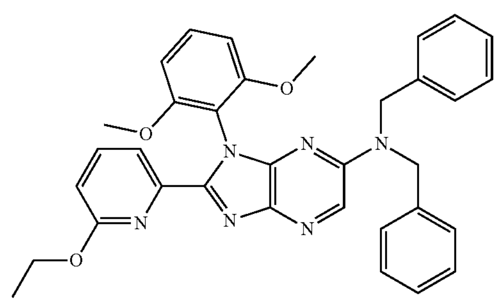 [SMILES: CCOc1cccc(-c2nc3ncc(N(Cc4ccccc4)Cc4ccccc4)nc3n2-c2c(OC)cccc2OC)n1] | N,N-dibenzyl-1-(2,6-dimethoxyphenyl)-2-(6-ethoxypyridin-2-yl)-1H-imidazo[4,5-b]pyrazin-6-amine | B |
| 12 | 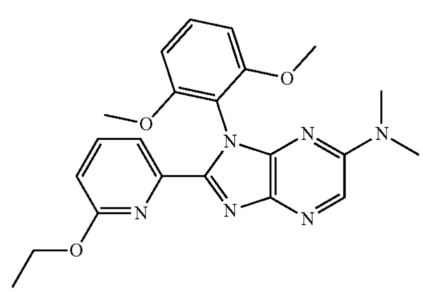 [SMILES: CCOc1cccc(-c2nc3ncc(N(C)C)nc3n2-c2c(OC)cccc2OC)n1] | 1-(2,6-dimethoxyphenyl)-2-(6-ethoxypyridin-2-yl)-N,N-dimethyl-1H-imidazo[4,5-b]pyrazin-6-amine | C |
| 13 | 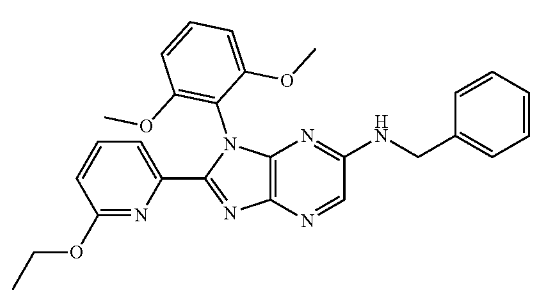 [SMILES: CCOc1cccc(-c2nc3ncc(NCc4ccccc4)nc3n2-c2c(OC)cccc2OC)n1] | N-benzyl-1-(2,6-dimethoxyphenyl)-2-(6-ethoxypyridin-2-yl)-1H-imidazo[4,5-b]pyrazin-6-amine | B |

TABLE 1-continued

Example compounds and their potency range

| Example # | Structure | IUPAC Name | Potency Range |
|---|---|---|---|
| 14 | 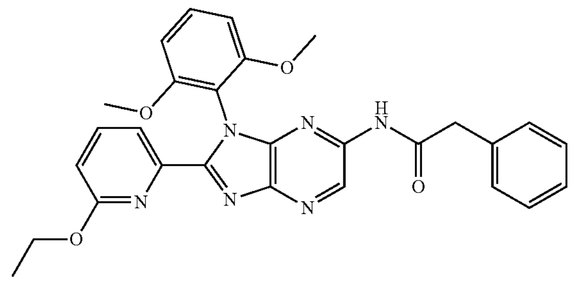 [SMILES: CCOc1cccc(-c2nc3ncc(NC(=O)Cc4ccccc4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-2-phenylacetamide | B |
| 15 | 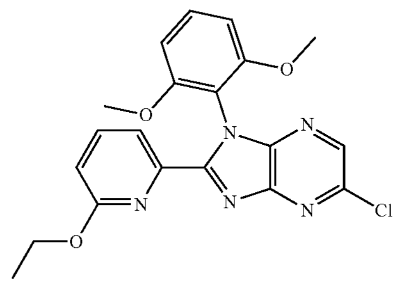 [SMILES: CCOc1cccc(-c2nc3nc(Cl)cnc3n2-c2c(OC)cccc2OC)n1] | 5-chloro-1-(2,6-dimethoxyphenyl)-2-(6-ethoxypyridin-2-yl)-1H-imidazo[4,5-b]pyrazine | C |
| 16 | 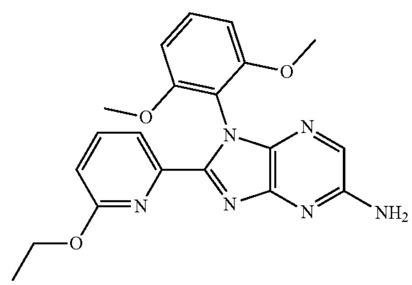 [SMILES: CCOc1cccc(-c2nc3nc(N)cnc3n2-c2c(OC)cccc2OC)n1] | 1-(2,6-dimethoxyphenyl)-2-(6-ethoxypyridin-2-yl)-1H-imidazo[4,5-b]pyrazin-5-amine | B |
| 17 | 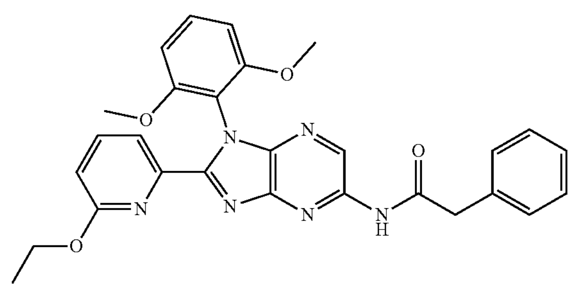 [SMILES: CCOc1cccc(-c2nc3nc(NC(=O)Cc4ccccc4)cnc3n2-c2c(OC)cccc2OC)n1] | N-(1-(2,6-dimethoxyphenyl)-2-(6-ethoxypyridin-2-yl)-1H-imidazo[4,5-b]pyrazin-5-yl)-2-phenylacetamide | B |
| 18 | 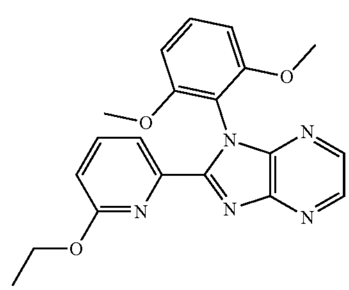 [SMILES: CCOc1cccc(-c2nc3nccnc3n2-c2c(OC)cccc2OC)n1] | 1-(2,6-dimethoxyphenyl)-2-(6-ethoxypyridin-2-yl)-1H-imidazo[4,5-b]pyrazine | C |

TABLE 1-continued

Example compounds and their potency range

| Example # | Structure | IUPAC Name | Potency Range |
|---|---|---|---|
| 19 | 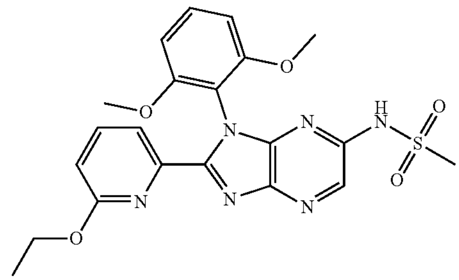 [SMILES: CCOc1cccc(-c2nc3ncc(NS(C)(=O)=O)nc3n2-c2c(OC)cccc2OC)n1] | N-(5-(2,6-dimethoxyphenyl)-6-(6-ethoxypyridin-2-yl)-5H-pyrrolo[2,3-b]pyrazin-3-yl)methanesulfonamide | C |
| 20 | 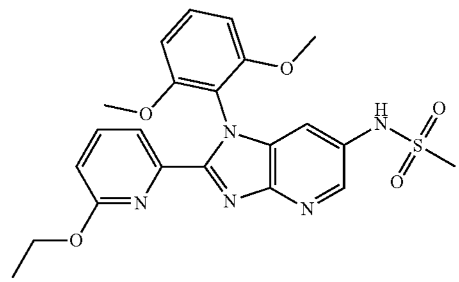 [SMILES: CCOc1cccc(-c2nc3ncc(NS(C)(=O)=O)cc3n2-c2c(OC)cccc2OC)n1] | N-(1-(2,6-dimethoxyphenyl)-2-(6-ethoxypyridin-2-yl)-1H-imidazo[4,5-b]pyridin-6-yl)methanesulfonamide | B |
| 21 | 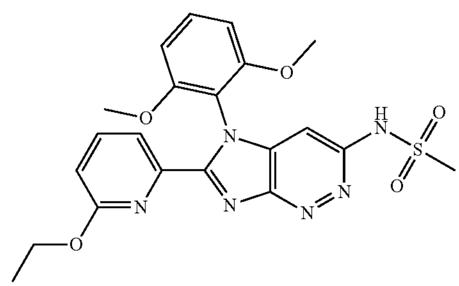 | N-(5-(2,6-dimethoxyphenyl)-6-(6-ethoxypyridin-2-yl)-5H-imidazo[4,5-c]pyridazin-3-yl)methanesulfonamide | B |
| 22 | 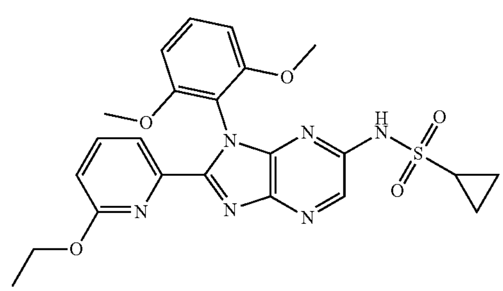 [SMILES: CCOc1cccc(-c2nc3ncc(NS(=O)(=O)C4CC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)cyclopropanesulfonamide | B |
| 23 | 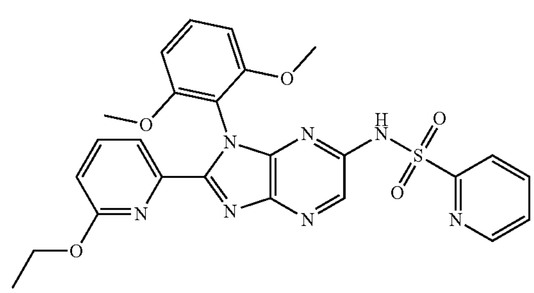 | N-(1-(2,6-dimethoxyphenyl)-2-(6-ethoxypyridin-2-yl)-1H-imidazo[4,5-b]pyrazin-6-yl)pyridine-2-sulfonamide | A |

TABLE 1-continued

Example compounds and their potency range

| Example # | Structure | IUPAC Name | Potency Range |
|---|---|---|---|
| 24 | 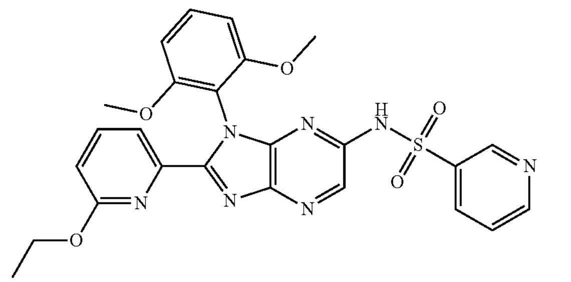 [SMILES: CCOc1cccc(-c2nc3ncc(NS(=O)(=O)c4cccnc4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)pyridine-3-sulfonamide | B |
| 25 | 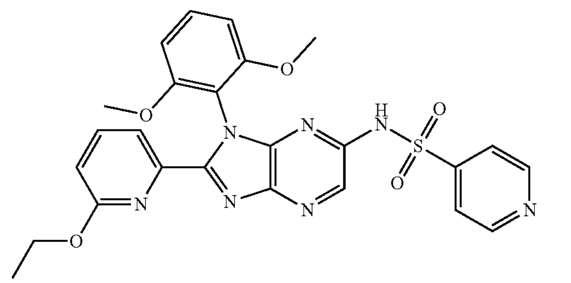 [SMILES: CCOc1cccc(-c2nc3ncc(NS(=O)(=O)c4ccncc4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)pyridine-4-sulfonamide | B |
| 26 | 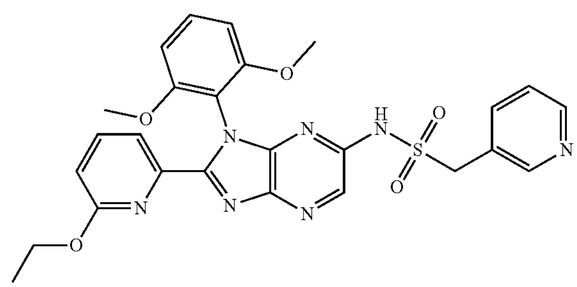 [SMILES: CCOc1cccc(-c2nc3ncc(NS(=O)(=O)Cc4cccnc4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-1-(pyridin-3-yl)methanesulfonamide | B |
| 27 | 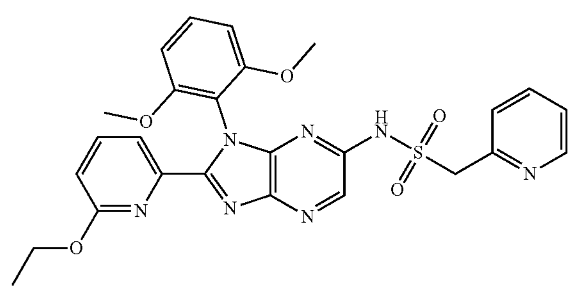 | N-(1-(2,6-dimethoxyphenyl)-2-(6-ethoxypyridin-2-yl)-1H-imidazo[4,5-b]pyrazin-6-yl)-1-(pyridin-2-yl)methanesulfonamide | B |
| 28 | 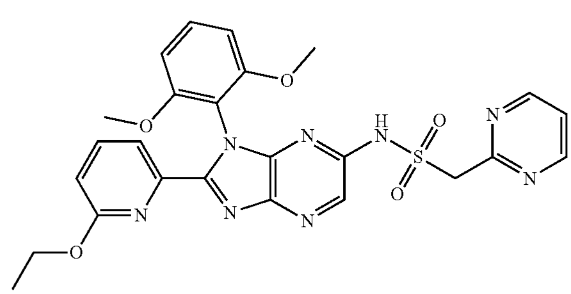 [SMILES: CCOc1cccc(-c2nc3ncc(NS(=O)(=O)Cc4ncccn4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-1-(pyrimidin-2-yl)methanesulfonamide | A |

TABLE 1-continued

Example compounds and their potency range

| Example # | Structure | IUPAC Name | Potency Range |
|---|---|---|---|
| 29 | 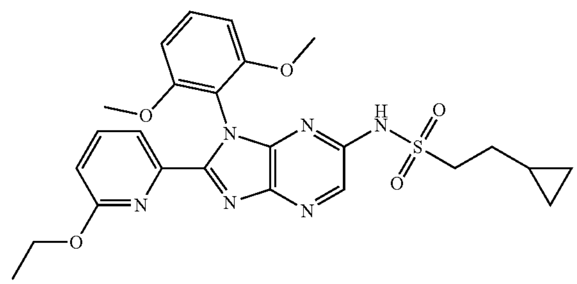 [SMILES: CCOc1cccc(-c2nc3ncc(NS(=O)(=O)CCC4CC4)nc3n2-c2c(OC)cccc2OC)n1] | 2-cyclopropyl-N-(1-(2,6-dimethoxyphenyl)-2-(6-ethoxypyridin-2-yl)-1H-imidazo[4,5-b]pyrazin-6-yl)ethanesulfonamide | A |
| 30 | 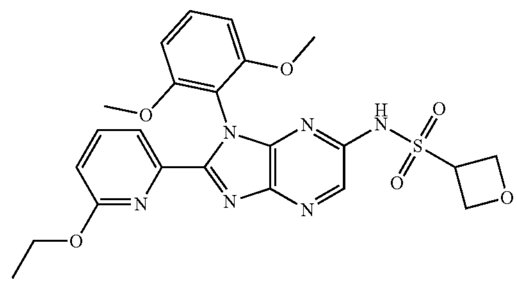 [SMILES: CCOc1cccc(-c2nc3ncc(NS(=O)(=O)C4COC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)oxetane-3-sulfonamide | B |
| 31 | 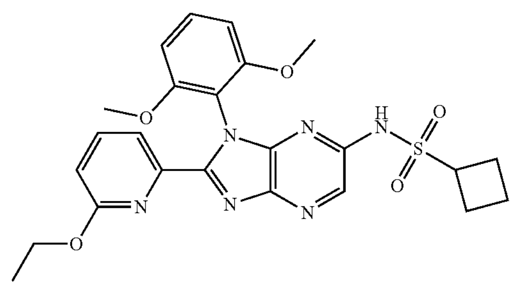 [SMILES: CCOc1cccc(-c2nc3ncc(NS(=O)(=O)C4CCC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)cyclobutanesulfonamide | B |
| 32 | 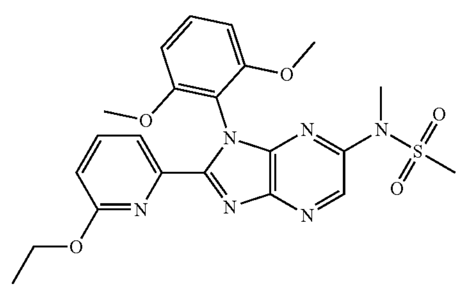 [SMILES: CCOc1cccc(-c2nc3ncc(N(C)S(C)(=O)=O)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-N-methylmethanesulfonamide | C |
| 33 | 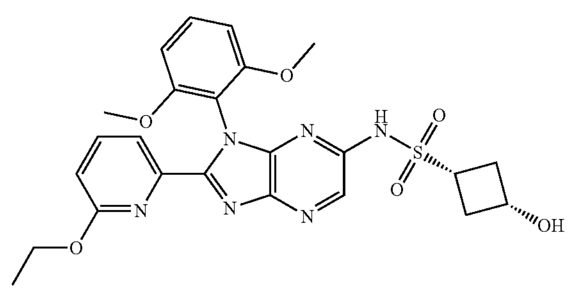 [SMILES: CCOc1cccc(-c2nc3ncc(NS(=O)(=O)[C@H]4C[C@@H](O)C4)nc3n2-c2c(OC)cccc2OC)n1] | cis-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide | B |

TABLE 1-continued

Example compounds and their potency range

| Example # | Structure | IUPAC Name | Potency Range |
|---|---|---|---|
| 34 | 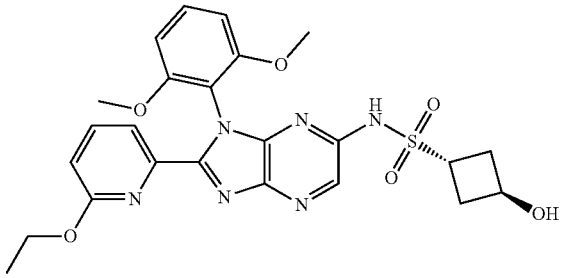 [SMILES: CCOc1cccc(-c2nc3ncc(NS(=O)(=O)[C@H]4C[C@H](O)C4)nc3n2-c2c(OC)cccc2OC)n1] | trans-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide | B |
| 35 | 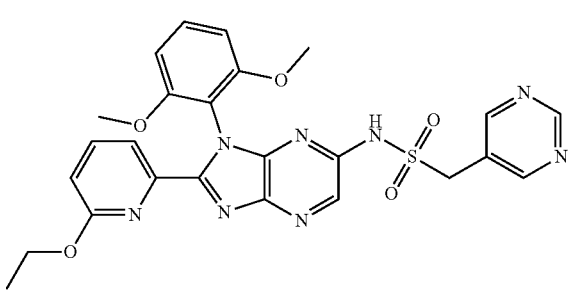 [SMILES: CCOc1cccc(-c2nc3ncc(NS(=O)(=O)Cc4cncnc4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-1-(pyrimidin-5-yl)methanesulfonamide | B |
| 36 | 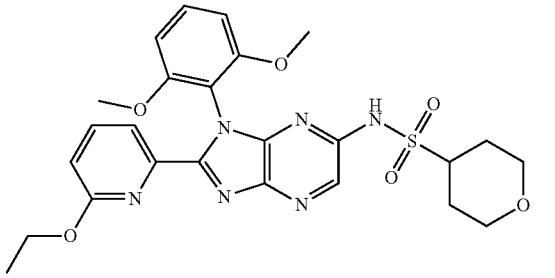 | N-(1-(2,6-dimethoxyphenyl)-2-(6-ethoxypyridin-2-yl)-1H-imidazo[4,5-b]pyrazin-6-yl)tetrahydro-2H-pyran-4-sulfonamide | B |
| 37 | 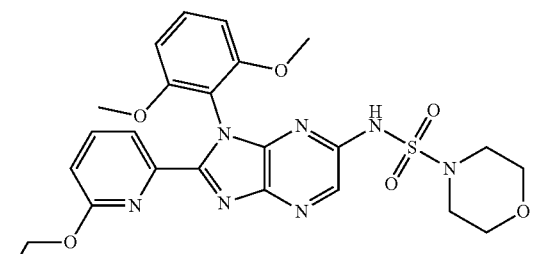 | N-(1-(2,6-dimethoxyphenyl)-2-(6-ethoxypyridin-2-yl)-1H-imidazo[4,5-b]pyrazin-6-yl)morpholine-4-sulfonamide | A |
| 38 | 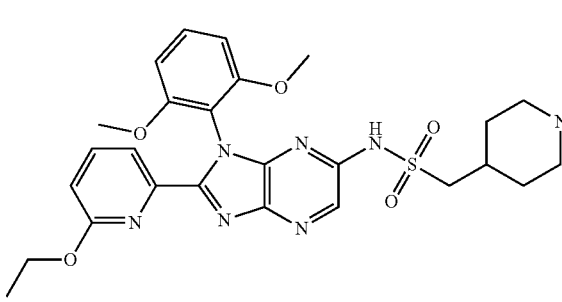 | N-(1-(2,6-dimethoxyphenyl)-2-(6-ethoxypyridin-2-yl)-1H-imidazo[4,5-b]pyrazin-6-yl)-1-(piperidin-4-yl)methanesulfonamide | B |

TABLE 1-continued

Example compounds and their potency range

| Example # | Structure | IUPAC Name | Potency Range |
|---|---|---|---|
| 39 | 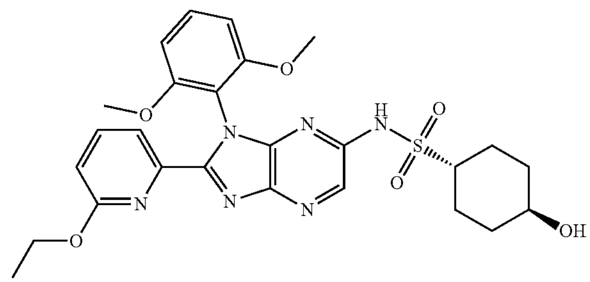 [SMILES: CCOc1cccc(-c2nc3ncc(NS(=O)(=O)[C@H]4CC[C@H](O)CC4)nc3n2-c2c(OC)cccc2OC)n1] | trans-N-(1-(2,6-dimethoxyphenyl)-2-(6-ethoxypyridin-2-yl)-1H-imidazo[4,5-b]pyrazin-6-yl)-4-hydroxycyclohexane-1-sulfonamide | A |
| 40 | 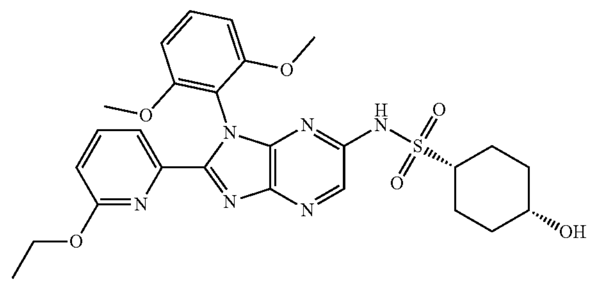 [SMILES: CCOc1cccc(-c2nc3ncc(NS(=O)(=O)[C@H]4CC[C@@H](O)CC4)nc3n2-c2c(OC)cccc2OC)n1] | cis-N-(1-(2,6-dimethoxyphenyl)-2-(6-ethoxypyridin-2-yl)-1H-imidazo[4,5-b]pyrazin-6-yl)-4-hydroxycyclohexane-1-sulfonamide | B |
| 41 | 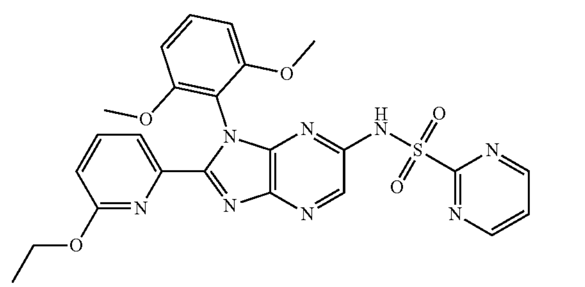 [SMILES: CCOc1cccc(-c2nc3ncc(NS(=O)(=O)c4ncccn4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)pyrimidine-2-sulfonamide | B |
| 42 | 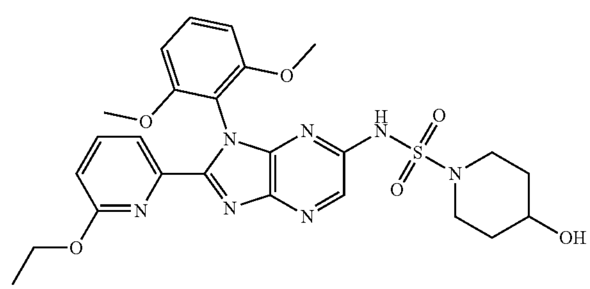 [SMILES: CCOc1cccc(-c2nc3ncc(NS(=O)(=O)N4CCC(O)CC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-4-hydroxypiperidine-1-sulfonamide | B |
| 43 | 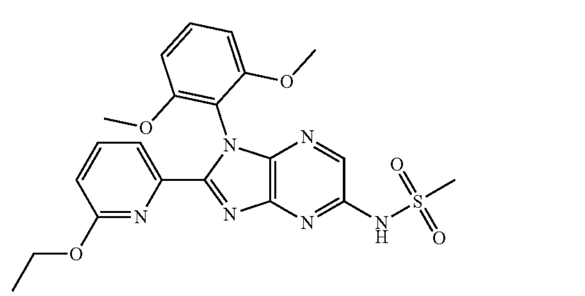 [SMILES: CCOc1cccc(-c2nc3nc(NS(C)(=O)=O)cnc3n2-c2c(OC)cccc2OC)n1] | N-(1-(2,6-dimethoxyphenyl)-2-(6-ethoxypyridin-2-yl)-1H-imidazo[4,5-b]pyrazin-5-yl)methanesulfonamide | B |

TABLE 1-continued

Example compounds and their potency range

| Example # | Structure | IUPAC Name | Potency Range |
|---|---|---|---|
| 44 | 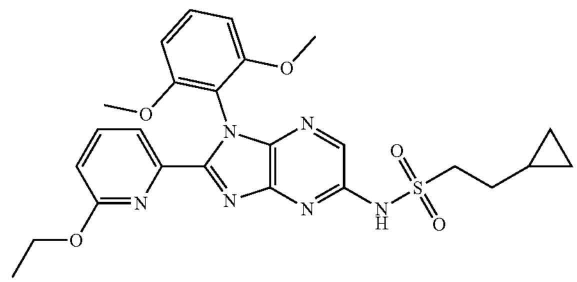 [SMILES: CCOc1cccc(-c2nc3nc(NS(=O)(=O)CCC4CC4)cnc3n2-c2c(OC)cccc2OC)n1] | N-(1-(2,6-dimethoxyphenyl)-2-(6-ethoxypyridin-2-yl)-1H-imidazo[4,5-b]pyrazin-5-yl)methanesulfonamide | A |
| 45 | 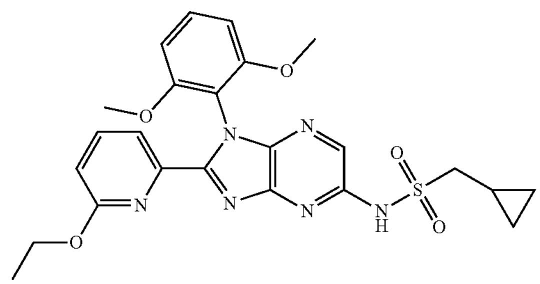 [SMILES: CCOc1cccc(-c2nc3nc(NS(=O)(=O)CC4CC4)cnc3n2-c2c(OC)cccc2OC)n1] | 1-cyclopropyl-N-(1-(2,6-dimethoxyphenyl)-2-(6-ethoxypyridin-2-yl)-1H-imidazo[4,5-b]pyrazin-5-yl)methanesulfonamide | A |
| 46 | 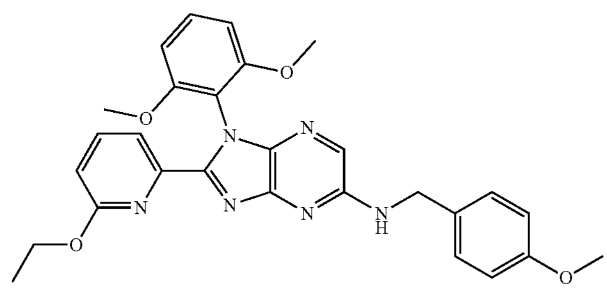 [SMILES: CCOc1cccc(-c2nc3nc(NCc4ccc(OC)cc4)cnc3n2-c2c(OC)cccc2OC)n1] | 1-(2,6-dimethoxyphenyl)-2-(6-ethoxypyridin-2-yl)-N-(4-methoxybenzyl)-1H-imidazo[4,5-b]pyrazin-5-amine | A |
| 47 | 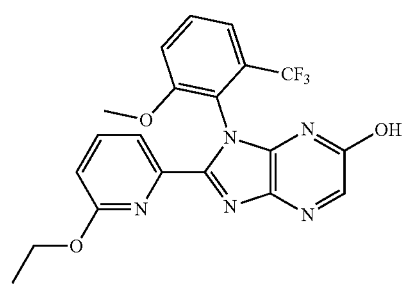 [SMILES: CCOc1cccc(-c2nc3ncc(O)nc3n2-c2c(OC)cccc2C(F)(F)F)n1] | 2-(6-ethoxypyridin-2-yl)-1-(2-methoxy-6-(trifluoromethyl)phenyl)-1H-imidazo[4,5-b]pyrazin-6-ol | C |
| 48 | 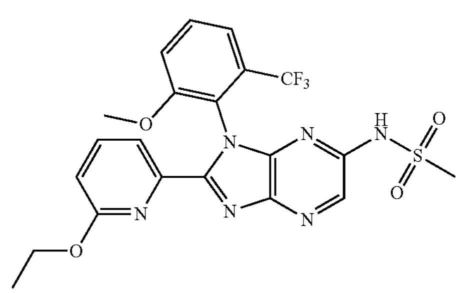 [SMILES: CCOc1cccc(-c2nc3ncc(NS(C)(=O)=O)nc3n2-c2c(OC)cccc2C(F)(F)F)n1] | N-(2-(6-ethoxypyridin-2-yl)-1-(2-methoxy-6-(trifluoromethyl)phenyl)-1H-imidazo[4,5-b]pyrazin-6-yl)methanesulfonamide | B |

TABLE 1-continued

Example compounds and their potency range

| Example # | Structure | IUPAC Name | Potency Range |
|---|---|---|---|
| 49 | 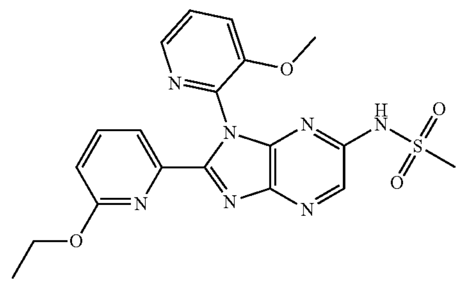 [SMILES: CCOc1cccc(-c2nc3ncc(NS(C)(=O)=O)nc3n2-c2ncccc2OC)n1] | N-(2-(6-ethoxypyridin-2-yl)-1-(3-methoxypyridin-2-yl)-1H-imidazo[4,5-b]pyrazin-6-yl)methanesulfonamide | C |
| 50 | 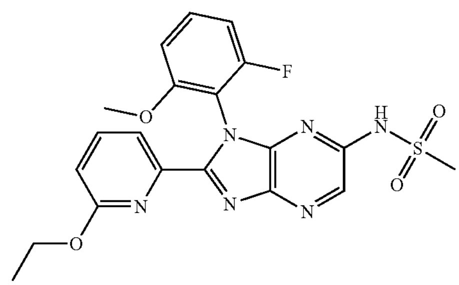 | N-(benzylsulfonyl)-4-(2-fluoro-6-methoxyphenyl)-5-(6-methoxypyridin-2-yl)-4H-1,2,4-triazole-3-carboxamide | B |
| 51 | 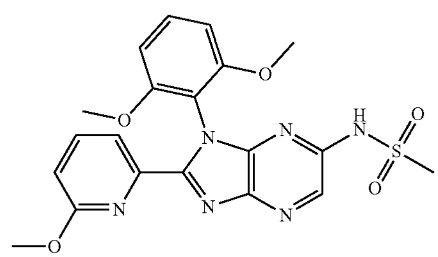 | N-(1-(2,6-dimethoxyphenyl)-2-(6-methoxypyridin-2-yl)-1H-imidazo[4,5-b]pyrazin-6-yl)methanesulfonamide | B |
| 52 | 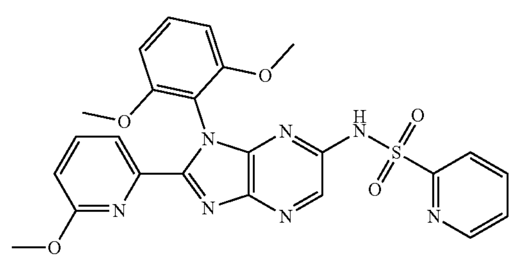 [SMILES: COc1cccc(-c2nc3ncc(NS(=O)(=O)c4ccccn4)nc3n2-c2c(OC)cccc2OC)n1] | N-(1-(2,6-dimethoxyphenyl)-2-(6-methoxypyridin-2-yl)-1H-imidazo[4,5-b]pyrazin-6-yl)pyridine-2-sulfonamide | B |
| 53 | 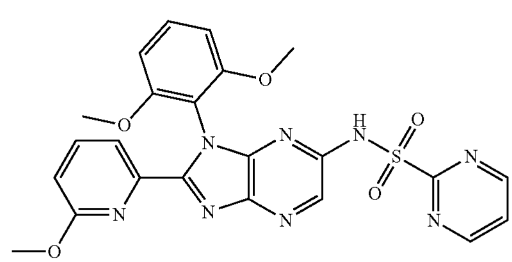 | N-(1-(2,6-dimethoxyphenyl)-2-(6-methoxypyridin-2-yl)-1H-imidazo[4,5-b]pyrazin-6-yl)pyrimidine-2-sulfonamide | B |

TABLE 1-continued

Example compounds and their potency range

| Example # | Structure | IUPAC Name | Potency Range |
|---|---|---|---|
| 54 | 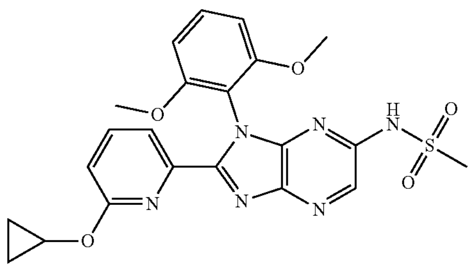 [SMILES: COc1cccc(OC)c1-n1c(-c2cccc(OC3CC3)n2)nc2ncc(NS(C)(=O)=O)nc21] | N-(2-(6-cyclopropoxypyridin-2-yl)-1-(2,6-dimethoxyphenyl)-1H-imidazo[4,5-b]pyrazin-6-yl)methanesulfonamide | B |
| 55 | 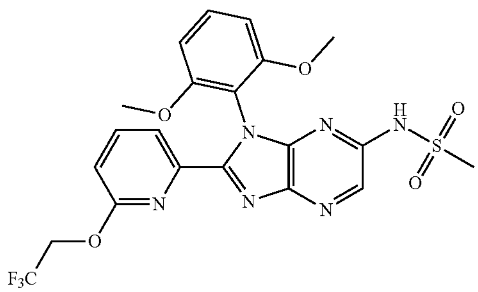 [SMILES: COc1cccc(OC)c1-n1c(-c2cccc(OCC(F)(F)F)n2)nc2ncc(NS(C)(=O)=O)nc21] | N-(1-(2,6-dimethoxyphenyl)-2-(6-(trifluoroethoxy)pyridin-2-yl)-1H-imidazo[4,5-b]pyrazin-6-yl)methanesulfonamide | B |
| 56 | 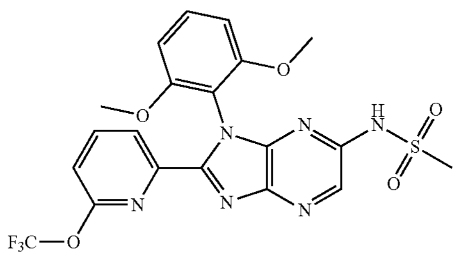 [SMILES: COc1cccc(OC)c1-n1c(-c2cccc(OC(F)(F)F)n2)nc2ncc(NS(C)(=O)=O)nc21] | N-(1-(2,6-dimethoxyphenyl)-2-(6-(trifluoromethoxy)pyridin-2-yl)-1H-imidazo[4,5-b]pyrazin-6-yl)methanesulfonamide | C |
| 57 | 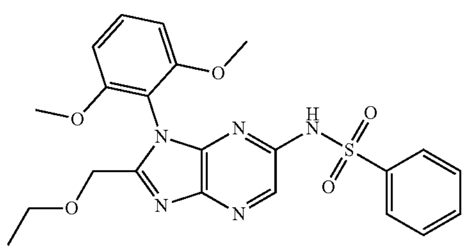 | N-(1-(2,6-dimethoxyphenyl)-2-(ethoxymethyl)-1H-imidazo[4,5-b]pyrazin-6-yl)benzenesulfonamide | C |
| 58 | 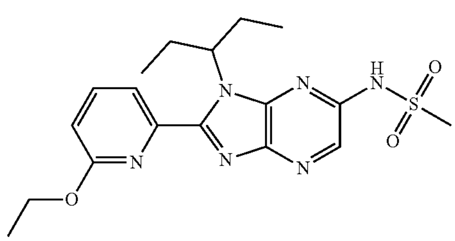 [SMILES: CCOc1cccc(-c2nc3ncc(NS(C)(=O)=O)nc3n2C(CC)CC)n1] | N-(2-(6-ethoxypyridin-2-yl)-1-(pentan-3-yl)-1H-imidazo[4,5-b]pyrazin-6-yl)methanesulfonamide | B |
| 59 | 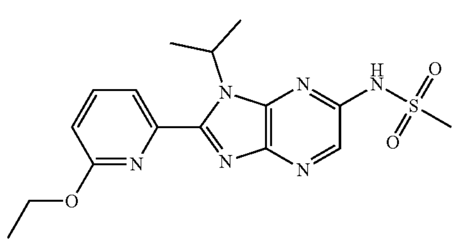 [SMILES: CCOc1cccc(-c2nc3ncc(NS(C)(=O)=O)nc3n2C(C)C)n1] | N-(2-(6-ethoxypyridin-2-yl)-1-isopropyl-1H-imidazo[4,5-b]pyrazin-6-yl)methanesulfonamide | C |

TABLE 1-continued

Example compounds and their potency range

| Example # | Structure | IUPAC Name | Potency Range |
|---|---|---|---|
| 60 | 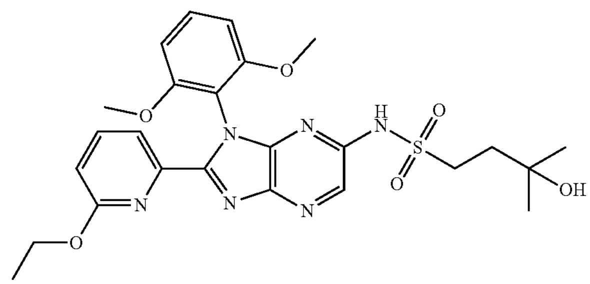 [SMILES: CCOc1cccc(-c2nc3ncc(NS(=O)(=O)CCC(C)(C)O)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-3-hydroxy-3-methylbutane-1-sulfonamide | B |
| 61 | 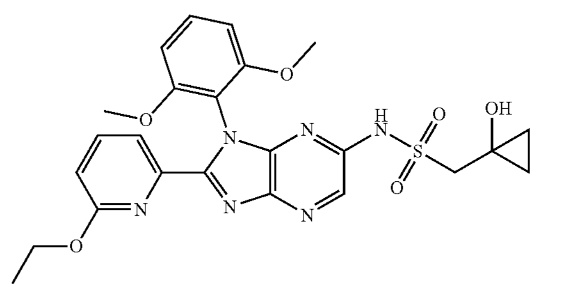 [SMILES: CCOc1cccc(-c2nc3ncc(NS(=O)(=O)CC4(O)CC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-1-(1-hydroxycyclopropyl)methanesulfonamide | B |
| 62 | 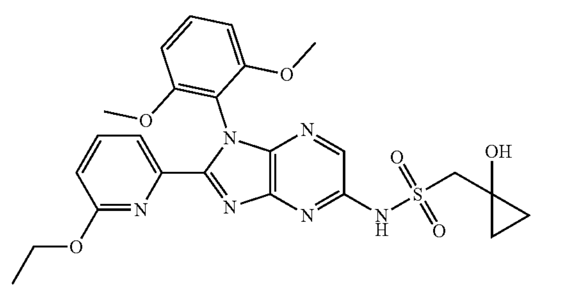 [SMILES: CCOc1cccc(-c2nc3nc(NS(=O)(=O)CC4(O)CC4)cnc3n2-c2c(OC)cccc2OC)n1] | N-(1-(2,6-dimethoxyphenyl)-2-(6-ethoxypyridin-2-yl)-1H-imidazo[4,5-b]pyrazin-5-yl)-1-(1-hydroxycyclopropyl)methanesulfonamide | B |
| 63 | 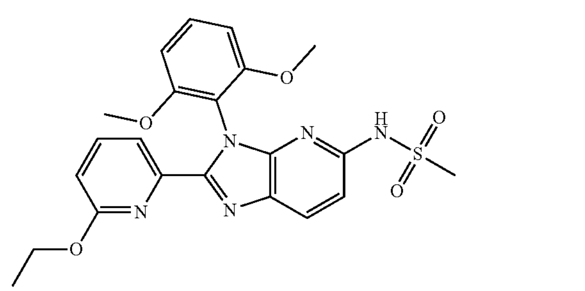 [SMILES: CCOc1cccc(-c2nc3ccc(NS(C)(=O)=O)nc3n2-c2c(OC)cccc2OC)n1] | N-(3-(2,6-dimethoxyphenyl)-2-(6-ethoxypyridin-2-yl)-3H-imidazo[4,5-b]pyridin-5-yl)methanesulfonamide | B |
| 64 | 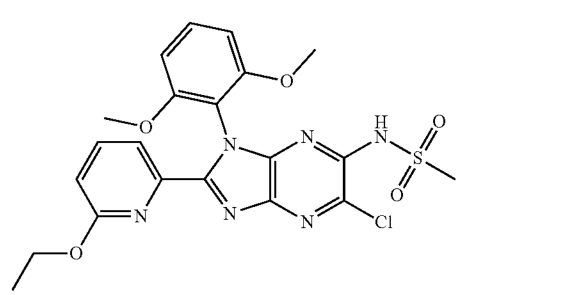 [SMILES: CCOc1cccc(-c2nc3nc(Cl)c(NS(C)(=O)=O)nc3n2-c2c(OC)cccc2OC)n1] | N-(5-chloro-1-(2,6-dimethoxyphenyl)-2-(6-ethoxypyridin-2-yl)-1H-imidazo[4,5-b]pyrazin-6-yl)methanesulfonamide | B |

TABLE 1-continued

Example compounds and their potency range

| Example # | Structure | IUPAC Name | Potency Range |
|---|---|---|---|
| 65 | 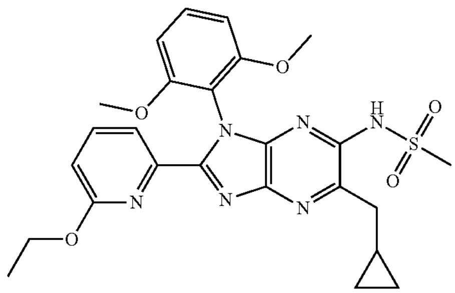 [SMILES: CCOc1cccc(-c2nc3nc(CC4CC4)c(NS(C)(=O)=O)nc3n2-c2c(OC)cccc2OC)n1] | N-(5-(cyclopropylmethyl)-1-(2,6-dimethoxyphenyl)-2-(6-ethoxypyridin-2-yl)-1H-imidazo[4,5-b]pyrazin-6-yl)methanesulfonamide | A |
| 66 | 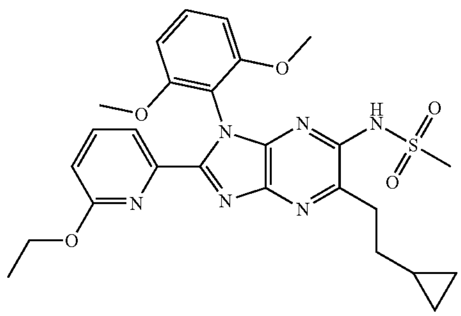 [SMILES: CCOc1cccc(-c2nc3nc(CCC4CC4)c(NS(C)(=O)=O)nc3n2-c2c(OC)cccc2OC)n1] | N-(5-(2-cyclopropylethyl)-1-(2,6-dimethoxyphenyl)-2-(6-ethoxypyridin-2-yl)-1H-imidazo[4,5-b]pyrazin-6-yl)methanesulfonamide | A |
| 67 | 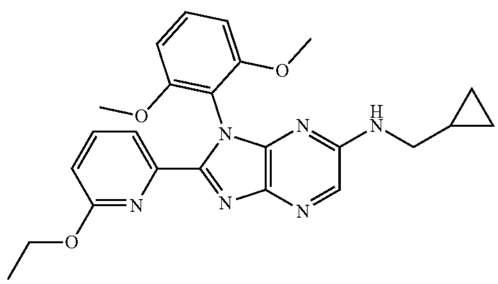 [SMILES: CCOc1cccc(-c2nc3ncc(NCC4CC4)nc3n2-c2c(OC)cccc2OC)n1] | N-(cyclopropylmethyl)-1-(2,6-dimethoxyphenyl)-2-(6-ethoxypyridin-2-yl)-1H-imidazo[4,5-b]pyrazin-6-amine | B |
| 68 | 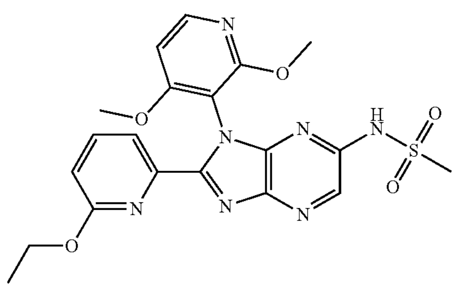 | N-(1-(2,4-dimethoxypyridin-3-yl)-2-(6-ethoxypyridin-2-yl)-1H-imidazo[4,5-b]pyrazin-6-yl)methanesulfonamide | B |
| 69 | 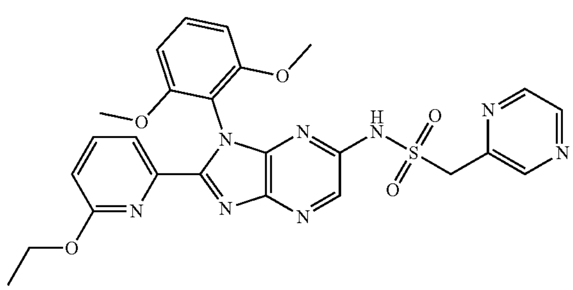 [SMILES: CCOc1cccc(-c2nc3ncc(NS(=O)(=O)Cc4cnccn4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-1-(pyrazin-2-yl)methanesulfonamide | B |

TABLE 1-continued

Example compounds and their potency range

| Example # | Structure | IUPAC Name | Potency Range |
|---|---|---|---|
| 70 | 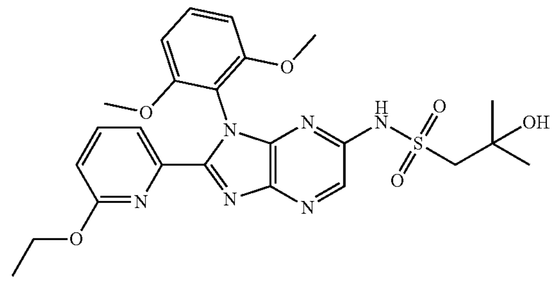 [SMILES: CCOc1cccc(-c2nc3ncc(NS(=O)(=O)CC(C)(C)O)nc3n2-c2c(OC)cccc2OC)n1] | N-(1-(2,6-Dimethoxyphenyl)-2-(6-ethoxypyridin-2-yl)-1H-imidazo[4,5-b]pyrazin-6-yl)-2-hydroxy-2-methylpropane-1-sulfonamide | B |
| 71 | 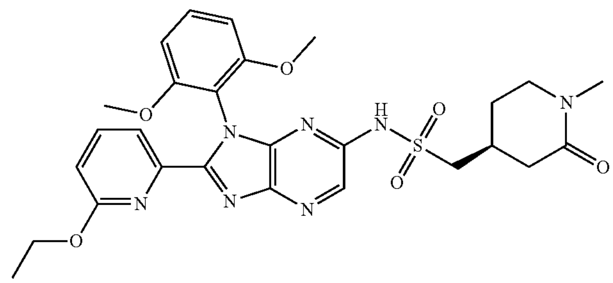 [SMILES: CCOc1cccc(-c2nc3ncc(NS(=O)(=O)C[C@H]4CCN(C)C(=O)C4)nc3n2-c2c(OC)cccc2OC)n1] | (S)-N-(1-(2,6-Dimethoxyphenyl)-2-(6-ethoxypyridin-2-yl)-1H-imidazo[4,5-b]pyrazin-6-yl)-1-(1-methyl-2-oxopiperidin-4-yl)methanesulfonamide | A |
| 72 | 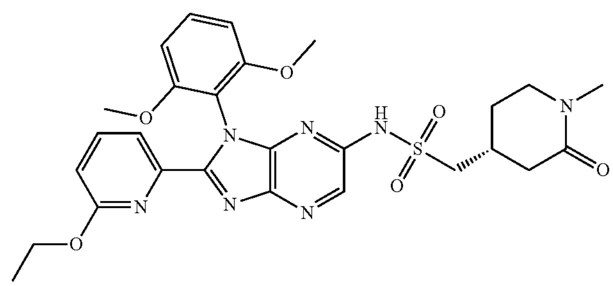 [SMILES: CCOc1cccc(-c2nc3ncc(NS(=O)(=O)C[C@@H]4CCN(C)C(=O)C4)nc3n2-c2c(OC)cccc2OC)n1] | (R)-N-(1-(2,6-dimethoxyphenyl)-2-(6-ethoxypyridin-2-yl)-1H-imidazo[4,5-b]pyrazin-6-yl)-1-(1-methyl-2-oxopiperidin-4-yl)methanesulfonamide | A |
| 73 | 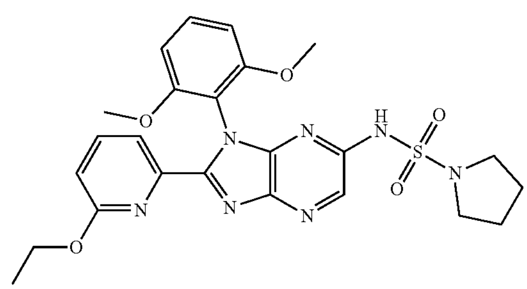 [SMILES: CCOc1cccc(-c2nc3ncc(NS(=O)(=O)N4CCCC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)pyrrolidine-1-sulfonamide | B |
| 74 | 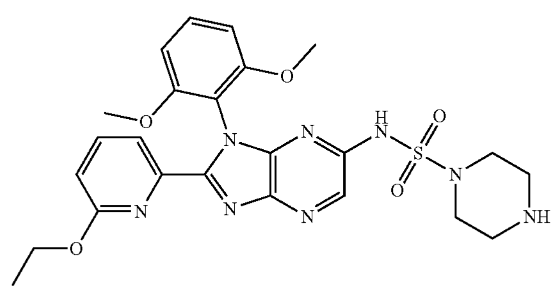 [SMILES: CCOc1cccc(-c2nc3ncc(NS(=O)(=O)N4CCNCC4)nc3n2-c2c(OC)cccc2OC)n1] | N-(1-(2,6-Dimethoxyphenyl)-2-(6-ethoxypyridin-2-yl)-1H-imidazo[4,5-b]pyrazin-6-yl)piperazine-1-sulfonamide | B |

TABLE 1-continued

Example compounds and their potency range

| Example # | Structure | IUPAC Name | Potency Range |
|---|---|---|---|
| 75 | 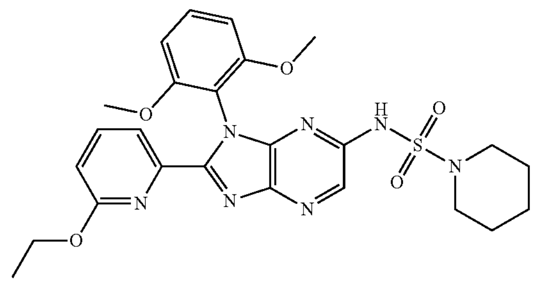 [SMILES: CCOc1cccc(-c2nc3ncc(NS(=O)(=O)N4CCCCC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)piperidine-1-sulfonamide | A |
| 76 | 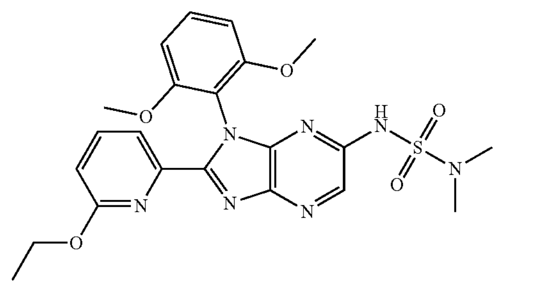 [SMILES: CCOc1cccc(-c2nc3ncc(NS(=O)(=O)N(C)C)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-N',N'-dimethylsulfamide | B |
| 77 | 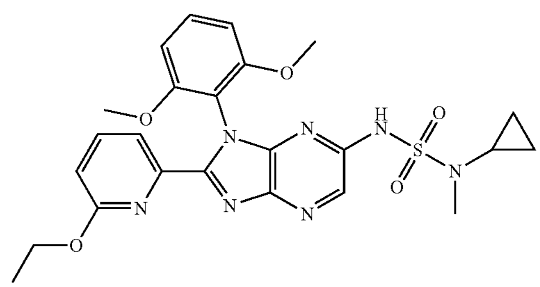 [SMILES: CCOc1cccc(-c2nc3ncc(NS(=O)(=O)N(C)C4CC4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-N'-methyl-N'-cyclopropylsulfamide | A |
| 78 | 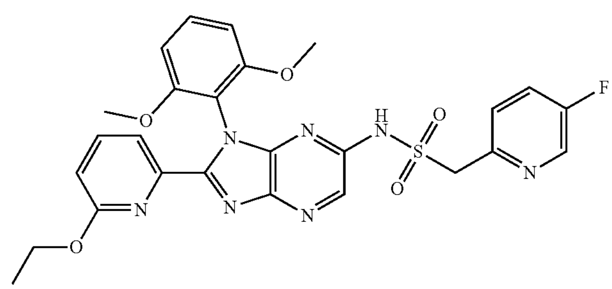 | N-(1-(2,6-dimethoxyphenyl)-2-(6-ethoxypyridin-2-yl)-1H-imidazo[4,5-b]pyrazin-6-yl)-1-(5-fluoropyridin-2-yl)methanesulfonamide | A |
| 79 | 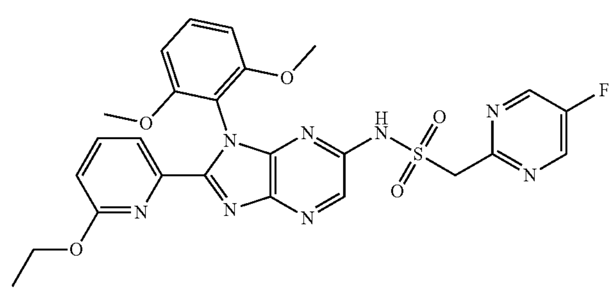 | N-(1-(2,6-dimethoxyphenyl)-2-(6-ethoxypyridin-2-yl)-1H-imidazo[4,5-b]pyrazin-6-yl)-1-(5-fluoropyrimidin-2-yl)methanesulfonamide | A |

TABLE 1-continued

Example compounds and their potency range

| Example # | Structure | IUPAC Name | Potency Range |
|---|---|---|---|
| 80 | 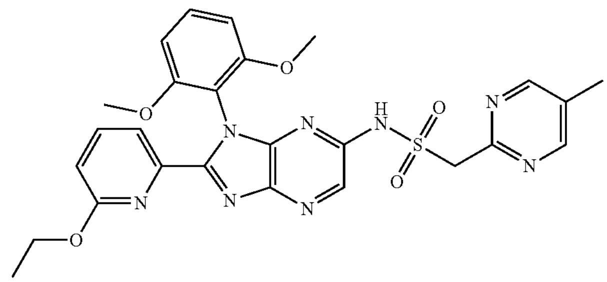 [SMILES: CCOc1cccc(-c2nc3ncc(NS(=O)(=O)Cc4ncc(C)cn4)nc3n2-c2c(OC)cccc2OC)n1] | N-(1-(2,6-dimethoxyphenyl)-2-(6-ethoxypyridin-2-yl)-1H-imidazo[4,5-b]pyrazin-6-yl)-1-(5-methylpyrimidin-2-yl)methanesulfonamide | A |
| 81 | 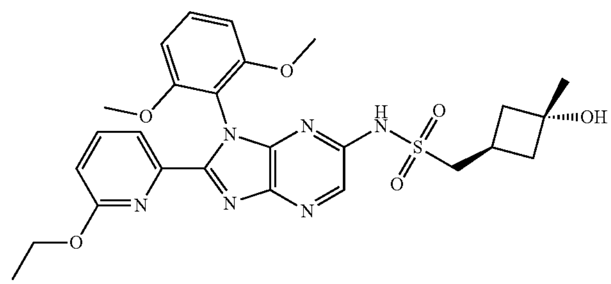 [SMILES: CCOc1cccc(-c2nc3ncc(NS(=O)(=O)C[C@H]4C[C@](C)(O)C4)nc3n2-c2c(OC)cccc2OC)n1] | trans-N-(1-(2,6-Dimethoxyphenyl)-2-(6-ethoxypyridin-2-yl)-1H-imidazo[4,5-b]pyrazin-6-yl)-1-((1r,3r)-3-hydroxy-3-methylcyclobutyl)methane-sulfonamide | B |
| 82 | 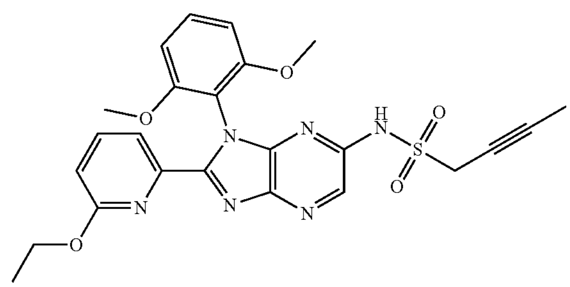 [SMILES: CC#CCS(=O)(=O)Nc1cnc2nc(-c3cccc(OCC)n3)n(-c3c(OC)cccc3OC)c2n1] | N-(1-(2,6-Dimethoxyphenyl)-2-(6-ethoxypyridin-2-yl)-1H-imidazo[4,5-b]pyrazin-6-yl)but-2-yne-1-sulfonamide | B |
| 83 | 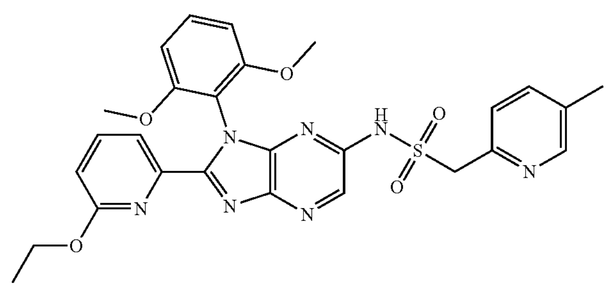 [SMILES: CCOc1cccc(-c2nc3ncc(NS(=O)(=O)Cc4ccc(C)cn4)nc3n2-c2c(OC)cccc2OC)n1] | N-(1-(2,6-Dimethoxyphenyl)-2-(6-ethoxypyridin-2-yl)-1H-imidazo[4,5-b]pyrazin-6-yl)-1-(5-methylpyridin-2-yl)methanesulfonamide | A |
| 84 | 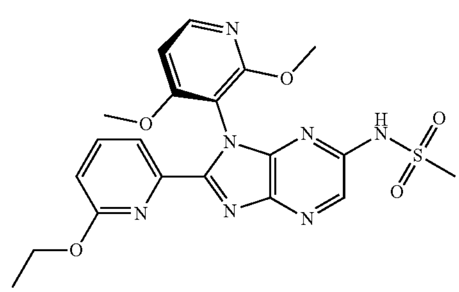 | N-(1-(2,4-Dimethoxypyridin-3-yl)-2-(6-ethoxypyridin-2-yl)-1H-imidazo[4,5-b]pyrazin-6-yl)methanesulfonamide | B |

TABLE 1-continued

Example compounds and their potency range

| Example # | Structure | IUPAC Name | Potency Range |
|---|---|---|---|
| 85 | 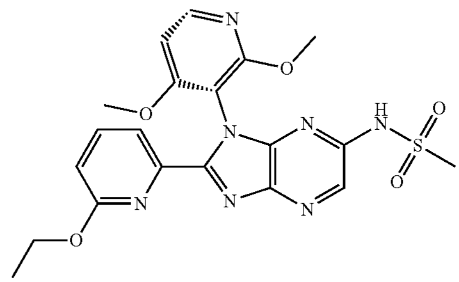 | N-(1-(2,4-Dimethoxypyridin-3-yl)-2-(6-ethoxypyridin-2-yl)-1H-imidazo[4,5-b]pyrazin-6-yl)methanesulfonamide] | C |
| 86 | 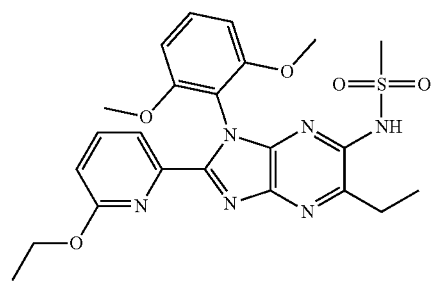 [SMILES: CCOc1cccc(-c2nc3nc(CC)c(NS(C)(=O)=O)nc3n2-c2c(OC)cccc2OC)n1] | N-(1-(2,6-dimethoxyphenyl)-2-(6-ethoxypyridin-2-yl)-5-ethyl-1H-imidazo[4,5-b]pyrazin-6-yl)methanesulfonamide | B |
| 87 | 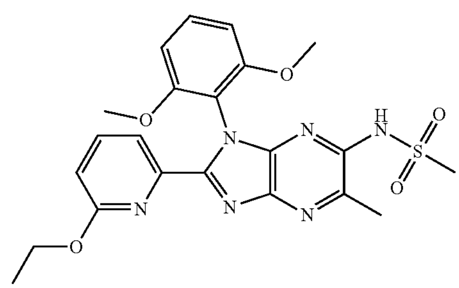 [SMILES: CCOc1cccc(-c2nc3nc(C)c(NS(C)(=O)=O)nc3n2-c2c(OC)cccc2OC)n1] | N-(1-(2,6-Dimethoxyphenyl)-2-(6-ethoxypyridin-2-yl)-5-methyl-1H-imidazo[4,5-b]pyrazin-6-yl)methanesulfonamide | B |
| 88 | 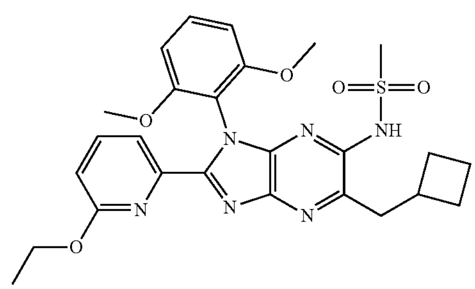 [SMILES: CCOc1cccc(-c2nc3nc(CC4CCC4)c(NS(C)(=O)=O)nc3n2-c2c(OC)cccc2OC)n1] | N-(5-(Cyclobutylmethyl)-1-(2,6-dimethoxyphenyl)-2-(6-ethoxypyridin-2-yl)-1H-imidazo[4,5-b]pyrazin-6-yl)methanesulfonamide | A |
| 89 | 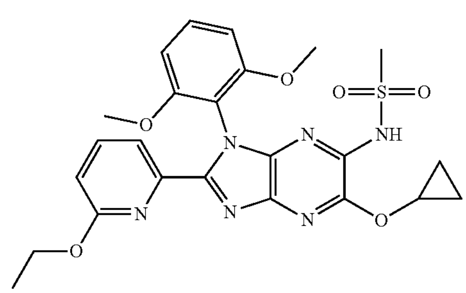 [SMILES: CCOc1cccc(-c2nc3nc(OC4CC4)c(NS(C)(=O)=O)nc3n2-c2c(OC)cccc2OC)n1] | N-(5-Cyclopropoxy-1-(2,6-dimethoxyphenyl)-2-(6-ethoxypyridin-2-yl)-1H-imidazo[4,5-b]pyrazin-6-yl)methanesulfonamide | C |

TABLE 1-continued

Example compounds and their potency range

| Example # | Structure | IUPAC Name | Potency Range |
|---|---|---|---|
| 90 | 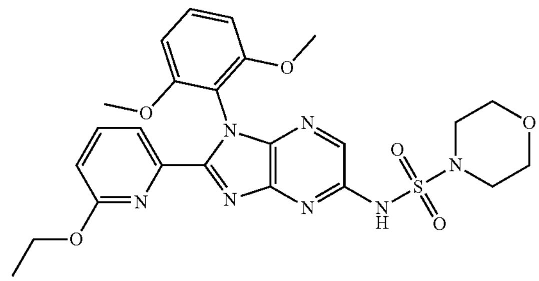 [SMILES: CCOc1cccc(-c2nc3nc(NS(=O)(=O)N4CCOCC4)cnc3n2-c2c(OC)cccc2OC)n1] | N-(1-(2,6-Dimethoxyphenyl)-2-(6-ethoxypyridin-2-yl)-1H-imidazo[4,5-b]pyrazin-5-yl)morpholine-4-sulfonamide | A |
| 91 | 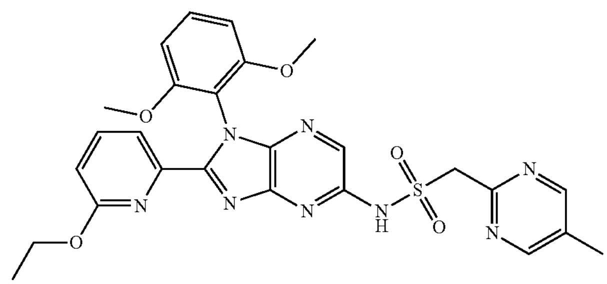 [SMILES: CCOc1cccc(-c2nc3nc(NS(=O)(=O)Cc4ncc(C)cn4)cnc3n2-c2c(OC)cccc2OC)n1] | N-(1-(2,6-Dimethoxyphenyl)-2-(6-ethoxypyridin-2-yl)-1H-imidazo[4,5-b]pyrazin-5-yl)-1-(5-methylpyrimidin-2-yl)methanesulfonamide | A |
| 92 | 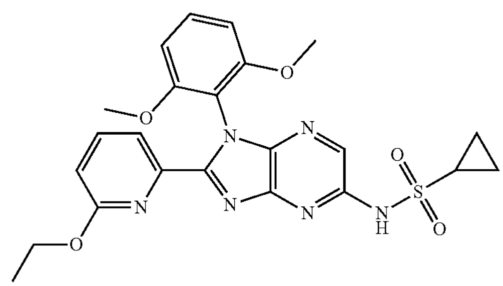 [SMILES: CCOc1cccc(-c2nc3nc(NS(=O)(=O)C4CC4)cnc3n2-c2c(OC)cccc2OC)n1] | N-(1-(2,6-Dimethoxyphenyl)-2-(6-ethoxypyridin-2-yl)-1H-imidazo[4,5-b]pyrazin-5-yl)cyclopropanesulfonamide | B |
| 93 | 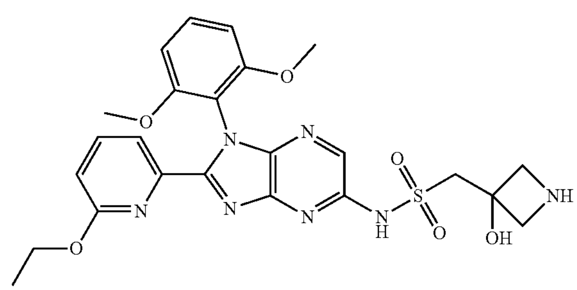 [SMILES: CCOc1cccc(-c2nc3nc(NS(=O)(=O)CC4(O)CNC4)cnc3n2-c2c(OC)cccc2OC)n1] | N-(1-(2,6-Dimethoxyphenyl)-2-(6-ethoxypyridin-2-yl)-1H-imidazo[4,5-b]pyrazin-5-yl)-1-(3-hydroxyazetidin-3-yl)methanesulfonamide | A |
| 94 | 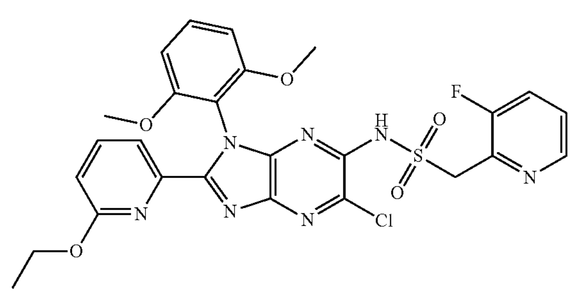 [SMILES: CCOc1cccc(-c2nc3nc(Cl)c(NS(=O)(=O)Cc4ncccc4F)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(3-fluoropyridin-2-yl)methanesulfonamide | B |

TABLE 1-continued

Example compounds and their potency range

| Example # | Structure | IUPAC Name | Potency Range |
|---|---|---|---|
| 95 | 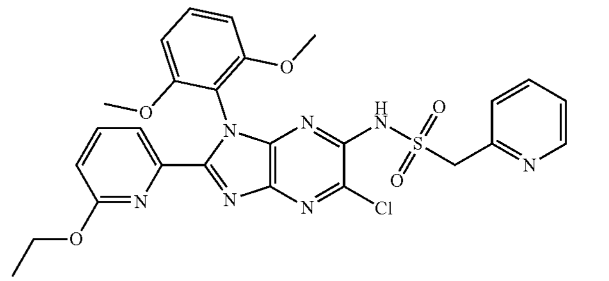 | N-(5-Chloro-1-(2,6-dimethoxyphenyl)-2-(6-ethoxypyridin-2-yl)-1H-imidazo[4,5-b]pyrazin-6-yl)-1-(pyridin-2-yl)methanesulfonamide | B |
| 96 | 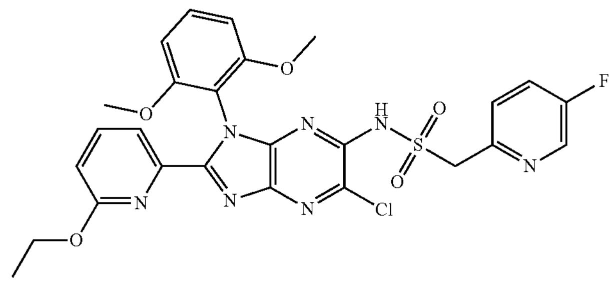 | N-(5-Chloro-1-(2,6-dimethoxyphenyl)-2-(6-ethoxypyridin-2-yl)-1H-imidazo[4,5-b]pyrazin-6-yl)-1-(5-fluoropyridin-2-yl)methanesulfonamide | A |
| 97 | 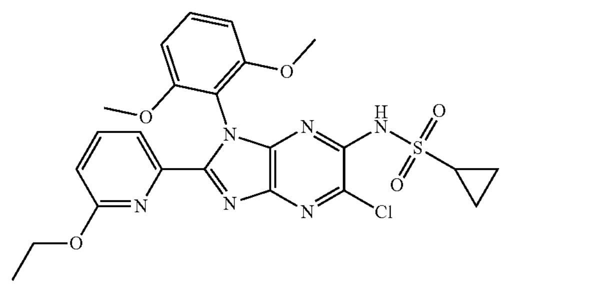 [SMILES: CCOc1cccc(-c2nc3nc(Cl)c(NS(=O)(=O)C4CC4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)cyclopropanesulfonamide | B |
| 98 | 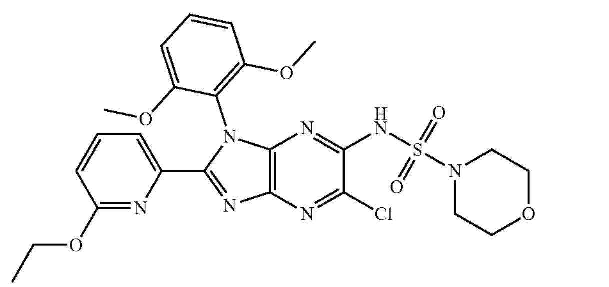 | N-(5-Chloro-1-(2,6-dimethoxyphenyl)-2-(6-ethoxypyridin-2-yl)-1H-imidazo[4,5-b]pyrazin-6-yl)morpholine-4-sulfonamide | B |
| 99 | 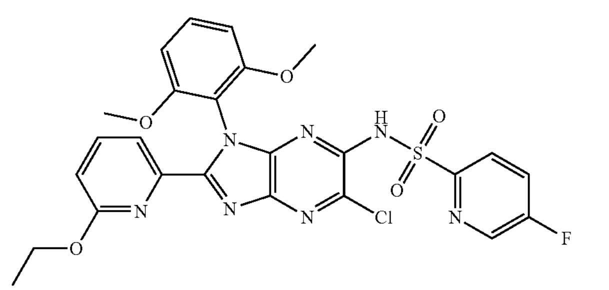 [SMILES: CCOc1cccc(-c2nc3nc(Cl)c(NS(=O)(=O)c4ccc(F)cn4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-5-fluoropyridine-2-sulfonamide | B |

TABLE 1-continued

Example compounds and their potency range

| Example # | Structure | IUPAC Name | Potency Range |
|---|---|---|---|
| 100 | 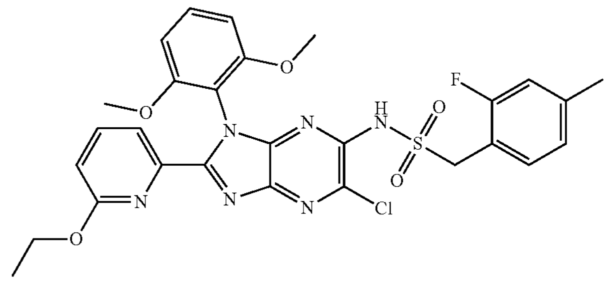 [SMILES: CCOc1cccc(-c2nc3nc(Cl)c(NS(=O)(=O)Cc4ccc(C)cc4F)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(2-fluoro-4-methylphenyl)methanesulfonamide | B |
| 101 | 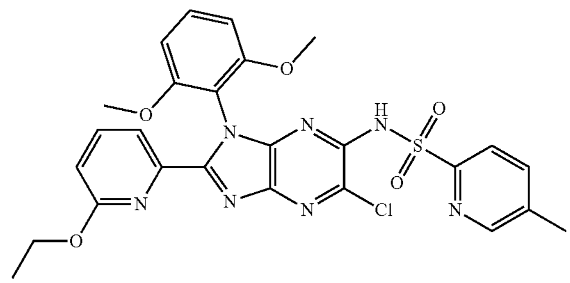 [SMILES: CCOc1cccc(-c2nc3nc(Cl)c(NS(=O)(=O)c4ccc(C)cn4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-5-methylpyridine-2-sulfonamide | A |
| 102 | 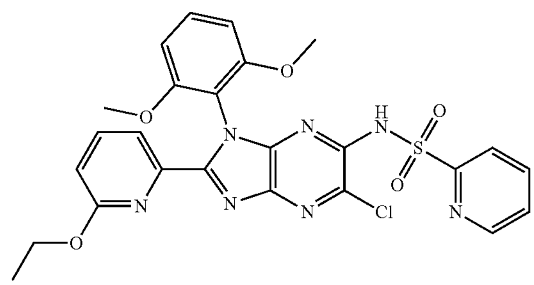 [SMILES: CCOc1cccc(-c2nc3nc(Cl)c(NS(=O)(=O)c4ccccn4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)pyridine-2-sulfonamide | B |
| 103 | 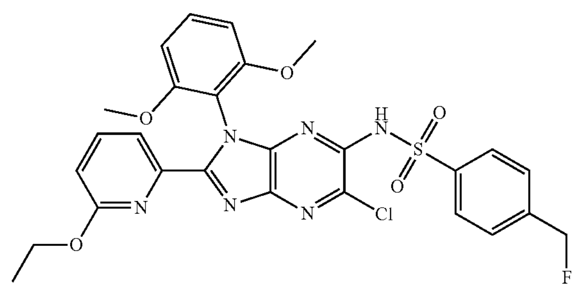 [SMILES: CCOc1cccc(-c2nc3nc(Cl)c(NS(=O)(=O)c4ccc(CF)cc4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-4-(fluoromethyl)benzenesulfonamide | A |
| 104 | 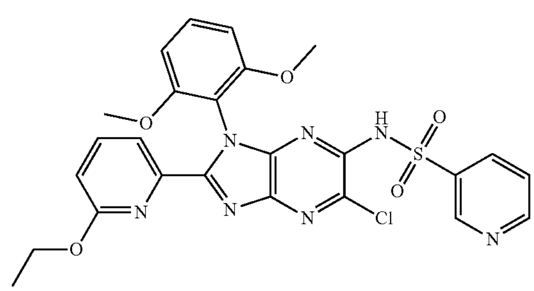 [SMILES: CCOc1cccc(-c2nc3nc(Cl)c(NS(=O)(=O)c4cccnc4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)pyridine-3-sulfonamide | B |

TABLE 1-continued

Example compounds and their potency range

| Example # | Structure | IUPAC Name | Potency Range |
|---|---|---|---|
| 105 | 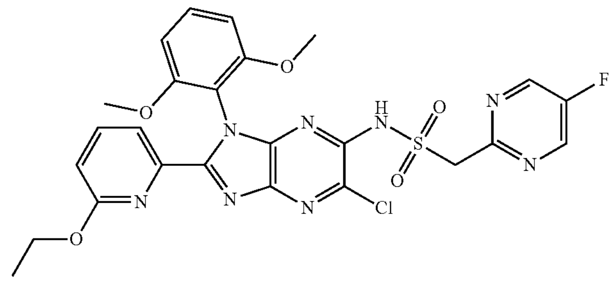 [SMILES: CCOc1cccc(-c2nc3nc(Cl)c(NS(=O)(=O)Cc4ncc(F)cn4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(5-fluoropyrimidin-2-yl)methanesulfonamide | A |
| 106 | 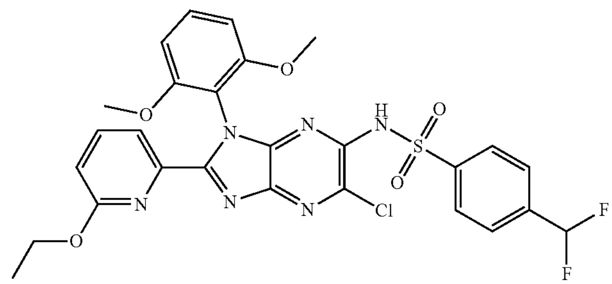 [SMILES: CCOc1cccc(-c2nc3nc(Cl)c(NS(=O)(=O)c4ccc(C(F)F)cc4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-4-(difluoromethyl)benzenesulfonamide | B |
| 107 | 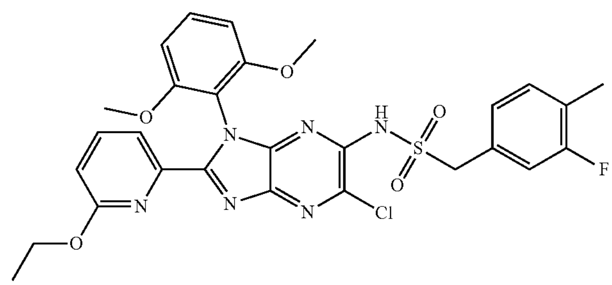 [SMILES: CCOc1cccc(-c2nc3nc(Cl)c(NS(=O)(=O)Cc4ccc(C)c(F)c4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(3-fluoro-4-methylphenyl)methanesulfonamide | A |
| 108 | 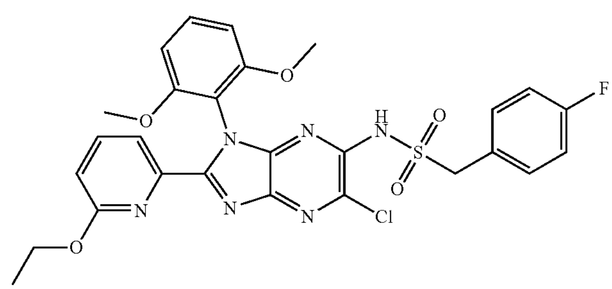 [SMILES: CCOc1cccc(-c2nc3nc(Cl)c(NS(=O)(=O)Cc4ccc(F)cc4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(4-fluorophenyl)methanesulfonamide | A |
| 109 | 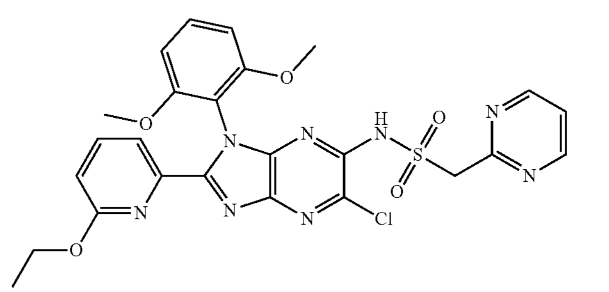 [SMILES: CCOc1cccc(-c2nc3nc(Cl)c(NS(=O)(=O)Cc4ncccn4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(pyrimidin-2-yl)methanesulfonamide | B |

TABLE 1-continued

Example compounds and their potency range

| Example # | Structure | IUPAC Name | Potency Range |
|---|---|---|---|
| 110 | 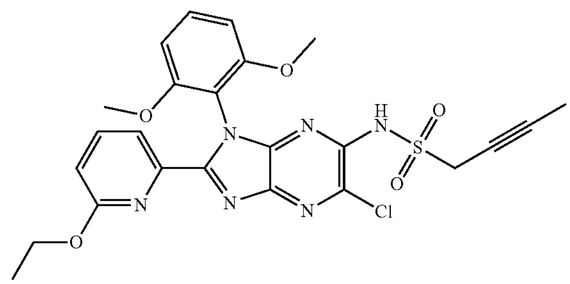 [SMILES: CC#CCS(=O)(=O)Nc1nc2c(nc1Cl)nc(-c1cccc(OCC)n1)n2-c1c(OC)cccc1OC] | N-(5-Chloro-1-(2,6-dimethoxyphenyl)-2-(6-ethoxypyridin-2-yl)-1H-imidazo[4,5-b]pyrazin-6-yl)but-2-yne-1-sulfonamide | A |
| 111 | 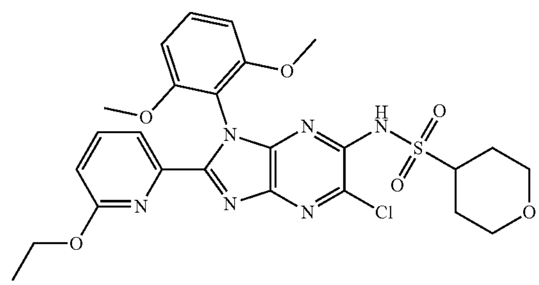 [SMILES: CCOc1cccc(-c2nc3nc(Cl)c(NS(=O)(=O)C4CCOCC4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)tetrahydro-2H-pyran-4-sulfonamide | B |
| 112 | 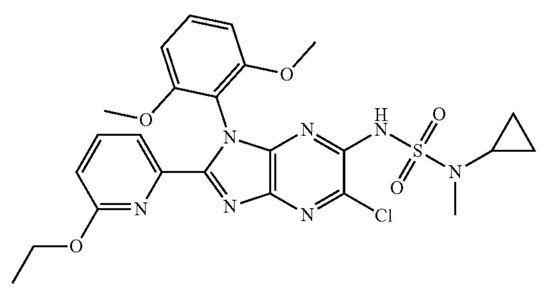 [SMILES: CCOc1cccc(-c2nc3nc(Cl)c(NS(=O)(=O)N(C)C4CC4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-N'-methyl-N'-cyclopropylsulfamide | A |
| 113 | 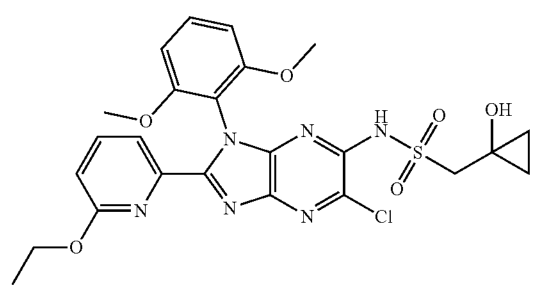 [SMILES: CCOc1cccc(-c2nc3nc(Cl)c(NS(=O)(=O)CC4(O)CC4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(1-hydroxycyclopropyl)methanesulfonamide(ANPA-0003489) | B |
| 114 | 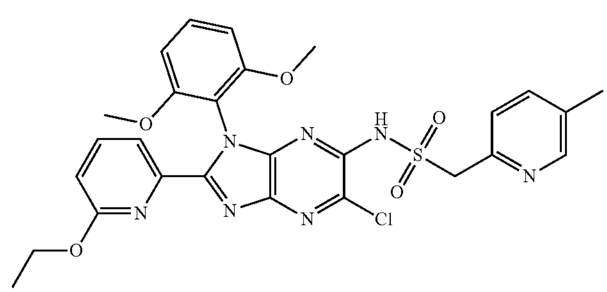 [SMILES: CCOc1cccc(-c2nc3nc(Cl)c(NS(=O)(=O)Cc4ccc(C)cn4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-(5-methylpyridin-2-yl)methanesulfonamide | B |

TABLE 1-continued

Example compounds and their potency range

| Example # | Structure | IUPAC Name | Potency Range |
|---|---|---|---|
| 115 | 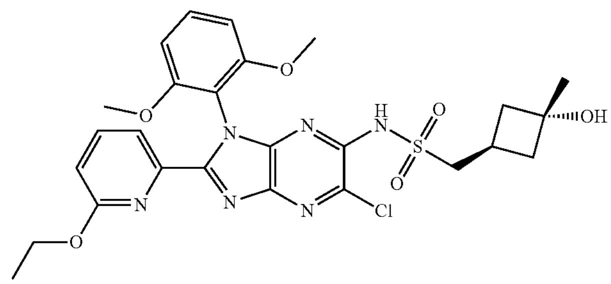 [SMILES: CCOc1cccc(-c2nc3nc(Cl)c(NS(=O)(=O)C[C@H]4C[C@](C)(O)C4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-1-((1r,3r)-3-hydroxy-3-methylcyclobutyl)methanesulfonamide | A |
| 116 | 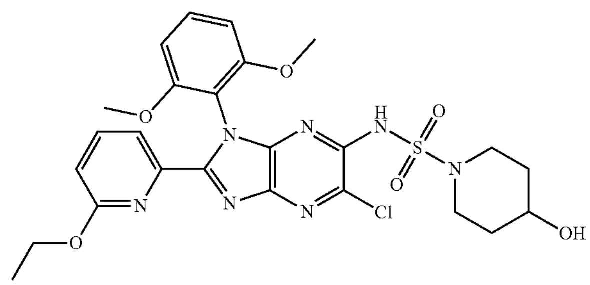 [SMILES: CCOc1cccc(-c2nc3nc(Cl)c(NS(=O)(=O)N4CCC(O)CC4)nc3n2-c2c(OC)cccc2OC)n1] | N-(5-Chloro-1-(2,6-dimethoxyphenyl)-2-(6-ethoxypyridin-2-yl)-1H-imidazo[4,5-b]pyrazin-6-yl)-4-hydroxypiperidine-1-sulfonamide | B |
| 117 | 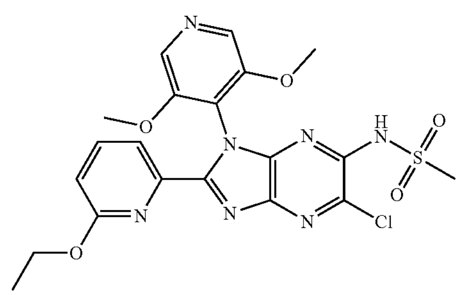 [SMILES: CCOc1cccc(-c2nc3nc(Cl)c(NS(C)(=O)=O)nc3n2-c2c(OC)cncc2OC)n1] | N-(5-Chloro-1-(3,5-dimethoxypyridin-4-yl)-2-(6-ethoxypyridin-2-yl)-1H-imidazo[4,5-b]pyrazin-6-yl)methanesulfonamide | B |
| 118 | 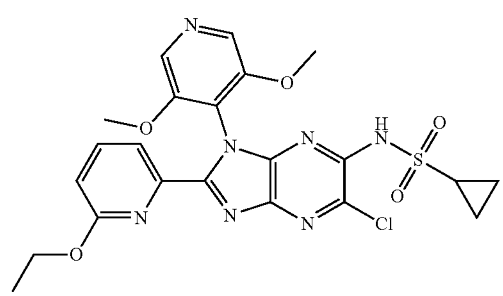 [SMILES: CCOc1cccc(-c2nc3nc(Cl)c(NS(=O)(=O)C4CC4)nc3n2-c2c(OC)cncc2OC)n1] | N-(5-Chloro-1-(3,5-dimethoxypyridin-4-yl)-2-(6-ethoxypyridin-2-yl)-1H-imidazo[4,5-b]pyrazin-6-yl)cyclopropanesulfonamide | B |
| 119 | 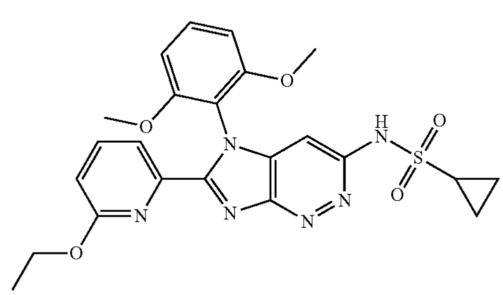 [SMILES: CCOc1cccc(-c2nc3nnc(NS(=O)(=O)C4CC4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)cyclopropanesulfonamide | B |

TABLE 1-continued

Example compounds and their potency range

| Example # | Structure | IUPAC Name | Potency Range |
|---|---|---|---|
| 120 | 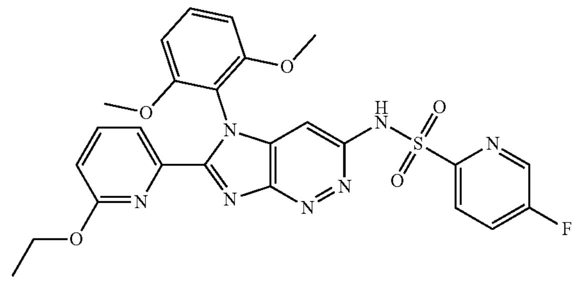 [SMILES: CCOc1cccc(-c2nc3nnc(NS(=O)(=O)c4ccc(F)cn4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)-5-fluoropyridine-2-sulfonamide | A |
| 121 | 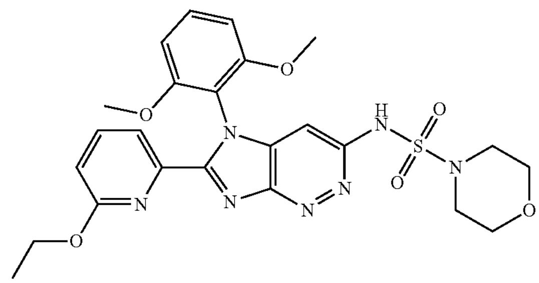 [SMILES: CCOc1cccc(-c2nc3nnc(NS(=O)(=O)N4CCOCC4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)morpholine-4-sulfonamide | B |
| 122 | 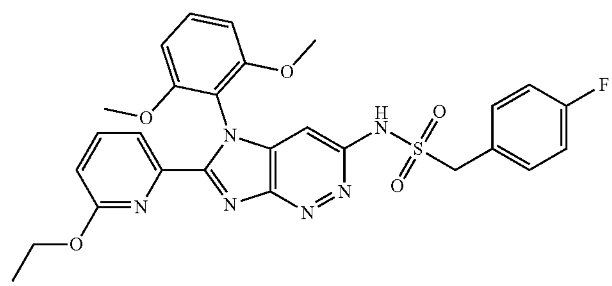 [SMILES: CCOc1cccc(-c2nc3nnc(NS(=O)(=O)Cc4ccc(F)cc4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)-1-(4-fluorophenyl)methanesulfonamide | A |
| 123 | 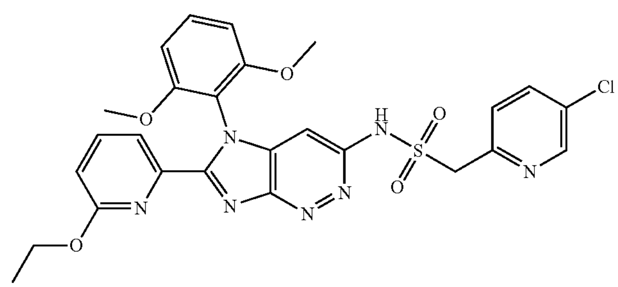 | 1-(5-Chloropyridin-2-yl)-N-(7-(2,6-dimethoxyphenyl)-8-(6-ethoxypyridin-2-yl)-7H-imidazo[4,5-c]pyridazinyl)methanesulfonamide | A |
| 124 | 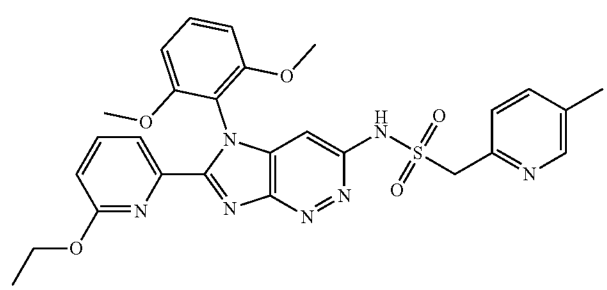 [SMILES: CCOc1cccc(-c2nc3nnc(NS(=O)(=O)Cc4ccc(C)cn4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)-1-(5-methylpyridin-2-yl)methanesulfonamide | A |

TABLE 1-continued

Example compounds and their potency range

| Example # | Structure | IUPAC Name | Potency Range |
|---|---|---|---|
| 125 | 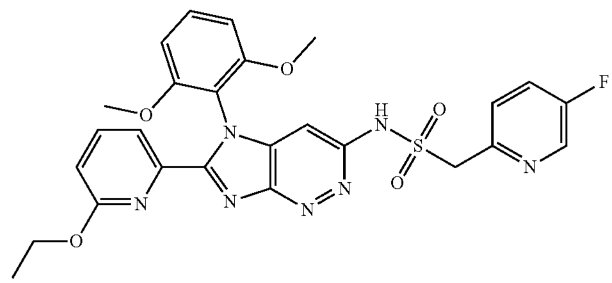 [SMILES: CCOc1cccc(-c2nc3nnc(NS(=O)(=O)Cc4ccc(F)cn4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)-1-(5-fluoropyridin-2-yl)methanesulfonamide | A |
| 126 | 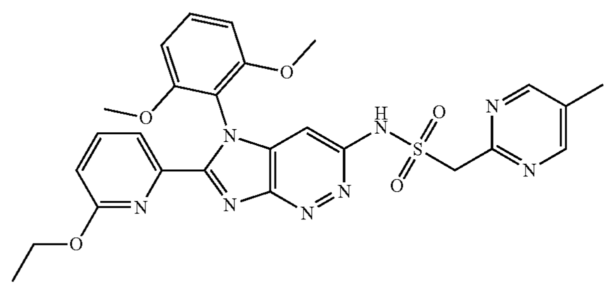 [SMILES: CCOc1cccc(-c2nc3nnc(NS(=O)(=O)Cc4ncc(C)cn4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)-1-(5-methylpyrimidin-2-yl)methanesulfonamide | A |
| 127 | 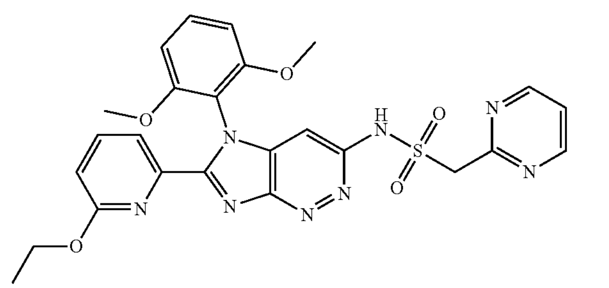 [SMILES: CCOc1cccc(-c2nc3nnc(NS(=O)(=O)Cc4ncccn4)cc3n2-c2c(OC)cccc2OC)n1] | N-(5-(2,6-Dimethoxyphenyl)-6-(6-ethoxypyridin-2-yl)-5H-imidazo[4,5-c]pyridazin-3-yl)-1-(pyrimidin-2-yl)methanesulfonamide | A |
| 128 | 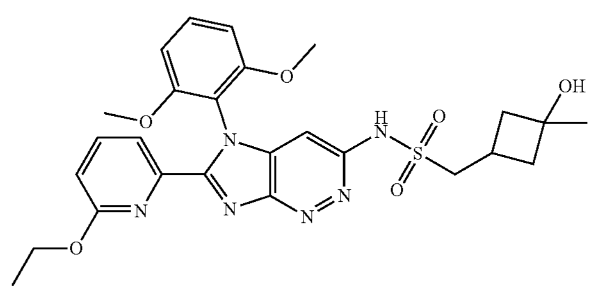 [SMILES: CCOc1cccc(-c2nc3nnc(NS(=O)(=O)CC4CC(C)(O)C4)cc3n2-c2c(OC)cccc2OC)n1] | N-(5-(2,6-Dimethoxyphenyl)-6-(6-ethoxypyridin-2-yl)-5H-imidazo[4,5-c]pyridazin-3-yl)-1-(3-hydroxy-3-methylcyclobutyl)methanesulfonamide | A |
| 129 | 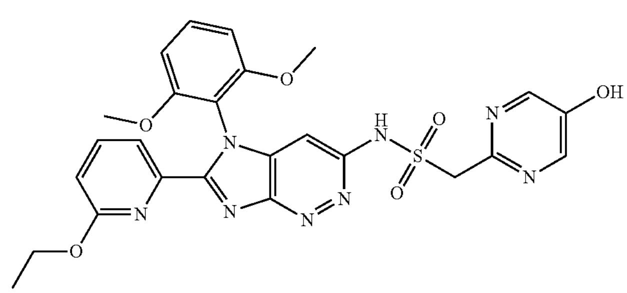 [SMILES: CCOc1cccc(-c2nc3nnc(NS(=O)(=O)Cc4ncc(O)cn4)cc3n2-c2c(OC)cccc2OC)n1] | N-(7-(2,6-Dimethoxyphenyl)-8-(6-ethoxypyridin-2-yl)-7H-imidazo[4,5-c]pyridazinyl)-1-(5-hydroxypyrimidin-2-yl)methanesulfonamide | B |

TABLE 1-continued

Example compounds and their potency range

| Example # | Structure | IUPAC Name | Potency Range |
|---|---|---|---|
| 130 | 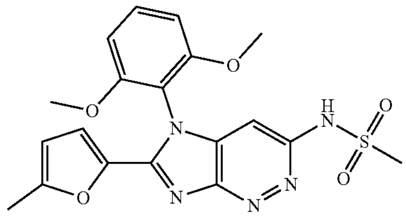 | N-(7-(2,6-Dimethoxyphenyl)-8-(5-methylfuran-2-yl)-7H-imidazo[4,5-c]pyridazinyl)methane-sulfonamide | C |
| 131 | 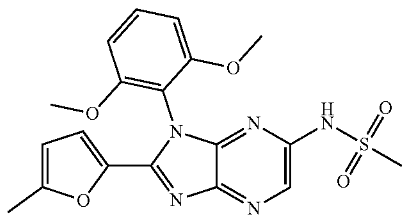 | N-(1-(2,6-dimethoxyphenyl)-2-(5-methylfuran-2-yl)-1H-imidazo[4,5-b]pyrazin-6-yl)methanesulfonamide | B |
| 132 | 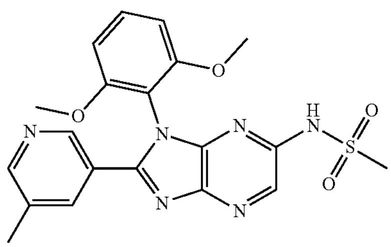 | N-(1-(2,6-dimethoxyphenyl)-2-(5-methylpyridin-3-yl)-1H-imidazo[4,5-b]pyrazin-6-yl)methanesulfonamide | C |
| 133 | 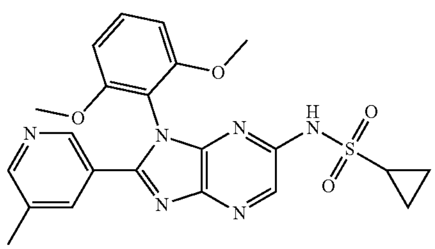 | N-(1-(2,6-dimethoxyphenyl)-2-(5-methylpyridin-3-yl)-1H-imidazo[4,5-b]pyrazin-6-yl)cyclopropanesulfon-amide | C |
| 134 | 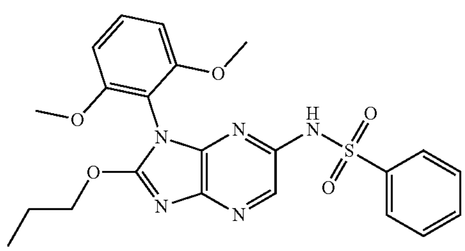 | N-(1-(2,6-Dimethoxyphenyl)-2-propoxy-1H-imidazo[4,5-b]pyrazin-6-yl)benzenesulfonamide | C |
| 135 | 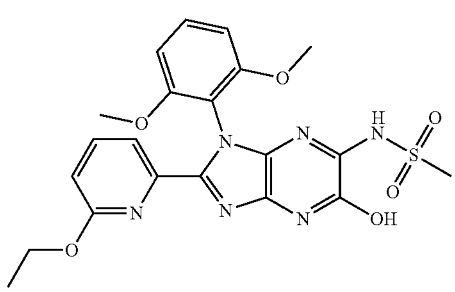 | N-(1-(2,6-Dimethoxyphenyl)-2-(6-ethoxypyridin-2-yl)-5-hydroxy-1H-imidazo[4,5-b]pyrazin-6-yl)methanesulfonamide | B |

TABLE 1-continued

Example compounds and their potency range

| Example # | Structure | IUPAC Name | Potency Range |
|---|---|---|---|
| 136 | 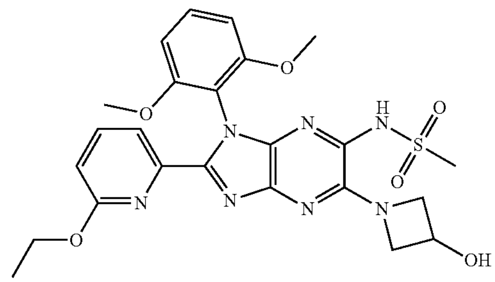 | N-(1-(2,6-Dimethoxyphenyl)-2-(6-ethoxypyridin-2-yl)-5-(3-hydroxyazetidin-1-yl)-1H-imidazo[4,5-b]pyrazin-6-yl)methanesulfonamide | C |
| 137 | 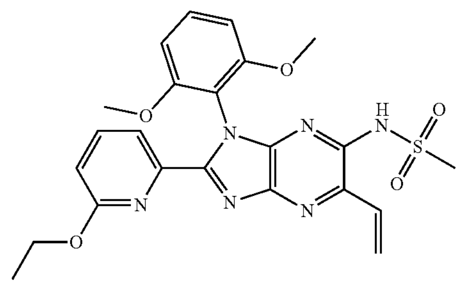 | N-(1-(2,6-Dimethoxyphenyl)-2-(6-ethoxypyridin-2-yl)-5-vinyl-1H-imidazo[4,5-b]pyrazin-6-yl)methanesulfonamide | B |
| 138 | 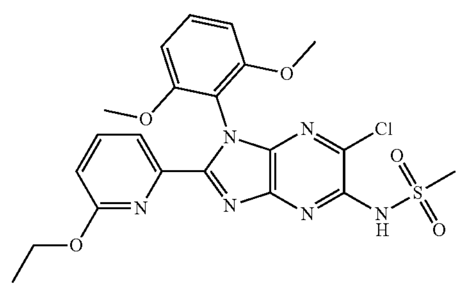 | N-(6-Chloro-1-(2,6-dimethoxyphenyl)-2-(6-ethoxypyridin-2-yl)-1H-imidazo[4,5-b]pyrazin-5-yl)methanesulfonamide | B |
| 139 | 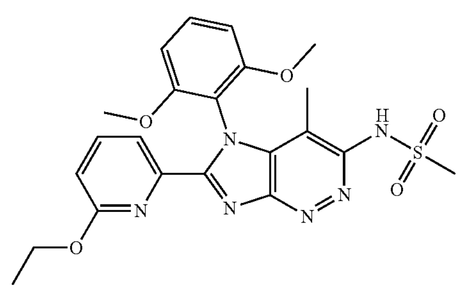 | N-(7-(2,6-Dimethoxyphenyl)-8-(6-ethoxypyridin-2-yl)-6-methyl-7H-imidazo[4,5-c]pyridazinyl)methanesulfonamide | B |
| 140 | 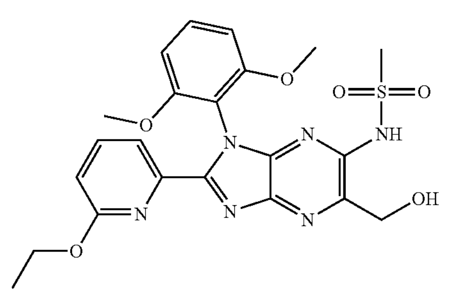 [SMILES: CCOc1cccc(-c2nc3nc(CO)c(NS(C)(=O)=O)nc3n2-c2c(OC)cccc2OC)n1] | N-(1-(2,6-Dimethoxyphenyl)-2-(6-ethoxypyridin-2-yl)-5-(hydroxymethyl)-1H-imidazo[4,5-b]pyrazin-6-yl)methanesulfonamide | B |

TABLE 1-continued

Example compounds and their potency range

| Example # | Structure | IUPAC Name | Potency Range |
|---|---|---|---|
| 141 | 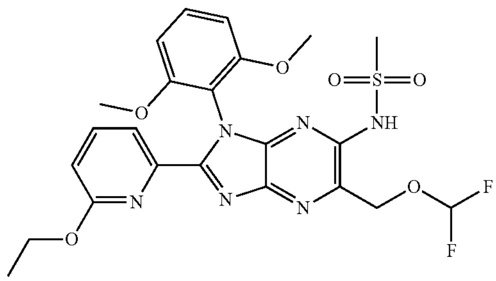 [SMILES: CCOc1cccc(-c2nc3nc(COC(F)F)c(NS(C)(=O)=O)nc3n2-c2c(OC)cccc2OC)n1] | N-(5-((Difluoromethoxy)methyl)-1-(2,6-dimethoxyphenyl)-2-(6-ethoxypyridin-2-yl)-1H-imidazo[4,5-b]pyrazin-6-yl)methanesulfonamide | B |
| 142 | 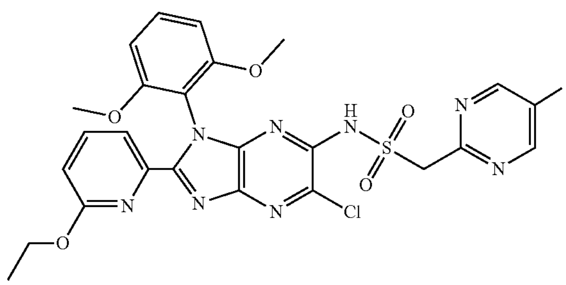 | N-(5-Chloro-1-(2,6-dimethoxyphenyl)-2-(6-ethoxypyridin-2-yl)-1H-imidazo[4,5-b]pyrazin-6-yl)-1-(5-methylpyrimidin-2-yl)methanesulfonamide | A |
| 143 | 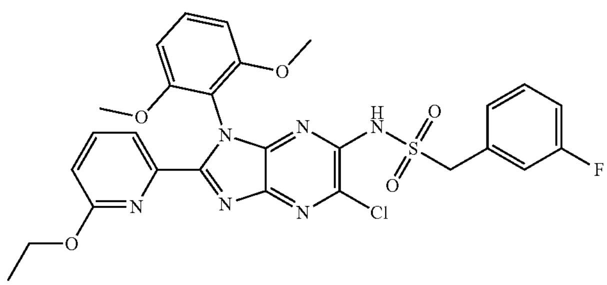 | N-(5-Chloro-1-(2,6-dimethoxyphenyl)-2-(6-ethoxypyridin-2-yl)-1H-imidazo[4,5-b]pyrazin-6-yl)-1-(3-fluorophenyl)methanesulfonamide | B |
| 144 | 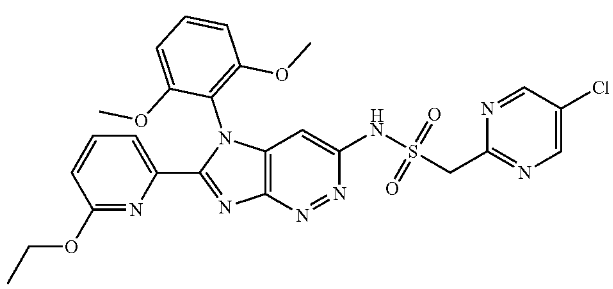 | 1-(5-chloropyrimidin-2-yl)-N-(7-(2,6-dimethoxyphenyl)-8-(6-ethoxypyridin-2-yl)-7H-imidazo[4,5-c]pyridazinyl)methanesulfonamide | A |
| 145 | 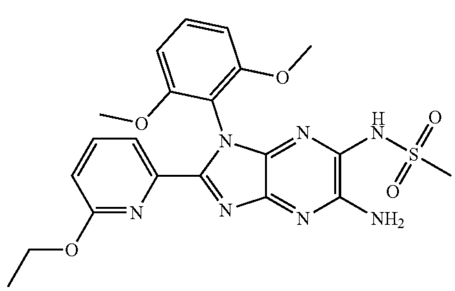 | N-(5-Amino-1-(2,6-dimethoxyphenyl)-2-(6-ethoxypyridin-2-yl)-1H-imidazo[4,5-b]pyrazin-6-yl)methanesulfonamide | B |

TABLE 1-continued

Example compounds and their potency range

| Example # | Structure | IUPAC Name | Potency Range |
|---|---|---|---|
| 146 | 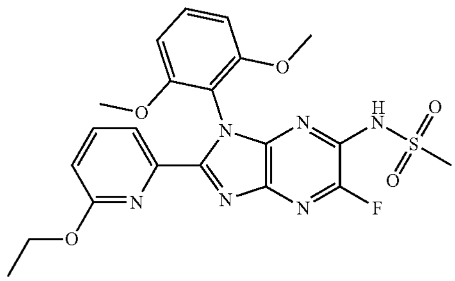 | N-(1-(2,6-Dimethoxyphenyl)-2-(6-ethoxypyridin-2-yl)-5-fluoro-1H-imidazo[4,5-b]pyrazin-6-yl)methanesulfonamide | B |

A number of embodiments of the invention have been described. Nevertheless, it will be understood that various modifications may be made without departing from the spirit and scope of the invention. Accordingly, other embodiments are within the scope of the following claims

What is claimed is:

1. A compound which is:

| 359 -continued | | 360 -continued | |
|---|---|---|---|
| 27 | 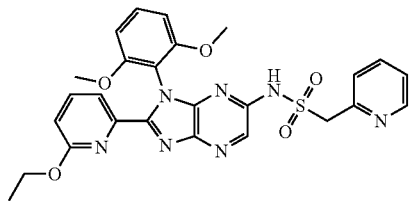 [SMILES: CCOc1cccc(-c2nc3ncc(NS(=O)(=O)Cc4ccccn4)nc3n2-c2c(OC)cccc2OC)n1] | 34 | 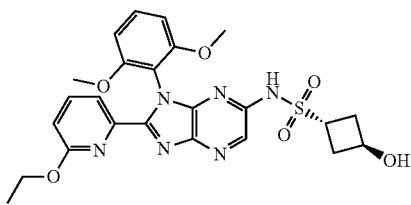 |
| 28 | 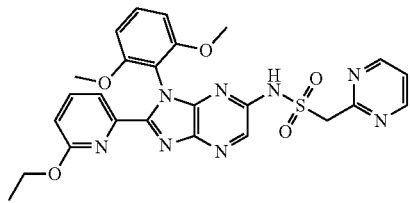 | 35 | 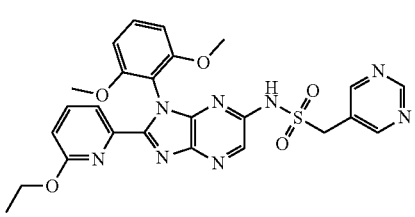 |
| 29 | 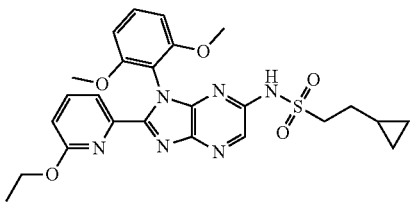 [SMILES: CCOc1cccc(-c2nc3ncc(NS(=O)(=O)CCC4CC4)nc3n2-c2c(OC)cccc2OC)n1] | 36 | 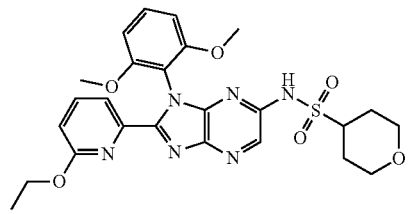 |
| 30 | 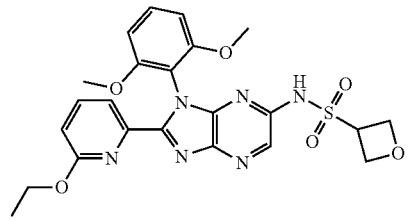 [SMILES: CCOc1cccc(-c2nc3ncc(NS(=O)(=O)C4COC4)nc3n2-c2c(OC)cccc2OC)n1] | 37 | 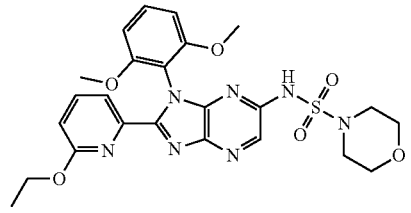 |
| 31 | 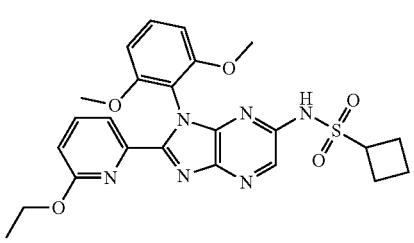 [SMILES: CCOc1cccc(-c2nc3ncc(NS(=O)(=O)C4CCC4)nc3n2-c2c(OC)cccc2OC)n1] | 38 | 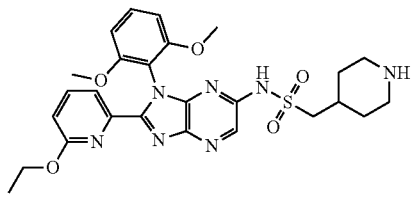 |
| 32 | 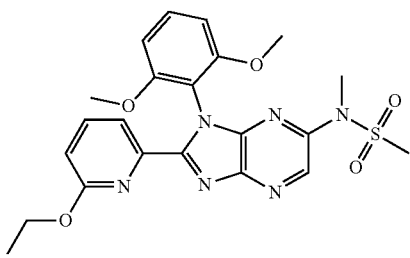 [SMILES: CCOc1cccc(-c2nc3ncc(N(C)S(C)(=O)=O)nc3n2-c2c(OC)cccc2OC)n1] | 39 | 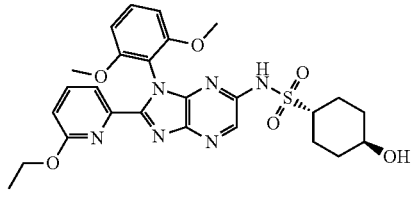 |
| 33 | 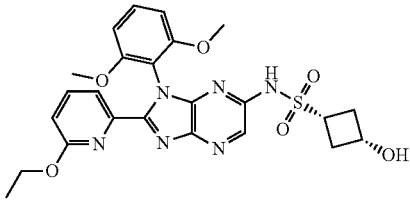 [SMILES: CCOc1cccc(-c2nc3ncc(NS(=O)(=O)[C@H]4C[C@@H](O)C4)nc3n2-c2c(OC)cccc2OC)n1] | 40 | 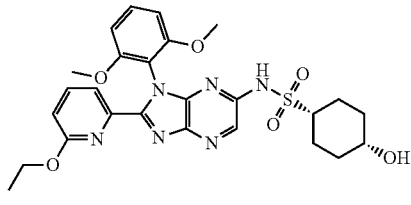 [SMILES: CCOc1cccc(-c2nc3ncc(NS(=O)(=O)[C@H]4CC[C@@H](O)CC4)nc3n2-c2c(OC)cccc2OC)n1] |

| | |
|---|---|
| 41 | 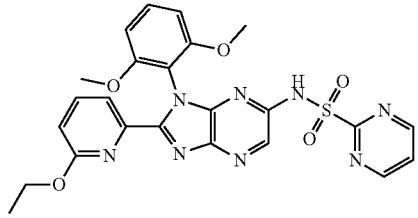 |
| 42 | 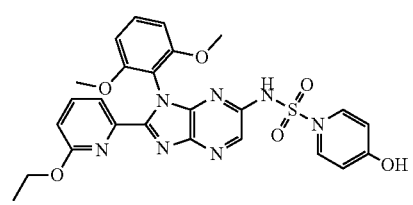 |
| 60 | 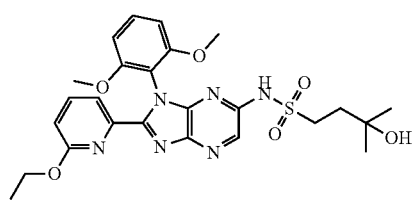 |
| 61 | 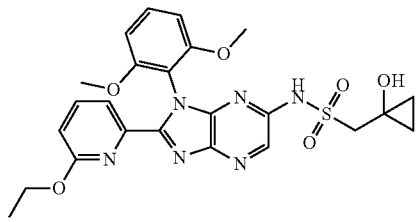 |
| 64 | 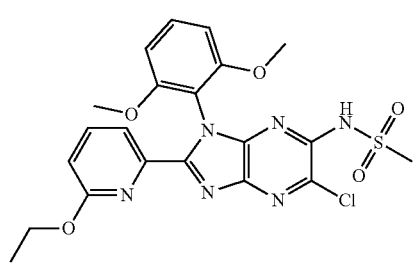 |
| 69 | 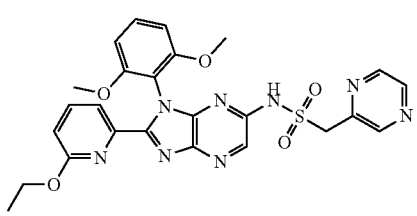 |
| 70 | 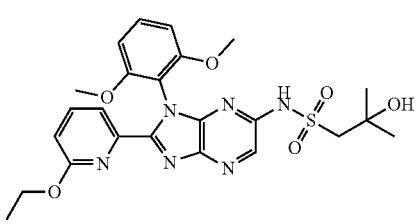 |
| 71 | 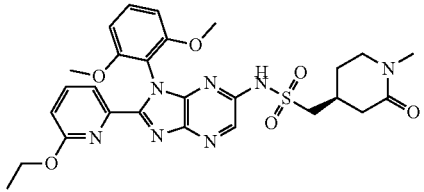 |
| 72 | 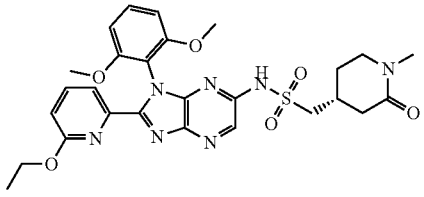 |
| 73 | 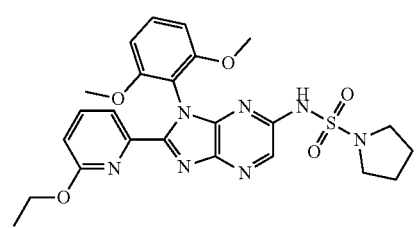 |
| 74 | 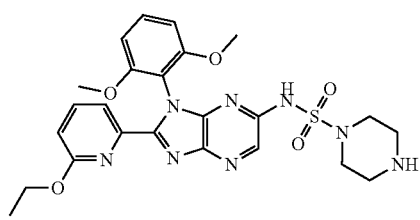 |
| 75 | 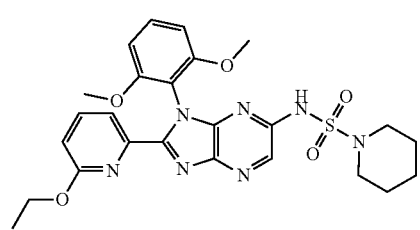 |
| 76 | 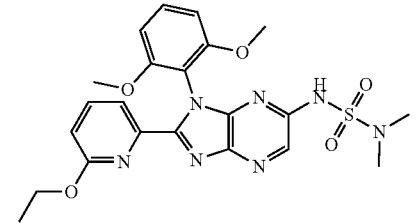 |
| 77 | 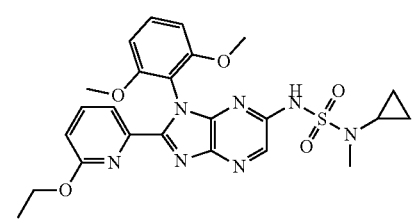 |

363
-continued
| | |
|---|---|
| 78 | 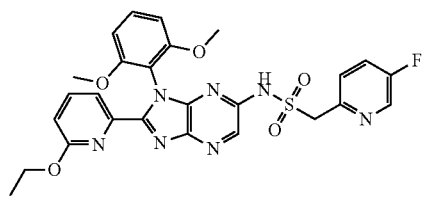 |
| 79 | 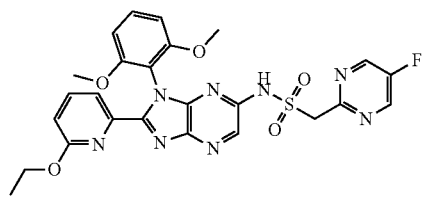 |
| 80 | 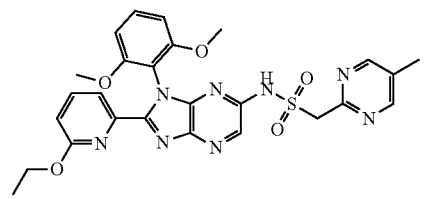 |
| 81 | 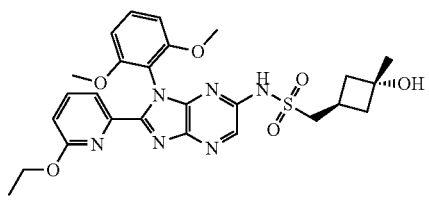 |
| 82 | 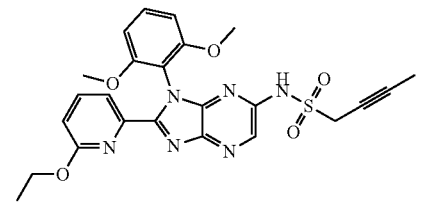 |
| 83 | 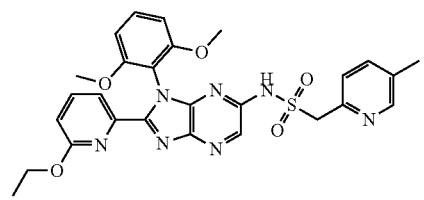 |
| 94 | 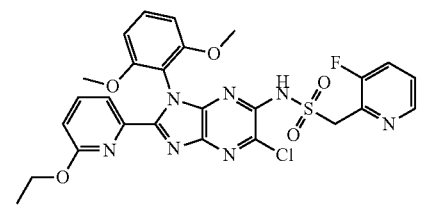 |
364
-continued
| | |
|---|---|
| 95 | 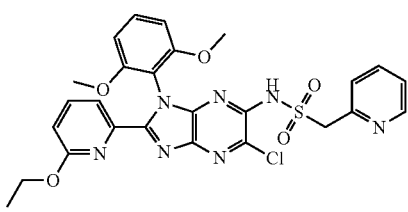 |
| 96 | 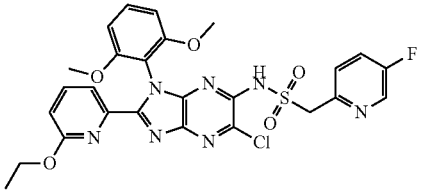 |
| 97 | 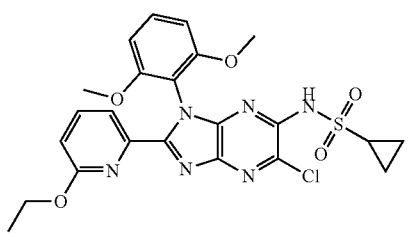 |
| 98 | 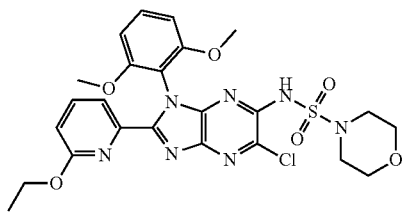 |
| 99 | 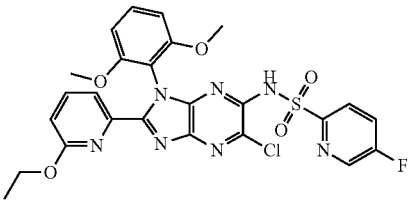 |
| 100 | 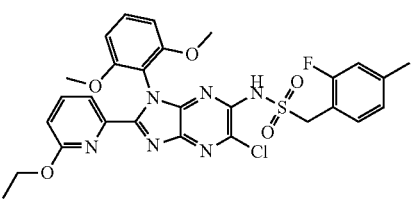 |
| 101 | 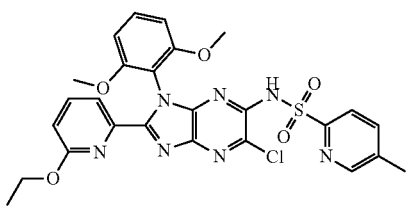 |

365
-continued
102 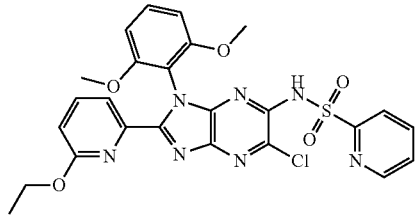
103 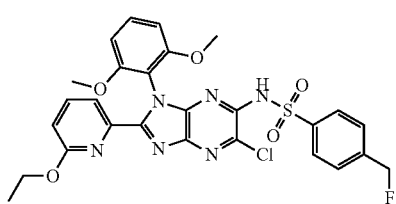
104 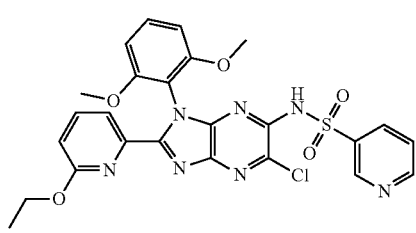 [SMILES: CCOc1cccc(-c2nc3nc(Cl)c(NS(=O)(=O)c4cccnc4)nc3n2-c2c(OC)cccc2OC)n1]
105 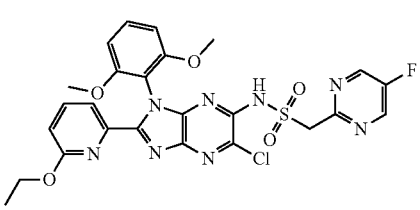 [SMILES: CCOc1cccc(-c2nc3nc(Cl)c(NS(=O)(=O)Cc4ncc(F)cn4)nc3n2-c2c(OC)cccc2OC)n1]
106 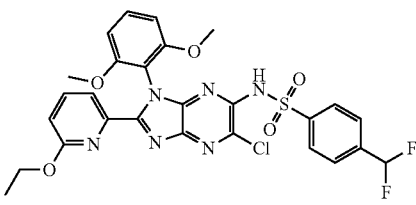 [SMILES: CCOc1cccc(-c2nc3nc(Cl)c(NS(=O)(=O)c4ccc(C(F)F)cc4)nc3n2-c2c(OC)cccc2OC)n1]
107 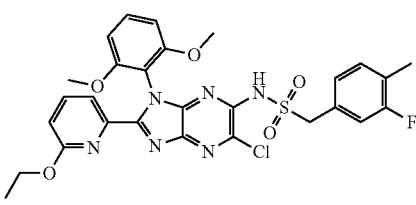 [SMILES: CCOc1cccc(-c2nc3nc(Cl)c(NS(=O)(=O)Cc4ccc(C)c(F)c4)nc3n2-c2c(OC)cccc2OC)n1]
108 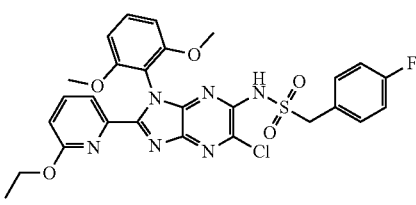 [SMILES: CCOc1cccc(-c2nc3nc(Cl)c(NS(=O)(=O)Cc4ccc(F)cc4)nc3n2-c2c(OC)cccc2OC)n1]
366
-continued
109 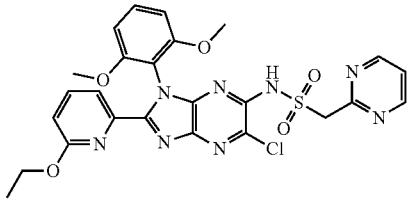 [SMILES: CCOc1cccc(-c2nc3nc(Cl)c(NS(=O)(=O)Cc4ncccn4)nc3n2-c2c(OC)cccc2OC)n1]
110 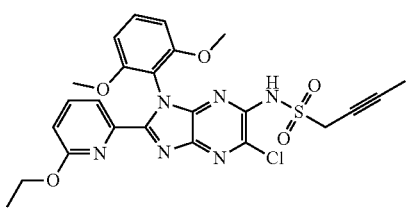 [SMILES: CC#CCS(=O)(=O)Nc1nc2c(nc1Cl)nc(-c1cccc(OCC)n1)n2-c1c(OC)cccc1OC]
111 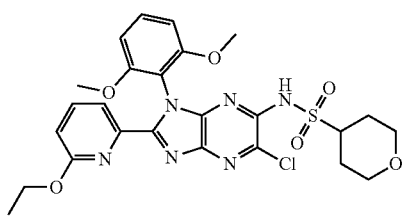 [SMILES: CCOc1cccc(-c2nc3nc(Cl)c(NS(=O)(=O)C4CCOCC4)nc3n2-c2c(OC)cccc2OC)n1]
112 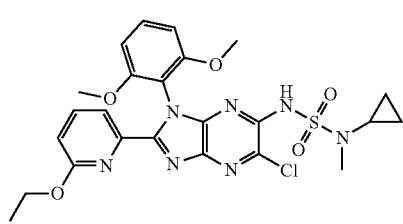 [SMILES: CCOc1cccc(-c2nc3nc(Cl)c(NS(=O)(=O)N(C)C4CC4)nc3n2-c2c(OC)cccc2OC)n1]
113 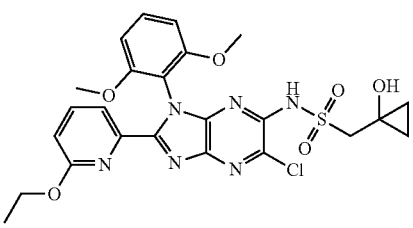 [SMILES: CCOc1cccc(-c2nc3nc(Cl)c(NS(=O)(=O)CC4(O)CC4)nc3n2-c2c(OC)cccc2OC)n1]
114 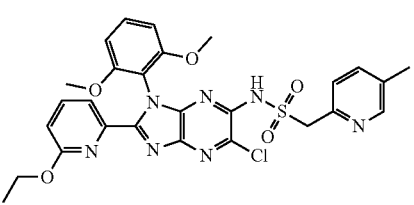 [SMILES: CCOc1cccc(-c2nc3nc(Cl)c(NS(=O)(=O)Cc4ccc(C)cn4)nc3n2-c2c(OC)cccc2OC)n1]
115 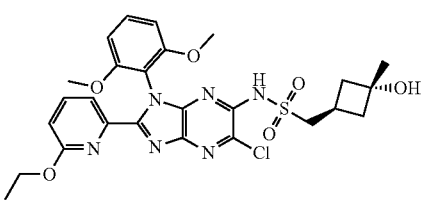 [SMILES: CCOc1cccc(-c2nc3nc(Cl)c(NS(=O)(=O)C[C@H]4C[C@](C)(O)C4)nc3n2-c2c(OC)cccc2OC)n1]

| | |
|---|---|
| 116 | 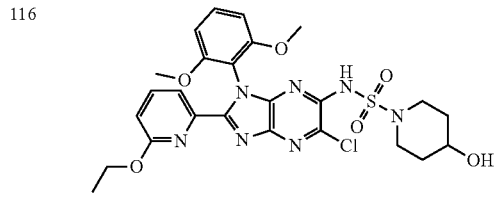 |
| 142 | 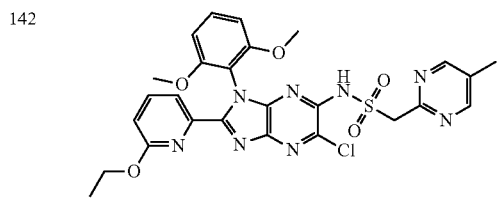 |
| or | |
| 143 | 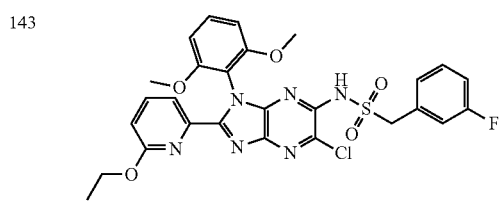 |

| | |
|---|---|
| 2 | N-(1-(2,6-dimethoxyphenyl)-2-(6-ethoxypyridin-2-yl)-1H-imidazo[4,5-b]pyrazin-6-yl)methanesulfonamide, |
| 3 | N-(1-(2,6-dimethoxyphenyl)-2-(6-ethoxypyridin-2-yl)-1H-imidazo[4,5-b]pyrazin-6-yl)-1-phenylmethanesulfonamide, |
| 4 | 1-cyclopropyl-N-(1-(2,6-dimethoxyphenyl)-2-(6-ethoxypyridin-2-yl)-1H-imidazo[4,5-b]pyrazin-6-yl)methanesulfonamide, |
| 5 | N-(1-(2,6-dimethoxyphenyl)-2-(6-ethoxypyridin-2-yl)-1H-imidazo[4,5-b]pyrazin-6-yl)benzenesulfonamide, |
| 22 | N-(1-(2,6-dimethoxyphenyl)-2-(6-ethoxypyridin-2-yl)-1H-imidazo[4,5-b]pyrazin-6-yl)cyclopropanesulfonamide, |
| 23 | N-(1-(2,6-dimethoxyphenyl)-2-(6-ethoxypyridin-2-yl)-1H-imidazo[4,5-b]pyrazin-6-yl)pyridine-2-sulfonamide, |
| 24 | N-(1-(2,6-dimethoxyphenyl)-2-(6-ethoxypyridin-2-yl)-1H-imidazo[4,5-b]pyrazin-6-yl)pyridine-3-sulfonamide, |
| 25 | N-(1-(2,6-dimethoxyphenyl)-2-(6-ethoxypyridin-2-yl)-1H-imidazo[4,5-b]pyrazin-6-yl)pyridine-4-sulfonamide, |
| 26 | N-(1-(2,6-dimethoxyphenyl)-2-(6-ethoxypyridin-2-yl)-1H-imidazo[4,5-b]pyrazin-6-yl)-1-(pyridin-3-yl)methanesulfonamide, |
| 27 | N-(1-(2,6-dimethoxyphenyl)-2-(6-ethoxypyridin-2-yl)-1H-imidazo[4,5-b]pyrazin-6-yl)-1-(pyridin-2-yl)methanesulfonamide, |
| 28 | N-(1-(2,6-dimethoxyphenyl)-2-(6-ethoxypyridin-2-yl)-1H-imidazo[4,5-b]pyrazin-6-yl)-1-(pyrimidin-2-yl)methanesulfonamide, |
| 29 | 2-cyclopropyl-N-(1-(2,6-dimethoxyphenyl)-2-(6-ethoxypyridin-2-yl)-1H-imidazo[4,5-b]pyrazin-6-yl)ethanesulfonamide, |
| 30 | N-(1-(2,6-dimethoxyphenyl)-2-(6-ethoxypyridin-2-yl)-1H-imidazo[4,5-b]pyrazin-6-yl)oxetane-3-sulfonamide, |
| 31 | N-(1-(2,6-dimethoxyphenyl)-2-(6-ethoxypyridin-2-yl)-1H-imidazo[4,5-b]pyrazin-6-yl)cyclobutanesulfonamide, |
| 32 | N-(1-(2,6-dimethoxyphenyl)-2-(6-ethoxypyridin-2-yl)-1H-imidazo[4,5-b]pyrazin-6-yl)-N-methylmethanesulfonamide, |
| 33 | cis-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide, |
| 34 | trans-N-(1-(2,6-dimethoxyphenyl)-2-(6-ethoxypyridin-2-yl)-1H-imidazo[4,5-b]pyrazin-6-yl)-3-hydroxycyclobutane-1-sulfonamide, |
| 35 | N-(1-(2,6-dimethoxyphenyl)-2-(6-ethoxypyridin-2-yl)-1H-imidazo[4,5-b]pyrazin-6-yl)-1-(pyrimidin-5-yl)methanesulfonamide, |
| 36 | N-(1-(2,6-dimethoxyphenyl)-2-(6-ethoxypyridin-2-yl)-1H-imidazo[4,5-b]pyrazin-6-yl)tetrahydro-2H-pyran-4-sulfonamide, |
| 37 | N-(1-(2,6-dimethoxyphenyl)-2-(6-ethoxypyridin-2-yl)-1H-imidazo[4,5-b]pyrazin-6-yl)morpholine-4-sulfonamide, |
| 38 | N-(1-(2,6-dimethoxyphenyl)-2-(6-ethoxypyridin-2-yl)-1H-imidazo[4,5-b]pyrazin-6-yl)-1-(piperidin-4-yl)methanesulfonamide, |
| 39 | trans-N-(1-(2,6-dimethoxyphenyl)-2-(6-ethoxypyridin-2-yl)-1H-imidazo[4,5-b]pyrazin-6-yl)-4-hydroxycyclohexane-1-sulfonamide, |
| 40 | cis-N-(1-(2,6-dimethoxyphenyl)-2-(6-ethoxypyridin-2-yl)-1H-imidazo[4,5-b]pyrazin-6-yl)-4-hydroxycyclohexane-1-sulfonamide, |
| 41 | N-(1-(2,6-dimethoxyphenyl)-2-(6-ethoxypyridin-2-yl)-1H-imidazo[4,5-b]pyrazin-6-yl)pyrimidine-2-sulfonamide, |
| 42 | N-(1-(2,6-dimethoxyphenyl)-2-(6-ethoxypyridin-2-yl)-1H-imidazo[4,5-b]pyrazin-6-yl)-4-hydroxypiperidine-1-sulfonamide, |
| 60 | N-(1-(2,6-dimethoxyphenyl)-2-(6-ethoxypyridin-2-yl)-1H-imidazo[4,5-b]pyrazin-6-yl)-3-hydroxy-3-methylbutane-1-sulfonamide, |
| 61 | N-(1-(2,6-dimethoxyphenyl)-2-(6-ethoxypyridin-2-yl)-1H-imidazo[4,5-b]pyrazin-6-yl)-1-(1-hydroxycyclopropyl)methanesulfonamide, |
| 64 | N-(5-chloro-1-(2,6-dimethoxyphenyl)-2-(6-ethoxypyridin-2-yl)-1H-imidazo[4,5-b]pyrazin-6-yl)methanesulfonamide, |
| 69 | N-(1-(2,6-dimethoxyphenyl)-2-(6-ethoxypyridin-2-yl)-1H-imidazo[4,5-b]pyrazin-6-yl)-1-(pyrazin-2-yl)methanesulfonamide, |
| 70 | N-(1-(2,6-Dimethoxyphenyl)-2-(6-ethoxypyridin-2-yl)-1H-imidazo[4,5-b]pyrazin-6-yl)-2-hydroxy-2-methylpropane-1-sulfonamide, |
| 71 | (S)-N-(1-(2,6-Dimethoxyphenyl)-2-(6-ethoxypyridin-2-yl)-1H-imidazo[4,5-b]pyrazin-6-yl)-1-(1-methyl-2-oxopiperidin-4-yl)methanesulfonamide, |
| 72 | (R)-N-(1-(2,6-dimethoxyphenyl)-2-(6-ethoxypyridin-2-yl)-1H-imidazo[4,5-b]pyrazin-6-yl)-1-(1-methyl-2-oxopiperidin-4-yl)methanesulfonamide, |
| 73 | N-(1-(2,6-dimethoxyphenyl)-2-(6-ethoxypyridin-2-yl)-1H-imidazo[4,5-b]pyrazin-6-yl)pyrrolidine-1-sulfonamide, |
| 74 | N-(1-(2,6-Dimethoxyphenyl)-2-(6-ethoxypyridin-2-yl)-1H-imidazo[4,5-b]pyrazin-6-yl)piperazine-1-sulfonamide, |
| 75 | N-(1-(2,6-dimethoxyphenyl)-2-(6-ethoxypyridin-2-yl)-1H-imidazo[4,5-b]pyrazin-6-yl)piperidine-1-sulfonamide, |
| 76 | N-(1-(2,6-dimethoxyphenyl)-2-(6-ethoxypyridin-2-yl)-1H-imidazo[4,5-b]pyrazin-6-yl)-N',N'-dimethylsulfamide, |
| 77 | N-(1-(2,6-dimethoxyphenyl)-2-(6-ethoxypyridin-2-yl)-1H-imidazo[4,5-b]pyrazin-6-yl)-N'-methyl-N'-cyclopropylsulfamide, |
| 78 | N-(1-(2,6-dimethoxyphenyl)-2-(6-ethoxypyridin-2-yl)-1H-imidazo[4,5-b]pyrazin-6-yl)-1-(5-fluoropyridin-2-yl)methanesulfonamide, |
| 79 | N-(1-(2,6-dimethoxyphenyl)-2-(6-ethoxypyridin-2-yl)-1H-imidazo[4,5-b]pyrazin-6-yl)-1-(5-fluoropyrimidin-2-yl)methanesulfonamide, |
| 80 | N-(1-(2,6-dimethoxyphenyl)-2-(6-ethoxypyridin-2-yl)-1H-imidazo[4,5-b]pyrazin-6-yl)-1-(5-methylpyrimidin-2-yl)methanesulfonamide, |

| | |
|---|---|
| 81 | trans-N-(1-(2,6-Dimethoxyphenyl)-2-(6-ethoxypyridin-2-yl)-1H-imidazo[4,5-b]pyrazin-6-yl)-1-((1r,3r)-3-hydroxy-3-methylcyclobutyl)methanesulfonamide, |
| 82 | N-(1-(2,6-Dimethoxyphenyl)-2-(6-ethoxypyridin-2-yl)-1H-imidazo[4,5-b]pyrazin-6-yl)but-2-yne-1-sulfonamide, |
| 83 | N-(1-(2,6-Dimethoxyphenyl)-2-(6-ethoxypyridin-2-yl)-1H-imidazo[4,5-b]pyrazin-6-yl)-1-(5-methylpyridin-2-yl)methanesulfonamide, |
| 94 | N-(5-Chloro-1-(2,6-dimethoxyphenyl)-2-(6-ethoxypyridin-2-yl)-1H-imidazo[4,5-b]pyrazin-6-yl)-1-(3-fluoropyridin-2-yl)methanesulfonamide, |
| 95 | N-(5-Chloro-1-(2,6-dimethoxyphenyl)-2-(6-ethoxypyridin-2-yl)-1H-imidazo[4,5-b]pyrazin-6-yl)-1-(pyridin-2-yl)methanesulfonamide, |
| 96 | N-(5-Chloro-1-(2,6-dimethoxyphenyl)-2-(6-ethoxypyridin-2-yl)-1H-imidazo[4,5-b]pyrazin-6-yl)-1-(5-fluoropyridin-2-yl)methanesulfonamide, |
| 97 | N-(5-Chloro-1-(2,6-dimethoxyphenyl)-2-(6-ethoxypyridin-2-yl)-1H-imidazo[4,5-b]pyrazin-6-yl)cyclopropanesulfonamide, |
| 98 | N-(5-Chloro-1-(2,6-dimethoxyphenyl)-2-(6-ethoxypyridin-2-yl)-1H-imidazo[4,5-b]pyrazin-6-yl)morpholine-4-sulfonamide, |
| 99 | N-(5-Chloro-1-(2,6-dimethoxyphenyl)-2-(6-ethoxypyridin-2-yl)-1H-imidazo[4,5-b]pyrazin-6-yl)-5-fluoropyridine-2-sulfonamide, |
| 100 | N-(5-Chloro-1-(2,6-dimethoxyphenyl)-2-(6-ethoxypyridin-2-yl)-1H-imidazo[4,5-b]pyrazin-6-yl)-1-(2-fluoro-4-methylphenyl)methanesulfonamide, |
| 101 | N-(5-Chloro-1-(2,6-dimethoxyphenyl)-2-(6-ethoxypyridin-2-yl)-1H-imidazo[4,5-b]pyrazin-6-yl)-5-methylpyridine-2-sulfonamide, |
| 102 | N-(5-Chloro-1-(2,6-dimethoxyphenyl)-2-(6-ethoxypyridin-2-yl)-1H-imidazo[4,5-b]pyrazin-6-yl)pyridine-2-sulfonamide, |
| 103 | N-(5-Chloro-1-(2,6-dimethoxyphenyl)-2-(6-ethoxypyridin-2-yl)-1H-imidazo[4,5-b]pyrazin-6-yl)-4-(fluoromethyl)benzenesulfonamide, |
| 104 | N-(5-Chloro-1-(2,6-dimethoxyphenyl)-2-(6-ethoxypyridin-2-yl)-1H-imidazo[4,5-b]pyrazin-6-yl)pyridine-3-sulfonamide, |
| 105 | N-(5-Chloro-1-(2,6-dimethoxyphenyl)-2-(6-ethoxypyridin-2-yl)-1H-imidazo[4,5-b]pyrazin-6-yl)-1-(5-fluoropyrimidin-2-yl)methanesulfonamide, |
| 106 | N-(5-Chloro-1-(2,6-dimethoxyphenyl)-2-(6-ethoxypyridin-2-yl)-1H-imidazo[4,5-b]pyrazin-6-yl)-4-(difluoromethyl)benzenesulfonamide, |
| 107 | N-(5-Chloro-1-(2,6-dimethoxyphenyl)-2-(6-ethoxypyridin-2-yl)-1H-imidazo[4,5-b]pyrazin-6-yl)-1-(3-fluoro-4-methylphenyl)methanesulfonamide, |
| 108 | N-(5-Chloro-1-(2,6-dimethoxyphenyl)-2-(6-ethoxypyridin-2-yl)-1H-imidazo[4,5-b]pyrazin-6-yl)-1-(4-fluorophenyl)methanesulfonamide, |
| 109 | N-(5-Chloro-1-(2,6-dimethoxyphenyl)-2-(6-ethoxypyridin-2-yl)-1H-imidazo[4,5-b]pyrazin-6-yl)-1-(pyrimidin-2-yl)methanesulfonamide, |
| 110 | N-(5-Chloro-1-(2,6-dimethoxyphenyl)-2-(6-ethoxypyridin-2-yl)-1H-imidazo[4,5-b]pyrazin-6-yl)but-2-yne-1-sulfonamide, |
| 111 | N-(5-Chloro-1-(2,6-dimethoxyphenyl)-2-(6-ethoxypyridin-2-yl)-1H-imidazo[4,5-b]pyrazin-6-yl)tetrahydro-2H-pyran-4-sulfonamide, |
| 112 | N-(5-Chloro-1-(2,6-dimethoxyphenyl)-2-(6-ethoxypyridin-2-yl)-1H-imidazo[4,5-b]pyrazin-6-yl)-N'-methyl-N'-cyclopropylsulfamide, |
| 113 | N-(5-Chloro-1-(2,6-dimethoxyphenyl)-2-(6-ethoxypyridin-2-yl)-1H-imidazo[4,5-b]pyrazin-6-yl)-1-(1-hydroxycyclopropyl)methanesulfonamide, |
| 114 | N-(5-Chloro-1-(2,6-dimethoxyphenyl)-2-(6-ethoxypyridin-2-yl)-1H-imidazo[4,5-b]pyrazin-6-yl)-1-(5-methylpyridin-2-yl)methanesulfonamide, |
| 115 | N-(5-Chloro-1-(2,6-dimethoxyphenyl)-2-(6-ethoxypyridin-2-yl)-1H-imidazo[4,5-b]pyrazin-6-yl)-1-((1r,3r)-3-hydroxy-3-methylcyclobutyl)methanesulfonamide, |
| 116 | N-(5-Chloro-1-(2,6-dimethoxyphenyl)-2-(6-ethoxypyridin-2-yl)-1H-imidazo[4,5-b]pyrazin-6-yl)-4-hydroxypiperidine-1-sulfonamide, |
| 142 | N-(5-Chloro-1-(2,6-dimethoxyphenyl)-2-(6-ethoxypyridin-2-yl)-1H-imidazo[4,5-b]pyrazin-6-yl)-1-(5-methylpyrimidin-2-yl)methanesulfonamide, |
| or | |
| 143 | N-(5-Chloro-1-(2,6-dimethoxyphenyl)-2-(6-ethoxypyridin-2-yl)-1H-imidazo[4,5-b]pyrazin-6-yl)-1-(3-fluorophenyl)methanesulfonamide, | or a pharmaceutically acceptable salt thereof.

2. A pharmaceutical composition comprising a compound of claim 1, or a pharmaceutically acceptable salt thereof, and one or more pharmaceutically acceptable excipients.

3. A compound which is:

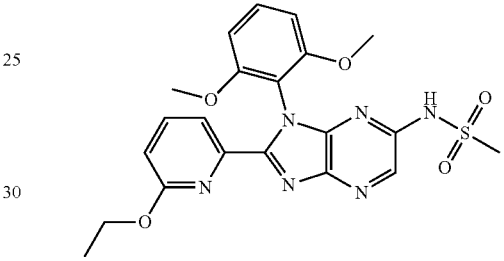

or a pharmaceutically acceptable salt thereof.

4. A compound which is:

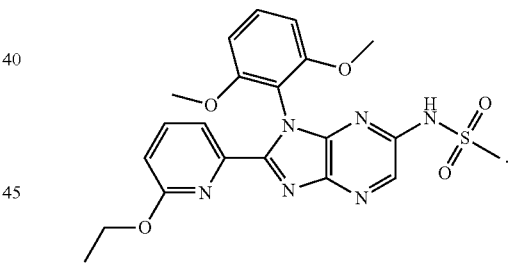

5. A pharmaceutical composition comprising the compound of claim 3, or a pharmaceutically acceptable salt thereof, and a pharmaceutically acceptable excipient.

6. A compound which is:

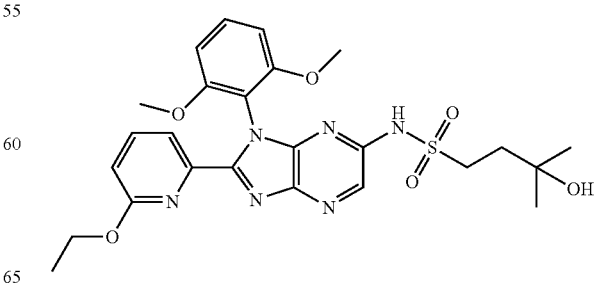

or a pharmaceutically acceptable salt thereof.

7. A compound which is:

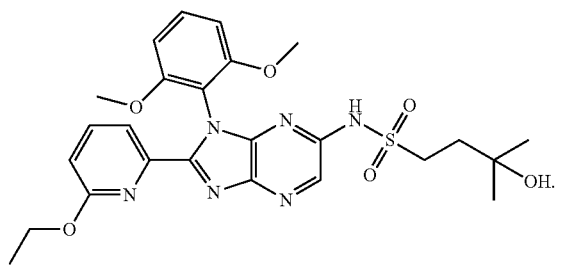 [SMILES: CCOc1cccc(-c2nc3ncc(NS(=O)(=O)CCC(C)(C)O)nc3n2-c2c(OC)cccc2OC)n1]

8. A pharmaceutical composition comprising the compound of claim 6, or a pharmaceutically acceptable salt thereof, and a pharmaceutically acceptable excipient.

9. A compound which is:

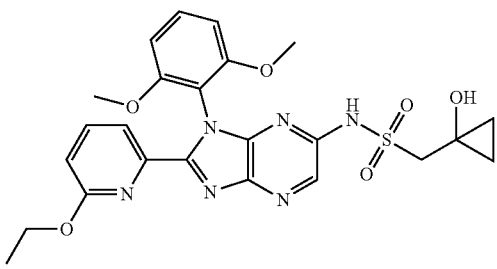 [SMILES: CCOc1cccc(-c2nc3ncc(NS(=O)(=O)CC4(O)CC4)nc3n2-c2c(OC)cccc2OC)n1]

or a pharmaceutically acceptable salt thereof.

10. A compound which is:

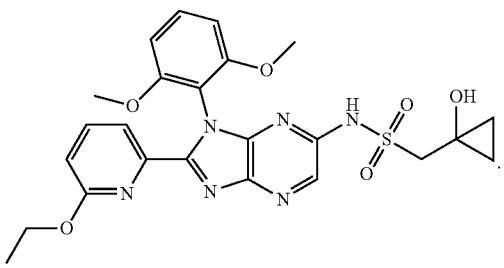 [SMILES: CCOc1cccc(-c2nc3ncc(NS(=O)(=O)CC4(O)CC4)nc3n2-c2c(OC)cccc2OC)n1]

11. A pharmaceutical composition comprising the compound of claim 9, or a pharmaceutically acceptable salt thereof, and a pharmaceutically acceptable excipient.

12. A compound which is:

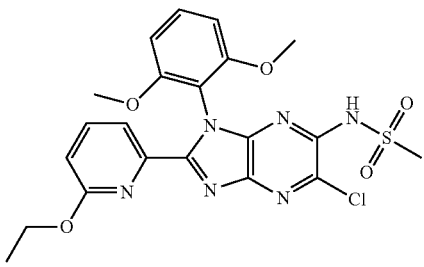 [SMILES: CCOc1cccc(-c2nc3nc(Cl)c(NS(C)(=O)=O)nc3n2-c2c(OC)cccc2OC)n1]

or a pharmaceutically acceptable salt thereof.

13. A compound which is:

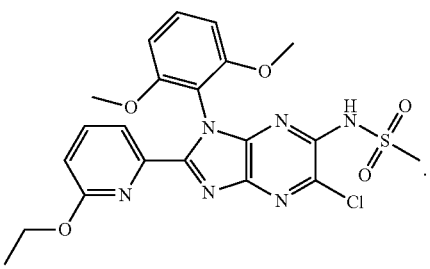 [SMILES: CCOc1cccc(-c2nc3nc(Cl)c(NS(C)(=O)=O)nc3n2-c2c(OC)cccc2OC)n1]

14. A pharmaceutical composition comprising the compound of claim 12, or a pharmaceutically acceptable salt thereof, and a pharmaceutically acceptable excipient.

15. A compound which is:

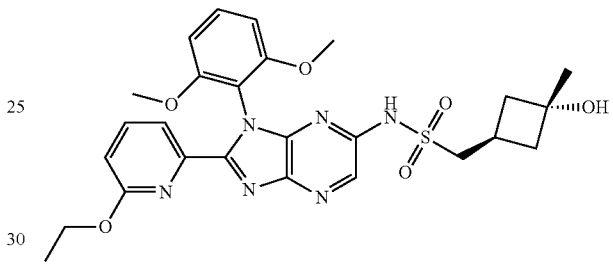

or a pharmaceutically acceptable salt thereof.

16. A compound which is:

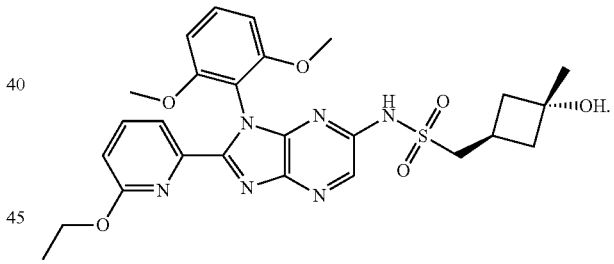

17. A pharmaceutical composition comprising the compound of claim 15, or a pharmaceutically acceptable salt thereof, and a pharmaceutically acceptable excipient.

18. A compound which is:

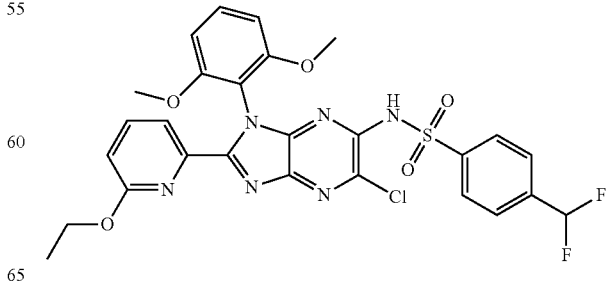

or a pharmaceutically acceptable salt thereof.

19. A compound which is:
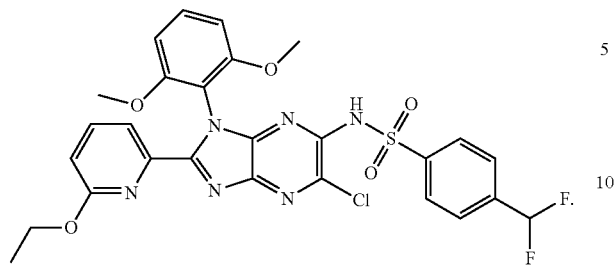
20. A pharmaceutical composition comprising the compound of claim 19, or a pharmaceutically acceptable salt thereof, and a pharmaceutically acceptable excipient.
* * * * *